US006534535B1

(12) United States Patent
Zhu et al.

(10) Patent No.: US 6,534,535 B1
(45) Date of Patent: Mar. 18, 2003

(54) INHIBITORS OF FACTOR XA

(75) Inventors: Bing-Yan Zhu, Belmont, CA (US); Robert M. Scarborough, Half Moon Bay, CA (US); Lane Clizbe, Redwood City, CA (US); Brandon Doughan, San Francisco, CA (US); Zhaozhong Jon Jia, South San Franscisco, CA (US); Kim Kane-Maguire, Belmont, CA (US); Charles Marlowe, Redwood City, CA (US); Yonghong Song, Foster City, CA (US); Ting Su, Belmont, CA (US); Willy Teng, San Francisco, CA (US); Penglie Zhang, San Francisco, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 6 days.

(21) Appl. No.: 09/636,804

(22) Filed: Aug. 10, 2000

Related U.S. Application Data

(60) Provisional application No. 60/202,202, filed on May 5, 2000, and provisional application No. 60/148,627, filed on Aug. 12, 1999.

(51) Int. Cl.[7] ........................ A61K 31/40; A61K 31/47; C07D 209/02; C07D 209/04; C07D 217/22

(52) U.S. Cl. ........................ 514/414; 514/312; 514/313; 514/310; 514/379; 514/405; 514/414; 514/415; 514/416; 546/143; 546/153; 548/454; 548/465; 548/483; 548/484; 548/492; 548/494; 548/503; 548/362.1; 548/241

(58) Field of Search .............................. 548/152.1, 454, 548/465, 483, 484, 492, 494, 503, 362.1, 241; 546/143, 153; 514/312, 313, 310, 379, 405, 414, 415, 416

(56) References Cited

U.S. PATENT DOCUMENTS

| | | | | |
|---|---|---|---|---|
| 5,391,566 A | * | 2/1995 | Chakravarty | |
| 5,486,525 A | | 1/1996 | Summers, Jr. et al. | 514/303 |
| 5,849,759 A | * | 12/1998 | Arnaiz | |
| 5,886,194 A | * | 3/1999 | Dominguez | |
| 6,043,257 A | * | 3/2000 | Dominguez | |
| 6,207,695 B1 | * | 3/2001 | Nelson | |

FOREIGN PATENT DOCUMENTS

| | | | |
|---|---|---|---|
| DE | 19718181 | * | 11/1998 |
| EP | 574174 | | 12/1993 |
| EP | 620214 | | 10/1994 |
| EP | 781774 | | 7/1997 |
| WO | WO 93/01813 | | 2/1992 |
| WO | WO 95/16687 | | 6/1995 |
| WO | WO 97/14682 | | 4/1997 |
| WO | WO 97/17333 | | 5/1997 |
| WO | WO 97/40846 | | 11/1997 |
| WO | 98/01428 | * | 1/1998 |
| WO | 99/00128 | * | 1/1999 |
| WO | 99/12903 | * | 3/1999 |

OTHER PUBLICATIONS

Han, CA 134:86116, abstract of J Med Chem, 43(23), pp4398–4415, 2000.*

Zhao, CA 133:144480, abstract of Bioorg Med Chem Lett, 10(9), 963–966, 2000.*

Database CA on STN, Chemical Abstracts, (Columbus, OH, USA), No. 125:167737, Katritzky, A.R. 'A new indole synthesis via [3+3] annulation of 2–(benzotriazol–1–ylmethyl)pyrroles with .alpha . . . beta.–unsaturated aldehydes and ketones,' abstract Tetrahedron Let. vol. 37, No. 32, pp. 5641–5644, 1996.

Database CA on STN, Chemical Abstracts, (Columbus, OH, USA), No. 124:175907, Sheppard, G.S., 'Synthesis and evaluation of water soluble indole pyrrolothiazole PAF antagonists,' abstract, Bioorg. Med. Chem. Lett. vol. 5, No. 23, pp. 2913–1918, 1995.

Database CA on STN, Chemical Abstracts, (Columbus, OH, USA), No. 99:157, Kolasa, K. 'Preliminary pharmacological studies of the central action of phenyl and piperidinomethyl derivatives of 2–benzoxazolone,' abstract Ann. Univ. mariae Curie–Sklodowska, Sect. D. vol. 36 pp. 73–81, 1981.

* cited by examiner

*Primary Examiner*—D. Margaret Seaman
(74) *Attorney, Agent, or Firm*—Townsend and Townsend and Crew LLP

(57) ABSTRACT

Novel compounds, their salts and compositions related thereto having activity against mammalian factor Xa are disclosed. The compounds of formula (I) below:

(I)

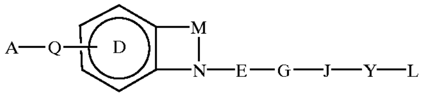

are useful in vitro or in vivo for preventing or treating coagulation disorders.

42 Claims, No Drawings

INHIBITORS OF FACTOR XA

RELATED APPLICATIONS

This application claims benefit of priority under 35 USC § 119(e) to U.S. Provisional Application No. 60/202,202 filed on May 5, 2000 and U.S. Provisional Application No. 60/148,627 filed on Aug. 12, 1999, which are both herein incorporated in their entirety by reference.

FIELD OF THE INVENTION

This invention relates to novel compounds which are potent and highly selective inhibitors of isolated factor Xa or factor Xa when assembled in the prothrombinase complex. These compounds show selectivity for factor Xa versus other proteases of the coagulation (e.g. thrombin, fVIIa, fIXa) or the fibrinolytic cascades (e.g. plasminogen activators, plasmin). In another aspect, the present invention relates to novel monoamidino-containing compounds, their pharmaceutically acceptable salts, and pharmaceutically acceptable compositions thereof which are useful as potent and specific inhibitors of blood coagulation in mammals. In yet another aspect, the invention relates to methods for using these inhibitors as therapeutic agents for disease states in mammals characterized by coagulation disorders.

BACKGROUND OF THE INVENTION

Hemostasis, the control of bleeding, occurs by surgical means, or by the physiological properties of vasoconstriction and coagulation. This invention is particularly concerned with blood coagulation and ways in which it assists in maintaining the integrity of mammalian circulation after injury, inflammation, disease, congenital defect, dysfunction or other disruption. Although platelets and blood coagulation are both involved in thrombus formation, certain components of the coagulation cascade are primarily responsible for the amplification or acceleration of the processes involved in platelet aggregation and fibrin deposition.

Thrombin is a key enzyme in the coagulation cascade as well as in hemostasis. Thrombin plays a central role in thrombosis through its ability to catalyze the conversion of fibrinogen into fibrin and through its potent platelet activation activity. Direct or indirect inhibition of thrombin activity has been the focus of a variety of recent anticoagulant strategies as reviewed by Claeson, G., "Synthetic Peptides and Peptidomimetics as Substrates and Inhibitors of Thrombin and Other Proteases in the Blood Coagulation System", Blood Coag. Fibrinol. 5, 411–436 (1994). Several classes of anticoagulants currently used in the clinic directly or indirectly affect thrombin (i.e. heparins, low-molecular weight heparins, heparin-like compounds and coumarins).

A prothrombinase complex, including Factor Xa (a serine protease, the activated form of its Factor X precursor and a member of the calcium ion binding, gamma carboxyglutamyl (Gla)-containing, vitamin K dependent, blood coagulation glycoprotein family), converts the zymogen prothrombin into the active procoagulant thrombin. Unlike thrombin, which acts on a variety of protein substrates as well as at a specific receptor, factor Xa appears to have a single physiologic substrate, namely prothrombin. Since one molecule of factor Xa may be able to generate up to 138 molecules of thrombin (Elodi et al., *Thromb. Res.* 15, 617–619 (1979)), direct inhibition of factor Xa as a way of indirectly inhibiting the formation of thrombin may be an efficient anticoagulant strategy. Therefore, it has been suggested that compounds which selectively inhibit factor Xa may be useful as in vitro diagnostic agents, or for therapeutic administration in certain thrombotic disorders, see e.g., WO 94/13693.

Polypeptides derived from hematophagous organisms have been reported which are highly potent and specific inhibitors of factor Xa. U.S. Pat. No. 4,588,587 describes anticoagulant activity in the saliva of the Mexican leech, *Haementeria officinalis*. A principal component of this saliva was shown to be the polypeptide factor Xa inhibitor, antistasin (ATS), by Nutt, E. et al., "The Amino Acid Sequence of Antistasin, a Potent Inhibitor of Factor Xa Reveals a Repeated Internal Structure", J. Biol. Chem., 263, 10162–10167 (1988). Another potent and highly specific inhibitor of Factor Xa, called tick anticoagulant peptide (TAP), has been isolated from the whole body extract of the soft tick *Omnithidoros moubata*, as reported by Waxman, L., et al., "Tick Anticoagulant Peptide (TAP) is a Novel Inhibitor of Blood Coagulation Factor Xa" Science, 248 593–596 (1990).

Factor Xa inhibitory compounds which are not large polypeptide-type inhibitors have also been reported including: Tidwell, R. R. et al., "Strategies for Anticoagulation With Synthetic Protease Inhibitors. Xa Inhibitors Versus Thrombin Inhibitors", Thromb. Res., 19, 339–349 (1980); Turner, A. D. et al., "p-Amidino Esters as Irreversible Inhibitors of Factor IXa and Xa and Thrombin", Biochemistry, 25, 4929–4935 (1986); Hitomi, Y. et al., "Inhibitory Effect of New Synthetic Protease Inhibitor (FUT-175) on the Coagulation System", Haemostasis, 15, 164–168 (1985); Sturzebecher, J. et al., "Synthetic Inhibitors of Bovine Factor Xa and Thrombin. Comparison of Their Anticoagulant Efficiency", Thromb. Res., 54, 245–252 (1989); Kam, C. M. et al., "Mechanism Based Isocoumarin Inhibitors for Trypsin and Blood Coagulation Serine Proteases: New Anticoagulants", Biochemistry, 27, 2547–2557 (1988); Hauptmann, J. et al., "Comparison of the Anticoagulant and Antithrombotic Effects of Synthetic Thrombin and Factor Xa Inhibitors", Thromb. Haemost., 63, 220–223 (1990); and the like.

Others have reported Factor Xa inhibitors which are small molecule organic compounds, such as nitrogen containing heterocyclic compounds which have amidino substituent groups, wherein two functional groups of the compounds can bind to Factor Xa at two of its active sites. For example, WO 98/28269 describes pyrazole compounds having a terminal $C(=NH)-NH_2$ group; WO 97/21437 describes benzimidazole compounds substituted by a basic radical which are connected to a naththyl group via a straight or branched chain alkylene, $-C(=O)$ or $-S(=O)_2$ bridging group; WO 99/10316 describes compounds having a 4-phenyl-N-alkylamidino-piperidine and 4-phenoxy-N-alkylarnidino-piperidine group connected to a 3-amidinophenyl group via a carboxamidealkyleneamino bridge; and EP 798295 describes compounds having a 4-phenoxy-N-alkylamidino-piperidine group connected to an amidinonaphthyl group via a substituted or unsubstituted sulfonamide or carboxamide bridging group.

There exists a need for effective therapeutic agents for the regulation of hemostasis, and for the prevention and treatment of thrombus formation and other pathological processes in the vasculature induced by thrombin such as restenosis and inflammation. In particular, there continues to be a need for compounds which selectively inhibit factor Xa or its precursors. Compounds that have different combinations of bridging groups and functional groups than compounds previously discovered are needed, particularly compounds which selectively or preferentially bind to Factor Xa.

Compounds with a higher degree of binding to Factor Xa than to thrombin are desired, especially those compounds having good bioavailability and/or solubility.

SUMMARY OF THE INVENTION

The present invention relates to novel compounds which inhibit factor Xa, their pharmaceutically acceptable isomers, salts, hydrates, solvates and prodrug derivatives, and pharmaceutically acceptable compositions thereof which have particular biological properties and are useful as potent and specific inhibitors of blood coagulation in mammals. Pharmaceutical compositions of the invention may be used to prevent or treat a condition in a mammal characterized by undesired thrombosis. In another aspect, the invention relates to methods of using these inhibitors as diagnostic reagents or as therapeutic agents for disease states in mammals which have coagulation disorders, such as in the treatment or prevention of a condition in a mammal characterized by undesired thrombosis such as, for example, any thrombotically mediated acute coronary or cerebrovascular syndrome, any thrombotic syndrome occurring in the venous system, any coagulopathy, and any thrombotic complications associated with extracorporeal circulation or instrumentation, and for the inhibition of coagulation of biological samples and blood in biological samples.

In certain embodiments, this invention relates to novel compounds which are potent and highly selective inhibitors of isolated factor Xa or factor Xa when assembled in the prothrombinase complex. These compounds show selectivity for factor Xa versus other proteases of the coagulation cascade (e.g. thrombin, etc.) or the fibrinolytic cascade, and are useful as diagnostic reagents as well as antithrombotic agents.

In a preferred embodiment, the present invention provides a compound of the formula I:

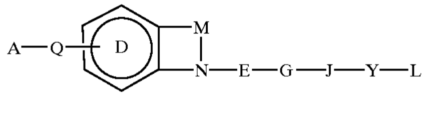

wherein:

A is selected from:

(a) $C_1$–$C_6$-alkyl;

(b) $C_3$–$C_8$-cycloalkyl;

(c) —N(—$R^2$,—$R^3$), $R^3$—C(=N—$R^2$)—, (—$R^2$, —$R^3$)N—C(=N—$R^2$)—, (—$R^2$, —$R^3$)N—C(=N—$R^2$)—N(—R—)—

(d) phenyl, which is independently substituted with 0–2 $R^1$ substituents;

(e) naphthyl, which is independently substituted with 0–2 $R^1$ substituents; and (f) a monocyclic or fused bicyclic heterocyclic ring system having from 5 to 10 ring atoms, wherein 1–4 ring atoms of the ring system are selected from N, O and S, and wherein the ring system may be substituted with 0–2 $R^1$ substituents;

$R^1$ is selected from:

Halo, $C_{1-4}$alkyl, $C_{2-6}$alkenyl, $C_{2-6}$alkynyl, $C_{3-8}$scycloalkyl, $C_{0-4}$alkyl$C_{3-8}$cycloalkyl, —CN, —$NO_2$, $R^2$—C(=N—$R^3$)—, (—$R^2$, —$R^3$)N—C(=N—$R^2$)—, (—$CH_2$)$_m$N$R^2R^3$, —C(=O)—N(—$R^2$, —$R^3$), —$SO_2$N(—$R^2$, —$R^3$), —$SO_2R^2$, —$CF_3$, —O$R^2$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_1$–$C_4$-alkyl, —CN $C_{1-4}$alkyl, $C_{2-6}$alkenyl, $C_{2-6}$alkenyl, $C_{3-8}$cycloalkyl, $C_{0-4}$alkyl$C_{3-8}$cycloalkyl and —$NO_2$;

$R^2$ and $R^3$ are independently selected from the group consisting of:

H, —O$R^2$, —N(—$R^2$, —$R^3$), —$C_{1-4}$alkyl, —$C_{2-6}$ alkenyl, —$C_{2-6}$alkynyl, —$C_{3-8}$cycloalkyl, —$C_{0-4}$ alkyl$C_{3-8}$cycloalkyl, —$C_{0-4}$alkylphenyl and —$C_{0-4}$ alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$ cycloalkyl, —$C_{0-4}$alkyl$C_{3-8}$cycloalkyl, —CN, and —$NO_2$;

or $R^2$ and $R^3$ taken together can form a 3–8 membered cycloalkyl or a heterocyclic ring system, wherein the heterocyclic ring system may have from 5 to 10 ring atoms, with 1 to 2 rings being in the ring system and contain from 1–4 heteroatoms selected from N, O and S, wherein from 1–4 hydrogen atoms on the heterocyclic ring system may be independently replaced with a member selected from the group consisting of halo, $C_1$–$C_4$-alkyl, —CN —$C_{1-4}$alkyl, —$C_{2-6}$alkenyl, —$C_{2-6}$ alkynyl, —$C_{3-8}$cycloalkyl, —$C_{0-4}$alkyl$C_{3-8}$cycloalkyl and —$NO_2$;

m is an integer of 0–2;

Q is a member selected from the group consisting of:

a direct link, —CH2—, —C(=O)—, —N($R^4$)—, —N($R^4$)CH2—, —C=N(R4)—, —C(=O)—N($R^4$)—, —N($R^4$)—C(=O)—, —$SO_2$—, —O—, —$SO_2$—N($R^4$)— and —N($R^4$)—$SO_2$—;

$R^4$ is selected from:

H, —$C_{1-4}$alkyl, —$C_{2-6}$alkenyl, —$C_{2-6}$alkynyl, —$C_{3-8}$ cycloalkyl, —$C_{0-4}$alkyl$C_{3-8}$cycloalkyl, —$C_{0-4}$ alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —$NO_2$;

D is a member selected from the group consisting of:

(a) phenyl, which is independently substituted with 0–2 $R^{1a}$ substituents; and (b) an aromatic six-membered heterocyclic ring having from 1–2 ring nitrogen atoms, and wherein the ring atoms may be substituted with 0–2 $R^{1a}$ substituents;

$R^{1a}$ is selected from:

Halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —$NO_2$, $(CH_2)_m$N$R^{2a}R^{3a}$, $SO_2$N$R^{2a}R^{3a}$, $SO_2R^{2a}$, $CF_3$, O$R^{2a}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

$R^{2a}$ and $R^{3a}$ are independently selected from the group consisting of:

$C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

M is a member selected from the group consisting of:

—N($R^{16}$)—C(=O)—, —N($R^{16}$)—C(=S)—, —C(—$R^{17}$,—$R^{18}$)—C(=O)—, —C(—$R^{17}$,—$R^{18}$)—C(=S)—, —C(—$R^{17}$,$R^{17a}$)—C(—$R^{18}$,—$R^{18a}$)—, —C(—$R^{19}$,—$R^{19a}$)—C(—$R^{17}$,—$R^{17a}$)—C(—$R^{18}$,—$R^{18a}$)—, —C(—$R^{17}$)=C(—$R^{18}$)—C(=O)—, —C(—$R^{17}$)=C(—$R^{18}$)—C(=S)—, —C(—$R^{17}$)=C(—$R^{18}$)—, —O—C(—$R^{17}$,—$R^{18}$)—C(=O)—, —O—C(—$R^{17}$,—$R^{18}$)—C(=S)—, —S—C(—$R^{17}$,—$R^{18}$)—C(=O)—, —S(=O)$_2$—C(—$R^{17}$,—$R^{18}$)—C(=O)—, —S(=O)—C(—$R^{17}$,—$R^{18}$)—C(=O)—, —S—C(—$R^{17}$,—$R^{18}$)—C(=S)—, —S(=O)$_2$—C(—$R^{17}$,—$R^{18}$)—C(=S)—, —S(=O)—C(—$R^{17}$,—$R^{18}$)—C(=S)—, —C(=O)—C(=O)—, —N($R^{16}$)—C(—$R^{17}$,—$R^{18}$)—C(=O)—, —N($R^{16}$)—C(—$R^{17}$,—$R^{18}$)—C(=S)—, —C(=S)—C(=S)—, —C(=S)—C(=O)—, —C(=O)—C(=S)—, —N=C(—$R^{17}$)—C(=O)—, —N=C(—$R^{17}$)—C(=S)—, —C(—$R^{17}$)=N—, —N(—$R^{16}$)—C(=O)—C(—$R^{18}$,—$R^{18a}$)—C(—$R^{17}$,—$R^{17a}$)—, —O—C(—$R^{18}$,—$R^{18a}$)—C(—$R^{17}$,—$R^{17a}$)—, —N(—$R^{16}$)—C(=S)—C(—$R^{18}$,—$R^{18a}$)—C(—$R^{17}$,—$R^{17a}$)—, —S(=O)—C(—$R^{18}$,—$R^{18a}$)—C(—$R^{17}$,—$R^{17a}$)—, —S(=O)$_2$—C(—$R^{18}$,—$R^{18a}$)—C(—$R^{17}$,—$R^{17a}$)—, —C(=C($R^{17b}$,—$R^{17c}$))—C(=O)—, —C(=C($R^{17b}$,—$R^{17c}$))—C(=S)—, —N(—$R^{16}$)—C(—$R^{18}$,—$R^{18a}$)—C(—$R^{17}$,—$R^{17a}$)—C(=S)—, —N(—$R^{16}$)—C(—$R^{18}$,—$R^{18a}$)—C(—(N(—H,—$R^{18b}$)),—$R^{17a}$)—C(=O)—; —N=C(—$R^{17}$)— and —N(—$R^{16}$)—C(—$R^{18}$,—$R^{18a}$)—C(—(N(—H,—$R^{18b}$)), —$R^{17a}$)—C(=S)—; wherein the first named atom of the chain is directly attached to D, and wherein D, M and the N atom attached to the last chain atom of M collectively form a bicyclic ring structure;

$R^{16}$, $R^{17}$, $R^{17a}$, $R^{18}$, $R^{18a}$, $R^{18b}$, $R^{19}$, and $R^{19a}$ are each independently selected from the consisting of:

hydrogen, halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —$NO_2$, $(CH_2)_m NR^2R^3$, $SO_2NR^2R^3$, $SO_2R^2$, $CF_3$, $OR^2$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_1$–$C_4$-alkyl, —CN, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl and —$NO_2$;

$R^{17b}$ and $R^{17c}$ are each independently a member selected from the group consisting of hydrogen, -halo, hydroxy, —$C_{1-4}$alkyl, $C_{2-6}$alkenyl, —$C_{2-6}$alkynyl, —$C_{3-8}$cycloalkyl, —$C_{0-4}$alkyl-$C_{3-8}$cycloalkyl, —CN, —$NO_2$, —$(CH_2)_m NR^2R^3$, —$SO_2NR^2R^3$, —$SO_2R^2$, —$CF_3$, —$OR^2$, phenyl, and a 5–6 membered aromatic heterocyclic ring containing from 1–4 heteroatoms selected from N, O and S, wherein from 1–4 hydrogen atoms on the cycloalkyl, the phenyl ring, or the aromatic heterocyclic ring may be independently replaced with a member selected from the group consisting of halo, $C_1$–$C_4$-alkyl, —CN, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl and —$NO_2$;

E is a member selected from the group consisting of:

a direct link, —C(=O)—, —C(=O)—N($R^5$)—, —C(—$R^{5a}$,—$R^{6a}$)— and —C(—$R^{5b}$,—$R^{6b}$)—C(—$R^{5c}$,—$R^{6c}$)—;

wherein $R^5$, $R^{5a}$, $R^{6a}$, $R^{5b}$, $R^{6b}$, $R^{5c}$ and $R^{6c}$ are independently selected from:

H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl, $C_{0-4}$alkylnaphthyl, $C_{0-4}$alkylheteroaryl, $C_{1-4}$alkylCOOH and $C_{1-4}$alkylCOO$C_{1-4}$alkyl, wherein from 0–4 hydrogen atoms on the ring atoms of the phenyl, naphthyl and heteroaryl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —OH, —O—$C_{1-4}$alkyl, —SH, —S—$C_{1-4}$alkyl, —CN and —$NO_2$;

G is selected from:

a direct link, —C($R^7$,$R^8$)—, —C($R^{7a}$,$R^{8a}$)—C($R^{7b}$, $R^{8b}$)— and —C($R^{7c}$)=C($R^{8c}$)—;

wherein $R^7$, $R^8$, $R^{7a}$, $R^{8a}$, $R^{7b}$, $R^{8b}$, $R^{7c}$ and $R^{8c}$ are independently a member selected from from the group consisting of:

hydrogen, halogen, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, $C_{0-4}$alkylphenyl, $C_{0-4}$alkylnaphthyl, —$OR^9$, —N($R^9R^{10}$), —$C_{0-4}$alkylCOO$R^9$, —$C_{0-4}$alkylC(=O)N$R^9R^{10}$, —$C_{0-4}$alkylC(=O)O$R^9$, —$C_{0-4}$alkylC(=O)N$R^9$—$CH_2$—$CH_2$—O—$R^{10}$, —$C_{0-4}$alkylC(=O)N$R^9$(—$CH_2$—$CH_2$—O—$R^{10}$—)$_2$, —N($R^9$)CO$R^{10}$, —N($R^9$)C(=O)$R^{10}$,—N($R^9$)$SO_2R^{10}$, a naturally occurring or synthetic amino acid side chain, and $C_{0-4}$alkylheterocyclic ring having from 1 to 4 hetero ring atoms selected from the group consisting of N, O and S, $CH_2COOC_{1-4}$alkyl, $CH_2COOC_{1-4}$alkylphenyl and $CH_2COOC_{1-4}$alkylnaphthyl, wherein from 1–4 hydrogen atoms on the $C_{0-4}$alkylheterocyclic ring may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

wherein from 1–4 hydrogen atoms on the ring atoms of the phenyl and naphthyl moieties may be independently replaced with a member selected from the group consisting of halo, —$OR^9$, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, —CN and —$NO_2$;

$R^9$ and $R^{10}$ are independently selected from:

H, $C_{1-4}$alkyl, $C_{0-4}$alkylphenyl, $C_{0-4}$alkylnaphthyl, $C_{3-8}$cycloalkyl, and $C_{1-4}$alkyl-O—$C_{1-4}$alkyl, $C_{1-4}$alkyl-COOH wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, C26alkynyl, $C_{3-8}$cycloalkyl, $C_{0-4}$alkyl-$C_{3-8}$cycloalkyl, —CN and —$NO_2$, and wherein $R^9$ and $R^{10}$ taken together can form a 5–8 membered heterocylic ring;

J is a member selected from the group consisting of:

a direct link, —O—, —O—C(—$R^{11}$, —$R^{11a}$)—, —S—, —S(=O)—,—S(=O)$_2$—, —S—C(—$R^{11}$, —$R^{11a}$)—, —S(=O)—C(—$R^{11}$, —$R^{11a}$)—, —$S(=O)_2$—(—$R^{11}$, —$R^{11a}$)—, —C(=O)—, —C(=O)—N($R^{11b}$)—, —N($R^{11b}$)—C(=O)—, —N($R^{11b}$)—, —N($R^{11b}$)—C(—$R^{11}$, —$R^{11a}$)— and a monocyclic aromatic or non-aromatic heterocyclic ring having from 5 to 8 ring atoms, wherein 1–4 ring atoms of the ring system are selected from N, O and S, and wherein the ring system may be substituted with 0–2 $R^{11}$ substituents;

$R^{11}$, $R^{11a}$, $R^{11b}$, and $R^{11}$ are a member independently selected from the group consisting of:

hydrogen, halo, —$CF_3$, —CN, —$NR^9R^{10}$, —$SO_2$Me, —$NO_2$, —OH, —O—$C_{1-4}$alkyl, —O—$C_{2-6}$alkenyl, —O—$C_{2-6}$alkynyl, —O—$C_{3-8}$cycloalkyl, —O—$C_{1-4}$ alkyl-O—$C_{1-4}$alkyl, —O—$C_{1-4}$alkyl-COOH, —O—$C_{1-4}$alkyl-phenyl, —COOH, —C(=O)—O—$C_{1-4}$alkyl, —C(=O)—O—$C_{2-6}$alkenyl, —C(=O)—O—$C_{2-6}$alkynyl, —C(=O)—O—$C_{3-8}$ cycloalkyl, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, $C_{0-4}$alkylphenyl, $C_{0-4}$alkylnaphthyl, $C_{0-4}$alkylC(=O)$NR^9R^{10}$, $C_{0-4}$alkylC(=O)$OR^9$, $C_{0-4}$alkylheterocyclic ring having from 1 to 4 hetero ring atoms selected from the group consisting of N, O and S, $CH_2COOC_{1-4}$alkyl, $CH_2COOC_{1-4}$ alkylphenyl and $CH_2COOC_{1-4}$alkylnaphthyl; wherein from 1–4 hydrogen atoms on the $C_{0-4}$alkylheterocyclic ring may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl-phenyl, $C_{0-4}$alkyl$C_{3-8}$cycloalkyl, —CN and —$NO_2$;

wherein from 1–4 hydrogen atoms on the ring atoms of the phenyl and naphthyl moieties may be independently replaced with a member selected from the group consisting of halo, —$OR^9$, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, —CN and —$NO_2$;

Y is a member selected from the group consisting of:

(a) phenyl, which is independently substituted with 0–2 $R^{1b}$ substituents;

(b) naphthyl, which is independently substituted with 0–2 $R^{1b}$ substituents; and (c) a monocyclic or fused bicyclic heterocyclic ring system having from 5 to 10 ring atoms, wherein 1–4 ring atoms of the ring system are selected from N, O and S, and wherein the ring system may be substituted with 0–2 $R^{1b}$ substituents;

$R^{1b}$ is a member selected from the group consisting of:

halo, $C_{1-4}$alkyl, $C_{2-6}$alkenyl, $C_{2-6}$alkynyl, $C_{3-8}$cycloaklyl, $C_{0-4}$alkyl$C_{3-8}$cycloalkyl, —CN, —$NO_2$, $NR^{2b}R^{3b}$, $SO_2NR^{2b}R^{3b}$, $SO_2R^{2b}$, $CF_3$, $OR^{2b}$, O—$CH_2$—$CH_2$—$OR^{2b}$, O—$CH_2$-$COOR^{2b}$, N($^{2b}$)—$CH_2$—$CH_2$—$OR^{2b}$, N(—$CH_2$—$CH_2$—$OR^{2b})_2$, N($R^{2b}$)—C(=O)$R^{3b}$, N($R^{2b}$)—$SO_2$—$R^{3b}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$ cycloalkyl, $C_{0-4}$alkyl-phenyl, —CN and —$NO_2$;

$R^{2b}$ and $R^{3b}$ are independently selected from the group consisting of:

H, $C_4$alkyl, $C_{2-6}$alkenyl, $C_{2-6}$alkynyl, $C_{3-8}$cycloaklyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, —$OR^9$, $C_{1-4}$alkyl, $C_{2-6}$alkenyl, $C_{2-6}$alkynyl, $C_{3-8}$cycloalkyl, $C_{0-4}$alkyl$C_{3-8}$cycoalkyl, —CN and —$NO_2$;

L is selected from:

H, —CN, C(=O)$NR^{12}R^{13}$, —$(CH_2)_n$$NR^{12}R^{13}$, C(=$NR^{12}$)$NR^{12}R^{13}$, $OR^{12}$, —$NR^{12}$C(=$NR^{12}$)$NR^{12}R^{13}$, and $NR^{12}$C(=$NR^{12}$)—$R^{13}$;

n is an integer from 0 to 8;

$R^{12}$ and $R^{13}$ are independently selected from:

hydrogen, —$OR^{14}$, —$NR^{14}R^{15}$, $C_{1-4}$alkyl, $C_{0-4}$alkylphenyl, $C_{0-4}$alkylnaphthyl, $COOC_{1-4}$alkyl, COO—$C_{0-4}$alkylphenyl and COO—$C_{0-4}$ alkylnaphthyl, wherein from 1–4 hydrogen atoms on the ring atoms of the phenyl and naphthyl moieties may be independently replaced with a member selected from the group consisting of halo, —OH, —O—$C_{1-4}$alkyl, $C_{1-4}$alkyl, $C_{2-6}$alkenyl, $C_{2-6}$alkynyl, $C_{3-8}$cycloalkyl, $C_{0-4}$alkyl$C_{3-8}$ cycloalkyl, —CN, and —$NO_2$;

$R^{14}$ and $R^{15}$ are independently selected from:

H, $C_{1-4}$alkyl, $C_{2-6}$alkenyl, $C_{2-6}$alkynyl, $C_{3-8}$cycloalkyl, CO4alkylC3-8cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —$NO_2$;

and all pharmaceutically acceptable isomers, salts, hydrates, solvates and prodrug derivatives thereof.

In certain aspects of this invention, compounds are provided which are useful as diagnostic reagents. In another aspect, the present invention includes pharmaceutical compositions comprising a pharmaceutically effective amount of the compounds of this invention and a pharmaceutically acceptable carrier. In yet another aspect, the present invention includes methods comprising using the above compounds and pharmaceutical compositions for preventing or treating disease states characterized by disorders of the blood coagulation process in mammals, or for preventing coagulation in stored blood products and samples. Optionally, the methods of this invention comprise administering the pharmaceutical composition in combination with an additional therapeutic agent such as an antithrombotic and/or a thrombolytic agent and/or an anticoagulant.

The preferred compounds also include their pharmaceutically acceptable isomers, hydrates, solvates, salts and prodrug derivatives.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical. The term "alkinyl" (or "alkynyl") refers to a straight or branched chain aliphatic radical that includes at least two carbons joined by a triple bond. If no number of carbons is specified alkenyl and alkinyl each refer to radicals having from 2–12 carbon atoms.

The term "alkyl" refers to saturated aliphatic groups including straight-chain, branched-chain and cyclic groups having the number of carbon atoms specified, or if no number is specified, having up to 12 carbon atoms. The term "cycloalkyr" as used herein refers to a mono-, bi-, or tricyclic aliphatic ring having 3 to 14 carbon atoms and preferably 3 to 7 carbon atoms.

As used herein, the terms "carbocyclic ring structure" and "$C_{3-16}$carbocyclic mono, bicyclic or tricyclic ring structure" or the like are each intended to mean stable ring structures having only carbon atoms as ring atoms wherein the ring structure is a substituted or unsubstituted member selected from the group consisting of: a stable monocyclic ring which is aromatic ring ("aryl") having six ring atoms; a stable monocyclic non-aromatic ring having from 3 to 7 ring atoms in the ring; a stable bicyclic ring structure having a total of from 7 to 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from 10 to 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), 2.2.2] bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the substituents indicated for that structure if such substitution(s) would result in a stable compound.

The term "aryl" which is included with the term "carbocyclic ring structure" refers to an unsubstituted or substituted aromatic ring, substituted with one, two or three substituents selected from loweralkoxy, loweralkyl, loweralkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, loweralkylphenyl, napthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzyhydryl, trityl, and the like, all of which may be optionally substituted.

As used herein, the term "heterocyclic ring" or "heterocyclic ring system" is intended to mean a substituted or unsubstituted member selected from the group consisting of stable monocyclic ring having from 5–7 members in the ring itself and having from 1 to 4 hetero ring atoms selected from the group consisting of N, O and S; a stable bicyclic ring structure having a total of from 7 to 12 atoms in the two rings wherein at least one of the two rings has from 1 to 4 hetero atoms selected from N, O and S, including bicyclic ring structures wherein any of the described stable monocyclic heterocyclic rings is fused to a hexane or benzene ring; and a stable tricyclic heterocyclic ring structure having a total of from 10 to 16 atoms in the three rings wherein at least one of the three rings has from 1 to 4 hetero atoms selected from the group consisting of N, O and S. Any nitrogen and sulfur atoms present in a heterocyclic ring of such a heterocyclic ring structure may be oxidized. Unless indicated otherwise the terms "heterocyclic ring" or "heterocyclic ring system" include aromatic rings, as well as non-aromatic rings which can be saturated, partially saturated or fully saturated non-aromatic rings. Also, unless indicated otherwise the term "heterocyclic ring system" includes ring structures wherein all of the rings contain at least one hetero atom as well as structures having less than all of the rings in the ring structure containing at least one hetero atom, for example bicyclic ring structures wherein one ring is a benzene ring and one of the rings has one or more hetero atoms are included within the term "heterocyclic ring systems" as well as bicyclic ring structures wherein each of the two rings has at least one hetero atom. Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of the each of the rings in the ring structures described herein may be replaced by one or more of the indicated substituents if such replacement (s) would result in a stable compound. Nitrogen atoms in a ring structure may be quaternized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more that I O or S ring atoms in the same ring of a given heterocyclic ring structure.

Examples of monocylic and bicyclic heterocylic ring systems, in alphabetical order, are acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl, indolyl, benzimidazolyl, 1H-indazolyl, oxazolinyl, or isatinoyl. Also included are fused ring and spiro compounds containing, for example, the above heterocylic ring structures.

As used herein the term "aromatic heterocyclic ring system" has essentially the same definition as for the monocyclic and bicyclic ring systems except that at least one ring of the ring system is an aromatic heterocyclic ring or the bicyclic ring has an aromatic or non-aromatic heterocyclic ring fused to an aromatic carbocyclic ring structure.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like as preferred radicals, for example.

The term "methylene" refers to $—CH_2—$. The term "Bu" refers to "butyl" or $—CH_2CH_2CH_2CH_2—$; the term "Ph" refers to "phenyl"; the term "Me" refers to "methyl" or $—CH_3$; the term "Et" refers to "ethyl" or $—CH_2CH_3$; the term "Bu(t)" or "t-Bu" refers to "tert-butyl" or $—C(CH_3)_4$.

The term "amino acid side chain" includes any naturally occurring or synthetic side chain, i.e. the side chain "R" of an amino acid having the formula: $NM_2—CHR—COOH$. Synthetic amino acids include both (R) and (S) enantiomers, as well as derivatives of the naturally-occuring amino acid side chains. The side chain may be any synthetic amino acid side chain known in the art, including but not limited to, those produced by recombinant DNA techniques, fermentation, or by solid phase synthesis techniques. Such synthetic amino acid side chains may contain one or more functional groups selected from the following: alky, aryl, alkenyl, alkinyl, thiols, primary and secondary amines, aldehydes, carboxylates, nitrites, aromatic amines, aromatic carboxylates, primary alcohols, and the like.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

In the compounds of this invention, carbon atoms bonded to four non-identical substituents are asymmetric. Accordingly, the compounds may exist as diastereoisomers, enantiomers or mixtures thereof The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention.

Preferred Embodiments

In a preferred embodiment, the present invention provides a compound according to the formula I:

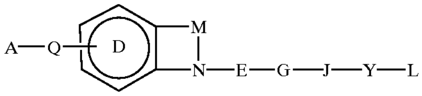

wherein:

A is selected from:

(a) $C_1$–$C_6$-alkyl;

(b) $C_3$–$C_8$-cycloalkyl;

(c) phenyl, which is independently substituted with 0–2 $R^1$ substituents;

(d) naphthyl, which is independently substituted with 0–2 $R^1$ substituents; and (e) a monocyclic or fused bicyclic heterocyclic ring system having from 5 to 10 ring atoms, wherein 1–4 ring atoms of the ring system are selected from the group consisting of N, O and S, and wherein the ring system may be substituted with 0–2 $R^1$ substituents;

$R^1$ is selected from:

halo, $—C_{1-4}$alkyl, $—C_{2-6}$alkenyl, $—C_{2-6}$alkynyl, $—C_{3-8}$ cycloalkyl, $—C_{0-4}$alkyl$C_{3-8}$cycloalkyl, —CN, $—NO_2$, $—(CH_2)_mNR^2R^3$, $—SO_2NR^2R^3$, $—SO_2R^2$, —$CF_3$, —$OR^2$, and a 5–6 membered aromatic heterocyclic system containing from 1–4 heteroatoms selected from the group consisting of N, O and S, wherein from 1–4 hydrogen atoms on the aromatic heterocyclic system may be independently replaced with a member selected from the group consisting of halo, —$C_1$–$C_4$-alkyl, —CN, —$C_{1-4}$alkyl, —$C_{2-6}$ alkenyl, —$C_{2-6}$alkynyl, —$C_{3-8}$cycloalkyl, —$C_{0-4}$ alkyl$C_{3-8}$cycloalkyl and —$NO_2$;

$R^2$ and $R^3$ are independently selected from the group consisting of:

H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —$NO_2$;

m is an integer of 0–2;

Q is a member selected from the group consisting of:

a direct link, —C(=O)—, —N($R^4$)—, —C(=O)—N($R^4$)—, —N($R^4$)—C(=O)—, —$SO_2$—, —O—, —$SO_2$—N($R^4$)— and —N($R^4$)—$SO_2$—;

$R^4$ is selected from:

H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —$NO_2$;

D is a member selected from the group consisting of:

(a) phenyl, which is independently substituted with 0–2 $R^{1a}$ substituents; and (b) an aromatic six-membered heterocyclic ring having from 1–2 ring nitrogen atoms, and wherein the ring atoms may be substituted with 0–2 $R^{1a}$ substituents;

$R^{1a}$ is selected from:

halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —$NO_2$, $(CH_2)_m NR^{2a}R^{3a}$, $SO_2NR^{2a}R^{3a}$, $SO_2R^{2a}$, $CF_3$, $OR^{2a}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

$R^{2a}$ and $R^{3a}$ are independently selected from the group consisting of:

H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

M, D and N collectively form a bicyclic ring structure selected from the group consisting of:

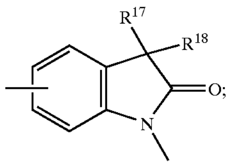
;
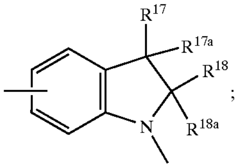
;
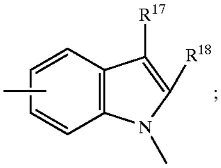
;
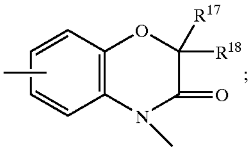
;
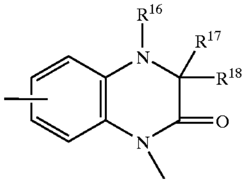
;
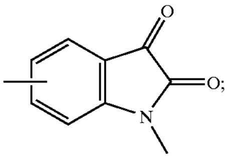
;
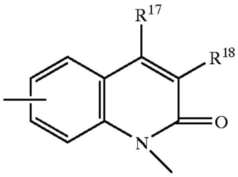
;
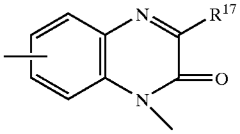
;
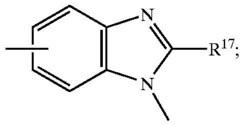
;
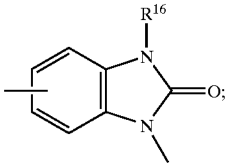
;
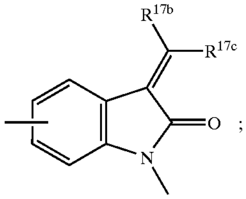
;
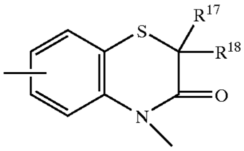
;
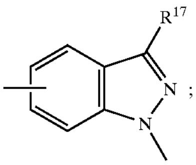
;
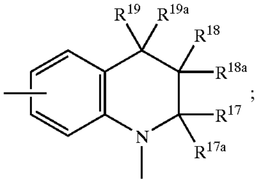
;
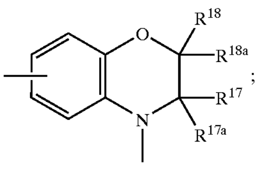
;
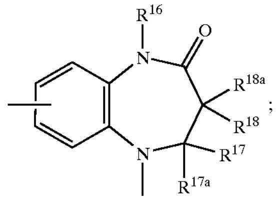
;
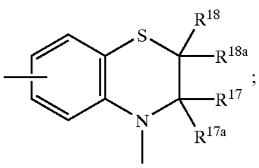
;
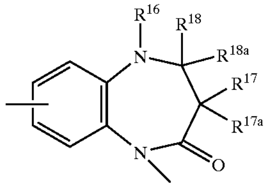
and -continued

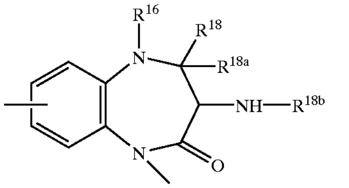

and the like, wherein the aromatic carbocyclic ring corresponding to the D portion for each of the bicyclic rings may be replaced with an aromatic heterocylic ring as defined above for D, and wherein 0 to 2 of the hydrogen atoms on the D portion of the bicyclic ring may be replaced by $R^{1a}$ substituents as defined above;

$R^{16}$, $R^{17}$, $R^{17a}$, $R^{18}$, $R^{18a}$, $R^{18b}$, $R^{19}$ and $R^{19a}$ are each independently selected form the group consisting of:

halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —$NO_2$, $(CH_2)_mNR^2R^3$, $SO_2NR^2R^3$, $SO_2R^2$, $CF_3$, $OR^2$, and a 5–6 membered aromatic heterocyclic system containing from 1–4 heteroatoms selected from N, O and S, wherein from 1–4 hydrogen atoms on the aromatic heterocyclic system may be independently replaced with a member selected form the group consisting of halo, $C_1$–$C_4$-alkyl, —CN, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl and —$NO_2$;

$R^{17b}$ and $R^{17c}$ are each independently a member selected from the group consisting of:

hydrogen, -halo, hydroxy, —$C_{1-4}$alkyl, $C_{2-6}$alkenyl, —$C_{2-6}$alkynyl, —$C_{3-8}$cycloalkyl, —$C_{0-4}$alkyl-$C_{3-8}$ cycloalkyl, —CN, —$NO_2$, —$(CH_2)_mNR^2R^3$, —$SO_2NR^2R^3$, —$SO_2R^2$, —$CF_3$, —$OR^2$, phenyl, and a 5–6 membered aromatic heterocyclic ring containing from 1–4 heteroatoms selected from N, O and S, wherein from 1–4 hydrogen atoms on the cycloalkyl, the phenyl ring, or the aromatic heterocyclic ring may be independently replaced with a member selected from the group consisting of halo, $C_1$–$C_4$-alkyl, —CN, $C_{1-4}$alkyl, $C_{2-6}$alkenyl, $C_{2-6}$alkynyl, $C_{3-8}$cycloalkyl, $C_{0-4}$alkylC3-8 cycloalkyl and —$NO_2$;

E is a member selected from the group consisting of:

a direct link, —C(=O)—, —C(=O)—N($R^5$)—, —C(—$R^{5a}$, —$R^{6a}$)— and —(—C(—$R^{5b}$, —$R^{6b}$)—C(—$R^{5c}$, —$R^{6c}$)—;

wherein $R^5$, $R^{5a}$, $R^{6a}$, $R^{5b}$ $R^{6b}$, $R^{5c}$ and $R^{6c}$ are independently selected from:

H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl, $C_{0-4}$alkylnaphthyl, $C_{0-4}$alkylheteroaryl, $C_{1-4}$alkylCOOH and $C_{1-4}$alkylCOO$C_{1-4}$alkyl, wherein from 0–4 hydrogen atoms on the ring atoms of the phenyl, naphthyl and heteroaryl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —OH, —O—$C_{1-4}$alkyl, —SH, —S—$C_{1-4}$alkyl, —CN and —$NO_2$;

G is selected from:

a direct link, —C($R^7$, $R^8$)—, —C($R^{7a}$, $R^{8a}$)—C($R^{7b}$, $R^{8b}$) and —C($R^{7c}$)=C($R^{8c}$)—;

wherein $R^7$, $R^8$, $R^{7a}$, $R^{8a}$, $R^{7b}$, $R^{8b}$, $R^{7c}$ and $R^{8c}$ are independently a member selected from from the group consisting of:

hydrogen, halogen, $C_{1-4}$alkyl, $C_{2-6}$alkenyl, $C_{2-6}$alkynyl, $C_{3-8}$cycloalkyl, $C_{0-4}$alkyl-$C_{3-8}$ cycloalkyl, $C_{0-4}$alkylphenyl, $C_{0-4}$alkylnaphthyl, —$OR^9$, —N($R^9R^{10}$), —$C_{0-4}$alkylCOO$R^9$, —$C_{0-4}$ alkylC(=O)$NR^9R^{10}$, —$C_{0-4}$alkylC(=O)$NR^9$—$CH_2$—$CH_2$—O—$R^{10}$, —$C_{0-4}$alkylC(=O)$NR^9$(—$CH_2$—$CH_2$—O—$R^{10}$—$)_2$, —N($R^9$)CO$R^{10}$, N($R^9$)C(=O)$R^{10}$, —N($R^9$)$SO_2R^{10}$, and a naturally occurring or synthetic amino acid side chain, wherein from 1–4 hydrogen atoms on the ring atoms of the phenyl and naphthyl moieties may be independently replaced with a member selected from the group consisting of halo, —$OR^9$, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, —CN and —$NO_2$;

$R^9$ and $R^{10}$ are independently selected from:

H, $C_{1-4}$alkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl-$C_{3-8}$ cycloalkyl, —CN and —$NO_2$, and wherein $R^9$ and $R^{10}$ taken together can form a 5–8 membered heterocylic ring;

J is a member selected from the group consisting of:

a direct link, —O—, —O—C(—$R^{11}$, —$R^{11a}$)—, —S—, —S(=O)—, —S(=O$)_2$—, —S—C(—$R^{11}$, —$R^{11a}$)—, —S(=O)—C(—$R^{11}$, —$R^{11a}$)—, —S(=O$)_2$—(—$R^{11}$, —$R^{11a}$)—, —C(=O)—, —C(=O)—N($R^{11b}$)—, —N($R^{11b}$)—C(=O)—, —N($R^{11b}$)—, —N($R^{11b}$)—C(—$R^{11}$, —$R^{11a}$)— and a monocyclic aromatic or non-aromatic heterocyclic ring having from 5 to 8 ring atoms, wherein 1–4 ring atoms of the ring system are selected from N, O and S, and wherein the ring system may be substituted with 0–2 $R^{11c}$ substituents;

$R^{11}$, $R^{11a}$, $R^{11b}$ and $R^{11c}$ are a member independently selected from the group consisting of:

hydrogen, halo, —CN, —$NO_2$, —OH, —O—$C_{1-4}$ alkyl, —O—$C_{2-6}$alkenyl, —O—$C_{2-6}$alkynyl, —O—$C_{3-8}$cycloalkyl, —COOH, —C(=O)—O—$C_{1-4}$alkyl, —C(=O)—O—$C_{2-6}$alkenyl, —C(=O)—O—$C_{2-6}$akynyl, —C(=O)—O—$C_{3-8}$ cycloalkyl, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, $C_{0-4}$alkylphenyl, $C_{0-4}$alkylnaphthyl, $C_{0-4}$alkylheterocyclic ring having from 1 to 4 hetero ring atoms selected from the group consisting of N, O and S, $CH_2COOC_{1-4}$alkyl, $CH_2COOC_{1-4}$ alkylphenyl and $CH_2COOC_{1-4}$alkylnaphthyl;

Y is a member selected from the group consisting of:

(a) phenyl, which is independently substituted with 0–2 $R^{1b}$ substituents;

(b) naphthyl, which is independently substituted with 0–2 $R^{1b}$ substituents; and (c) a monocyclic or fused bicyclic heterocyclic ring system having from 5 to 10 ring atoms, wherein 1–4 ring atoms of the ring system are selected from N, O and S, and wherein the ring system may be substituted with 0–2 $R^{1b}$ substituents;

$R^{1b}$ is a member selected from the group consisting of:

halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —$NO_2$, $NR^{2b}R^{3b}$, $SO_2NR^{2b}R^{3b}$, $SO_2R^{2b}$, $CF_3$, $OR^{2b}$, O—$CH_2$—$CH_2$—$OR^{2b}$, O—$CH_2$—$COOR^{2b}$, $N(R^{2b})—CH_2—CH_2—OR^{2b}$, $N(—CH_2—CH_2—OR^{2b})_2$, $N(R^{2b})—C(=O)R^{3b}$, $N(R^{2b})—SO_2R^{3b}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and $—NO_2$;

$R^{2b}$ and $R^{3b}$ are independently selected from the group consisting of:

H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and $—NO_2$;

L is selected from:

H, —CN, $C(=O)NR^{12}R^{13}$, $(CH_2)_bNR^{12}R^{13}$, $C(=NR^{12})NR^{12}R^{13}$, $OR^{12}$, $—NR^{12}C(=NR^{12})NR^{12}R^{13}$, and $NR^{12}C(=NR^{12})—R^{13}$;

n is an integer from 0 to 8;

$R^{12}$ and $R^{13}$ are independently selected from:

hydrogen, $—OR^{14}$, $—NR^{14}R^{15}$, $C_{1-4}$alkyl, $C_{0-4}$alkylphenyl, $C_{0-4}$alkylnaphthyl, $COOC_{1-4}$alkyl, $COO—C_{0-4}$alkylphenyl and $COO—C_{0-4}$alkylnaphthyl, wherein from 1–4 hydrogen atoms on the ring atoms of the phenyl and naphthyl moieties may be independently replaced with a member selected from the group consisting of halo, —OH, $—O—C_{1-4}$alkyl, $C_{1-4}$alkyl, $C_{2-6}$alkenyl, $C_{2-6}$alkynyl, $C_{3-8}$cycloalkyl, $C_{0-4}$aklyl$C_{3-8}$cycloalkyl, —CN, and $—NO_2$;

$R^{14}$ and $R^{15}$ are independently selected from:

H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and $—NO_2$;

and all pharmaceutically acceptable isomers, salts, hydrates, solvates and prodrug derivatives thereof.

In a further preferred embodiment, the present invention provides a compound according to the formula I:

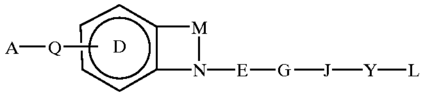

wherein:

A is selected from:

(a) $C_1$–$C_6$-alkyl;

(b) $C_3$–$C_8$-cycloalkyl;

(c) phenyl, which is independently substituted with 0–2 $R^1$ substituents;

(d) naphthyl, which is independently substituted with 0–2 $R^1$ substituents; and (e) a monocyclic or fused bicyclic heterocyclic ring system having from 5 to 10 ring atoms, wherein 1–4 ring atoms of the ring system are selected from N, O and S, and wherein the ring system may be substituted with 0–2 $R^1$ substituents;

$R^1$ is selected from:

halo, $C_{1-4}$alkyl, —CN, $—NO_2$, $(CH_2)_mNR^2R^3$, $SO_2NR^2R^3$, $SO_2R^2$, $CF_3$, $OR^2$, and a 5–6 membered aromatic heterocyclic system containing from 1–4 heteroatoms selected from N, O and S;

$R^2$ and $R^3$ are independently selected from the group consisting of:

H, $C_{1-4}$alkyl, $C_{0-4}$alkylphenyl and $C_{0-4}$alkylnaphthyl;

m is an integer of 0–2;

B is a member selected from the group consisting of:

a direct link, —C(=O)—, $—N(R^4)—$, $—C(=O)—N(R^4)—$, $—N(R^4)—C(=O)—$, $—SO_2—$, —O—, $—SO_2—N(R^4)—$ and $—N(R^4)—SO_2—$;

$R^4$ is selected from:

H, $C_{1-4}$alkyl, $C_{0-4}$alkylphenyl and $C_{0-4}$alkylnaphthyl;

D is phenyl, which is independently substituted with 0–2 $R^{1a}$ substituents;

$R^{1a}$ is selected from:

halo, $C_{1-4}$alkyl, —CN, $—NO_2$, $—(CH_2)_mNR^{2a}R^{3a}$, $—SO_2NR^{2a}R^{3a}$, $—SO_2R^{2a}$, $CF_3$, $—OR^{2a}$, and a 5–6 membered aromatic heterocyclic system containing from 1–4 heteroatoms selected from N, O and S;

$R^{2a}$ and $R^{3a}$ are independently selected from the group consisting of:

H, $C_{1-4}$alkyl, $C_{0-4}$alkylphenyl and $C_{0-4}$alkylnaphthyl;

M, D and N collectively form a bicyclic ring structure selected from the group consisting of:

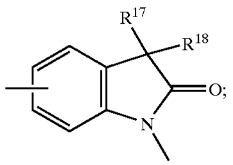
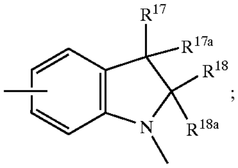
;

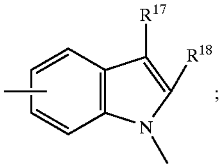
;
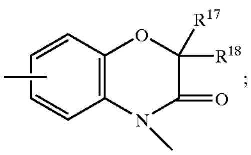
;

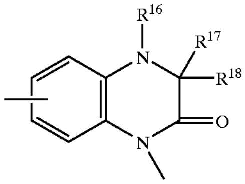
;
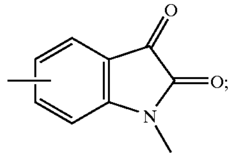

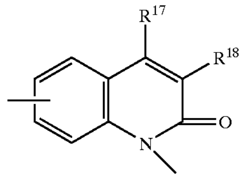
;
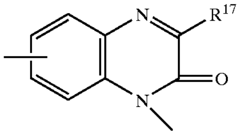
;

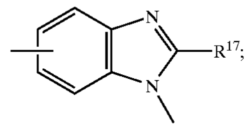
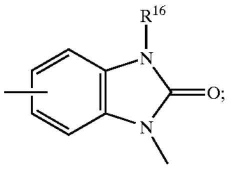

-continued

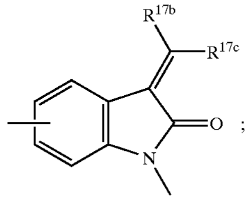 ; 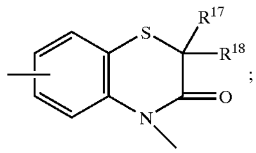 ;

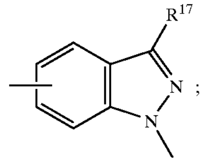 ; 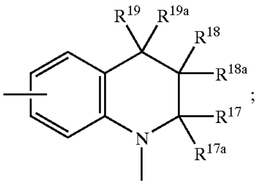 ;

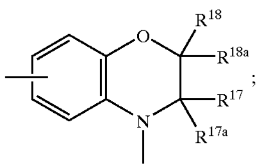 ; 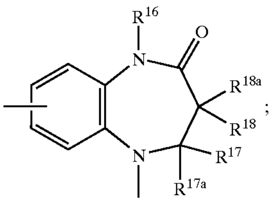 ;

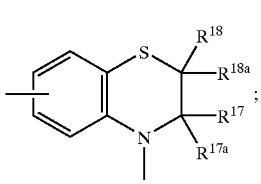 ; 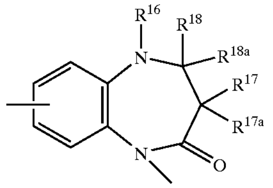 and

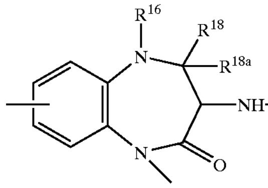

wherein 0 to 2 of the hydrogen atoms on the D portion of the bicyclic ring may be replaced by $R^{1a}$ substituents as defined above;

$R^{16}$, $R^{17}$, $R^{17a}$, $R^{18}$, $R^{18a}$, $R^{18b}$, $R^{19}$ and $R^{19a}$ are each independently selected from the group consisting of:

halo, $C_{1-4}$alkyl, —CN, —$NO_2$, $(CH_2)_mNR^2R^3$, $SO_2NR^2R^3$, $SO_2R^2$, $CF_3$, $OR^2$, and a5–6 membered aromatic heterocyclic system containing from 1–4 heteroatoms selected from N, O and S;

$R^{17b}$ and $R^{17c}$ are each independently a member selected from the group consisting of:

hydrogen, -halo, hydroxy, —$C_{1-4}$alkyl, —CN, —$NO_2$, —$(CH_2)_mNR^2R^3$, —$SO_2NR^2R^3$, —$SO_2R^2$, —$CF_3$, —$OR^2$, phenyl, and a 5–6 membered aromatic heterocyclic ring containing from 1–4 heteroatoms selected from N, O and S;

m is an integer from 0–6;

E is a member selected from the group consisting of:

a direct link, —C(=O)—, —C(=O)—N($R^5$)—, —C(—$R^{5a}$,—$R^{6a}$)—and —(—C(—$R^{5b}$,—$R^{6b}$)—C(—$R^{5c}$,—$R^{6c}$)—;

wherein $R^5$, $R^{5a}$, $R^{6a}$, $R^{5b}$, $R^{6b}$, $R^{5c}$ and $R^{6c}$ are independently selected from:

H, $C_{1-4}$alkyl, $C_{0-4}$alkylphenyl, $C_{0-4}$alkylnaphthyl, $C_{0-4}$alkylheteroaryl, $C_{1-4}$alkylCOOH and $C_{1-4}$alkylCOO$C_{1-4}$alkyl, wherein from 0–2 hydrogen atoms on the ring atoms of the phenyl, naphthyl and heteroaryl moieties may be independently replaced with a member selected from the group consisting of halo, $C_{1-4}$alkyl, —OH, —O—$C_{1-4}$alkyl, —SH, —S—$C_{1-4}$alkyl, —CN and —$NO_2$;

G is selected from:

a direct link, —C($R^7$,$R^8$)—, —C($R^{7a}$,$R^{8a}$)—C($R^{7b}$, $R^{8b}$)— and —C($R^{7c}$)=C($R^{8c}$)—;

wherein $R^7$, $R^8$, $R^{7a}$, $R^{8a}R^{7b}$, $R^{8b}$, $R^{7c}$ and $R^{8c}$ are independently a member selected from from the group consisting of:

hydrogen, halogen, $C_{1-4}$alkyl, $C_{0-4}$alkyl—$C_{3-8}$cycloalkyl, $C_{0-4}$alkylphenyl, $C_{0-4}$alkylnaphthyl, —$OR^9$, —N($R^9R^{10}$), —$C_{0-4}$alkylCOOR$^9$, —$C_{0-4}$alkylC (=O)$NR^9R^{10}$, —$C_{0-4}$alkylC(=O)$NR^9$—$CH_2$—$CH_2$—O—$R^{10}$, —$C_{0-4}$alkyC(=O)$NR^9$(—$CH_2$—$CH_2$—O—$R^{10}$—$)_2$, —N($R^9$)COR$^{10}$, —N($R^9$)C(=O)$R^{10}$,—N($R^9$)$SO_2R^{10}$, and a naturally occurring or synthetic amino acid side chain;

$R^9$ and $R^{10}$ are independently selected from:

H, $C_{1-4}$alkyl, $C_{0-4}$alkylphenyl and $C_{0-4}$alkylnaphthyl;

J is a member selected from the group consisting of:

a direct link, —O—, —O—C(—$R^{11}$, —$R^{11a}$)—, —S—, —S(=O)$_2$—, —S—C(—$R^{11}$, —$R^{11a}$)—, —S(=O)$_2$—(—$R^{11}$, —$R^{11a}$)—, —C(=O)—N($R^{11b}$)—, —N($R^{11b}$)—, —N($R^{11b}$)—C(—$R^{11}$, —$R^{11a}$)— and a monocyclic aromatic or non-aromatic heterocyclic ring having from 5 to 8 ring atoms, wherein 1–4 ring atoms of the ring system are selected from N, O and S, and wherein the ring system may be substituted with 0–2 $R^{11c}$ substituents;

$R^{11}$, $R^{11a}$, $R^{11b}$ and $R^{11c}$ are a member independently selected from the group consisting of:

hydrogen, halo, —CN, —$NO_2$, —OH, —O—$C_{14}$alkyl, —O—$C_{3-8}$cycloalkyl, —COOH, —C(=O)—O—$C_{1-4}$alkyl, —C(=O)—O—$C_{3-8}$cycloalkyl, $C_{1-4}$alkyl, $C_{3-8}$cycloalkyl, $C_{0-4}$alkyl—$C_{3-8}$cycloalkyl, $C_{0-4}$alkylphenyl, $C_{0-4}$alkylnaphthyl, and a $C_{0-4}$alkyl heterocyclic ring having from 1 to 4 hetero ring atoms selected from the group consisting of N, O and S, $CH_2COOC_{1-4}$alkyl, $CH_2$ $COOC_{1-4}$alkylphenyl and $CH_2$ $COOC_{1-4}$alkylnaphthyl;

Y is a member selected from the group consisting of:

(a) phenyl, which is independently substituted with 0–2 $R^{1b}$ substituents;

(b) naphthyl, which is independently substituted with 0–2 $R^{1b}$ substituents; and (c) a monocyclic or fused bicyclic heterocyclic ring system having from 5 to 10 ring atoms, wherein 1–4 ring atoms of the ring system are selected from N, O and S, and wherein the ring system may be substituted with 0–2 $R^{1b}$ substituents;

$R^{1b}$ is a member selected from the group consisting of:

halo, $C_{1-4}$ alkyl, $C_{2-6}$ alkenyl, $C_{2-6}$ alkynyl, $C_{3-8}$ cycloalkyl, $C_{0-4}$alkyl$C_{3-8}$cycloalkyl, —CN, —$NO_2$, $NR^{2b}$ $R^{3b}$, $SO_2$ $R^{2b}$, $CF_3$, $OR^{2b}$, O—$CH_2$—$CH_2$—$OR^{2b}$, O—$CH_2$—$COOR^{2b}$, N($R^{2b}$)—$CH_2$—$CH_2$—$OR^{2b}$, N(—$CH_2$—$CH_2$—$OR^{2b}$) $_2$, N($R^{2b}$)—C(=O) $R^{3b}$, N($R^{2b}$)—$SO_2$—$R^{3b}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

$R^{2b}$ and $R^{3b}$ are independently selected from the group consisting of:

H, $C_{1-4}$alkyl, $C_{3-8}$cycloalkyl, $C_{0-4}$alkyl$C_{3-8}$cycloalkyl, $C_{0-4}$alkylphenyl and $C_{0-4}$alkylnaphthyl;

L is selected from:

H, —CN, C(=O)$NR^{12}R^{13}$, $(CH_2)_n NR^{12}R^{13}$, C(=$NR^{12}$) $NR^{12}R^{13}$, $OR^{12}$, —$NR^{12}$C(=$NR^{12}$) $NR^{12}R^{13}$, and $NR^{12}$C(=$NR^{12}$)—$R^{13}$;

n is an integer from 0 to 6;

$R^{12}$ and $R^{13}$ are independently selected from:

hydrogen, —$OR^{14}$, —$NR^{14}R^{15}$, $C_{1-4}$alky, $C_{0-4}$alkylphenyl, $C_{0-4}$alkylnaphthyl, $COOC_{1-4}$alkyl, COO—$Co_{0-4}$alkylphenyl and COO—$CO_{0-4}$ alkylnaphthyl, wherein from 0–4 hydrogen atoms on the ring atoms of the phenyl and naphthyl moieties may be independently replaced with a member selected from the group consisting of halo, —OH, —O—$C_{1-4}$alkyl, $C_{1-4}$alkyl, $C_{3-8}$cycloalkyl, $C_{0-4}$alkyl$C_{3-8}$cycloalkyl, —CN, and —$NO_2$;

$R^{14}$ and $R^{15}$ are independently selected from:

H, $C_{1-4}$alkyl, $C_{0-4}$alkyl$C_{3-8}$cycloalkyl, $C_{0-4}$alkylphenyl and $C_{0-4}$alkylnaphthyl;

and all pharmaceutically acceptable isomers, salts, hydrates, solvates and prodrug derivatives thereof In a still further preferred embodiment, the present invention provides a compound according to the formula I:

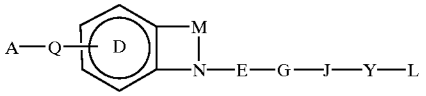

wherein:

A is selected from:

(a) phenyl, which is independently substituted with 0–2 $R^1$ substituents; and (b) a monocyclic or fused bicyclic heterocyclic ring system having from 5 to 10 ring atoms, wherein 1–4 ring atoms of the ring system are selected from N, O and S, and wherein the ring system may be substituted with 0–2 $R^1$ substituents;

$R^1$ is selected from:

halo, $(CH_2)_m NR^2R^3$, $SO_2NR^2R^3$ and $SO_2R^2$;

$R^2$ and $R^3$ are independently selected from the group consisting of:

H and $C_{1-4}$alkyl;

m is an integer of 0–2;

Q is a member selected from the group consisting of:

a direct link, —C(=O)—, —$SO_2$—, and —O—;

D is phenyl, which is independently substituted with 0–2 $R^{1a}$ substituents;

$R^{1a}$ is selected from:

halo and $C_{1-4}$alkyl;

M, D and N collectively form a bicyclic ring structure selected from the group consisting of:

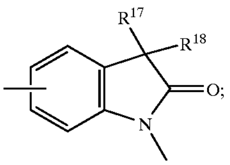

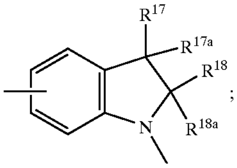 ;

-continued

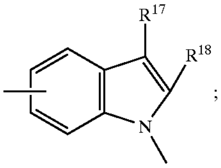 ; 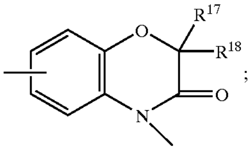 ;

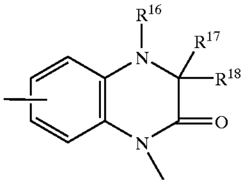 ; 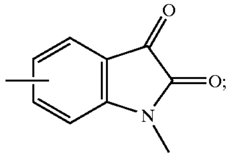

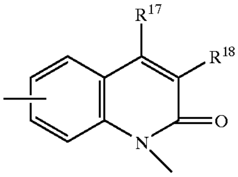 ; 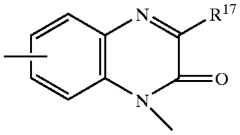 ;

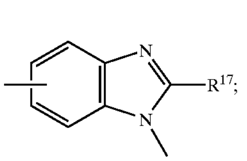 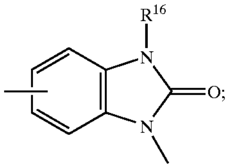

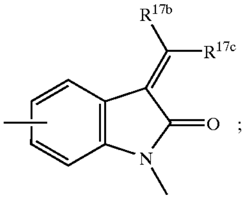 ; 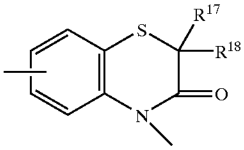 ;

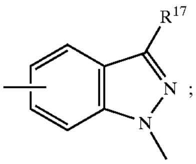 ; 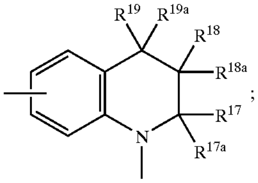 ;

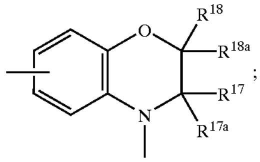 ; 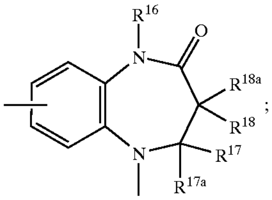 ;

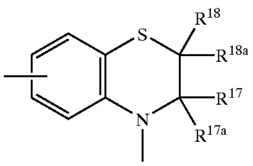 ; 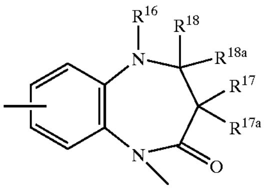 and

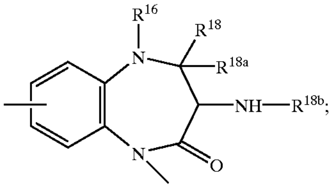

$R^{16}$, $R^{17}$, $R^{17a}$, $R^{18}$, $R^{18a}$, $^{18}$ $R^{19}$ and $R^{19a}$ are each independently selected from the group consisting of:

halo, $C_{1-4}$alkyl, —CN, —$NO_2$, $(CH_2)_mNR^2R^3$, $SO_2NR^2R^3$, $SO_2R^2$, $CF_3$ and $OR^2$;

$R^{17b}$ and $R^{17c}$ are each independently a member selected from the group consisting of:

hydrogen, —halo, hydroxy, —$C_{1-4}$alkyl, —CN, —$NO_2$, —$(CH_2)_mNR^2R^3$, —$SO_2NR^2R^3$, —$SO_2R^2$, —$CF_3$, —$OR^2$, phenyl, and a 5–6 membered aromatic heterocyclic ring containing from 1–3 N atoms;

E is a member selected from the group consisting of:

a direct link, —C(=O)—, —C(=O)—N($R^5$)—, —C(—$R^{5a}$,—$R^{6a}$)—and —(—C(—$R^{5b}$,—$R^{6b}$)—C(—$R^{5c}$,—$R^{6c}$)—;

wherein $R^5$, $R^{5a}$, $R^{6a}$, $R^{5b}R^{6b}$, $R^{5c}$ and $R^{6c}$ are independently selected from:

H, $C_{1-4}$alkyl, $C_{0-4}$alkylphenyl, $C_{0-4}$alkylnaphthyl, $C_{0-4}$alkylheteroaryl, $C_{1-4}$alkylCOOH and $C_{1-4}$alkylCOO$C_{1-4}$alkyl;

G is selected from:

a direct link, —C($R^7$,$R^8$)—, —C($R^{7a}$,$R^{8a}$)—C($R^{7b}$, $R^{8b}$)—and —C($R^{7c}$)=C($R^{8c}$)—;

wherein $R^7$, $R^8$, $R^{7a}$, $R^{8a}$, $R^{7b}$, $R^{8b}$, $R^{7c}$ and $R^{8c}$ are independently a member selected from from the group consisting of:

hydrogen, halogen, $C_{1-4}$alkyl, $C_{0-4}$alkyl—$C_{3-8}$ cycloalkyl, $C_{0-4}$alkylphenyl, $C_{0-4}$alkylnaphthyl, —$OR^9$, —N($R^9R^{10}$), —$C_{0-4}$alkylCOOR$^9$, —$C_{0-4}$ alkyC(=O)$NR^9R^{10}$, —$CO_{0-4}$alkylC(=O)$NR^9$—$CH_2$—$CH_2$—O—$R^{10}$, —$C_{0-4}$alkylC(=O)$NR^9$(—$CH_2$—$CH_2$—O—$R^{10}$—$)_2$, —N($R^9$)COR$^{10}$, —N($R^9$)C(=O)$R^{10}$,—N($R^9$)$SO_2R^{10}$, and a naturally occurring or synthetic amino acid side chain;

$R^9$ and $R^{10}$ are independently selected from:

H, $C_{1-4}$alkyl, $C_{0-4}$alkylphenyl and $C_{0-4}$alkylnaphthyl;

J is a member selected from the group consisting of:

a direct link, —O—, —S—, —C(=O)—N($R^{11b}$)—, —N($R^{11b}$)—, —N($R^{11b}$)—C(—$R^{11}$, —$R^{11a}$) and a monocyclic aromatic or non-aromatic heterocyclic ring having from 5 to 8 ring atoms, wherein 1–4 ring atoms of the ring system are selected from N, O and S, and wherein the ring system may be substituted with 0–2 $R^{11c}$ substituents;

$R^{11}$, $R^{11a}$, $R^{11b}$ and $R^{11c}$ are a member independently selected from the group consisting of:

hydrogen, halo, —CN, —$NO_2$, —OH, —O—$C_{1-4}$ alkyl, —O—$C_{3-8}$cycloalkyl, —COOH, —C(=O)—O—$C_{1-4}$alkyl, —C(=O)—O—$C_{3-8}$ cycloalkyl, $C_{1-4}$alky, $C_{3-8}$cycloalkyl, $C_{0-4}$alkyl—$C_{3-8}$cycloalkyl, $C_{0-4}$alkylphenyl, $C_{0-4}$alkylnaphthyl, and a $C_{0-4}$alkyl heterocyclic ring having from 1 to 4 hetero ring atoms selected from the group consisting of N, O and S, $CH_2COOC_{1-4}$alkyl, $CH_2COOC_{1-4}$ alkylphenyl and $CH_2COOC_{1-4}$alkylnaphthyl;

Y is a member selected from the group consisting of:

(a) phenyl, which is independently substituted with 0–2 $R^{1b}$ substituents;

(b) an aromatic heterocyclic ring having from 5 to 10 ring atoms, wherein 1–4 ring atoms of the ring system are selected from N, O and S, and wherein the ring may be substituted with 0–2 $R^{1b}$ substituents;

2(c) a fused aromatic bicyclic heterocyclic ring system having from 5 to 10 ring atoms, wherein 1–4 ring atoms of the ring system are selected from N, O and S, and wherein the bicyclic ring system may be substituted with 0–2 $R^{1b}$ substituents;

$R^{1b}$ is a member selected from the group consisting of:

halo, —$C_{1-4}$alkyl, —OH, —OBn, —O—$CH_2$—$CH_2$—OH, —O—$CH_2$—$CH_2$—$OCH_3$, —O—$CH_2$—COOH, —O—$CH_2$—C(=O)—O—$CH_3$, —$NH_2$, —NH—$CH_2$—$CH_2$—O—$CH_3$, —NH—C(=O)—O—$CH_3$ and —NH—$SO_2$—$CH_3$;

L is selected from:

H, —C(=O)$NR^{12}R^{13}$, —$(CH_2)_nNR^{12}R^{13}$ and —C(=$NR^{12}$)$NR^{12}R^{13}$;

n is an integer from 0 to 6;

$R^{12}$ and R—are independently selected from:

hydrogen and $C_{1-4}$alkyl;

and all pharmaceutically acceptable isomers, salts, hydrates, solvates and prodrug derivatives thereof In yet another preferred embodiment, the present invention provides a compound according to formula I:

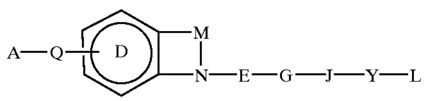

wherein:

A is a member selected from the group consisting of:

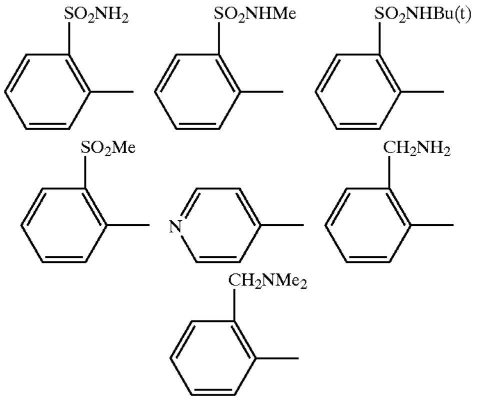

D is a member selected from the group consisting of:

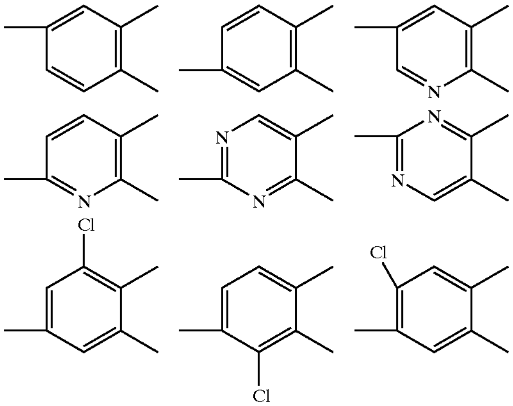

-continued

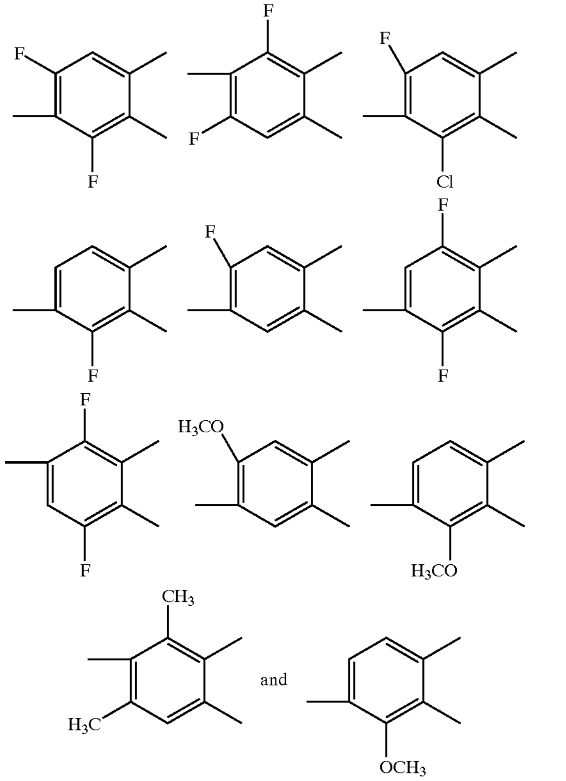

E is a member selected from the group consisting of
a direct link, —C(═O)—, —C(═O)—N($R^5$)—, —C(—$R^{5a}$,—$R^{6a}$)—and —(—C(—$R^{5b}$,—$R^{6b}$)—C (—$R^{5c}$,—$R^{6c}$)—;

wherein $R^5$, $R^{5a}$, $R^{6a}$, $R^{5b}$ $R^{6b}$, $R^{5c}$ and $R^{6c}$ are independently selected from:
H, $C_{1-4}$alkyl, $C_{0-4}$alkylphenyl, $C_{0-4}$alkylnaphthyl, $C_{0-4}$alkylheteroaryl, $C_{1-4}$alkylCOOH and $C_{1-4}$alkylCOO$C_{1-4}$alkyl;

G is selected from:
a direct link, —C($R^7$,$R^8$)—, —C($R^{7a}$,$R^{8a}$)—C($R^{7b}$, $R^{8b}$)—and —C($R^{7c}$)═C($R^{8c}$)—;

wherein $R^7$, $R^8$, $R^{7a}$, $R^{8a}$, $R^{7b}$, $R^{8b}$, $R^{7c}$ and $R^{8c}$ are independently a member selected from from the group consisting of:
hydrogen, halogen, $C_{1-4}$alkyl $C_{0-4}$alkyl—$C_{3-8}$ cycloalkyl, $C_{0-4}$alkylphenyl, $C_{0-4}$alkylnaphthyl, —$OR^9$, —N($R^9R^{10}$), —$C_{0-4}$alkylCOO$R^9$, —$C_{0-4}$ alkylC(═O)N$R^9R^{10}$, —$C_{0-4}$alkylC(═O)N$R^9$—$CH_2$—$CH_2$—O—$R^{10}$, —$C_{0-4}$alkylC (═O)N$R^9$(—$CH_2$—$CH_2$—O—$R^{10}$—$)_2$, —N($R^9$)CO$R^{10}$, —N($R^9$)C(═O)$R^{10}$,—N($R^9$)$SO_2R^{10}$, and a naturally occurring or synthetic amino acid side chain;

$R^9$ and $R^{10}$ are independently selected from:
H, $C_{1-4}$alkyl, $C_{0-4}$alkylphenyl and $C_{0-4}$alkylnaphthyl;

J is a member selected from the group consisting of:
a direct link, —O—, —S—, —C(═O)—N($R^{11b}$)—, —N($R^{11b}$)—, —N($R^{11b}$)—C (—$R^{11}$, —$R^{11a}$)—and a monocyclic aromatic or non-aromatic heterocyclic ring having from 5 to 8 ring atoms, wherein 1–4 ring atoms of the ring system are selected from N, O and S, and wherein the ring system may be substituted with 0–2 $R^{11c}$ substitutuents;

$R^{11}$, $R^{11a}$, $R^{11b}$ and $R^{11c}$ are a member independently selected from the group consisting of:
hydrogen, halo, —CN, —$NO_2$, —OH, —O—$C_{1-4}$alkyl, —$C_{1-4}$alkyl, —COOH,phenyl, and benzyl wherein the aromatic ring of the phenyl or benzyl is substituted with 0–2 members independently selected from the group consisting of halo, —CN, —$NO_2$, —OH, —O—$C_{1-4}$alkyl, —$C_{1-4}$alkyl, —COOH and —C(═O)—O—$C_{1-4}$alkyl;

Y and L taken together are a member selected from the group consisting of:

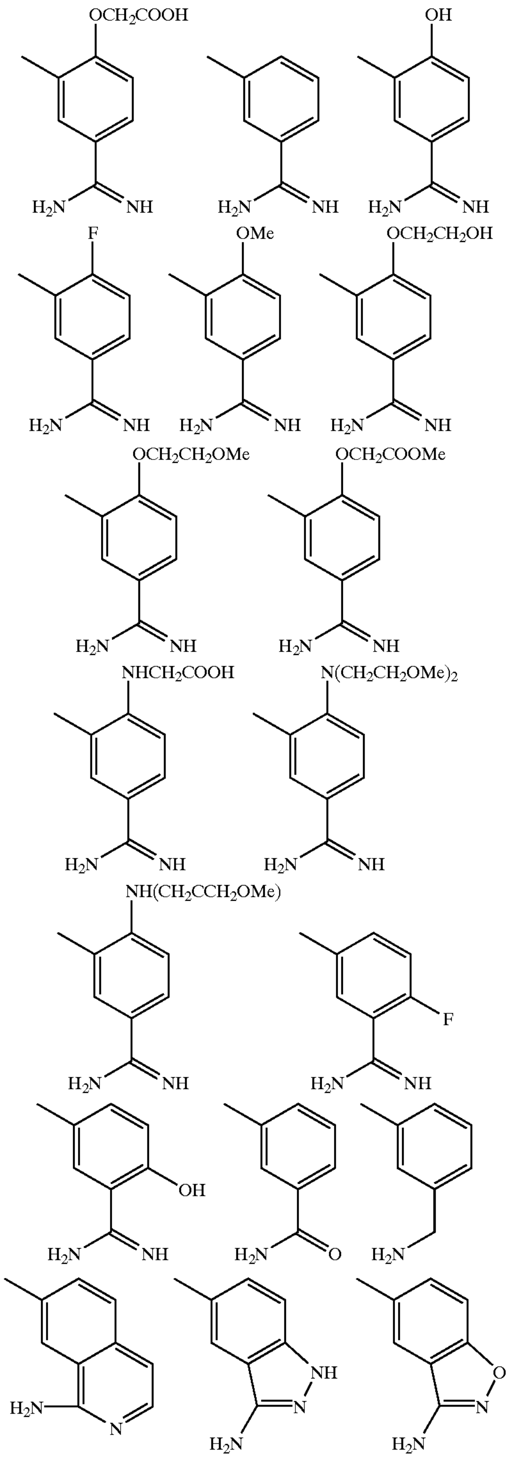

-continued

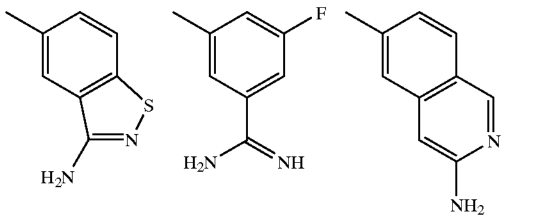
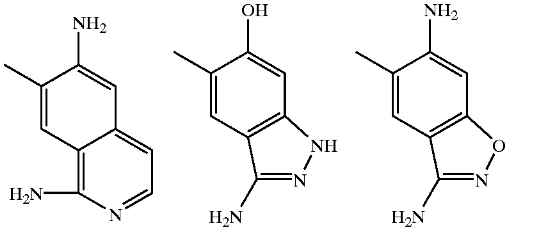
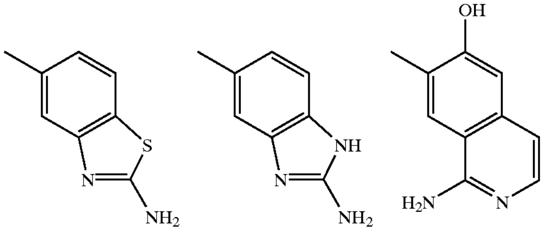
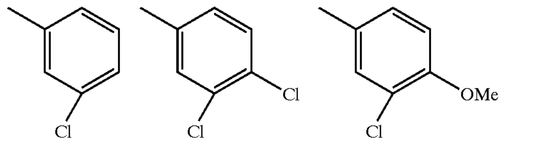
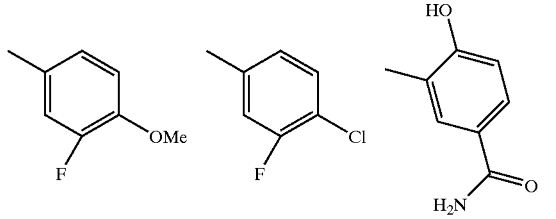
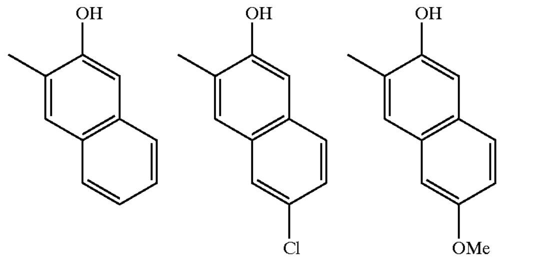
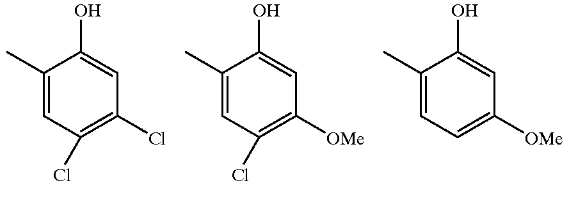

M and Q are as defined elsewhere in the specification; and all pharmaceutically acceptable isomers, salts, hydrates, solvates and prodrug derivatives thereof.

The following non-limiting tables illustrate representative compounds of the present invention wherein the "Y-L" portions for each of the formula in each of the tables are taken together and are independently selected from the group consisting of:

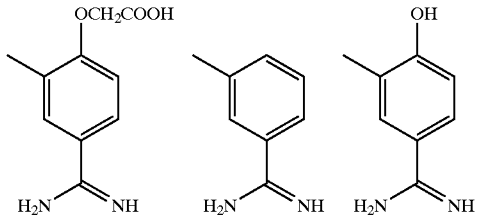
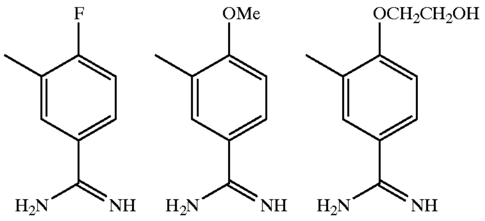
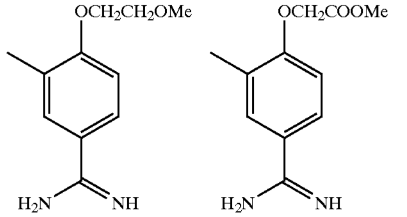
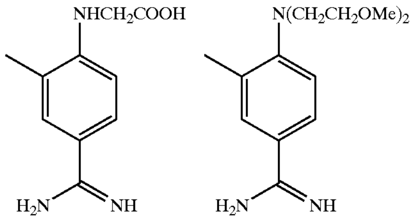
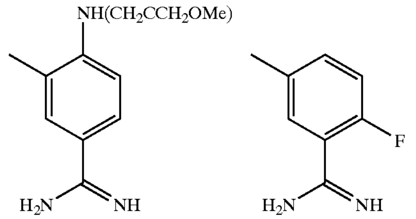
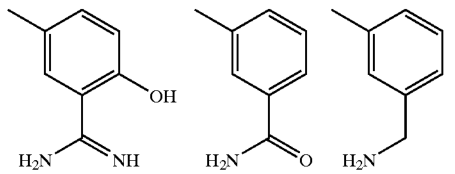
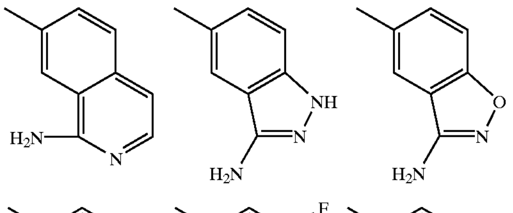
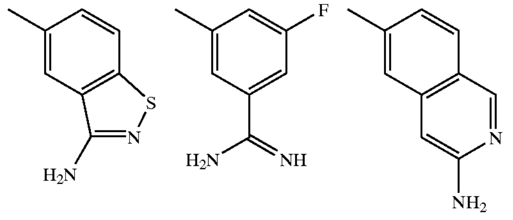

-continued
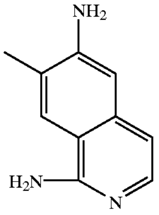
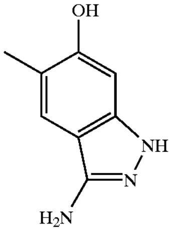
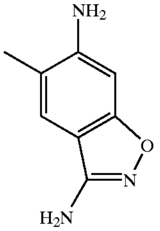
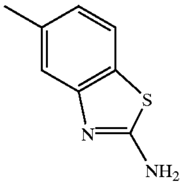
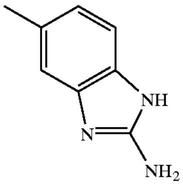
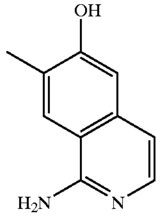
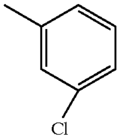
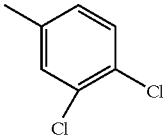
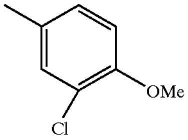
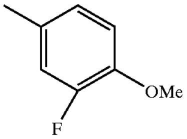
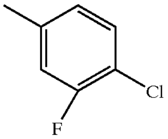
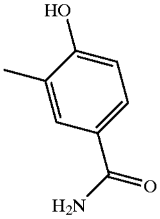
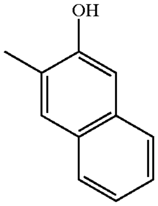
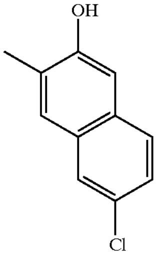
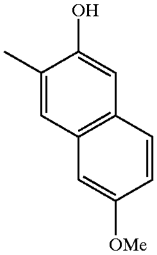
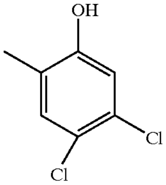
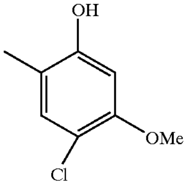
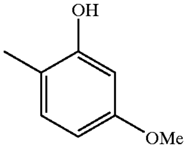
TABLE 1
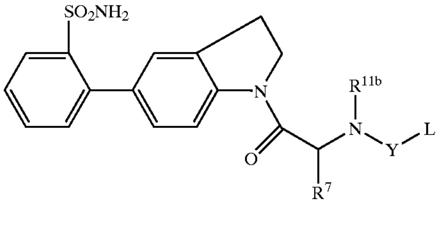
Formula II
| $R^7$ | $R^{11b}$ |
|---|---|
| H | H |
| Me | Me |
TABLE 1-continued
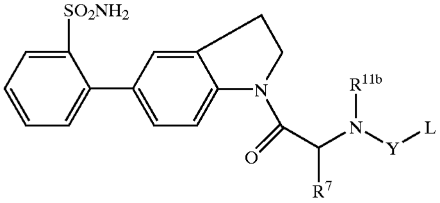
Formula II
| $R^7$ | $R^{11b}$ |
|---|---|
| 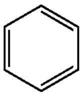 | 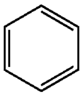 |
| 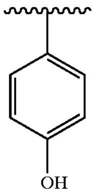 | 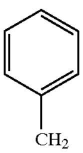 |
| 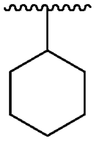 | 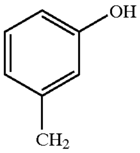 |
| 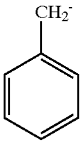 | 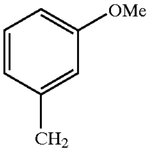 |
| 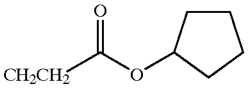 | 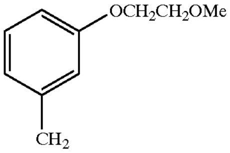 |
| 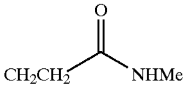 | 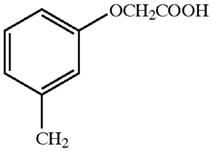 |
| 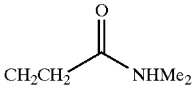 | 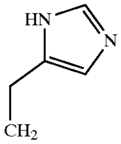 |
| 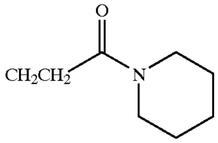 | 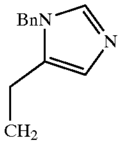 |

TABLE 1-continued
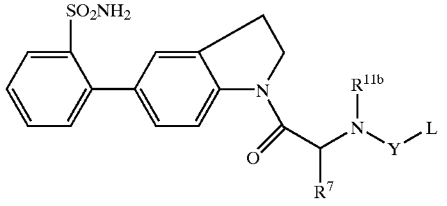
Formula II
| $R^7$ | $R^{11b}$ |
|---|---|
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 1a
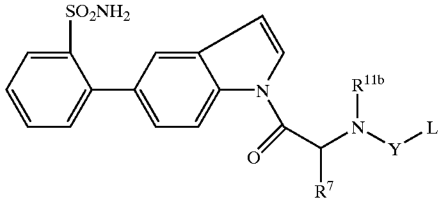
Formula IIa
| $R^7$ | $R^{11b}$ |
|---|---|
| H | H |
| Me | Me |
| 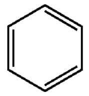 | 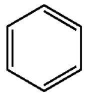 |
| 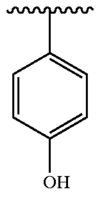 | 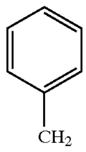 |
| 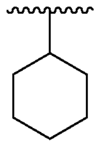 | 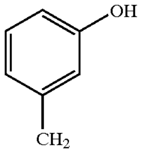 |
| 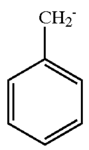 | 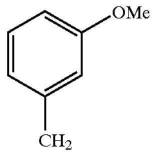 |
TABLE 1a-continued
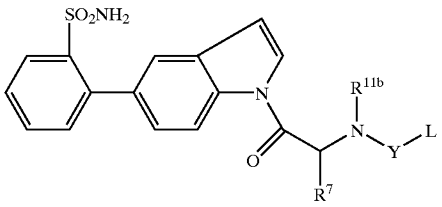
Formula IIa
| $R^7$ | $R^{11b}$ |
|---|---|
| 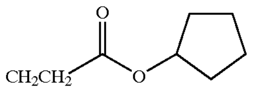 | 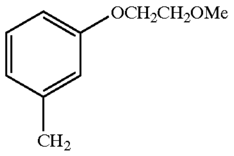 |
| 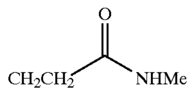 | 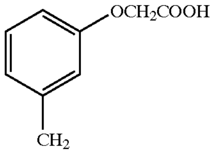 |
| 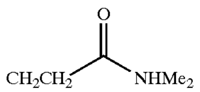 | 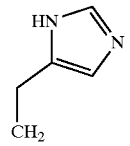 |
| 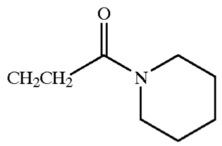 | 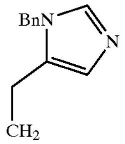 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 1b
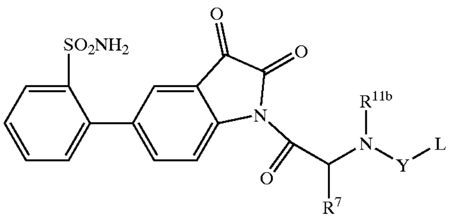
Formula IIb
| $R^7$ | $R^{11b}$ |
|---|---|
| H | H |
| Me | Me |

TABLE 1b-continued
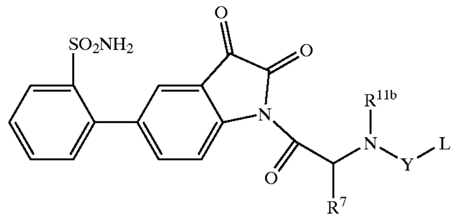
Formula IIb
| $R^7$ | $R^{11b}$ |
|---|---|
| 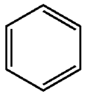 | 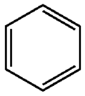 |
| 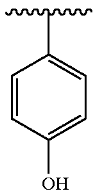 | 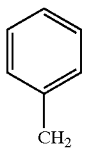 |
| 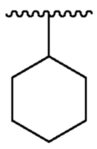 | 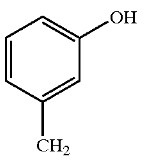 |
| 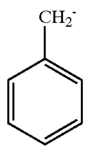 | 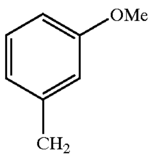 |
| 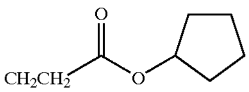 | 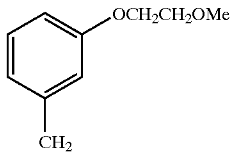 |
| 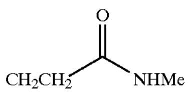 | 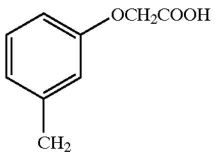 |
| 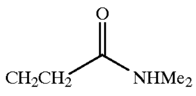 | 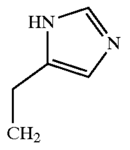 |
| 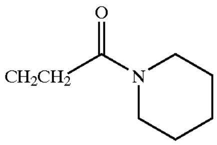 | 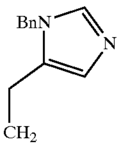 |
TABLE 1b-continued
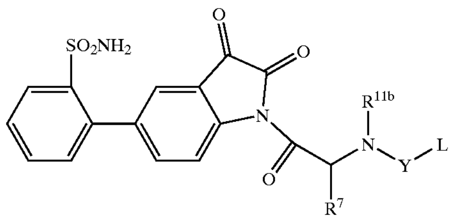
Formula IIb
| $R^7$ | $R^{11b}$ |
|---|---|
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 1c
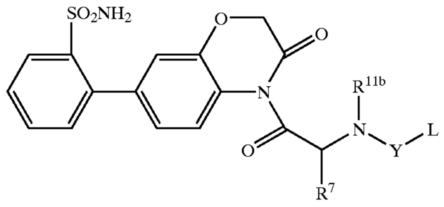
Formula IIc
| $R^7$ | $R^{11b}$ |
|---|---|
| H | H |
| Me | Me |
| 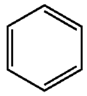 | 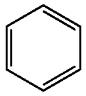 |
| 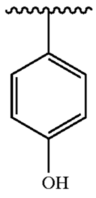 | 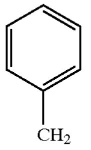 |
| 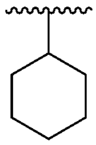 | 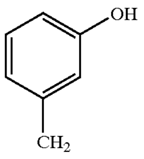 |
| 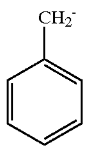 | 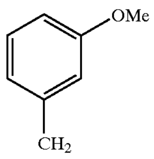 |

TABLE 1c-continued
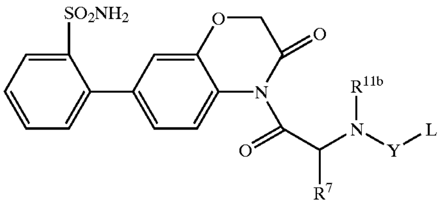
Formula IIc
| $R^7$ | $R^{11b}$ |
|---|---|
| 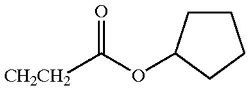 | 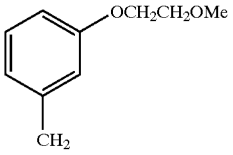 |
| 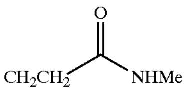 | 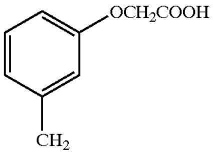 |
| 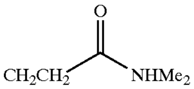 | 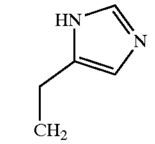 |
| 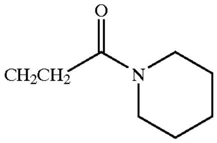 | 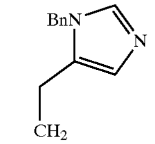 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 1d
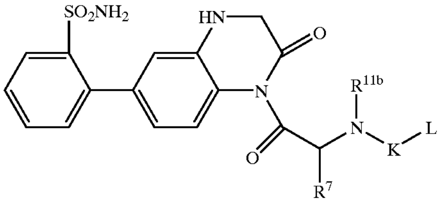
Formula IId
| $R^7$ | $R^{11b}$ |
|---|---|
| H | H |
| Me | Me |
TABLE 1d-continued
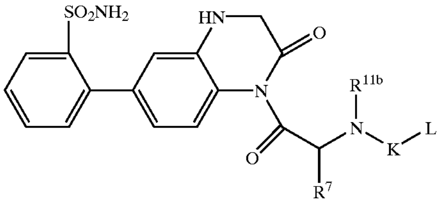
Formula IId
| $R^7$ | $R^{11b}$ |
|---|---|
| 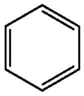 | 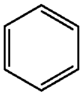 |
| 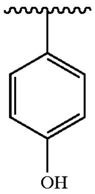 | 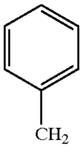 |
| 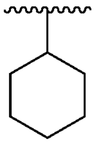 | 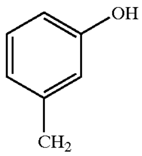 |
| 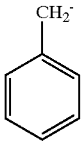 | 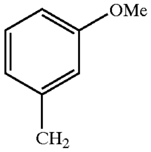 |
| 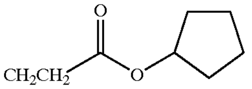 | 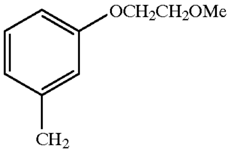 |
| 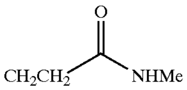 | 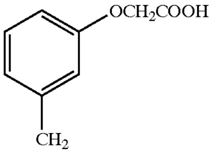 |
| 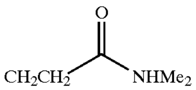 | 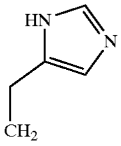 |
| 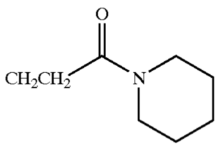 | 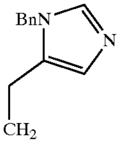 |
| OMe | H |

TABLE 1d-continued
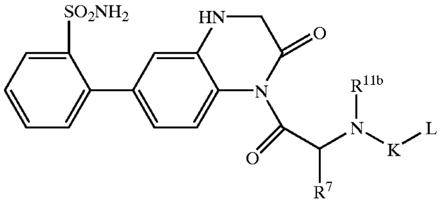
Formula IId
| $R^7$ | $R^{11b}$ |
|---|---|
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 1e
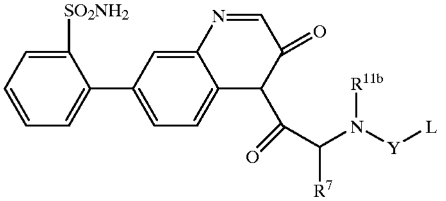
Formula IIe
| $R^7$ | $R^{11b}$ |
|---|---|
| H | H |
| Me | Me |
| 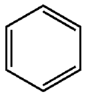 | 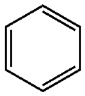 |
| 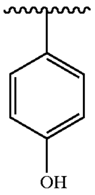 | 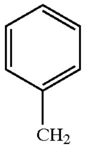 |
| 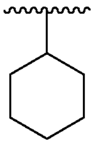 | 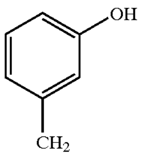 |
| 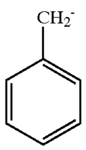 | 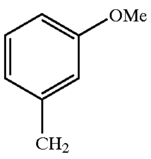 |
TABLE 1e-continued
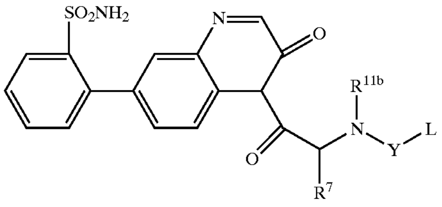
Formula IIe
| $R^7$ | $R^{11b}$ |
|---|---|
| 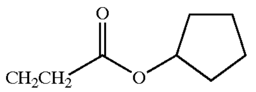 | 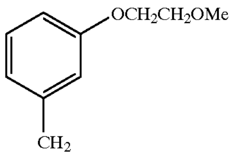 |
| 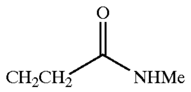 | 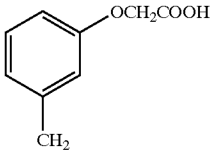 |
| 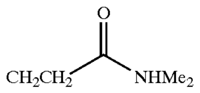 | 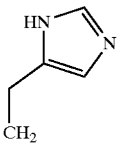 |
| 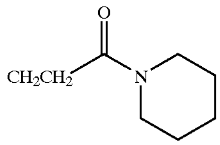 | 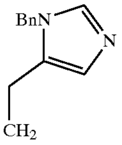 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 1f
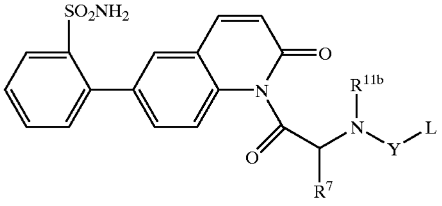
Formula IIf
| $R^7$ | $R^{11b}$ |
|---|---|
| H | H |
| Me | Me |

TABLE 1f-continued
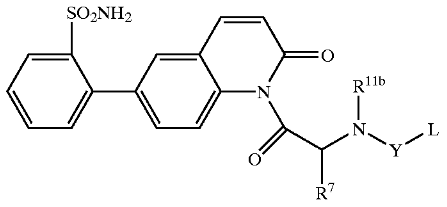
Formula IIf
| $R^7$ | $R^{11b}$ |
|---|---|
| 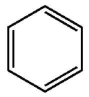 | 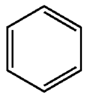 |
| 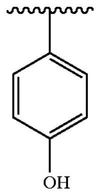 | 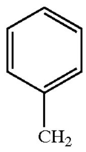 |
| 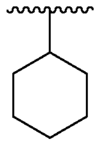 | 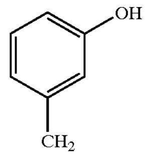 |
| 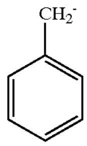 | 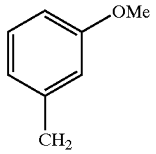 |
| 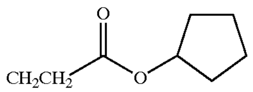 | 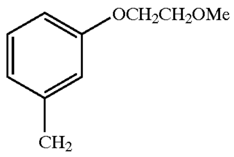 |
| 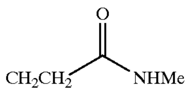 | 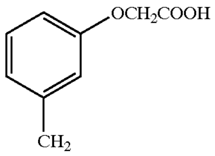 |
| 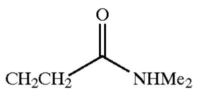 | 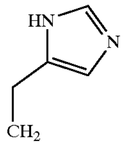 |
| 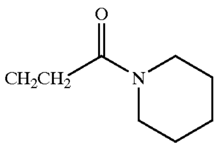 | 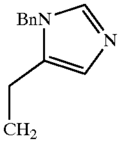 |
| OMe | H |
TABLE 1f-continued
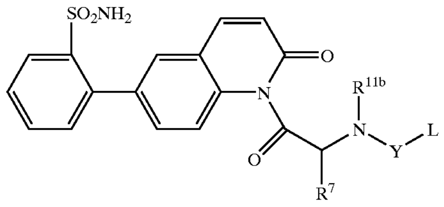
Formula IIf
| $R^7$ | $R^{11b}$ |
|---|---|
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 1g
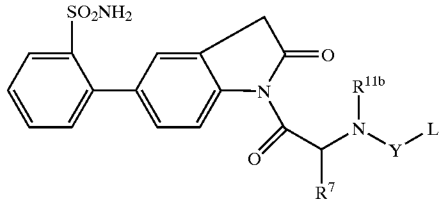
Formula IIg
| $R^7$ | $R^{11b}$ |
|---|---|
| H | H |
| Me | Me |
| 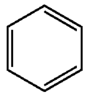 | 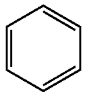 |
| 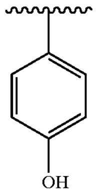 | 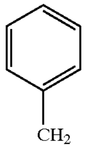 |
| 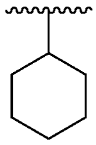 | 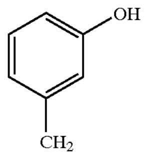 |
| 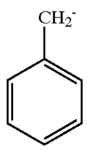 | 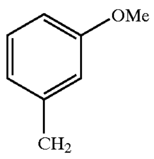 |

TABLE 1g-continued
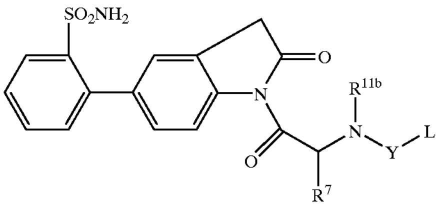
Formula IIg
| $R^7$ | $R^{11b}$ |
|---|---|
| 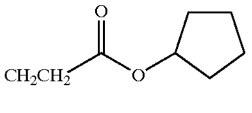 | 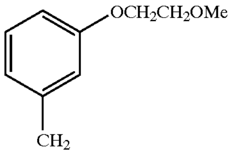 |
| 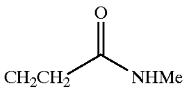 | 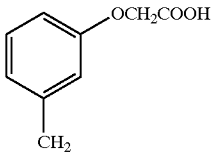 |
| 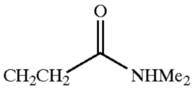 | 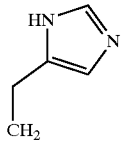 |
| 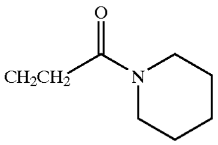 | 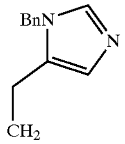 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 1h
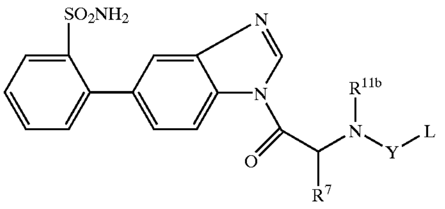
Formula IIh
| $R^7$ | $R^{11b}$ |
|---|---|
| H | H |
| Me | Me |
TABLE 1h-continued
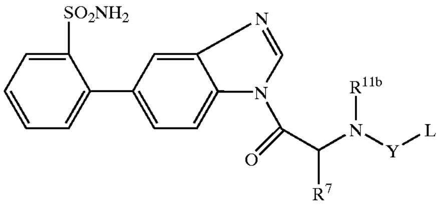
Formula IIh
| $R^7$ | $R^{11b}$ |
|---|---|
| 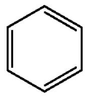 | 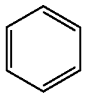 |
| 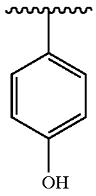 | 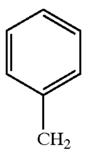 |
| 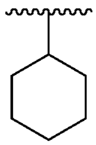 | 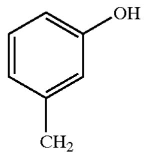 |
| 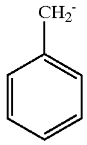 | 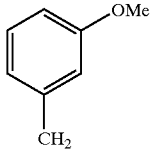 |
| 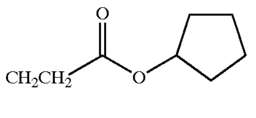 | 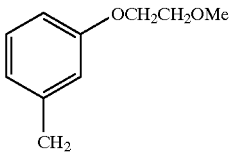 |
| 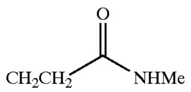 | 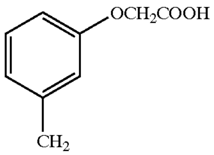 |
| 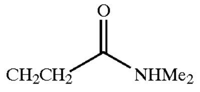 | 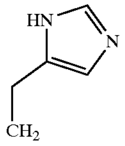 |
| 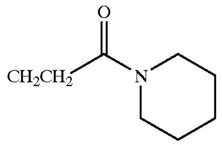 | 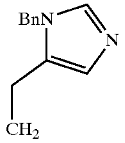 |
| OMe | H |

TABLE 1h-continued
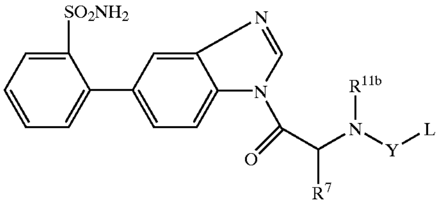
Formula IIh
| $R^7$ | $R^{11b}$ |
|---|---|
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 1i
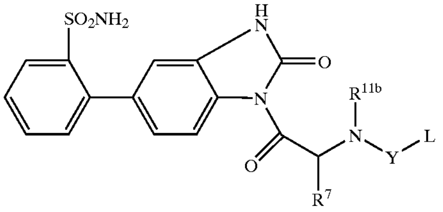
Formula IIi
| $R^7$ | $R^{11b}$ |
|---|---|
| H | H |
| Me | Me |
| 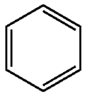 | 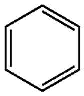 |
| 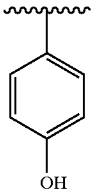 | 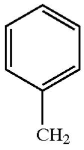 |
| 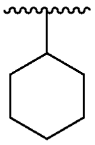 | 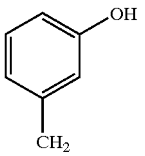 |
| 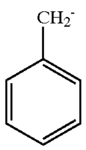 | 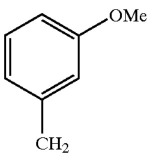 |
TABLE 1i-continued
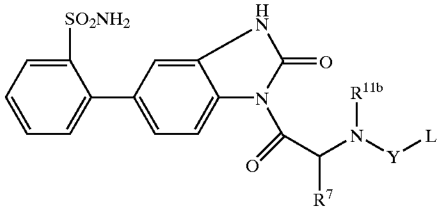
Formula IIi
| $R^7$ | $R^{11b}$ |
|---|---|
| 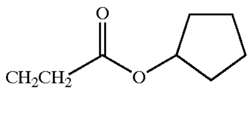 | 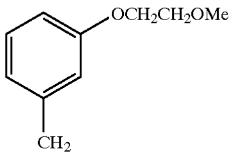 |
| 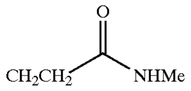 | 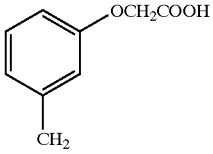 |
| 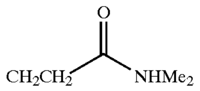 | 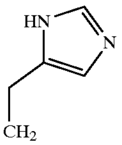 |
| 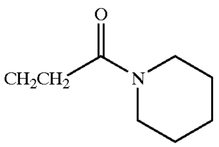 | 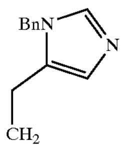 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 1j
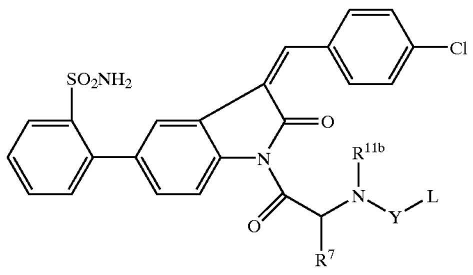
Formula IIj
| $R^7$ | $R^{11b}$ |
|---|---|
| H | H |

TABLE 1j-continued
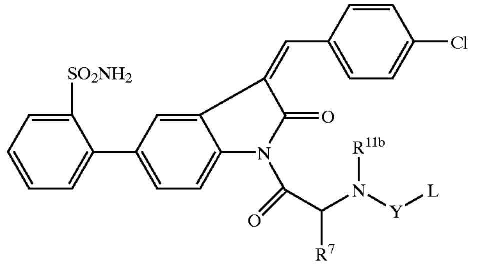
Formula IIj
| $R^7$ | $R^{11b}$ |
|---|---|
| Me | Me |
| 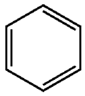 | 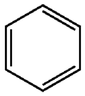 |
| 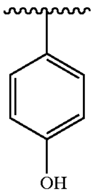 | 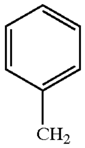 |
| 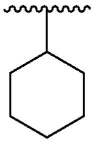 | 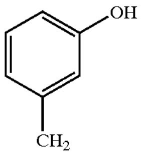 |
| 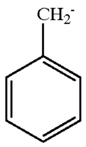 | 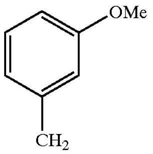 |
| 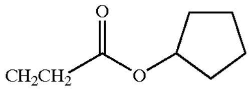 | 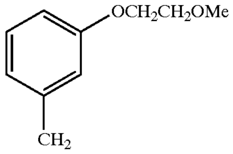 |
| 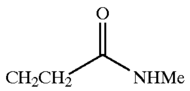 | 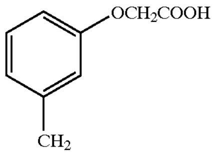 |
| 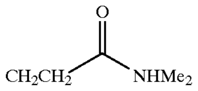 | 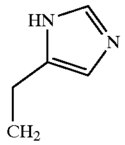 |
TABLE 1j-continued
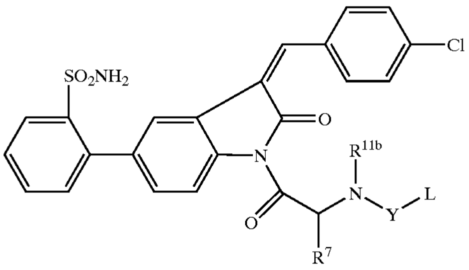
Formula IIj
| $R^7$ | $R^{11b}$ |
|---|---|
| 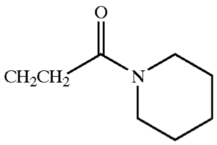 | 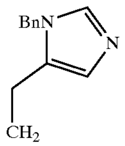 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 1k
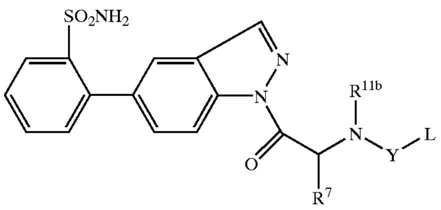
Formula IIk
| $R^7$ | $R^{11b}$ |
|---|---|
| H | H |
| Me | Me |
| 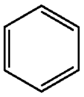 | 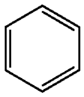 |
| 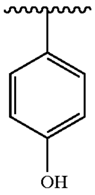 | 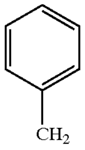 |
| 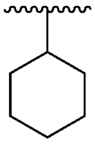 | 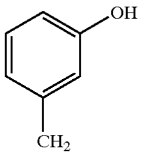 |

TABLE 1k-continued
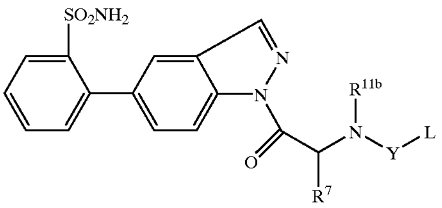
Formula IIk
| $R^7$ | $R^{11b}$ |
| --- | --- |
| 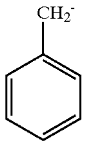 | 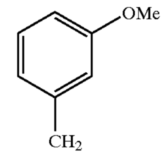 |
| 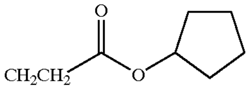 | 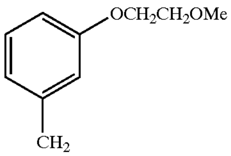 |
| 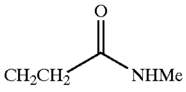 | 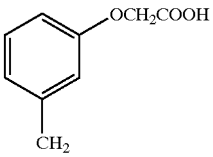 |
| 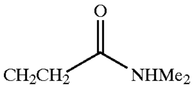 | 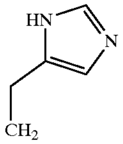 |
| 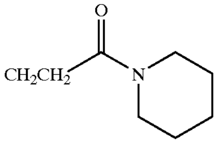 | 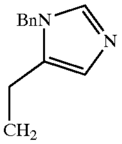 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 1(l)
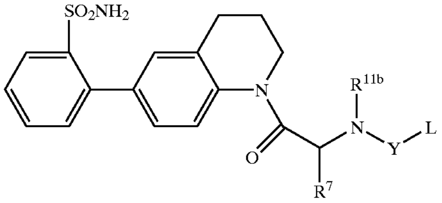
Formula II(l)
| $R^7$ | $R^{11b}$ |
| --- | --- |
| H | H |
| Me | Me |
| 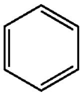 | 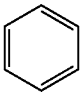 |
| 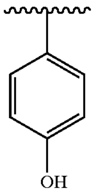 | 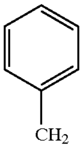 |
| 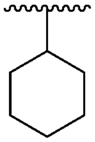 | 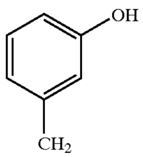 |
| 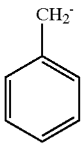 | 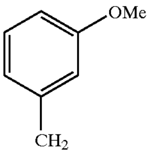 |
| 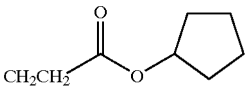 | 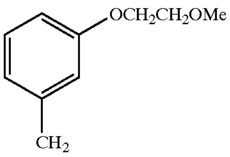 |
| 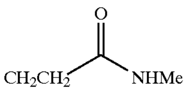 | 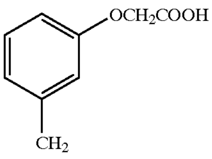 |
| 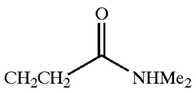 | 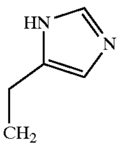 |

TABLE 1(l)-continued
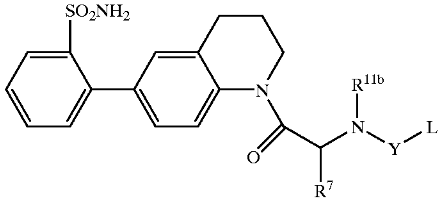
Formula II(l)
| $R^7$ | $R^{11b}$ |
|---|---|
| 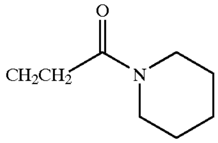 | 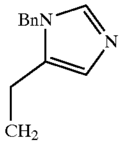 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 1m
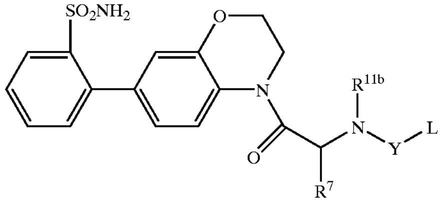
Formula IIm
| $R^7$ | $R^{11b}$ |
|---|---|
| H | H |
| Me | Me |
| 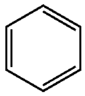 | 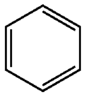 |
| 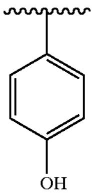 | 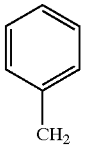 |
| 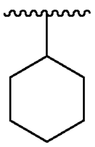 | 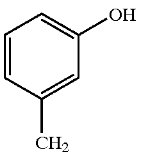 |
TABLE 1m-continued
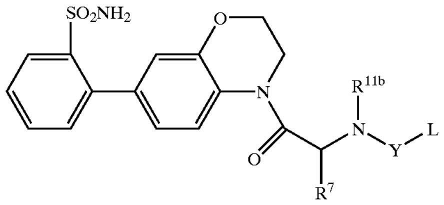
Formula IIm
| $R^7$ | $R^{11b}$ |
|---|---|
| 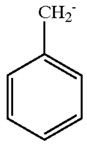 | 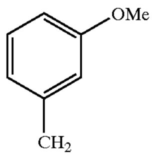 |
| 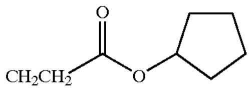 | 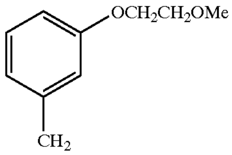 |
| 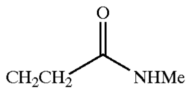 | 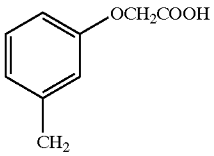 |
| 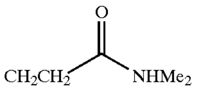 | 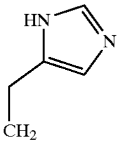 |
| 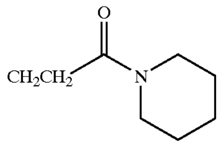 | 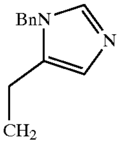 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |

TABLE 1n
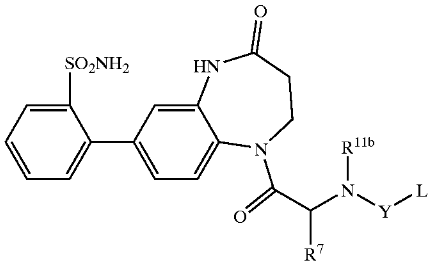
Formula IIn
| $R^7$ | $R^{11b}$ |
|---|---|
| H | H |
| Me | Me |
| 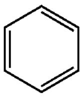 | 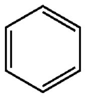 |
| 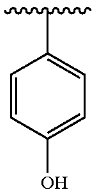 | 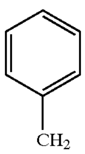 |
| 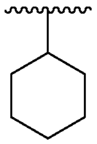 | 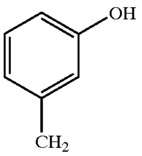 |
| 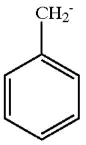 | 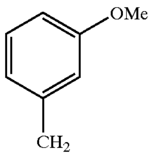 |
| 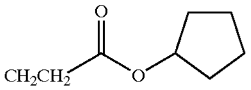 | 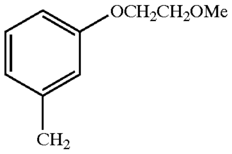 |
| 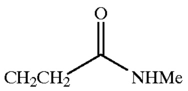 | 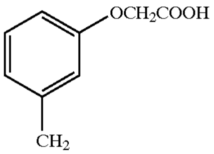 |
| 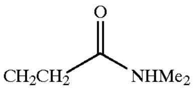 | 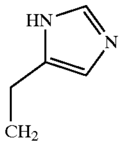 |
TABLE 1n-continued
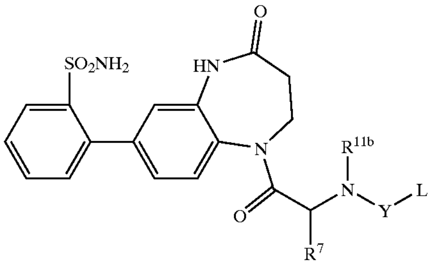
Formula IIn
| $R^7$ | $R^{11b}$ |
|---|---|
| 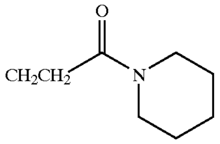 | 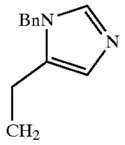 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 1o
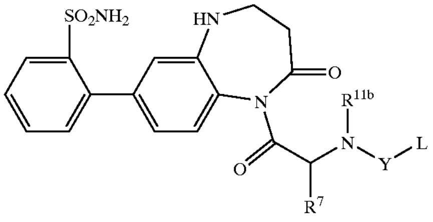
Formula IIo
| $R^7$ | $R^{11b}$ |
|---|---|
| H | H |
| Me | Me |
| 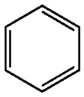 | 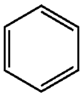 |
| 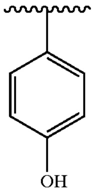 | 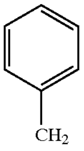 |

TABLE 1o-continued
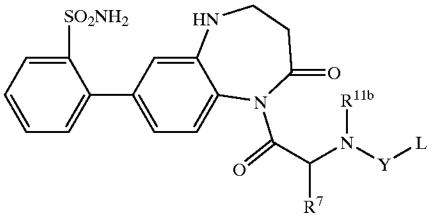
Formula IIo
| $R^7$ | $R^{11b}$ |
|---|---|
| 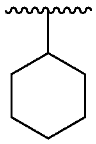 | 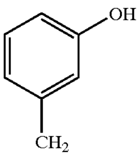 |
| 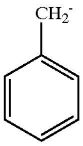 | 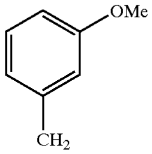 |
| 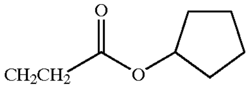 | 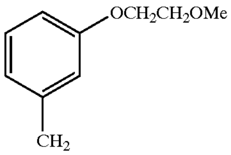 |
| 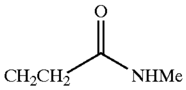 | 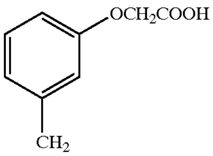 |
| 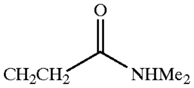 | 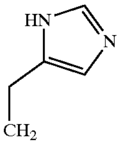 |
| 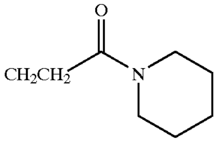 | 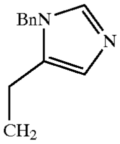 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 1p
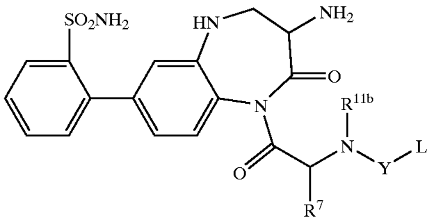
Formula IIp
| $R^7$ | $R^{11b}$ |
|---|---|
| H | H |
| Me | Me |
| 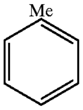 | 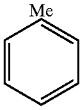 |
| 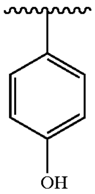 | 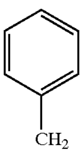 |
| 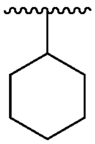 | 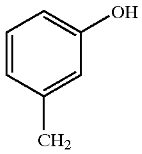 |
| 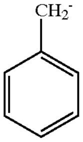 | 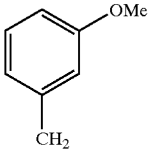 |
| 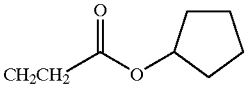 | 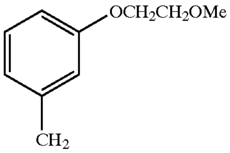 |
| 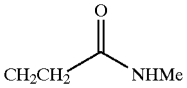 | 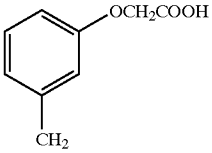 |
| 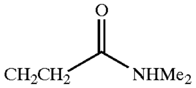 | 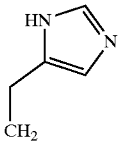 |
| 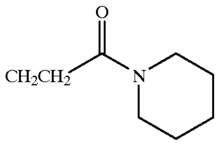 | 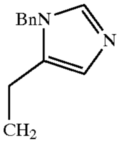 |

| | |
|---|---|
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 1q
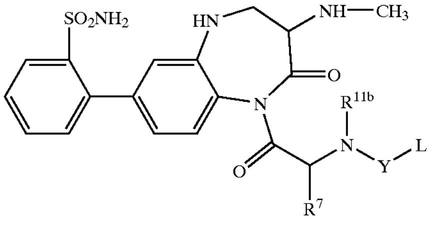
Formula IIq
| $R^7$ | $R^{11b}$ |
|---|---|
| H | H |
| Me | Me |
| 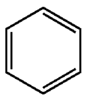 | 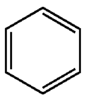 |
| 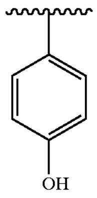 | 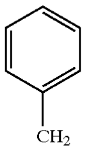 |
| 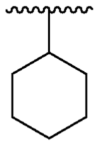 | 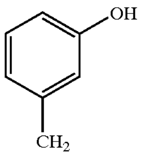 |
| 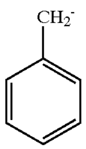 | 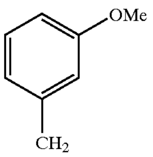 |
| 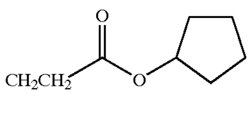 | 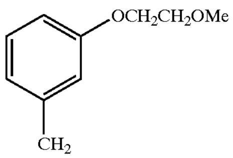 |
| 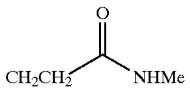 | 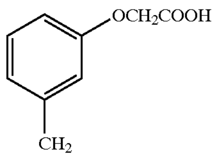 |
TABLE 1q-continued
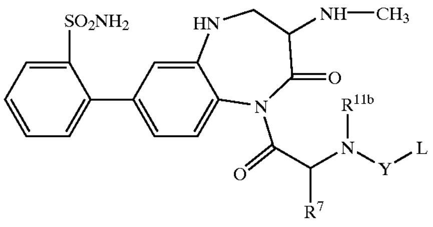
Formula IIq
| $R^7$ | $R^{11b}$ |
|---|---|
| 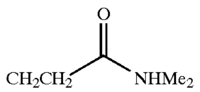 | 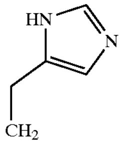 |
| 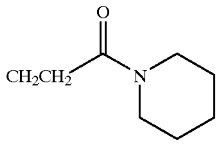 | 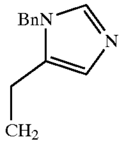 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 2
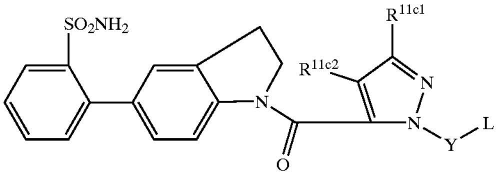
Formula III
| $R^{11c1}$ | $R^{11c2}$ |
|---|---|
| H | H |
| Me | Me |
| Br | Me |
| H | Cl |
| Me | Cl |
| Et | Cl |
| 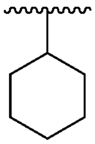 | 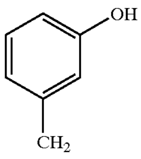 |

TABLE 2-continued
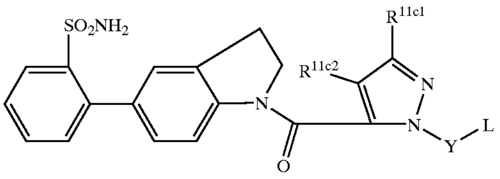
Formula III
| $R^{11c1}$ | $R^{11c2}$ |
|---|---|
| 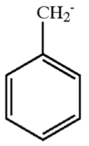 | 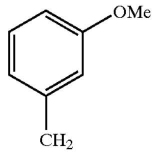 |
| 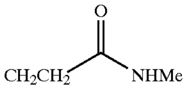 | 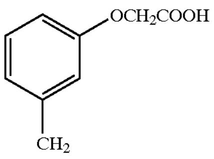 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 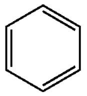 | 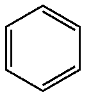 |
| 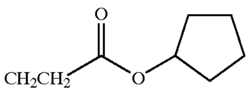 | 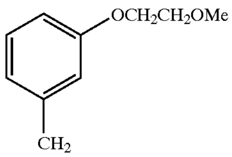 |
| 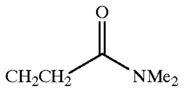 | 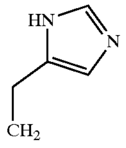 |
| —NH2 | H |
| H | Et |
| Et | F |
| Me | Et |
| SO2Me | Cl |
TABLE 2a
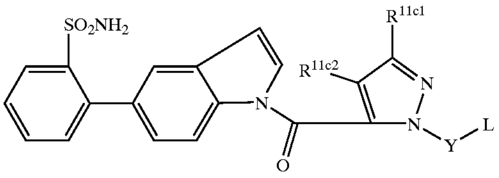
Formula IIIa
| $R^{11c1}$ | $R^{11c2}$ |
|---|---|
| H | H |
| Me | Me |
| Br | Me |
| H | Cl |
| Me | Cl |
| Et | Cl |
| 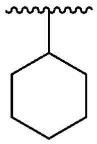 | 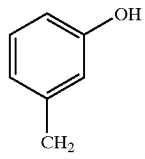 |
| 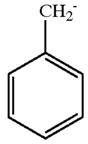 | 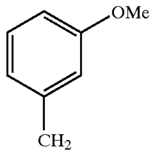 |
| 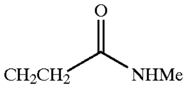 | 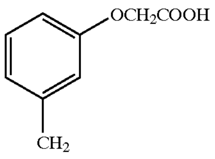 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 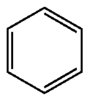 | 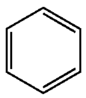 |
| 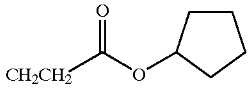 | 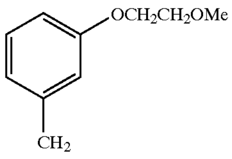 |
| 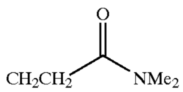 | 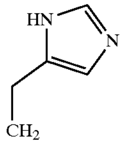 |
| —NH2 | H |

TABLE 2a-continued
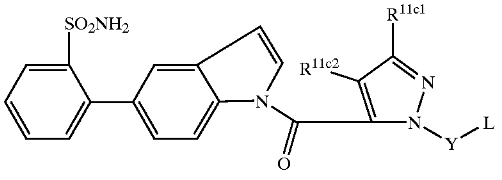
Formula IIIa
| $R^{11c1}$ | $R^{11c2}$ |
| --- | --- |
| H | Et |
| Et | F |
| Me | Et |
| SO2Me | Cl |
TABLE 2b
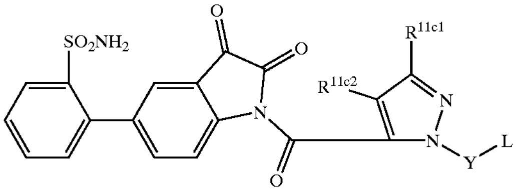
Formula IIIb
| $R^{11c1}$ | $R^{11c2}$ |
| --- | --- |
| H | H |
| Me | Me |
| Br | Me |
| H | Cl |
| Me | Cl |
| Et | Cl |
| 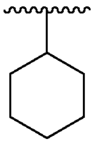 | 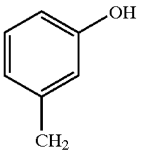 |
| 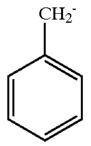 | 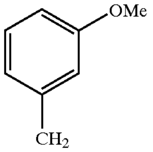 |
| 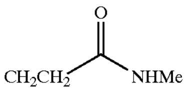 | 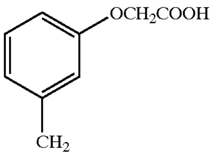 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
TABLE 2b-continued
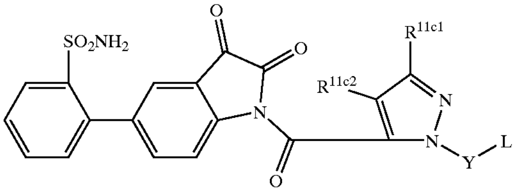
Formula IIIb
| $R^{11c1}$ | $R^{11c2}$ |
| --- | --- |
| 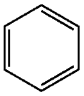 | 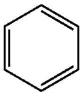 |
| 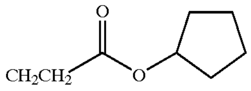 | 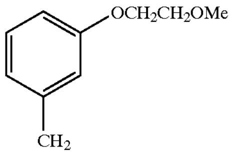 |
| 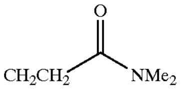 | 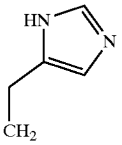 |
| —NH2 | H |
| H | Et |
| Et | F |
| Me | Et |
| SO2Me | Cl |
TABLE 2c
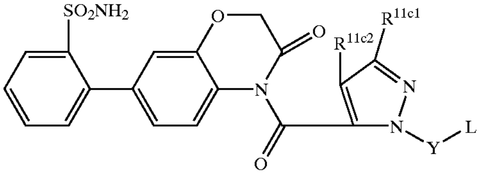
Formula IIIc
| $R^{11c1}$ | $R^{11c2}$ |
| --- | --- |
| H | H |
| Me | Me |
| Br | Me |
| H | Cl |
| Me | Cl |
| Et | Cl |
| 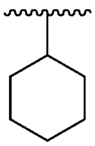 | 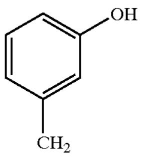 |

TABLE 2c-continued
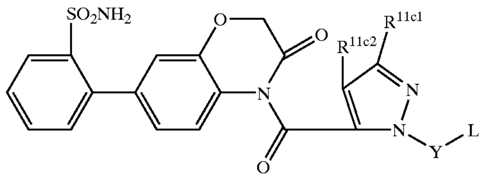
Formula IIIc
| $R^{11c1}$ | $R^{11c2}$ |
|---|---|
| 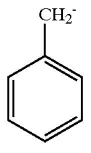 | 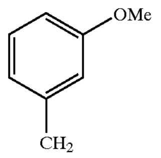 |
| 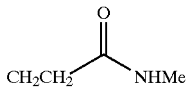 | 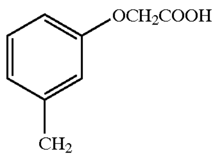 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 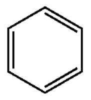 | 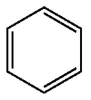 |
| 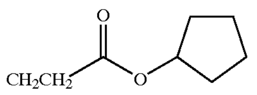 | 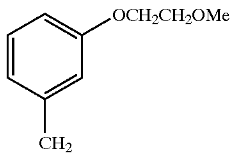 |
| 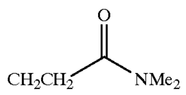 | 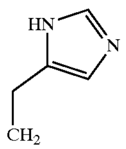 |
| —NH2 | H |
| H | Et |
| Et | F |
| Me | Et |
| SO2Me | Cl |
TABLE 2d
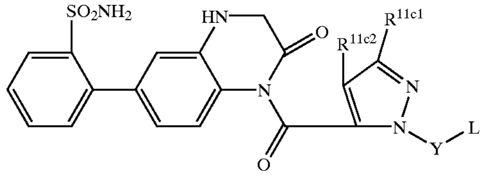
Formula IIId
| $R^{11c1}$ | $R^{11c2}$ |
|---|---|
| H | H |
| Me | Me |
| Br | Me |
| H | Cl |
| Me | Cl |
| Et | Cl |
| 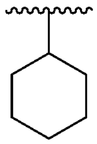 | 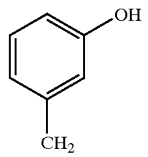 |
| 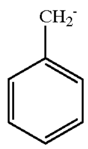 | 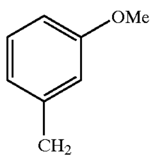 |
| 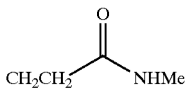 | 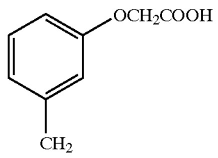 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 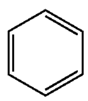 | 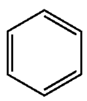 |
| 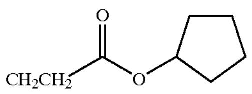 | 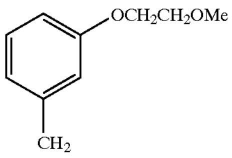 |
| 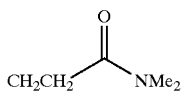 | 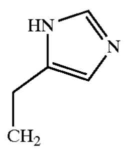 |
| —NH2 | H |

TABLE 2d-continued
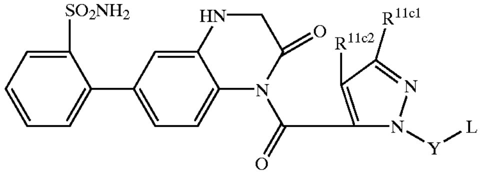
Formula IIId
| $R^{11c1}$ | $R^{11c2}$ |
|---|---|
| H | Et |
| Et | F |
| Me | Et |
| SO2Me | Cl |
TABLE 2e
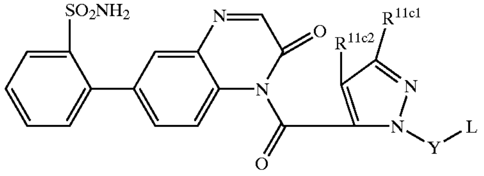
Formula IIIe
| $R^{11c1}$ | $R^{11c2}$ |
|---|---|
| H | H |
| Me | Me |
| Br | Me |
| H | Cl |
| Me | Cl |
| Et | Cl |
| 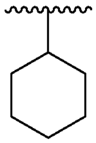 | 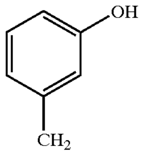 |
| 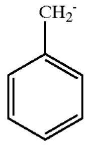 | 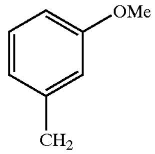 |
| 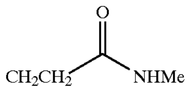 | 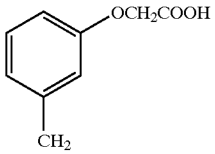 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
TABLE 2e-continued
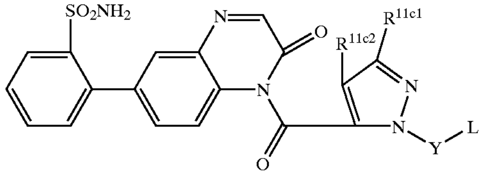
Formula IIIe
| $R^{11c1}$ | $R^{11c2}$ |
|---|---|
| 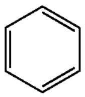 | 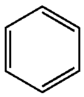 |
| 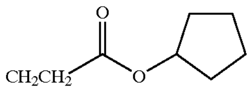 | 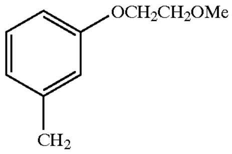 |
| 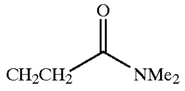 | 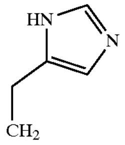 |
| —NH2 | H |
| H | Et |
| Et | F |
| Me | Et |
| SO2Me | Cl |
TABLE 2f
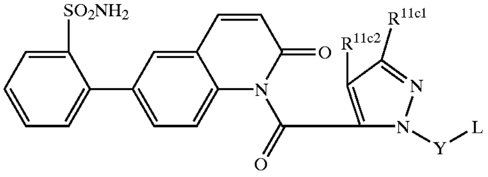
Formula IIIf
| $R^{11c1}$ | $R^{11c2}$ |
|---|---|
| H | H |
| Me | Me |
| Br | Me |
| H | Cl |
| Me | Cl |
| Et | Cl |
| 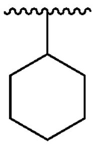 | 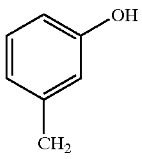 |

TABLE 2f-continued
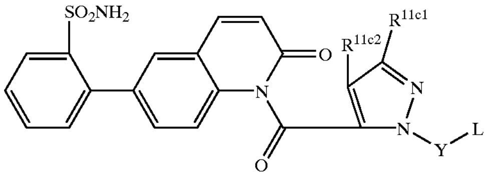
Formula IIIf
| $R^{11c1}$ | $R^{11c2}$ |
| --- | --- |
| 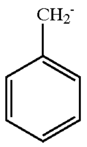 | 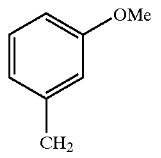 |
| 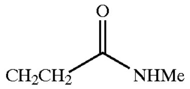 | 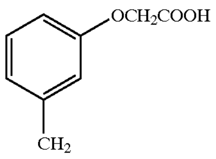 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 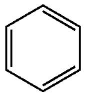 | 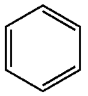 |
| 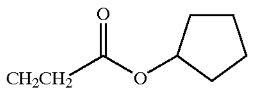 | 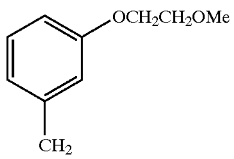 |
| 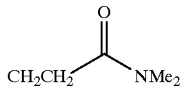 | 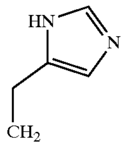 |
| —NH2 | H |
| H | Et |
| Et | F |
| Me | Et |
| SO2Me | Cl |
TABLE 2g
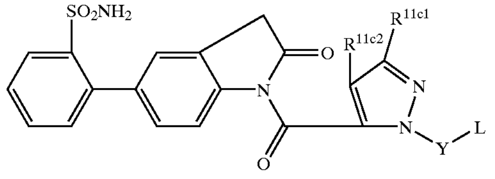
Formula IIIg
| $R^{11c1}$ | $R^{11c2}$ |
| --- | --- |
| H | H |
| Me | Me |
| Br | Me |
| H | Cl |
| Me | Cl |
| Et | Cl |
| 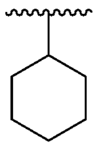 | 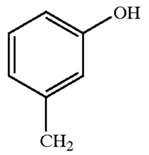 |
| 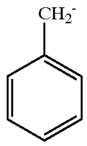 | 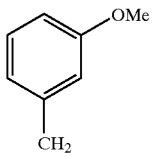 |
| 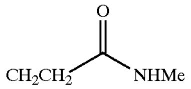 | 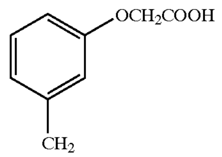 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 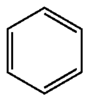 | 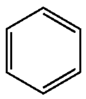 |
| 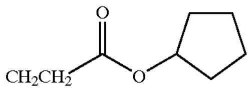 | 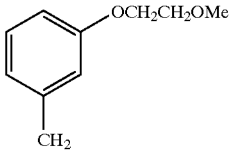 |
| 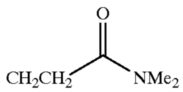 | 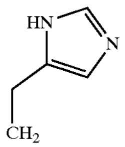 |
| —NH2 | H |

TABLE 2g-continued
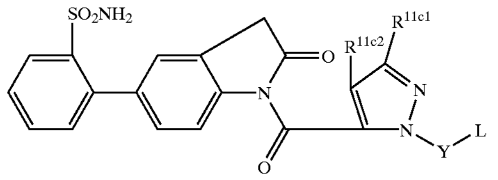
Formula IIIg
| $R^{11c1}$ | $R^{11c2}$ |
|---|---|
| H | Et |
| Et | F |
| Me | Et |
| SO2Me | Cl |
TABLE 2h
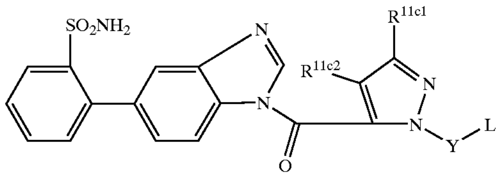
Formula IIIh
| $R^{11c1}$ | $R^{11c2}$ |
|---|---|
| H | H |
| Me | Me |
| Br | Me |
| H | Cl |
| Me | Cl |
| Et | Cl |
| 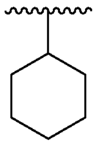 | 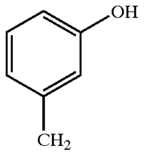 |
| 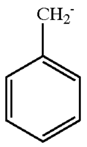 | 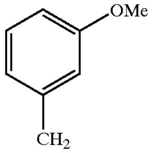 |
| 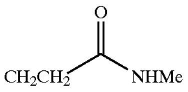 | 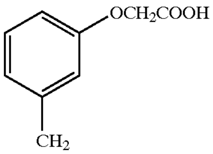 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
TABLE 2h-continued
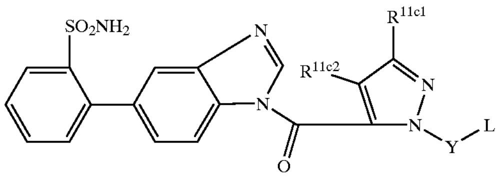
Formula IIIh
| $R^{11c1}$ | $R^{11c2}$ |
|---|---|
| 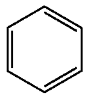 | 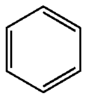 |
| 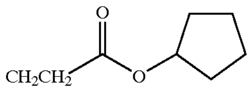 | 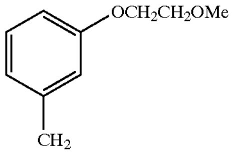 |
| 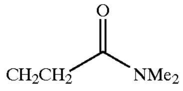 | 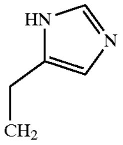 |
| —NH2 | H |
| H | Et |
| Et | F |
| Me | Et |
| SO2Me | Cl |
TABLE 2i
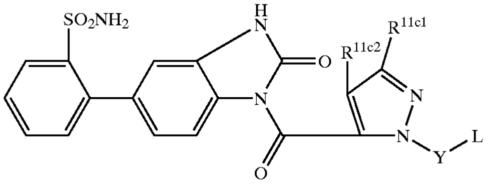
Formula IIIi
| $R^{11c1}$ | $R^{11c2}$ |
|---|---|
| H | H |
| Me | Me |
| Br | Me |
| H | Cl |
| Me | Cl |
| Et | Cl |
| 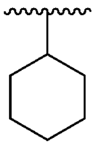 | 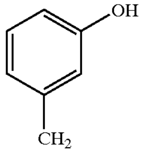 |

TABLE 2i-continued
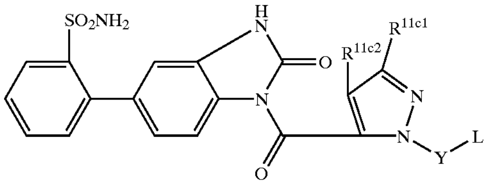
Formula IIIi
| $R^{11c1}$ | $R^{11c2}$ |
|---|---|
| 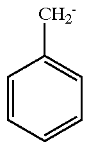 | 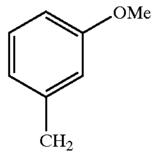 |
| 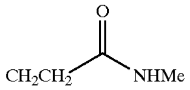 | 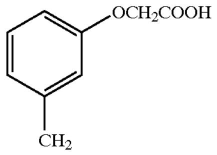 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 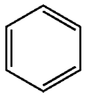 | 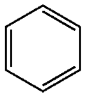 |
| 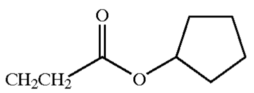 | 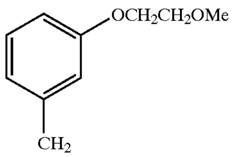 |
| 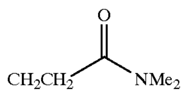 | 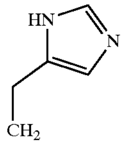 |
| —NH2 | H |
| H | Et |
| Et | F |
| Me | Et |
| SO2Me | Cl |
TABLE 2j
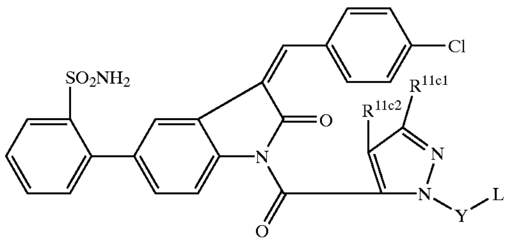
Formula IIIj
| $R^{11c1}$ | $R^{11c2}$ |
|---|---|
| H | H |
| Me | Me |
| Br | Me |
| H | Cl |
| Me | Cl |
| Et | Cl |
| 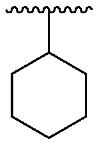 | 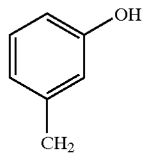 |
| 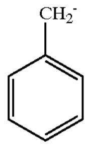 | 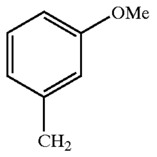 |
| 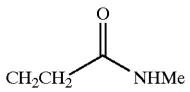 | 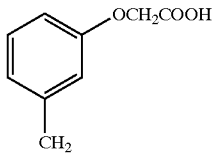 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 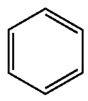 | 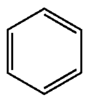 |
| 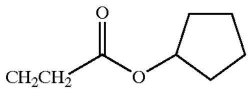 | 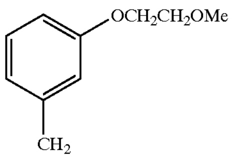 |

TABLE 2j-continued
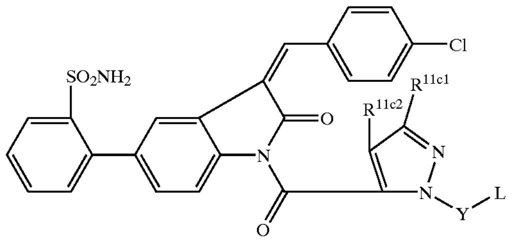
Formula IIIj
| $R^{11c1}$ | $R^{11c2}$ |
|---|---|
| 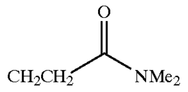 | 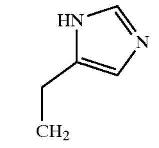 |
| —NH2 | H |
| H | Et |
| Et | F |
| Me | Et |
| SO2Me | Cl |
TABLE 2k
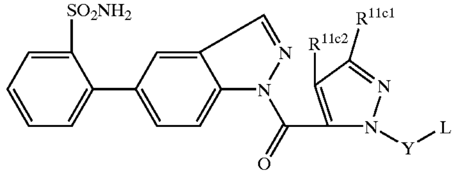
Formula IIIk
| $R^{11c1}$ | $R^{11c2}$ |
|---|---|
| H | H |
| Me | Me |
| Br | Me |
| H | Cl |
| Me | Cl |
| Et | Cl |
| 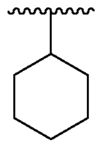 | 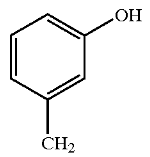 |
| 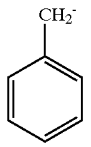 | 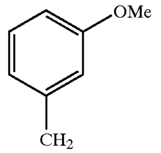 |
| 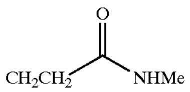 | 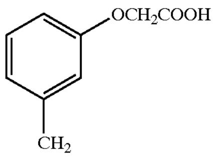 |
| OCH2Ph | H |
TABLE 2k-continued
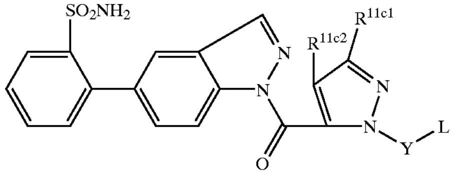
Formula IIIk
| $R^{11c1}$ | $R^{11c2}$ |
|---|---|
| OCH2CH2OMe | H |
| Me | F |
| Me | H |
| SO2Me | H |
| OMe | H |
| OMe | Me |
| F | H |
| Et | H |
| —OH | Me |
| Et | Br |
| 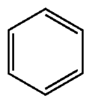 | 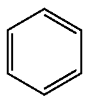 |
| 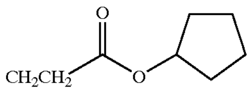 | 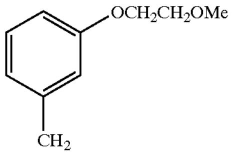 |
| 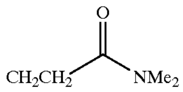 | 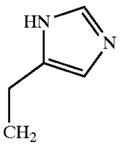 |
| —NH2 | H |
| H | Et |
| Et | F |
| Me | Et |
| SO2Me | Cl |
TABLE 2(l)
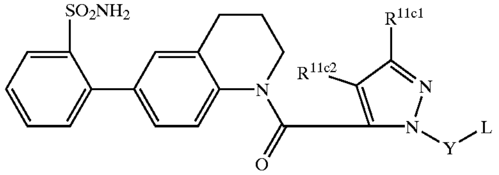
Formula III(l)
| $R^{11c1}$ | $R^{11c2}$ |
|---|---|
| H | H |
| Me | Me |
| Br | Me |
| H | Cl |
| Me | Cl |
| Et | Cl |

TABLE 2(l)-continued
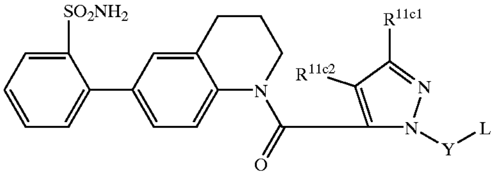
Formula III(l)
| $R^{11c1}$ | $R^{11c2}$ |
|---|---|
| 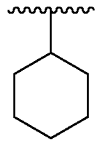 | 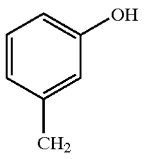 |
| 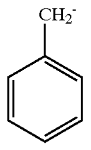 | 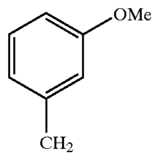 |
| 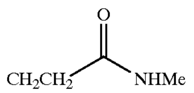 | 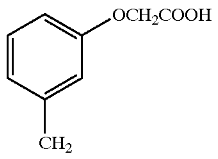 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 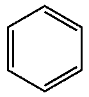 | 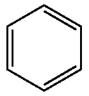 |
| 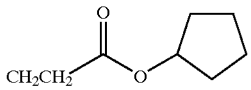 | 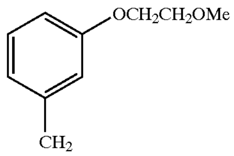 |
| 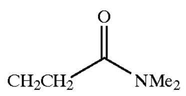 | 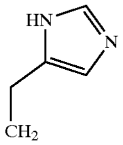 |
| —NH2 | H |
| H | Et |
| Et | F |
| Me | Et |
| SO2Me | Cl |
TABLE 2m
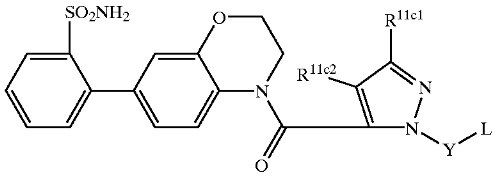
Formula IIIm
| $R^{11c1}$ | $R^{11c2}$ |
|---|---|
| H | H |
| Me | Me |
| Br | Me |
| H | Cl |
| Me | Cl |
| Et | Cl |
| 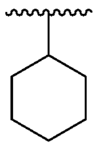 | 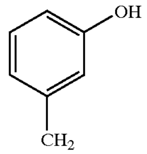 |
| 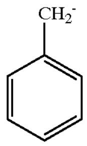 | 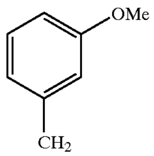 |
| 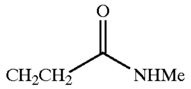 | 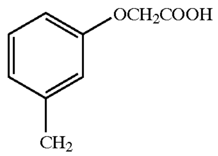 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 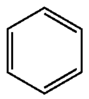 | 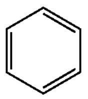 |
| 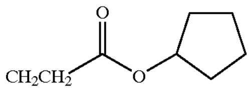 | 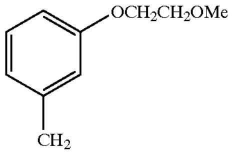 |
| 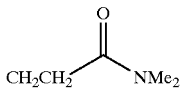 | 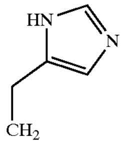 |
| —NH2 | H |

TABLE 2m-continued
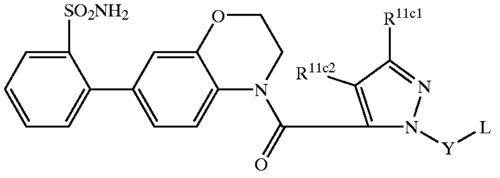
Formula IIIm
| $R^{11c1}$ | $R^{11c2}$ |
|---|---|
| H | Et |
| Et | F |
| Me | Et |
| SO2Me | Cl |
TABLE 2n
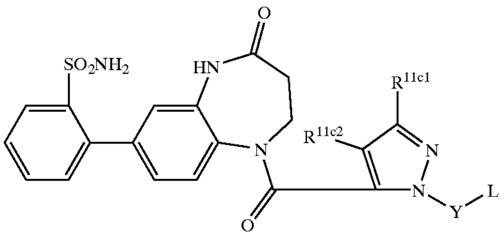
Formula IIIn
| $R^{11c1}$ | $R^{11c2}$ |
|---|---|
| H | H |
| Me | Me |
| Br | Me |
| H | Cl |
| Me | Cl |
| Et | Cl |
| 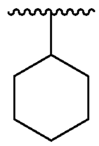 | 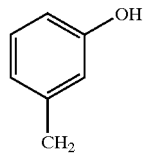 |
| 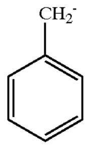 | 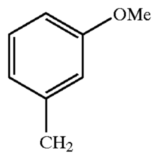 |
| 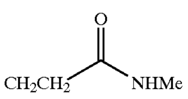 | 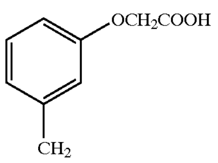 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
TABLE 2n-continued
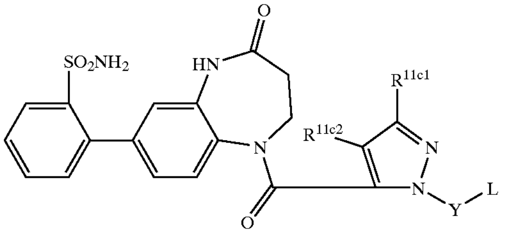
Formula IIIn
| $R^{11c1}$ | $R^{11c2}$ |
|---|---|
| Et | Br |
| 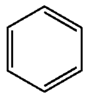 | 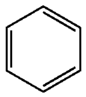 |
| 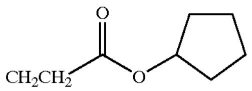 | 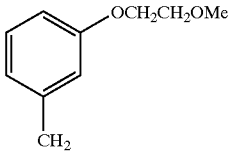 |
| 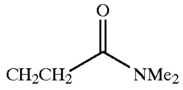 | 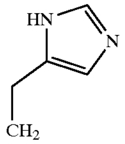 |
| —NH2 | H |
| H | Et |
| Et | F |
| Me | Et |
| SO2Me | Cl |
TABLE 2o
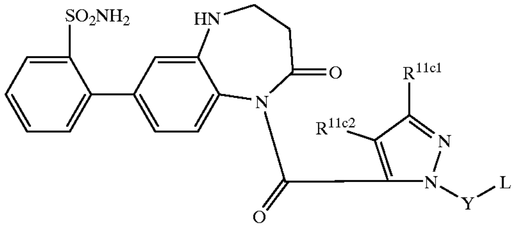
Formula IIIo
| $R^{11c1}$ | $R^{11c2}$ |
|---|---|
| H | H |
| Me | Me |
| Br | Me |
| H | Cl |
| Me | Cl |
| Et | Cl |
| 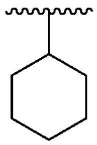 | 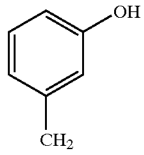 |

TABLE 2o-continued
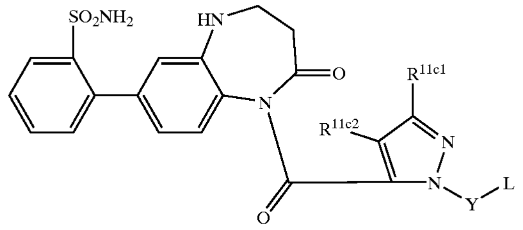
Formula IIIo
| $R^{11c1}$ | $R^{11c2}$ |
|---|---|
| 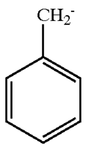 | 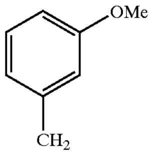 |
| 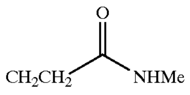 | 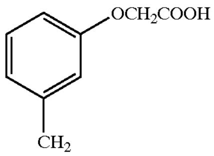 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 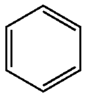 | 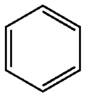 |
| 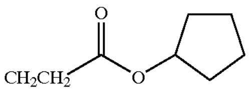 | 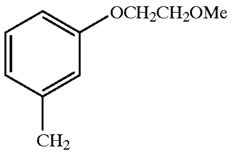 |
| 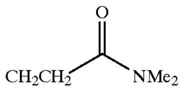 | 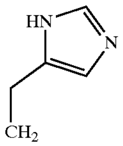 |
| —NH2 | H |
| H | Et |
| Et | F |
| Me | Et |
| SO2Me | Cl |
TABLE 2p
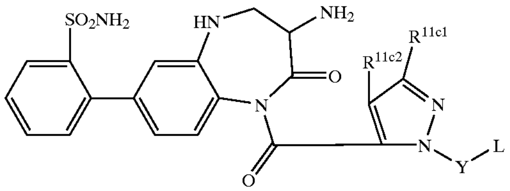
Formula IIIp
| $R^{11c1}$ | $R^{11c2}$ |
|---|---|
| H | H |
| Me | Me |
| Br | Me |
| H | Cl |
| Me | Cl |
| Et | Cl |
| 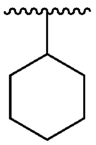 | 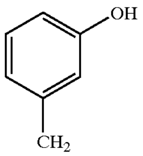 |
| 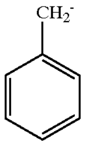 | 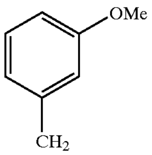 |
| 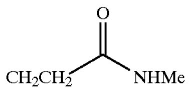 | 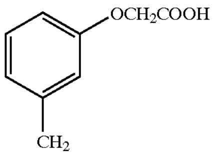 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 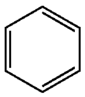 | 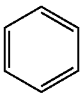 |
| 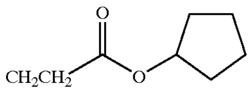 | 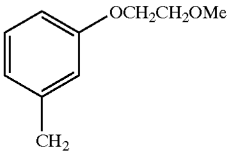 |
| 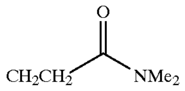 | 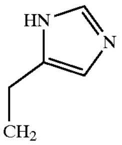 |

TABLE 2p-continued
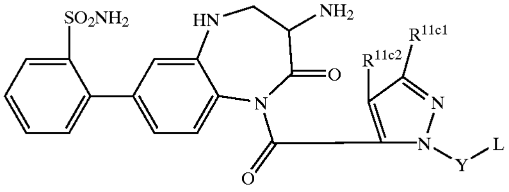
Formula IIIp
| $R^{11c1}$ | $R^{11c2}$ |
|---|---|
| —NH2 | H |
| H | Et |
| Et | F |
| Me | Et |
| SO2Me | Cl |
TABLE 2q
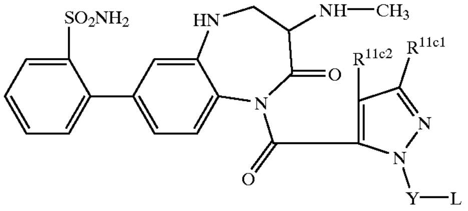
Formula IIIq
| $R^{11c1}$ | $R^{11c2}$ |
|---|---|
| H | H |
| Me | Me |
| Br | Me |
| H | Cl |
| Me | Cl |
| Et | Cl |
| 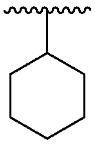 | 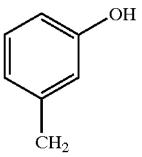 |
| 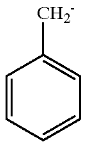 | 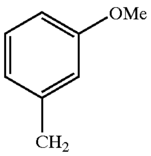 |
| 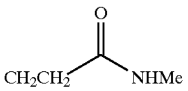 | 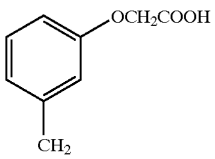 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
TABLE 2q-continued
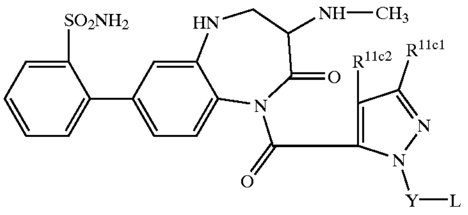
Formula IIIq
| $R^{11c1}$ | $R^{11c2}$ |
|---|---|
| Et | Br |
| 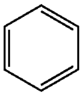 | 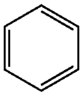 |
| 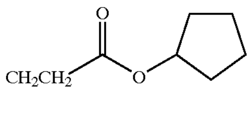 | 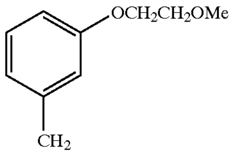 |
| 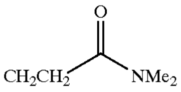 | 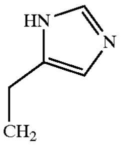 |
| —NH2 | H |
| H | Et |
| Et | F |
| Me | Et |
| SO2Me | Cl |
TABLE 3
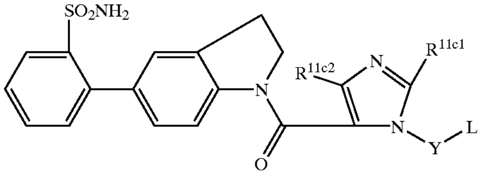
Formula IV
| $R^{11c1}$ | $R^{11c2}$ |
|---|---|
| H | H |
| Me | Me |
| 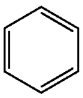 | 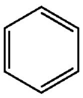 |
| 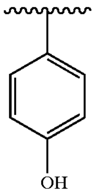 | 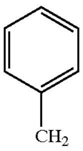 |

TABLE 3-continued
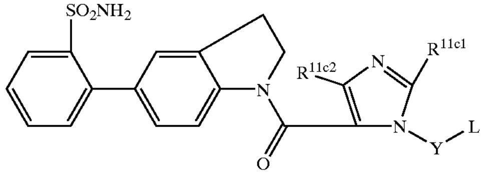
Formula IV
| $R^{11c1}$ | $R^{11c2}$ |
|---|---|
| 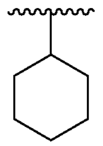 | 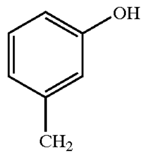 |
| 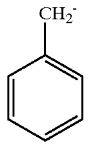 | 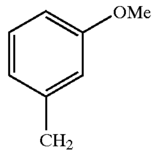 |
| 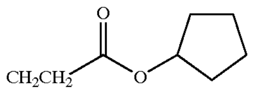 | 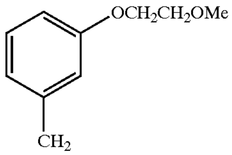 |
| 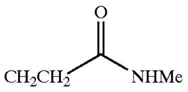 | 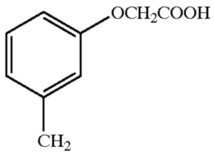 |
| 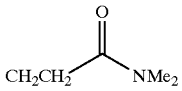 | 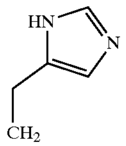 |
| 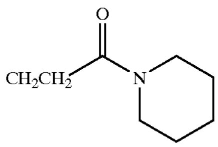 | 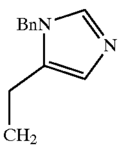 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 3a
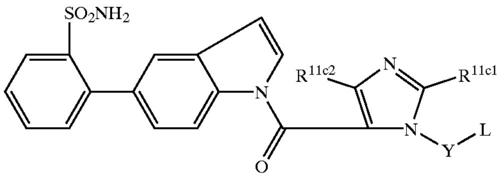
Formula IVa
| $R^{11c1}$ | $R^{11c2}$ |
|---|---|
| H | H |
| Me | Me |
| 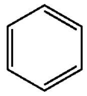 | 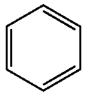 |
| 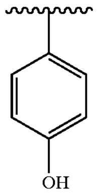 | 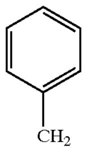 |
| 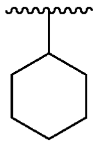 | 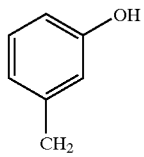 |
| 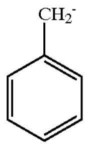 | 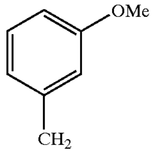 |
| 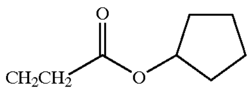 | 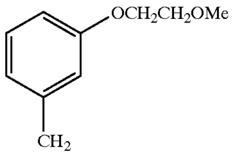 |
| 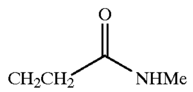 | 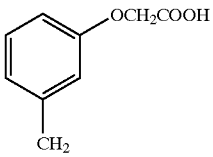 |
| 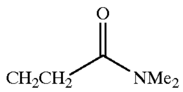 | 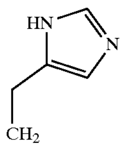 |
| 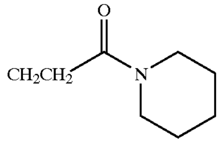 | 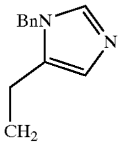 |

TABLE 3a-continued
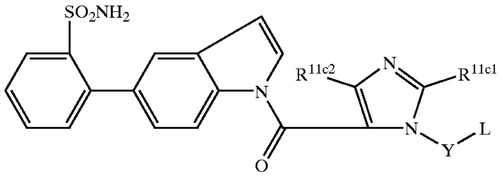
Formula IVa
| $R^{11c1}$ | $R^{11c2}$ |
|---|---|
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 3b
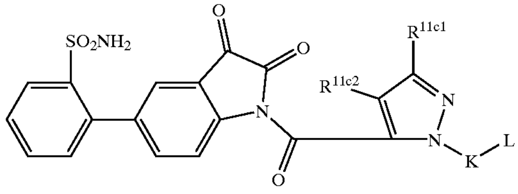
Formula IVb
| $R^{11c1}$ | $R^{11c2}$ |
|---|---|
| H | H |
| Me | Me |
| 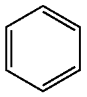 | 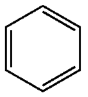 |
| 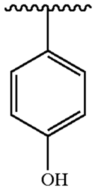 | 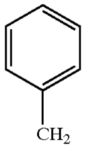 |
| 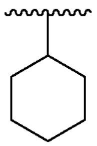 | 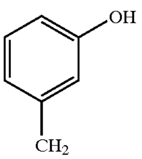 |
| 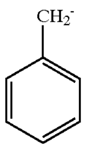 | 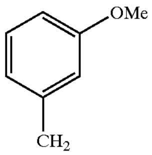 |
TABLE 3b-continued
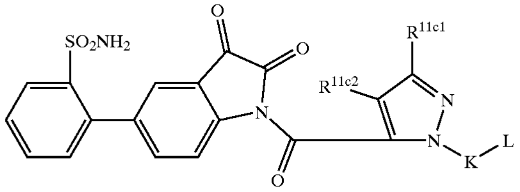
Formula IVb
| $R^{11c1}$ | $R^{11c2}$ |
|---|---|
| 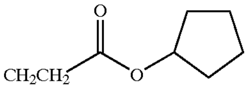 | 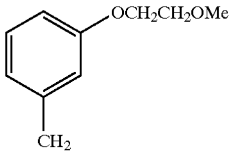 |
| 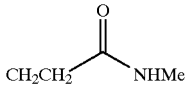 | 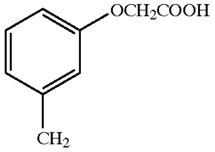 |
| 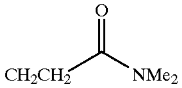 | 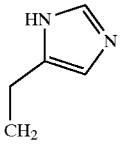 |
| 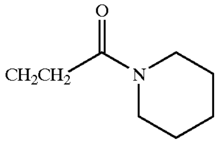 | 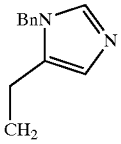 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 3c
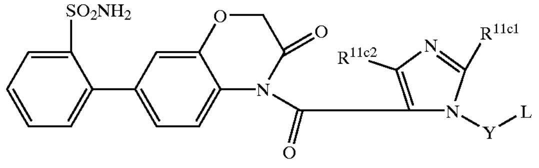
Formula IVc
| $R^{11c1}$ | $R^{11c2}$ |
|---|---|
| H | H |
| Me | Me |

TABLE 3c-continued
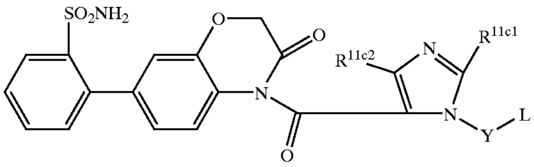
Formula IVc
| $R^{11c1}$ | $R^{11c2}$ |
|---|---|
| 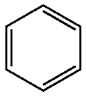 | 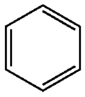 |
| 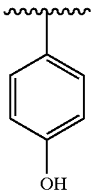 | 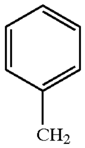 |
| 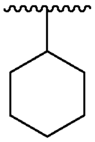 | 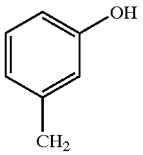 |
| 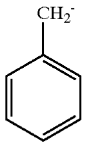 | 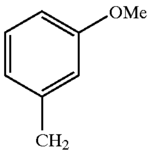 |
| 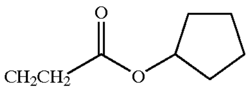 | 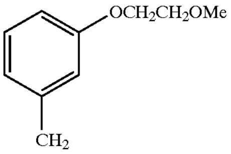 |
| 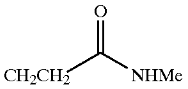 | 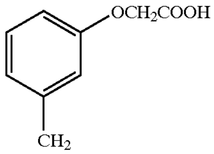 |
| 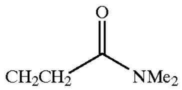 | 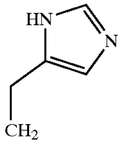 |
| 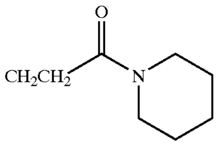 | 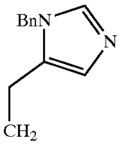 |
| OMe | H |
| OMe | Me |
TABLE 3c-continued
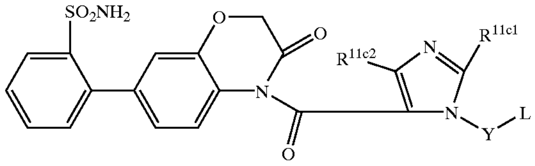
Formula IVc
| $R^{11c1}$ | $R^{11c2}$ |
|---|---|
| F | H |
| —OH | Me |
| Br | Me |
| —NH2 | H |
| OCH2Ph | H |
| OCH2CH2OMe | H |
| H | Et |
| Me | Et |
TABLE 3d
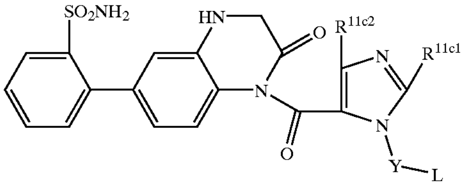
Formula IVd
| $R^{11c1}$ | $R^{11c2}$ |
|---|---|
| H | H |
| Me | Me |
| 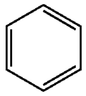 | 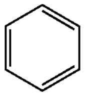 |
| 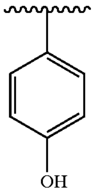 | 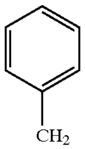 |
| 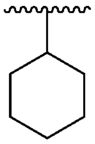 | 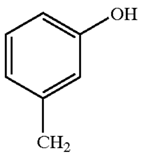 |
| 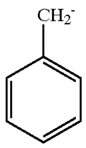 | 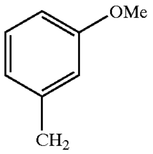 |

TABLE 3d-continued
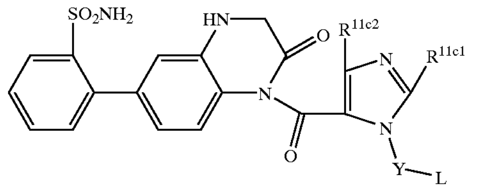
Formula IVd
| $R^{11c1}$ | $R^{11c2}$ |
|---|---|
| 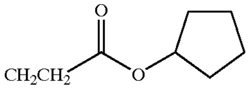 | 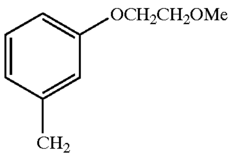 |
| 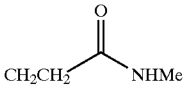 | 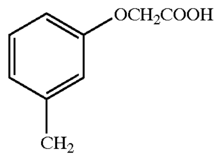 |
| 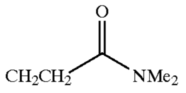 | 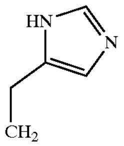 |
| 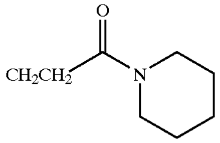 | 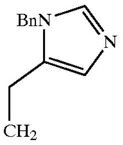 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 3e
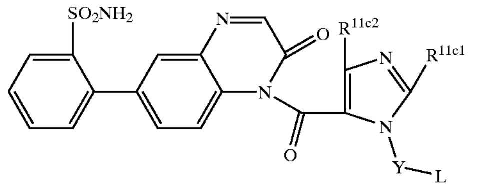
Formula IVe
| $R^{11c1}$ | $R^{11c2}$ |
|---|---|
| H | H |
| Me | Me |
TABLE 3e-continued
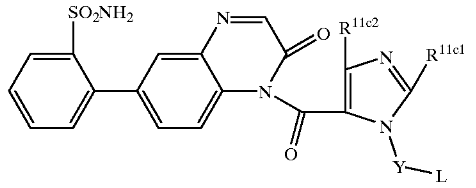
Formula IVe
| $R^{11c1}$ | $R^{11c2}$ |
|---|---|
| 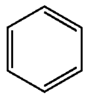 | 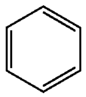 |
| 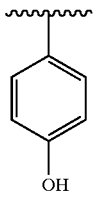 | 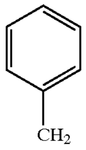 |
| 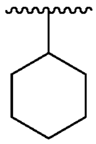 | 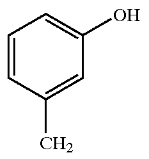 |
| 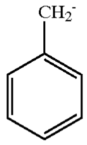 | 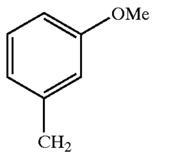 |
| 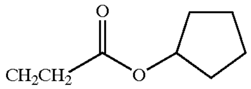 | 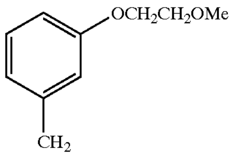 |
| 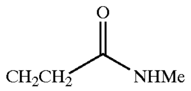 | 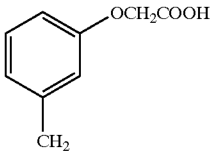 |
| 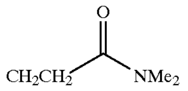 | 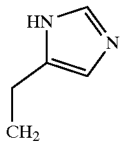 |
| 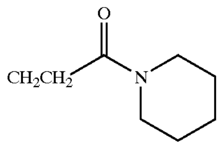 | 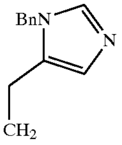 |
| OMe | H |

TABLE 3e-continued
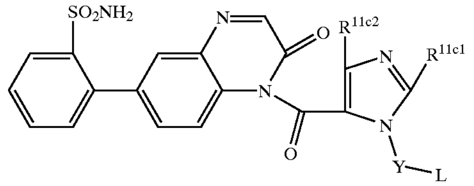
Formula IVe
| $R^{11c1}$ | $R^{11c2}$ |
|---|---|
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 3f
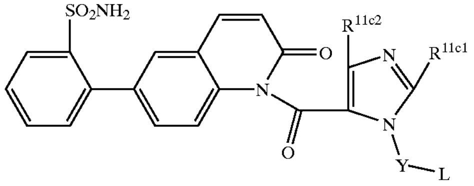
Formula IVf
| $R^{11c1}$ | $R^{11c2}$ |
|---|---|
| H | H |
| Me | Me |
| 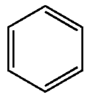 | 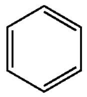 |
| 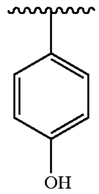 | 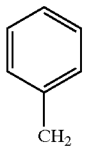 |
| 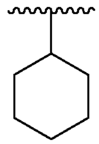 | 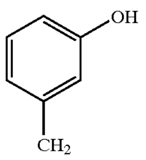 |
| 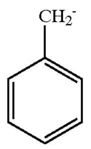 | 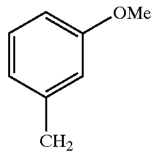 |
TABLE 3f-continued
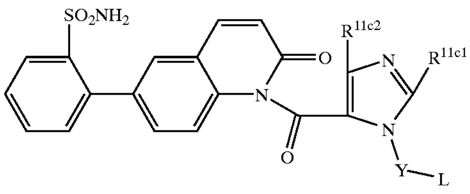
Formula IVf
| $R^{11c1}$ | $R^{11c2}$ |
|---|---|
| 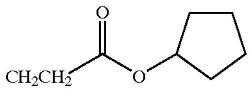 | 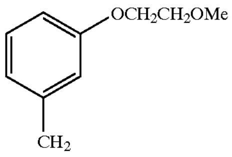 |
| 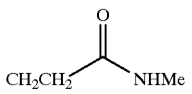 | 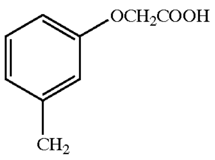 |
| 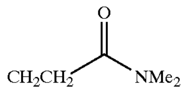 | 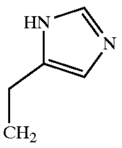 |
| 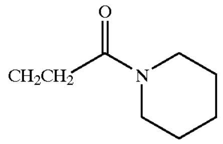 | 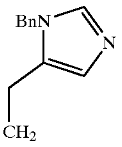 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 3g
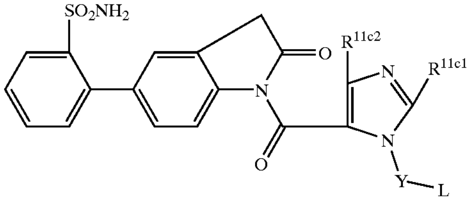
Formula IVg
| $R^{11c1}$ | $R^{11c2}$ |
|---|---|
| H | H |
| Me | Me |

TABLE 3g-continued
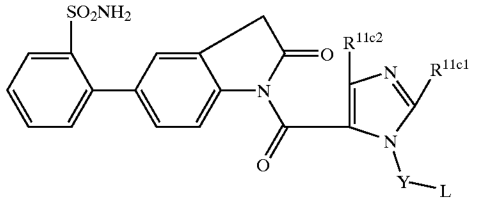
Formula IVg
| $R^{11c1}$ | $R^{11c2}$ |
|---|---|
| 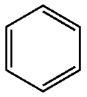 | 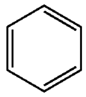 |
| 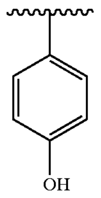 | 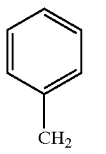 |
| 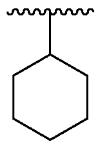 | 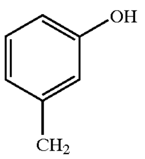 |
| 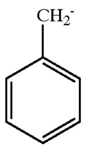 | 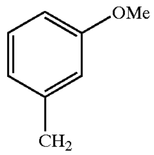 |
| 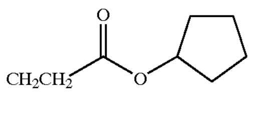 | 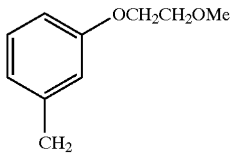 |
| 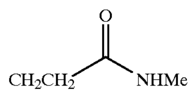 | 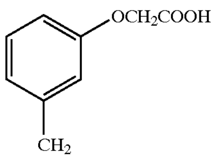 |
| 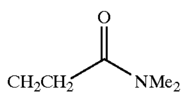 | 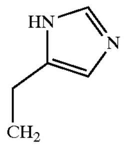 |
| 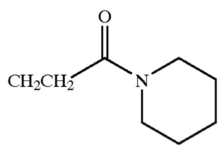 | 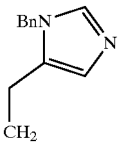 |
| OMe | H |
TABLE 3g-continued
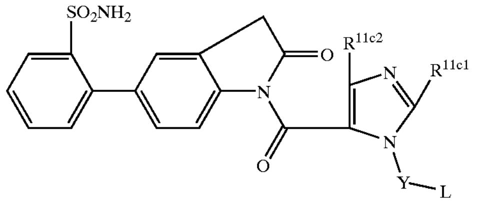
Formula IVg
| $R^{11c1}$ | $R^{11c2}$ |
|---|---|
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 3h
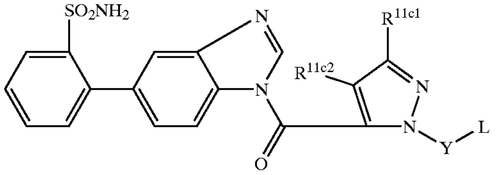
Formula IVh
| $R^{11c1}$ | $R^{11c2}$ |
|---|---|
| H | H |
| Me | Me |
| 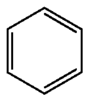 | 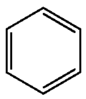 |
| 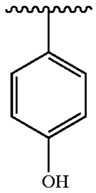 | 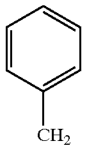 |
| 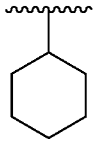 | 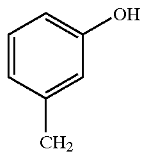 |
| 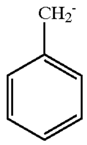 | 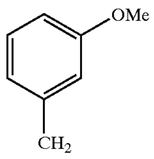 |

TABLE 3h-continued
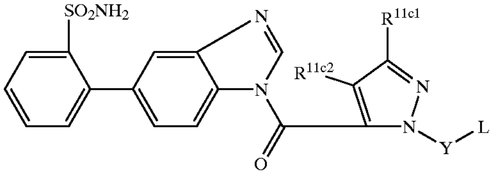
Formula IVh
| $R^{11c1}$ | $R^{11c2}$ |
|---|---|
| 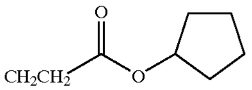 | 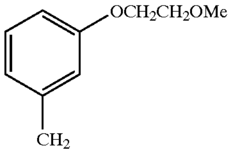 |
| 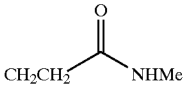 | 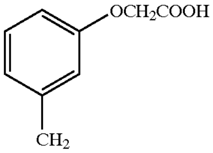 |
| 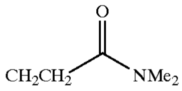 | 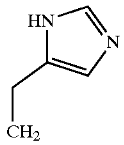 |
| 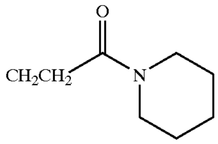 | 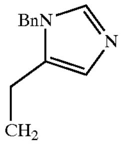 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 3i
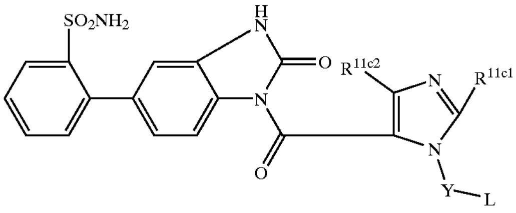
Formula IVi
| $R^{11c1}$ | $R^{11c2}$ |
|---|---|
| H | H |
| Me | Me |
TABLE 3i-continued
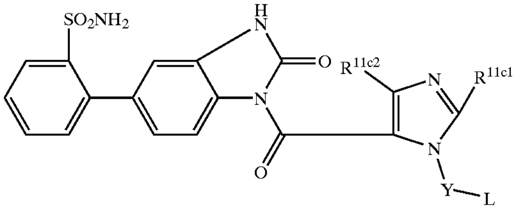
Formula IVi
| $R^{11c1}$ | $R^{11c2}$ |
|---|---|
| 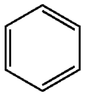 | 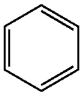 |
| 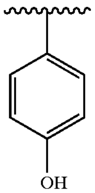 | 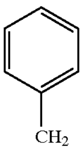 |
| 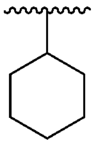 | 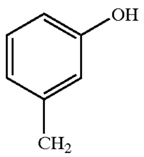 |
| 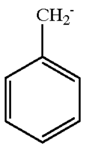 | 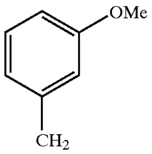 |
| 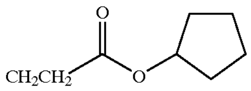 | 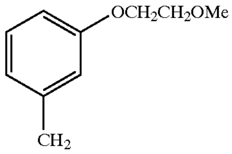 |
| 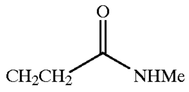 | 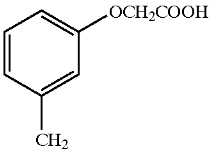 |
| 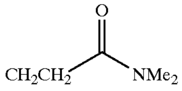 | 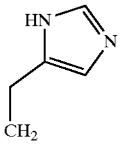 |
| 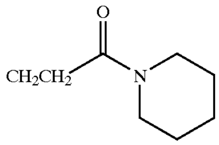 | 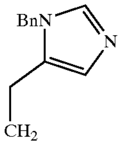 |

TABLE 3i-continued
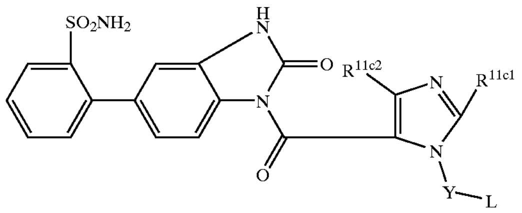
Formula IVi
| $R^{11c1}$ | $R^{11c2}$ |
|---|---|
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 3j
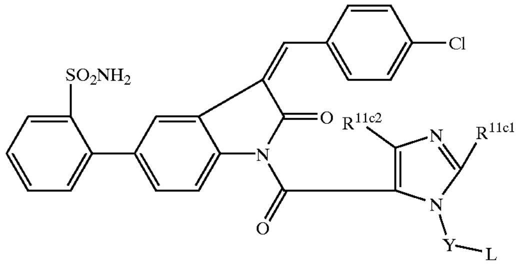
Formula IVj
| $R^{11c1}$ | $R^{11c2}$ |
|---|---|
| H | H |
| Me | Me |
| 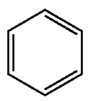 | 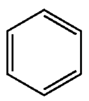 |
| 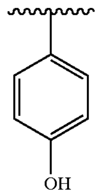 | 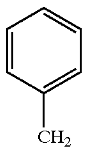 |
| 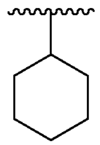 | 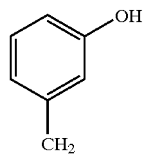 |
TABLE 3j-continued
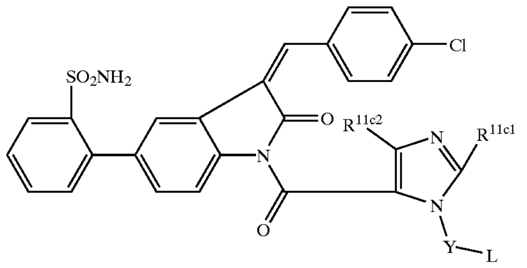
Formula IVj
| $R^{11c1}$ | $R^{11c2}$ |
|---|---|
| 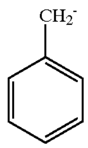 | 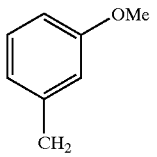 |
| 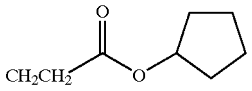 | 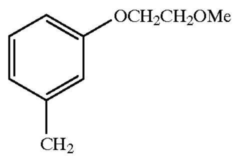 |
| 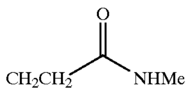 | 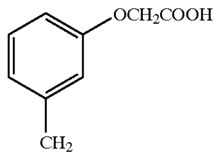 |
| 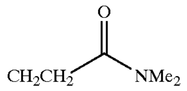 | 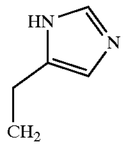 |
| 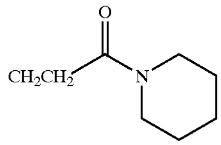 | 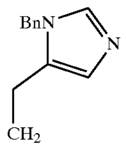 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |

TABLE 3k
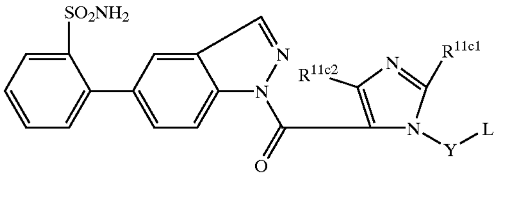
Formula IVk
| $R^{11c1}$ | $R^{11c2}$ |
|---|---|
| H | H |
| Me | Me |
| 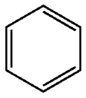 | 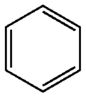 |
| 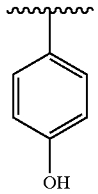 | 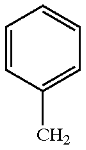 |
| 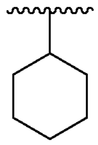 | 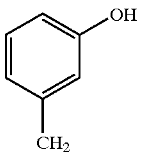 |
| 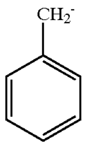 | 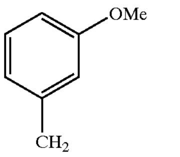 |
| 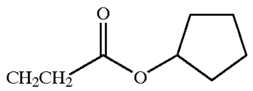 | 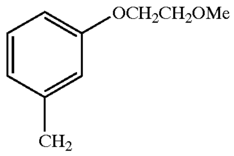 |
| 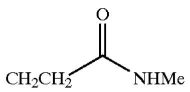 | 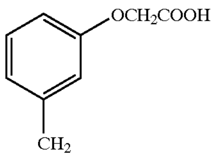 |
| 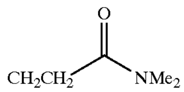 | 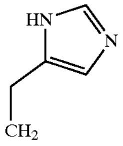 |
| 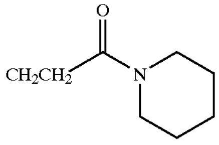 | 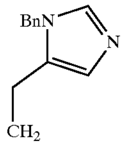 |
TABLE 3k-continued
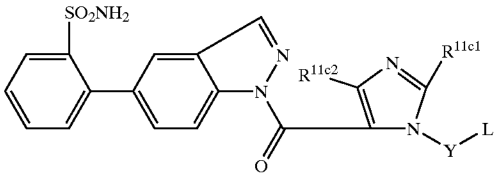
Formula IVk
| $R^{11c1}$ | $R^{11c2}$ |
|---|---|
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 3(l)
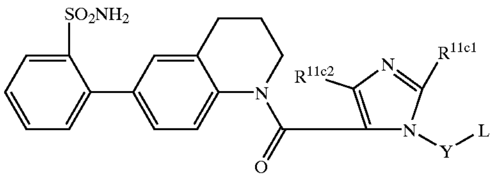
Formula IV(l)
| $R^{11c1}$ | $R^{11c2}$ |
|---|---|
| H | H |
| Me | Me |
| 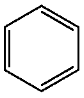 | 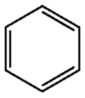 |
| 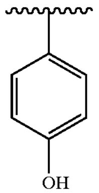 | 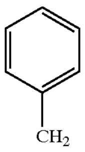 |
| 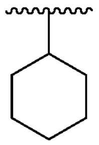 | 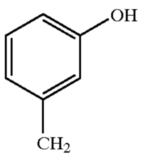 |
| 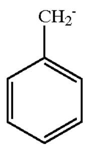 | 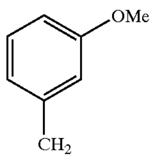 |

TABLE 3(l)-continued
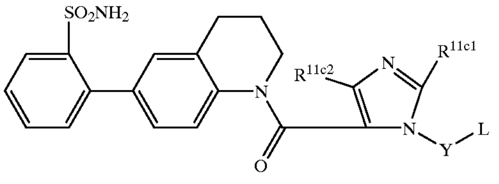
Formula IV(l)
| $R^{11c1}$ | $R^{11c2}$ |
| --- | --- |
| 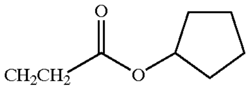 | 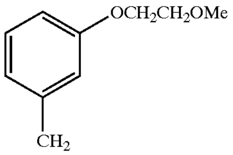 |
| 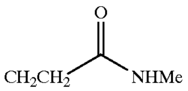 | 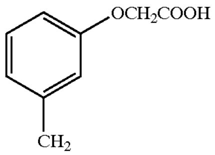 |
| 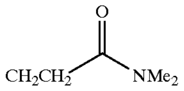 | 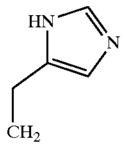 |
| 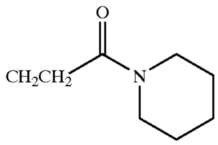 | 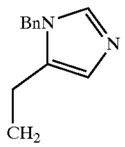 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 3m
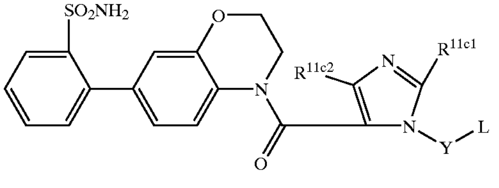
Formula IVm
| $R^{11c1}$ | $R^{11c2}$ |
| --- | --- |
| H | H |
| Me | Me |
TABLE 3m-continued
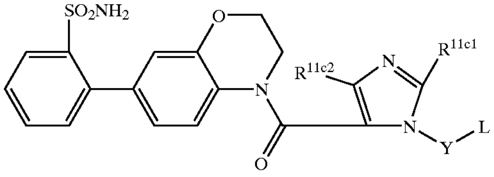
Formula IVm
| $R^{11c1}$ | $R^{11c2}$ |
| --- | --- |
| 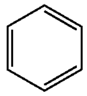 | 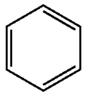 |
| 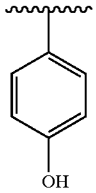 | 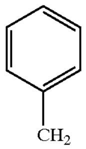 |
| 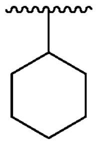 | 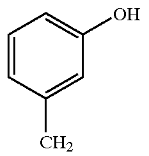 |
| 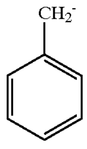 | 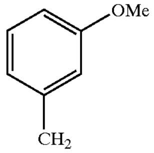 |
| 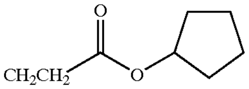 | 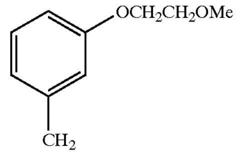 |
| 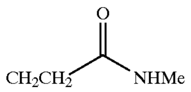 | 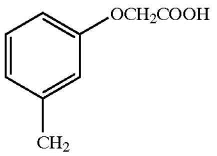 |
| 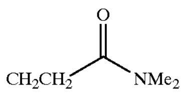 | 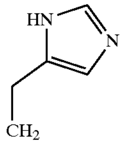 |
| 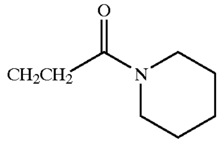 | 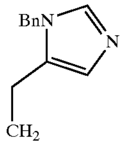 |
| OMe | H |
| OMe | Me |

TABLE 3m-continued
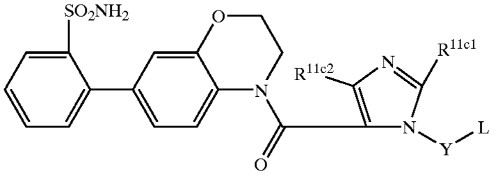
Formula IVm
| $R^{11c1}$ | $R^{11c2}$ |
|---|---|
| F | H |
| —OH | Me |
| Br | Me |
| —NH2 | H |
| OCH2Ph | H |
| OCH2CH2OMe | H |
| H | Et |
| Me | Et |
TABLE 3n
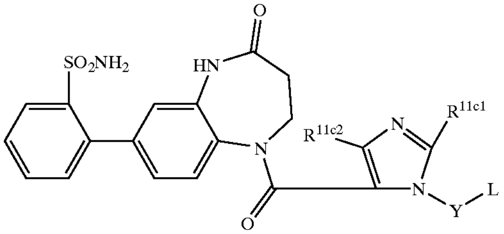
Formula IVn
| $R^{11c1}$ | $R^{11c2}$ |
|---|---|
| H | H |
| Me | Me |
| 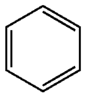 | 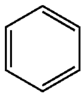 |
| 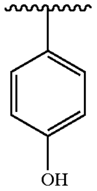 | 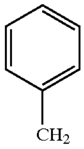 |
| 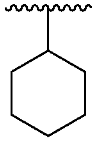 | 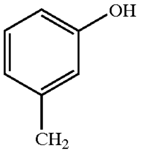 |
| 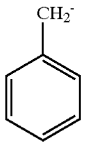 | 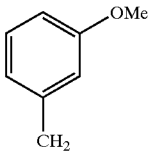 |
TABLE 3n-continued
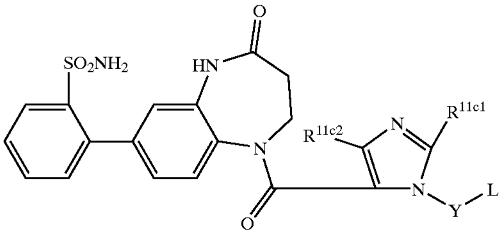
Formula IVn
| $R^{11c1}$ | $R^{11c2}$ |
|---|---|
| 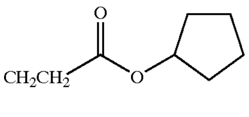 | 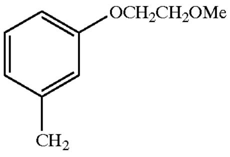 |
| 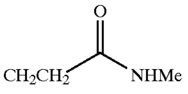 | 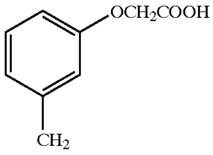 |
| 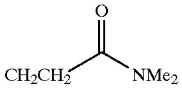 | 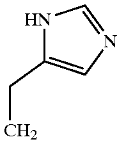 |
| 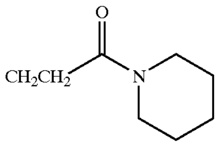 | 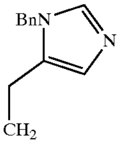 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 3o
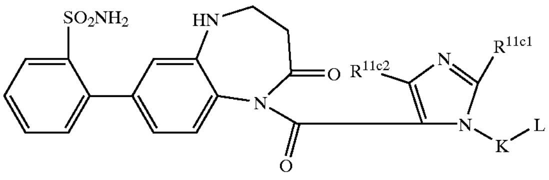
Formula IVo
| $R^{11c1}$ | $R^{11c2}$ |
|---|---|
| H | H |
| Me | Me |

TABLE 3o-continued
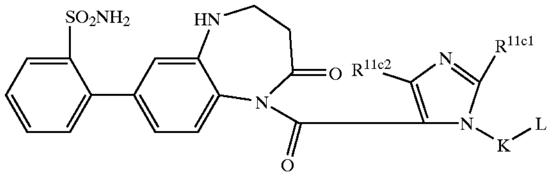
Formula IVo
| $R^{11c1}$ | $R^{11c2}$ |
|---|---|
| 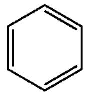 | 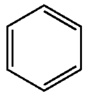 |
| 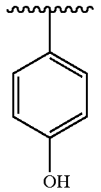 | 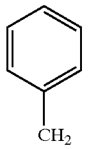 |
| 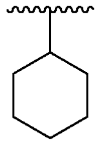 | 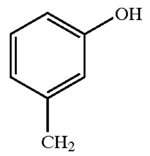 |
| 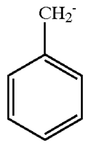 | 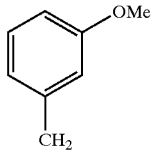 |
| 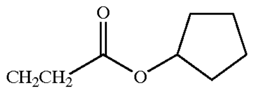 | 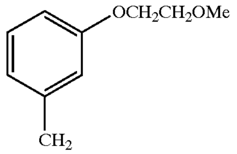 |
| 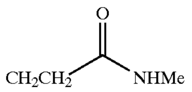 | 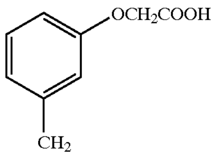 |
| 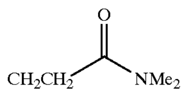 | 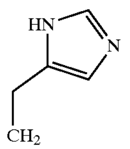 |
| 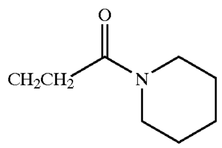 | 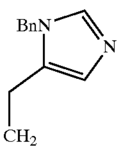 |
| OMe | H |
| OMe | Me |
TABLE 3o-continued
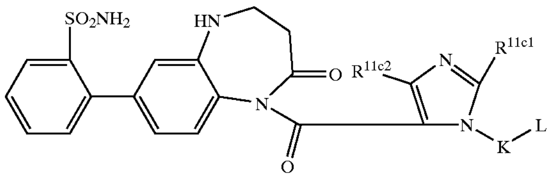
Formula IVo
| $R^{11c1}$ | $R^{11c2}$ |
|---|---|
| F | H |
| —OH | Me |
| Br | Me |
| —NH2 | H |
| OCH2Ph | H |
| OCH2CH2OMe | H |
| H | Et |
| Me | Et |
TABLE 3p
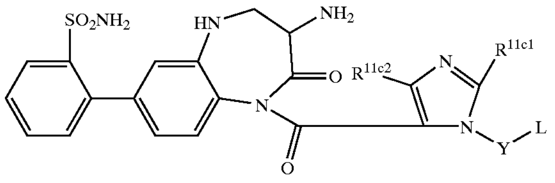
Formula IVp
| $R^{11c1}$ | $R^{11c2}$ |
|---|---|
| H | H |
| Me | Me |
| 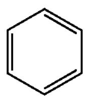 | 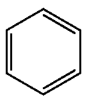 |
| 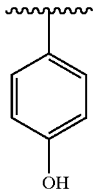 | 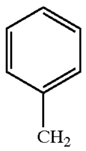 |
| 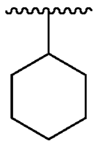 | 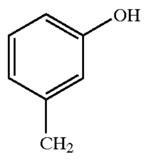 |
| 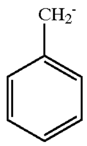 | 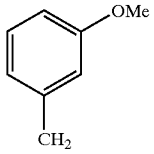 |

TABLE 3p-continued
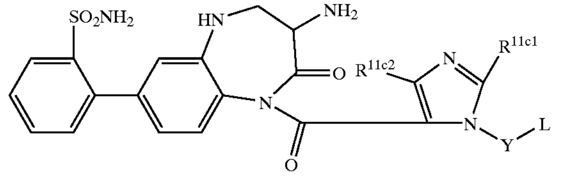
Formula IVp
| $R^{11c1}$ | $R^{11c2}$ |
|---|---|
| 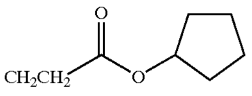 | 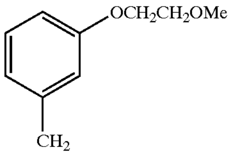 |
| 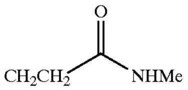 | 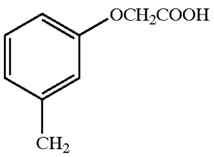 |
| 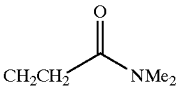 | 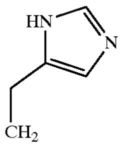 |
| 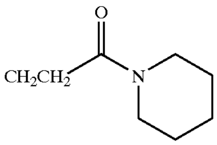 | 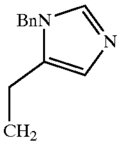 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 3q
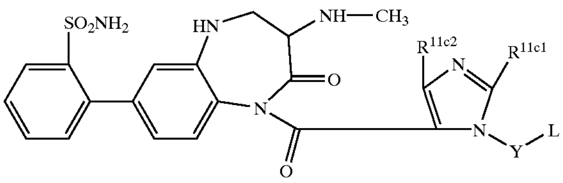
Formula IVq
| $R^{11c1}$ | $R^{11c2}$ |
|---|---|
| H | H |
| Me | Me |
TABLE 3q-continued
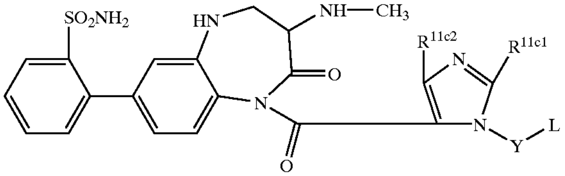
Formula IVq
| $R^{11c1}$ | $R^{11c2}$ |
|---|---|
| 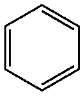 | 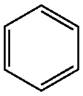 |
| 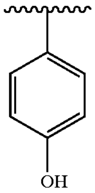 | 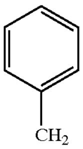 |
| 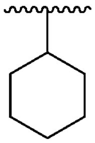 | 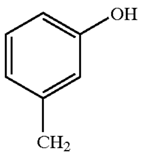 |
| 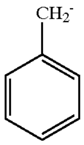 | 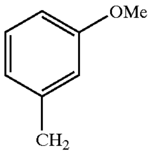 |
| 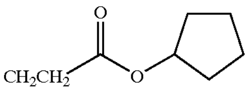 | 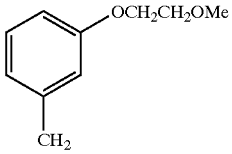 |
| 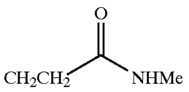 | 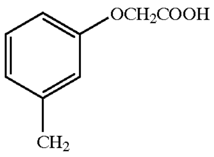 |
| 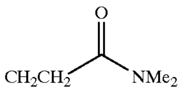 | 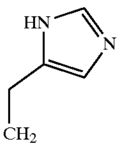 |
| 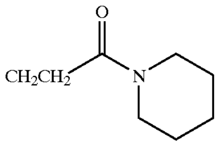 | 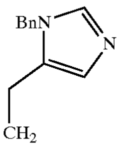 |
| OMe | H |
| OMe | Me |

TABLE 3q-continued
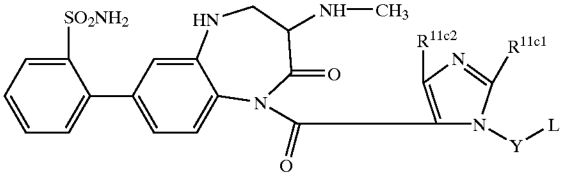
Formula IVq
| $R^{11c1}$ | $R^{11c2}$ |
|---|---|
| F | H |
| —OH | Me |
| Br | Me |
| —NH2 | H |
| OCH2Ph | H |
| OCH2CH2OMe | H |
| H | Et |
| Me | Et |
TABLE 4
Formula V
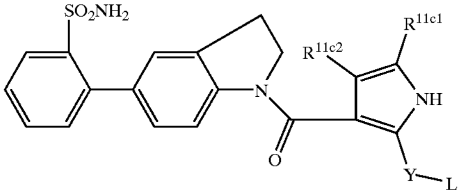
| $R^{11c1}$ | $R^{11c2}$ |
|---|---|
| H | H |
| Me | Me |
| 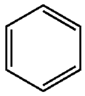 | 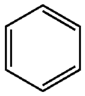 |
| 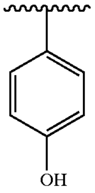 | 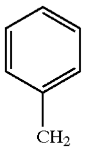 |
| 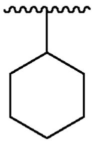 | 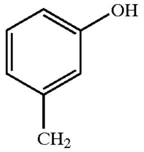 |
| 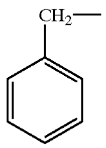 | 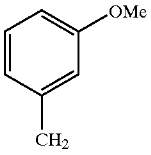 |
TABLE 4-continued
Formula V
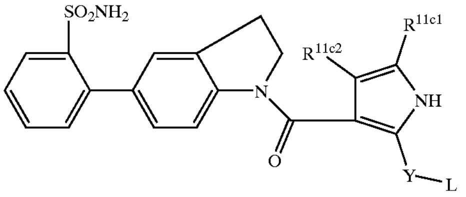
| $R^{11c1}$ | $R^{11c2}$ |
|---|---|
| 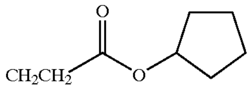 | 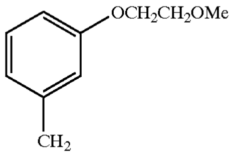 |
| 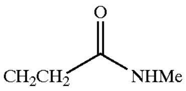 | 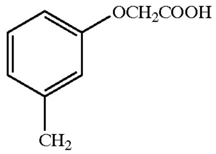 |
| 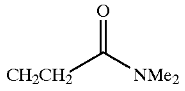 | 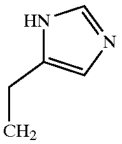 |
| 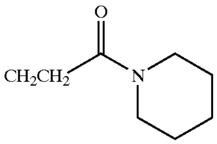 | 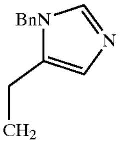 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 4a
Formula Va
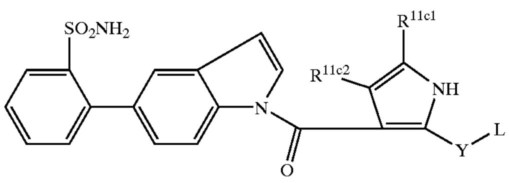
| $R^{11c1}$ | $R^{11c2}$ |
|---|---|
| H | H |
| Me | Me |

TABLE 4a-continued
Formula Va
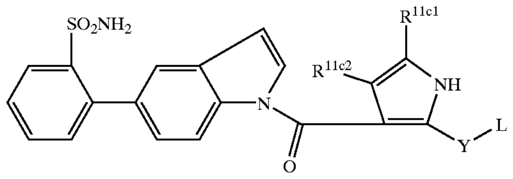
| $R^{11c1}$ | $R^{11c2}$ |
|---|---|
| 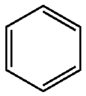 | 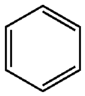 |
| 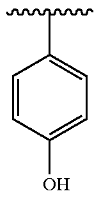 | 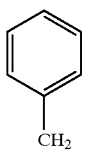 |
| 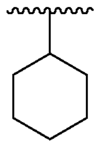 | 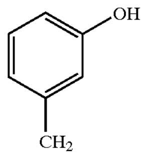 |
| 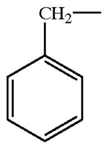 | 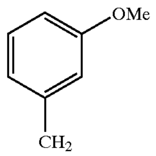 |
| 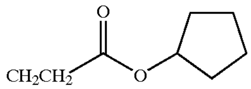 | 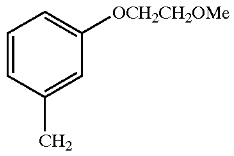 |
| 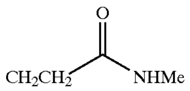 | 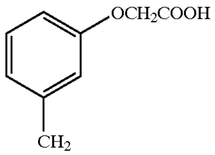 |
| 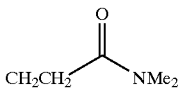 | 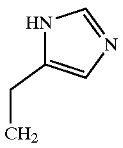 |
| 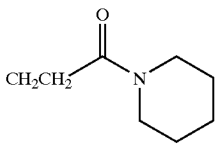 | 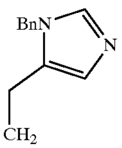 |
| OMe | H |
TABLE 4a-continued
Formula Va
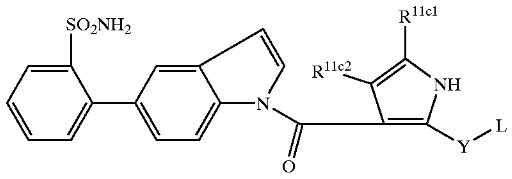
| $R^{11c1}$ | $R^{11c2}$ |
|---|---|
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 4b
Formula Vb
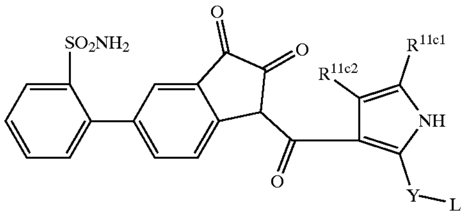
| $R^{11c1}$ | $R^{11c2}$ |
|---|---|
| H | H |
| Me | Me |
| 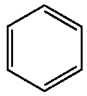 | 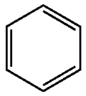 |
| 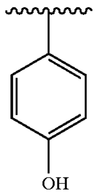 | 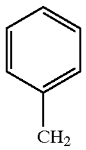 |
| 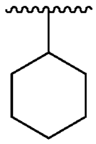 | 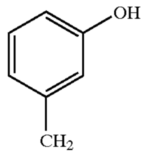 |
| 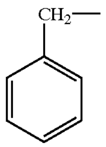 | 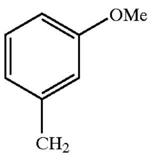 |

TABLE 4b-continued
Formula Vb
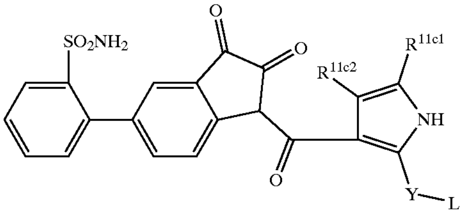
| $R^{11c1}$ | $R^{11c2}$ |
| --- | --- |
| 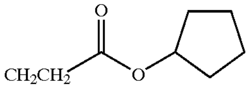 | 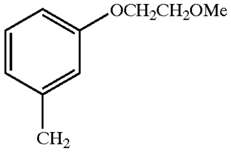 |
| 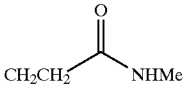 | 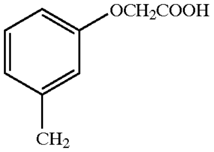 |
| 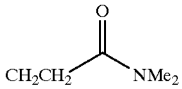 | 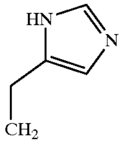 |
| 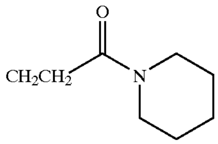 | 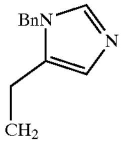 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 4c
Formula Vc
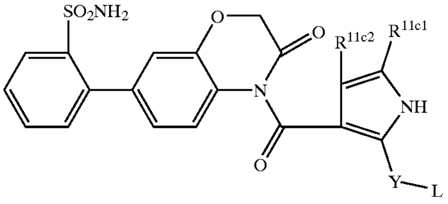
| $R^{11c1}$ | $R^{11c2}$ |
| --- | --- |
| H | H |
| Me | Me |
TABLE 4c-continued
Formula Vc
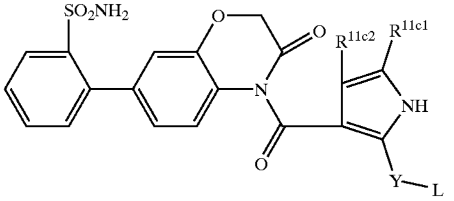
| $R^{11c1}$ | $R^{11c2}$ |
| --- | --- |
| 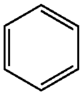 | 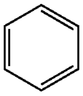 |
| 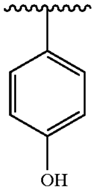 | 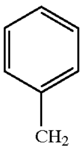 |
| 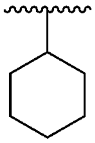 | 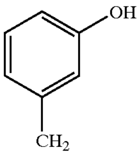 |
| 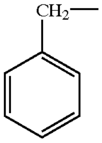 | 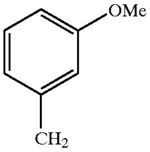 |
| 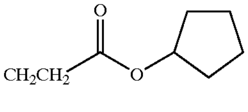 | 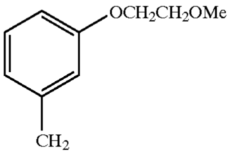 |
| 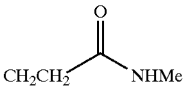 | 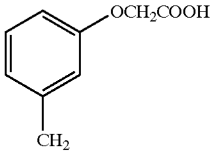 |
| 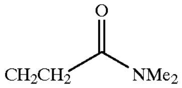 | 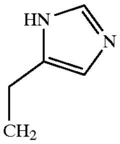 |
| 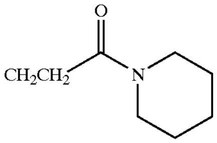 | 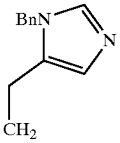 |
| OMe | H |

TABLE 4c-continued
Formula Vc
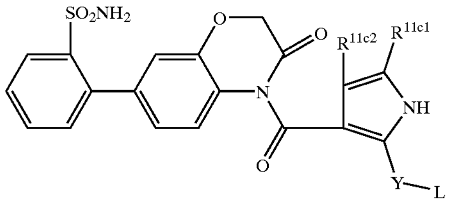
| $R^{11c1}$ | $R^{11c2}$ |
|---|---|
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 4d
Formula Vd
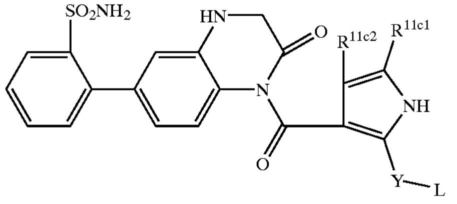
| $R^{11c1}$ | $R^{11c2}$ |
|---|---|
| H | H |
| Me | Me |
| 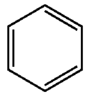 | 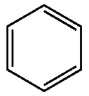 |
| 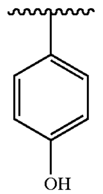 | 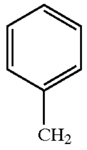 |
| 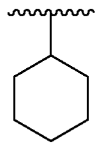 | 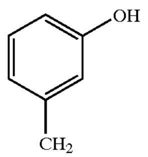 |
| 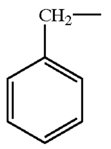 | 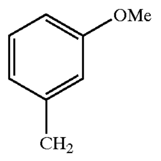 |
TABLE 4d-continued
Formula Vd
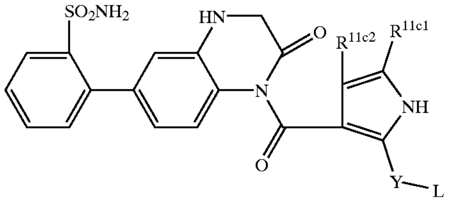
| $R^{11c1}$ | $R^{11c2}$ |
|---|---|
| 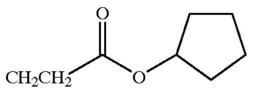 | 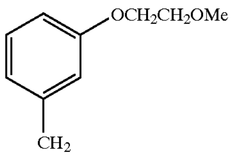 |
| 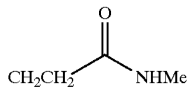 | 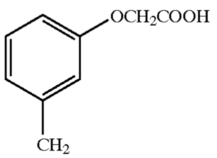 |
| 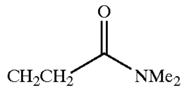 | 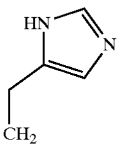 |
| 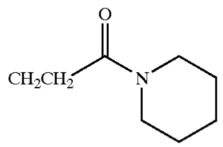 | 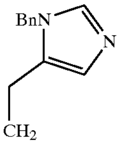 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 4e
Formula Ve
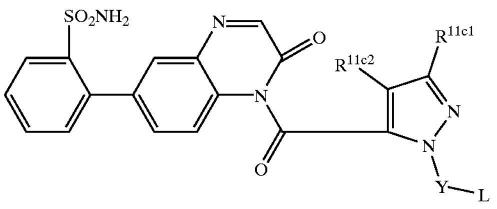
| $R^{11c1}$ | $R^{11c2}$ |
|---|---|
| H | H |
| Me | Me |

TABLE 4e-continued
Formula Ve
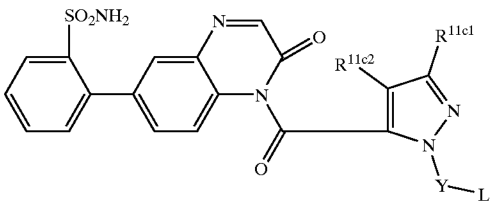
| $R^{11c1}$ | $R^{11c2}$ |
|---|---|
| 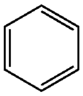 | 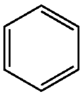 |
| 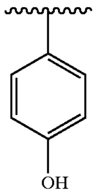 | 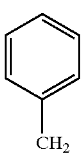 |
| 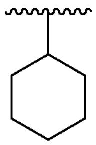 | 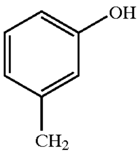 |
| 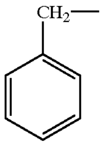 | 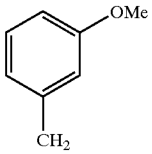 |
| 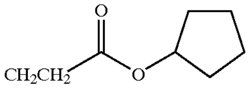 | 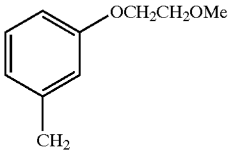 |
| 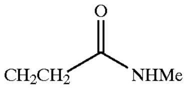 | 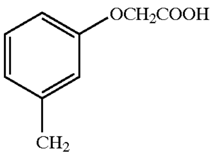 |
| 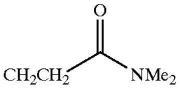 | 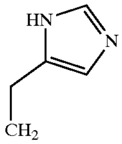 |
| 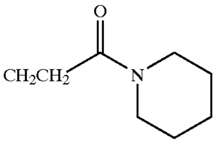 | 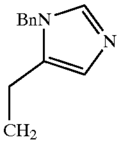 |
TABLE 4e-continued
Formula Ve
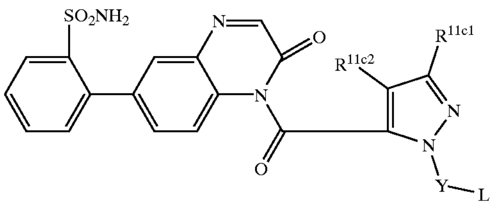
| $R^{11c1}$ | $R^{11c2}$ |
|---|---|
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 4f
Formula Vf
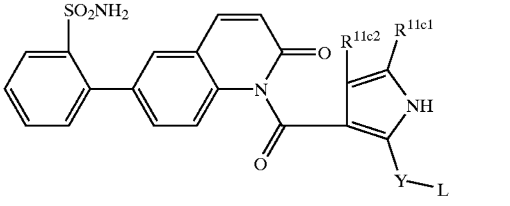
| $R^{11c1}$ | $R^{11c2}$ |
|---|---|
| H | H |
| Me | Me |
| 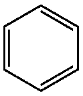 | 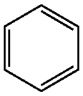 |
| 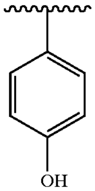 | 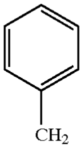 |
| 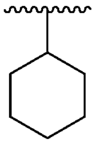 | 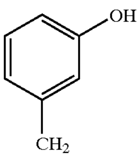 |
| 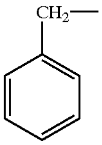 | 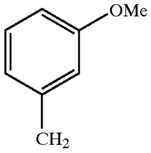 |

TABLE 4f-continued
Formula Vf
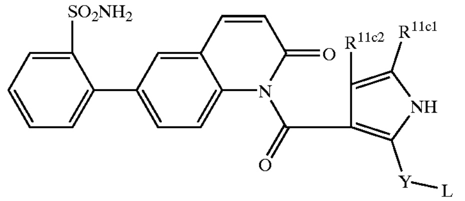
| $R^{11c1}$ | $R^{11c2}$ |
|---|---|
| 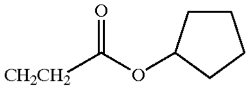 | 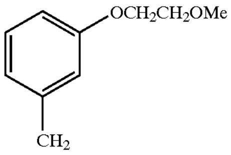 |
| 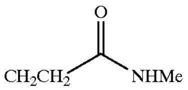 | 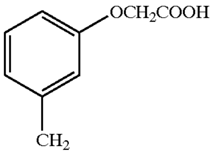 |
| 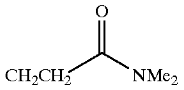 | 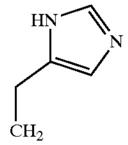 |
| 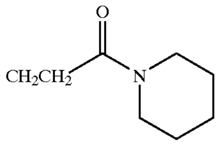 | 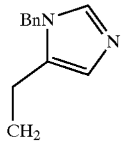 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 4g
Formula Vg
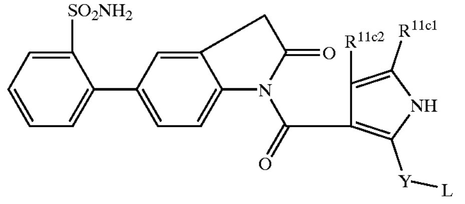
| $R^{11c1}$ | $R^{11c2}$ |
|---|---|
| H | H |
| Me | Me |
TABLE 4g-continued
Formula Vg
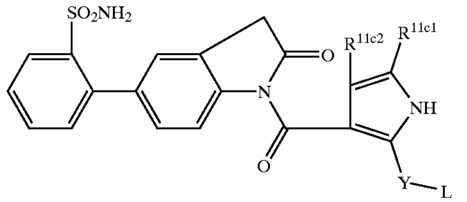
| $R^{11c1}$ | $R^{11c2}$ |
|---|---|
| 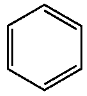 | 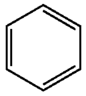 |
| 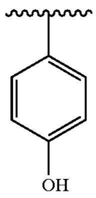 | 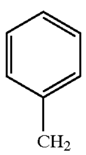 |
| 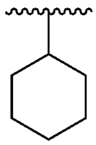 | 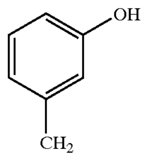 |
| 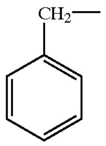 | 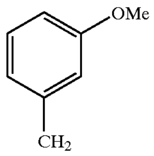 |
| 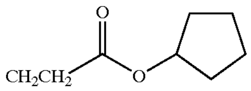 | 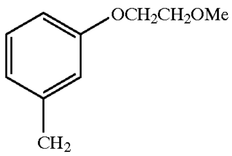 |
| 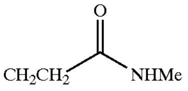 | 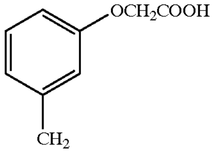 |
| 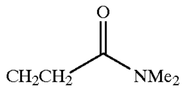 | 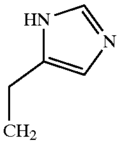 |
| 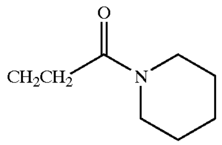 | 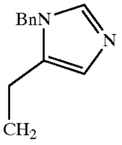 |
| OMe | H |

TABLE 4g-continued
Formula Vg
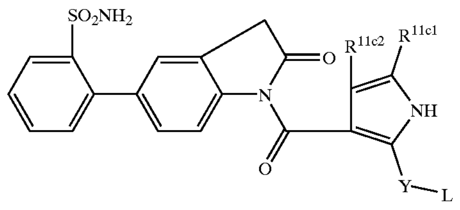
| $R^{11c1}$ | $R^{11c2}$ |
|---|---|
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 4h
Formula Vh
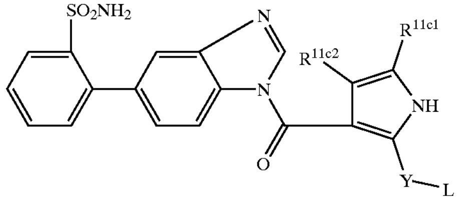
| $R^{11c1}$ | $R^{11c2}$ |
|---|---|
| H | H |
| Me | Me |
| 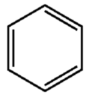 | 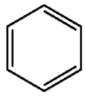 |
| 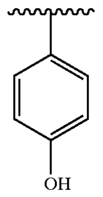 | 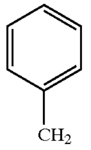 |
| 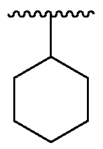 | 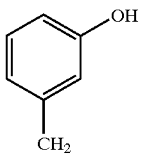 |
| 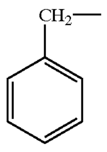 | 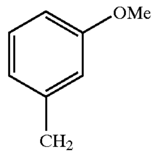 |
TABLE 4h-continued
Formula Vh
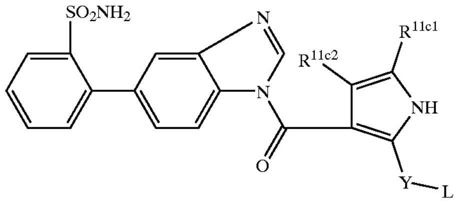
| $R^{11c1}$ | $R^{11c2}$ |
|---|---|
| 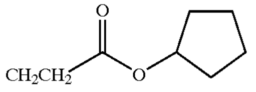 | 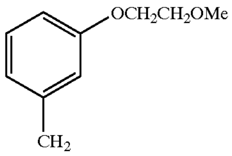 |
| 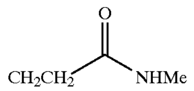 | 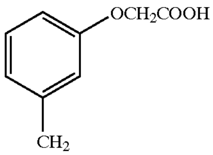 |
| 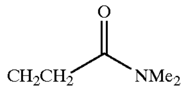 | 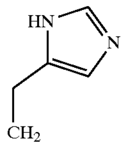 |
| 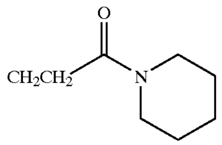 | 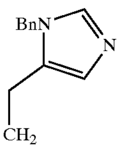 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 4i
Formula Vi
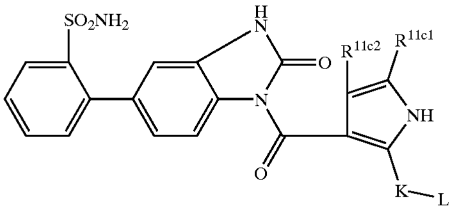
| $R^{11c1}$ | $R^{11c2}$ |
|---|---|
| H | H |
| Me | Me |

TABLE 4i-continued
Formula Vi
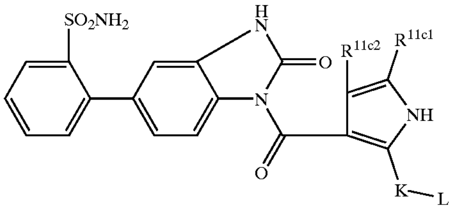
| $R^{11c1}$ | $R^{11c2}$ |
|---|---|
| 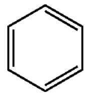 | 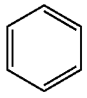 |
| 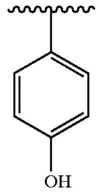 | 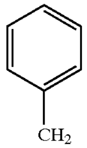 |
| 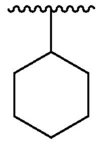 | 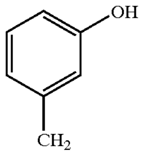 |
| 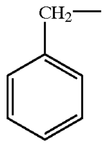 | 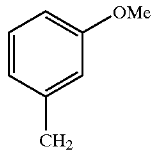 |
| 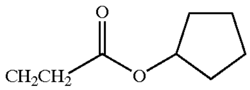 | 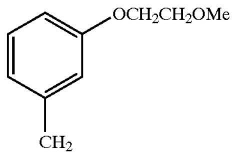 |
| 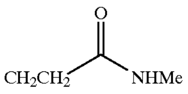 | 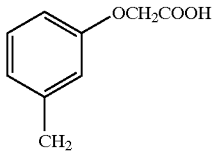 |
| 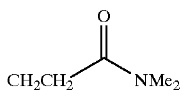 | 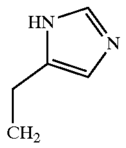 |
| 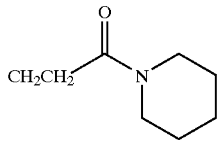 | 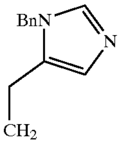 |
TABLE 4i-continued
Formula Vi
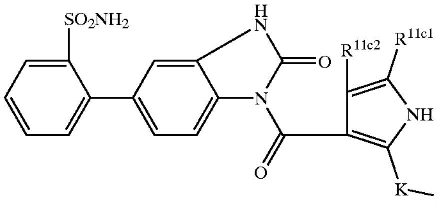
| $R^{11c1}$ | $R^{11c2}$ |
|---|---|
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 4j
Formula Vj
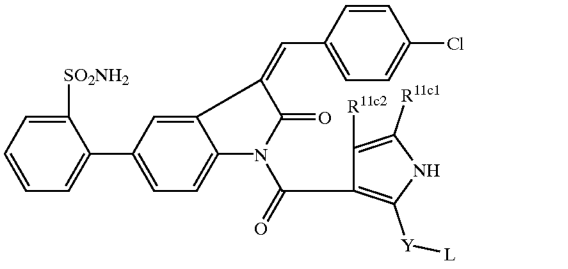
| $R^{11c1}$ | $R^{11c2}$ |
|---|---|
| H | H |
| Me | Me |
| 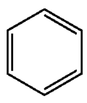 | 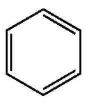 |
| 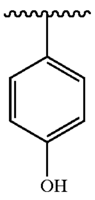 | 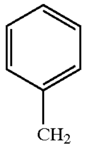 |
| 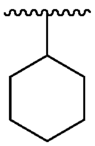 | 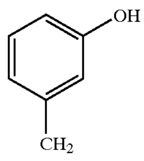 |

TABLE 4j-continued
Formula Vj
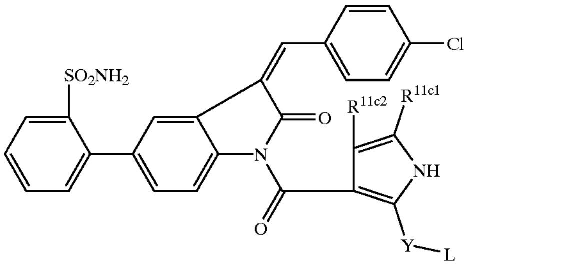
| $R^{11c1}$ | $R^{11c2}$ |
|---|---|
| 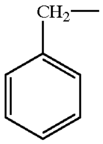 | 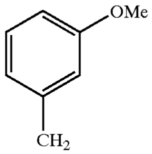 |
| 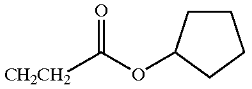 | 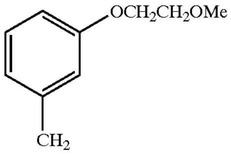 |
| 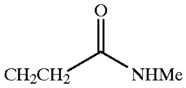 | 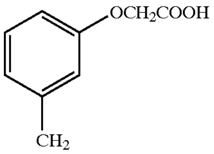 |
| 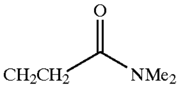 | 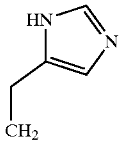 |
| 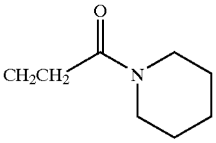 | 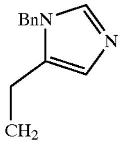 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 4k
Formula Vk
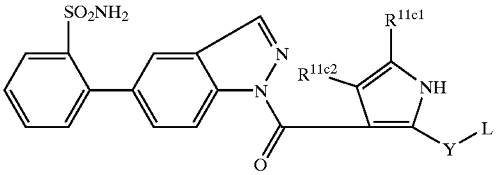
| $R^{11c1}$ | $R^{11c2}$ |
|---|---|
| H | H |
| Me | Me |
| 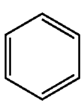 | 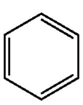 |
| 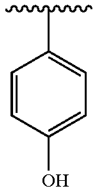 | 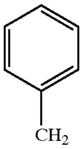 |
| 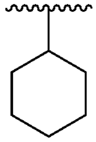 | 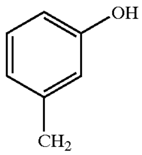 |
| 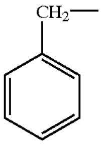 | 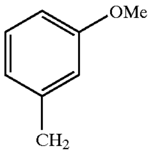 |
| 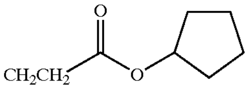 | 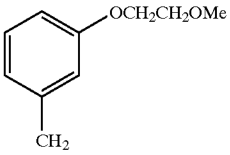 |
| 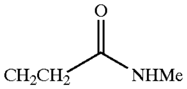 | 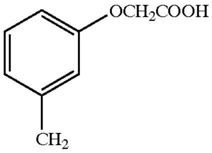 |
| 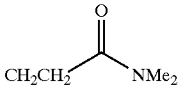 | 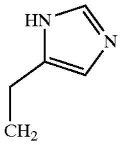 |
| 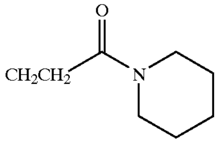 | 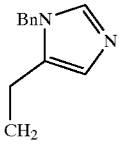 |
| OMe | H |
| OMe | Me |
| F | H |

| | |
|---|---|
| —OH | Me |
| Br | Me |
| —NH2 | H |
| OCH2Ph | H |
| OCH2CH2OMe | H |
| H | Et |
| Me | Et |
TABLE 4(l)
Formula V(l)
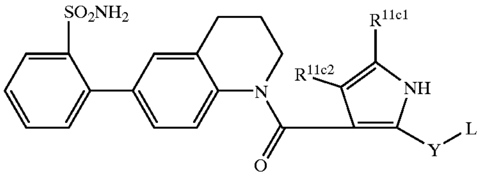
| $R^{11c1}$ | $R^{11c2}$ |
|---|---|
| H | H |
| Me | Me |
| 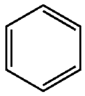 | 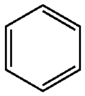 |
| 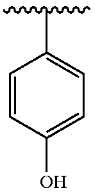 | 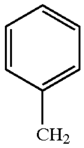 |
| 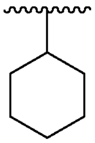 | 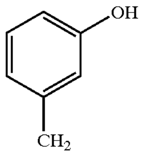 |
| 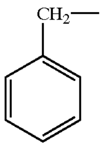 | 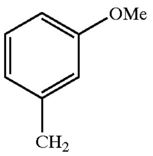 |
| 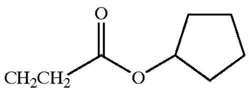 | 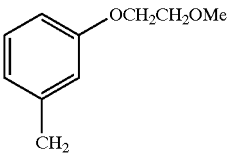 |
| 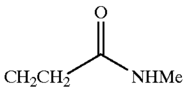 | 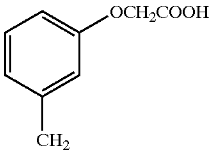 |
TABLE 4(l)-continued
Formula V(l)
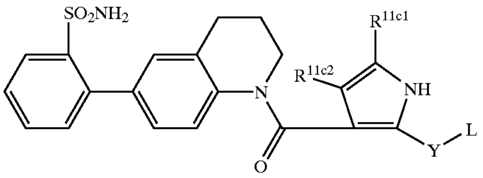
| $R^{11c1}$ | $R^{11c2}$ |
|---|---|
| 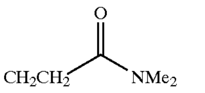 | 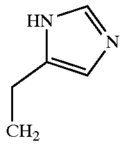 |
| 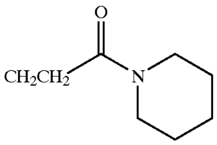 | 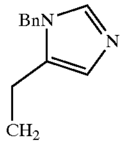 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 4m
Formula Vm
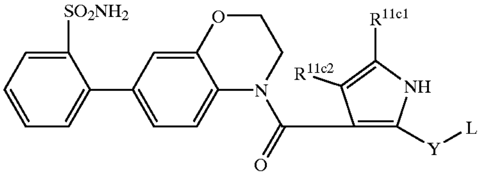
| $R^{11c1}$ | $R^{11c2}$ |
|---|---|
| H | H |
| Me | Me |
| 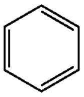 | 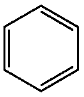 |
| 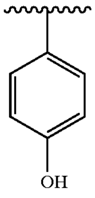 | 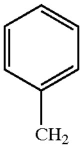 |

TABLE 4m-continued
Formula Vm
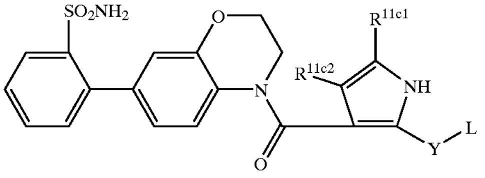
| $R^{11c1}$ | $R^{11c2}$ |
|---|---|
| 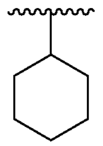 | 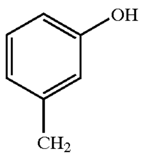 |
| 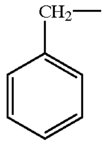 | 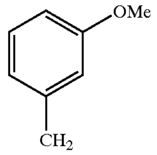 |
| 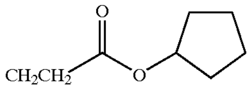 | 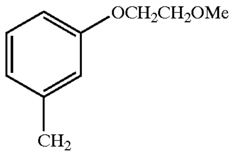 |
| 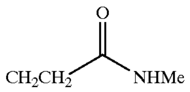 | 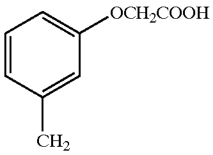 |
| 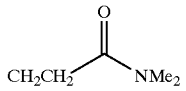 | 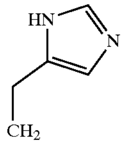 |
| 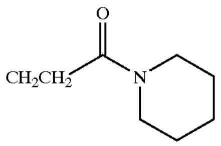 | 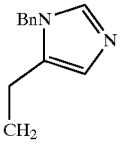 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 4n
Formula Vn
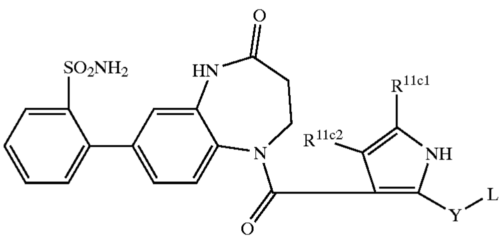
| $R^{11c1}$ | $R^{11c2}$ |
|---|---|
| H | H |
| Me | Me |
| 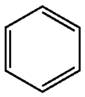 | 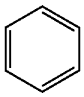 |
| 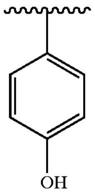 | 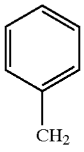 |
| 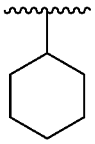 | 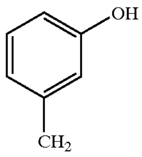 |
| 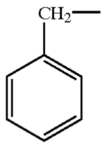 | 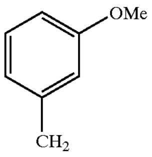 |
| 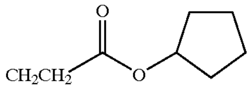 | 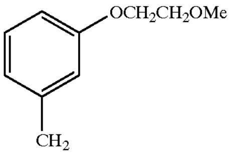 |
| 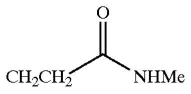 | 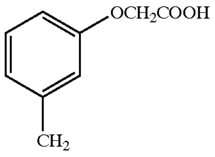 |
| 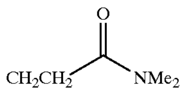 | 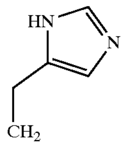 |

TABLE 4n-continued
Formula Vn
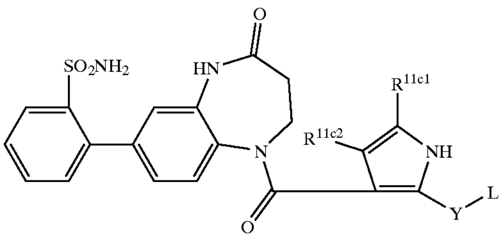
| $R^{11c1}$ | $R^{11c2}$ |
| --- | --- |
| 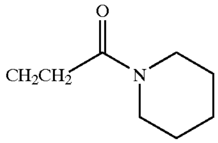 | 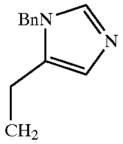 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 4o
Formula Vo
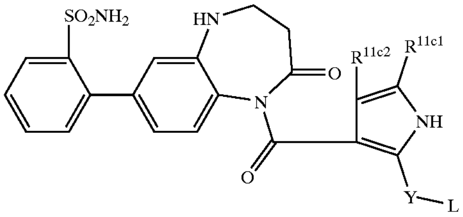
| $R^{11c1}$ | $R^{11c2}$ |
| --- | --- |
| H | H |
| Me | Me |
| 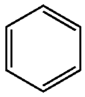 | 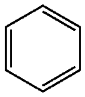 |
| 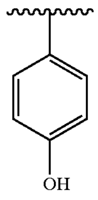 | 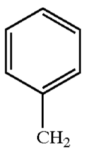 |
TABLE 4o-continued
Formula Vo
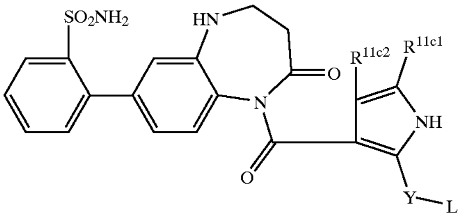
| $R^{11c1}$ | $R^{11c2}$ |
| --- | --- |
| 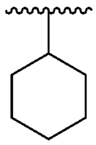 | 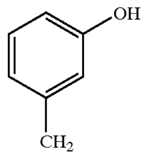 |
| 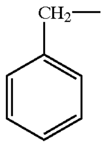 | 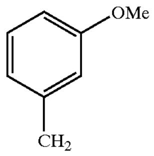 |
| 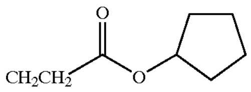 | 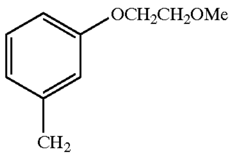 |
| 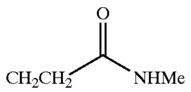 | 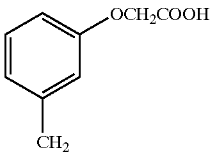 |
| 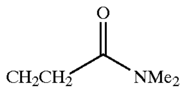 | 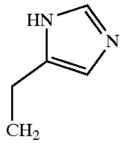 |
| 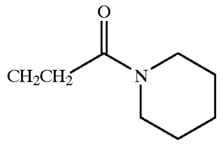 | 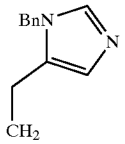 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |

TABLE 4p
Formula Vp
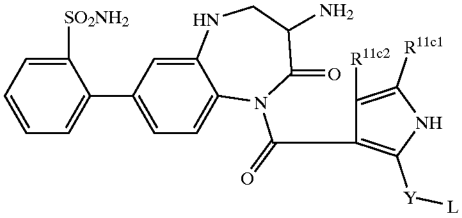
| $R^{11c1}$ | $R^{11c2}$ |
| --- | --- |
| H | H |
| Me | Me |
| 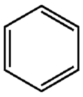 | 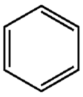 |
| 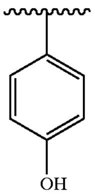 | 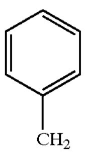 |
| 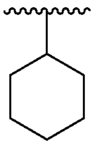 | 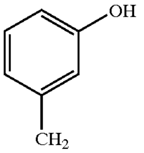 |
| 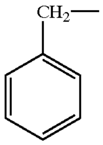 | 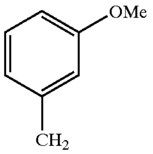 |
| 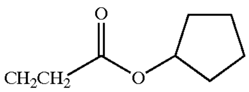 | 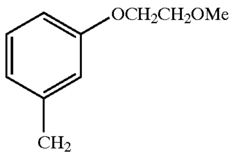 |
| 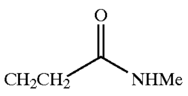 | 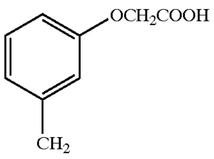 |
| 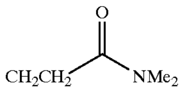 | 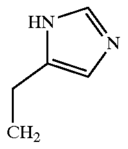 |
TABLE 4p-continued
Formula Vp
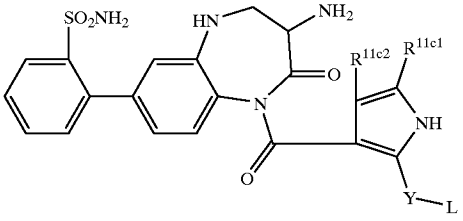
| $R^{11c1}$ | $R^{11c2}$ |
| --- | --- |
| 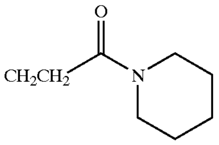 | 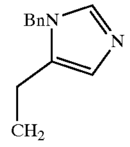 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 4q
Formula Vq
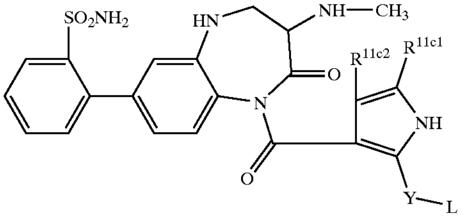
| $R^{11c1}$ | $R^{11c2}$ |
| --- | --- |
| H | H |
| Me | Me |
| 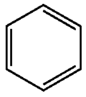 | 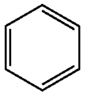 |
| 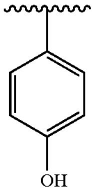 | 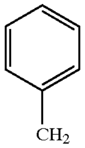 |
| 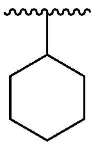 | 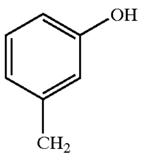 |

TABLE 4q-continued
Formula Vq
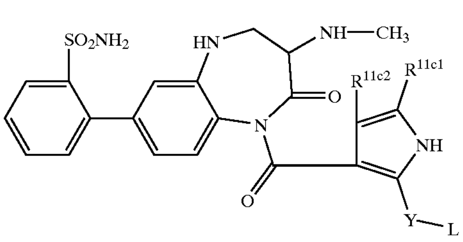
| $R^{11c1}$ | $R^{11c2}$ |
| --- | --- |
| 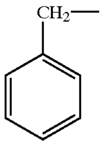 | 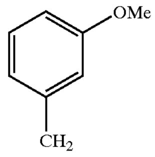 |
| 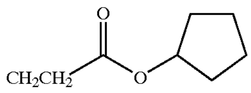 | 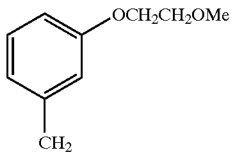 |
| 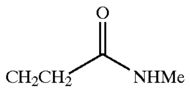 | 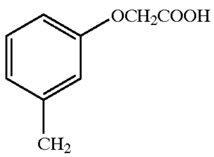 |
| 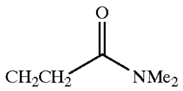 | 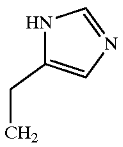 |
| 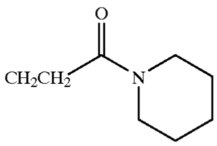 | 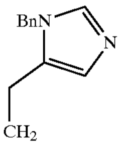 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 5
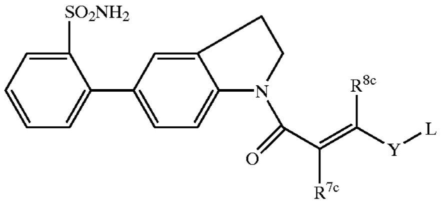
Formula VI
| $R^{7c}$ | $R^{8c}$ |
| --- | --- |
| H | H |
| Me | Me |
| 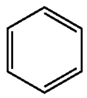 | 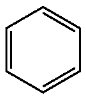 |
| 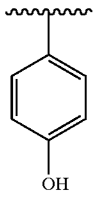 | 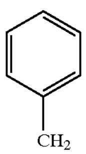 |
| 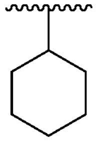 | 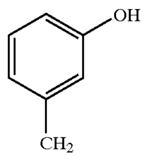 |
| 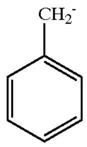 | 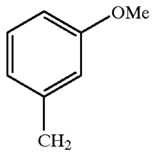 |
| 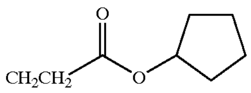 | 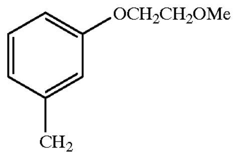 |
| 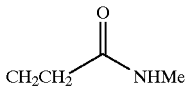 | 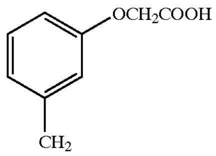 |
| 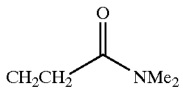 | 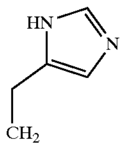 |

TABLE 5-continued
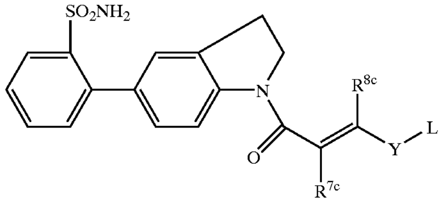
Formula VI
| $R^{7c}$ | $R^{8c}$ |
|---|---|
| 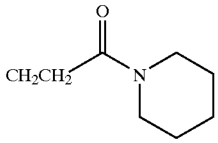 | 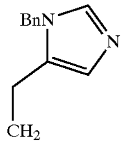 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 5a
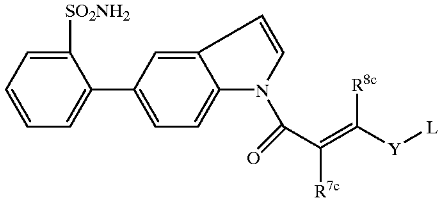
Formula VIa
| $R^{7c}$ | $R^{8c}$ |
|---|---|
| H | H |
| Me | Me |
| 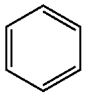 | 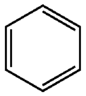 |
| 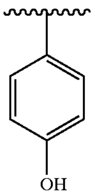 | 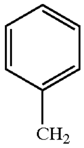 |
| 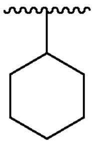 | 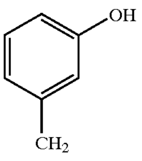 |
TABLE 5a-continued
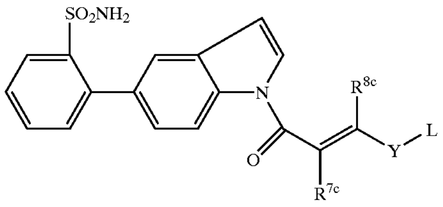
Formula VIa
| $R^{7c}$ | $R^{8c}$ |
|---|---|
| 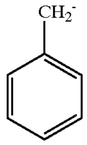 | 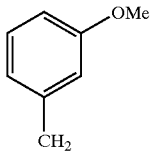 |
| 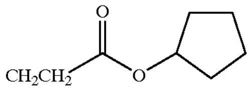 | 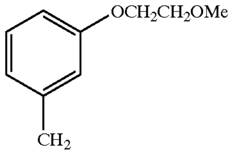 |
| 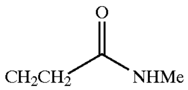 | 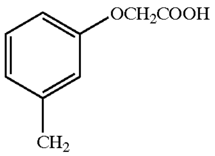 |
| 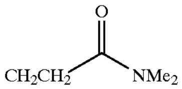 | 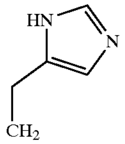 |
| 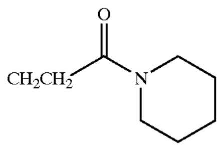 | 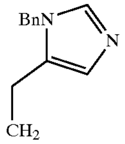 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |

TABLE 5b
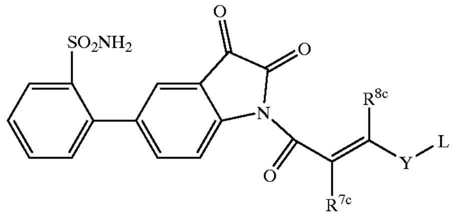
Formula VIb
| $R^{7c}$ | $R^{8c}$ |
|---|---|
| H | H |
| Me | Me |
| 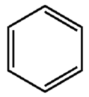 | 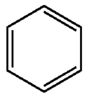 |
| 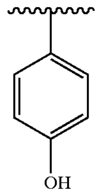 | 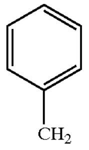 |
| 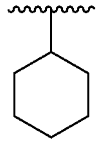 | 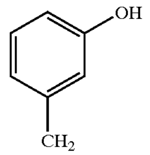 |
| 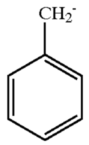 | 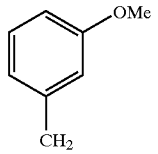 |
| 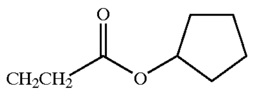 | 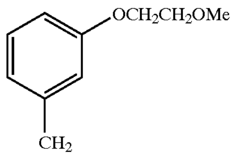 |
| 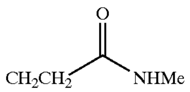 | 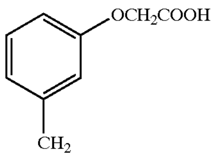 |
| 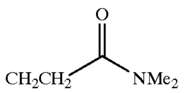 | 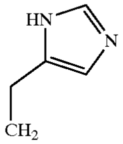 |
TABLE 5b-continued
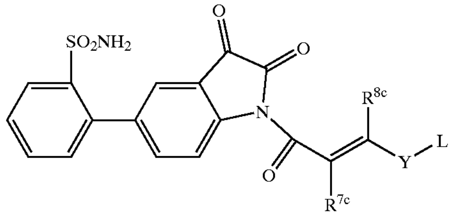
Formula VIb
| $R^{7c}$ | $R^{8c}$ |
|---|---|
| 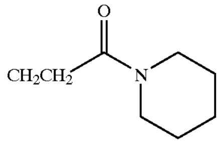 | 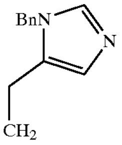 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 5c
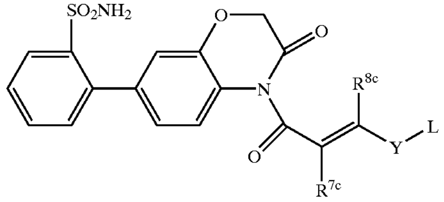
Formula VIc
| $R^{7c}$ | $R^{8c}$ |
|---|---|
| H | H |
| Me | Me |
| 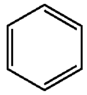 | 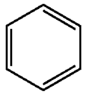 |
| 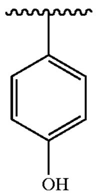 | 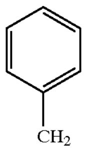 |
| 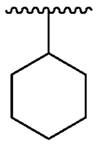 | 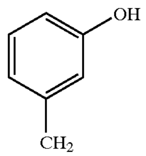 |

TABLE 5c-continued
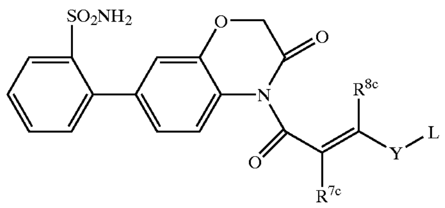
Formula VIc
| $R^{7c}$ | $R^{8c}$ |
|---|---|
| 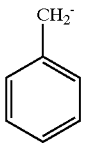 | 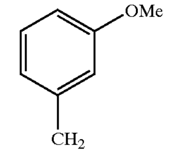 |
| 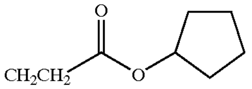 | 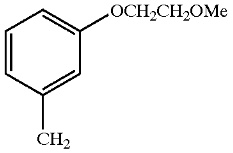 |
| 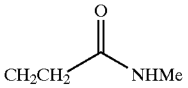 | 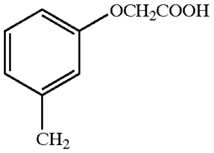 |
| 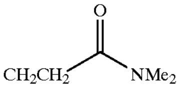 | 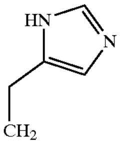 |
| 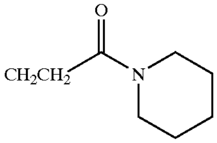 | 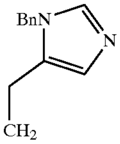 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 5d
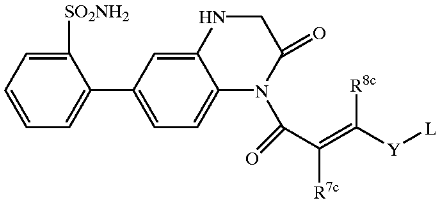
Formula VId
| $R^{7c}$ | $R^{8c}$ |
|---|---|
| H | H |
| Me | Me |
| 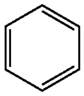 | 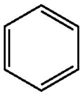 |
| 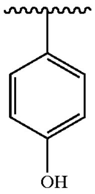 | 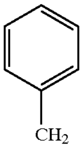 |
| 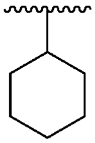 | 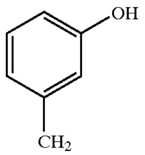 |
| 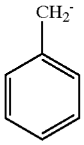 | 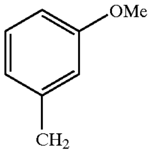 |
| 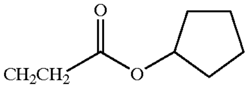 | 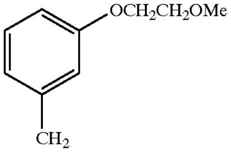 |
| 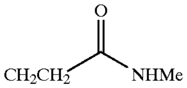 | 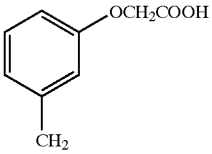 |
| 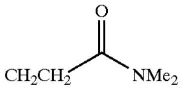 | 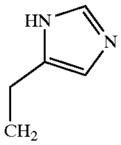 |

TABLE 5d-continued
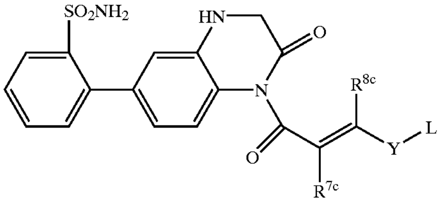
Formula VId
| $R^{7c}$ | $R^{8c}$ |
|---|---|
| 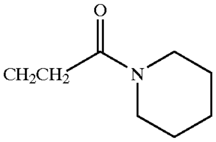 | 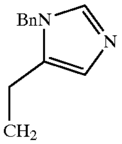 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 5e
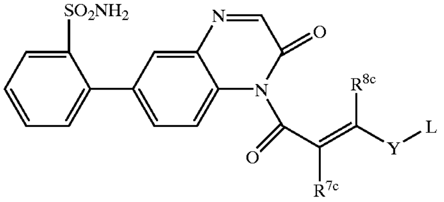
Formula VIe
| $R^{7c}$ | $R^{8c}$ |
|---|---|
| H | H |
| Me | Me |
| 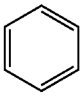 | 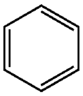 |
| 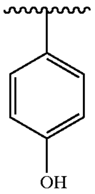 | 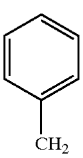 |
| 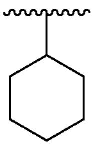 | 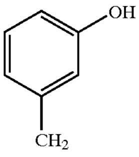 |
TABLE 5e-continued
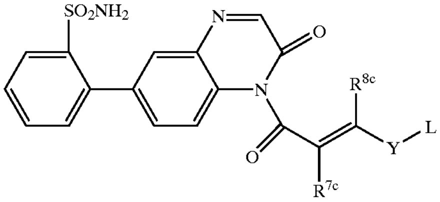
Formula VIe
| $R^{7c}$ | $R^{8c}$ |
|---|---|
| 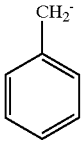 | 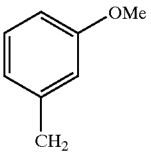 |
| 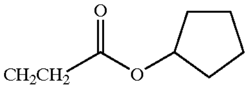 | 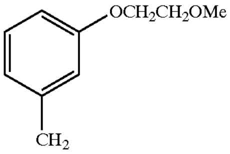 |
| 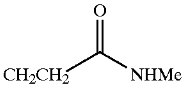 | 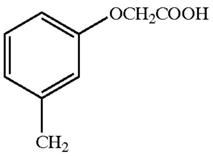 |
| 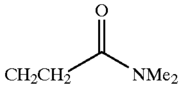 | 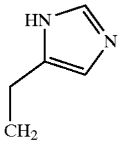 |
| 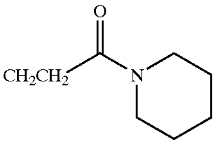 | 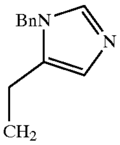 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |

TABLE 5f
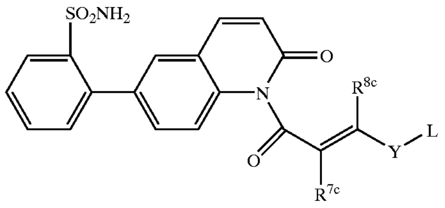
Formula VIf
| $R^{7c}$ | $R^{8c}$ |
|---|---|
| H | H |
| Me | Me |
| 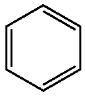 | 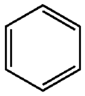 |
| 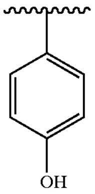 | 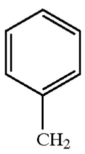 |
| 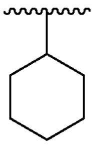 | 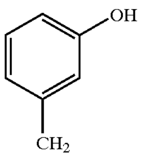 |
| 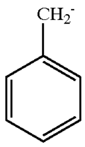 | 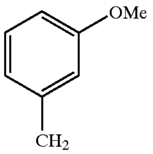 |
| 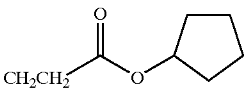 | 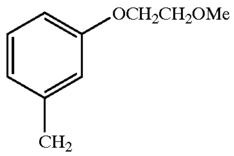 |
| 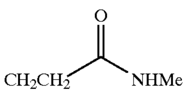 | 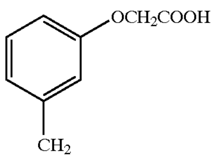 |
| 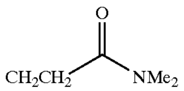 | 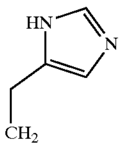 |
TABLE 5f-continued
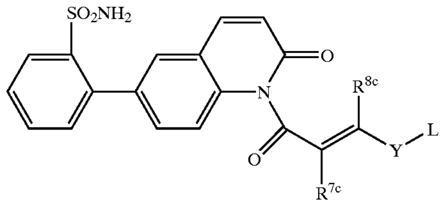
Formula VIf
| $R^{7c}$ | $R^{8c}$ |
|---|---|
| 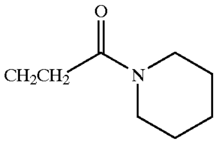 | 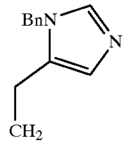 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 5g
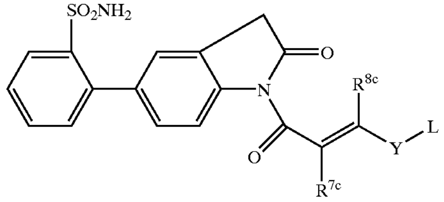
Formula VIg
| $R^{7c}$ | $R^{8c}$ |
|---|---|
| H | H |
| Me | Me |
| 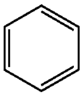 | 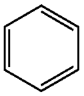 |
| 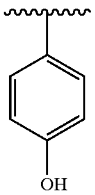 | 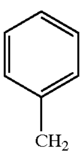 |
| 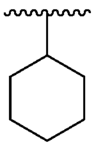 | 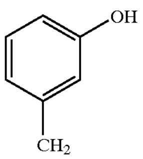 |

TABLE 5g-continued
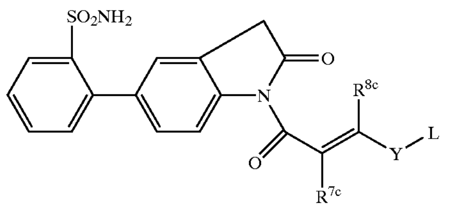
Formula VIg
| $R^{7c}$ | $R^{8c}$ |
|---|---|
| 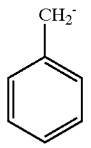 | 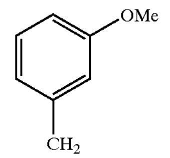 |
| 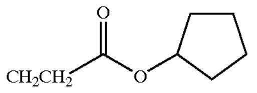 | 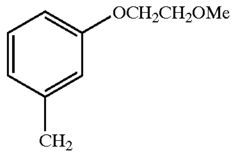 |
| 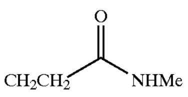 | 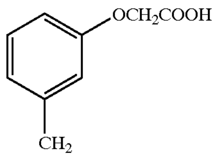 |
| 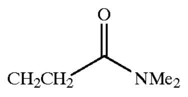 | 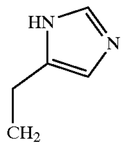 |
| 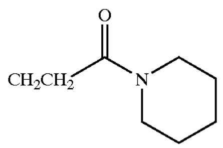 | 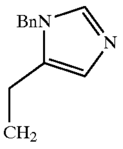 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 5h
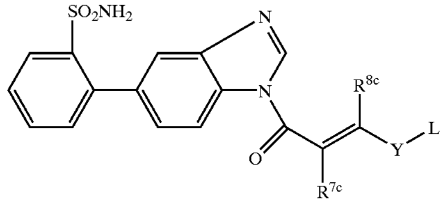
Formula VIh
| $R^{7c}$ | $R^{8c}$ |
|---|---|
| H | H |
| Me | Me |
| 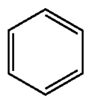 | 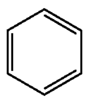 |
| 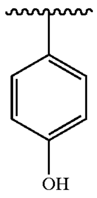 | 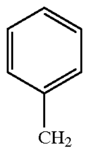 |
| 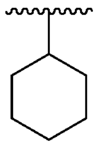 | 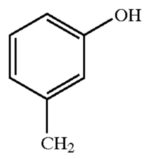 |
| 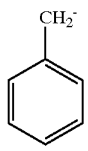 | 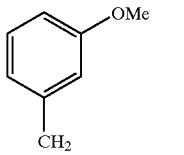 |
| 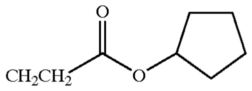 | 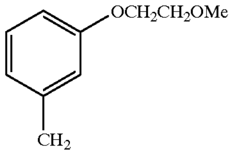 |
| 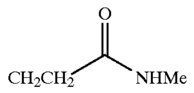 | 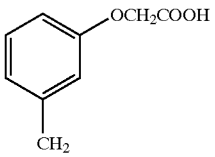 |
| 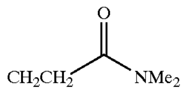 | 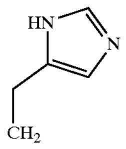 |

TABLE 5h-continued
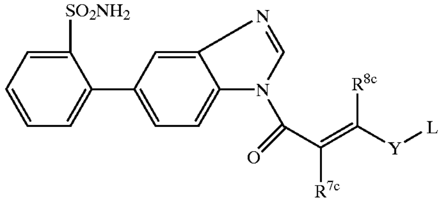
Formula VIh
| $R^{7c}$ | $R^{8c}$ |
|---|---|
| 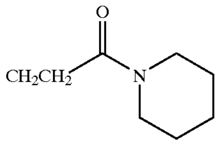 | 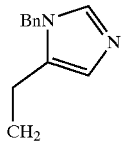 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 5i
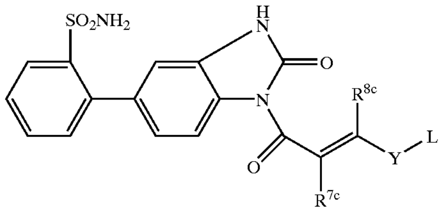
Formula VIi
| $R^{7c}$ | $R^{8c}$ |
|---|---|
| H | H |
| Me | Me |
| 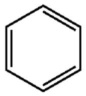 | 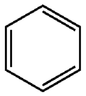 |
| 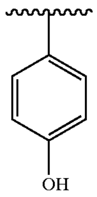 | 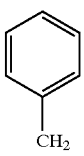 |
| 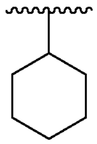 | 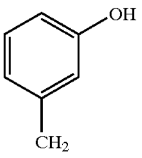 |
TABLE 5i-continued
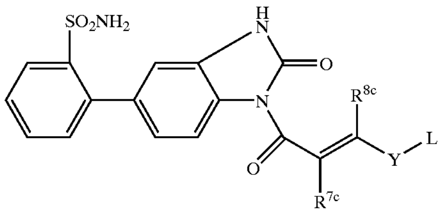
Formula VIi
| $R^{7c}$ | $R^{8c}$ |
|---|---|
| 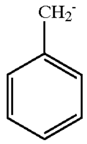 | 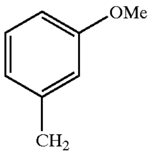 |
| 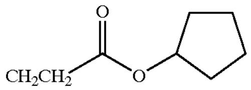 | 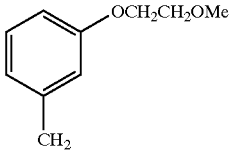 |
| 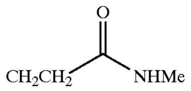 | 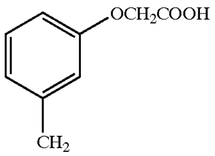 |
| 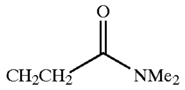 | 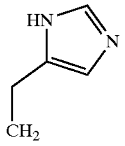 |
| 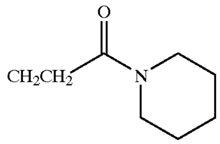 | 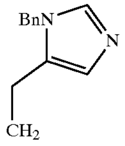 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |

TABLE 5j
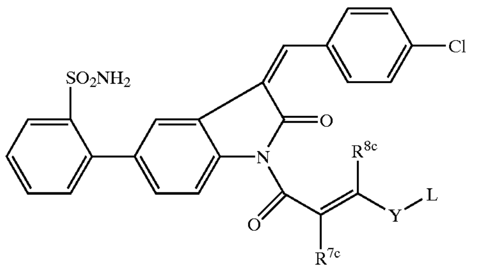
Formula VIj
| $R^{7c}$ | $R^{8c}$ |
|---|---|
| H | H |
| Me | Me |
| 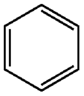 | 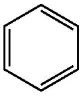 |
| 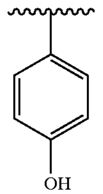 | 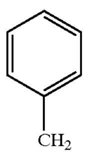 |
| 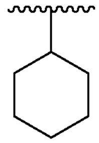 | 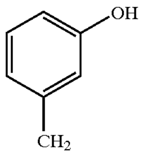 |
| 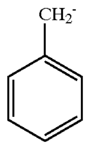 | 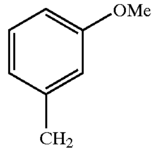 |
| 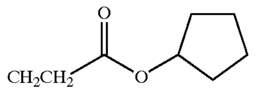 | 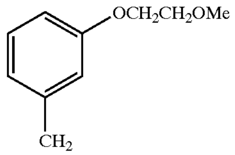 |
| 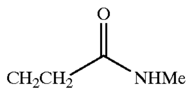 | 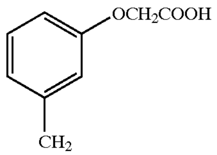 |
| 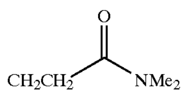 | 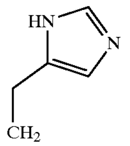 |
TABLE 5j-continued
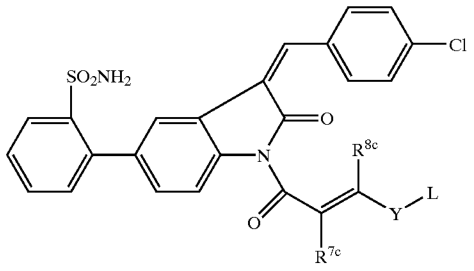
Formula VIj
| $R^{7c}$ | $R^{8c}$ |
|---|---|
| 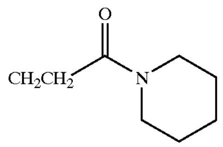 | 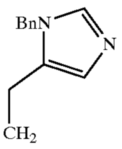 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 5k
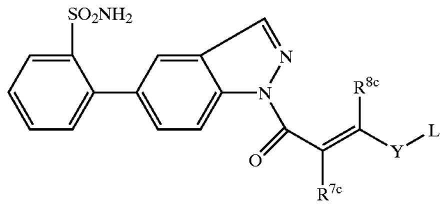
Formula VIk
| $R^{7c}$ | $R^{8c}$ |
|---|---|
| H | H |
| Me | Me |
| 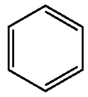 | 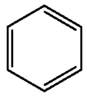 |
| 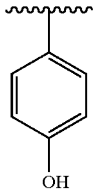 | 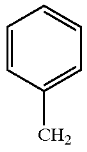 |
| 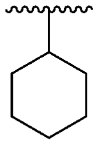 | 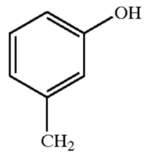 |

TABLE 5k-continued
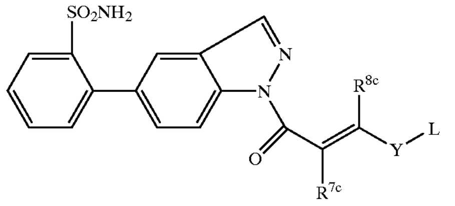
Formula VIk
| $R^{7c}$ | $R^{8c}$ |
|---|---|
| 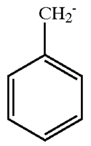 | 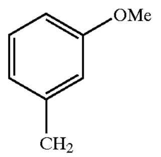 |
| 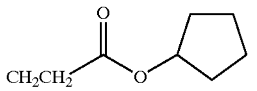 | 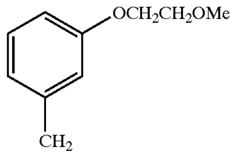 |
| 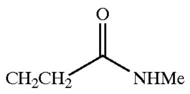 | 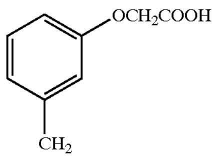 |
| 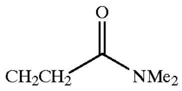 | 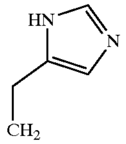 |
| 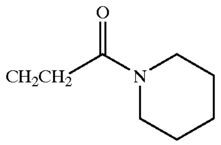 | 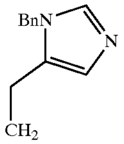 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 5(l)
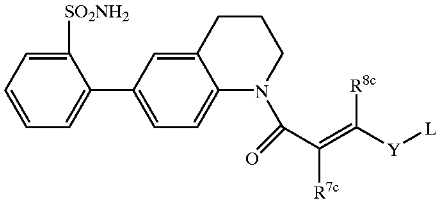
Formula VI(l)
| $R^{7c}$ | $R^{8c}$ |
|---|---|
| H | H |
| Me | Me |
| 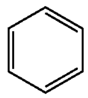 | 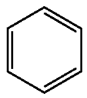 |
| 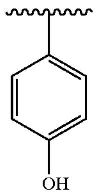 | 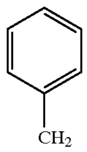 |
| 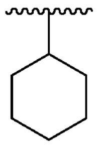 | 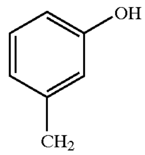 |
| 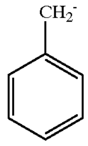 | 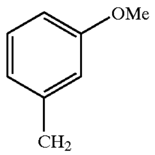 |
| 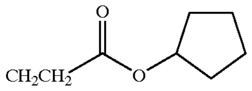 | 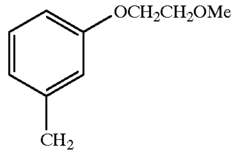 |
| 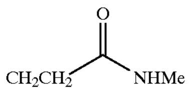 | 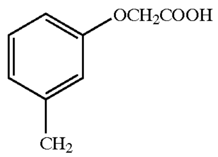 |
| 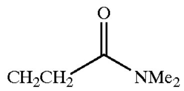 | 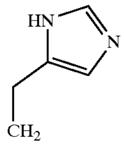 |

TABLE 5(l)-continued
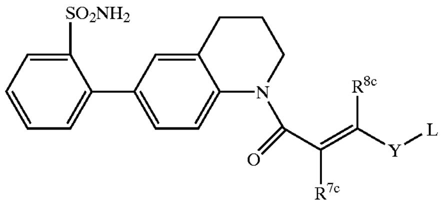
Formula VI(l)
| $R^{7c}$ | $R^{8c}$ |
|---|---|
| 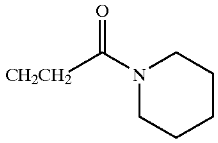 | 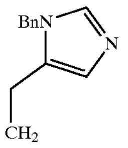 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 5m
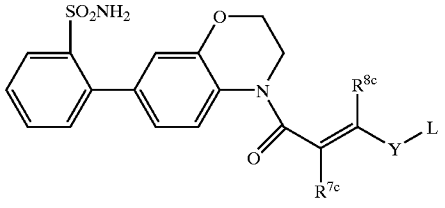
Formula VIm
| $R^{7c}$ | $R^{8c}$ |
|---|---|
| H | H |
| Me | Me |
| 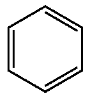 | 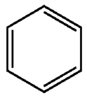 |
| 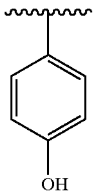 | 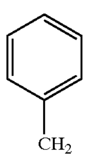 |
| 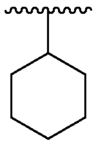 | 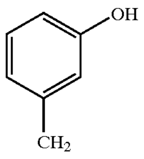 |
TABLE 5m-continued
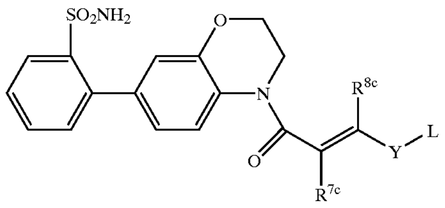
Formula VIm
| $R^{7c}$ | $R^{8c}$ |
|---|---|
| 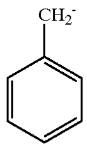 | 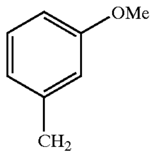 |
| 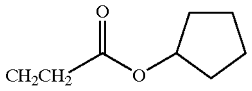 | 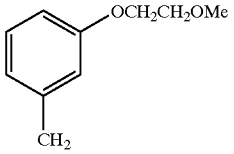 |
| 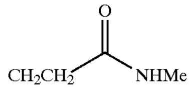 | 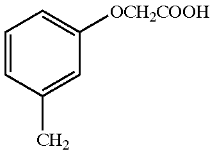 |
| 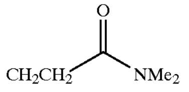 | 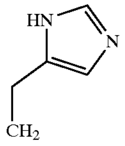 |
| 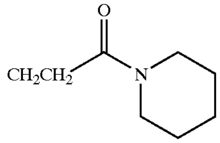 | 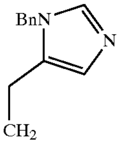 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |

TABLE 5n
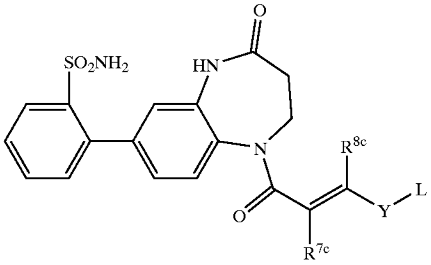
Formula VIn
| $R^{7c}$ | $R^{8c}$ |
|---|---|
| H | H |
| Me | Me |
| 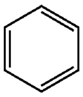 | 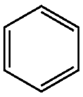 |
| 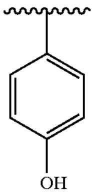 | 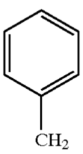 |
| 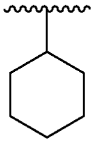 | 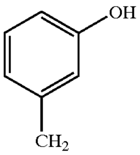 |
| 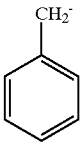 | 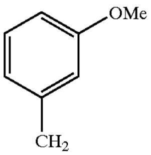 |
| 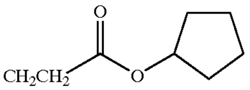 | 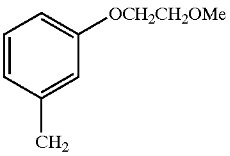 |
| 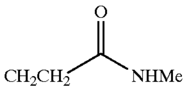 | 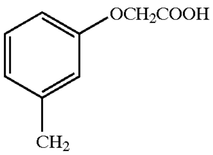 |
| 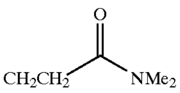 | 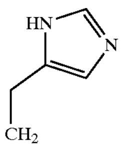 |
TABLE 5n-continued
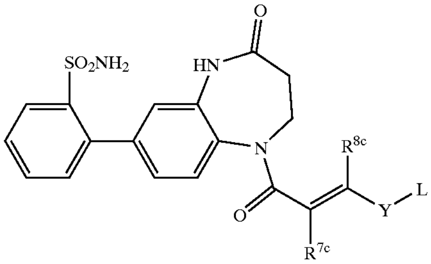
Formula VIn
| $R^{7c}$ | $R^{8c}$ |
|---|---|
| 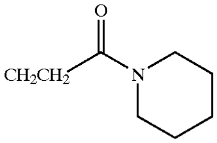 | 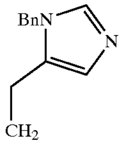 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 5o
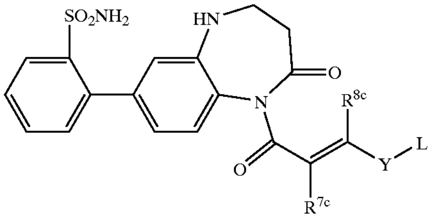
Formula VIo
| $R^{7c}$ | $R^{8c}$ |
|---|---|
| H | H |
| Me | Me |
| 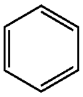 | 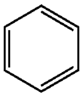 |
| 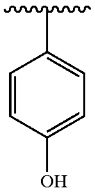 | 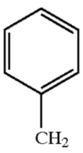 |

TABLE 5o-continued
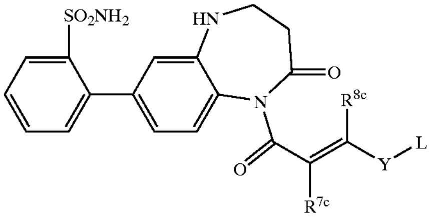
Formula VIo
| $R^{7c}$ | $R^{8c}$ |
|---|---|
| 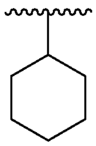 | 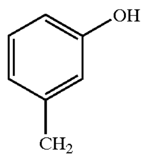 |
| 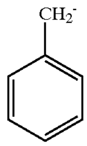 | 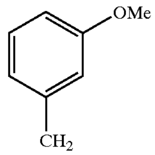 |
| 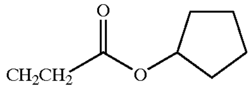 | 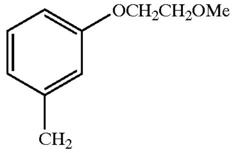 |
| 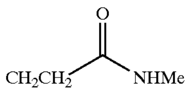 | 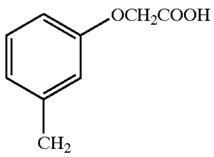 |
| 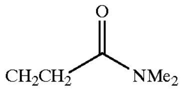 | 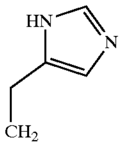 |
| 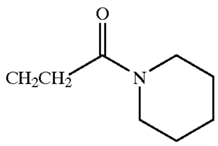 | 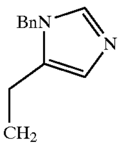 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 5p
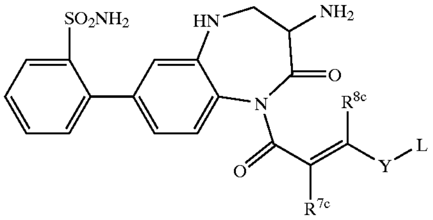
Formula VIp
| $R^{7c}$ | $R^{8c}$ |
|---|---|
| H | H |
| Me | Me |
| 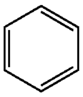 | 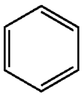 |
| 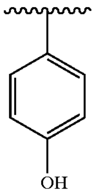 | 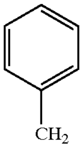 |
| 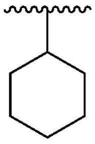 | 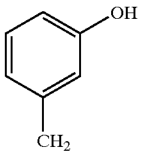 |
| 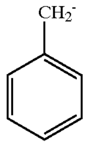 | 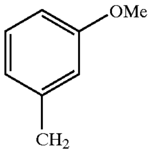 |
| 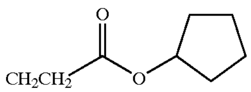 | 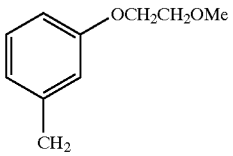 |
| 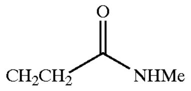 | 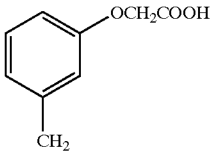 |
| 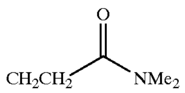 | 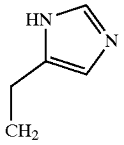 |

TABLE 5p-continued
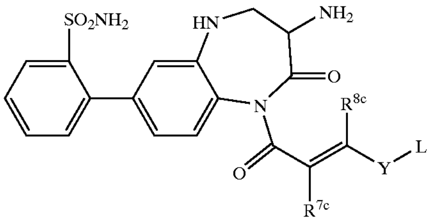
Formula VIp
| $R^{7c}$ | $R^{8c}$ |
| --- | --- |
| 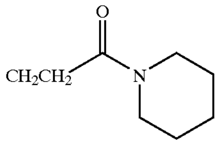 | 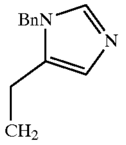 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 5q
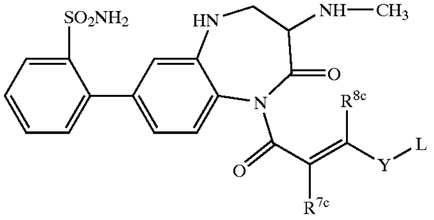
Formula VIq
| $R^{7c}$ | $R^{8c}$ |
| --- | --- |
| H | H |
| Me | Me |
| 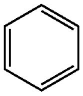 | 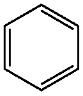 |
| 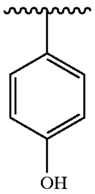 | 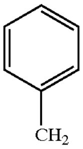 |
| 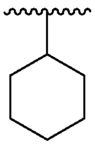 | 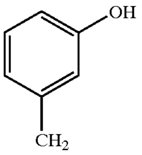 |
TABLE 5q-continued
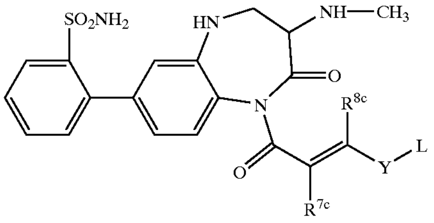
Formula VIq
| $R^{7c}$ | $R^{8c}$ |
| --- | --- |
| 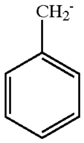 | 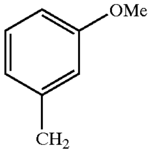 |
| 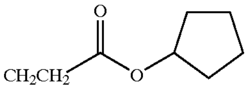 | 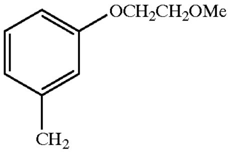 |
| 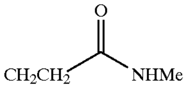 | 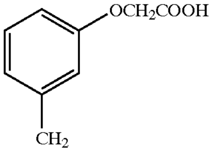 |
| 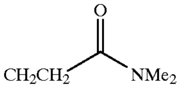 | 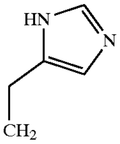 |
| 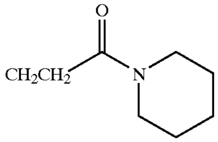 | 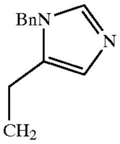 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |

TABLE 6
Formula VII
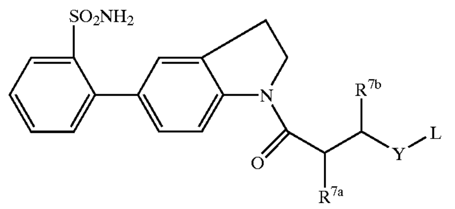
| $R^{7a}$ | $R^{7b}$ |
|---|---|
| H | H |
| Me | Me |
| 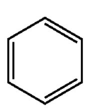 | 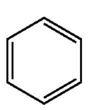 |
| 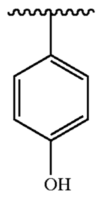 | 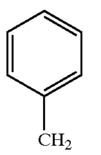 |
| 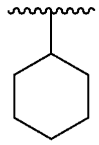 | 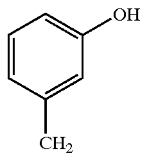 |
| 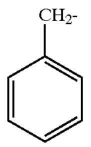 | 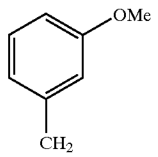 |
| 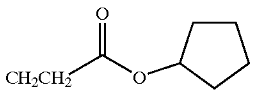 | 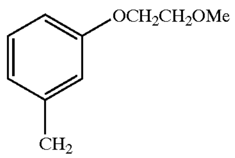 |
| 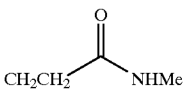 | 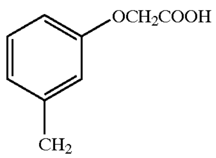 |
| 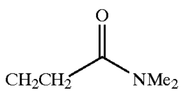 | 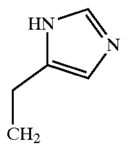 |
TABLE 6-continued
Formula VII
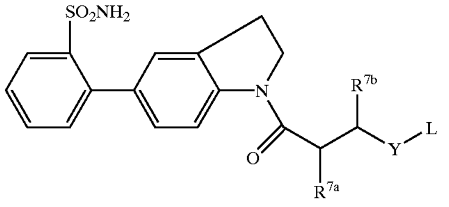
| $R^{7a}$ | $R^{7b}$ |
|---|---|
| 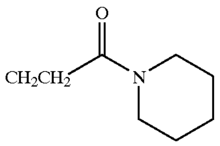 | 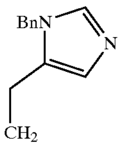 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 6a
Formula VIIa
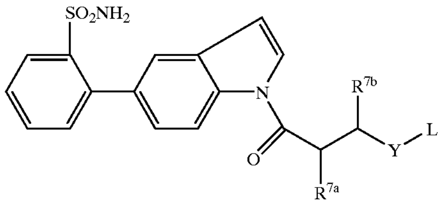
| $R^{7a}$ | $R^{7b}$ |
|---|---|
| H | H |
| Me | Me |
| 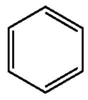 | 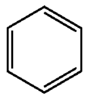 |
| 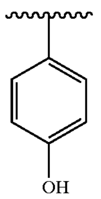 | 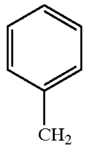 |
| 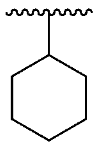 | 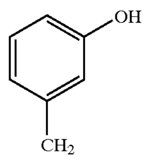 |

TABLE 6a-continued
Formula VIIa
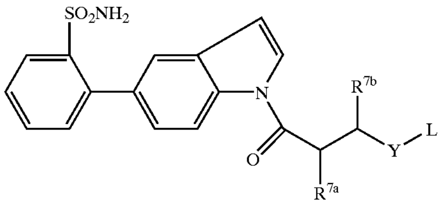
| $R^{7a}$ | $R^{7b}$ |
|---|---|
| 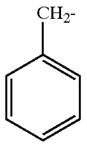 | 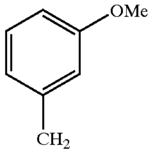 |
| 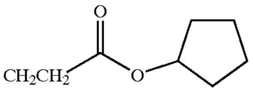 | 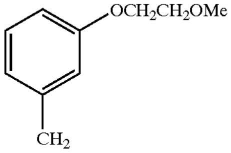 |
| 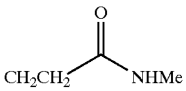 | 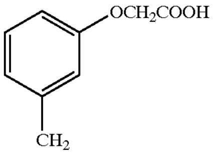 |
| 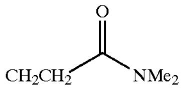 | 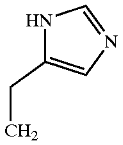 |
| 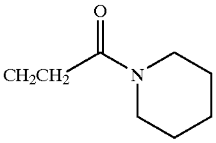 | 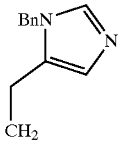 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 6b
Formula VIIb
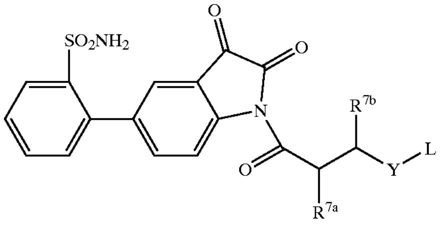
| $R^{7a}$ | $R^{7b}$ |
|---|---|
| H | H |
| Me | Me |
| 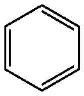 | 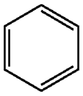 |
| 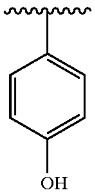 | 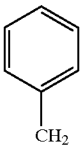 |
| 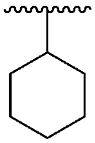 | 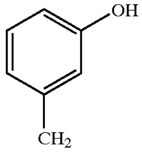 |
| 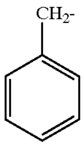 | 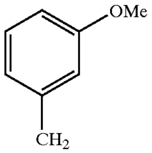 |
| 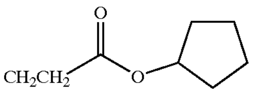 | 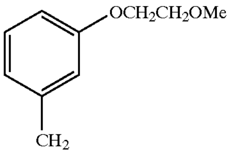 |
| 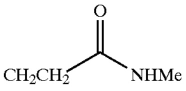 | 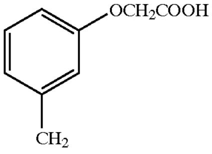 |
| 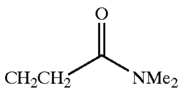 | 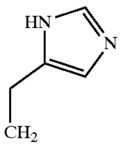 |

TABLE 6b-continued
Formula VIIb
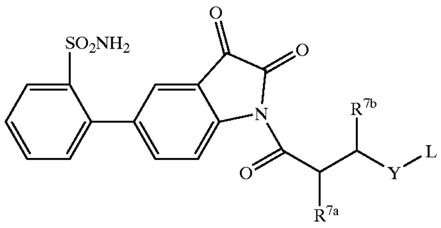
| $R^{7a}$ | $R^{7b}$ |
|---|---|
| 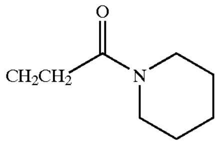 | 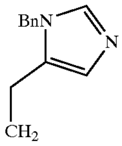 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 6c
Formula VIIc
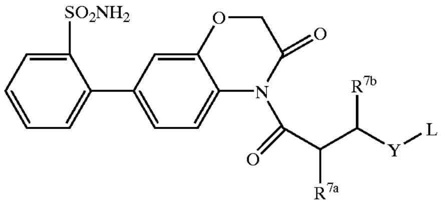
| $R^{7a}$ | $R^{7b}$ |
|---|---|
| H | H |
| Me | Me |
| 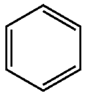 | 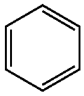 |
| 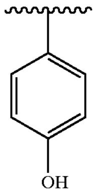 | 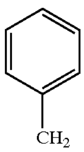 |
| 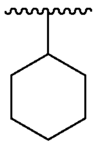 | 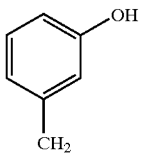 |
TABLE 6c-continued
Formula VIIc
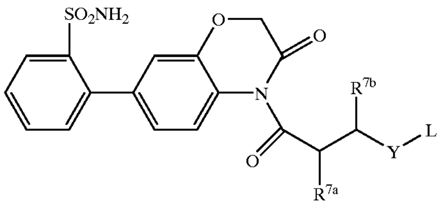
| $R^{7a}$ | $R^{7b}$ |
|---|---|
| 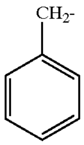 | 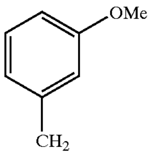 |
| 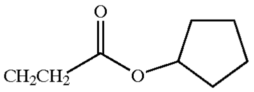 | 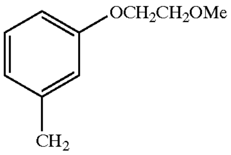 |
| 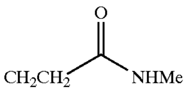 | 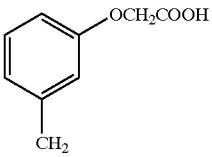 |
| 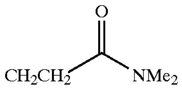 | 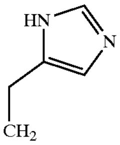 |
| 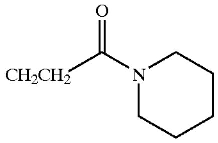 | 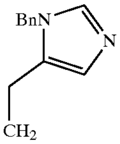 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |

TABLE 6d
Formula VIId
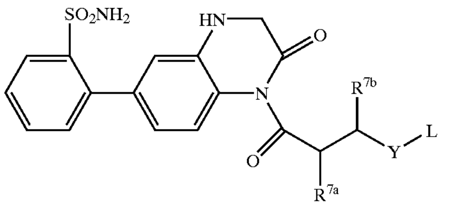
| $R^{7a}$ | $R^{7b}$ |
|---|---|
| H | H |
| Me | Me |
| 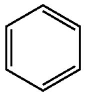 | 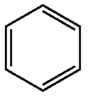 |
| 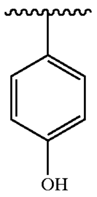 | 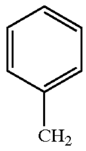 |
| 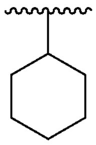 | 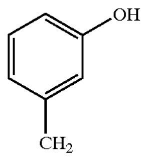 |
| 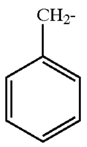 | 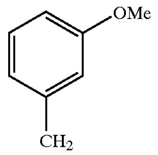 |
| 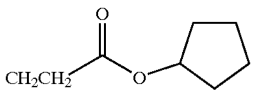 | 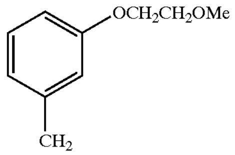 |
| 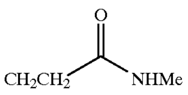 | 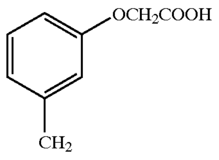 |
| 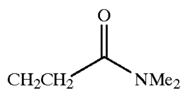 | 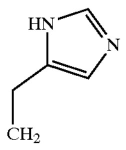 |
TABLE 6d-continued
Formula VIId
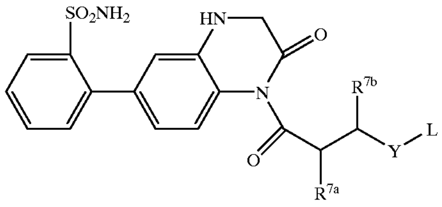
| $R^{7a}$ | $R^{7b}$ |
|---|---|
| 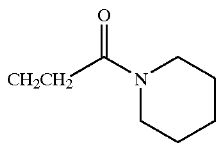 | 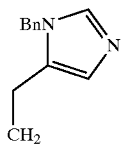 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 6e
Formula VIIe
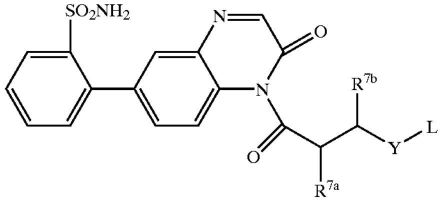
| $R^{7a}$ | $R^{7b}$ |
|---|---|
| H | H |
| Me | Me |
| 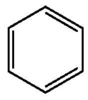 | 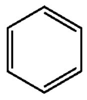 |
| 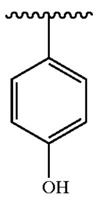 | 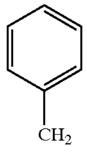 |
| 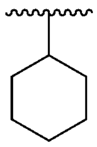 | 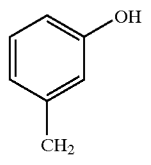 |

TABLE 6e-continued
Formula VIIe
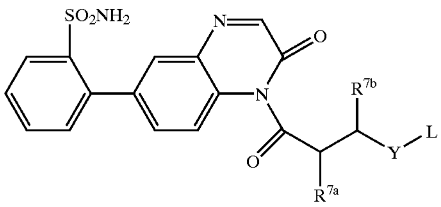
| $R^{7a}$ | $R^{7b}$ |
|---|---|
| 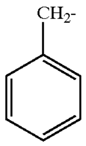 | 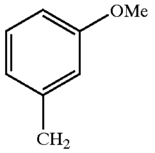 |
| 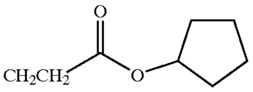 | 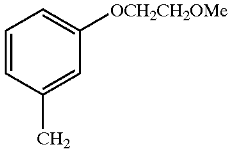 |
| 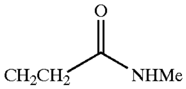 | 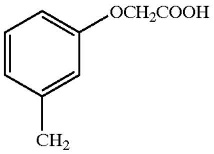 |
| 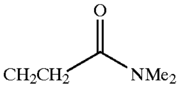 | 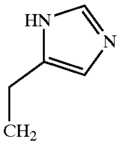 |
| 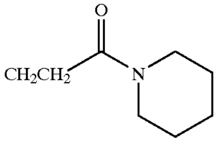 | 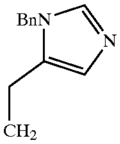 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 6f
Formula VIIf
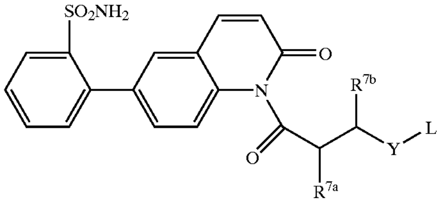
| $R^{7a}$ | $R^{7b}$ |
|---|---|
| H | H |
| Me | Me |
| 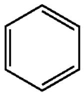 | 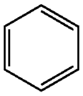 |
| 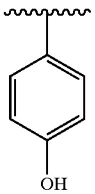 | 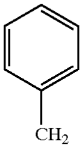 |
| 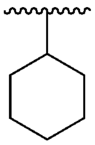 | 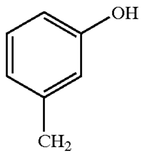 |
| 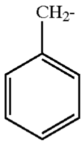 | 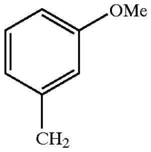 |
| 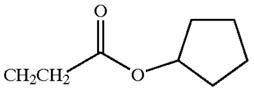 | 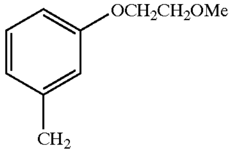 |
| 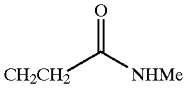 | 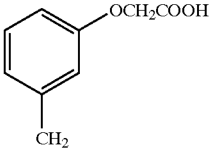 |
| 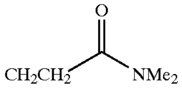 | 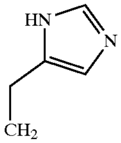 |

TABLE 6f-continued
Formula VIIf
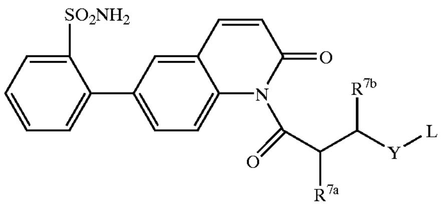
| $R^{7a}$ | $R^{7b}$ |
|---|---|
| 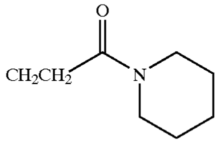 | 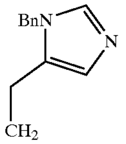 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 6g
Formula VIIg
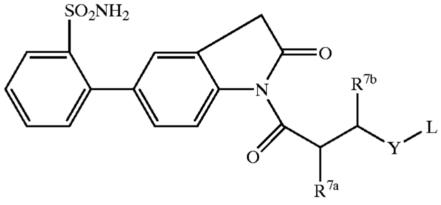
| $R^{7a}$ | $R^{7b}$ |
|---|---|
| H | H |
| Me | Me |
| 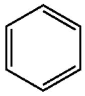 | 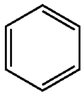 |
| 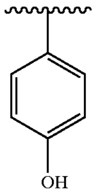 | 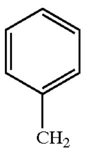 |
| 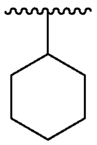 | 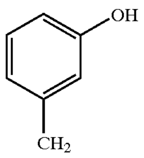 |
TABLE 6g-continued
Formula VIIg
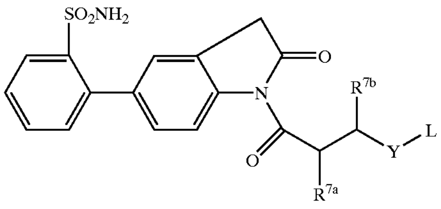
| $R^{7a}$ | $R^{7b}$ |
|---|---|
| 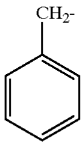 | 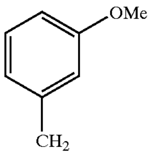 |
| 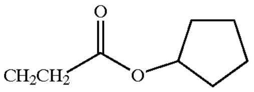 | 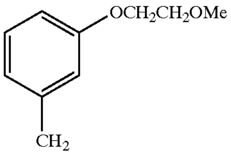 |
| 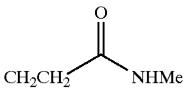 | 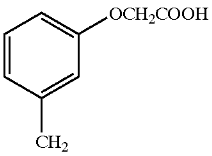 |
| 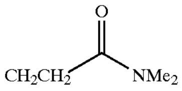 | 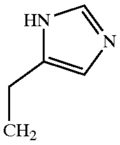 |
| 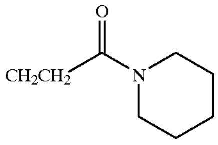 | 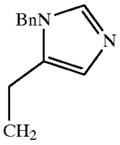 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |

TABLE 6h
Formula VIIh
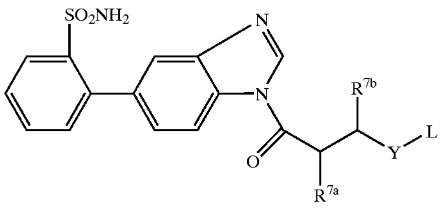
| $R^{7a}$ | $R^{7b}$ |
|---|---|
| H | H |
| Me | Me |
| 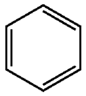 | 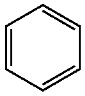 |
| 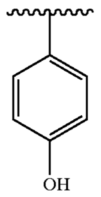 | 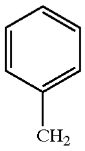 |
| 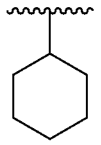 | 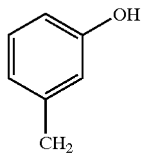 |
| 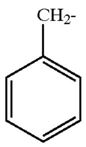 | 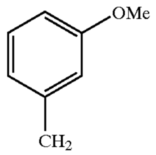 |
| 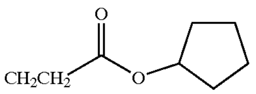 | 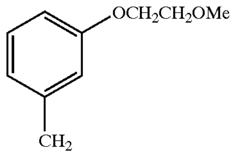 |
| 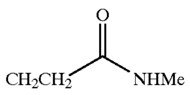 | 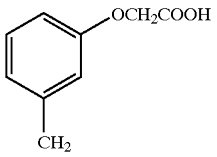 |
| 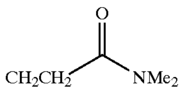 | 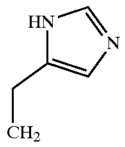 |
TABLE 6h-continued
Formula VIIh
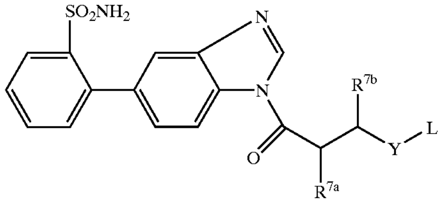
| $R^{7a}$ | $R^{7b}$ |
|---|---|
| 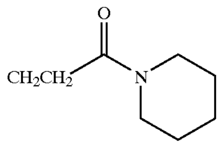 | 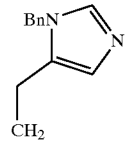 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 6i
Formula VIIi
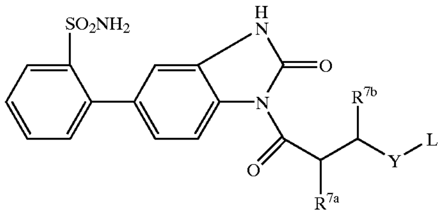
| $R^{7a}$ | $R^{7b}$ |
|---|---|
| H | H |
| Me | Me |
| 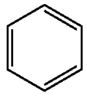 | 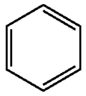 |
| 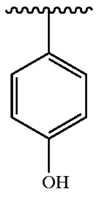 | 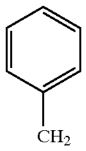 |
| 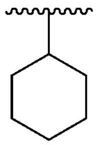 | 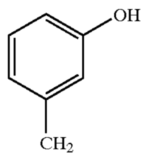 |

TABLE 6i-continued
Formula VIIi
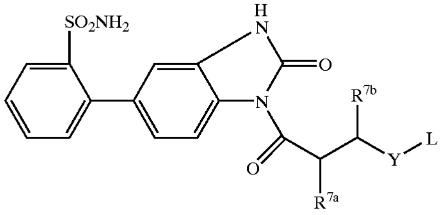
| $R^{7a}$ | $R^{7b}$ |
|---|---|
| 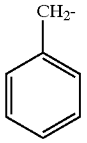 | 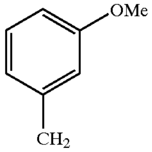 |
| 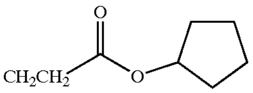 | 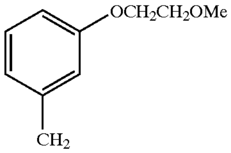 |
| 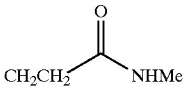 | 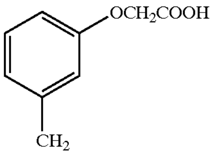 |
| 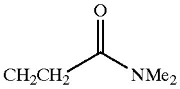 | 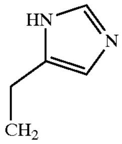 |
| 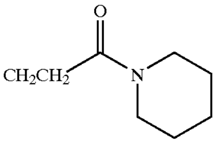 | 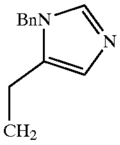 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 6j
Formula VIIj
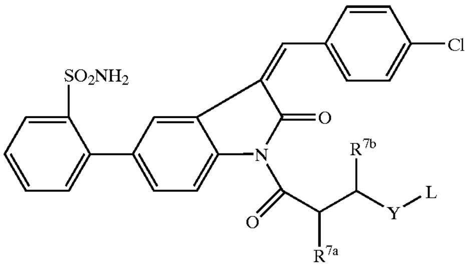
| $R^{7a}$ | $R^{7b}$ |
|---|---|
| H | H |
| Me | Me |
| 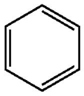 | 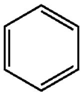 |
| 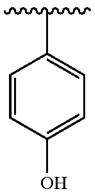 | 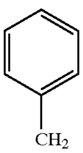 |
| 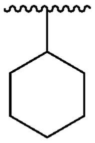 | 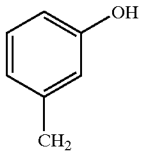 |
| 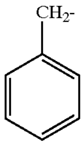 | 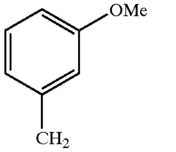 |
| 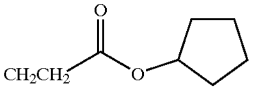 | 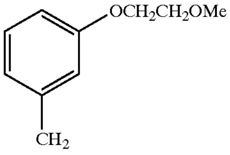 |
| 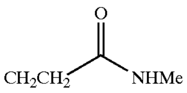 | 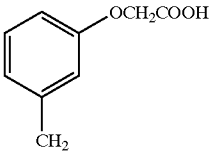 |
| 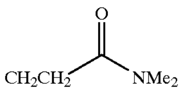 | 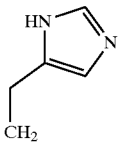 |

TABLE 6j-continued
Formula VIIj
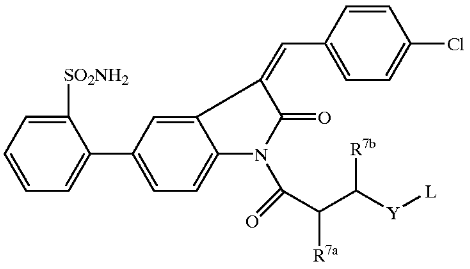
| $R^{7a}$ | $R^{7b}$ |
|---|---|
| 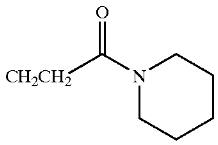 | 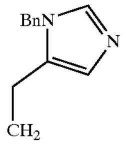 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 6k
Formula VIIk
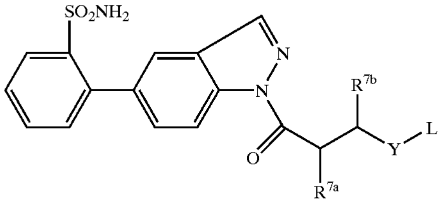
| $R^{7a}$ | $R^{7b}$ |
|---|---|
| H | H |
| Me | Me |
| 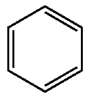 | 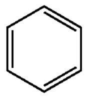 |
| 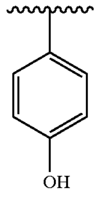 | 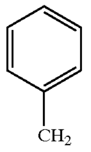 |
| 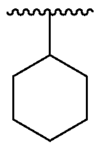 | 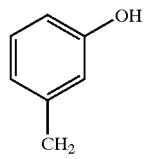 |
TABLE 6k-continued
Formula VIIk
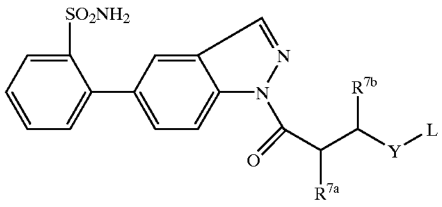
| $R^{7a}$ | $R^{7b}$ |
|---|---|
| 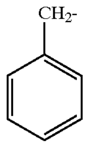 | 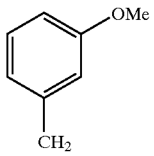 |
| 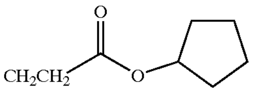 | 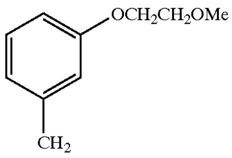 |
| 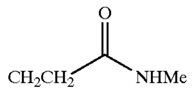 | 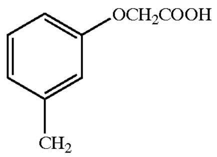 |
| 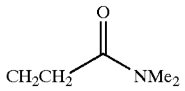 | 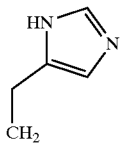 |
| 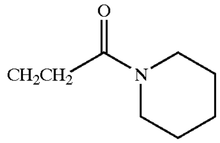 | 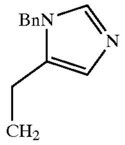 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |

TABLE 6(l)
Formula VII(l)
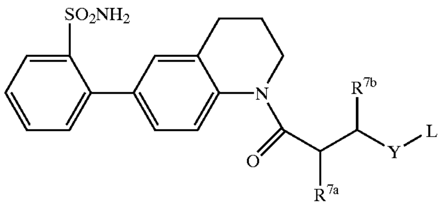
| $R^{7a}$ | $R^{7b}$ |
|---|---|
| H | H |
| Me | Me |
| 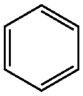 | 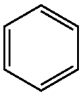 |
| 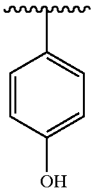 | 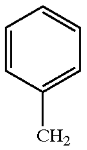 |
| 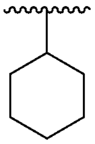 | 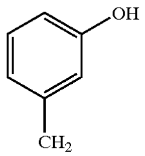 |
| 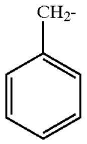 | 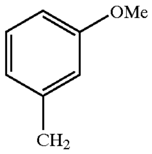 |
| 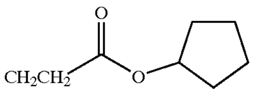 | 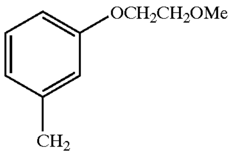 |
| 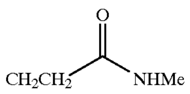 | 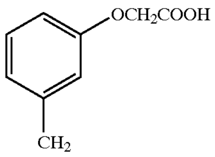 |
| 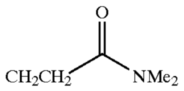 | 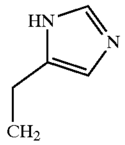 |
TABLE 6(l)-continued
Formula VII(l)
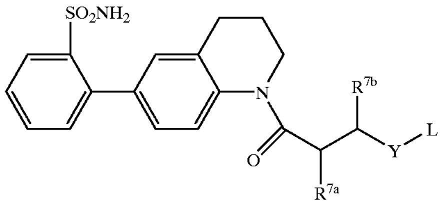
| $R^{7a}$ | $R^{7b}$ |
|---|---|
| 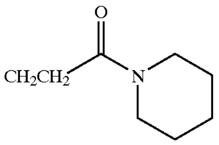 | 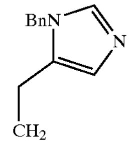 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 6m
Formula VIIm
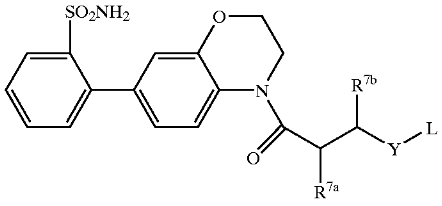
| $R^{7a}$ | $R^{7b}$ |
|---|---|
| H | H |
| Me | Me |
| 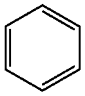 | 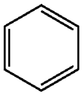 |
| 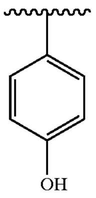 | 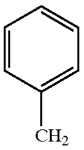 |
| 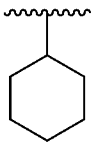 | 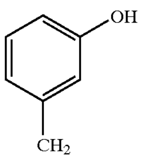 |

TABLE 6m-continued
Formula VIIm
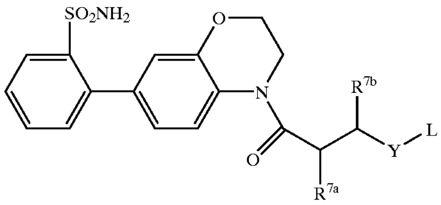
| $R^{7a}$ | $R^{7b}$ |
|---|---|
| 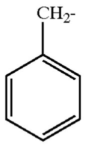 | 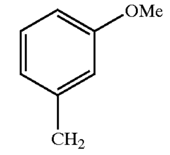 |
| 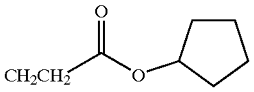 | 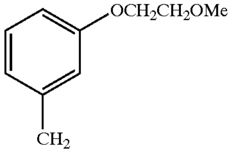 |
| 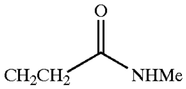 | 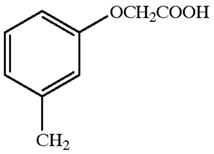 |
| 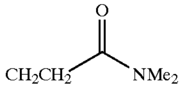 | 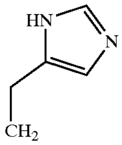 |
| 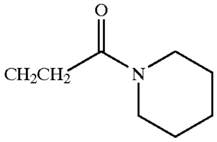 | 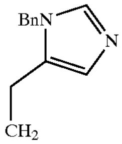 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 6n
Formula VIIn
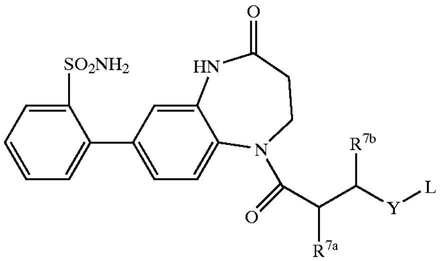
| $R^{7a}$ | $R^{7b}$ |
|---|---|
| H | H |
| Me | Me |
| 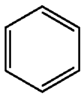 | 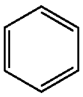 |
| 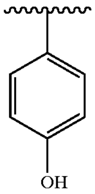 | 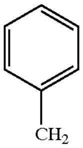 |
| 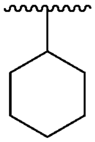 | 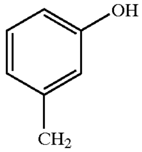 |
| 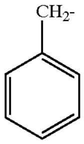 | 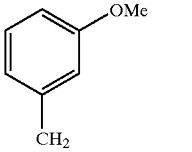 |
| 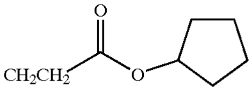 | 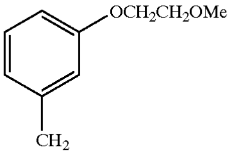 |
| 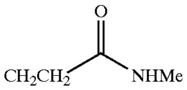 | 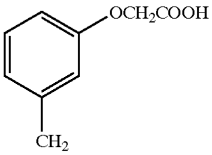 |
| 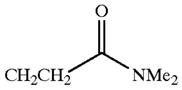 | 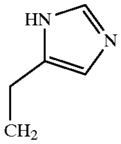 |

TABLE 6n-continued
Formula VIIn
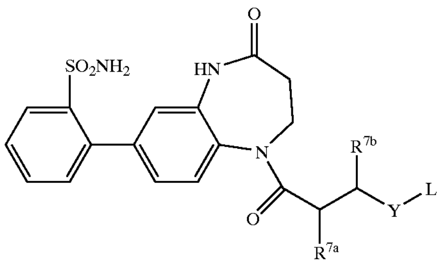
| $R^{7a}$ | $R^{7b}$ |
|---|---|
| 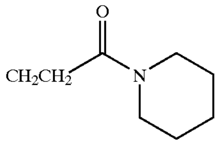 | 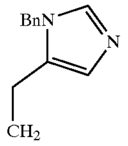 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 6o
Formula VIIo
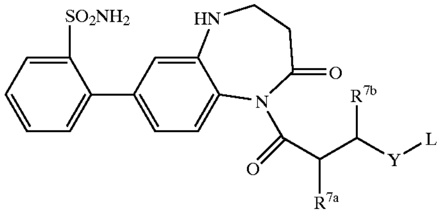
| $R^{7a}$ | $R^{7b}$ |
|---|---|
| H | H |
| Me | Me |
| 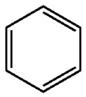 | 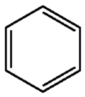 |
| 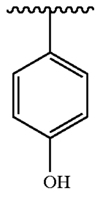 | 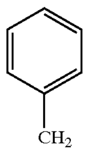 |
| 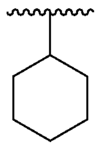 | 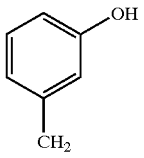 |
TABLE 6o-continued
Formula VIIo
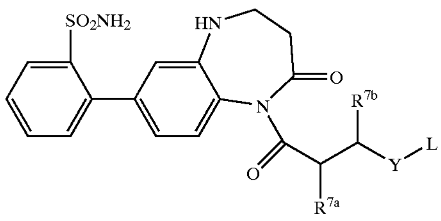
| $R^{7a}$ | $R^{7b}$ |
|---|---|
| 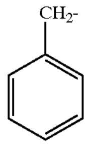 | 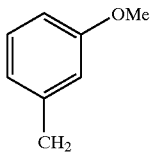 |
| 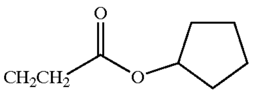 | 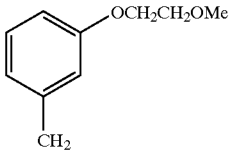 |
| 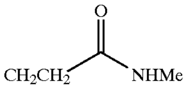 | 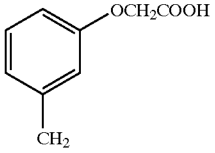 |
| 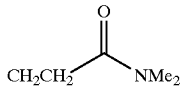 | 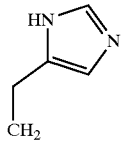 |
| 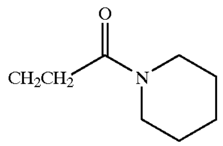 | 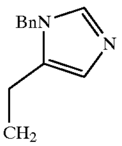 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |

TABLE 6p
Formula VIIp
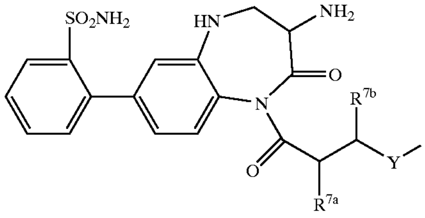
| $R^{7a}$ | $R^{7b}$ |
|---|---|
| H | H |
| Me | Me |
| 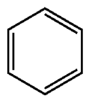 | 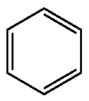 |
| 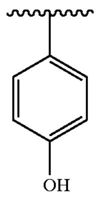 | 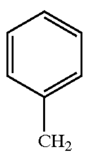 |
| 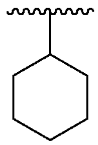 | 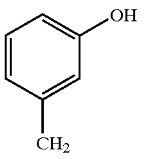 |
| 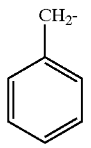 | 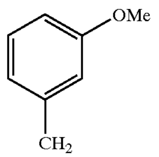 |
| 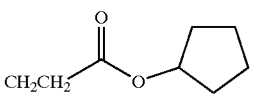 | 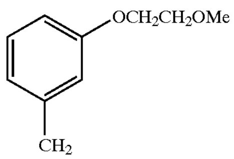 |
| 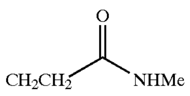 | 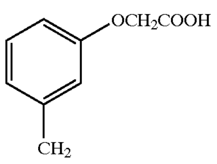 |
| 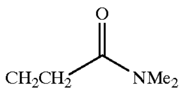 | 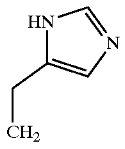 |
TABLE 6p-continued
Formula VIIp
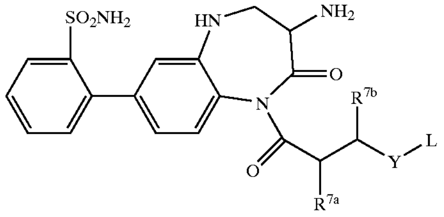
| $R^{7a}$ | $R^{7b}$ |
|---|---|
| 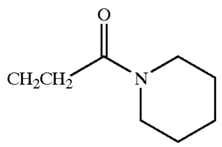 | 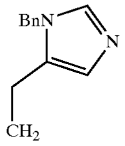 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 6q
Formula VIIq
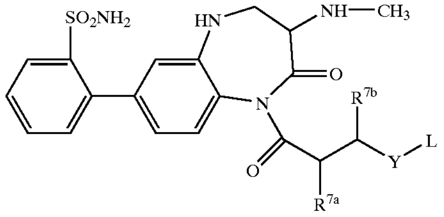
| $R^{7a}$ | $R^{7b}$ |
|---|---|
| H | H |
| Me | Me |
| 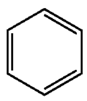 | 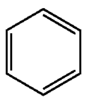 |
| 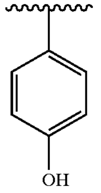 | 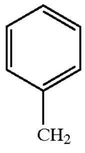 |
| 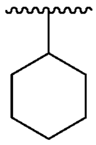 | 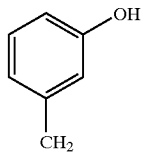 |

TABLE 6q-continued
Formula VIIq
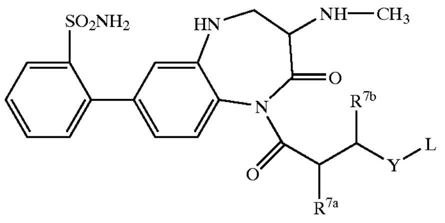
| $R^{7a}$ | $R^{7b}$ |
|---|---|
| 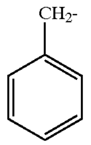 | 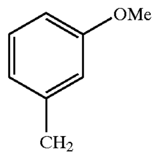 |
| 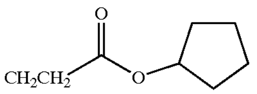 | 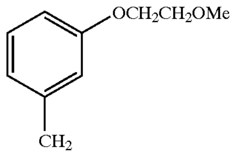 |
| 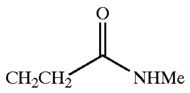 | 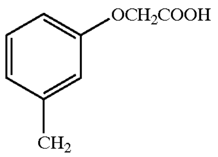 |
| 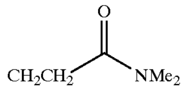 | 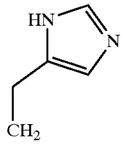 |
| 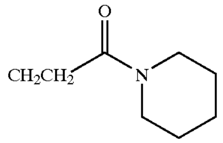 | 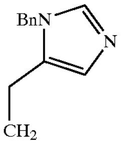 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 7
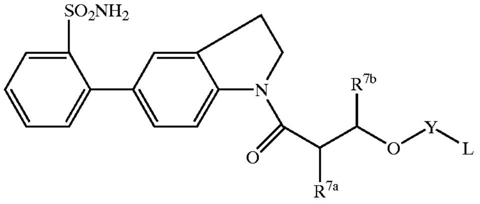
Formula VIII
| $R^{7a}$ | $R^{7b}$ |
|---|---|
| H | H |
| Me | Me |
| 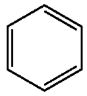 | 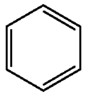 |
| 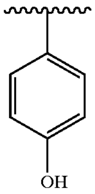 | 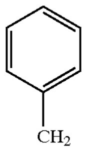 |
| 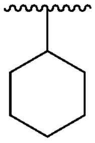 | 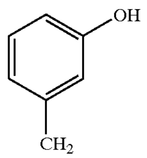 |
| 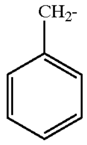 | 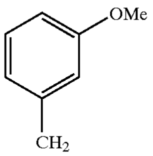 |
| 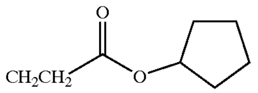 | 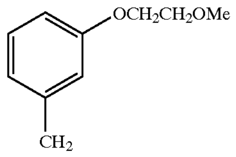 |
| 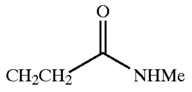 | 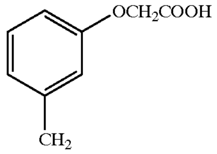 |
| 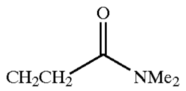 | 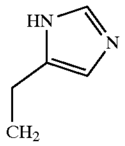 |

TABLE 7-continued
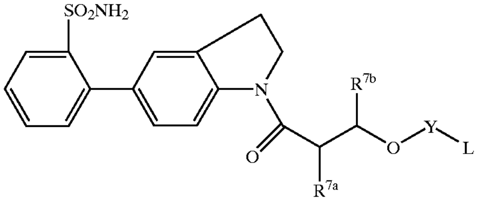
Formula VIII
| $R^{7a}$ | $R^{7b}$ |
| --- | --- |
| 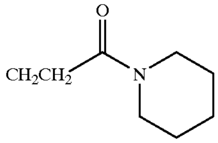 | 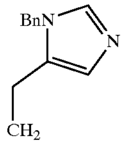 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 7a
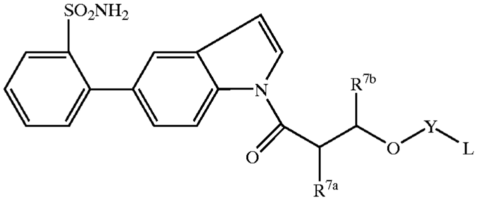
Formula VIIIa
| $R^{7a}$ | $R^{7b}$ |
| --- | --- |
| H | H |
| Me | Me |
| 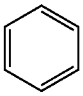 | 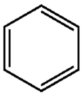 |
| 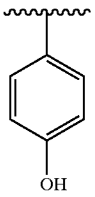 | 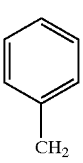 |
| 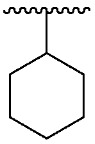 | 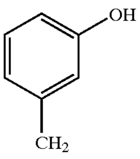 |
TABLE 7a-continued
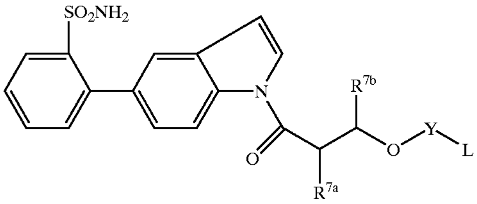
Formula VIIIa
| $R^{7a}$ | $R^{7b}$ |
| --- | --- |
| 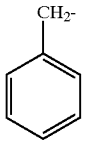 | 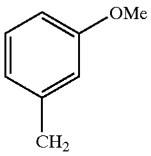 |
| 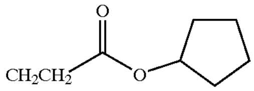 | 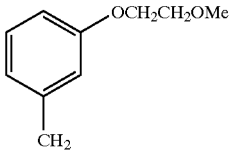 |
| 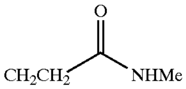 | 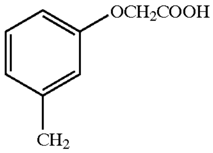 |
| 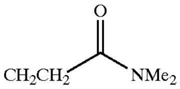 | 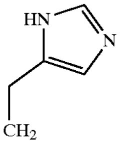 |
| 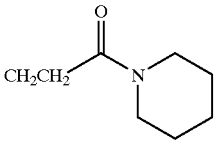 | 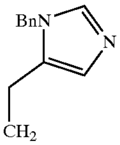 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |

TABLE 7b
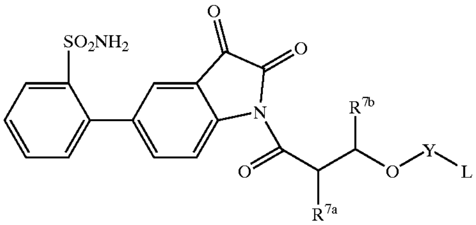
Formula VIIIb
| $R^{7a}$ | $R^{7b}$ |
| --- | --- |
| H | H |
| Me | Me |
| 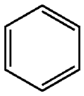 | 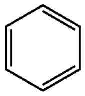 |
| 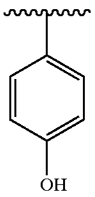 | 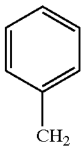 |
| 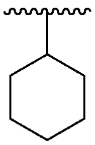 | 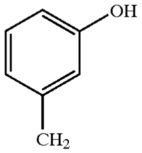 |
| 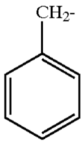 | 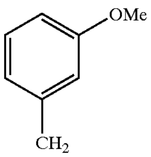 |
| 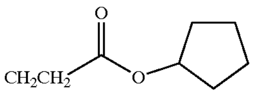 | 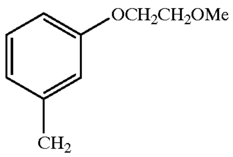 |
| 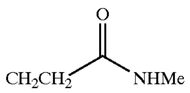 | 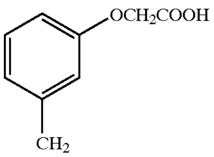 |
| 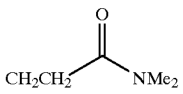 | 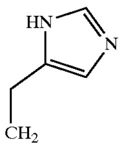 |
TABLE 7b-continued
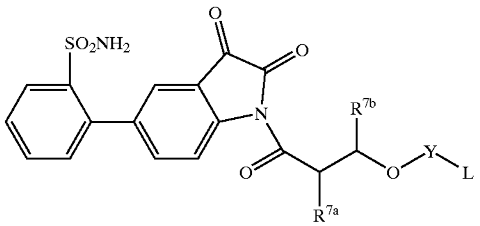
Formula VIIIb
| $R^{7a}$ | $R^{7b}$ |
| --- | --- |
| 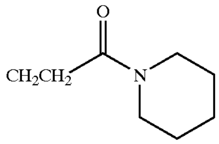 | 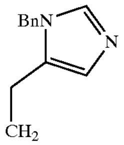 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 7c
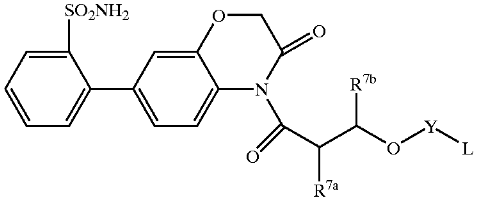
Formula VIIIc
| $R^{7a}$ | $R^{7b}$ |
| --- | --- |
| H | H |
| Me | Me |
| 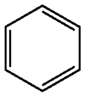 | 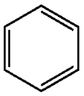 |
| 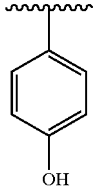 | 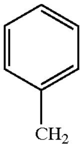 |
| 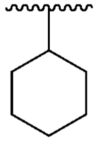 | 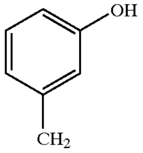 |

TABLE 7c-continued
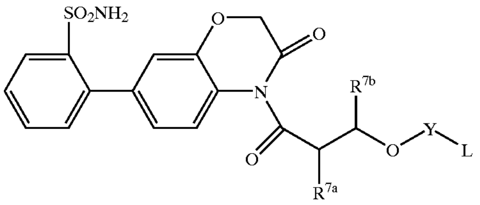
Formula VIIIc
| $R^{7a}$ | $R^{7b}$ |
|---|---|
| 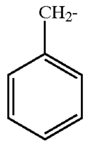 | 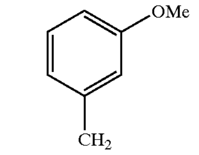 |
| 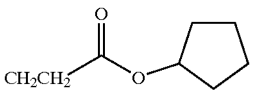 | 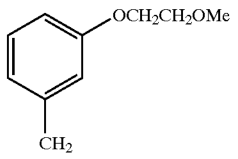 |
| 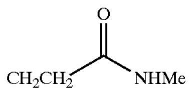 | 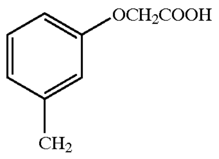 |
| 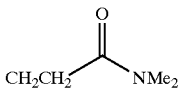 | 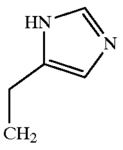 |
| 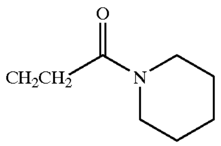 | 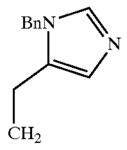 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 7d
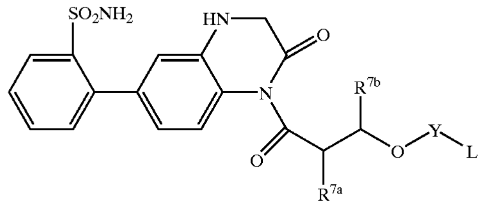
Formula VIIId
| $R^{7a}$ | $R^{7b}$ |
|---|---|
| H | H |
| Me | Me |
| 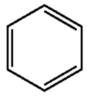 | 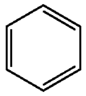 |
| 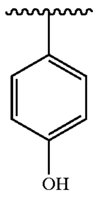 | 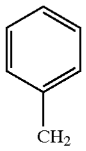 |
| 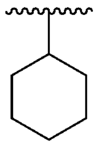 | 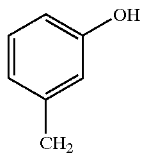 |
| 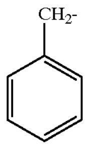 | 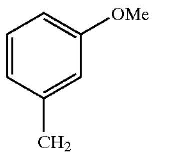 |
| 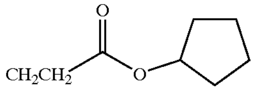 | 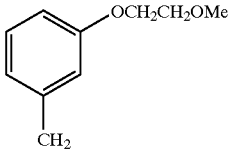 |
| 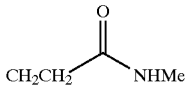 | 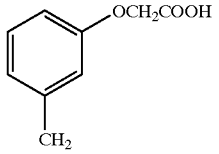 |
| 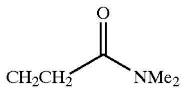 | 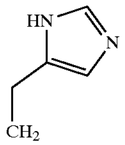 |

TABLE 7d-continued
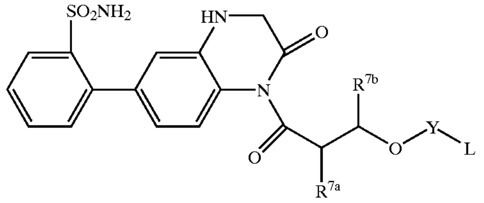
Formula VIIId
| $R^{7a}$ | $R^{7b}$ |
|---|---|
| 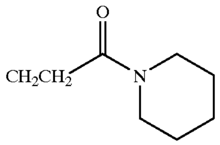 | 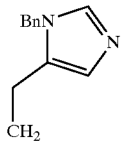 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 7e
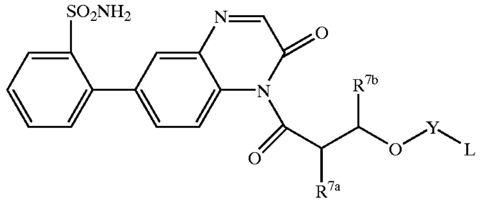
Formula VIIIe
| $R^{7a}$ | $R^{7b}$ |
|---|---|
| H | H |
| Me | Me |
| 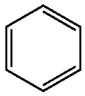 | 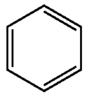 |
| 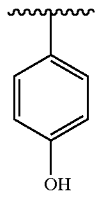 | 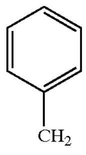 |
| 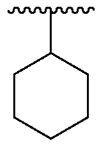 | 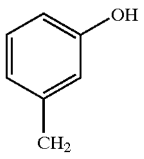 |
TABLE 7e-continued
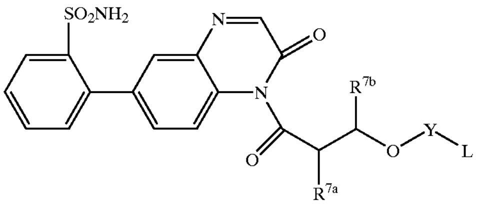
Formula VIIIe
| $R^{7a}$ | $R^{7b}$ |
|---|---|
| 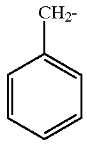 | 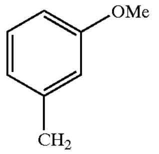 |
| 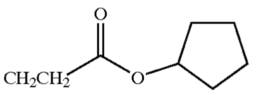 | 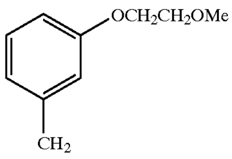 |
| 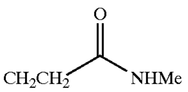 | 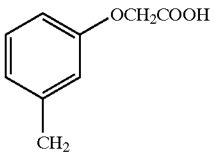 |
| 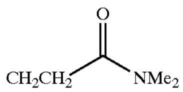 | 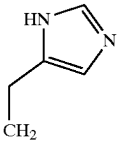 |
| 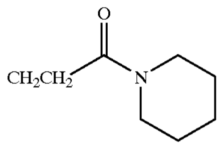 | 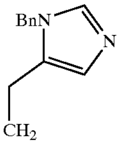 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |

TABLE 7f
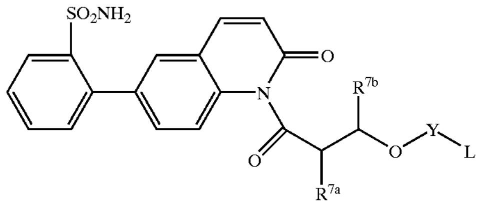
Formula VIIIf
| $R^{7a}$ | $R^{7b}$ |
|---|---|
| H | H |
| Me | Me |
| 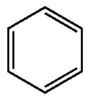 | 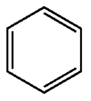 |
| 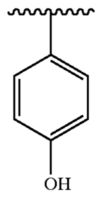 | 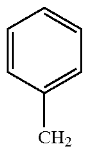 |
| 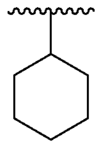 | 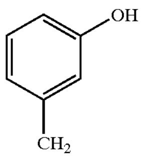 |
| 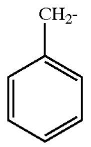 | 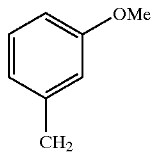 |
| 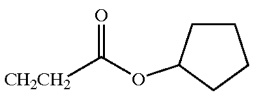 | 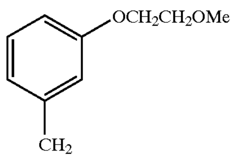 |
| 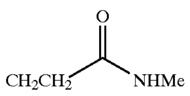 | 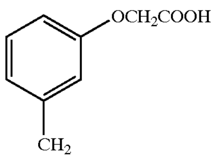 |
| 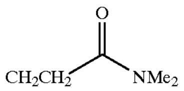 | 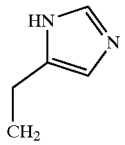 |
TABLE 7f-continued
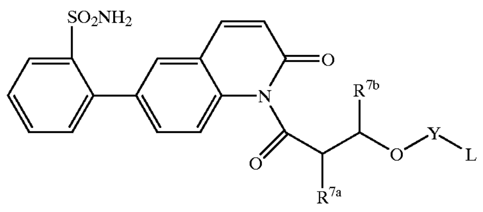
Formula VIIIf
| $R^{7a}$ | $R^{7b}$ |
|---|---|
| 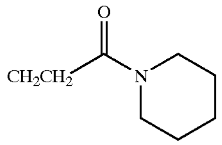 | 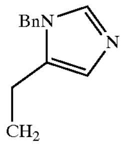 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 7g
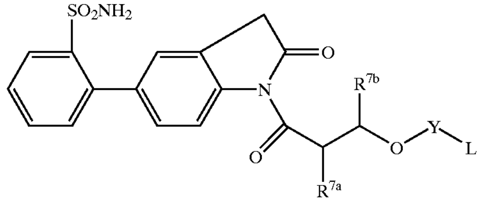
Formula VIIIg
| $R^{7a}$ | $R^{7b}$ |
|---|---|
| H | H |
| Me | Me |
| 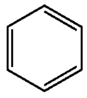 | 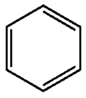 |
| 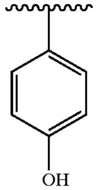 | 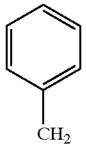 |
| 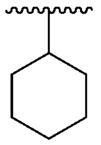 | 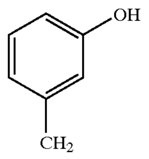 |

TABLE 7g-continued
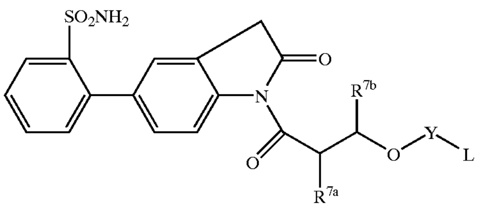
Formula VIIIg
| $R^{7a}$ | $R^{7b}$ |
|---|---|
| 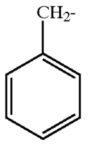 | 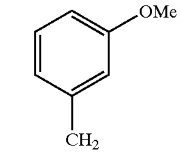 |
| 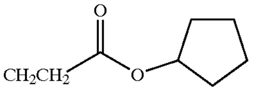 | 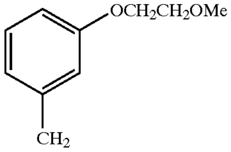 |
| 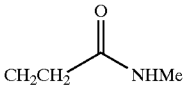 | 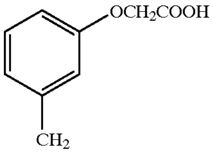 |
| 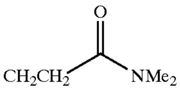 | 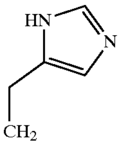 |
| 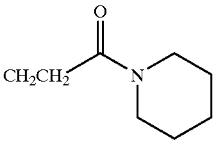 | 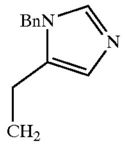 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 7h
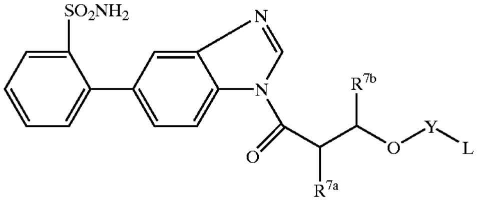
Formula VIIIh
| $R^{7a}$ | $R^{7b}$ |
|---|---|
| H | H |
| Me | Me |
| 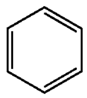 | 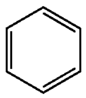 |
| 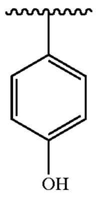 | 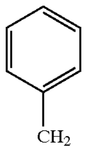 |
| 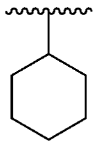 | 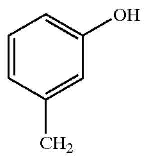 |
| 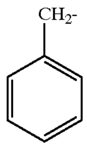 | 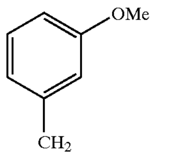 |
| 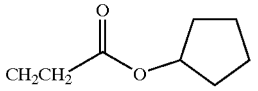 | 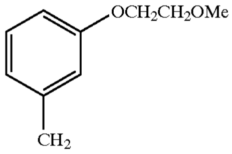 |
| 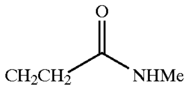 | 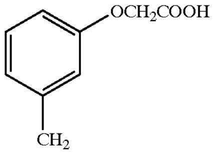 |
| 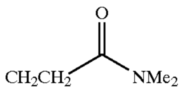 | 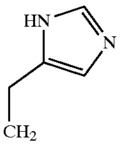 |

TABLE 7h-continued
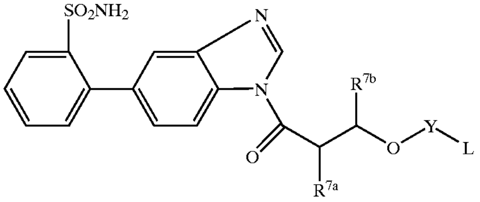
Formula VIIIh
| $R^{7a}$ | $R^{7b}$ |
|---|---|
| 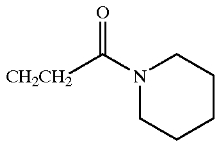 | 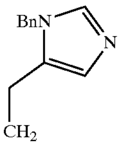 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 7i
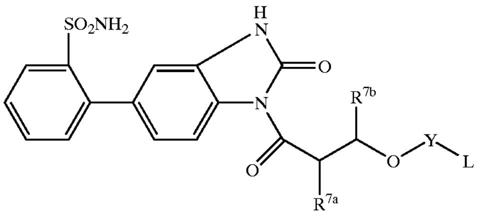
Formula VIIIi
| $R^{7a}$ | $R^{7b}$ |
|---|---|
| H | H |
| Me | Me |
| 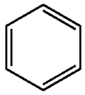 | 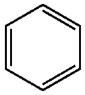 |
| 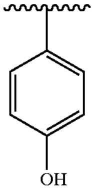 | 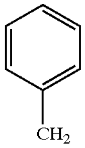 |
| 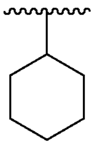 | 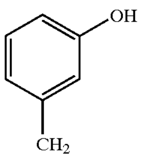 |
TABLE 7i-continued
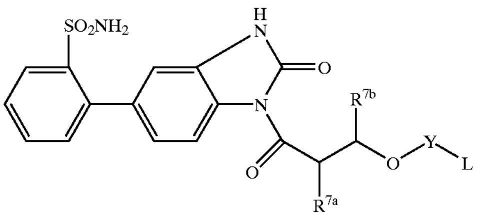
Formula VIIIi
| $R^{7a}$ | $R^{7b}$ |
|---|---|
| 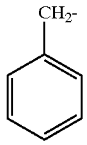 | 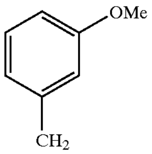 |
| 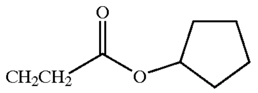 | 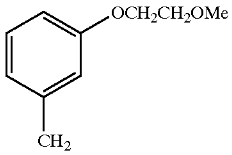 |
| 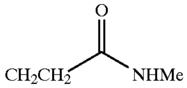 | 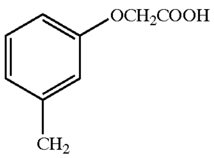 |
| 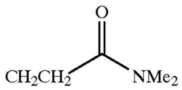 | 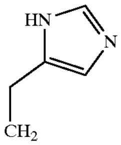 |
| 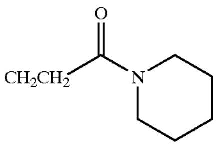 | 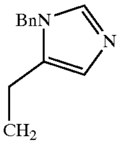 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |

TABLE 7j
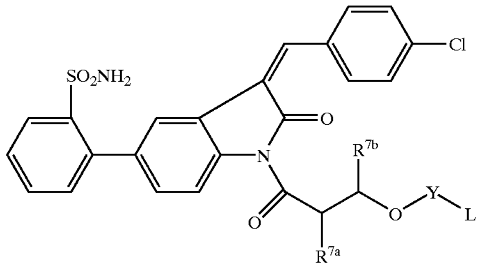
Formula VIIIj
| $R^{7a}$ | $R^{7b}$ |
| --- | --- |
| H | H |
| Me | Me |
| 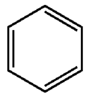 | 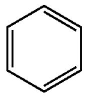 |
| 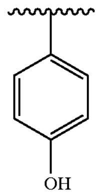 | 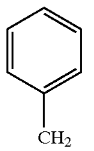 |
| 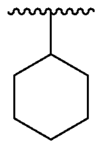 | 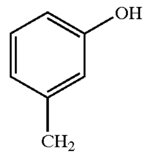 |
| 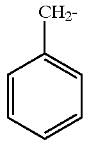 | 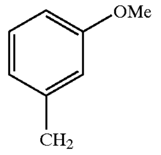 |
| 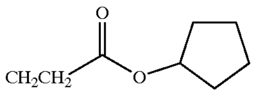 | 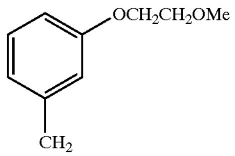 |
| 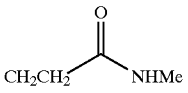 | 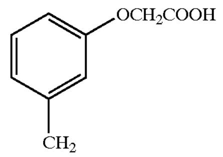 |
| 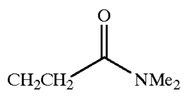 | 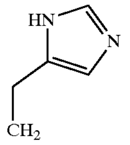 |
TABLE 7j-continued
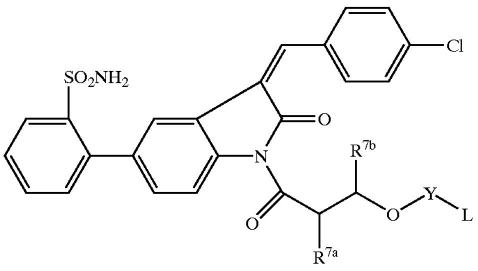
Formula VIIIj
| $R^{7a}$ | $R^{7b}$ |
| --- | --- |
| 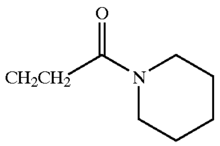 | 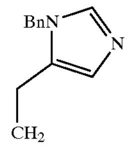 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 7k
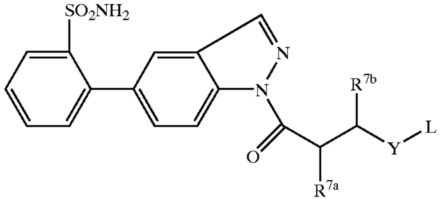
Formula VIIIk
| $R^{7a}$ | $R^{7b}$ |
| --- | --- |
| H | H |
| Me | Me |
| 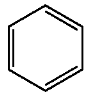 | 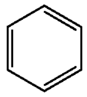 |
| 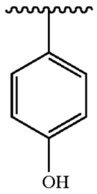 | 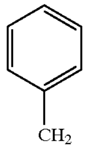 |
| 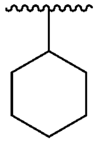 | 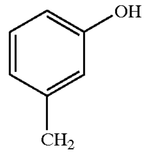 |

TABLE 7k-continued
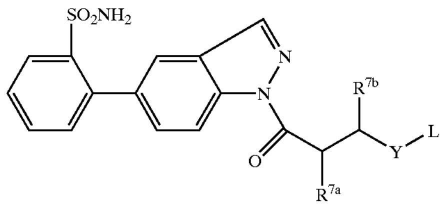
Formula VIIIk
| $R^{7a}$ | $R^{7b}$ |
| --- | --- |
| 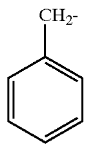 | 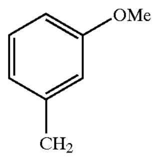 |
| 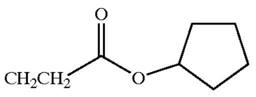 | 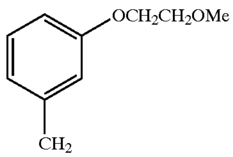 |
| 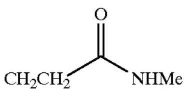 | 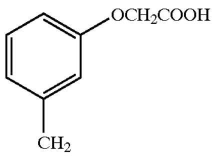 |
| 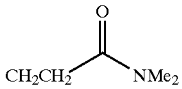 | 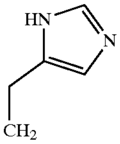 |
| 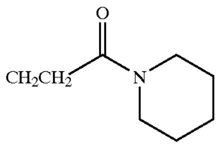 | 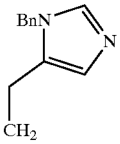 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 7(l)
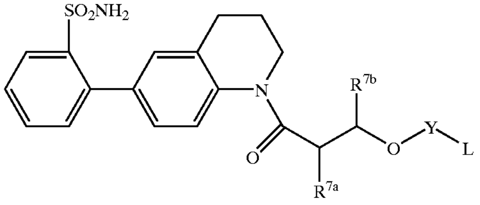
Formula VIII(l)
| $R^{7a}$ | $R^{7b}$ |
| --- | --- |
| H | H |
| Me | Me |
| 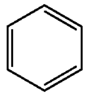 | 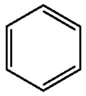 |
| 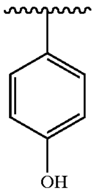 | 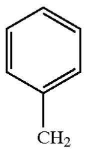 |
| 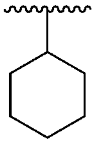 | 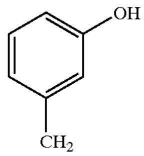 |
| 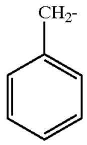 | 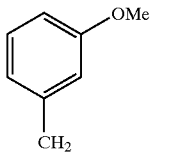 |
| 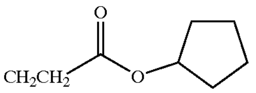 | 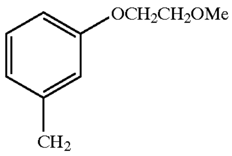 |
| 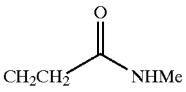 | 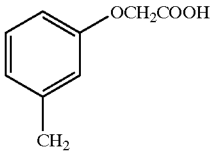 |
| 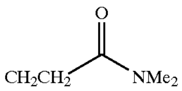 | 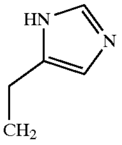 |

TABLE 7(l)-continued
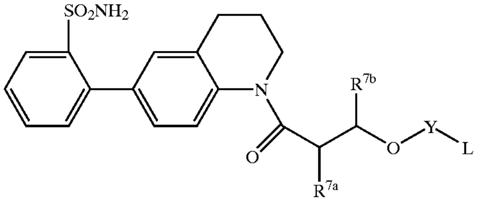
Formula VIII(l)
| R^7a | R^7b |
|---|---|
| 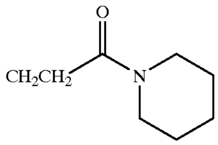 | 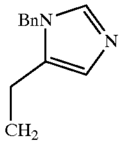 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 7m
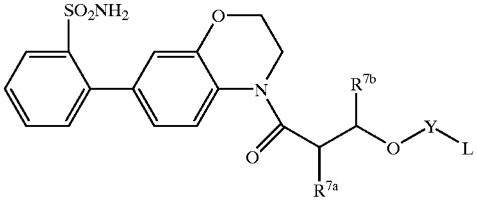
Formula VIIIm
| R^7a | R^7b |
|---|---|
| H | H |
| Me | Me |
| 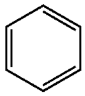 | 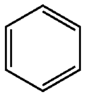 |
| 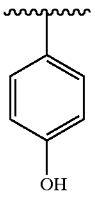 | 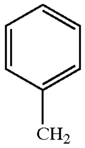 |
| 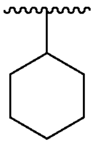 | 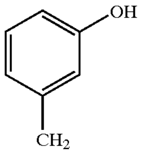 |
TABLE 7m-continued
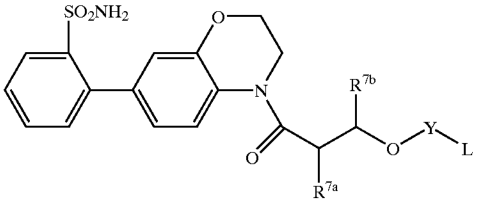
Formula VIIIm
| R^7a | R^7b |
|---|---|
| 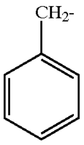 | 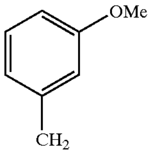 |
| 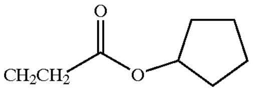 | 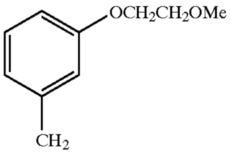 |
| 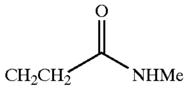 | 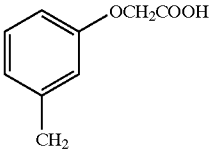 |
| 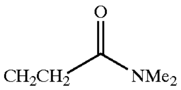 | 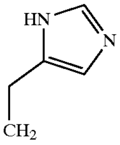 |
| 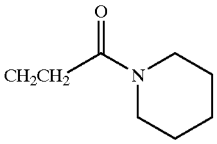 | 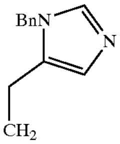 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |

TABLE 7n
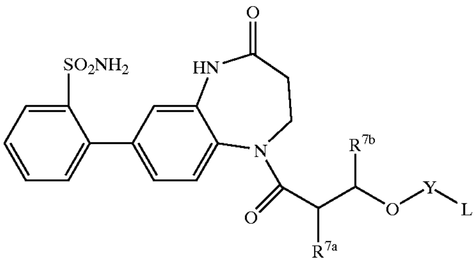
Formula VIIIn
| $R^{7a}$ | $R^{7b}$ |
|---|---|
| H | H |
| Me | Me |
| 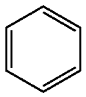 | 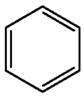 |
| 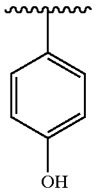 | 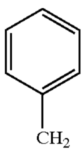 |
| 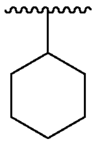 | 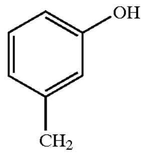 |
| 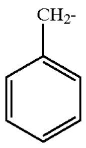 | 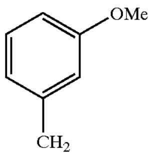 |
| 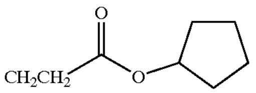 | 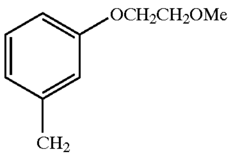 |
| 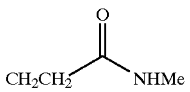 | 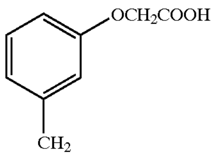 |
| 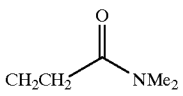 | 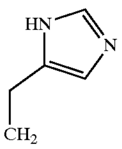 |
TABLE 7n-continued
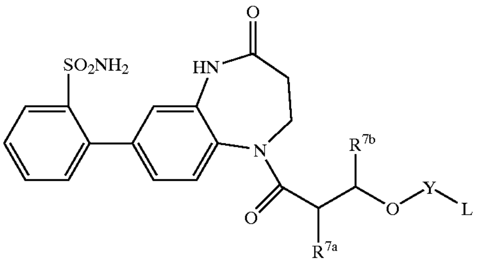
Formula VIIIn
| $R^{7a}$ | $R^{7b}$ |
|---|---|
| 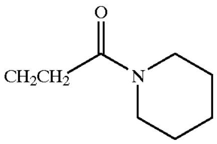 | 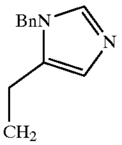 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 7o
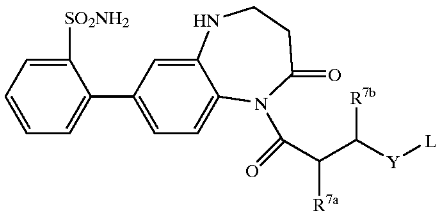
Formula VIIIo
| $R^{7a}$ | $R^{7b}$ |
|---|---|
| H | H |
| Me | Me |
| 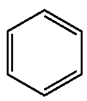 | 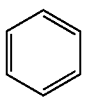 |
| 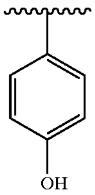 | 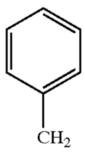 |

TABLE 7o-continued
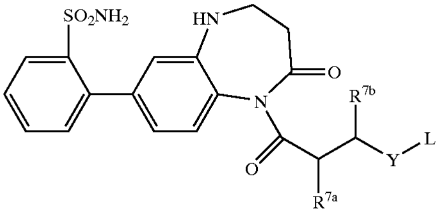
Formula VIIIo
| $R^{7a}$ | $R^{7b}$ |
|---|---|
| 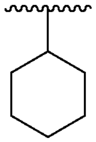 | 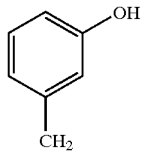 |
| 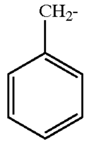 | 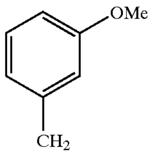 |
| 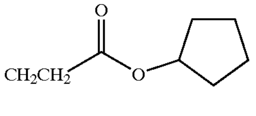 | 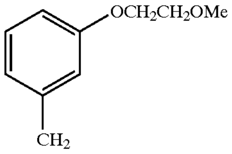 |
| 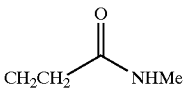 | 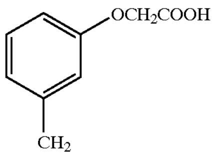 |
| 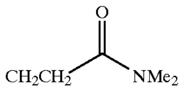 | 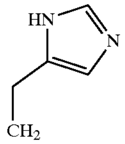 |
| 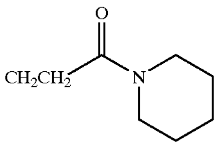 | 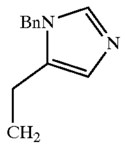 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 7p
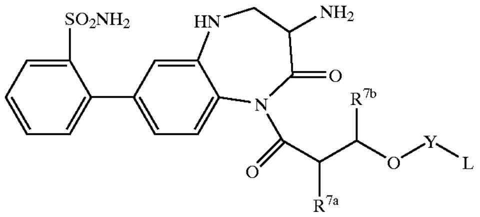
Formula VIIIp
| $R^{7a}$ | $R^{7b}$ |
|---|---|
| H | H |
| Me | Me |
| 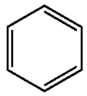 | 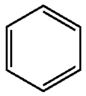 |
| 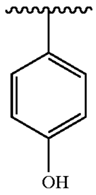 | 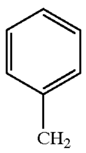 |
| 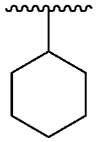 | 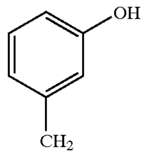 |
| 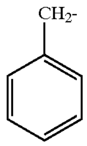 | 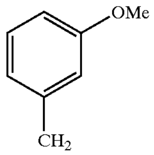 |
| 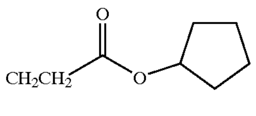 | 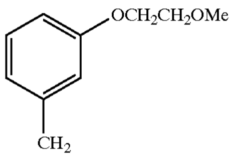 |
| 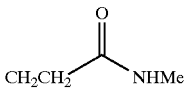 | 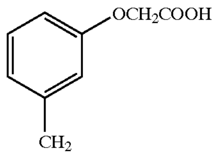 |
| 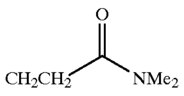 | 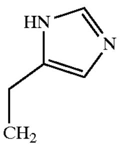 |

TABLE 7p-continued
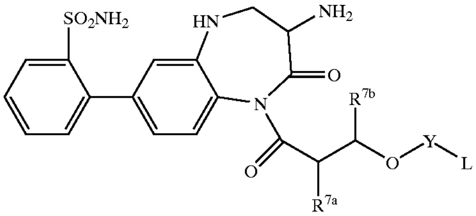
Formula VIIIp
| $R^{7a}$ | $R^{7b}$ |
|---|---|
| 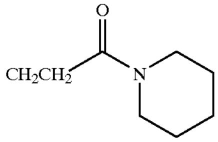 | 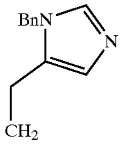 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 7q
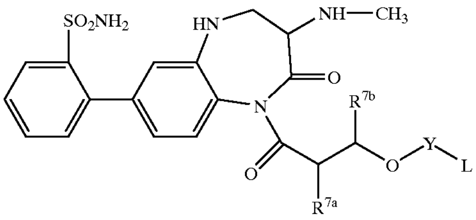
Formula VIIIq
| $R^{7a}$ | $R^{7b}$ |
|---|---|
| H | H |
| Me | Me |
| 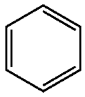 | 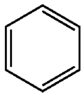 |
| 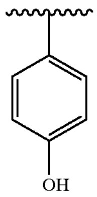 | 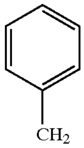 |
| 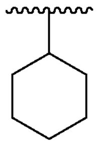 | 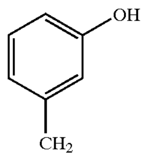 |
TABLE 7q-continued
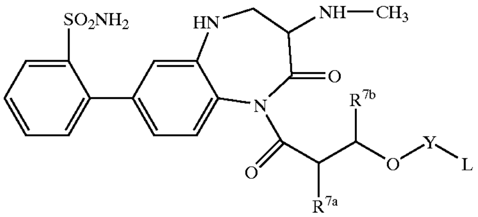
Formula VIIIq
| $R^{7a}$ | $R^{7b}$ |
|---|---|
| 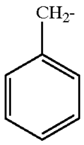 | 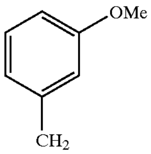 |
| 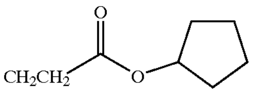 | 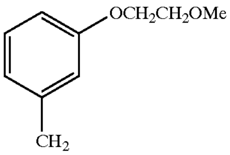 |
| 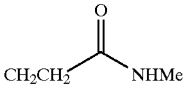 | 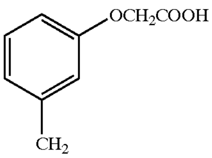 |
| 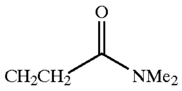 | 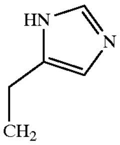 |
| 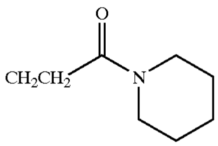 | 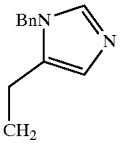 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |

TABLE 8
Formula IX
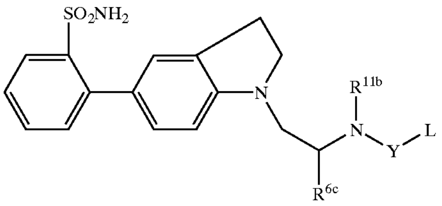
| $R^{6c}$ | $R^{11b}$ |
|---|---|
| H | H |
| Me | Me |
| Br | Me |
| H | Cl |
| Me | Cl |
| Et | Cl |
| 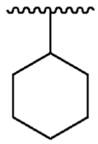 | 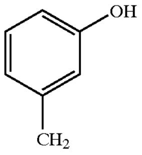 |
| 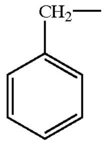 | 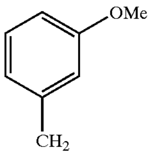 |
| 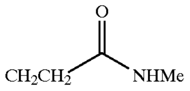 | 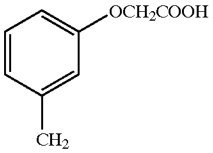 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 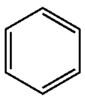 | 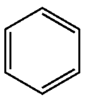 |
| 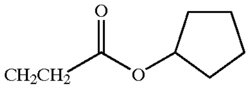 | 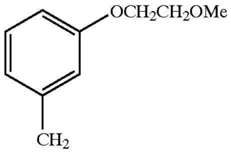 |
| 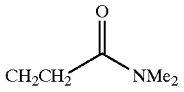 | 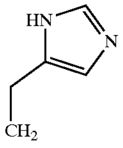 |
TABLE 8-continued
Formula IX
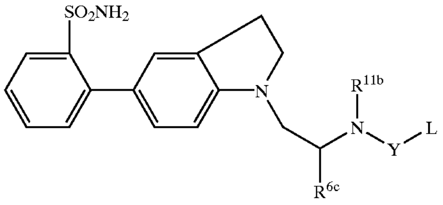
| $R^{6c}$ | $R^{11b}$ |
|---|---|
| —NH2 | H |
| H | Et |
| Et | F |
| Me | Et |
| SO2Me | Cl |
TABLE 8a
Formula IXa
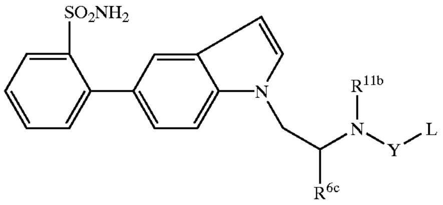
| $R^{6c}$ | $R^{11b}$ |
|---|---|
| H | H |
| Me | Me |
| Br | Me |
| H | Cl |
| Me | Cl |
| Et | Cl |
| 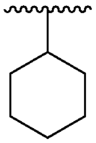 | 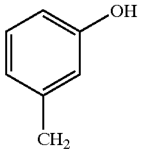 |
| 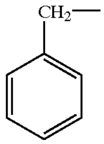 | 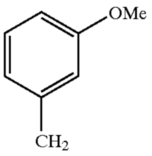 |
| 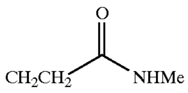 | 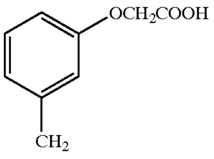 |
| OCH2Ph | H |
| OCH2CH2OMe | H |
| Me | F |
| Me | H |
| SO2Me | H |
| OMe | H |
| OMe | Me |
| F | H |
| Et | H |

TABLE 8a-continued
Formula IXa
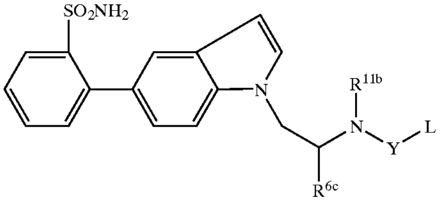
| $R^{6c}$ | $R^{11b}$ |
| --- | --- |
| —OH | Me |
| Et | Br |
| 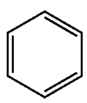 | 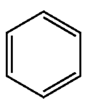 |
| 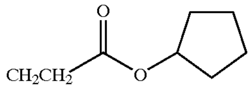 | 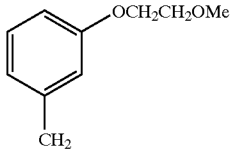 |
| 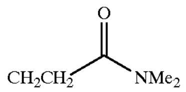 | 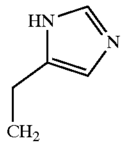 |
| —NH2 | H |
| H | Et |
| Et | F |
| Me | Et |
| SO2Me | Cl |
TABLE 8b
Formula IXb
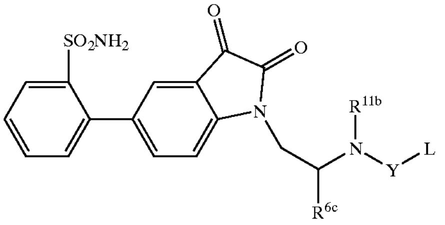
| $R^{6c}$ | $R^{11b}$ |
| --- | --- |
| H | H |
| Me | Me |
| Br | Me |
| H | Cl |
| Me | Cl |
| Et | Cl |
| 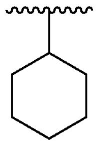 | 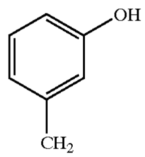 |
TABLE 8b-continued
Formula IXb
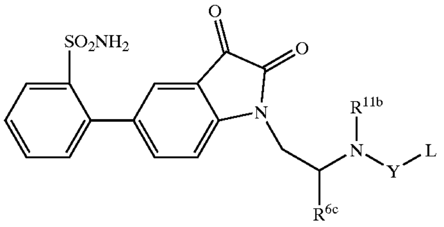
| $R^{6c}$ | $R^{11b}$ |
| --- | --- |
| 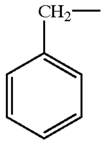 | 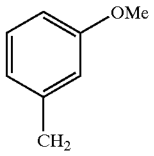 |
| 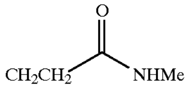 | 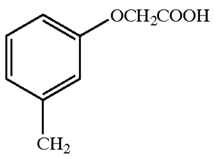 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 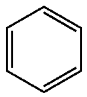 | 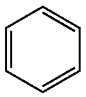 |
| 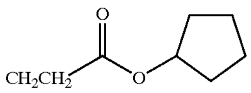 | 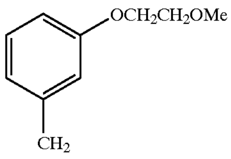 |
| 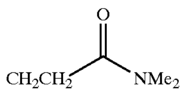 | 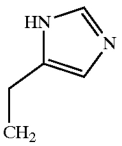 |
| —NH2 | H |
| H | Et |
| Et | F |
| Me | Et |
| SO2Me | Cl |

TABLE 8c
Formula IXc
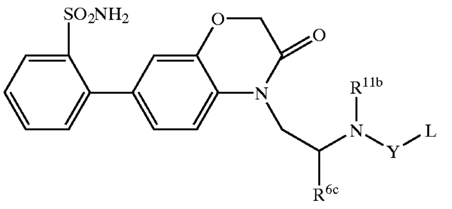
| $R^{6c}$ | $R^{11b}$ |
|---|---|
| H | H |
| Me | Me |
| Br | Me |
| H | Cl |
| Me | Cl |
| Et | Cl |
| 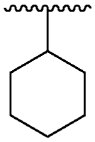 | 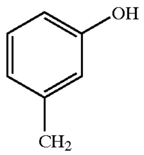 |
| 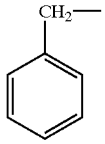 | 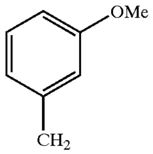 |
| 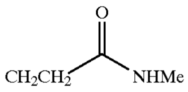 | 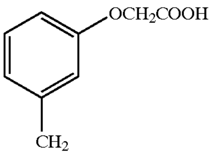 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 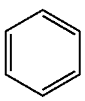 | 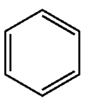 |
| 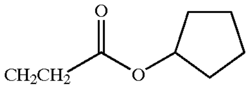 | 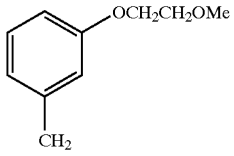 |
| 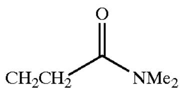 | 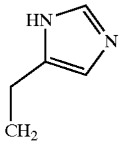 |
TABLE 8c-continued
Formula IXc
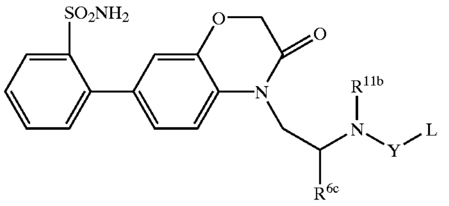
| $R^{6c}$ | $R^{11b}$ |
|---|---|
| —NH2 | H |
| H | Et |
| Et | F |
| Me | Et |
| SO2Me | Cl |
TABLE 8d
Formula IXd
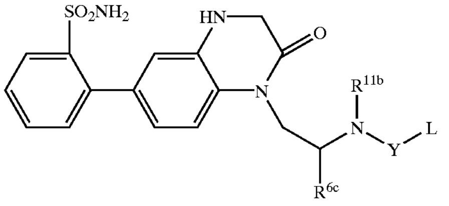
| $R^{6c}$ | $R^{11b}$ |
|---|---|
| H | H |
| Me | Me |
| Br | Me |
| H | Cl |
| Me | Cl |
| Et | Cl |
| 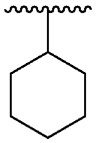 | 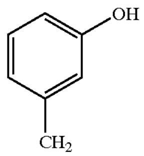 |
| 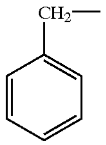 | 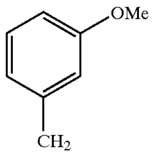 |
| 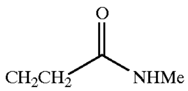 | 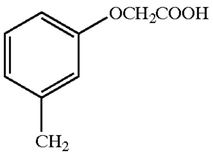 |
| OCH2Ph | H |
| OCH2CH2OMe | H |
| Me | F |
| Me | H |
| SO2Me | H |
| OMe | H |
| OMe | Me |
| F | H |
| Et | H |

TABLE 8d-continued
Formula IXd
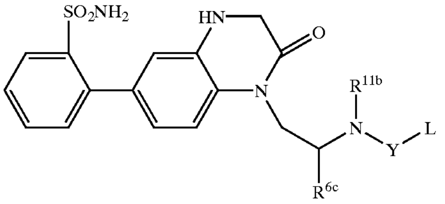
| $R^{6c}$ | $R^{11b}$ |
|---|---|
| —OH | Me |
| Et | Br |
| 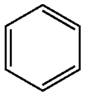 | 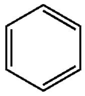 |
| 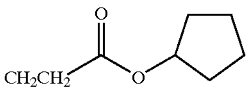 | 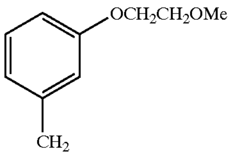 |
| 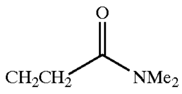 | 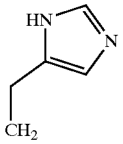 |
| —NH2 | H |
| H | Et |
| Et | F |
| Me | Et |
| SO2Me | Cl |
TABLE 8e
Formula IXe
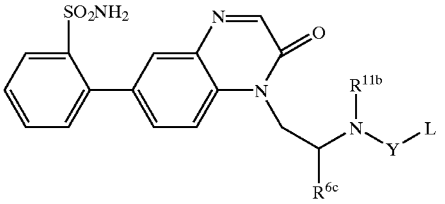
| $R^{6c}$ | $R^{11b}$ |
|---|---|
| H | H |
| Me | Me |
| Br | Me |
| H | Cl |
| Me | Cl |
| Et | Cl |
| 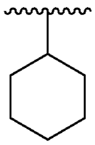 | 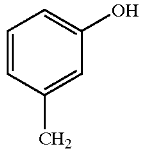 |
TABLE 8e-continued
Formula IXe
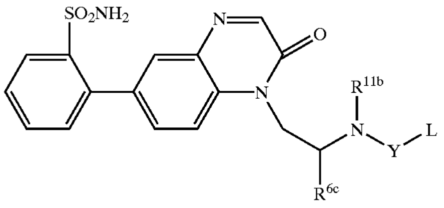
| $R^{6c}$ | $R^{11b}$ |
|---|---|
| 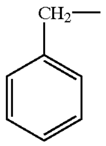 | 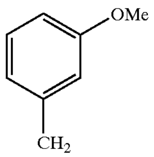 |
| 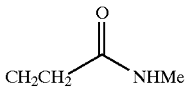 | 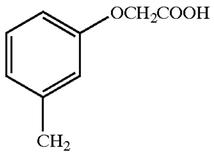 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 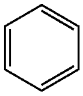 | 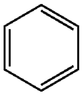 |
| 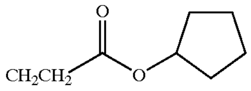 | 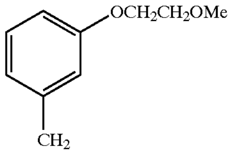 |
| 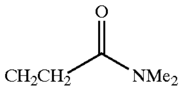 | 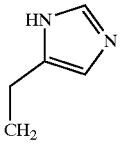 |
| —NH2 | H |
| H | Et |
| Et | F |
| Me | Et |
| SO2Me | Cl |

TABLE 8f
Formula IXf
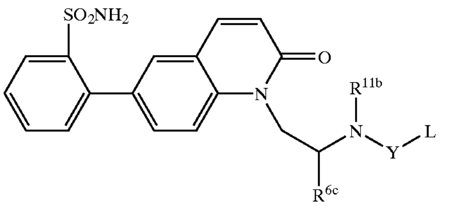
| $R^{6c}$ | $R^{11b}$ |
|---|---|
| H | H |
| Me | Me |
| Br | Me |
| H | Cl |
| Me | Cl |
| Et | Cl |
| 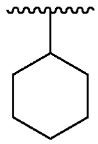 | 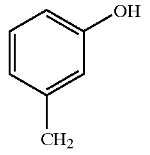 |
| 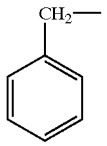 | 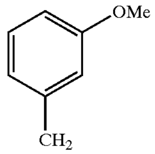 |
| 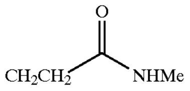 | 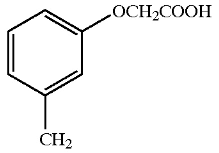 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 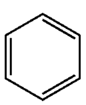 | 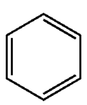 |
| 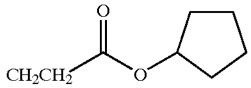 | 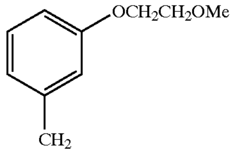 |
| 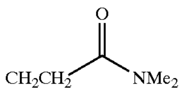 | 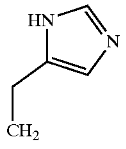 |
TABLE 8f-continued
Formula IXf
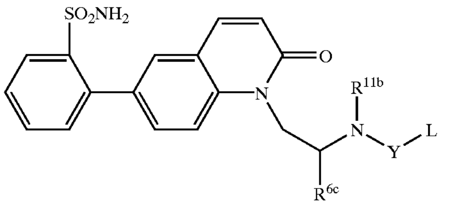
| $R^{6c}$ | $R^{11b}$ |
|---|---|
| —NH2 | H |
| H | Et |
| Et | F |
| Me | Et |
| SO2Me | Cl |
TABLE 8g
Formula IXg
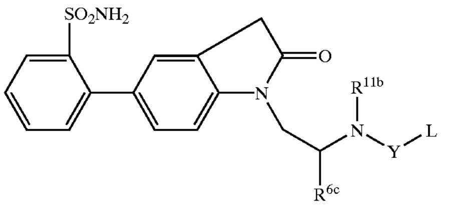
| $R^{6c}$ | $R^{11b}$ |
|---|---|
| H | H |
| Me | Me |
| Br | Me |
| H | Cl |
| Me | Cl |
| Et | Cl |
| 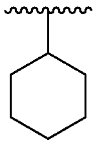 | 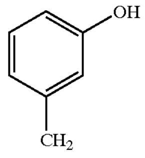 |
| 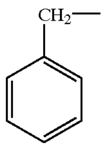 | 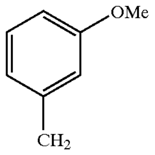 |
| 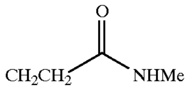 | 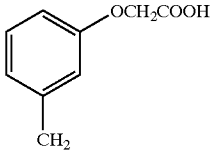 |
| OCH2Ph | H |
| OCH2CH2OMe | H |
| Me | F |
| Me | H |
| SO2Me | H |
| OMe | H |
| OMe | Me |
| F | H |
| Et | H |

TABLE 8g-continued
Formula IXg
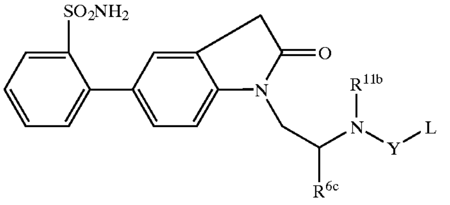
| $R^{6c}$ | $R^{11b}$ |
|---|---|
| —OH | Me |
| Et | Br |
| 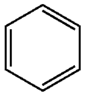 | 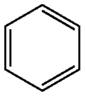 |
| 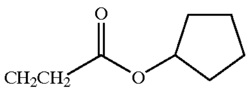 | 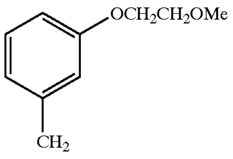 |
| 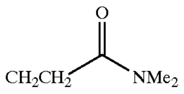 | 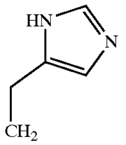 |
| —NH2 | H |
| H | Et |
| Et | F |
| Me | Et |
| SO2Me | Cl |
TABLE 8h
Formula IXh
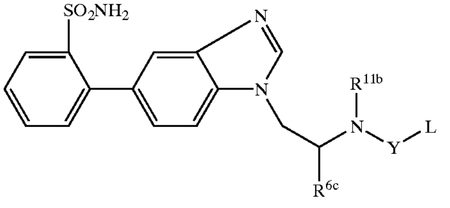
| $R^{6c}$ | $R^{11b}$ |
|---|---|
| H | H |
| Me | Me |
| Br | Me |
| H | Cl |
| Me | Cl |
| Et | Cl |
| 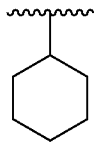 | 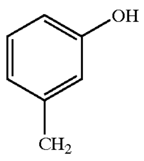 |
TABLE 8h-continued
Formula IXh
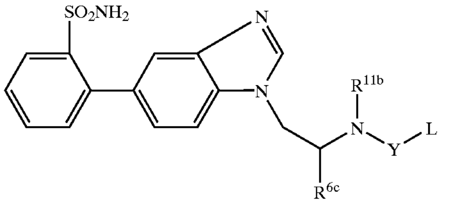
| $R^{6c}$ | $R^{11b}$ |
|---|---|
| 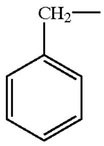 | 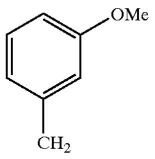 |
| 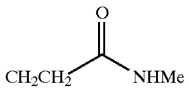 | 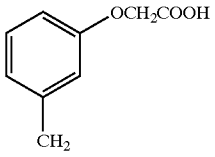 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 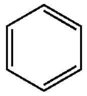 | 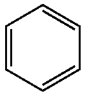 |
| 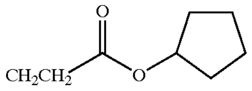 | 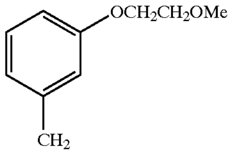 |
| 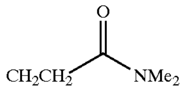 | 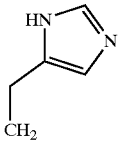 |
| —NH2 | H |
| H | Et |
| Et | F |
| Me | Et |
| SO2Me | Cl |

TABLE 8i
Formula IXi
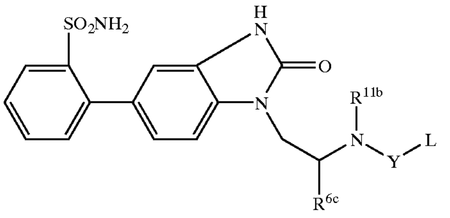
| $R^{6c}$ | $R^{11b}$ |
|---|---|
| H | H |
| Me | Me |
| Br | Me |
| H | Cl |
| Me | Cl |
| Et | Cl |
| 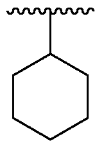 | 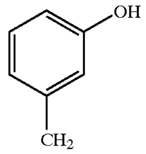 |
| 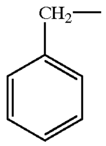 | 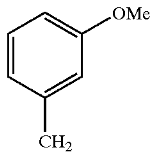 |
| 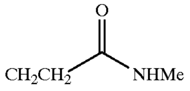 | 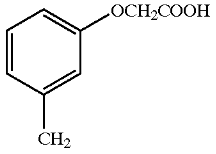 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 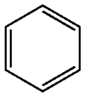 | 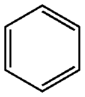 |
| 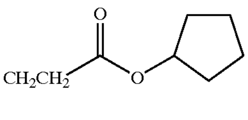 | 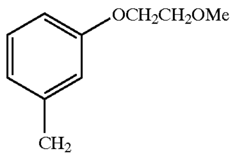 |
| 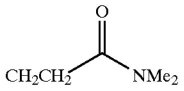 | 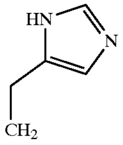 |
TABLE 8i-continued
Formula IXi
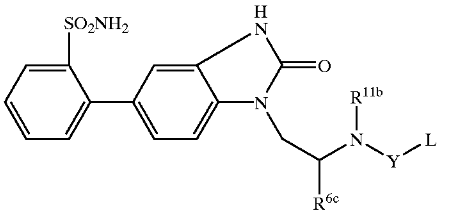
| $R^{6c}$ | $R^{11b}$ |
|---|---|
| —NH2 | H |
| H | Et |
| Et | F |
| Me | Et |
| SO2Me | Cl |
TABLE 8j
Formula IXj
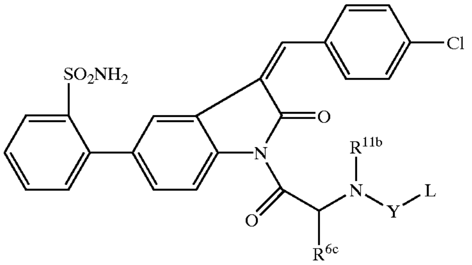
| $R^{6c}$ | $R^{11b}$ |
|---|---|
| H | H |
| Me | Me |
| Br | Me |
| H | Cl |
| Me | Cl |
| Et | Cl |
| 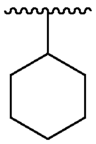 | 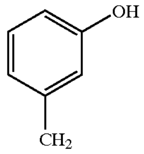 |
| 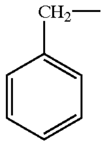 | 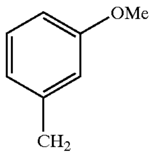 |
| 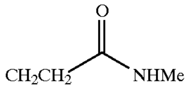 | 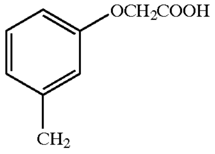 |
| OCH2Ph | H |
| OCH2CH2OMe | H |
| Me | F |
| Me | H |
| SO2Me | H |

TABLE 8j-continued
Formula IXj
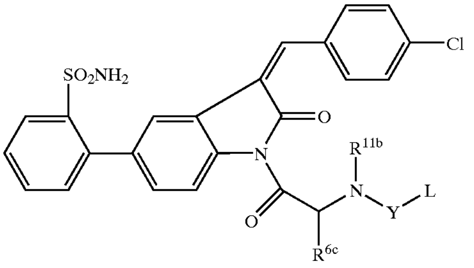
| $R^{6c}$ | $R^{11b}$ |
| --- | --- |
| OMe | H |
| OMe | Me |
| F | H |
| Et | H |
| —OH | Me |
| Et | Br |
| 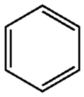 | 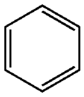 |
| 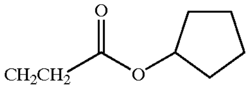 | 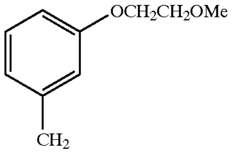 |
| 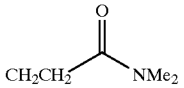 | 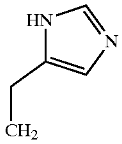 |
| —NH2 | H |
| H | Et |
| Et | F |
| Me | Et |
| SO2Me | Cl |
TABLE 8k
Formula IXk
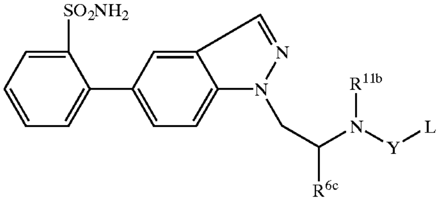
| $R^{6c}$ | $R^{11b}$ |
| --- | --- |
| H | H |
| Me | Me |
| Br | Me |
| H | Cl |
| Me | Cl |
| Et | Cl |
TABLE 8k-continued
Formula IXk
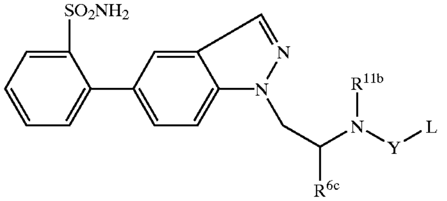
| $R^{6c}$ | $R^{11b}$ |
| --- | --- |
| 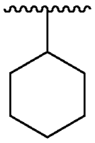 | 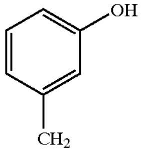 |
| 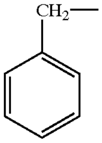 | 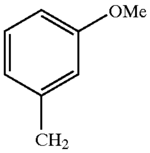 |
| 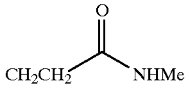 | 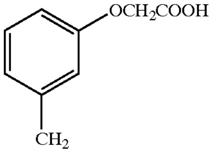 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 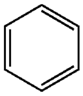 | 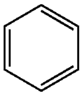 |
| 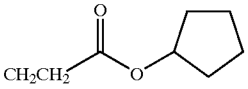 | 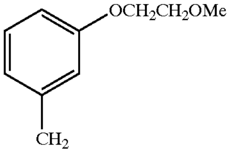 |
| 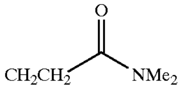 | 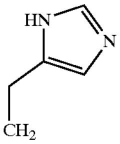 |
| —NH2 | H |
| H | Et |
| Et | F |
| Me | Et |
| SO2Me | Cl |

TABLE 8(l)
Formula IX(l)
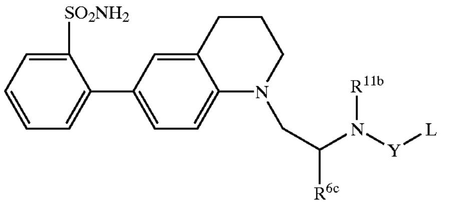
| $R^{6c}$ | $R^{11b}$ |
|---|---|
| H | H |
| Me | Me |
| Br | Me |
| H | Cl |
| Me | Cl |
| Et | Cl |
| 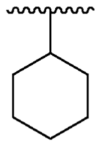 | 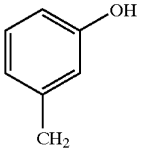 |
| 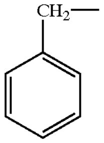 | 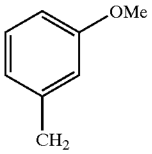 |
| 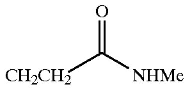 | 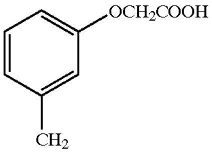 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 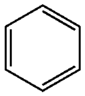 | 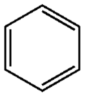 |
| 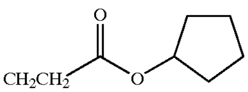 | 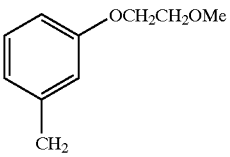 |
| 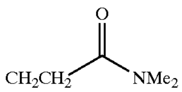 | 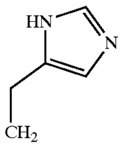 |
TABLE 8(l)-continued
Formula IX(l)
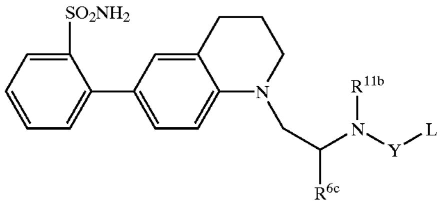
| $R^{6c}$ | $R^{11b}$ |
|---|---|
| —NH2 | H |
| H | Et |
| Et | F |
| Me | Et |
| SO2Me | Cl |
TABLE 8m
Formula IXm
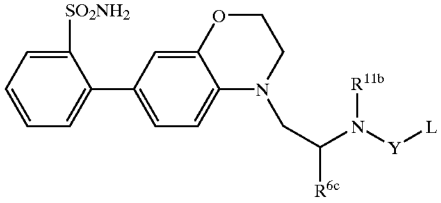
| $R^{6c}$ | $R^{11b}$ |
|---|---|
| H | H |
| Me | Me |
| 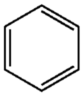 | 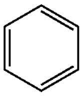 |
| 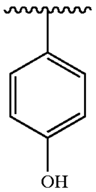 | 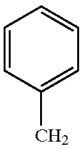 |
| 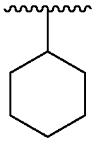 | 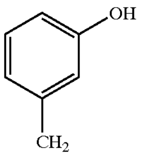 |
| 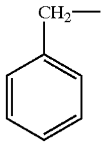 | 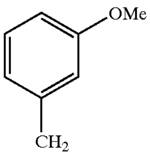 |

TABLE 8m-continued
Formula IXm
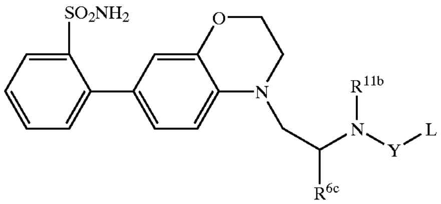
| $R^{6c}$ | $R^{11b}$ |
|---|---|
| 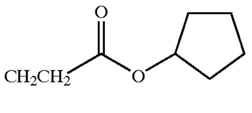 | 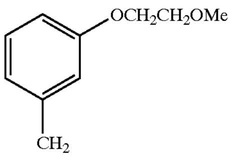 |
| 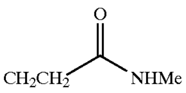 | 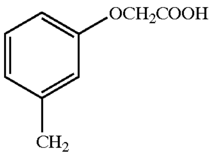 |
| 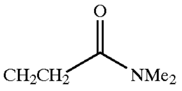 | 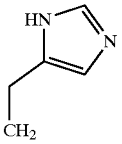 |
| 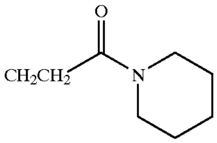 | 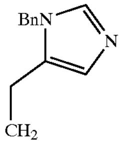 |
| OMe | H |
| OMe | Me |
| F | H |
| —OH | Me |
| Br | Me |
| —NH2 | H |
| OCH2Ph | H |
| OCH2CH2OMe | H |
| H | Et |
| Me | Et |
TABLE 8n
Formula IXn
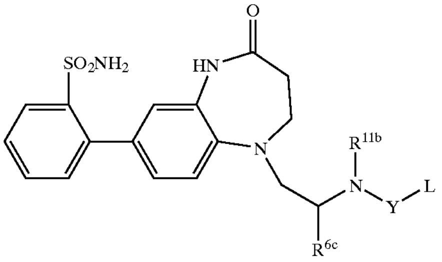
| $R^{6c}$ | $R^{11b}$ |
|---|---|
| H | H |
TABLE 8n-continued
Formula IXn
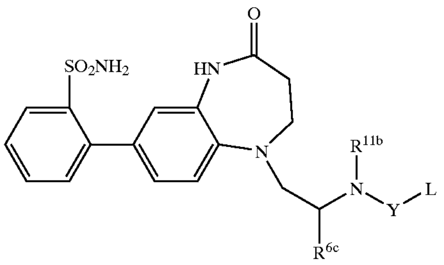
| $R^{6c}$ | $R^{11b}$ |
|---|---|
| Me | Me |
| Br | Me |
| H | Cl |
| Me | Cl |
| Et | Cl |
| 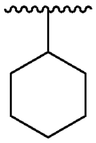 | 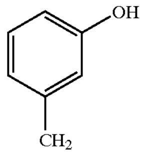 |
| 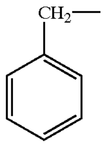 | 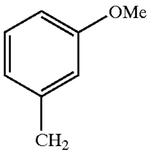 |
| 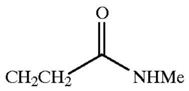 | 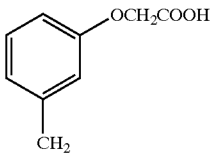 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 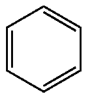 | 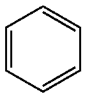 |
| 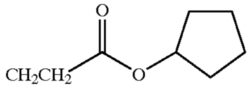 | 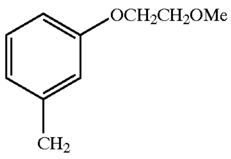 |

TABLE 8n-continued
Formula IXn
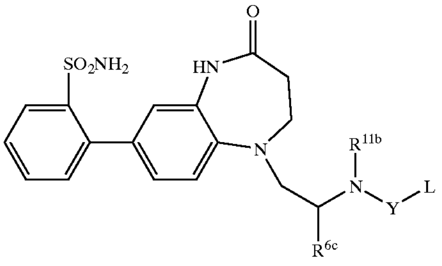
| $R^{6c}$ | $R^{11b}$ |
|---|---|
| 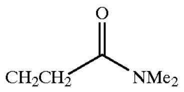 | 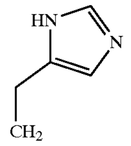 |
| —NH2 | H |
| H | Et |
| Et | F |
| Me | Et |
| SO2Me | Cl |
TABLE 8o
Formula IXo
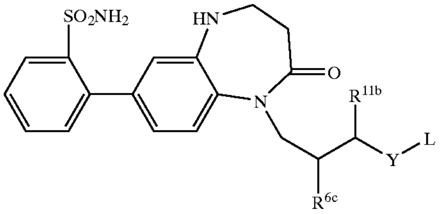
| $R^{6c}$ | $R^{11b}$ |
|---|---|
| H | H |
| Me | Me |
| Br | Me |
| H | Cl |
| Me | Cl |
| Et | Cl |
| 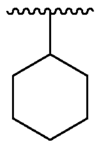 | 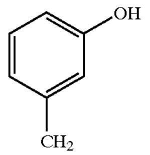 |
| 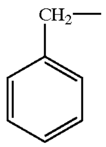 | 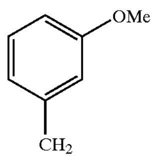 |
TABLE 8o-continued
Formula IXo
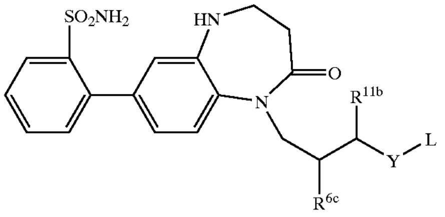
| $R^{6c}$ | $R^{11b}$ |
|---|---|
| 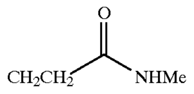 | 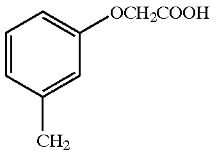 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 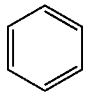 | 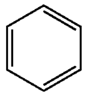 |
| 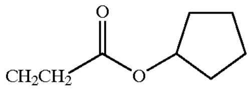 | 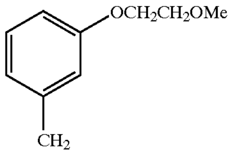 |
| 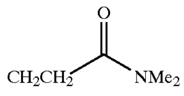 | 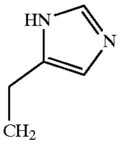 |
| —NH2 | H |
| H | Et |
| Et | F |
| Me | Et |
| SO2Me | Cl |

TABLE 8p
Formula IXp
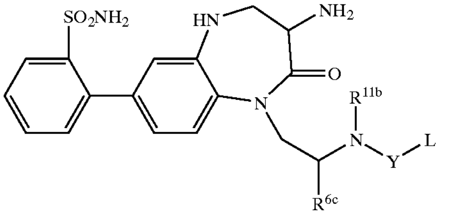
| $R^{6c}$ | $R^{11b}$ |
|---|---|
| H | H |
| Me | Me |
| Br | Me |
| H | Cl |
| Me | Cl |
| Et | Cl |
| 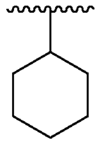 | 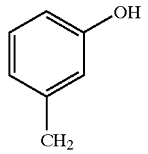 |
| 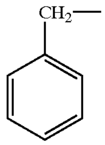 | 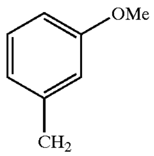 |
| 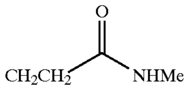 | 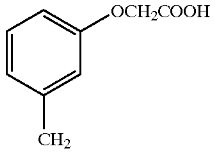 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 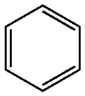 | 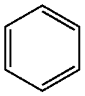 |
| 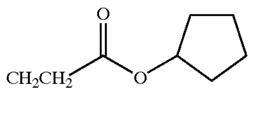 | 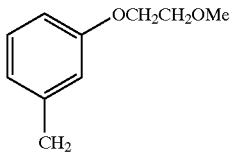 |
| 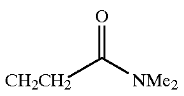 | 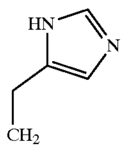 |
TABLE 8p-continued
Formula IXp
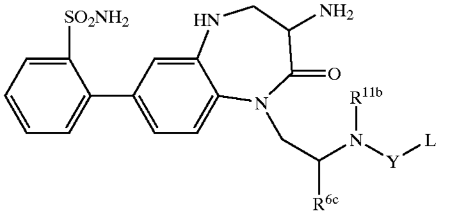
| $R^{6c}$ | $R^{11b}$ |
|---|---|
| —NH2 | H |
| H | Et |
| Et | F |
| Me | Et |
| SO2Me | Cl |
TABLE 8q
Formula IXq
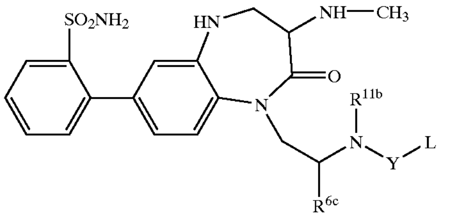
| $R^{6c}$ | $R^{11b}$ |
|---|---|
| H | H |
| Me | Me |
| Br | Me |
| H | Cl |
| Me | Cl |
| Et | Cl |
| 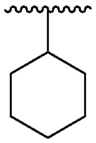 | 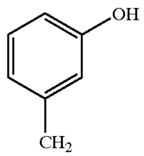 |
| 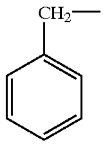 | 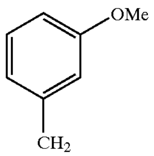 |
| 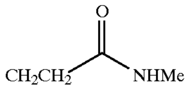 | 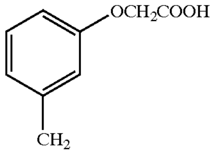 |
| OCH2Ph | H |
| OCH2CH2OMe | H |
| Me | F |
| Me | H |
| SO2Me | H |
| OMe | H |
| OMe | Me |

TABLE 8q-continued
Formula IXq
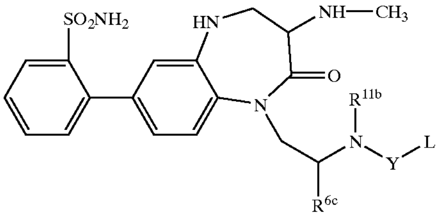
| $R^{6c}$ | $R^{11b}$ |
|---|---|
| F | H |
| Et | H |
| —OH | Me |
| Et | Br |
| 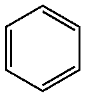 | 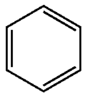 |
| 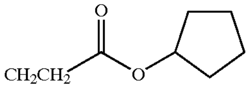 | 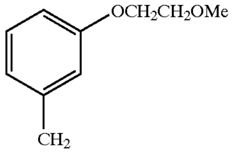 |
| 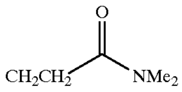 | 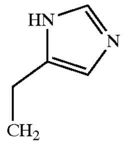 |
| —NH2 | H |
| H | Et |
| Et | F |
| Me | Et |
| SO2Me | Cl |
TABLE 9
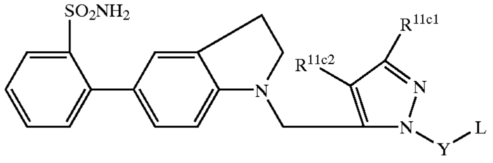
Formula X
| $R^{11c1}$ | $R^{11c2}$ |
|---|---|
| H | H |
| Me | Me |
| Br | Me |
| H | Cl |
| Me | Cl |
| Et | Cl |
| 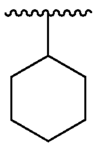 | 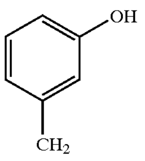 |
TABLE 9-continued
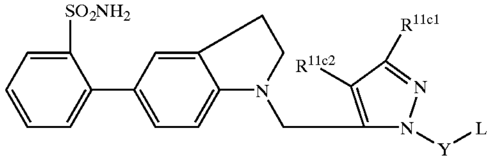
Formula X
| $R^{11c1}$ | $R^{11c2}$ |
|---|---|
| 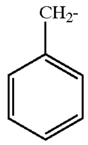 | 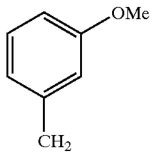 |
| 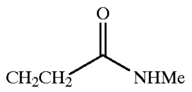 | 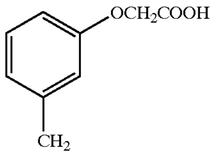 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 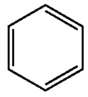 | 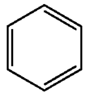 |
| 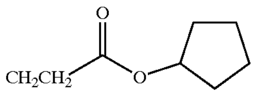 | 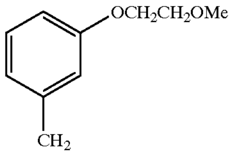 |
| 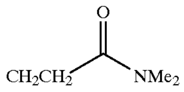 | 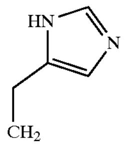 |
| —NH2 | H |
| H | Et |
| Et | F |
| Me | Et |
| SO2Me | Cl |

TABLE 9a
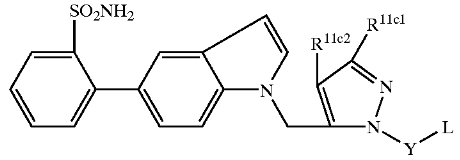
Formula Xa
| $R^{11c1}$ | $R^{11c2}$ |
|---|---|
| H | H |
| Me | Me |
| Br | Me |
| H | Cl |
| Me | Cl |
| Et | Cl |
| 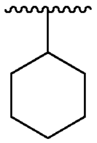 | 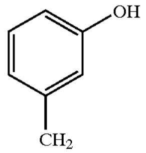 |
| 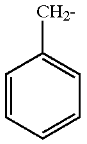 | 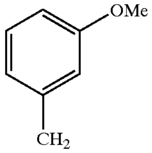 |
| 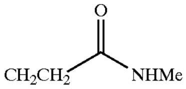 | 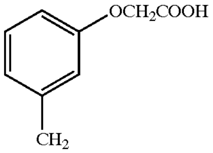 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 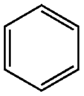 | 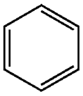 |
| 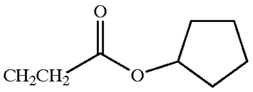 | 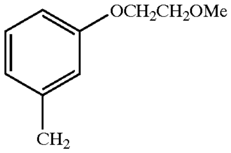 |
| 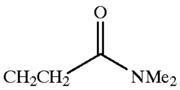 | 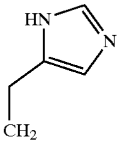 |
| —NH2 | H |
| H | Et |
TABLE 9a-continued
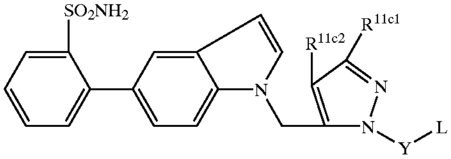
Formula Xa
| $R^{11c1}$ | $R^{11c2}$ |
|---|---|
| Et | F |
| Me | Et |
| SO2Me | Cl |
TABLE 9b
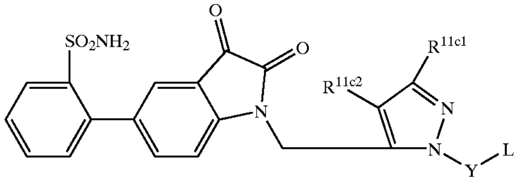
Formula Xb
| $R^{11c1}$ | $R^{11c2}$ |
|---|---|
| H | H |
| Me | Me |
| Br | Me |
| H | Cl |
| Me | Cl |
| Et | Cl |
| 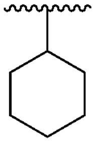 | 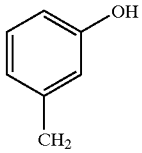 |
| 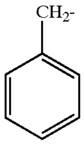 | 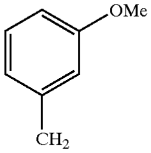 |
| 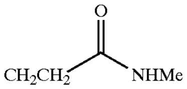 | 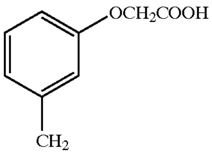 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |

TABLE 9b-continued
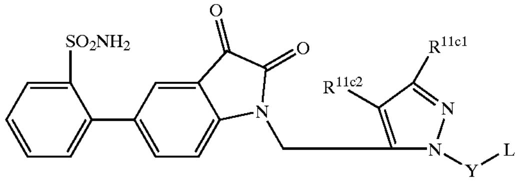
Formula Xb
| $R^{11c1}$ | $R^{11c2}$ |
|---|---|
| 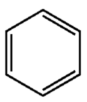 | 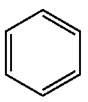 |
| 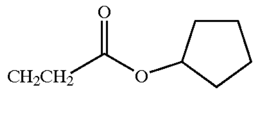 | 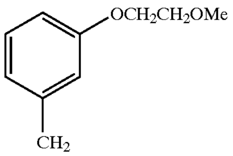 |
| 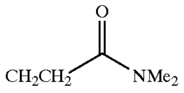 | 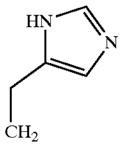 |
| —NH2 | H |
| H | Et |
| Et | F |
| Me | Et |
| SO2Me | Cl |
TABLE 9c
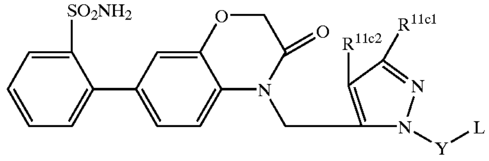
Formula Xc
| $R^{11c1}$ | $R^{11c2}$ |
|---|---|
| H | H |
| Me | Me |
| Br | Me |
| H | Cl |
| Me | Cl |
| Et | Cl |
| 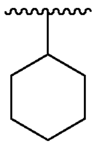 | 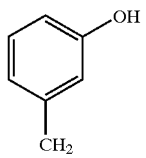 |
| 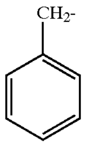 | 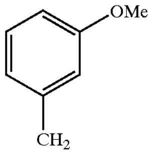 |
TABLE 9c-continued
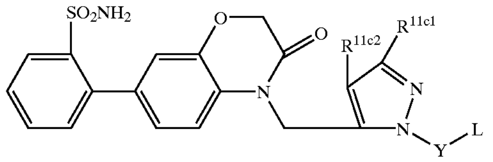
Formula Xc
| $R^{11c1}$ | $R^{11c2}$ |
|---|---|
| 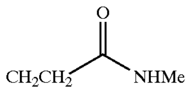 | 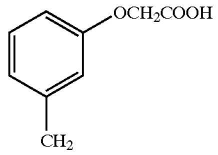 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 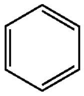 | 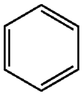 |
| 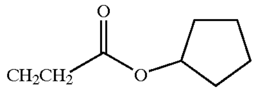 | 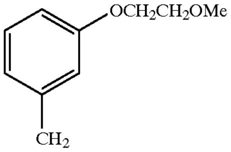 |
| 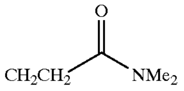 | 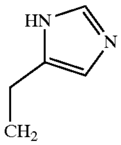 |
| —NH2 | H |
| H | Et |
| Et | F |
| Me | Et |
| SO2Me | Cl |
TABLE 9d
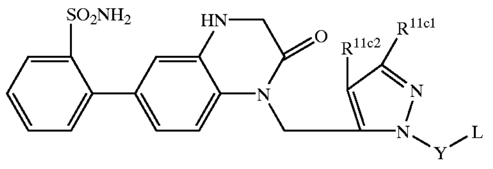
Formula Xd
| $R^{11c1}$ | $R^{11c2}$ |
|---|---|
| H | H |
| Me | Me |

TABLE 9d-continued
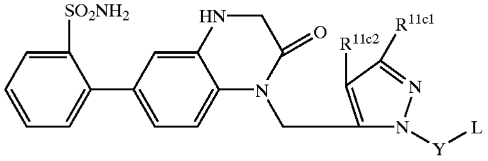
Formula Xd
| $R^{11c1}$ | $R^{11c2}$ |
|---|---|
| Br | Me |
| H | Cl |
| Me | Cl |
| Et | Cl |
| 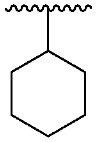 | 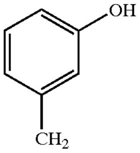 |
| 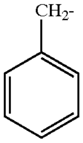 | 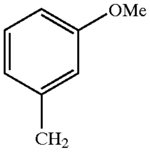 |
| 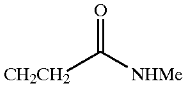 | 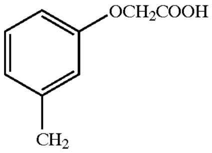 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 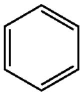 | 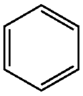 |
| 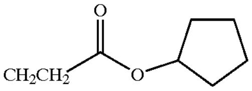 | 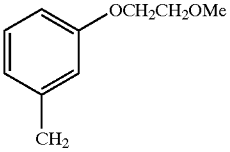 |
| 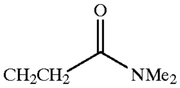 | 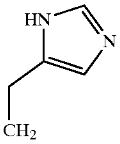 |
| —NH2 | H |
| H | Et |
| Et | F |
TABLE 9d-continued
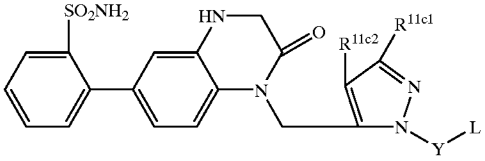
Formula Xd
| $R^{11c1}$ | $R^{11c2}$ |
|---|---|
| Me | Et |
| SO2Me | Cl |
TABLE 9e
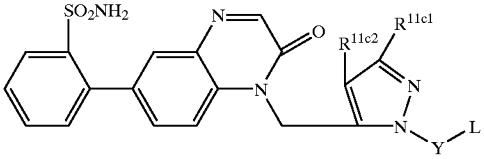
Formula Xe
| $R^{11c1}$ | $R^{11c2}$ |
|---|---|
| H | H |
| Me | Me |
| Br | Me |
| H | Cl |
| Me | Cl |
| Et | Cl |
| 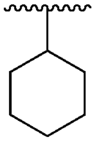 | 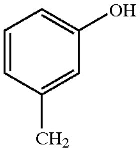 |
| 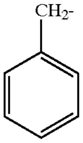 | 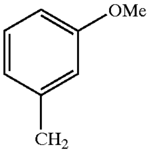 |
| 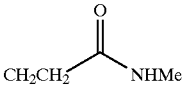 | 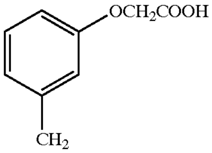 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 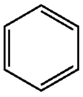 | 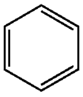 |

TABLE 9e-continued
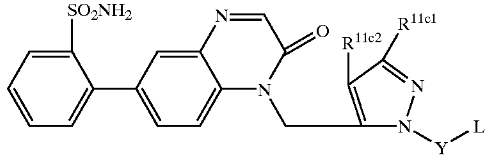
Formula Xe
| $R^{11c1}$ | $R^{11c2}$ |
|---|---|
| 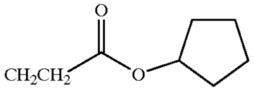 | 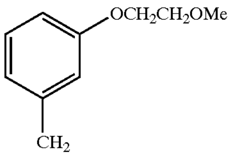 |
| 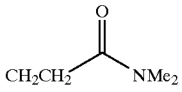 | 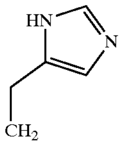 |
| —NH2 | H |
| H | Et |
| Et | F |
| Me | Et |
| SO2Me | Cl |
TABLE 9f
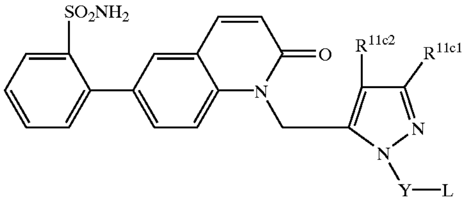
Formula Xf
| $R^{11c1}$ | $R^{11c2}$ |
|---|---|
| H | H |
| Me | Me |
| Br | Me |
| H | Cl |
| Me | Cl |
| Et | Cl |
| 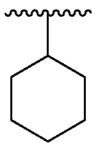 | 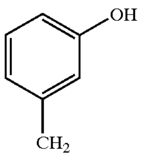 |
| 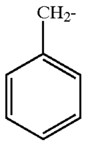 | 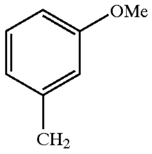 |
TABLE 9f-continued
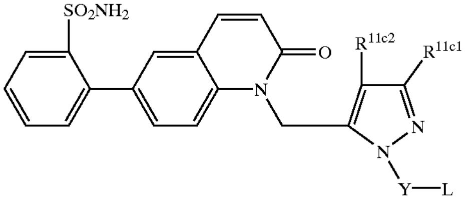
Formula Xf
| $R^{11c1}$ | $R^{11c2}$ |
|---|---|
| 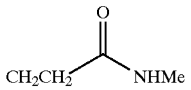 | 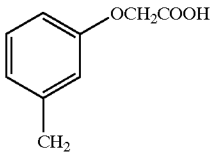 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 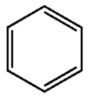 | 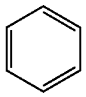 |
| 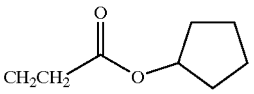 | 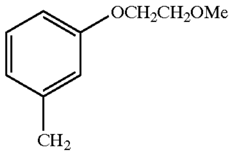 |
| 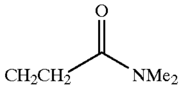 | 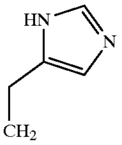 |
| —NH2 | H |
| H | Et |
| Et | F |
| Me | Et |
| SO2Me | Cl |

TABLE 9g
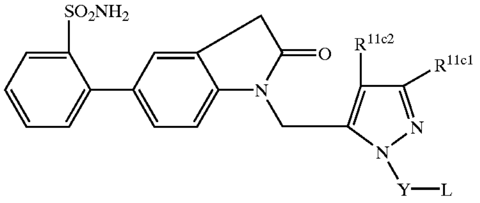
Formula Xg
| $R^{11c1}$ | $R^{11c2}$ |
|---|---|
| H | H |
| Me | Me |
| Br | Me |
| H | Cl |
| Me | Cl |
| Et | Cl |
| 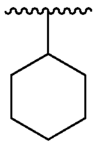 | 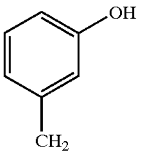 |
| 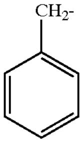 | 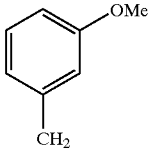 |
| 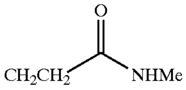 | 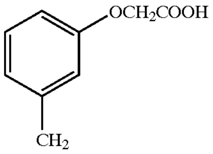 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 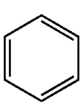 | 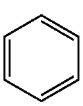 |
| 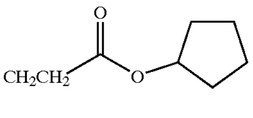 | 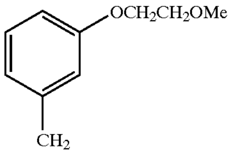 |
| 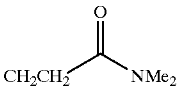 | 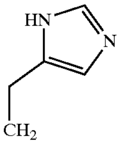 |
TABLE 9g-continued
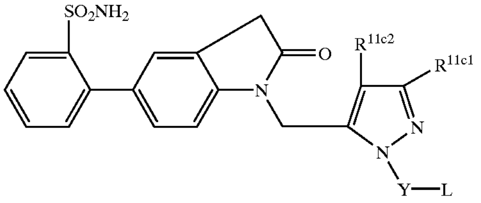
Formula Xg
| $R^{11c1}$ | $R^{11c2}$ |
|---|---|
| —NH2 | H |
| H | Et |
| Et | F |
| Me | Et |
| SO2Me | Cl |
TABLE 9h
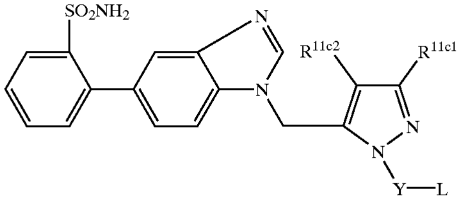
Formula Xh
| $R^{11c1}$ | $R^{11c2}$ |
|---|---|
| H | H |
| Me | Me |
| Br | Me |
| H | Cl |
| Me | Cl |
| Et | Cl |
| 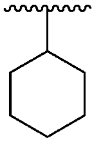 | 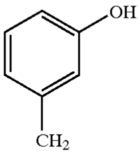 |
| 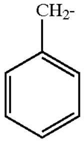 | 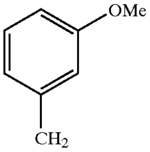 |
| 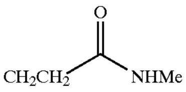 | 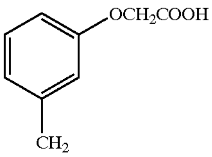 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |

TABLE 9h-continued
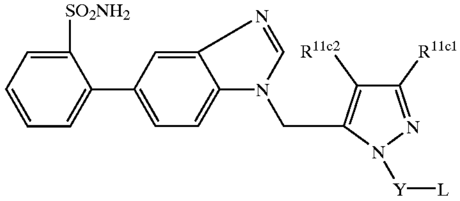
Formula Xh
| $R^{11c1}$ | $R^{11c2}$ |
|---|---|
| Et | Br |
| 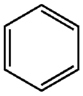 | 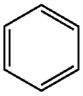 |
| 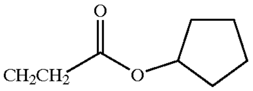 | 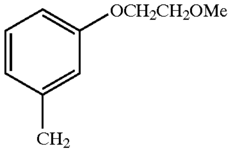 |
| 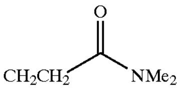 | 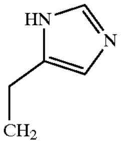 |
| —NH2 | H |
| H | Et |
| Et | F |
| Me | Et |
| SO2Me | Cl |
TABLE 9i
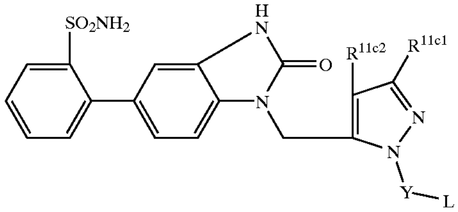
Formula Xi
| $R^{11c1}$ | $R^{11c2}$ |
|---|---|
| H | H |
| Me | Me |
| Br | Me |
| H | Cl |
| Me | Cl |
| Et | Cl |
| 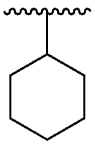 | 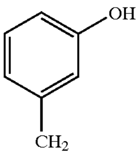 |
TABLE 9i-continued
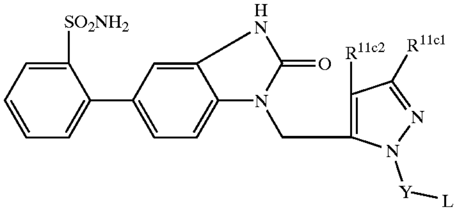
Formula Xi
| $R^{11c1}$ | $R^{11c2}$ |
|---|---|
| 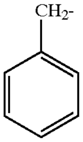 | 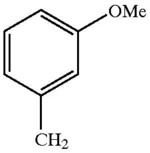 |
| 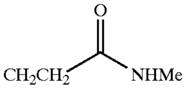 | 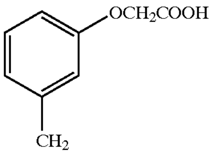 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 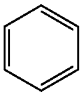 | 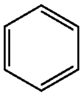 |
| 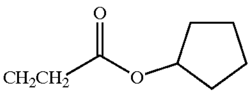 | 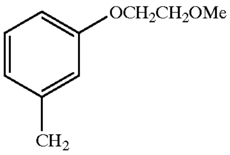 |
| 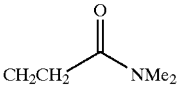 | 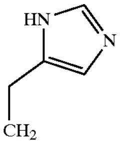 |
| —NH2 | H |
| H | Et |
| Et | F |
| Me | Et |
| SO2Me | Cl |

TABLE 9j
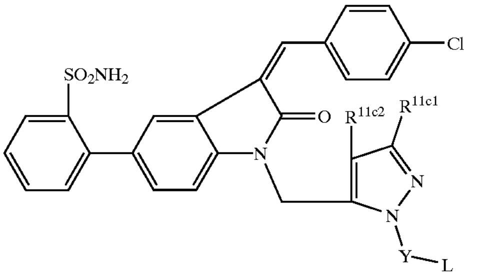
Formula Xj
| $R^{11c1}$ | $R^{11c2}$ |
|---|---|
| H | H |
| Me | Me |
| Br | Me |
| H | Cl |
| Me | Cl |
| Et | Cl |
| 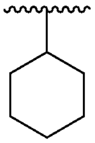 | 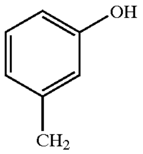 |
| 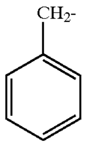 | 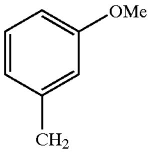 |
| 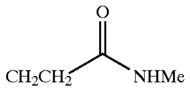 | 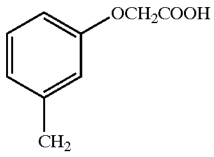 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 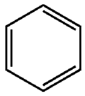 | 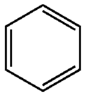 |
| 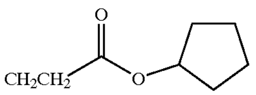 | 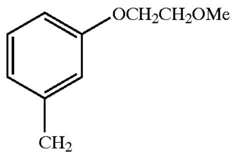 |
TABLE 9j-continued
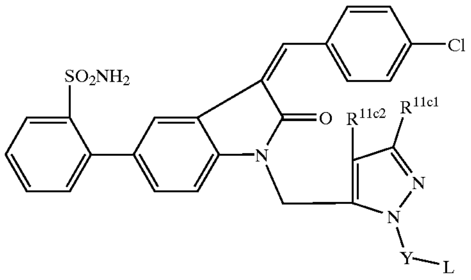
Formula Xj
| $R^{11c1}$ | $R^{11c2}$ |
|---|---|
| 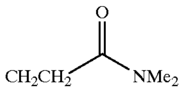 | 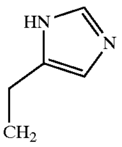 |
| —NH2 | H |
| H | Et |
| Et | F |
| Me | Et |
| SO2Me | Cl |
TABLE 9k
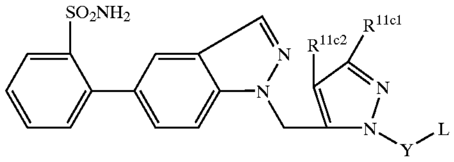
Formula Xk
| $R^{11c1}$ | $R^{11c2}$ |
|---|---|
| H | H |
| Me | Me |
| Br | Me |
| H | Cl |
| Me | Cl |
| Et | Cl |
| 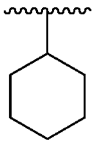 | 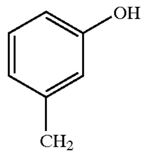 |
| 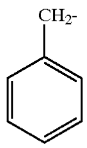 | 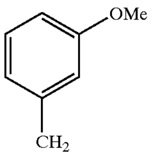 |
| 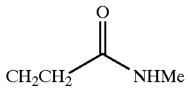 | 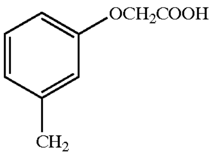 |

TABLE 9k-continued
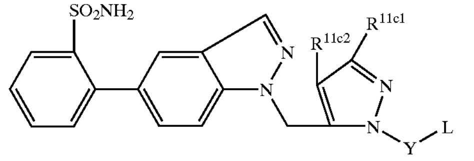
Formula Xk
| $R^{11c1}$ | $R^{11c2}$ |
|---|---|
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 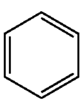 | 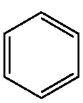 |
| 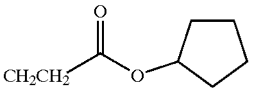 | 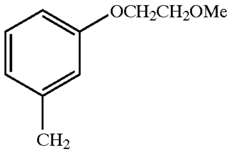 |
| 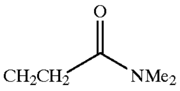 | 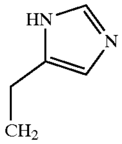 |
| —NH2 | H |
| H | Et |
| Et | F |
| Me | Et |
| SO2Me | Cl |
TABLE 9(l)
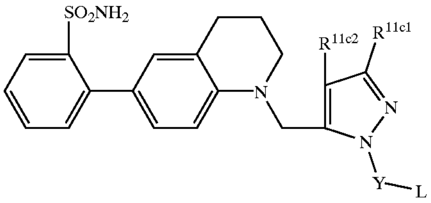
Formula X(l)
| $R^{11c1}$ | $R^{11c2}$ |
|---|---|
| H | H |
| Me | Me |
| Br | Me |
| H | Cl |
| Me | Cl |
| Et | Cl |
TABLE 9(l)-continued
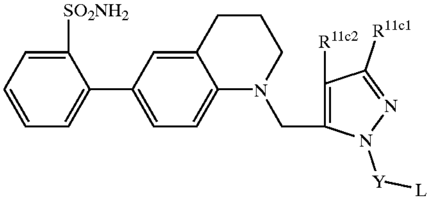
Formula X(l)
| $R^{11c1}$ | $R^{11c2}$ |
|---|---|
| 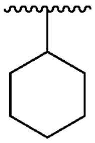 | 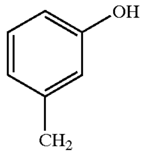 |
| 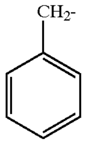 | 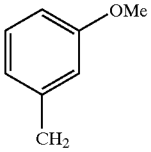 |
| 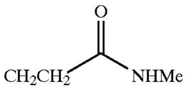 | 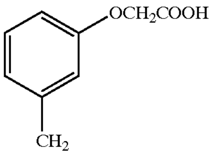 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 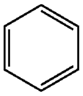 | 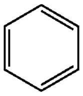 |
| 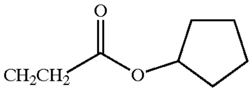 | 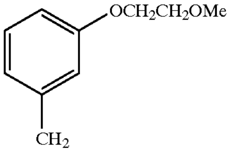 |
| 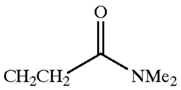 | 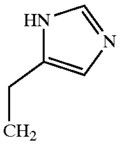 |
| —NH2 | H |
| H | Et |
| Et | F |
| Me | Et |
| SO2Me | Cl |

TABLE 9m
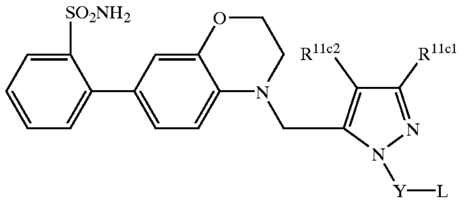
Formula Xm
| $R^{11c1}$ | $R^{11c2}$ |
|---|---|
| H | H |
| Me | Me |
| Br | Me |
| H | Cl |
| Me | Cl |
| Et | Cl |
| 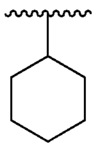 | 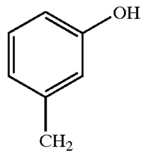 |
| 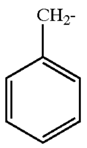 | 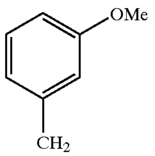 |
| 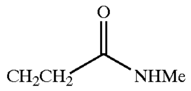 | 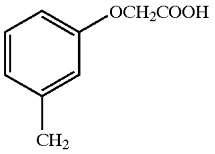 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 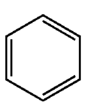 | 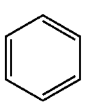 |
| 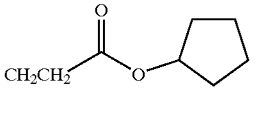 | 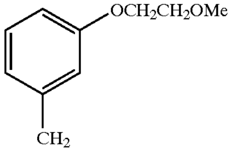 |
| 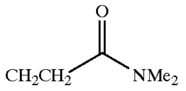 | 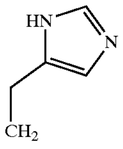 |
TABLE 9m-continued
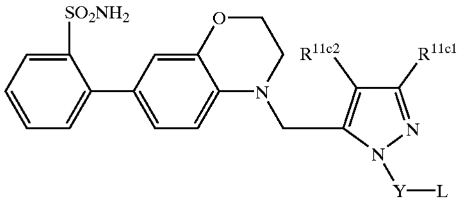
Formula Xm
| $R^{11c1}$ | $R^{11c2}$ |
|---|---|
| —NH2 | H |
| H | Et |
| Et | F |
| Me | Et |
| SO2Me | Cl |
TABLE 9n
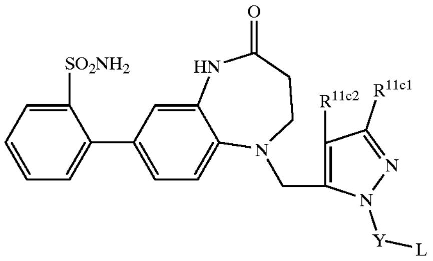
Formula Xn
| $R^{11c1}$ | $R^{11c2}$ |
|---|---|
| H | H |
| Me | Me |
| Br | Me |
| H | Cl |
| Me | Cl |
| Et | Cl |
| 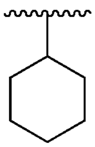 | 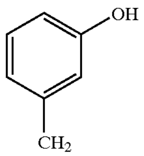 |
| 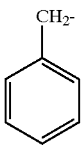 | 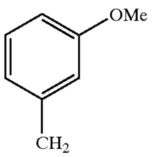 |
| 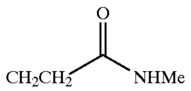 | 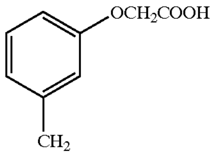 |
| OCH2Ph | H |
| OCH2CH2OMe | H |
| Me | F |
| Me | H |
| SO2Me | H |
| OMe | H |
| OMe | Me |

TABLE 9n-continued
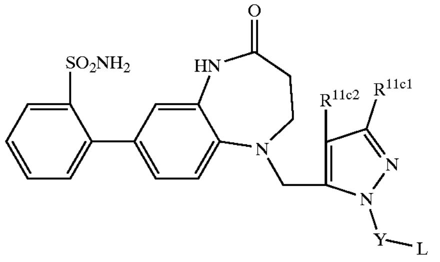
Formula Xn
| $R^{11c1}$ | $R^{11c2}$ |
|---|---|
| F | H |
| Et | H |
| —OH | Me |
| Et | Br |
| 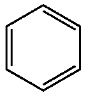 | 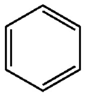 |
| 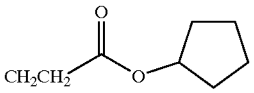 | 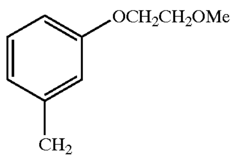 |
| 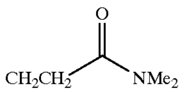 | 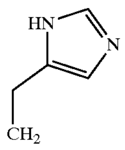 |
| —NH2 | H |
| H | Et |
| Et | F |
| Me | Et |
| SO2Me | Cl |
TABLE 9o
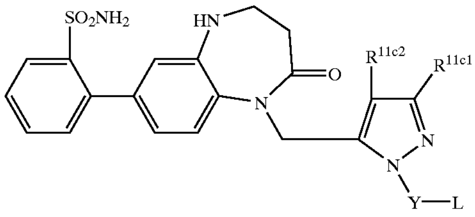
Formula Xo
| $R^{11c1}$ | $R^{11c2}$ |
|---|---|
| H | H |
| Me | Me |
| Br | Me |
| H | Cl |
| Me | Cl |
| Et | Cl |
TABLE 9o-continued
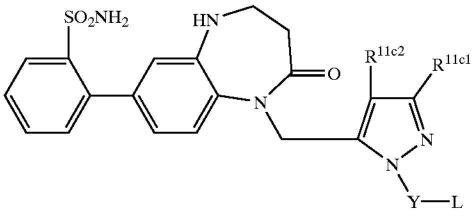
Formula Xo
| $R^{11c1}$ | $R^{11c2}$ |
|---|---|
| 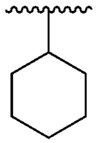 | 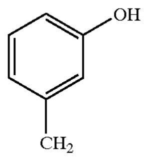 |
| 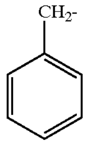 | 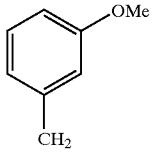 |
| 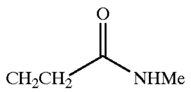 | 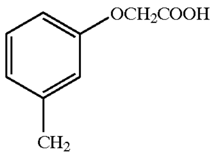 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 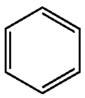 | 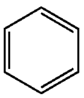 |
| 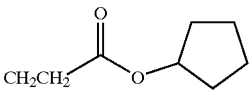 | 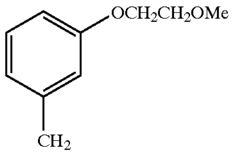 |
| 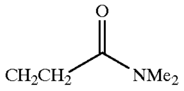 | 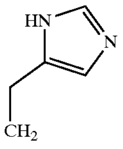 |
| —NH2 | H |
| H | Et |
| Et | F |
| Me | Et |
| SO2Me | Cl |

TABLE 9p
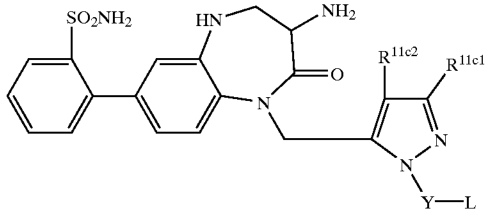
Formula Xp
| $R^{11c1}$ | $R^{11c2}$ |
|---|---|
| H | H |
| Me | Me |
| Br | Me |
| H | Cl |
| Me | Cl |
| Et | Cl |
| 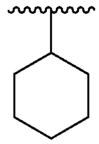 | 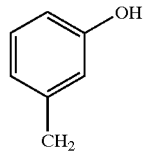 |
| 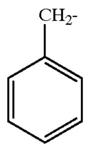 | 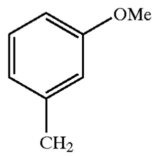 |
| 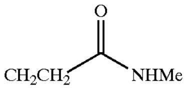 | 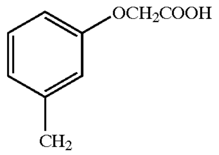 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 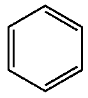 | 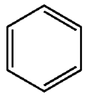 |
| 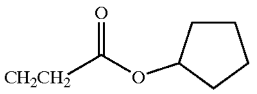 | 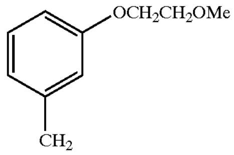 |
| 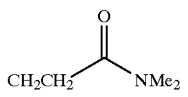 | 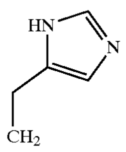 |
TABLE 9p-continued
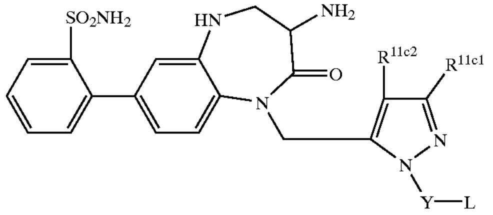
Formula Xp
| $R^{11c1}$ | $R^{11c2}$ |
|---|---|
| —NH2 | H |
| H | Et |
| Et | F |
| Me | Et |
| SO2Me | Cl |
TABLE 9q
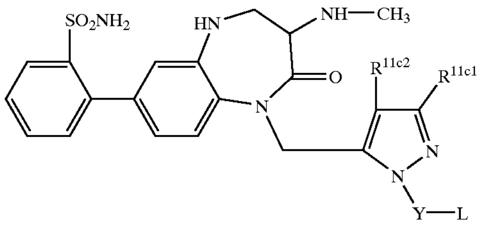
Formula Xq
| $R^{11c1}$ | $R^{11c2}$ |
|---|---|
| H | H |
| Me | Me |
| Br | Me |
| H | Cl |
| Me | Cl |
| Et | Cl |
| 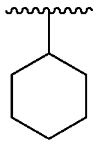 | 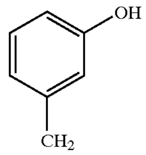 |
| 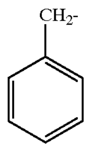 | 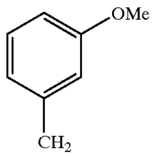 |
| 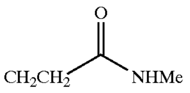 | 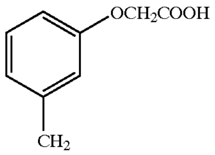 |
| OCH2Ph | H |
| OCH2CH2OMe | H |
| Me | F |
| Me | H |
| SO2Me | H |
| OMe | H |
| OMe | Me |

TABLE 9q-continued
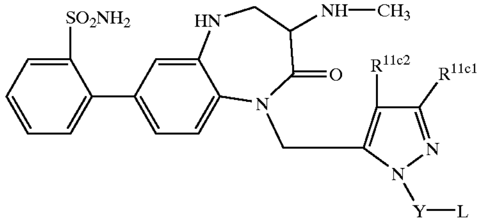
Formula Xq
| $R^{11c1}$ | $R^{11c2}$ |
|---|---|
| F | H |
| Et | H |
| —OH | Me |
| Et | Br |
| 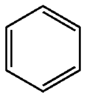 | 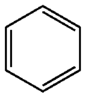 |
| 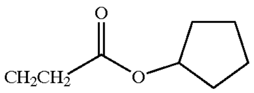 | 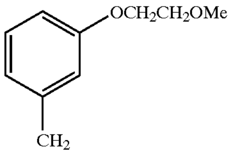 |
| 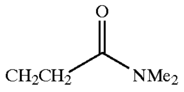 | 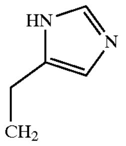 |
| —NH2 | H |
| H | Et |
| Et | F |
| Me | Et |
| SO2Me | Cl |
TABLE 10
Formula XI
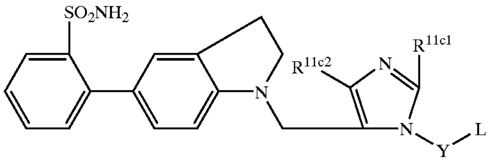
| $R^{11c1}$ | $R^{11c2}$ |
|---|---|
| H | H |
| Me | Me |
| Br | Me |
| H | Cl |
| Me | Cl |
| Et | Cl |
| 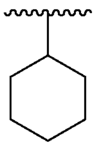 | 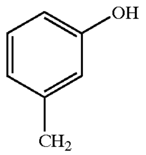 |
TABLE 10-continued
Formula XI
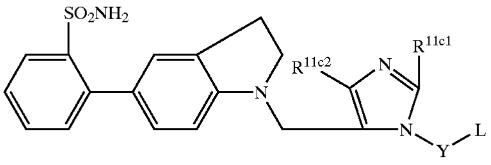
| $R^{11c1}$ | $R^{11c2}$ |
|---|---|
| 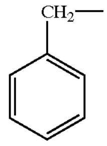 | 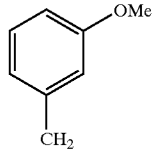 |
| 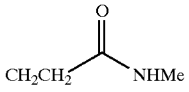 | 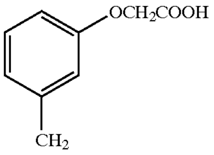 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 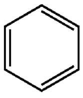 | 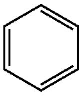 |
| 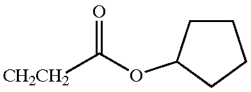 | 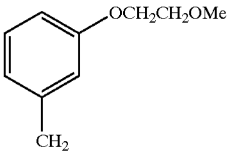 |
| 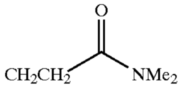 | 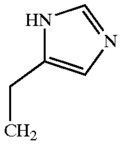 |
| —NH2 | H |
| H | Et |
| Et | F |
| Me | Et |
| SO2Me | Cl |

TABLE 10a
Formula XIa
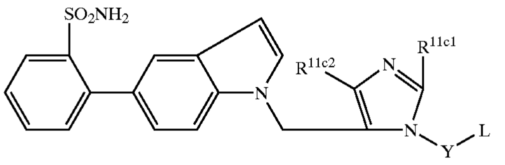
| $R^{11c1}$ | $R^{11c2}$ |
|---|---|
| H | H |
| Me | Me |
| Br | Me |
| H | Cl |
| Me | Cl |
| Et | Cl |
| 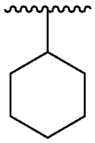 | 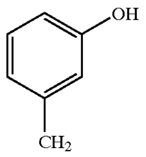 |
| 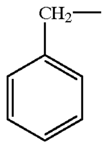 | 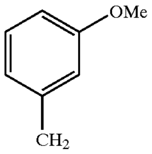 |
| 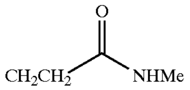 | 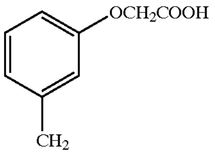 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 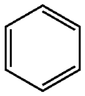 | 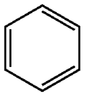 |
| 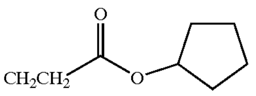 | 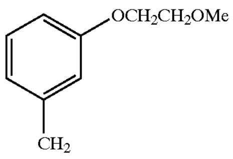 |
| 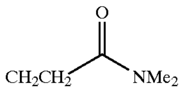 | 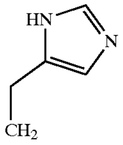 |
| —NH2 | H |
| H | Et |
TABLE 10a-continued
Formula XIa
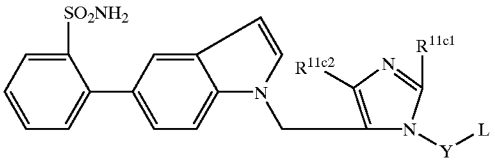
| $R^{11c1}$ | $R^{11c2}$ |
|---|---|
| Et | F |
| Me | Et |
| SO2Me | Cl |
TABLE 10b
Formula XIb
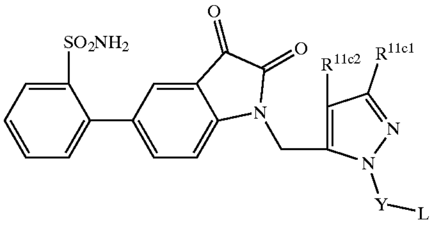
| $R^{11c1}$ | $R^{11c2}$ |
|---|---|
| H | H |
| Me | Me |
| Br | Me |
| H | Cl |
| Me | Cl |
| Et | Cl |
| 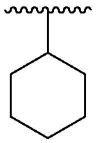 | 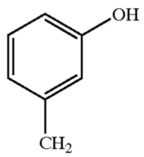 |
| 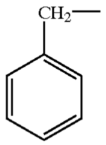 | 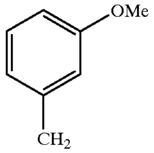 |
| 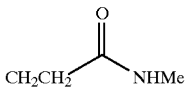 | 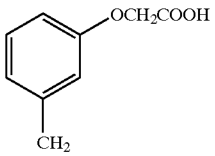 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |

TABLE 10b-continued
Formula XIb
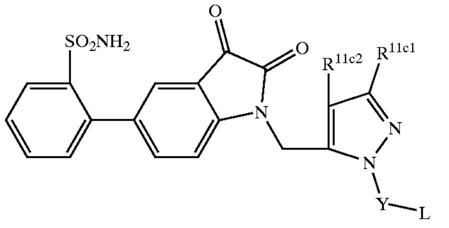
| $R^{11c1}$ | $R^{11c2}$ |
|---|---|
| 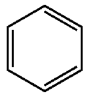 | 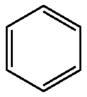 |
| 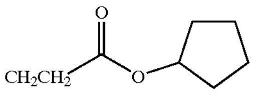 | 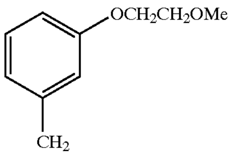 |
| 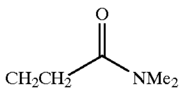 | 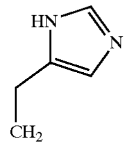 |
| —NH2 | H |
| H | Et |
| Et | F |
| Me | Et |
| SO2Me | Cl |
TABLE 10c
Formula XIc
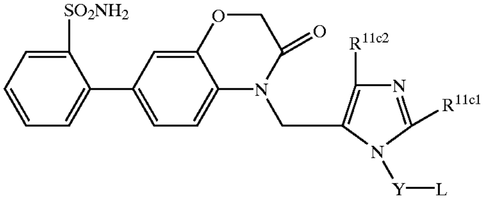
| $R^{11c1}$ | $R^{11c2}$ |
|---|---|
| H | H |
| Me | Me |
| Br | Me |
| H | Cl |
| Me | Cl |
| Et | Cl |
| 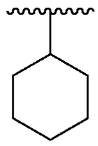 | 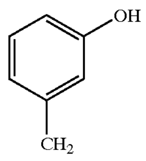 |
TABLE 10c-continued
Formula XIc
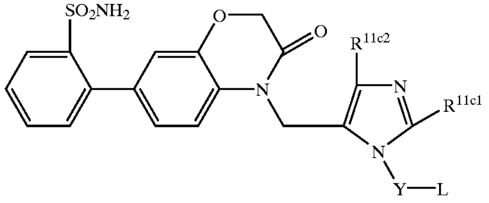
| $R^{11c1}$ | $R^{11c2}$ |
|---|---|
| 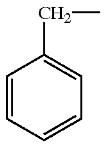 | 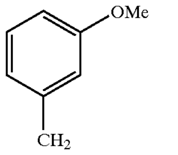 |
| 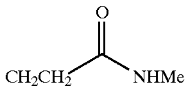 | 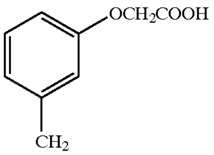 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 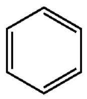 | 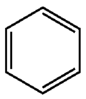 |
| 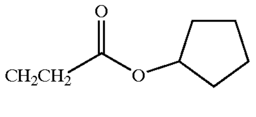 | 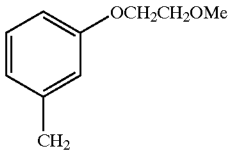 |
| 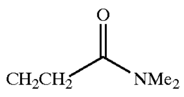 | 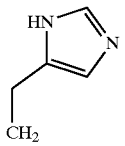 |
| —NH2 | H |
| H | Et |
| Et | F |
| Me | Et |
| SO2Me | Cl |

TABLE 10d
Formula XId
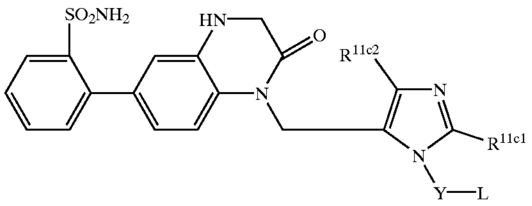
| $R^{11c1}$ | $R^{11c2}$ |
|---|---|
| H | H |
| Me | Me |
| Br | Me |
| H | Cl |
| Me | Cl |
| Et | Cl |
| 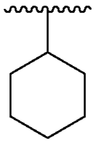 | 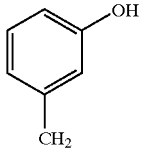 |
| 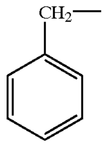 | 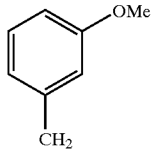 |
| 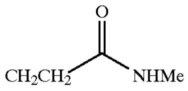 | 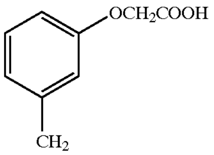 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 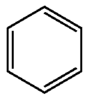 | 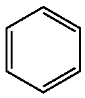 |
| 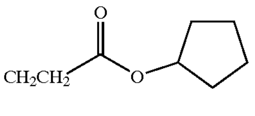 | 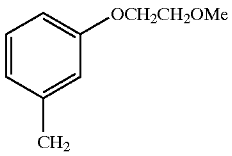 |
| 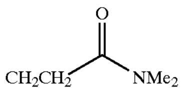 | 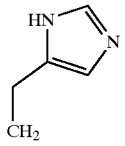 |
TABLE 10d-continued
Formula XId
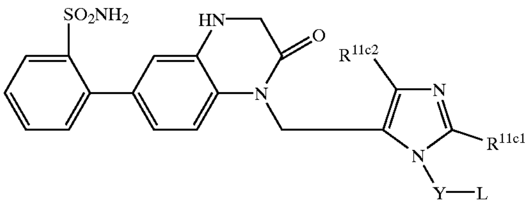
| $R^{11c1}$ | $R^{11c2}$ |
|---|---|
| —NH2 | H |
| H | Et |
| Et | F |
| Me | Et |
| SO2Me | Cl |
TABLE 10e
Formula XIe
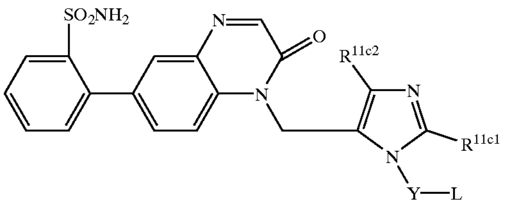
| $R^{11c1}$ | $R^{11c2}$ |
|---|---|
| H | H |
| Me | Me |
| Br | Me |
| H | Cl |
| Me | Cl |
| Et | Cl |
| 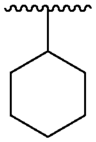 | 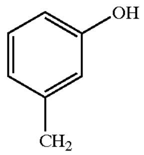 |
| 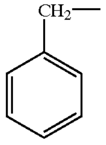 | 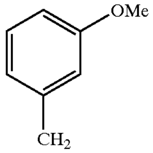 |
| 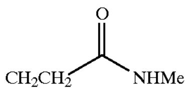 | 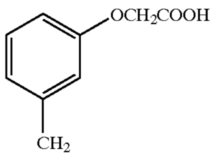 |
| OCH2Ph | H |
| OCH2CH2OMe | H |
| Me | F |
| Me | H |
| SO2Me | H |
| OMe | H |
| OMe | Me |

TABLE 10e-continued
Formula XIe
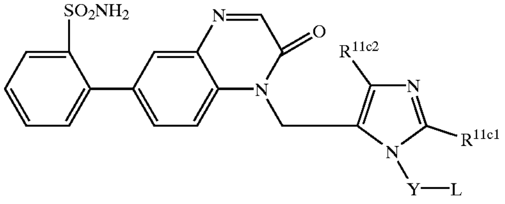
| R11c1 | R11c2 |
|---|---|
| F | H |
| Et | H |
| —OH | Me |
| Et | Br |
| 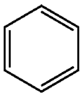 | 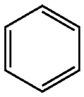 |
| 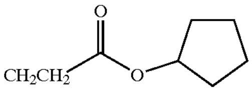 | 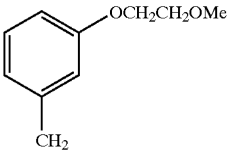 |
| 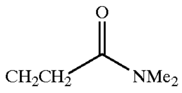 | 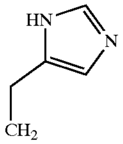 |
| —NH2 | H |
| H | Et |
| Et | F |
| Me | Et |
| SO2Me | Cl |
TABLE 10f
Formula XIf
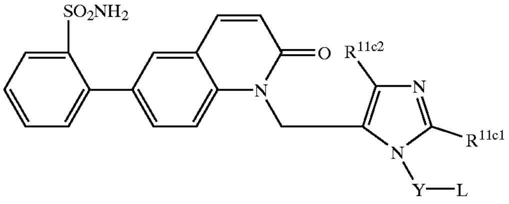
| R11c1 | R11c2 |
|---|---|
| H | H |
| Me | Me |
| Br | Me |
| H | Cl |
| Me | Cl |
| Et | Cl |
TABLE 10f-continued
Formula XIf
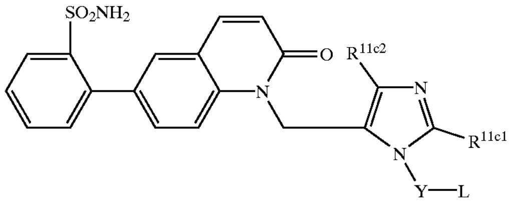
| R11c1 | R11c2 |
|---|---|
| 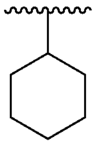 | 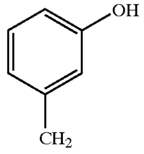 |
| 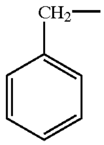 | 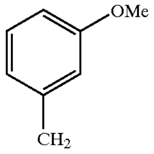 |
| 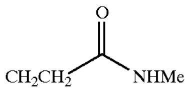 | 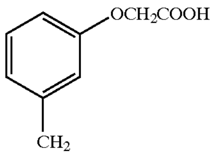 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 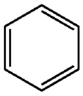 | 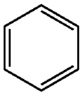 |
| 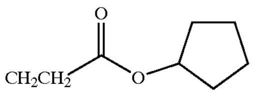 | 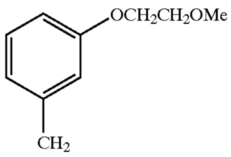 |
| 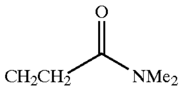 | 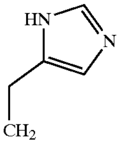 |
| —NH2 | H |
| H | Et |
| Et | F |
| Me | Et |
| SO2Me | Cl |

TABLE 10g
Formula XIg
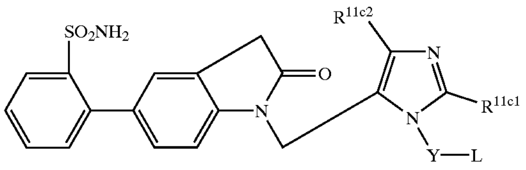
| $R^{11c1}$ | $R^{11c2}$ |
|---|---|
| H | H |
| Me | Me |
| Br | Me |
| H | Cl |
| Me | Cl |
| Et | Cl |
| 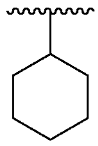 | 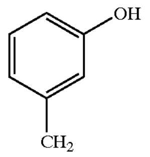 |
| 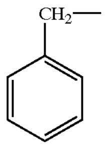 | 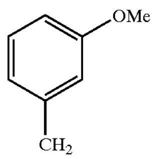 |
| 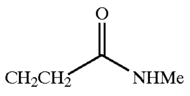 | 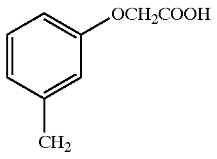 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 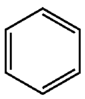 | 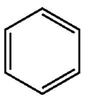 |
| 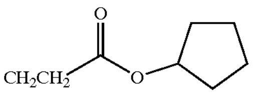 | 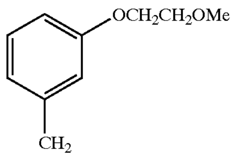 |
| 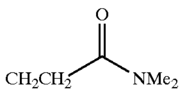 | 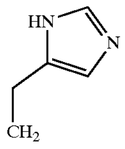 |
TABLE 10g-continued
Formula XIg
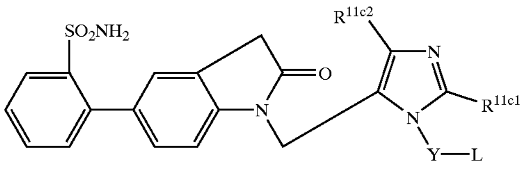
| $R^{11c1}$ | $R^{11c2}$ |
|---|---|
| —NH2 | H |
| H | Et |
| Et | F |
| Me | Et |
| SO2Me | Cl |
TABLE 10h
Formula XIh
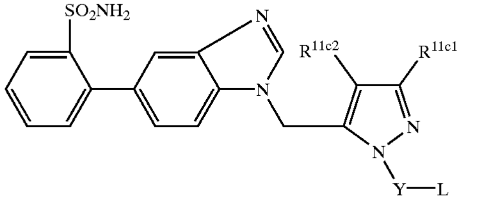
| $R^{11c1}$ | $R^{11c2}$ |
|---|---|
| H | H |
| Me | Me |
| Br | Me |
| H | Cl |
| Me | Cl |
| Et | Cl |
| 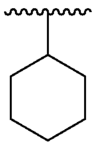 | 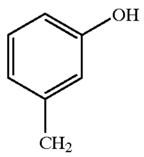 |
| 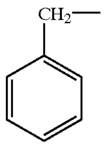 | 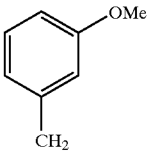 |
| 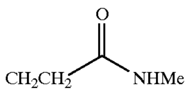 | 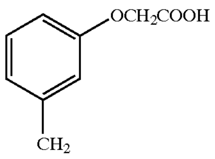 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |

TABLE 10h-continued
Formula XIh
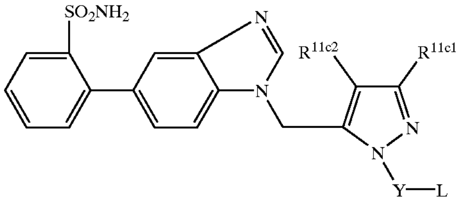
| $R^{11c1}$ | $R^{11c2}$ |
|---|---|
| Et | Br |
| 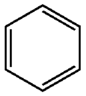 | 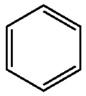 |
| 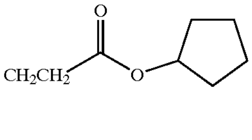 | 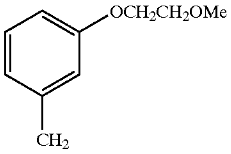 |
| 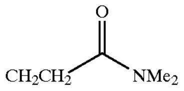 | 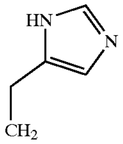 |
| —NH2 | H |
| H | Et |
| Et | F |
| Me | Et |
| SO2Me | Cl |
TABLE 10i
Formula XIi
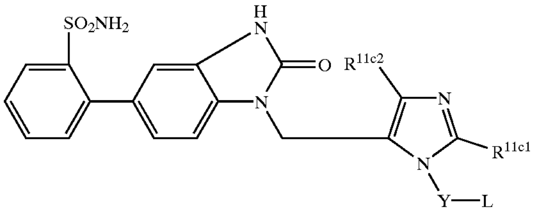
| $R^{11c1}$ | $R^{11c2}$ |
|---|---|
| H | H |
| Me | Me |
| Br | Me |
| H | Cl |
| Me | Cl |
| Et | Cl |
| 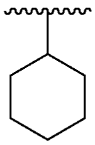 | 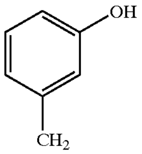 |
TABLE 10i-continued
Formula XIi
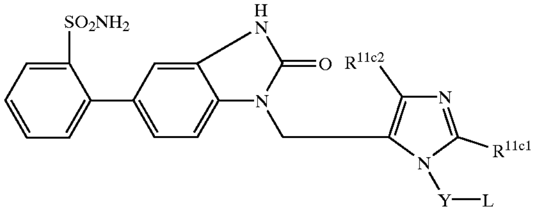
| $R^{11c1}$ | $R^{11c2}$ |
|---|---|
| 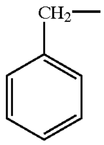 | 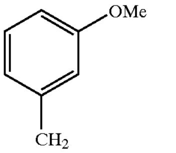 |
| 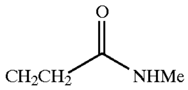 | 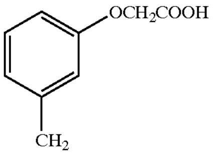 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 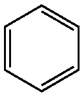 | 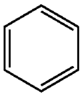 |
| 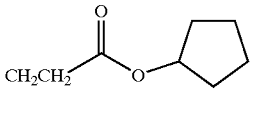 | 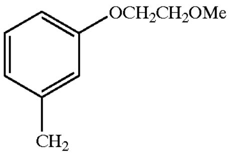 |
| 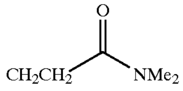 | 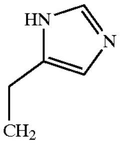 |
| —NH2 | H |
| H | Et |
| Et | F |
| Me | Et |
| SO2Me | Cl |

TABLE 10j
Formula XIj
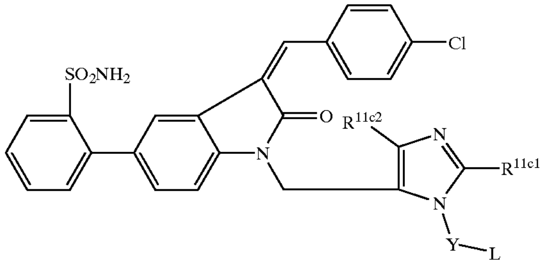
| $R^{11c1}$ | $R^{11c2}$ |
|---|---|
| H | H |
| Me | Me |
| Br | Me |
| H | Cl |
| Me | Cl |
| Et | Cl |
| 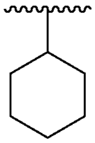 | 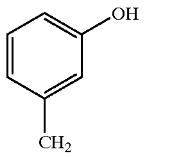 |
| 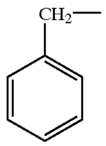 | 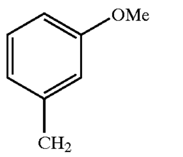 |
| 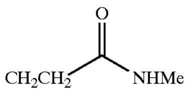 | 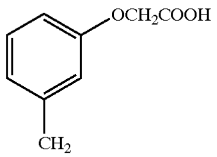 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 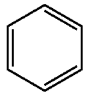 | 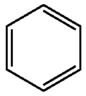 |
| 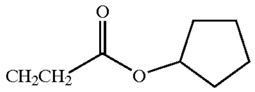 | 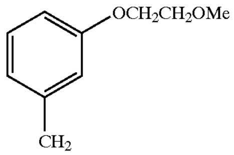 |
TABLE 10j-continued
Formula XIj
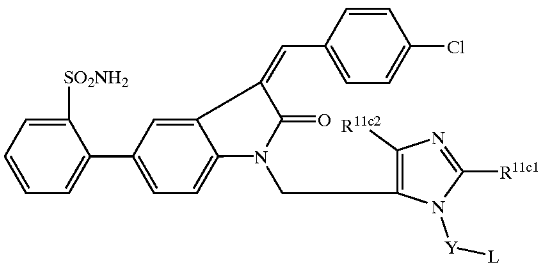
| $R^{11c1}$ | $R^{11c2}$ |
|---|---|
| 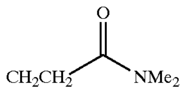 | 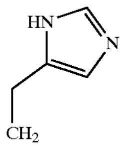 |
| —NH2 | H |
| H | Et |
| Et | F |
| Me | Et |
| SO2Me | Cl |
TABLE 10k
Formula XIk
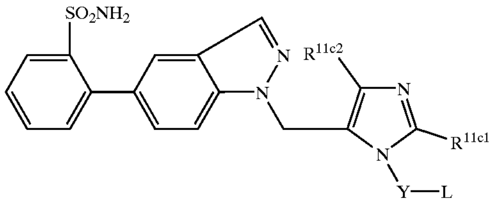
| $R^{11c1}$ | $R^{11c2}$ |
|---|---|
| H | H |
| Me | Me |
| Br | Me |
| H | Cl |
| Me | Cl |
| Et | Cl |
| 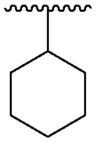 | 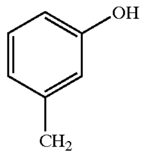 |
| 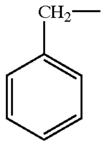 | 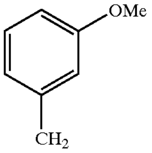 |

TABLE 10k-continued
Formula XIk
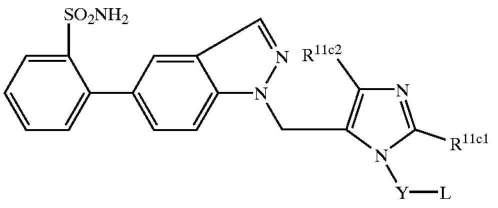
| $R^{11c1}$ | $R^{11c2}$ |
| --- | --- |
| 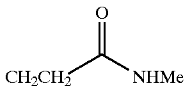 | 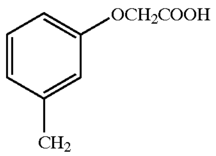 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 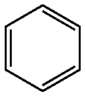 | 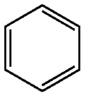 |
| 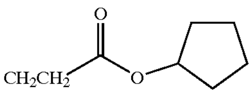 | 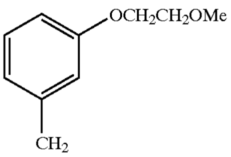 |
| 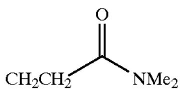 | 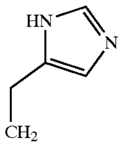 |
| —NH2 | H |
| H | Et |
| Et | F |
| Me | Et |
| SO2Me | Cl |
TABLE 10(l)
Formula XI(l)
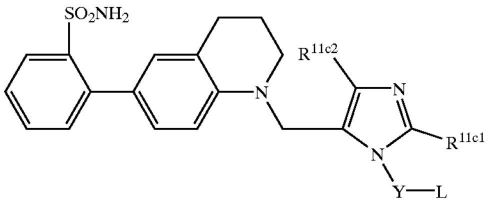
| $R^{11c1}$ | $R^{11c2}$ |
| --- | --- |
| H | H |
| Me | Me |
| Br | Me |
| H | Cl |
| Me | Cl |
| Et | Cl |
| 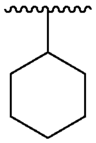 | 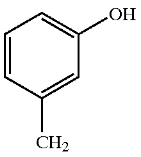 |
| 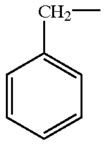 | 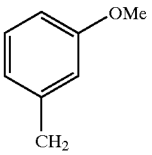 |
| 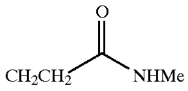 | 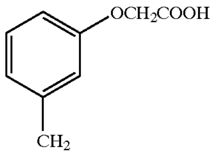 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 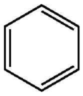 | 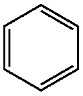 |
| 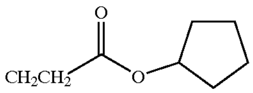 | 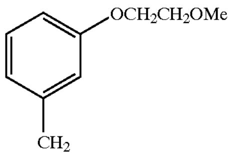 |
| 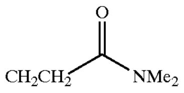 | 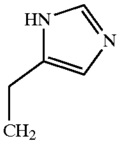 |

TABLE 10(l)-continued
Formula XI(l)
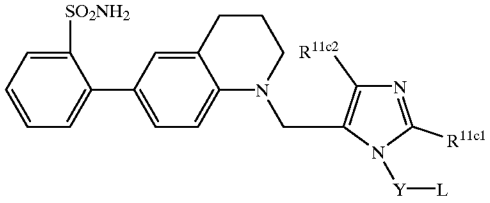
| $R^{11c1}$ | $R^{11c2}$ |
|---|---|
| —NH2 | H |
| H | Et |
| Et | F |
| Me | Et |
| SO2Me | Cl |
TABLE 10m
Formula XIm
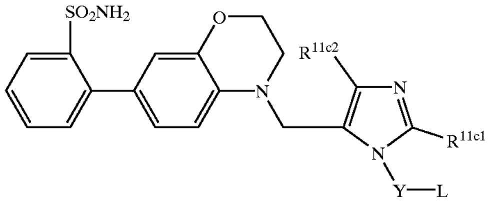
| $R^{11c1}$ | $R^{11c2}$ |
|---|---|
| H | H |
| Me | Me |
| Br | Me |
| H | Cl |
| Me | Cl |
| Et | Cl |
| 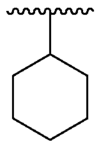 | 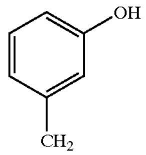 |
| 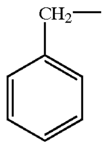 | 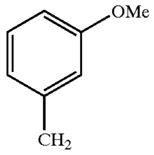 |
| 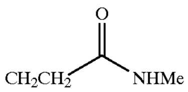 | 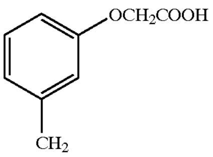 |
| OCH2Ph | H |
| OCH2CH2OMe | H |
| Me | F |
| Me | H |
| SO2Me | H |
| OMe | H |
| OMe | Me |
TABLE 10m-continued
Formula XIm
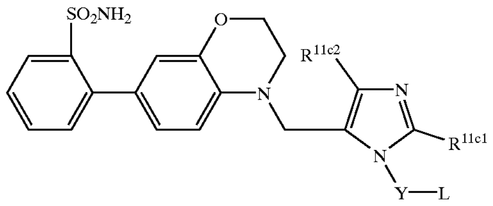
| $R^{11c1}$ | $R^{11c2}$ |
|---|---|
| F | H |
| Et | H |
| —OH | Me |
| Et | Br |
| 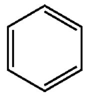 | 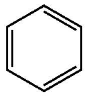 |
| 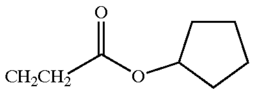 | 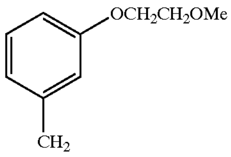 |
| 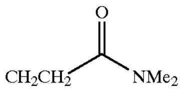 | 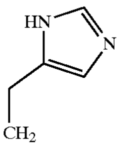 |
| —NH2 | H |
| H | Et |
| Et | F |
| Me | Et |
| SO2Me | Cl |
TABLE 10n
Formula XIn
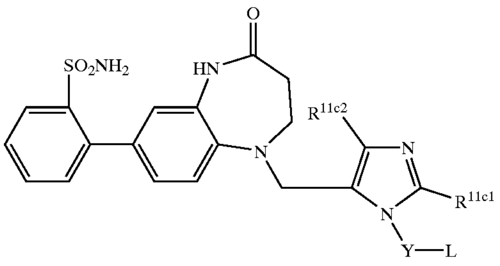
| $R^{11c1}$ | $R^{11c2}$ |
|---|---|
| H | H |
| Me | Me |
| Br | Me |
| H | Cl |
| Me | Cl |
| Et | Cl |

TABLE 10n-continued
Formula XIn
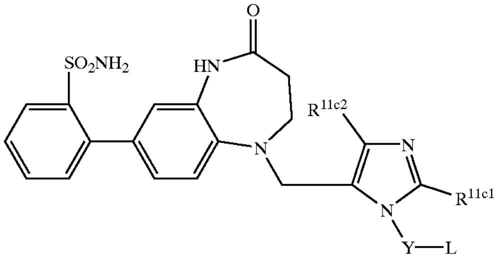
| $R^{11c1}$ | $R^{11c2}$ |
|---|---|
| 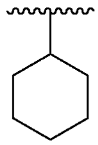 | 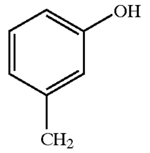 |
| 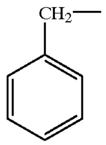 | 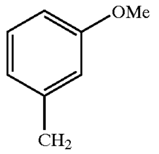 |
| 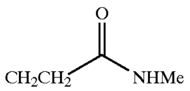 | 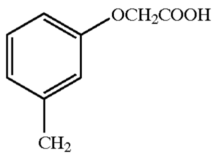 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 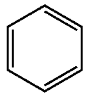 | 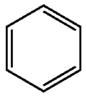 |
| 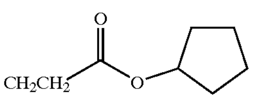 | 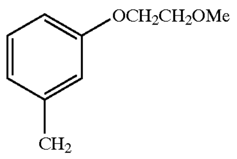 |
| 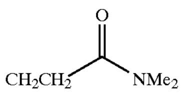 | 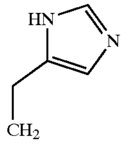 |
| —NH2 | H |
| H | Et |
| Et | F |
TABLE 10n-continued
Formula XIn
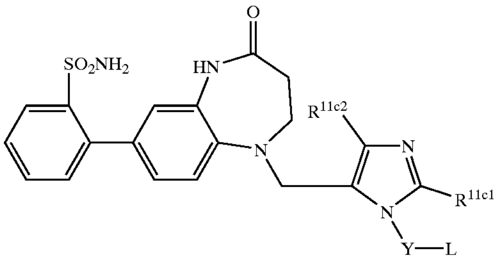
| $R^{11c1}$ | $R^{11c2}$ |
|---|---|
| Me | Et |
| SO2Me | Cl |
TABLE 10o
Formula XIo
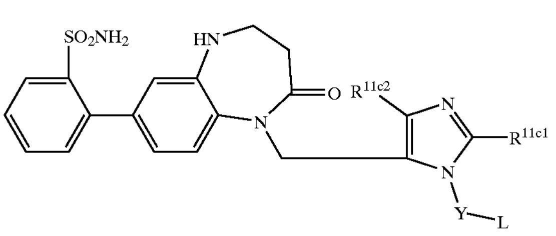
| $R^{11c1}$ | $R^{11c2}$ |
|---|---|
| H | H |
| Me | Me |
| Br | Me |
| H | Cl |
| Me | Cl |
| Et | Cl |
| 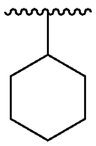 | 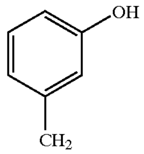 |
| 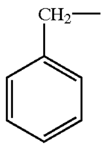 | 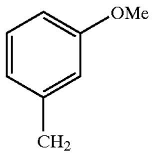 |
| 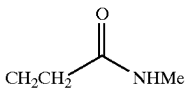 | 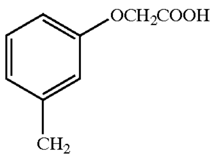 |
| OCH2Ph | H |
| OCH2CH2OMe | H |
| Me | F |
| Me | H |
| SO2Me | H |
| OMe | H |
| OMe | Me |

TABLE 10o-continued
Formula XIo
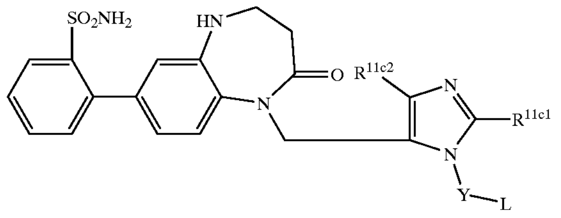
| $R^{11c1}$ | $R^{11c2}$ |
|---|---|
| F | H |
| Et | H |
| —OH | Me |
| Et | Br |
| 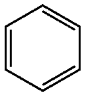 | 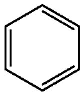 |
| 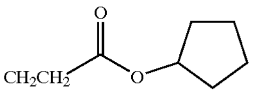 | 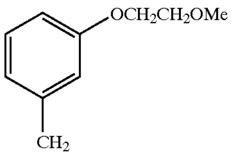 |
| 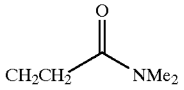 | 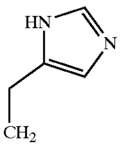 |
| —NH2 | H |
| H | Et |
| Et | F |
| Me | Et |
| SO2Me | Cl |
TABLE 10p
Formula XIp
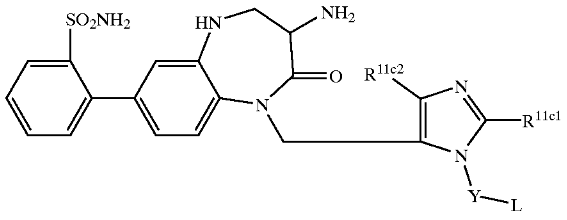
| $R^{11c1}$ | $R^{11c2}$ |
|---|---|
| H | H |
| Me | Me |
| Br | Me |
| H | Cl |
| Me | Cl |
| Et | Cl |
TABLE 10p-continued
Formula XIp
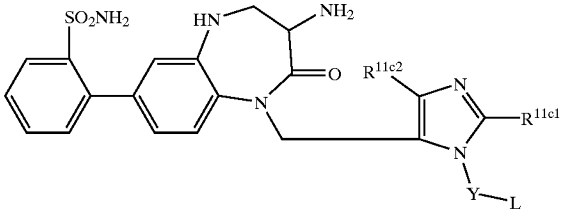
| $R^{11c1}$ | $R^{11c2}$ |
|---|---|
| 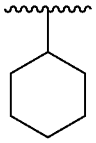 | 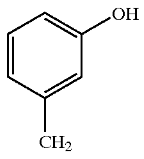 |
| 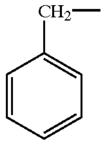 | 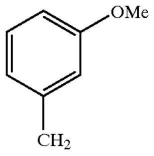 |
| 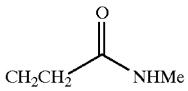 | 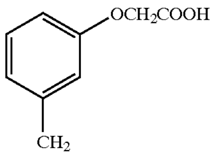 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 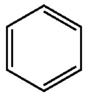 | 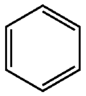 |
| 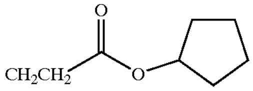 | 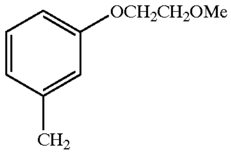 |
| 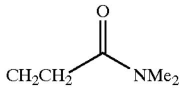 | 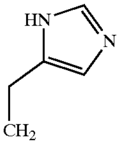 |
| —NH2 | H |
| H | Et |
| Et | F |
| Me | Et |

TABLE 10p-continued
Formula XIp
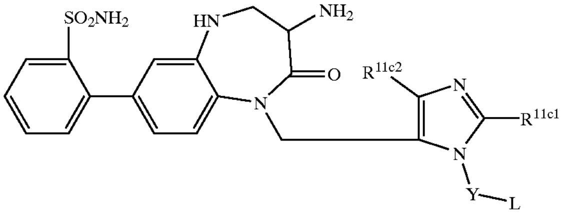
| $R^{11c1}$ | $R^{11c2}$ |
|---|---|
| SO2Me | Cl |
TABLE 10q
Formula XIq
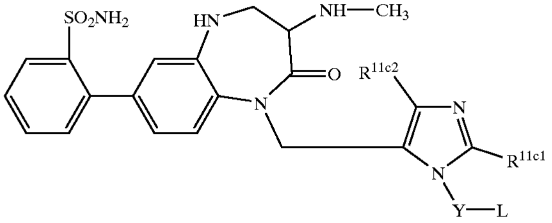
| $R^{11c1}$ | $R^{11c2}$ |
|---|---|
| H | H |
| Me | Me |
| Br | Me |
| H | Cl |
| Me | Cl |
| Et | Cl |
| 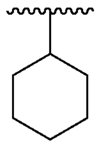 | 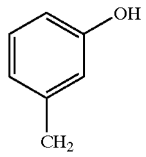 |
| 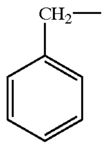 | 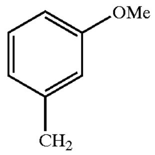 |
| 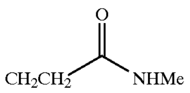 | 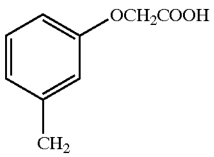 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
TABLE 10q-continued
Formula XIq
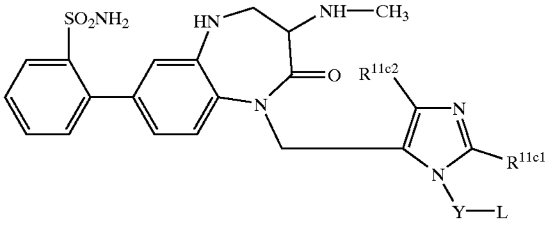
| $R^{11c1}$ | $R^{11c2}$ |
|---|---|
| Et | Br |
| 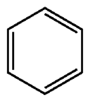 | 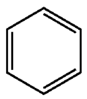 |
| 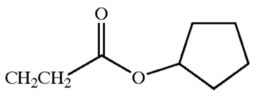 | 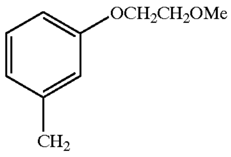 |
| 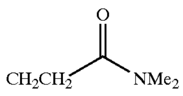 | 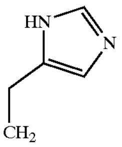 |
| —NH2 | H |
| H | Et |
| Et | F |
| Me | Et |
| SO2Me | Cl |
TABLE 11
Formula XII
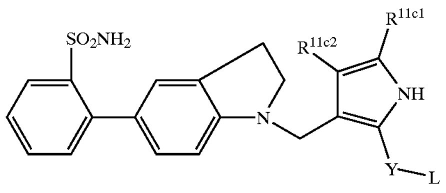
| $R^{11c1}$ | $R^{11c2}$ |
|---|---|
| H | H |
| Me | Me |
| Br | Me |
| H | Cl |
| Me | Cl |
| Et | Cl |
| 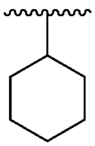 | 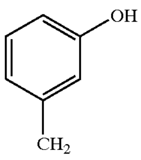 |

TABLE 11-continued
Formula XII
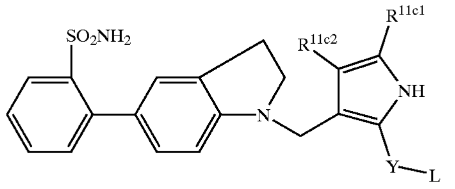
| $R^{11c1}$ | $R^{11c2}$ |
|---|---|
| 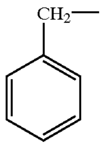 | 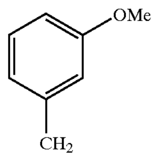 |
| 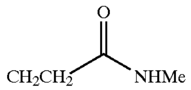 | 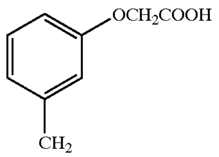 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 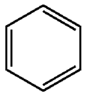 | 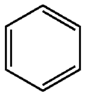 |
| 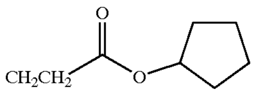 | 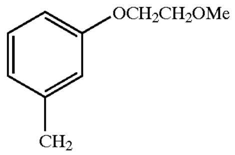 |
| 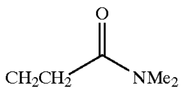 | 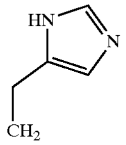 |
| —NH2 | H |
| H | Et |
| Et | F |
| Me | Et |
| SO2Me | Cl |
TABLE 11a
Formula XIa
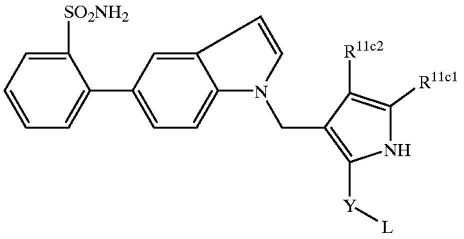
| $R^{11c1}$ | $R^{11c2}$ |
|---|---|
| H | H |
| Me | Me |
| Br | Me |
| H | Cl |
| Me | Cl |
| Et | Cl |
| 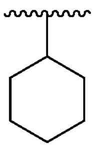 | 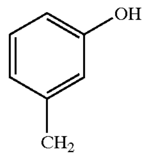 |
| 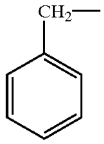 | 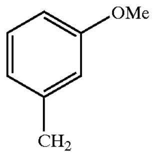 |
| 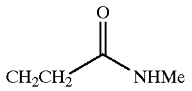 | 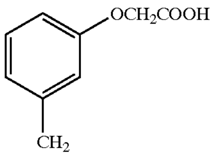 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 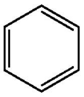 | 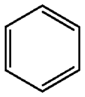 |
| 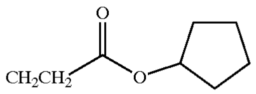 | 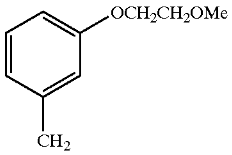 |

TABLE 11a-continued
Formula XIa
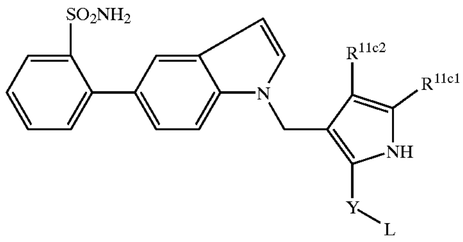
| $R^{11c1}$ | $R^{11c2}$ |
|---|---|
| 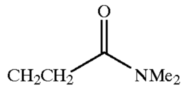 | 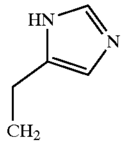 |
| —NH2 | H |
| H | Et |
| Et | F |
| Me | Et |
| SO2Me | Cl |
TABLE 11b
Formula XIb
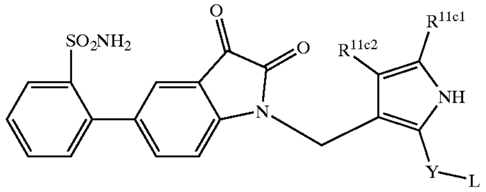
| $R^{11c1}$ | $R^{11c2}$ |
|---|---|
| H | H |
| Me | Me |
| Br | Me |
| H | Cl |
| Me | Cl |
| Et | Cl |
| 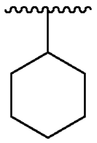 | 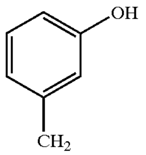 |
| 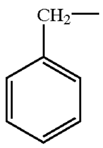 | 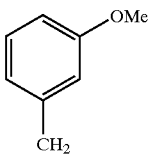 |
| 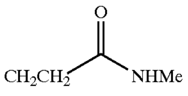 | 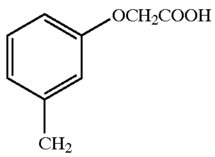 |
TABLE 11b-continued
Formula XIb
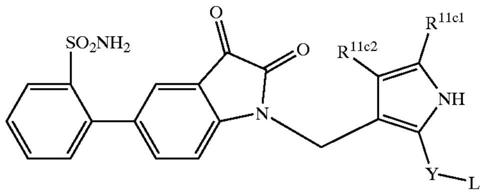
| $R^{11c1}$ | $R^{11c2}$ |
|---|---|
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 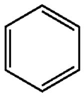 | 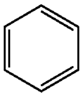 |
| 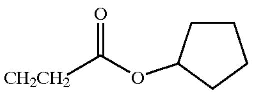 | 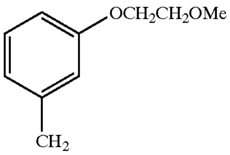 |
| 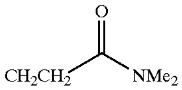 | 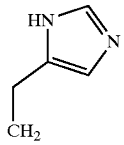 |
| —NH2 | H |
| H | Et |
| Et | F |
| Me | Et |
| SO2Me | Cl |
TABLE 11c
Formula XIc
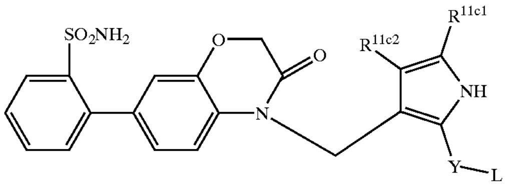
| $R^{11c1}$ | $R^{11c2}$ |
|---|---|
| H | H |
| Me | Me |
| Br | Me |
| H | Cl |
| Me | Cl |
| Et | Cl |

TABLE 11c-continued
Formula XIc
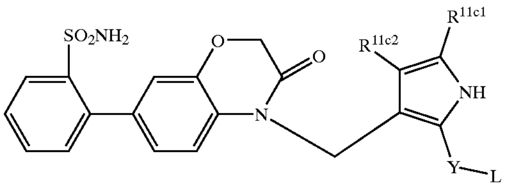
| $R^{11c1}$ | $R^{11c2}$ |
|---|---|
| 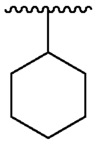 | 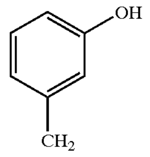 |
| 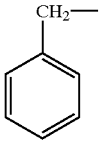 | 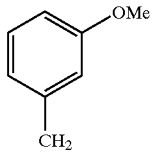 |
| 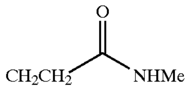 | 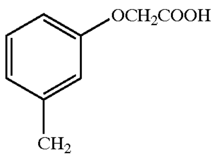 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 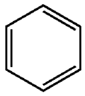 | 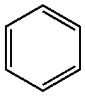 |
| 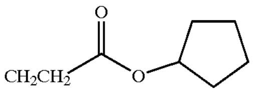 | 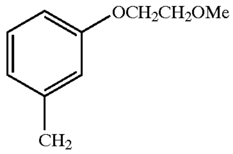 |
| 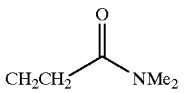 | 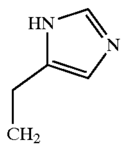 |
| —NH2 | H |
| H | Et |
| Et | F |
| Me | Et |
TABLE 11c-continued
Formula XIc
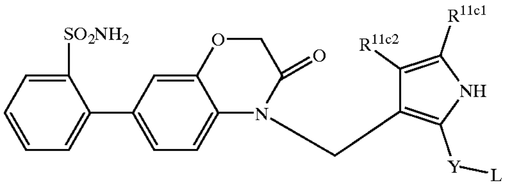
| $R^{11c1}$ | $R^{11c2}$ |
|---|---|
| SO2Me | Cl |
TABLE 11d
Formula XIId
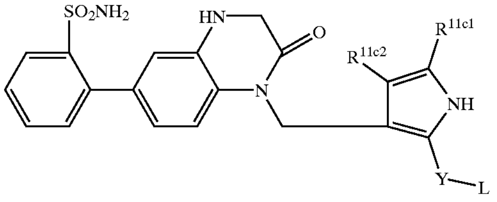
| $R^{11c1}$ | $R^{11c2}$ |
|---|---|
| H | H |
| Me | Me |
| Br | Me |
| H | Cl |
| Me | Cl |
| Et | Cl |
| 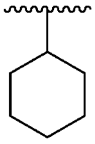 | 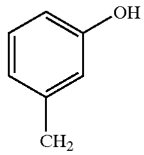 |
| 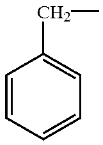 | 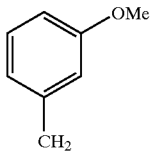 |
| 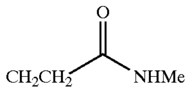 | 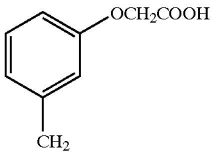 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |

TABLE 11d-continued
Formula XIId
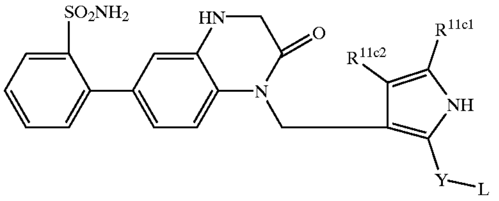
| $R^{11c1}$ | $R^{11c2}$ |
|---|---|
| 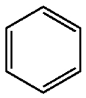 | 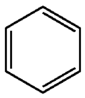 |
| 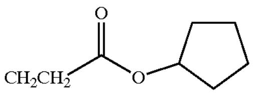 | 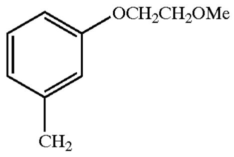 |
| 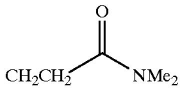 | 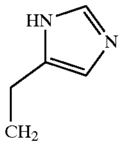 |
| —NH2 | H |
| H | Et |
| Et | F |
| Me | Et |
| SO2Me | Cl |
TABLE 11e
Formula XIIe
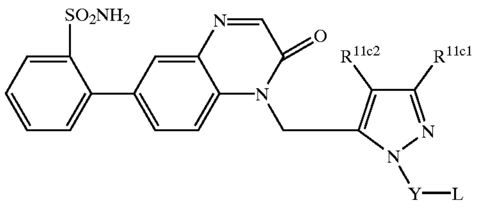
| $R^{11c1}$ | $R^{11c2}$ |
|---|---|
| H | H |
| Me | Me |
| Br | Me |
| H | Cl |
| Me | Cl |
| Et | Cl |
| 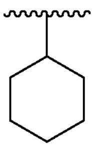 | 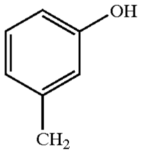 |
TABLE 11e-continued
Formula XIIe
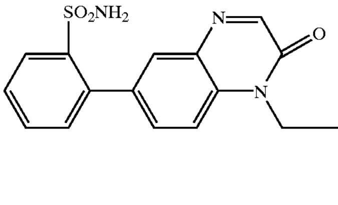
| $R^{11c1}$ | $R^{11c2}$ |
|---|---|
| 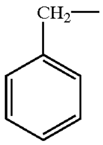 | 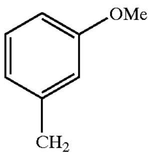 |
| 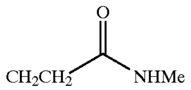 | 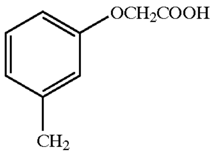 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 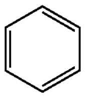 | 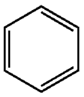 |
| 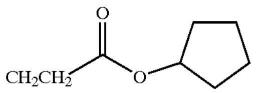 | 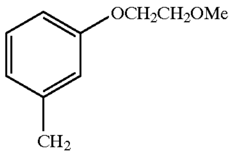 |
| 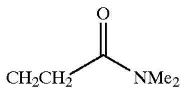 | 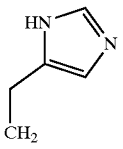 |
| —NH2 | H |
| H | Et |
| Et | F |
| Me | Et |
| SO2Me | Cl |

TABLE 11f
Formula XIIf
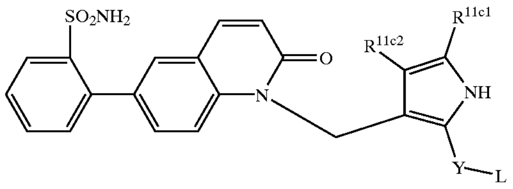
| $R^{11c1}$ | $R^{11c2}$ |
|---|---|
| H | H |
| Me | Me |
| Br | Me |
| H | Cl |
| Me | Cl |
| Et | Cl |
| 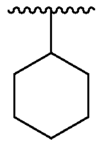 | 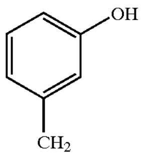 |
| 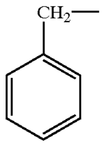 | 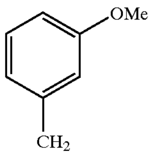 |
| 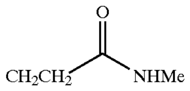 | 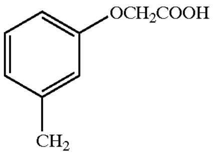 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 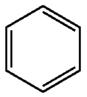 | 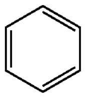 |
| 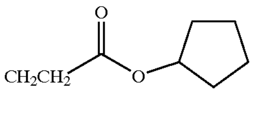 | 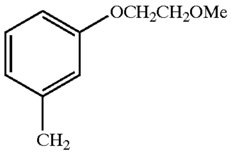 |
| 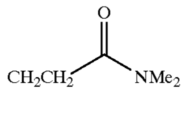 | 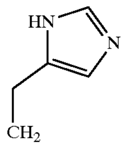 |
TABLE 11f-continued
Formula XIIf
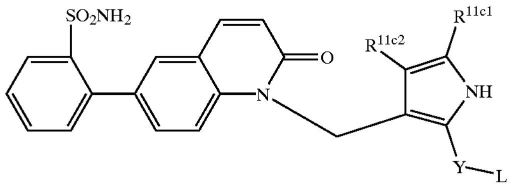
| $R^{11c1}$ | $R^{11c2}$ |
|---|---|
| —NH2 | H |
| H | Et |
| Et | F |
| Me | Et |
| SO2Me | Cl |
TABLE 11g
Formula XIIg
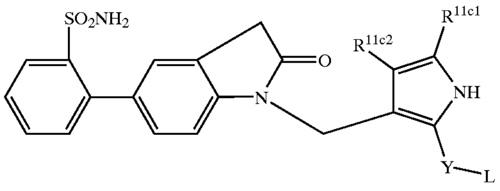
| $R^{11c1}$ | $R^{11c2}$ |
|---|---|
| H | H |
| Me | Me |
| Br | Me |
| H | Cl |
| Me | Cl |
| Et | Cl |
| 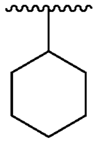 | 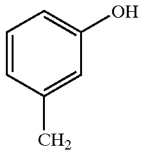 |
| 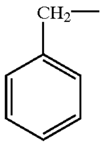 | 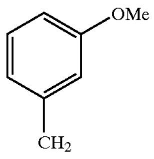 |
| 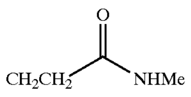 | 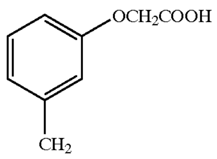 |
| OCH2Ph | H |
| OCH2CH2OMe | H |
| Me | F |
| Me | H |
| SO2Me | H |
| OMe | H |
| OMe | Me |
| F | H |

TABLE 11g-continued
Formula XIIg
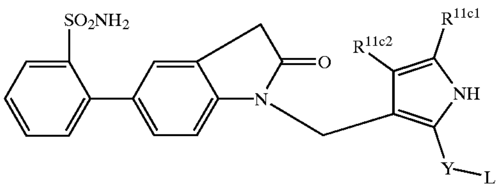
| $R^{11c1}$ | $R^{11c2}$ |
|---|---|
| Et | H |
| —OH | Me |
| Et | Br |
| 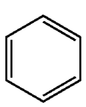 | 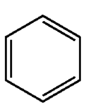 |
| 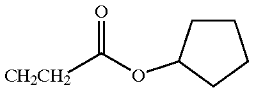 | 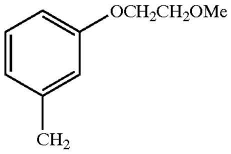 |
| 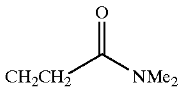 | 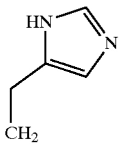 |
| —NH2 | H |
| H | Et |
| Et | F |
| Me | Et |
| SO2Me | Cl |
TABLE 11h
Formula XIIh
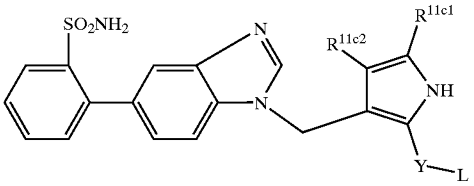
| $R^{11c1}$ | $R^{11c2}$ |
|---|---|
| H | H |
| Me | Me |
| Br | Me |
| H | Cl |
| Me | Cl |
| Et | Cl |
| 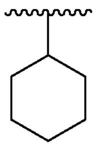 | 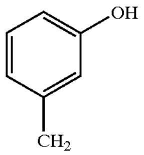 |
TABLE 11h-continued
Formula XIIh
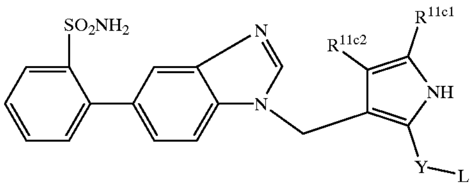
| $R^{11c1}$ | $R^{11c2}$ |
|---|---|
| 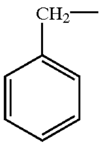 | 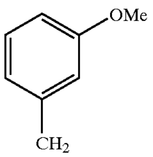 |
| 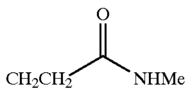 | 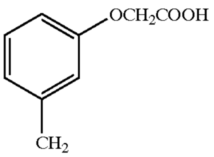 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 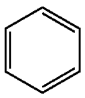 | 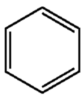 |
| 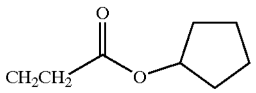 | 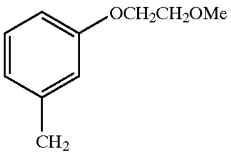 |
| 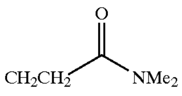 | 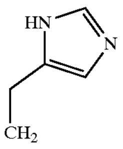 |
| —NH2 | H |
| H | Et |
| Et | F |
| Me | Et |
| SO2Me | Cl |

TABLE 11i
Formula XIIi
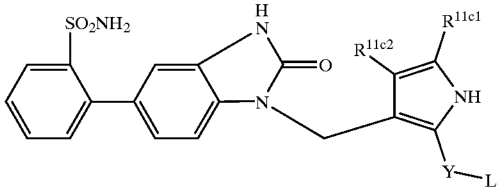
| $R^{11c1}$ | $R^{11c2}$ |
|---|---|
| H | H |
| Me | Me |
| Br | Me |
| H | Cl |
| Me | Cl |
| Et | Cl |
| 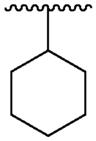 | 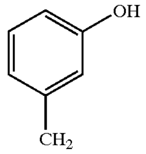 |
| 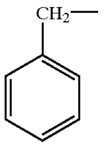 | 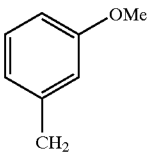 |
| 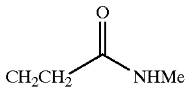 | 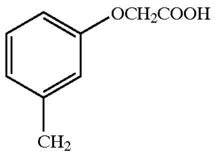 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 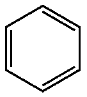 | 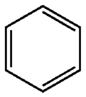 |
| 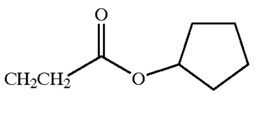 | 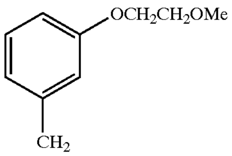 |
| 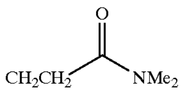 | 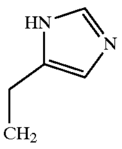 |
TABLE 11i-continued
Formula XIIi
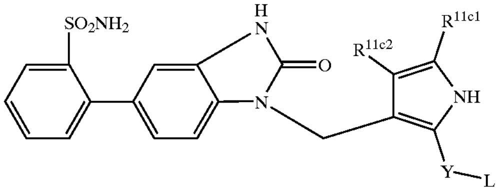
| $R^{11c1}$ | $R^{11c2}$ |
|---|---|
| —NH2 | H |
| H | Et |
| Et | F |
| Me | Et |
| SO2Me | Cl |
TABLE 11j
Formula XIIj
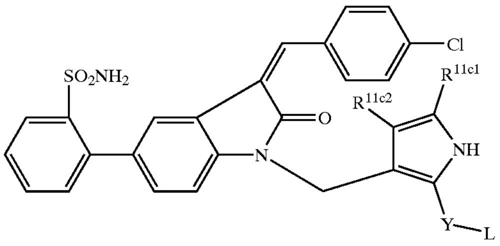
| $R^{11c1}$ | $R^{11c2}$ |
|---|---|
| H | H |
| Me | Me |
| Br | Me |
| H | Cl |
| Me | Cl |
| Et | Cl |
| 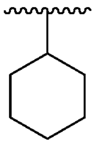 | 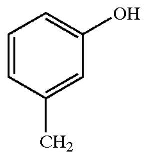 |
| 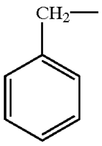 | 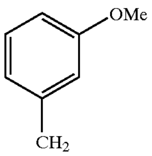 |
| 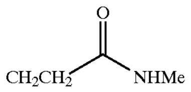 | 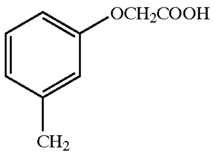 |
| OCH2Ph | H |
| OCH2CH2OMe | H |
| Me | F |
| Me | H |
| SO2Me | H |

TABLE 11j-continued
Formula XIIj
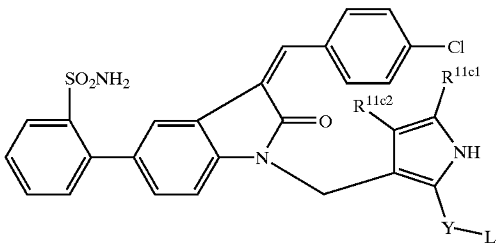
| $R^{11c1}$ | $R^{11c2}$ |
|---|---|
| OMe | H |
| OMe | Me |
| F | H |
| Et | H |
| —OH | Me |
| Et | Br |
| 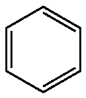 | 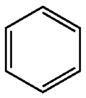 |
| 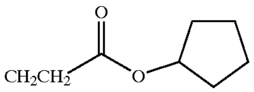 | 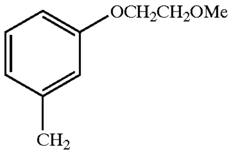 |
| 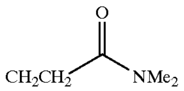 | 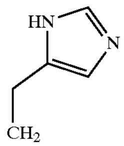 |
| —NH2 | H |
| H | Et |
| Et | F |
| Me | Et |
| SO2Me | Cl |
TABLE 11k
Formula XIIk
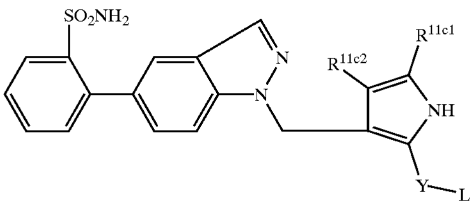
| $R^{11c1}$ | $R^{11c2}$ |
|---|---|
| H | H |
| Me | Me |
| Br | Me |
| H | Cl |
| Me | Cl |
| Et | Cl |
TABLE 11k-continued
Formula XIIk
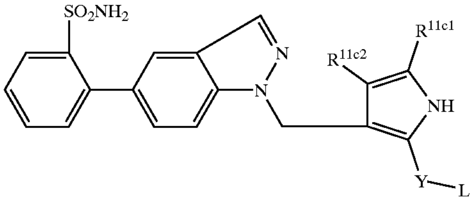
| $R^{11c1}$ | $R^{11c2}$ |
|---|---|
| 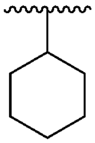 | 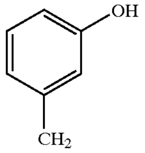 |
| 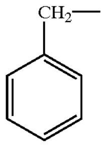 | 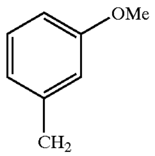 |
| 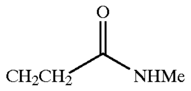 | 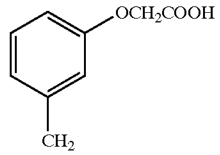 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 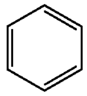 | 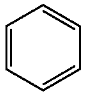 |
| 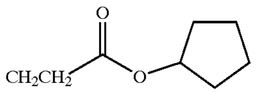 | 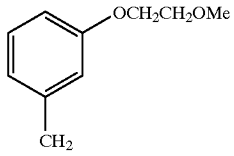 |
| 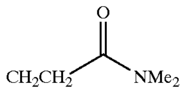 | 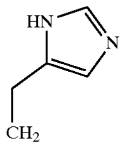 |
| —NH2 | H |
| H | Et |
| Et | F |
| Me | Et |
| SO2Me | Cl |

TABLE 11(l)
Formula XII(l)
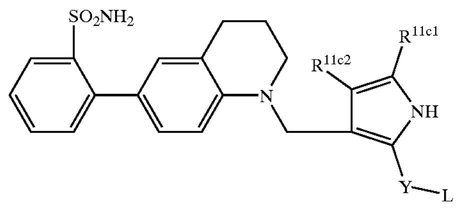
| $R^{11c1}$ | $R^{11c2}$ |
|---|---|
| H | H |
| Me | Me |
| Br | Me |
| H | Cl |
| Me | Cl |
| Et | Cl |
| 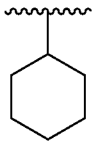 | 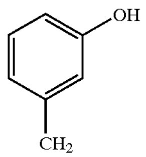 |
| 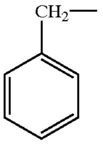 | 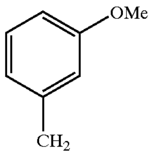 |
| 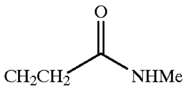 | 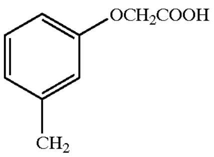 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 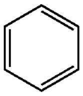 | 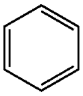 |
| 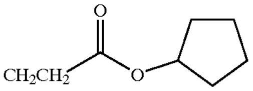 | 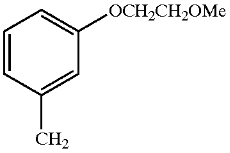 |
| 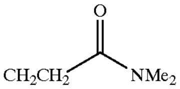 | 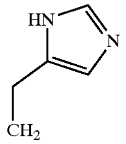 |
TABLE 11(l)-continued
Formula XII(l)
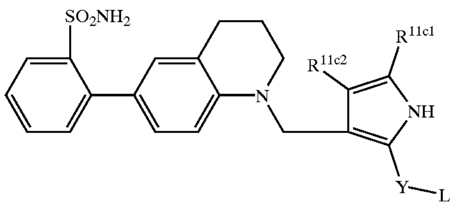
| $R^{11c1}$ | $R^{11c2}$ |
|---|---|
| —NH2 | H |
| H | Et |
| Et | F |
| Me | Et |
| SO2Me | Cl |
TABLE 11m
Formula XIIm
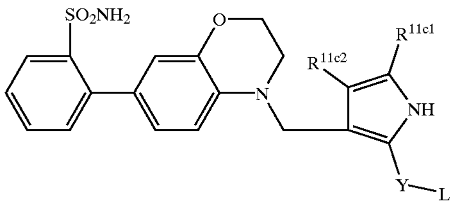
| $R^{11c1}$ | $R^{11c2}$ |
|---|---|
| H | H |
| Me | Me |
| Br | Me |
| H | Cl |
| Me | Cl |
| Et | Cl |
| 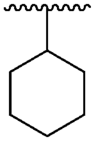 | 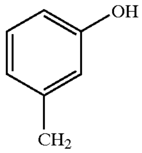 |
| 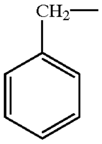 | 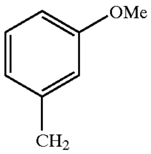 |
| 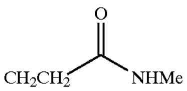 | 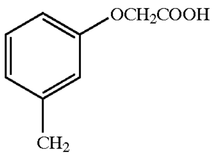 |
| OCH2Ph | H |
| OCH2CH2OMe | H |
| Me | F |
| Me | H |
| SO2Me | H |
| OMe | H |
| OMe | Me |

TABLE 11m-continued
Formula XIIm
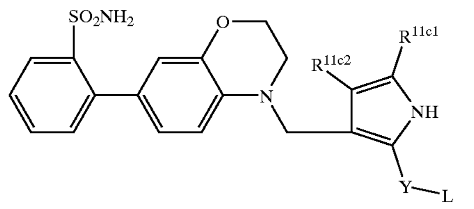
| $R^{11c1}$ | $R^{11c2}$ |
|---|---|
| F | H |
| Et | H |
| —OH | Me |
| Et | Br |
| 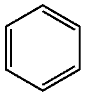 | 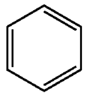 |
| 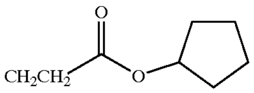 | 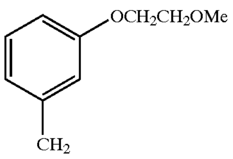 |
| 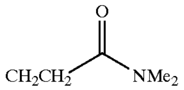 | 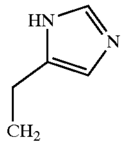 |
| —NH2 | H |
| H | Et |
| Et | F |
| Me | Et |
| SO2Me | Cl |
TABLE 11n
Formula XIIn
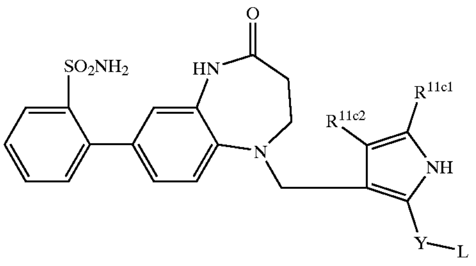
| $R^{11c1}$ | $R^{11c2}$ |
|---|---|
| H | H |
| Me | Me |
| Br | Me |
| H | Cl |
| Me | Cl |
| Et | Cl |
TABLE 11n-continued
Formula XIIn
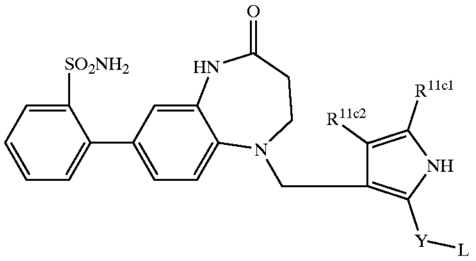
| $R^{11c1}$ | $R^{11c2}$ |
|---|---|
| 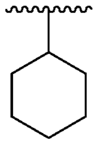 | 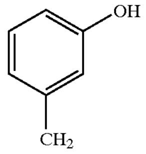 |
| 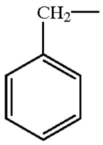 | 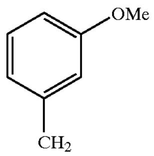 |
| 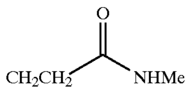 | 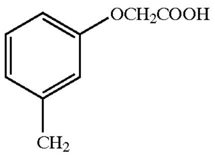 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 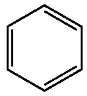 | 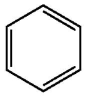 |
| 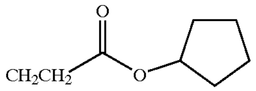 | 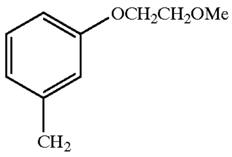 |
| 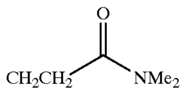 | 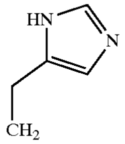 |
| —NH2 | H |
| H | Et |
| Et | F |

TABLE 11n-continued
Formula XIIn
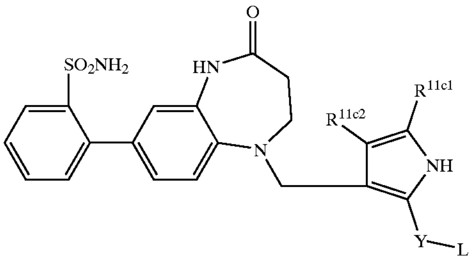
| $R^{11c1}$ | $R^{11c2}$ |
|---|---|
| Me | Et |
| SO2Me | Cl |
TABLE 11o
Formula XIIo
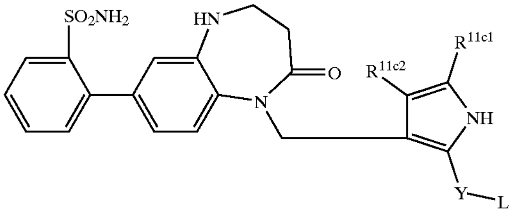
| $R^{11c1}$ | $R^{11c2}$ |
|---|---|
| H | H |
| Me | Me |
| Br | Me |
| H | Cl |
| Me | Cl |
| Et | Cl |
| 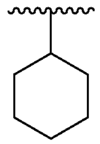 | 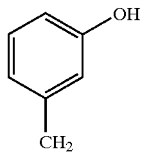 |
| 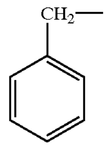 | 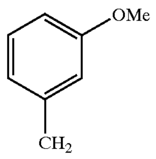 |
| 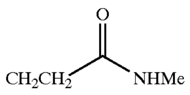 | 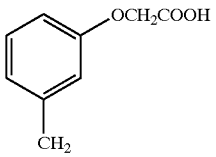 |
| OCH2Ph | H |
| OCH2CH2OMe | H |
| Me | F |
| Me | H |
| SO2Me | H |
| OMe | H |
| OMe | Me |
TABLE 11o-continued
Formula XIIo
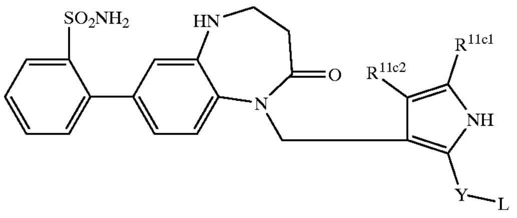
| $R^{11c1}$ | $R^{11c2}$ |
|---|---|
| F | H |
| Et | H |
| —OH | Me |
| Et | Br |
| 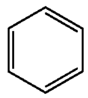 | 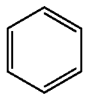 |
| 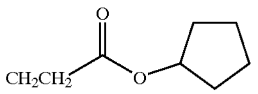 | 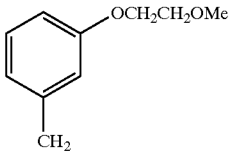 |
| 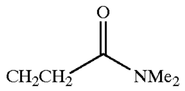 | 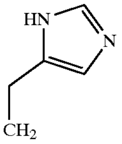 |
| —NH2 | H |
| H | Et |
| Et | F |
| Me | Et |
| SO2Me | Cl |
TABLE 11p
Formula XIIp
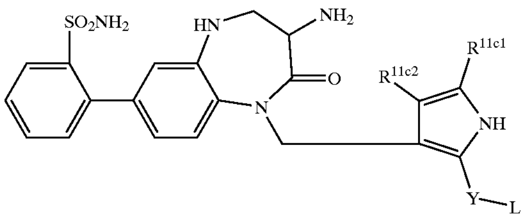
| $R^{11c1}$ | $R^{11c2}$ |
|---|---|
| H | H |
| Me | Me |
| Br | Me |
| H | Cl |
| Me | Cl |
| Et | Cl |

TABLE 11p-continued
Formula XIIp
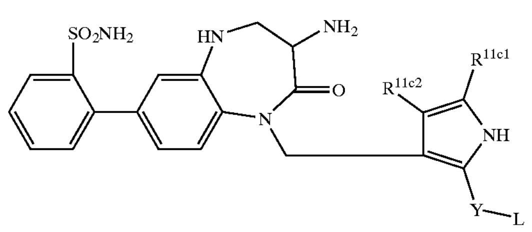
| $R^{11c1}$ | $R^{11c2}$ |
|---|---|
| 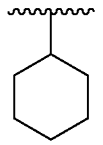 | 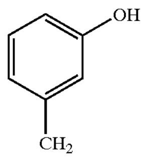 |
| 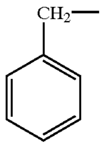 | 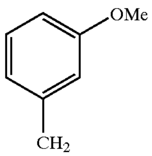 |
| 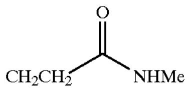 | 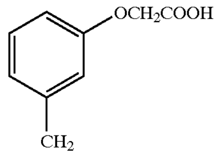 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |
| Et | Br |
| 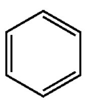 | 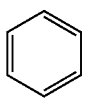 |
| 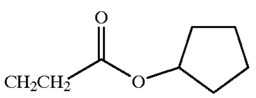 | 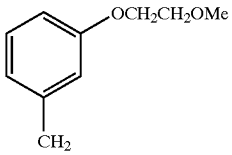 |
| 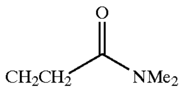 | 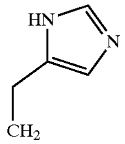 |
| —NH2 | H |
| H | Et |
| Et | F |
TABLE 11p-continued
Formula XIIp
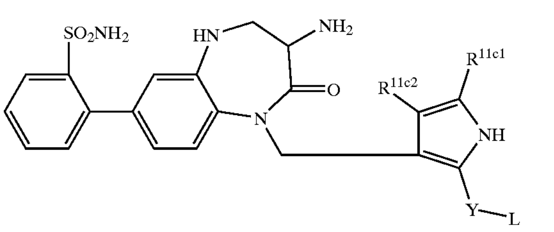
| $R^{11c1}$ | $R^{11c2}$ |
|---|---|
| Me | Et |
| SO2Me | Cl |
TABLE 11q
Formula XIIq
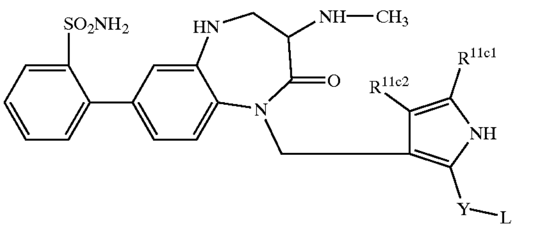
| $R^{11c1}$ | $R^{11c2}$ |
|---|---|
| H | H |
| Me | Me |
| Br | Me |
| H | Cl |
| Me | Cl |
| Et | Cl |
| 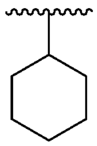 | 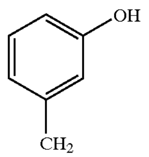 |
| 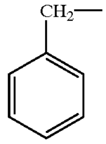 | 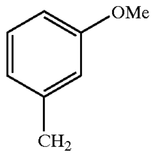 |
| 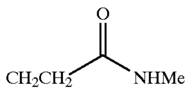 | 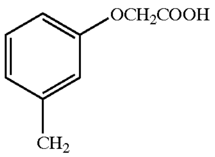 |
| OCH2Ph | H |
| OCH2CH2OMe | H |
| Me | F |
| Me | H |
| SO2Me | H |
| OMe | H |
| OMe | Me |
| F | H |
| Et | H |
| —OH | Me |

TABLE 11q-continued
Formula XIIq
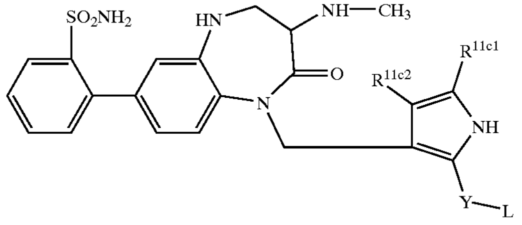
| $R^{11c1}$ | $R^{11c2}$ |
|---|---|
| Et | Br |
| 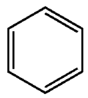 | 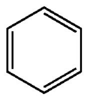 |
| 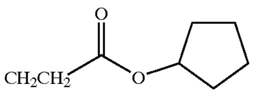 | 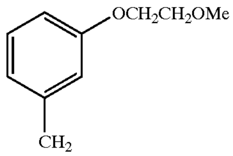 |
| 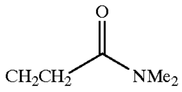 | 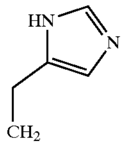 |
| —NH2 | H |
| H | Et |
| Et | F |
| Me | Et |
| SO2Me | Cl |
Also preferred are compounds according to Tables 1 through Table 11q, wherein
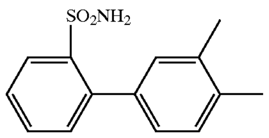
the biphenylene portions of their formulae:
are each replaced with the following ring structure:
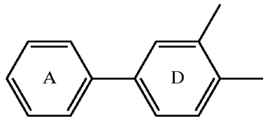
wherein each of the A and D ring portions are as follows:
| A | D |
|---|---|
| 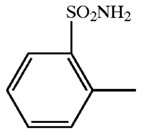 | 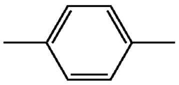 |
| 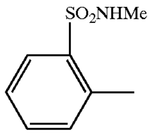 | 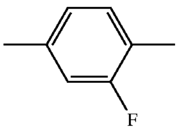 |
| 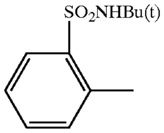 | 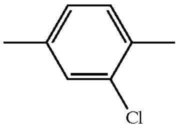 |
| 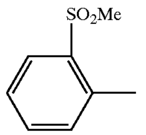 | 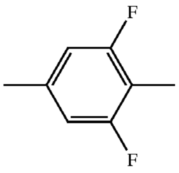 |
| 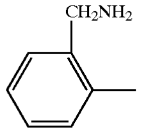 | 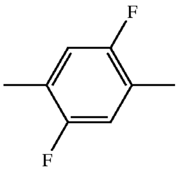 |
| 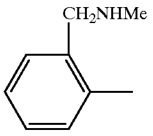 | 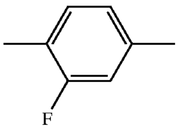 |
| 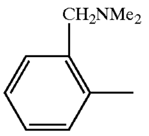 | 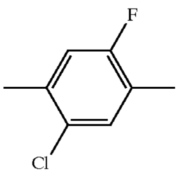 |

-continued
| A | D |
|---|---|
| 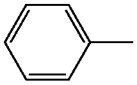 | 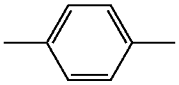 |
| 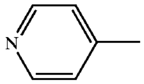 | 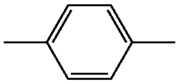 |
| 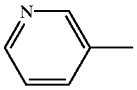 | 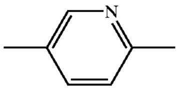 |
| 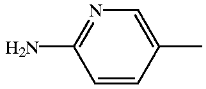 | 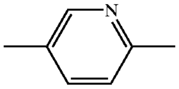 |
| 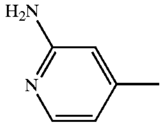 | 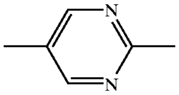 |
Even more preferred compounds are set forth in Tables 12–24, below.
TABLE 12
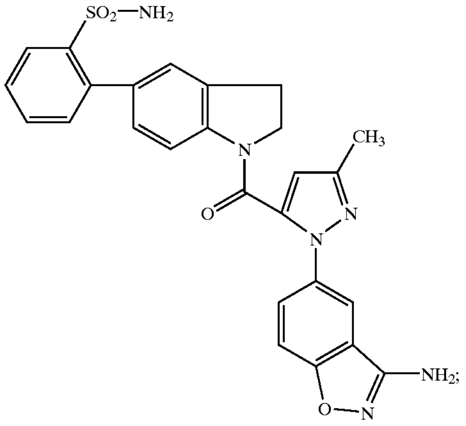
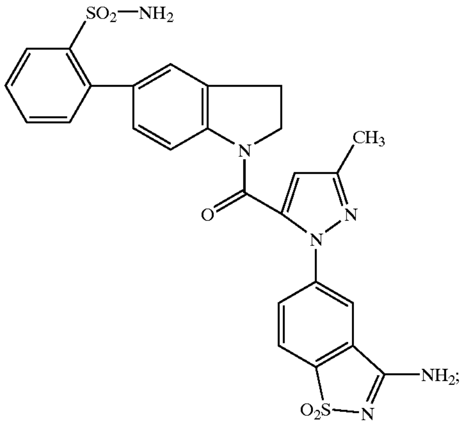
TABLE 12-continued
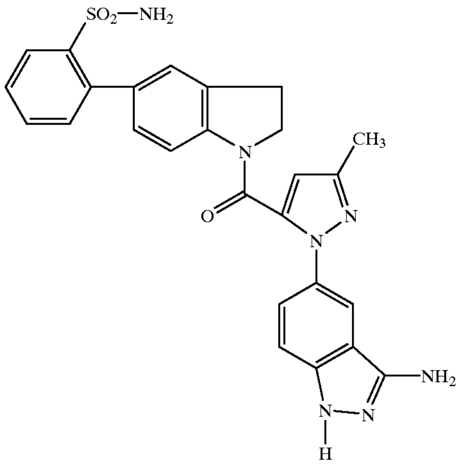
and
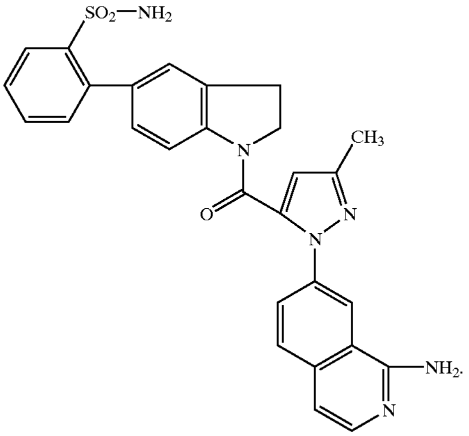
TABLE 13
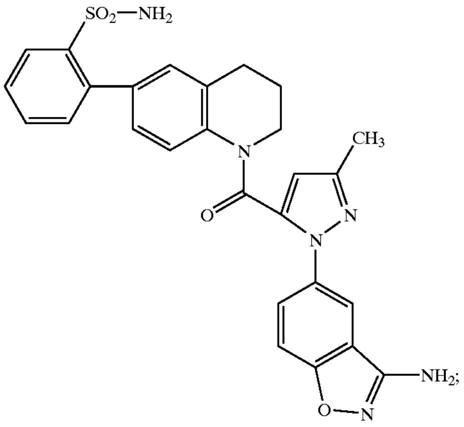

TABLE 13-continued
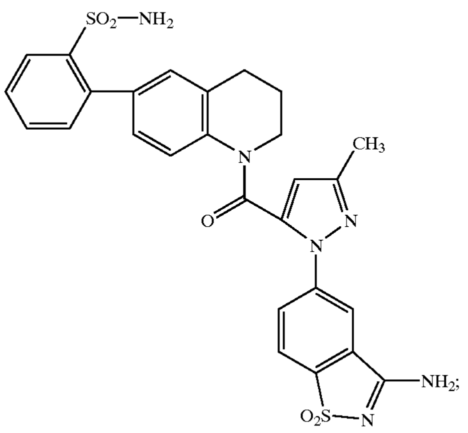
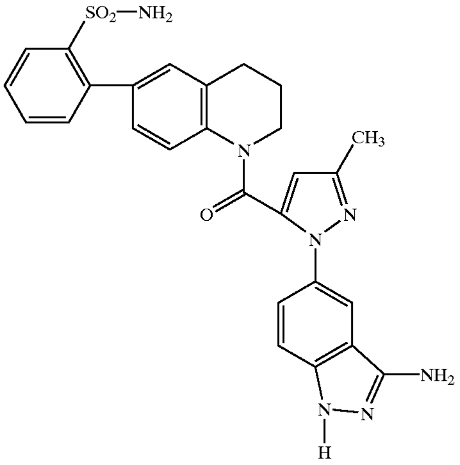
and
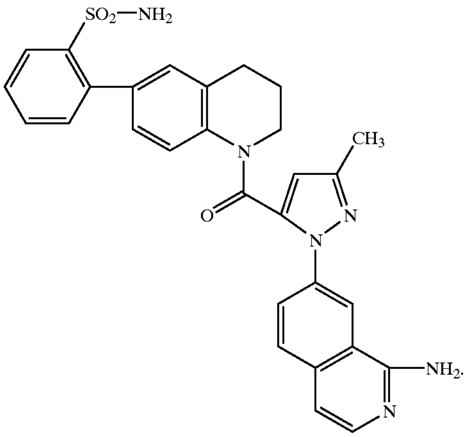
TABLE 14
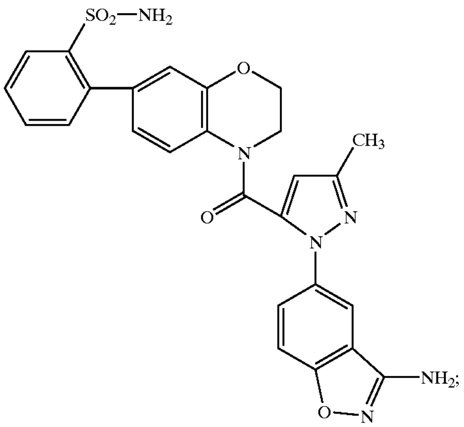
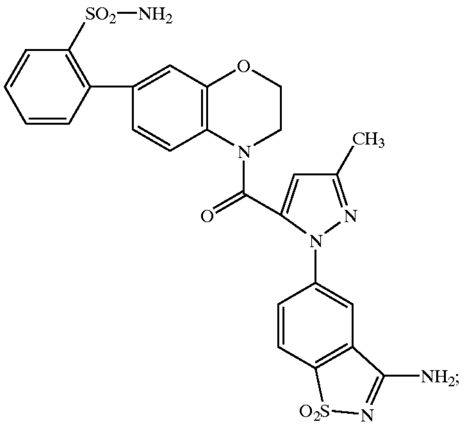
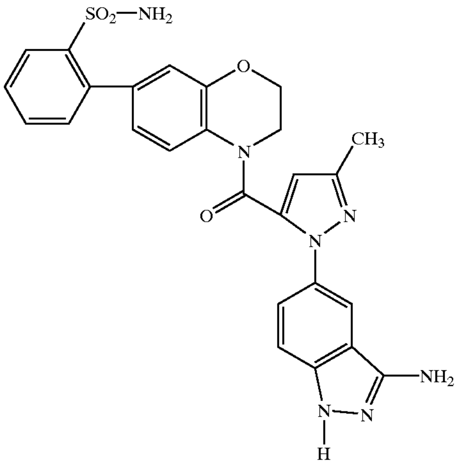
and TABLE 14-continued
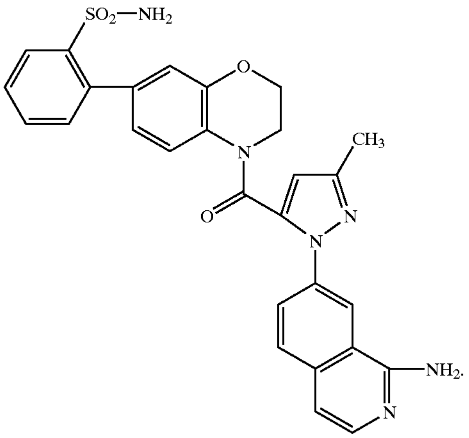
TABLE 15
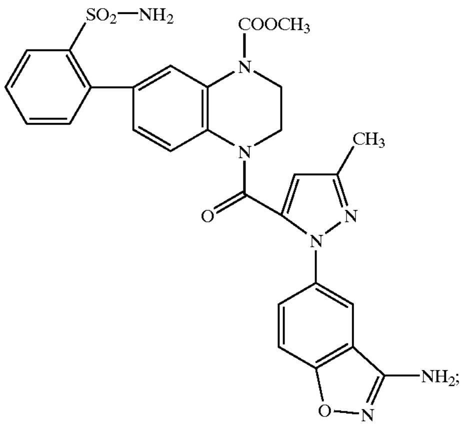
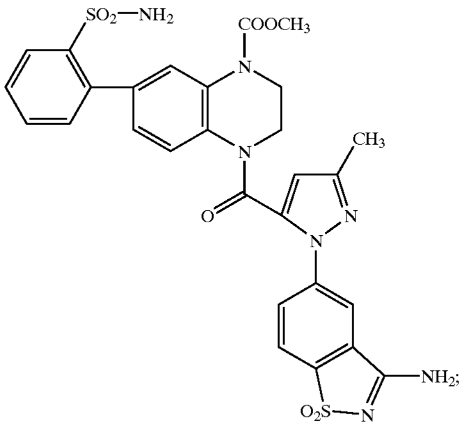
TABLE 15-continued
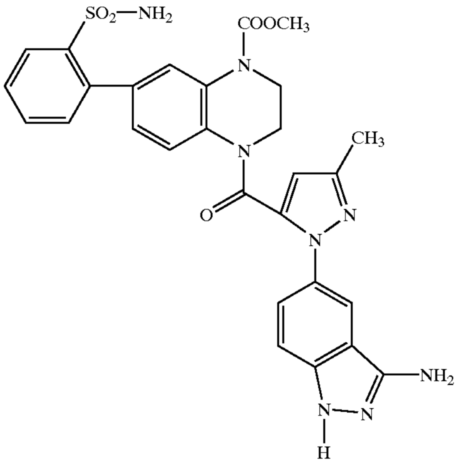
and
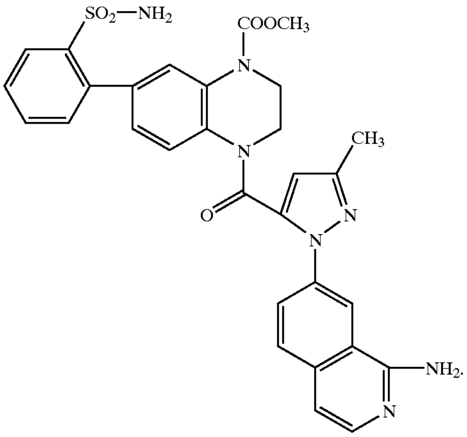
TABLE 16
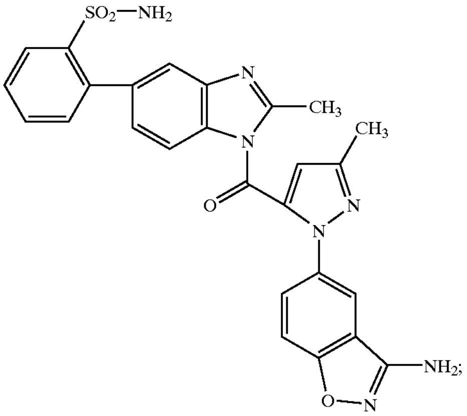

TABLE 16-continued
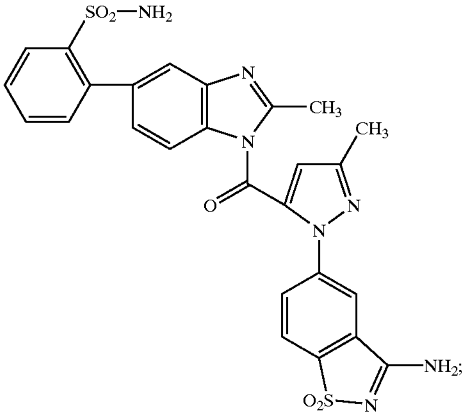
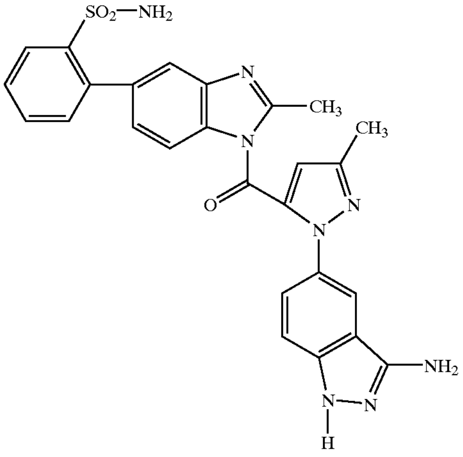
and
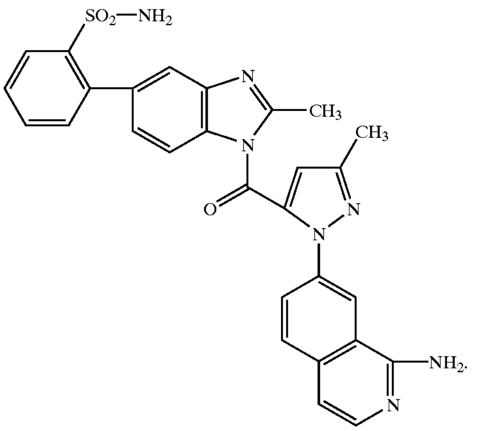
TABLE 17
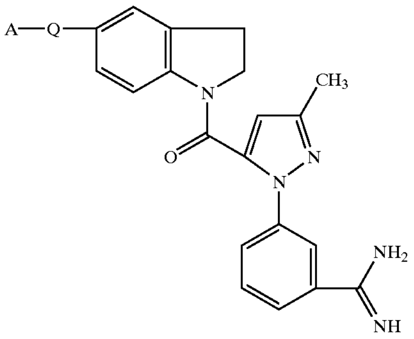
wherein A—Q— is selected from the group consisting of:
t-Bu; O-t-Bu; —$(CH_2)_{0-5}$-amino; OH; carboxylic acid ester; carboxamide;
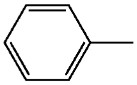 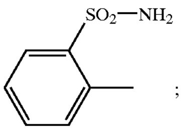 ; 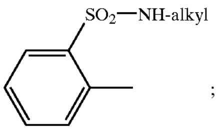 ;
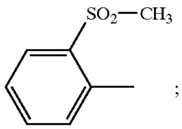 ; 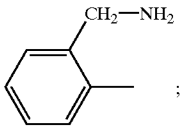 ; 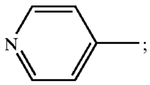 ;
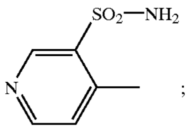 ; 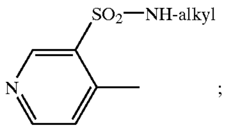 ;
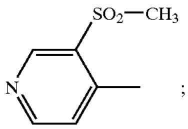 ; 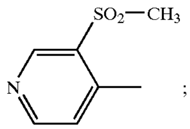 ; 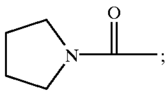 ;
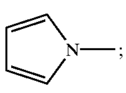 ; 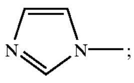 ; 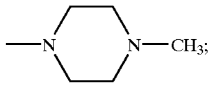
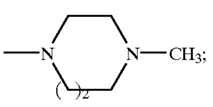 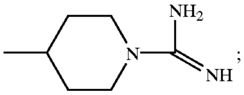 ;
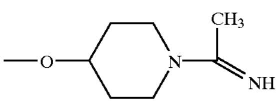 and 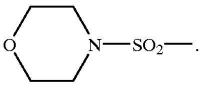 .

TABLE 18
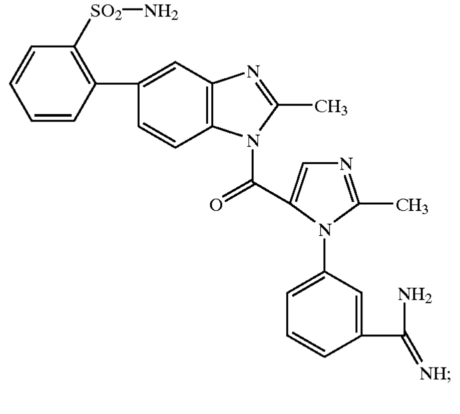
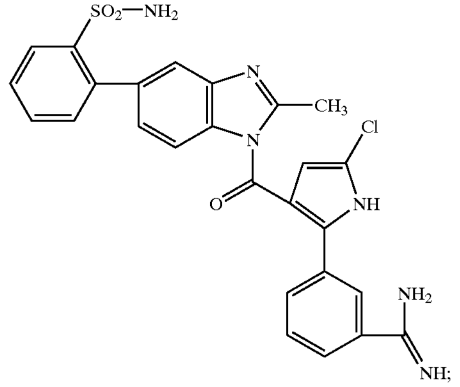
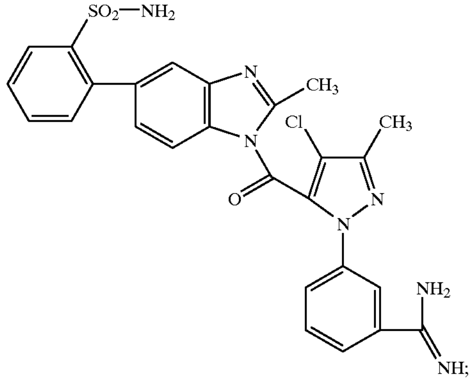
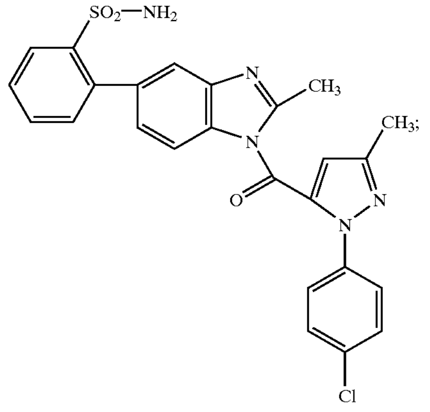
TABLE 18-continued
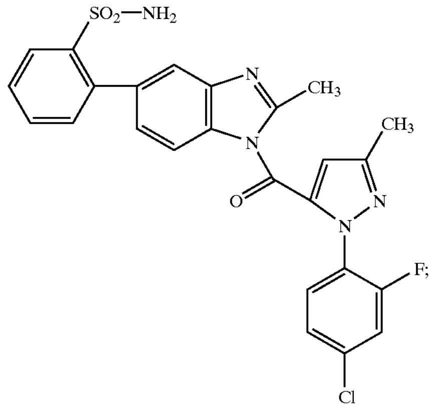
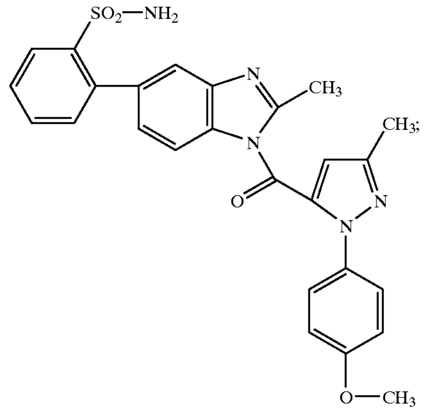
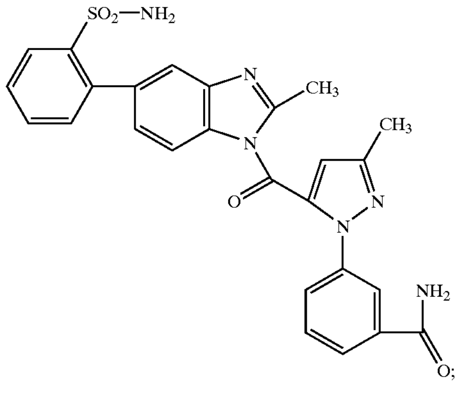
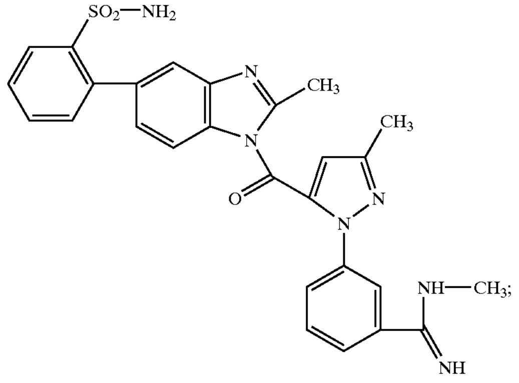

TABLE 18-continued
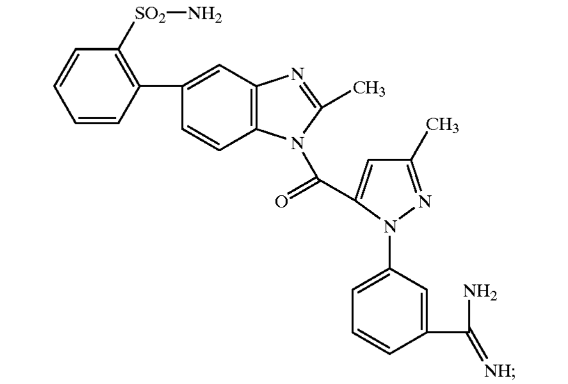
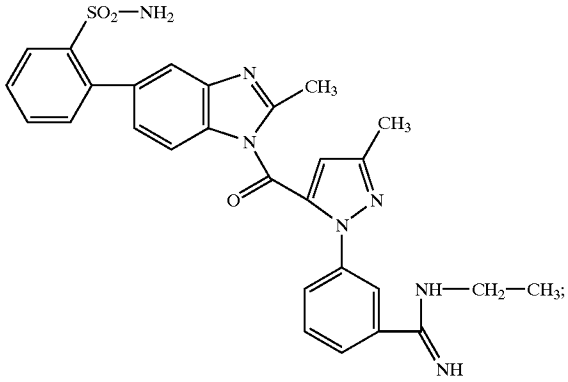
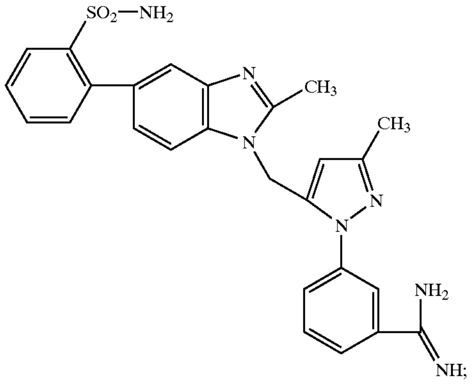
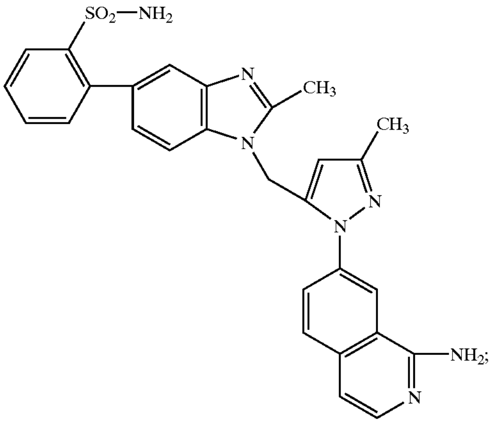
TABLE 18-continued
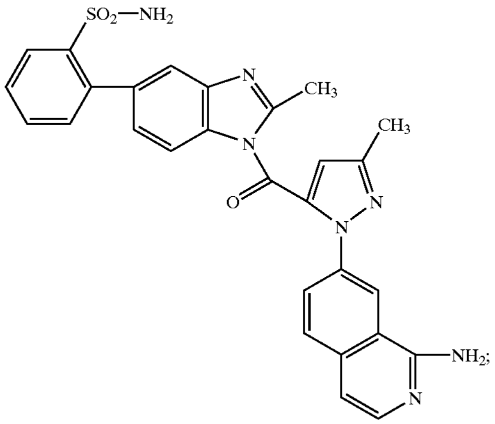
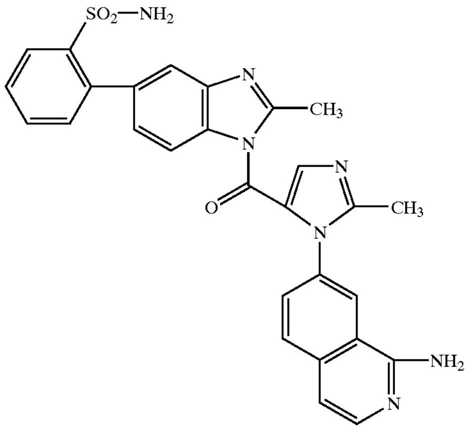
and
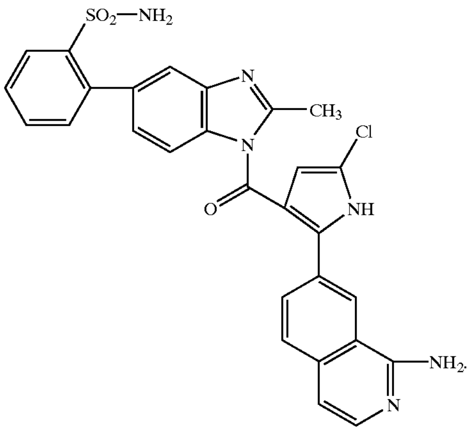

TABLE 19
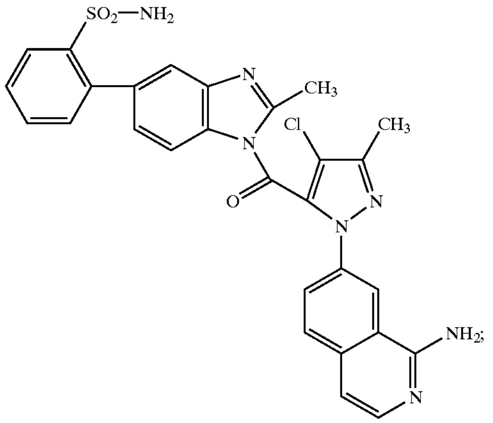
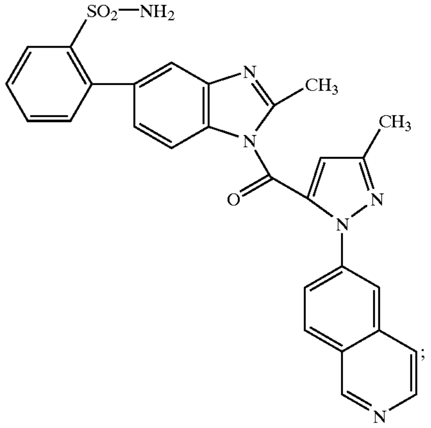
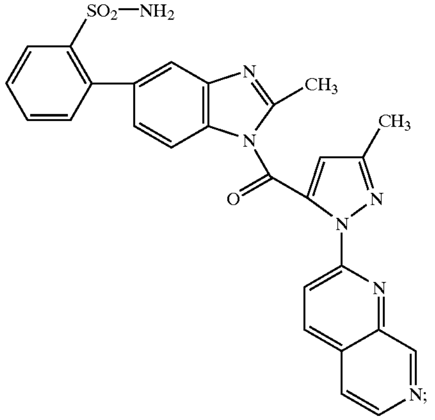
TABLE 19-continued
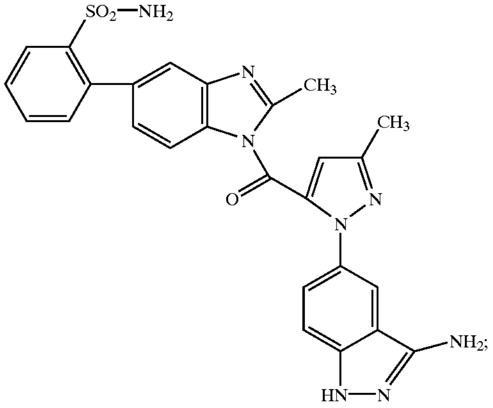
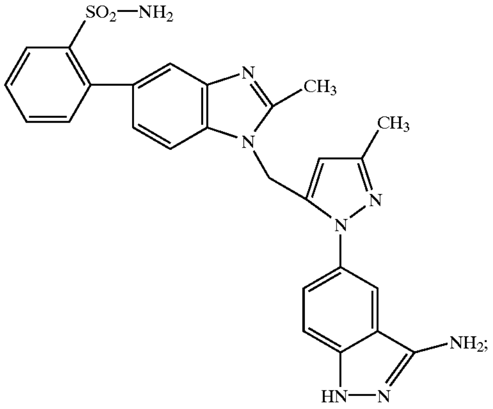
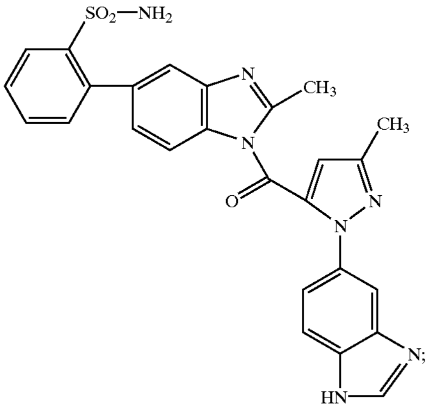

TABLE 19-continued
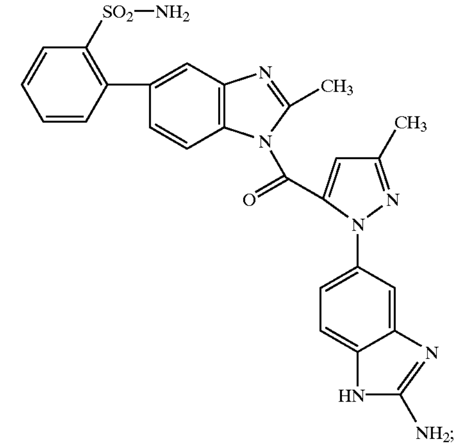
;
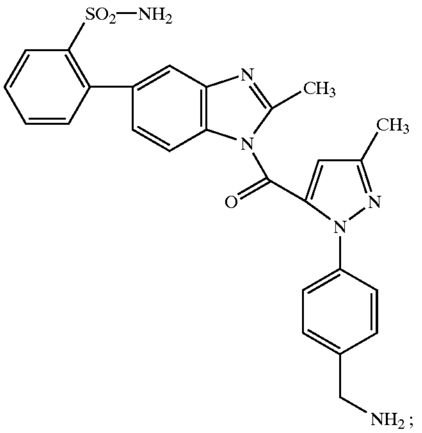
;
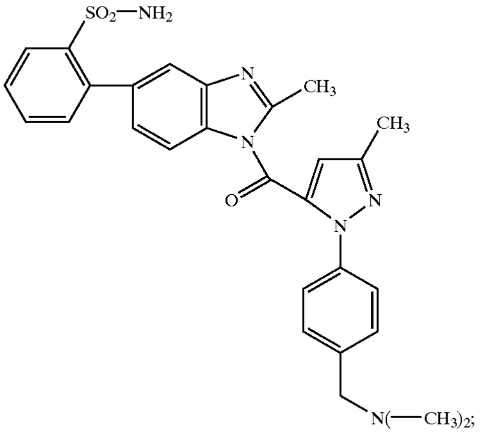
;
TABLE 19-continued
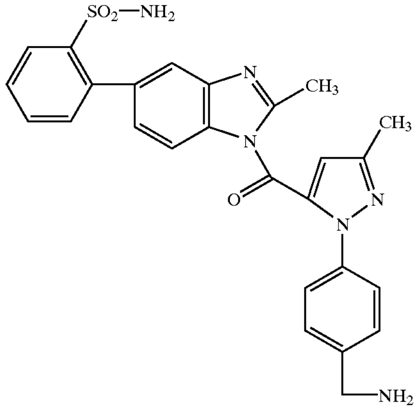
and
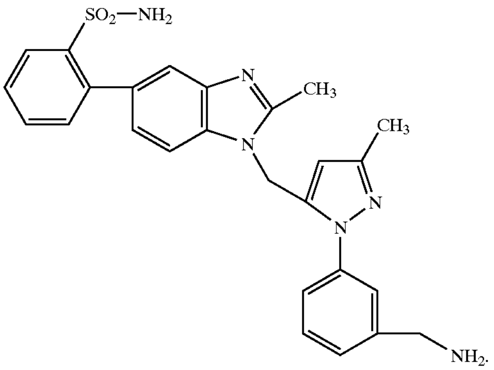
.
TABLE 20
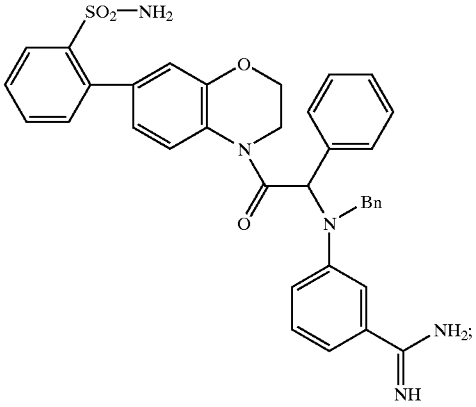
;

TABLE 20-continued
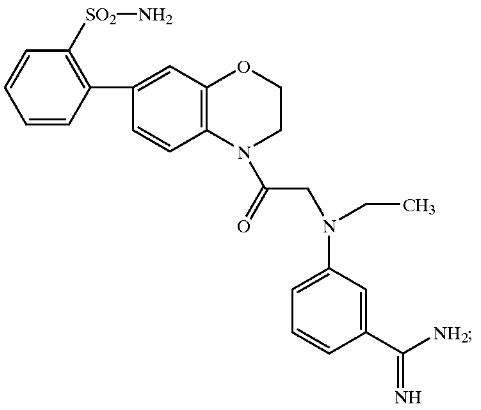
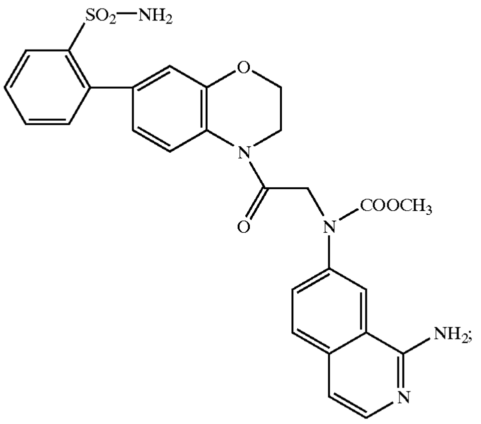
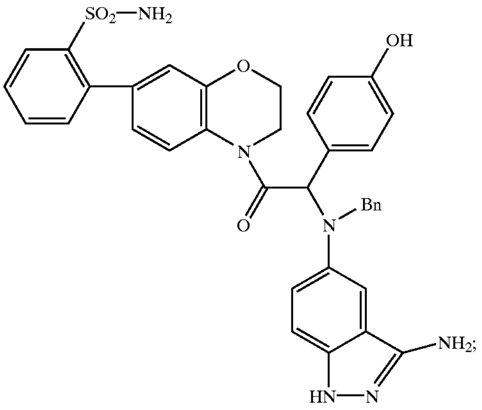
TABLE 20-continued
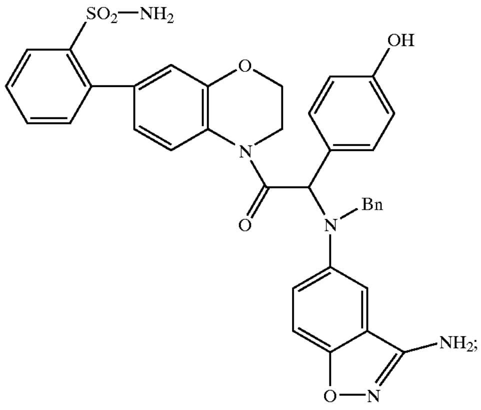
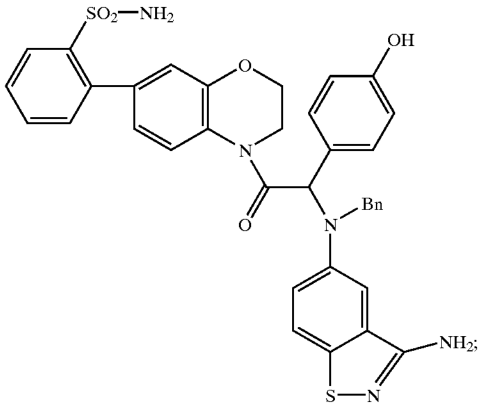
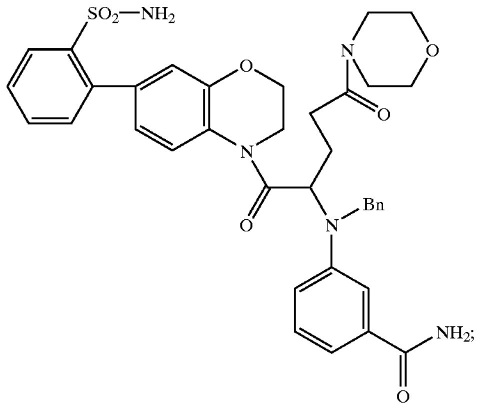

TABLE 20-continued
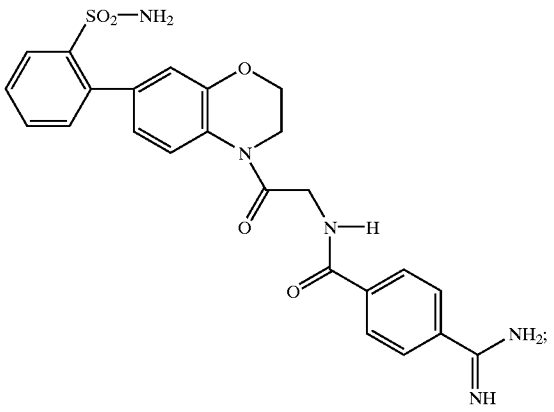
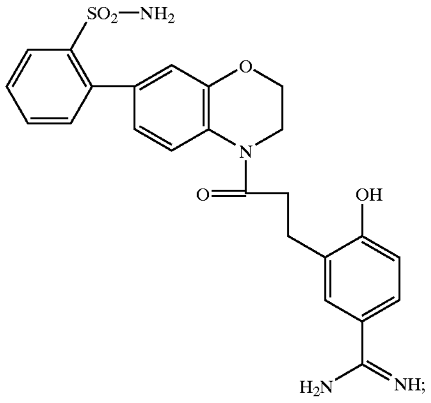
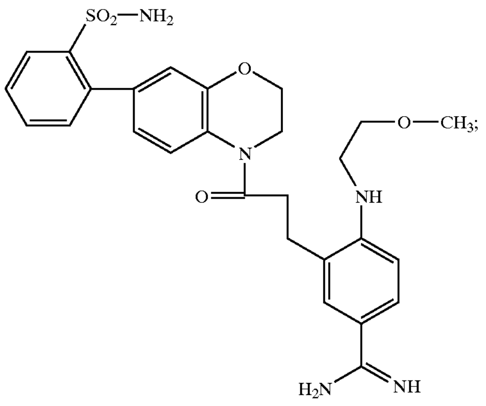
TABLE 20-continued
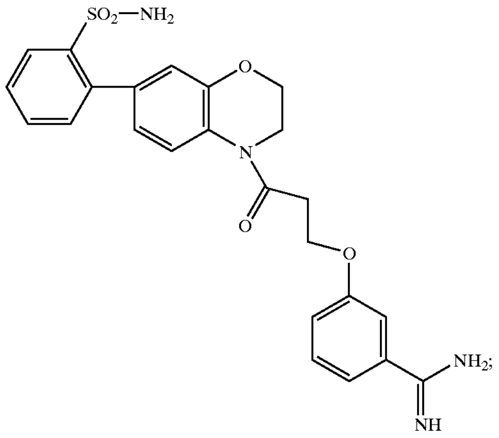
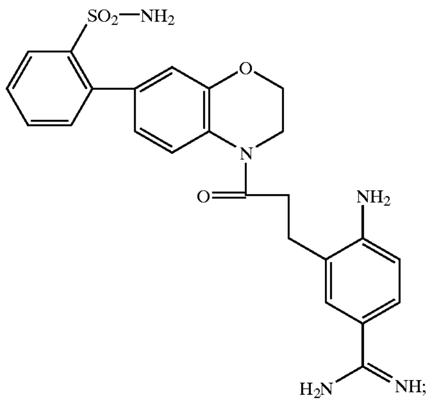
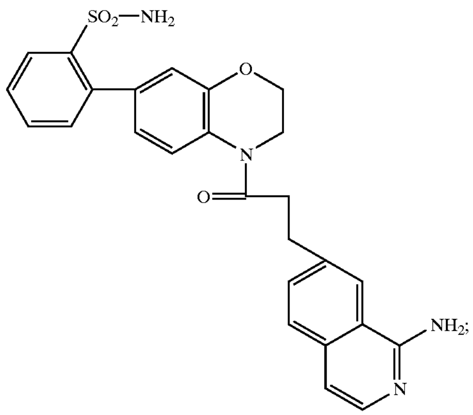

TABLE 20-continued
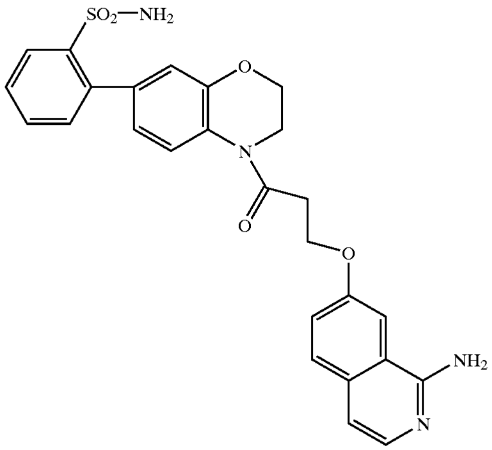
and
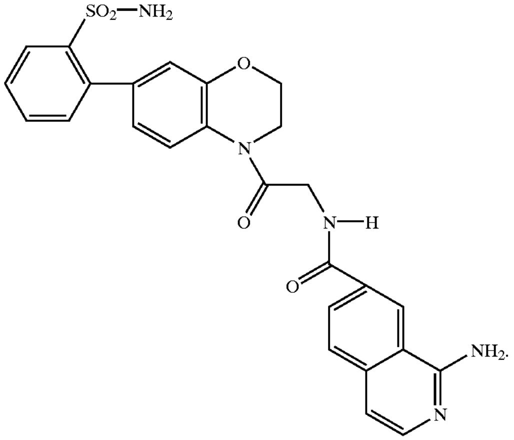
TABLE 21
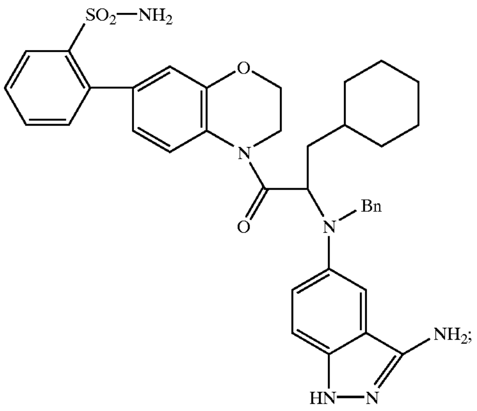
TABLE 21-continued
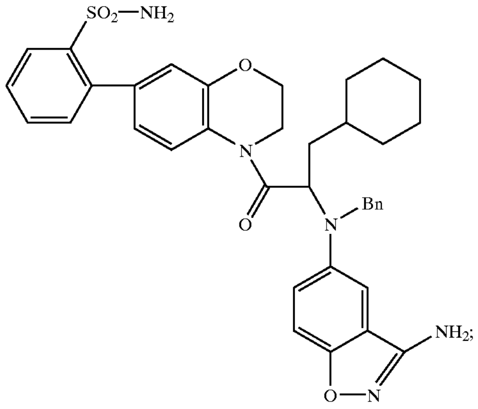
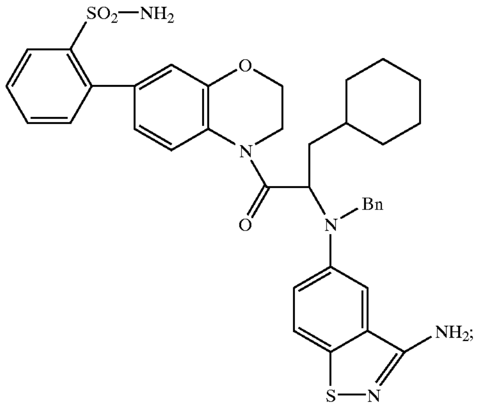
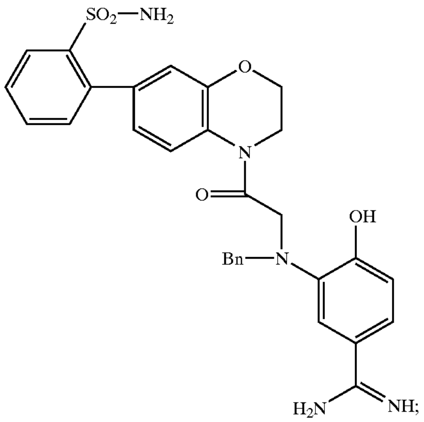

TABLE 21-continued
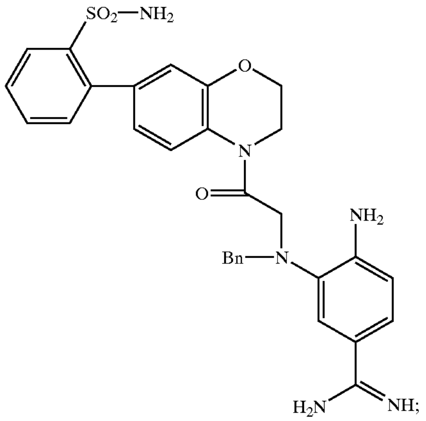
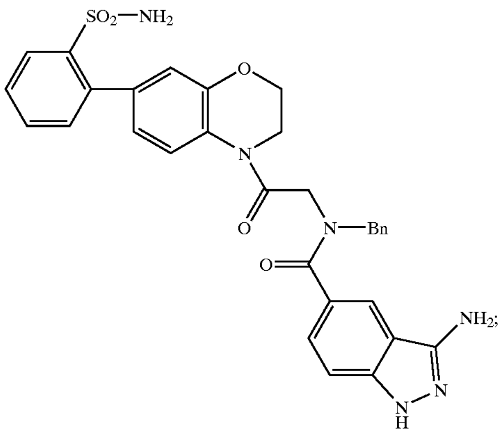
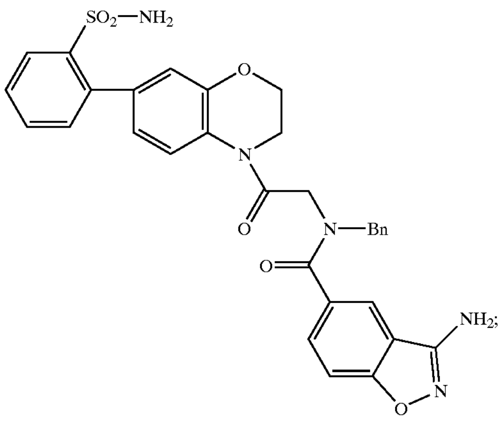
TABLE 21-continued
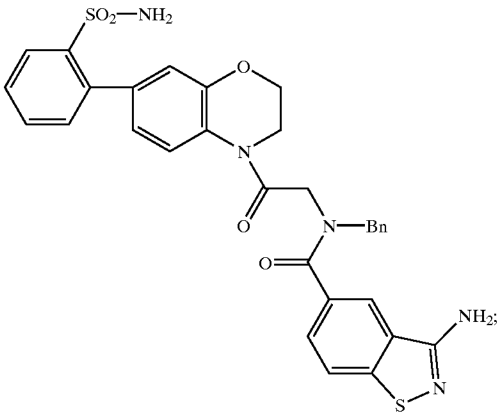
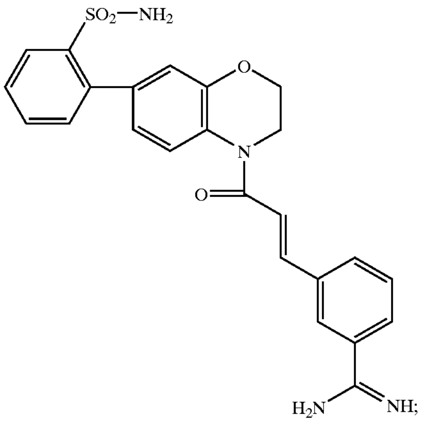
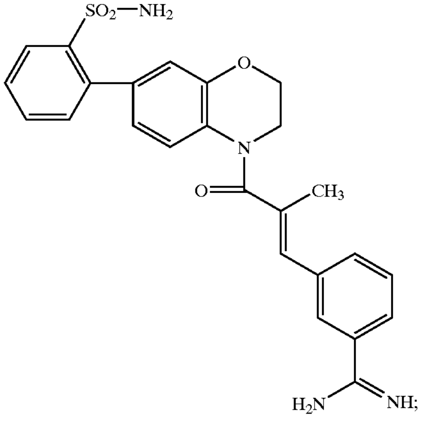

TABLE 21-continued
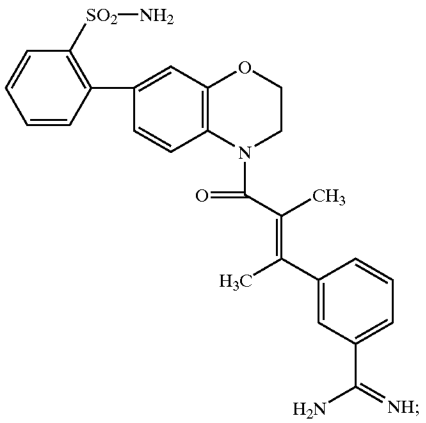
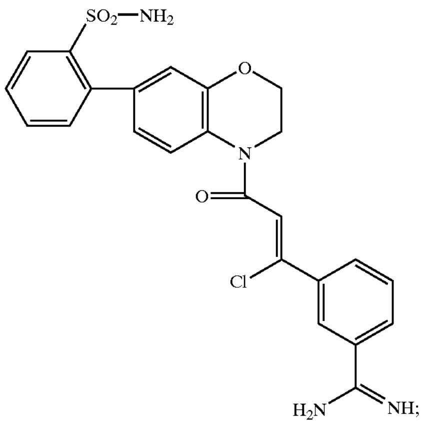
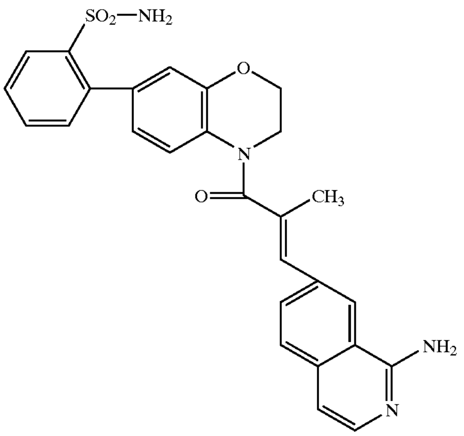
and
TABLE 21-continued
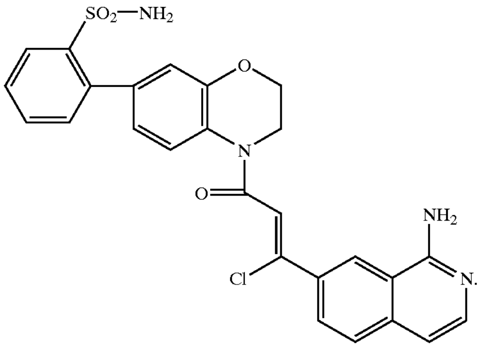
TABLE 22
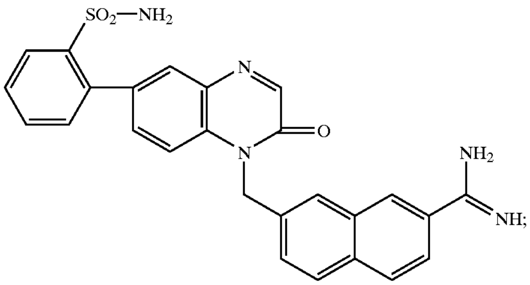
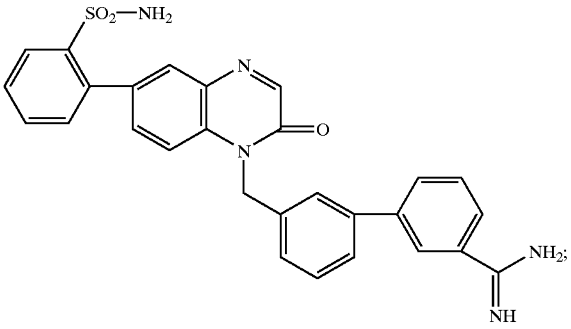
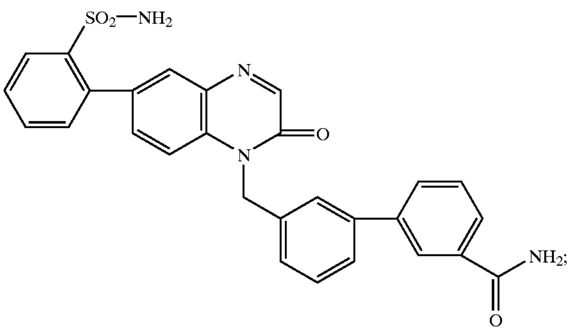

TABLE 22-continued
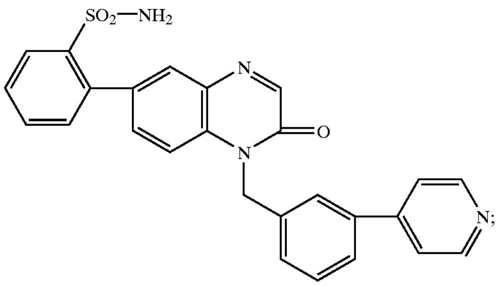
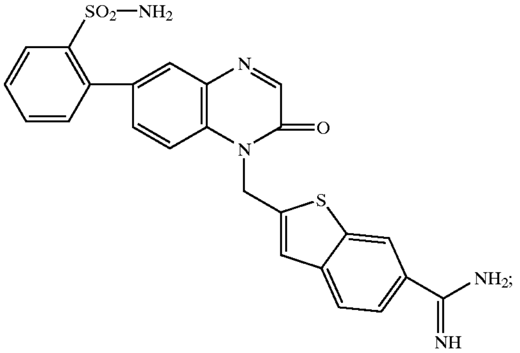
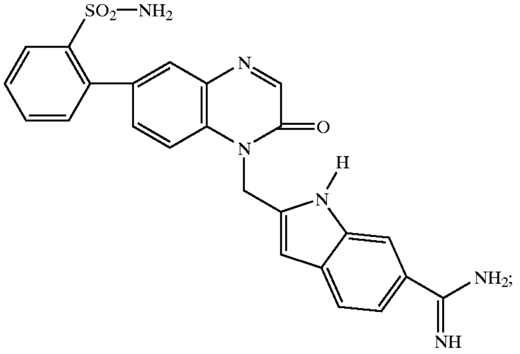
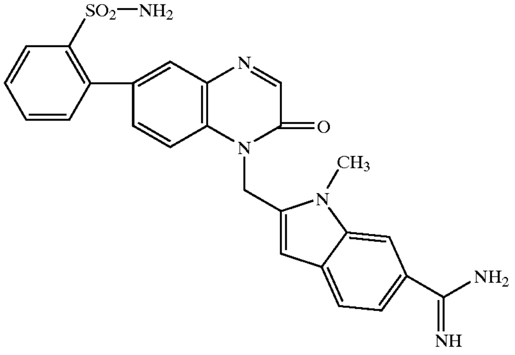
and
TABLE 22-continued
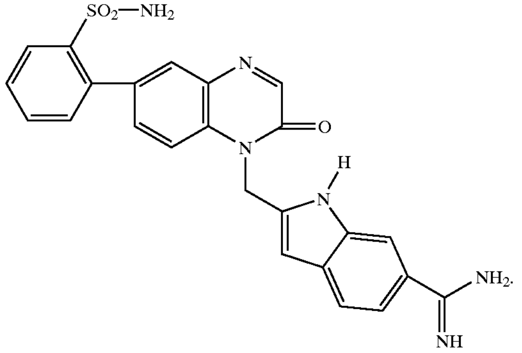
TABLE 23
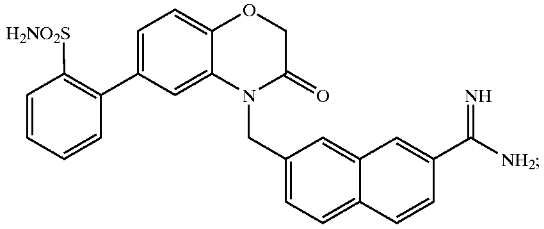
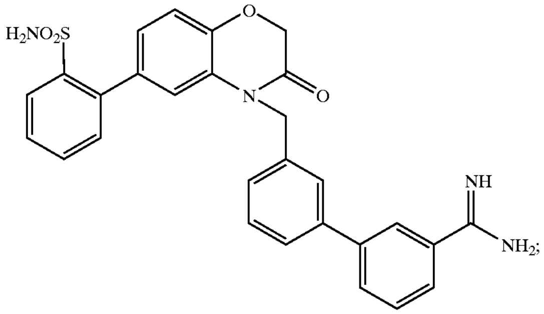
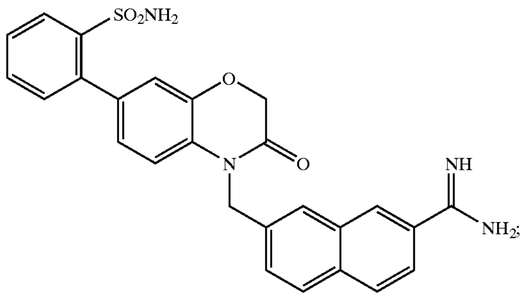
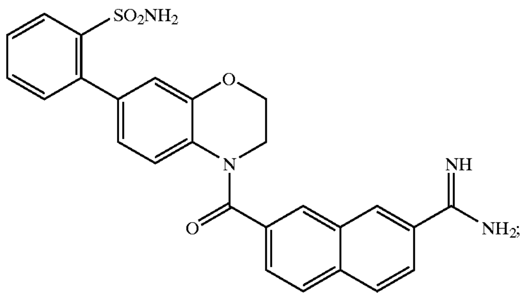

TABLE 23-continued
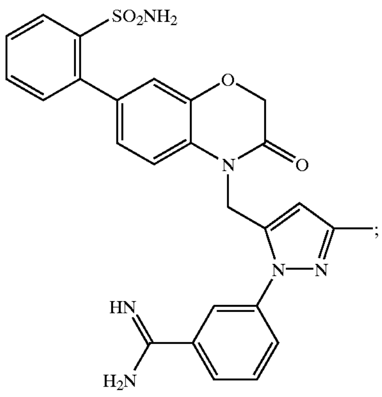
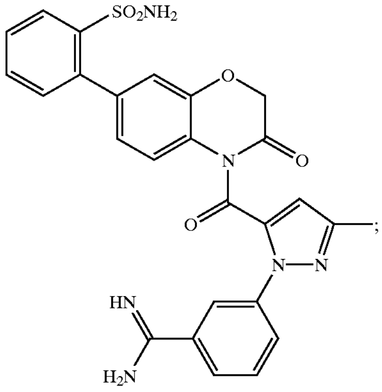
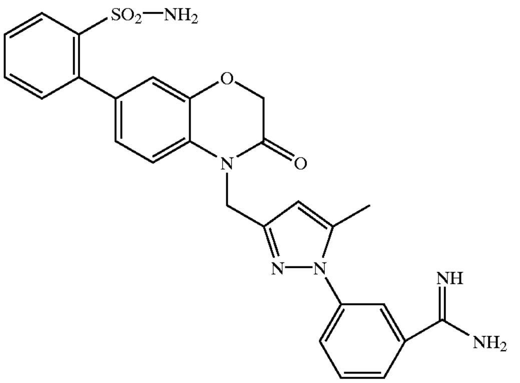
and
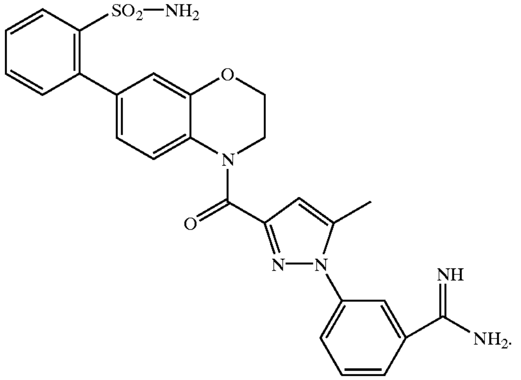
TABLE 24
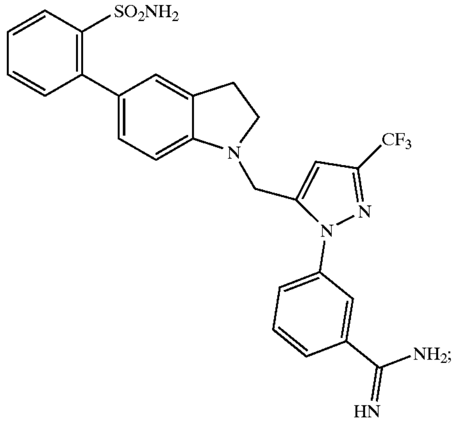
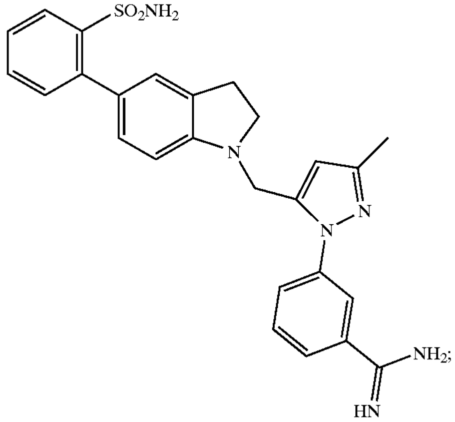
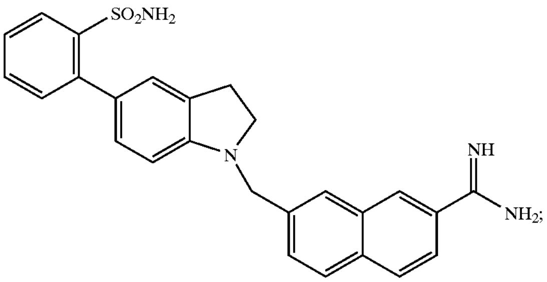
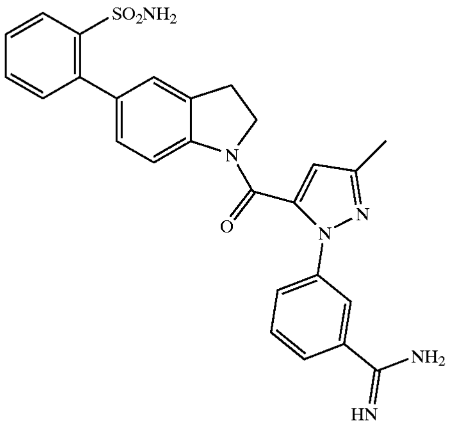
and TABLE 24-continued
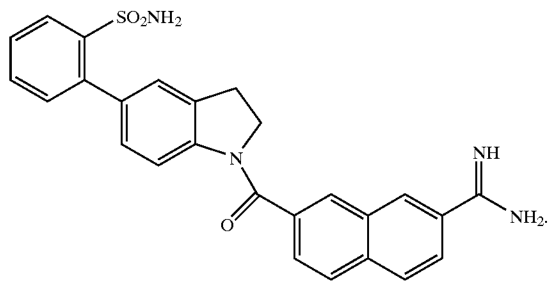
TABLE 25
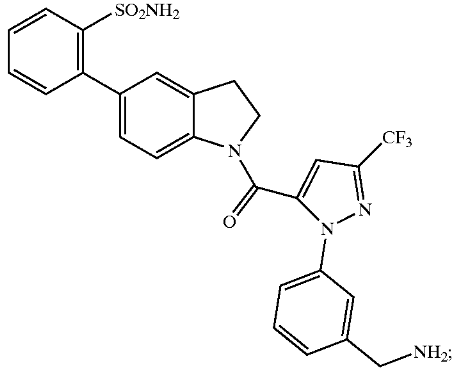
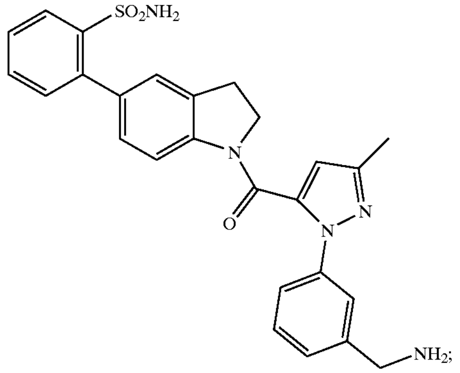
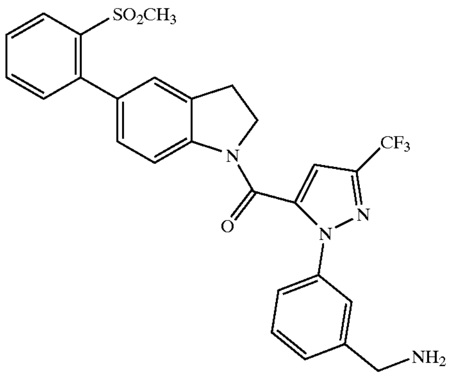
and
TABLE 25-continued
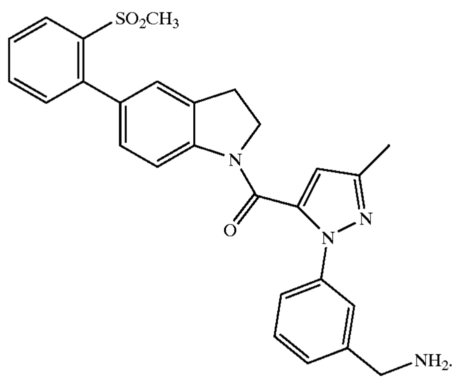
TABLE 26
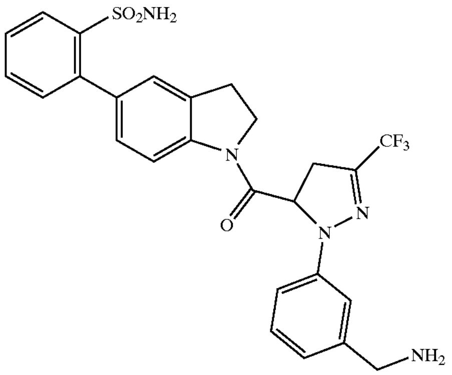
and
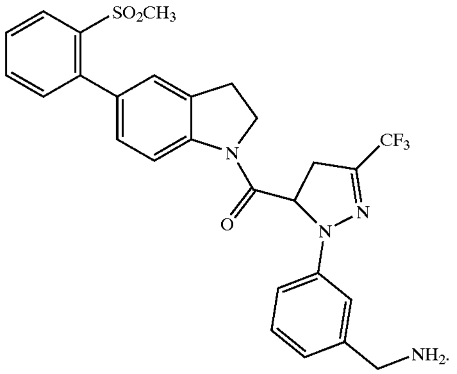
TABLE 27
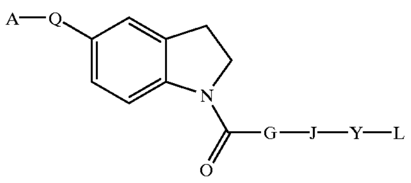
or TABLE 27-continued

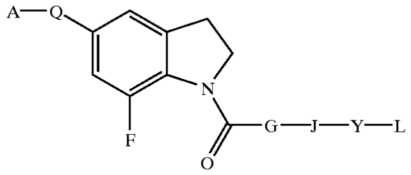

Wherein:

Q is a direct link, and A is a member selected from the group:

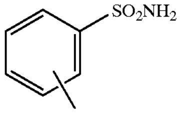 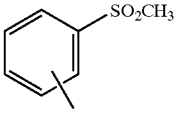 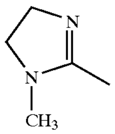 and

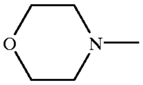

or Q is a —C(=NH)— group, and A is a member selected from the group:

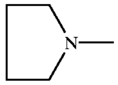 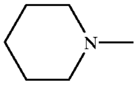 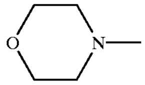 and

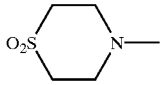

G is a direct link;

J is a member selected from the group:

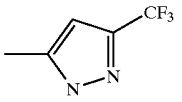 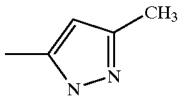 and

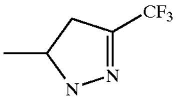 ; and

Y—L is a member selected from the group:

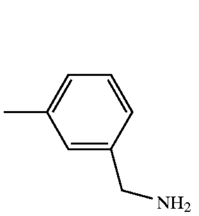 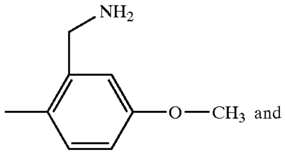 and

-continued

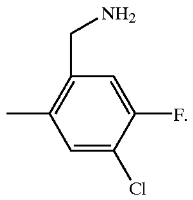

This invention also encompasses all pharmaceutically acceptable isomers, salts, hydrates and solvates of the compounds of formula I. In addition, the compounds of formula I can exist in various isomeric and tautomeric forms, and all such forms are meant to be included in the invention, along with pharmaceutically acceptable salts, hydrates and solvates of such isomers and tautomers.

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

A number of methods are useful for the preparation of the salts described above and are known to those skilled in the art. For example, the free acid or free base form of a compound of one of the formulas above can be reacted with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Prodrug Derivatives of Compounds

This invention also encompasses prodrug derivatives of the compounds contained herein. The term "prodrug" refers to a pharmacologically inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo, when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, Design of Prodrugs, pp. 7–9, 21–24, Elsevier, Amsterdam 1985 and Silverman, The Organic Chemistry of Drug Design and Drug Action, pp. 352–401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

As mentioned above, the compounds of this invention find utility as therapeutic agents for disease states in mammals which have disorders of coagulation such as in the treatment or prevention of unstable angina, refractory angina, myocardial infarction, transient ischemic attacks, thrombotic stroke, embolic stroke, disseminated intravascular coagulation including the treatment of septic shock, deep venous thrombosis in the prevention of pulmonary embolism or the treatment of reocclusion or restenosis of reperfused coronary arteries. Further, these compounds are useful for the treatment or prophylaxis of those diseases which involve the production and/or action of factor Xa/prothrombinase complex. This includes a number of thrombotic and prothrombotic states in which the coagulation cascade is activated which include but are not limited to, deep venous thrombosis, pulmonary embolism, myocardial infarction, stroke, thromboembolic complications of surgery and peripheral arterial occlusion.

Accordingly, a method for preventing or treating a condition in a mammal characterized by undesired thrombosis comprises administering to the mammal a therapeutically effective amount of a compound of this invention. In addition to the disease states noted above, other diseases treatable or preventable by the administration of compounds of this invention include, without limitation, occlusive coronary thrombus formation resulting from either thrombolytic therapy or percutaneous transluminal coronary angioplasty, thrombus formation in the venous vasculature, disseminated intravascular coagulopathy, a condition wherein there is rapid consumption of coagulation factors and systemic coagulation which results in the formation of life-threatening thrombi occurring throughout the microvasculature leading to widespread organ failure, hemorrhagic stroke, renal dialysis, blood oxygenation, and cardiac catheterization.

The compounds of the invention also find utility in a method for inhibiting the coagulation of biological samples, (e.g. blood) which comprises the administration of a compound of the invention.

The compounds of the present invention may also be used in combination with other therapeutic or diagnostic agents. In certain preferred embodiments, the compounds of this invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of the present invention may act in a synergistic fashion to prevent reocclusion following a successful thrombolytic therapy and/or reduce the time to reperfusion. These compounds may also allow for reduced doses of the thrombolytic agents to be used and therefore minimize potential hemorrhagic side-effects. The compounds of this invention can be utilized in vivo, ordinarily in mammals such as primates, (e.g. humans), sheep, horses, cattle, pigs, dogs, cats, rats and mice, or in vitro.

The biological properties of the compounds of the present invention can be readily characterized by methods that are well known in the art, for example by the in vitro protease activity assays and in vivo studies to evaluate antithrombotic efficacy, and effects on hemostasis and hematological parameters, such as are illustrated in the examples.

Diagnostic applications of the compounds of this invention will typically utilize formulations in the form of solutions or suspensions. In the management of thrombotic disorders the compounds of this invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be 3–11, more preferably 5–9 and most preferably 7–8. It will be understood that use of certain of the foregoing excipients, carriers, or stabilizers will result in the formation of cyclic polypeptide salts. While the preferred route of administration is by injection, other methods of administration are also anticipated such as orally, intravenously (bolus and/or infusion), subcutaneously, intramuscularly, colonically, rectally, nasally, transdermally or intraperitoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

The compounds of the invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can include polyvinylpyrrolidinone, pyran copolymer, polyhydroxypropyl-methacrylamide-phenol, polyhydroxyethyl-aspartamide-phenol, or polyethyleneoxide-polylysine substituted with palmitoyl residues. Furthermore, compounds of the invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Thetapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the body's fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be readily determined by one skilled in the art. Typically, applications of compound are commenced at lower dosage levels, with dosage levels being increased until the desired effect is achieved.

The compounds of the invention can be administered orally or parenterally in an effective amount within the dosage range of about 0.1 to 100 mg/kg, preferably about 0.5 to 50 mg/kg and more preferably about 1 to 20 mg/kg on a regimen in a single or 2 to 4 divided daily doses and/or continuous infusion.

Typically, about 5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Preparation of Compounds

The compounds of the present invention may be synthesized by either solid or liquid phase methods described and referenced in standard textbooks, or by a combination of both methods. These methods are well known in the art. See, Bodanszky, "The Principles of Peptide Synthesis", Hafner, et al., Eds., Springer-Verlag, Berlin, 1984.

Starting materials used in any of these methods are commercially available from chemical vendors such as Aldrich, Sigma, Nova Biochemicals, Bachem Biosciences, and the like, or may be readily synthesized by known procedures.

Reactions are carried out in standard laboratory glassware and reaction vessels under reaction conditions of standard temperature and pressure, except where otherwise indicated.

During the synthesis of these compounds, the functional groups of the amino acid derivatives used in these methods are protected by blocking groups to prevent cross reaction during the coupling procedure. Examples of suitable blocking groups and their use are described in "The Peptides: Analysis, Synthesis, Biology", Academic Press, Vol. 3 (Gross, et al., Eds., 1981) and Vol. 9 (1987), the disclosures of which are incorporated herein by reference.

Non-limiting exemplary synthesis schemes are outlined directly below, and specific steps are described in the Examples. The reaction products are isolated and purified by conventional methods, typically by solvent extraction into a compatible solvent. The products may be further purified by column chromatography or other appropriate methods.

Scheme 1

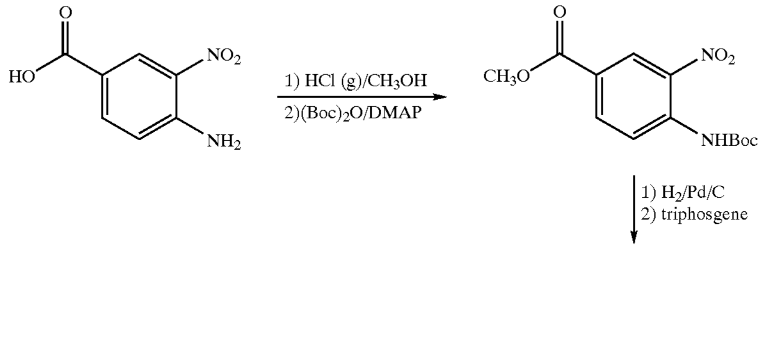

-continued
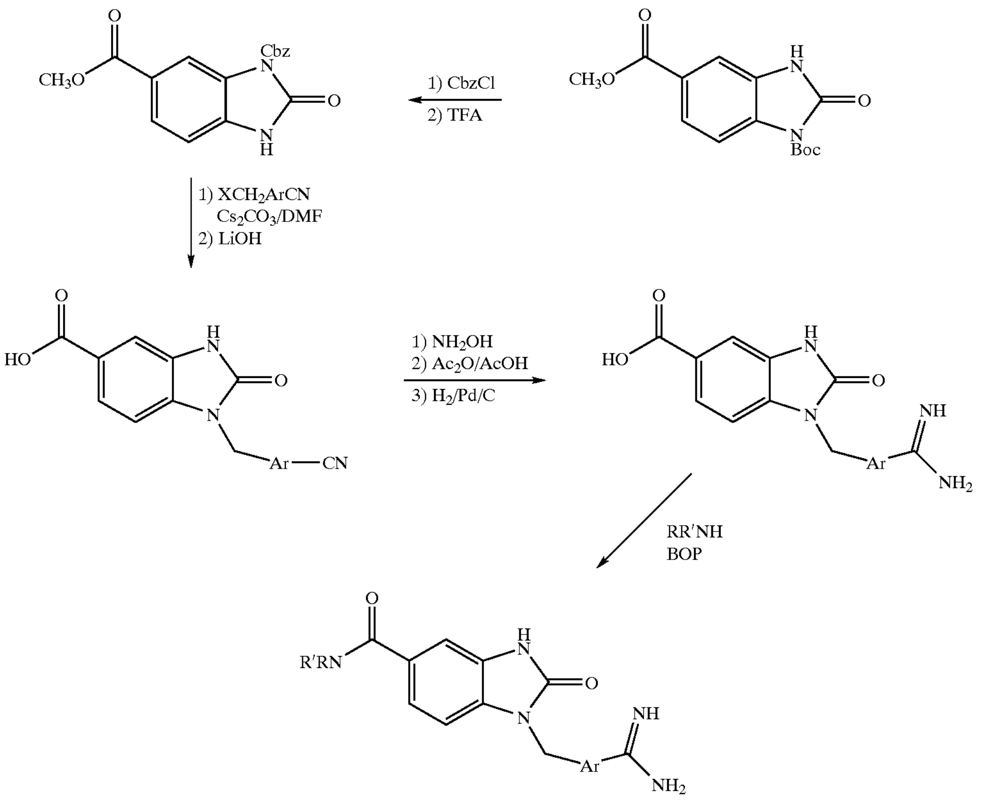
Scheme 2
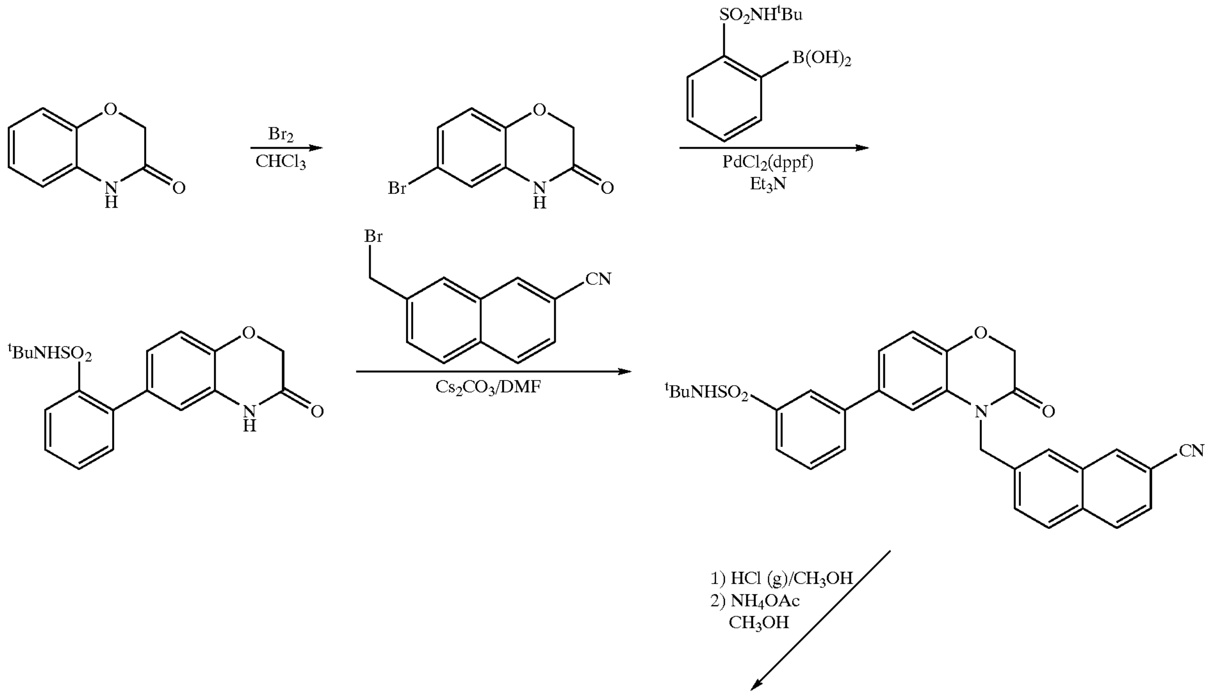

-continued
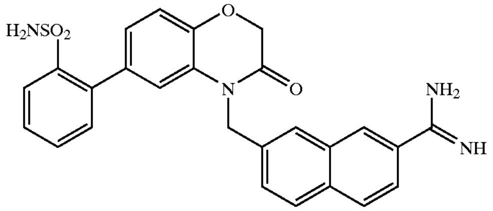
Scheme 3
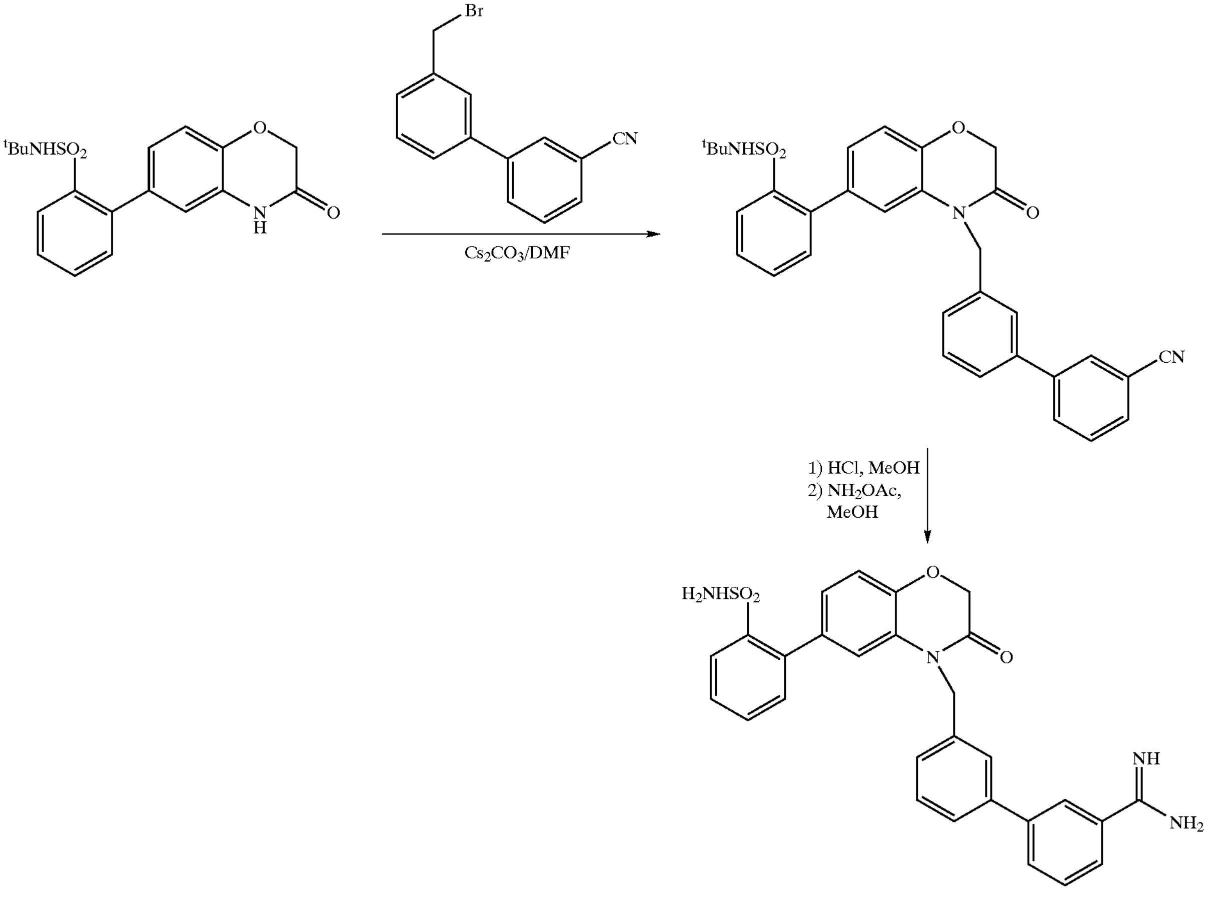
Scheme 4
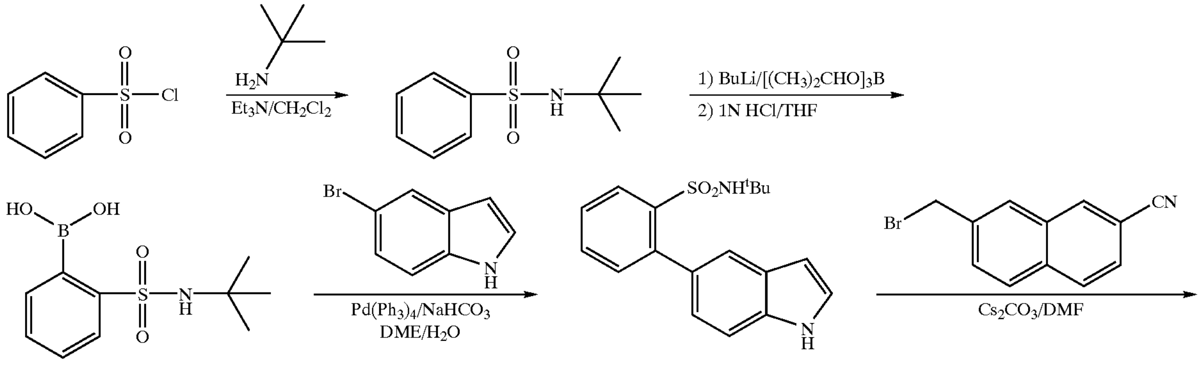

-continued
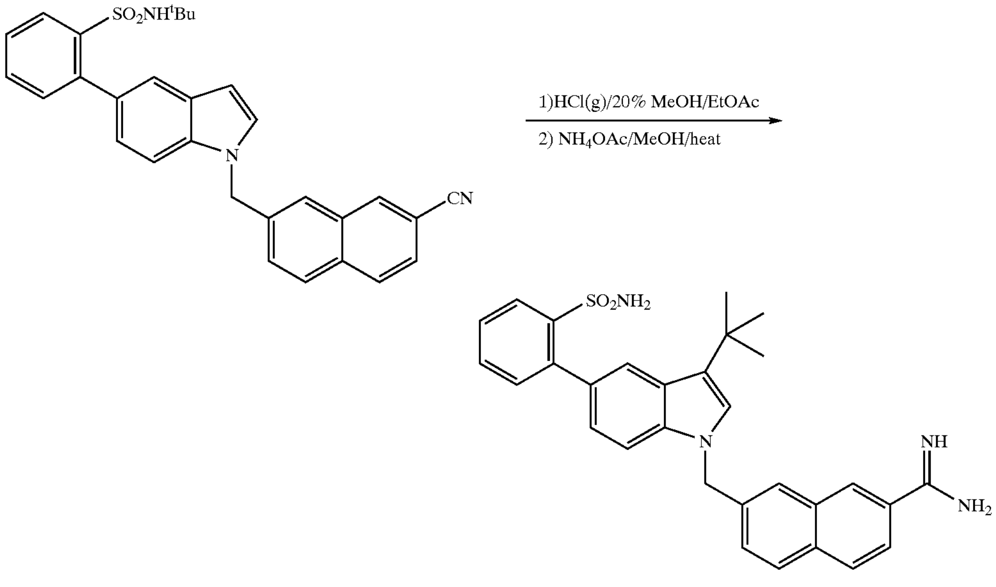
Scheme 5
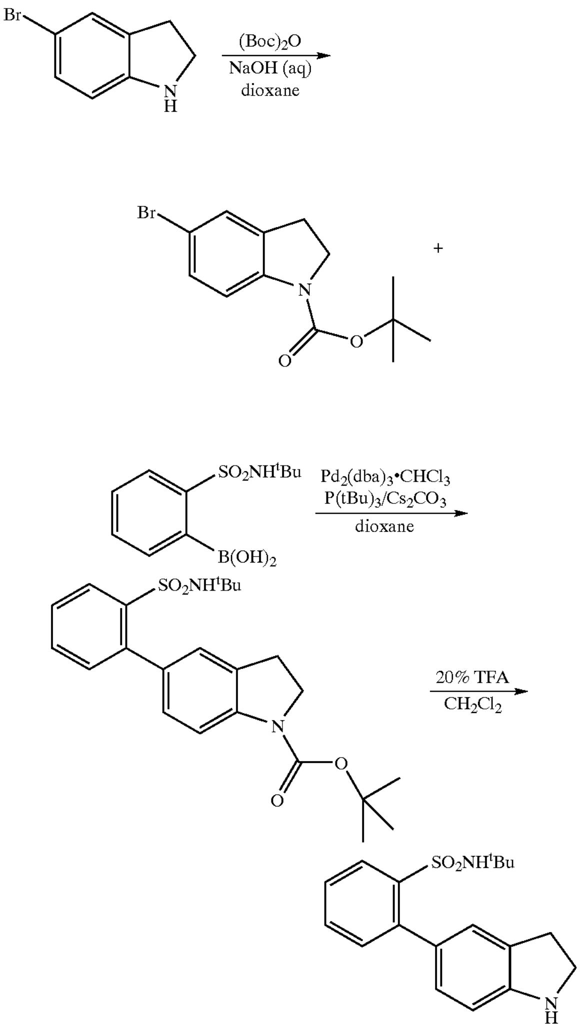
Scheme 6
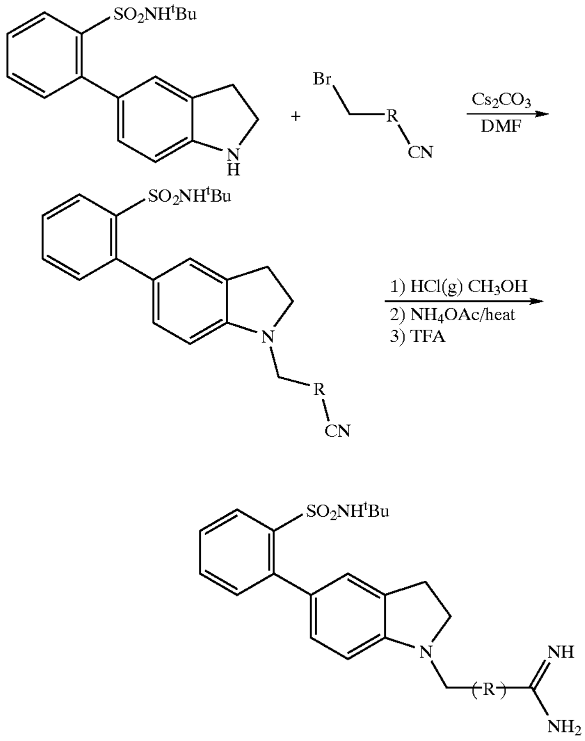
Scheme 7
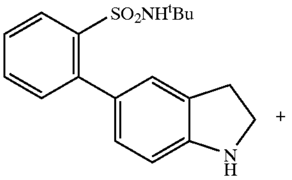

-continued
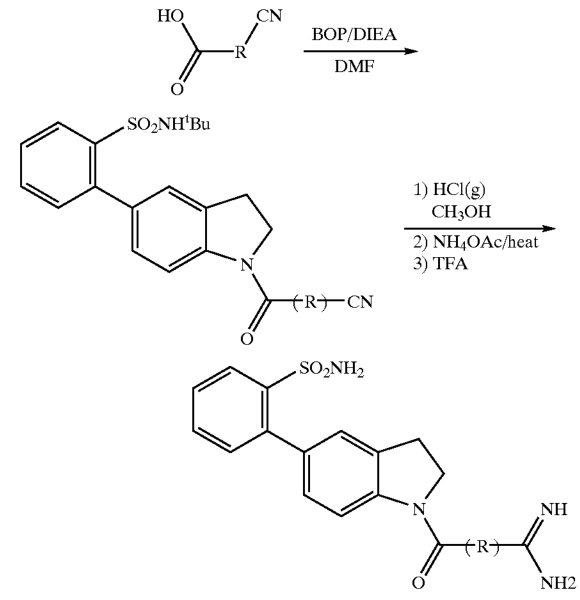
Scheme 8
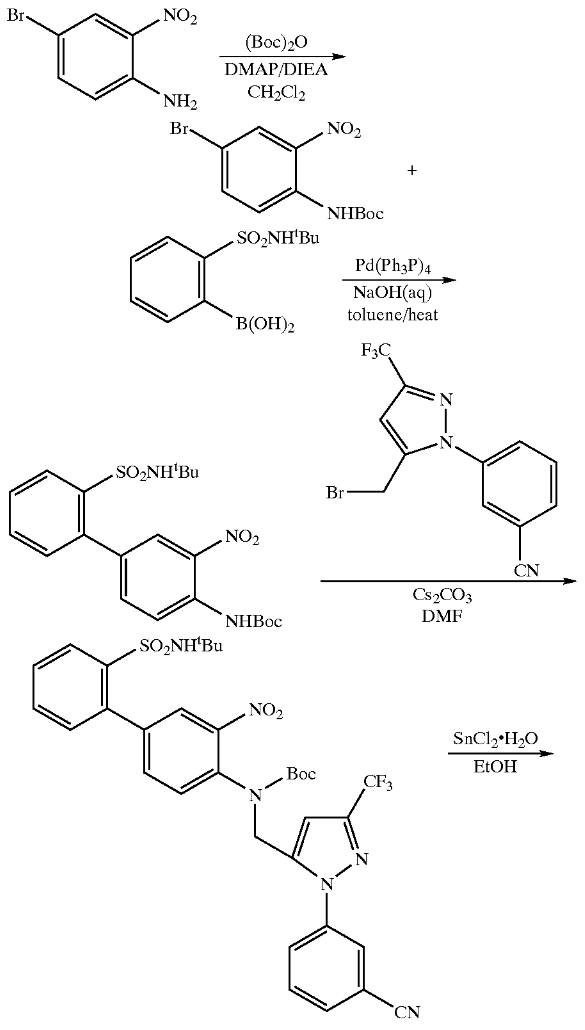
-continued
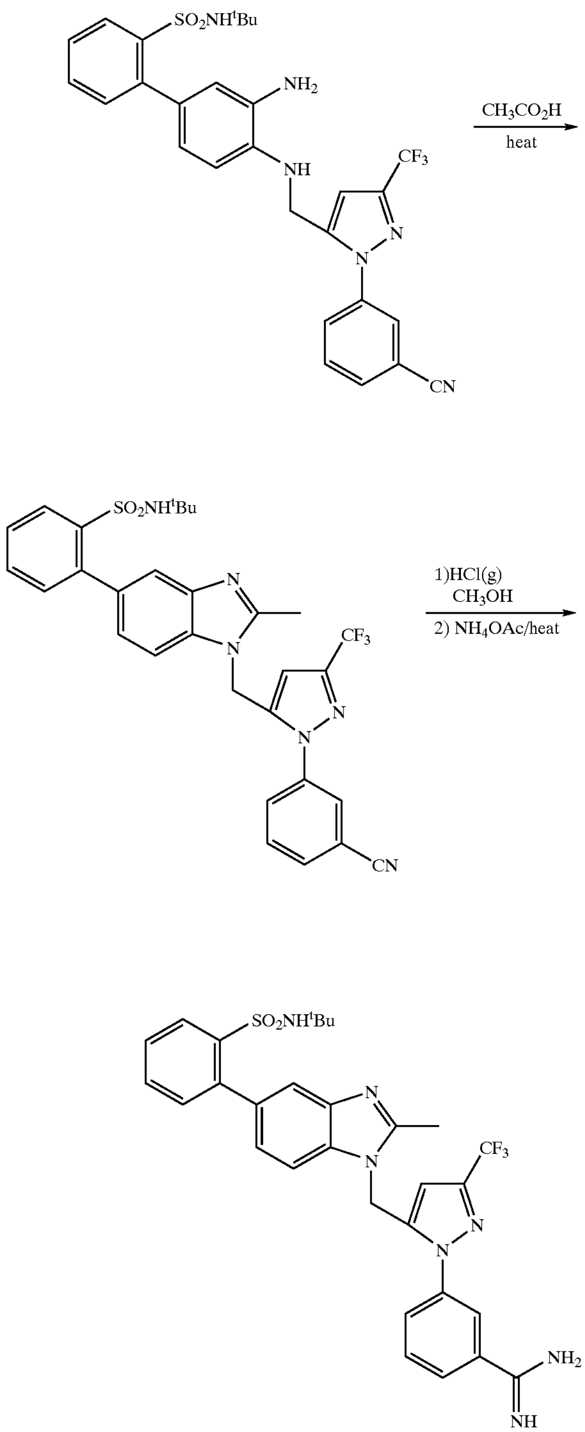
Scheme 9
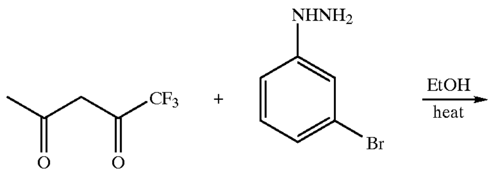

-continued
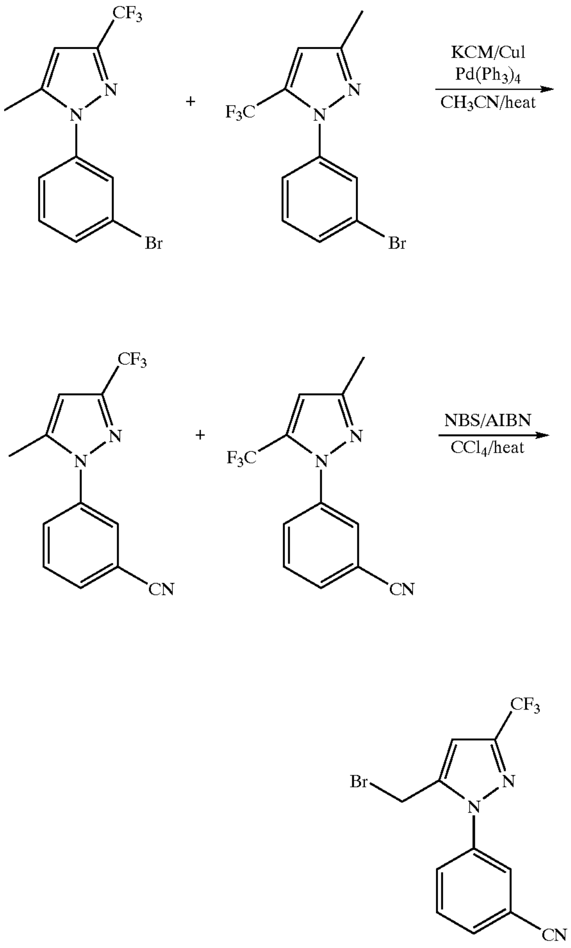
Scheme 10
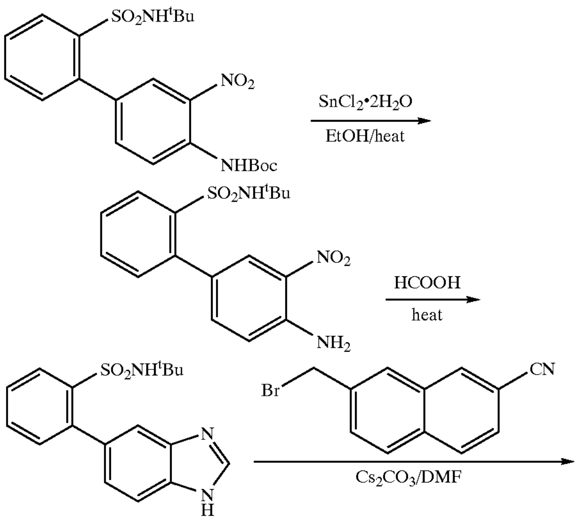
-continued
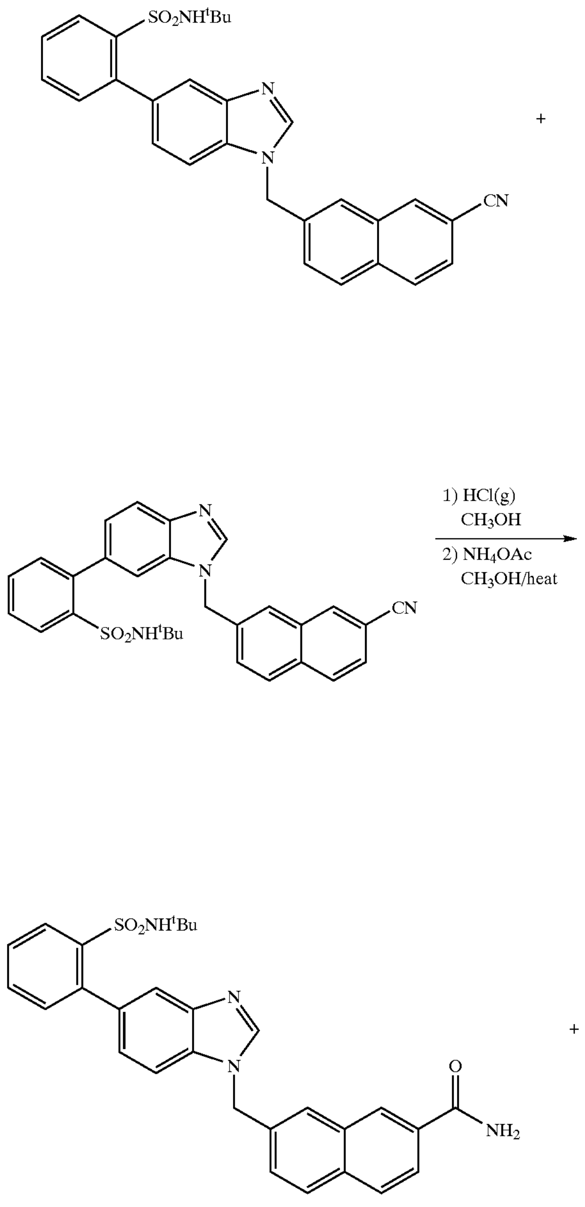
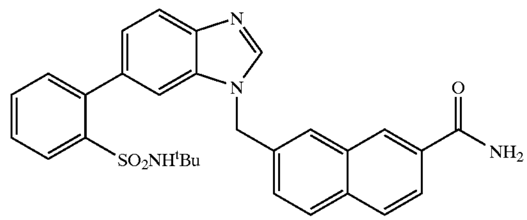

Scheme 11
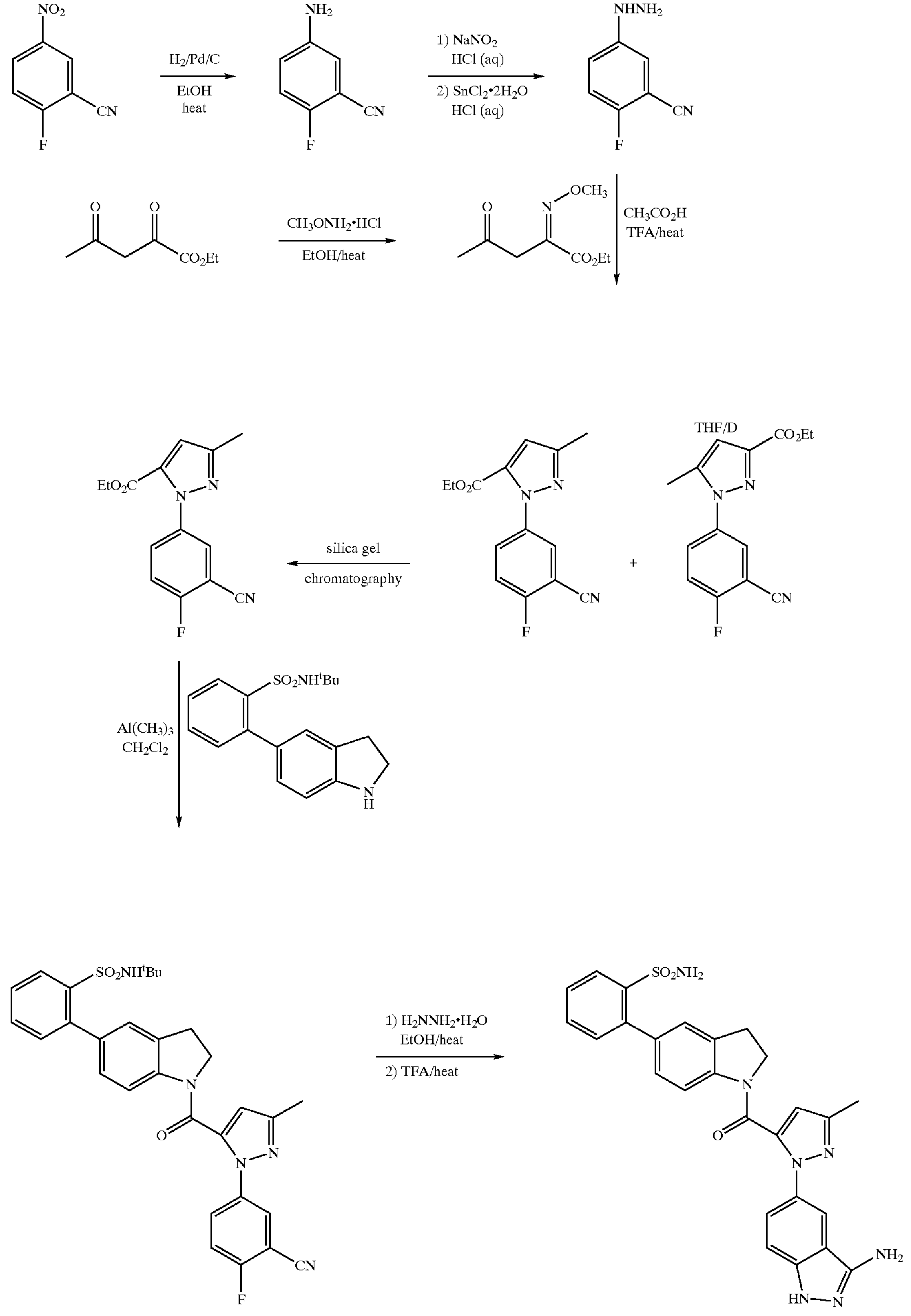

Scheme 12
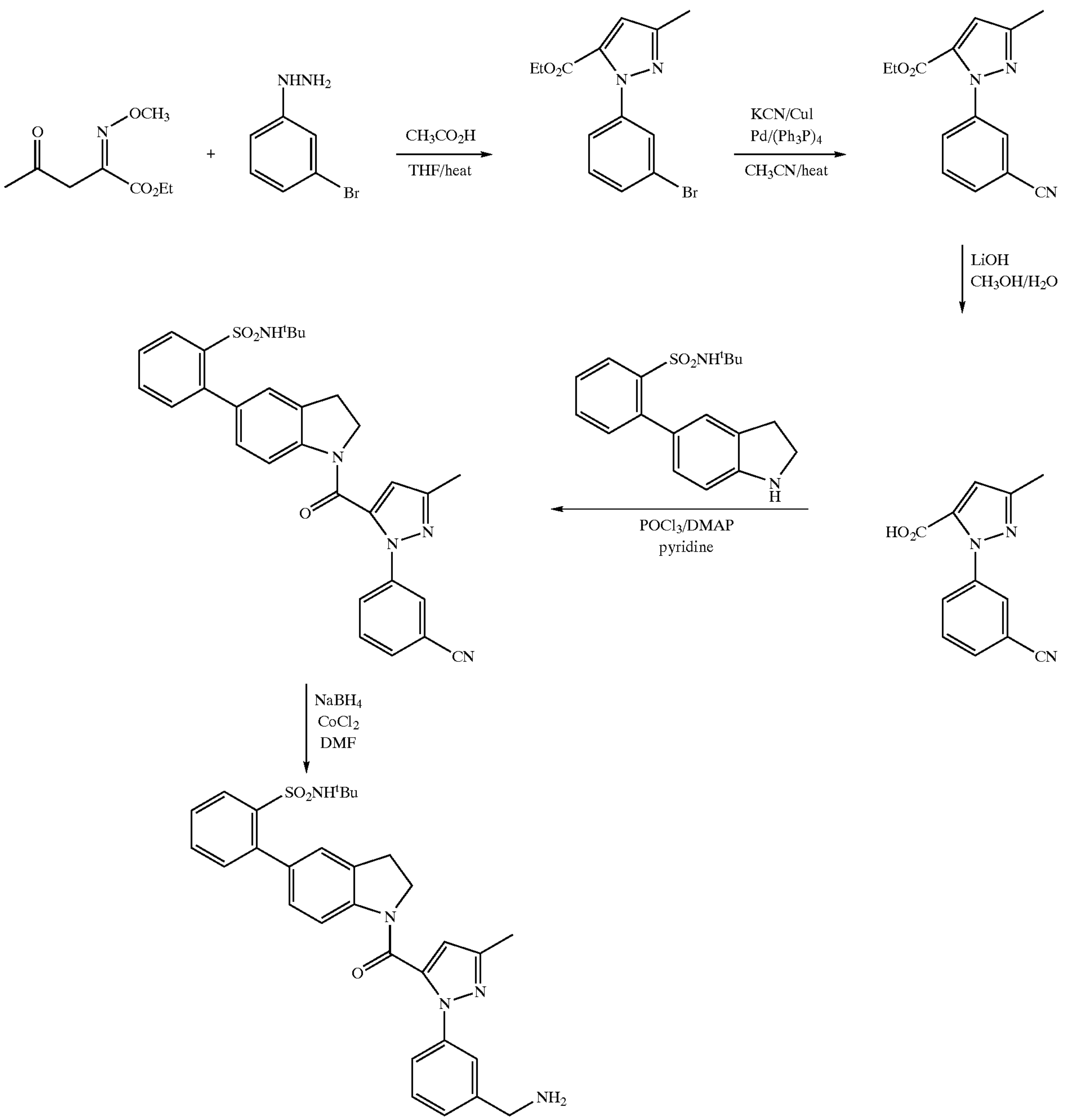
Scheme 13
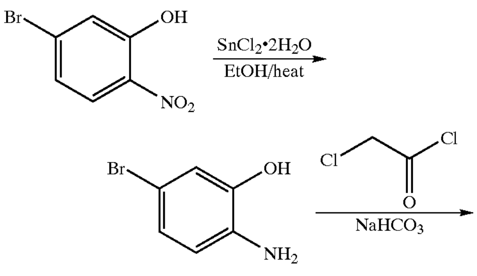
-continued
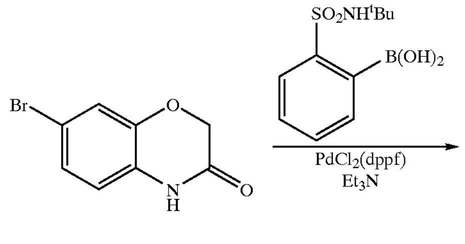

-continued
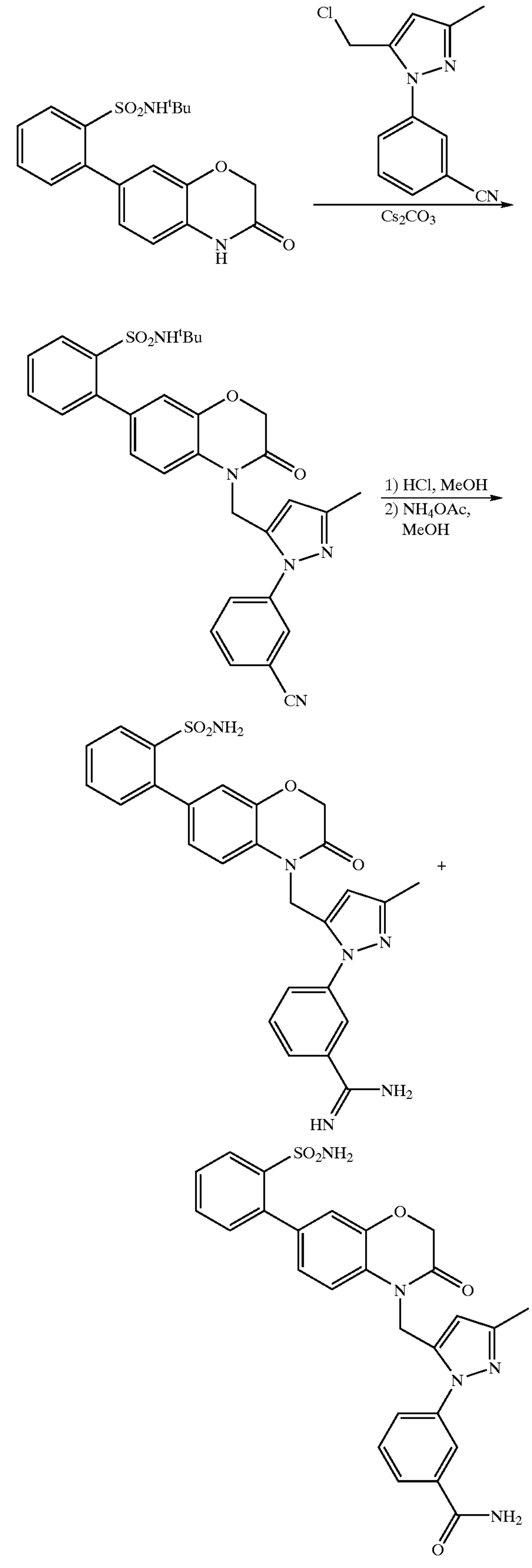
Scheme 14
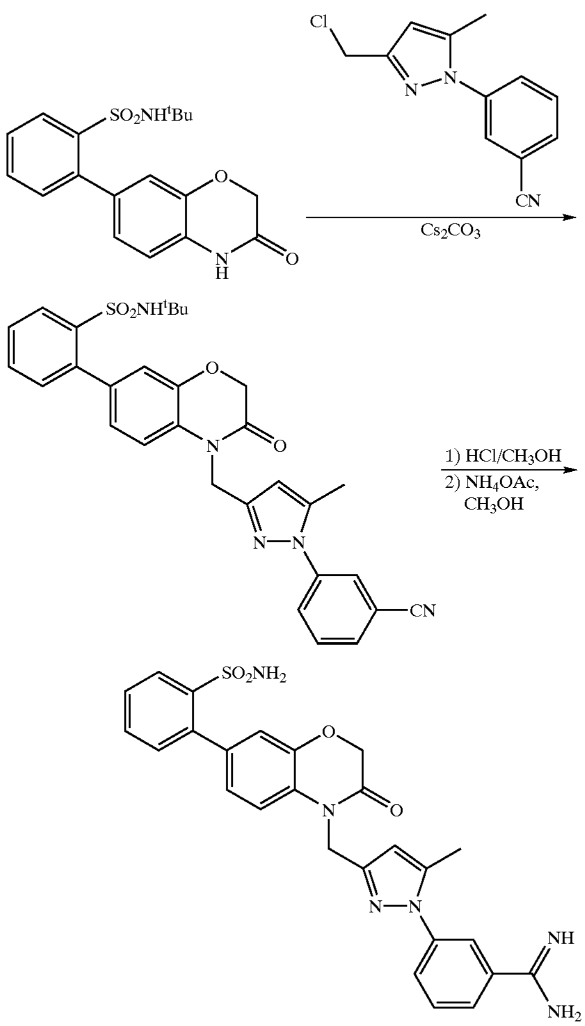
Scheme 15
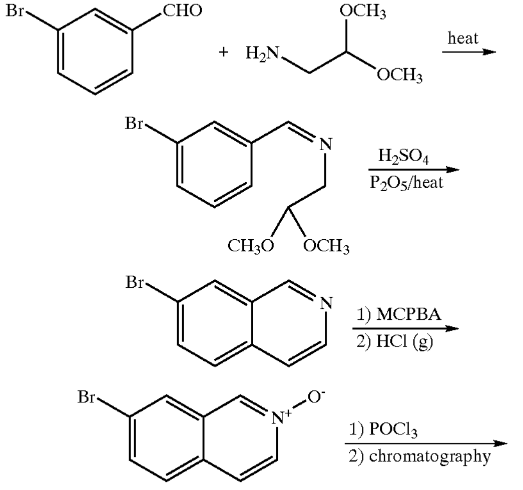

-continued
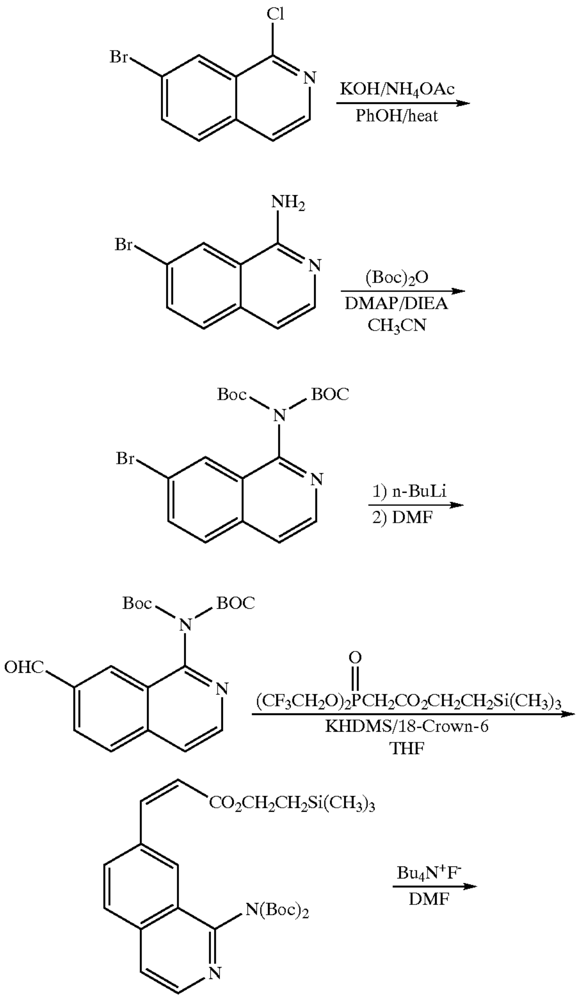
-continued
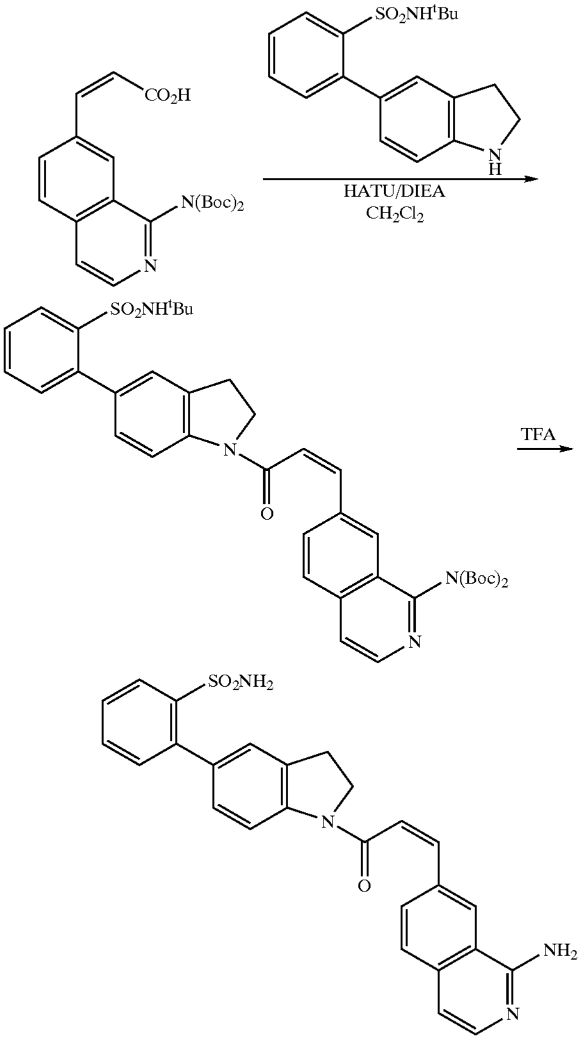
Scheme 16
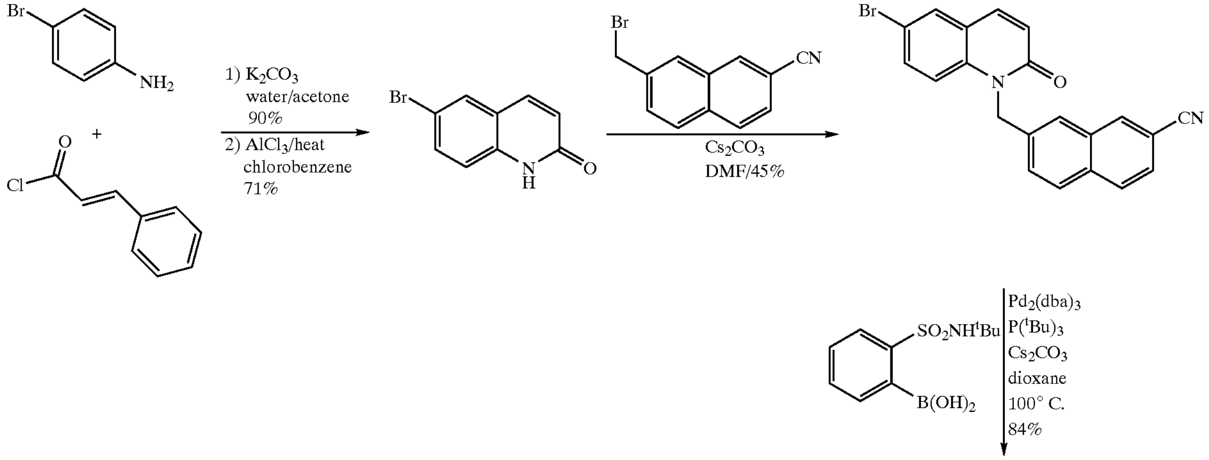

-continued

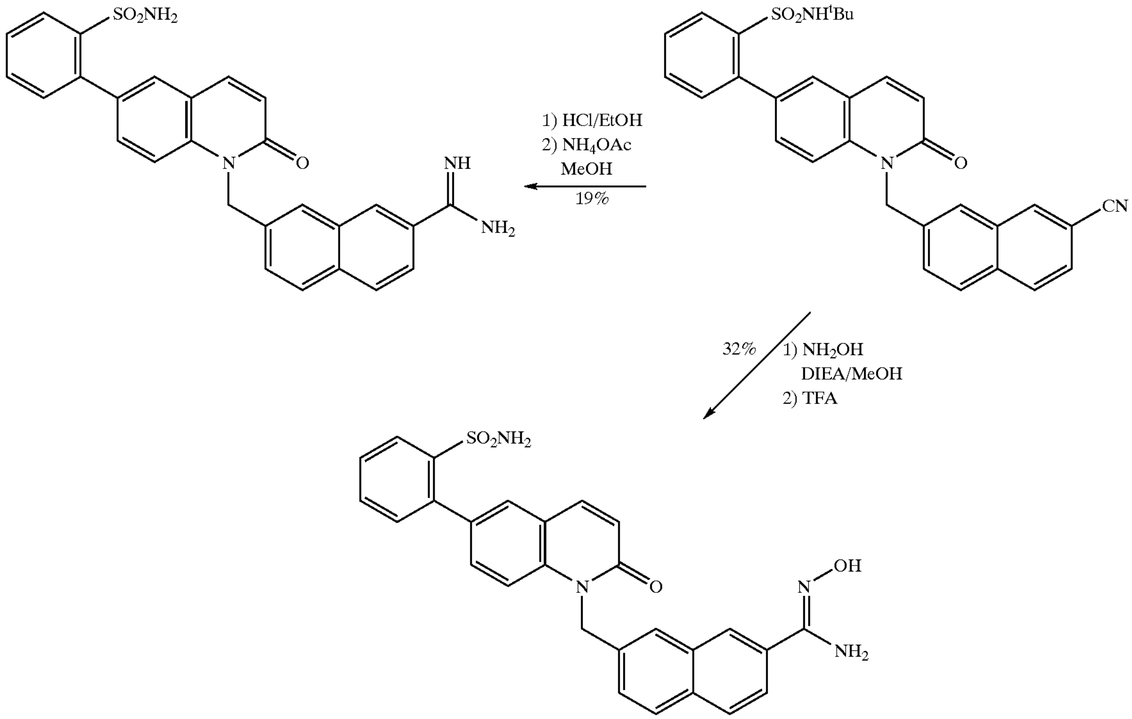

Compositions and Formulations

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

A number of methods are useful for the preparation of the salts described above and are known to those skilled in the art. For example, reaction of the free acid or free base form of a compound of the structures recited above with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Diagnostic applications of the compounds of this invention will typically utilize formulations such as solution or suspension. In the management of thrombotic disorders the compounds of this invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in *Remington's Pharmaceutical Sciences*, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by injection, other methods of administration are also anticipated such as intravenously (bolus and/or infusion), subcutaneously, intramuscularly, colonically, rectally, nasally or intraperitoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

The compounds of this invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can include polyvinylpyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the factor Xa inhibitors of this invention may be coupled to a class of biodegradable polymers useful in achieving controlled release of a drug, for example polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For injection by hypodermic needle, it may be assumed the dosage is delivered into the body's fluids. For other routes of administration, the absorption efficiency must be individually determined for each inhibitor by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds of this invention may be administered several times daily, and other dosage regimens may also be useful.

Typically, about 0.5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin, and excipient such as microcrystalline cellulose, a disintegrating agent like corn starch or alginic acid, a lubricant such as magnesium stearate, a sweetening agent such as sucrose or lactose, or a flavoring agent. When a dosage form is a capsule, in addition to the above materials it may also contain a liquid carrier such as water, saline, a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

In practicing the methods of this invention, the compounds of this invention may be used alone or in combination, or in combination with other therapeutic or diagnostic agents. In certain preferred embodiments, the compounds of this inventions may be coadministered along with other compounds typically prescribed for these conditions according to generally accepted medical practice, such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of this invention can be utilized in vivo, ordinarily in mammals such as primates, such as humans, sheep, horses, cattle, pigs, dogs, cats, rats and mice, or in vitro.

The preferred compounds of the present invention are characterized by their ability to inhibit thrombus formation with acceptable effects on classical measures of coagulation parameters, platelets and platelet function, and acceptable levels of bleeding complications associated with their use. Conditions characterized by undesired thrombosis would include those involving the arterial and venous vasculature.

With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA).

With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The compounds of this present invention, selected and used as disclosed herein, are believed to be useful for preventing or treating a condition characterized by undesired thrombosis, such as (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboangiitis obliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

Anticoagulant therapy is also useful to prevent coagulation of stored whole blood and to prevent coagulation in other biological samples for testing or storage. Thus the compounds of this invention can be added to or contacted with any medium containing or suspected to contain factor Xa and in which it is desired that blood coagulation be inhibited, e.g., when contacting the mammal's blood with material such as vascular grafts, stents, orthopedic prostheses, cardiac stents, valves and prostheses, extra corporeal circulation systems and the like.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

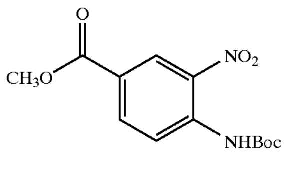

Part 1. Into a chilled suspension of 4-amino-3-nitrobenzoic acid (3.6 g, 20 mmol) in dry methanol (45 mL) was bubbled gaseous HCl for 10 min. The yellow suspension was stirred at room temperature for 2 days. The reaction mixture was filtered, washed with cold methanol and dried under high vacuum to give the HCl salt of methyl 4-amino-3-nitrobenzoate (3.25 g, 70%) as a yellow solid.

Part 2. To a chilled suspension of methyl 4-amino-3-nitrobenzoate (2.56 g, 11 mmol) and 4-dimethylaminopyridine (68 mg, 0.56 mmol) in $CH_2Cl_2$ (40 mL) and N,N-diisopropyl-ethylamine (1.9 mL, 11 mmol) was added a solution of di-tert-butyldicarbonate (2.2 g, 10 mmol) in $CH_2Cl_2$ (20 mL) dropwise over 20 min. The suspension was stirred at room temperature for 2 hours. Another solution of di-tert-butyldicarbonate (1.2 g, 5.5 mmol) in $CH_2Cl_2$ (10 mL) was added, and the resulting solution was stirred for another hour. The reaction was then concentrated, diluted with ethyl acetate, washed with 5% citric acid, water and brine, dried over sodium sulfate and concentrated in vacuo. The residue was purified by silica gel chromatography using 5% ethyl acetate in $CH_2Cl_2$ as eluent to yield methyl 4-[(tert-butoxy)carbonylamino]-3-nitrobenzoate (2.4 g, 74%). $^1H$ NMR ($CDCl_3$)δ: 1.54 (s, 9H); 3.93 (s, 3H); 8.19–8.22 (d, 1H); 8.66–8.68 (d, 1H); 8.86 (s, 1H); 9.87 (s, 1H).

Example 2

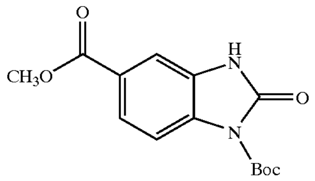

Part 1. To a solution of methyl 4-[(tert-butoxy) carbonylamino]-3-nitrobenzoate (0.44 g, 1.5 mmol) in methanol (2 mL), ethyl acetate (3 mL) and triethylamine (0.21 mL, 1.5 mmol) was added 10% Pd on carbon (159 mg, 0.15 mmol). The reaction mixture was hydrogenated under 1 atm $H_2$ for 3.5 hours, filtered, and concentrated in vacuo to yield methyl 3-amino-4-[(tert-butoxycarbonyl)amino] benzoate (0.40 g, 99%) as a white solid. ES-MS (M+H—$C_4H_8$)$^+$=211.1.

Part 2. To a chilled solution of methyl 3-amino-4-[(tert-butoxy)carbonylamino]benzoate (0.40 g, 1.5 mmol) in $CH_2Cl_2$ (10 mL) and triethylamine (0.21 mL, 1.5 mmol) was added a solution of triphosgene (161 mg, 0.54 mmol) in $CH_2Cl_2$ (6 mL) over 5 min. The reaction was stirred at room temperature for 2 hr, diluted with $CH_2Cl_2$, washed with water and brine, dried over sodium sulfate and concentrated in vacuo. The crude product was purified by silica gel chromatography using 50% ethyl acetate in $CH_2Cl_2$ as eluent to give methyl 1-[(tert-butyl)oxycarbonyl]-2-oxo-(3H)—benzimidazole-5-carboxylate (0.27 g, 61%).

$^1H$ NMR ($CDCl_3$) δ: 1.68 (s, 9H); 3.91 (s, 3H); 7.73 (s, 1H); 7.79–7.81 (d, 1H); 7.85–7.87 (dd, 1H); 8.9 (s, 1H). ES-MS (M+H—$C_4H_8$)$^+$=237.1.

Example 3

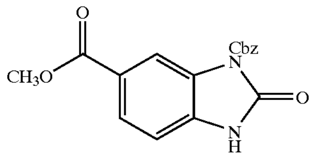

Part 1. To a chilled solution of methyl 1-[(tert-butyl) oxycarbonyl]-2-oxo-(3H)—benzimidazole-5-carboxylate (0.37 g, 1.28 mmol) in $CH_2Cl_2$ (8 mL) and N,N-diisopropylethylamine (0.23 mL, 1.3 mmol) was added a solution of benzyl chloroformate (0.208 mL, 1.46 mmol) in $CH_2Cl_2$ (2 mL). The reaction was stirred at room temperature for 2.5 hr, diluted with ethyl acetate, washed with water and brine, dried over sodium sulfate and concentrated in vacuo. This residue was dissolved in $CH_2Cl_2$ (9 mL) and treated with neat trifluoroacetic acid (2 mL) at 0° C. for 40 min, diluted with ethyl acetate, washed with 5% $NaHCO_3$, water and brine, dried over sodium sulfate and concentrated to yield methyl 2-oxo-3-[benzyloxycarbonyl]-(3H)—benzimidazole-5-carboxylate (0.37 g, 89%) as an off-white solid. $^1H$ NMR ($CDCl_3$) δ: 3.51 (s, 3H); 5.14 (s, 2H); 6.67–6.69 (d, 1H); 6.97–7.06 (m, 5H); 7.17–7.18 (d, 1H); 7.51–7.53 (d, 1H); 8.07 (s, 1H). ES-MS $(M+Na)^+$=349.0.

Example 4

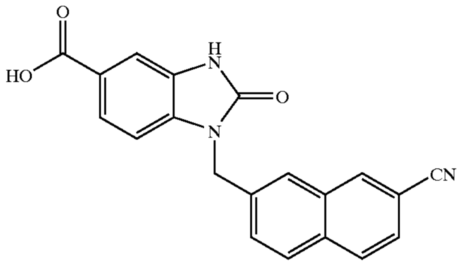

To a chilled solution of methyl 2-oxo-3-(benzyloxycarbonyl)—(3H)—benzimidazole-5-carboxylate (110 mg, 0.337 mmol) in DMF (3 mL) was added cesium carbonate (0.275 g, 0.84 mmol) followed by 7-(bromomethyl)naphthalene-2-carbonitrile (108 mg, 0.44 mmol). The reaction was stirred at room temperature for 1.5 hours, diluted with ethyl acetate, washed with water and brine, dried over sodium sulfate and concentrated in vacuo. This residue was redissolved in methanol (4 mL), $CH_3CN$ (3 mL) and IN LiOH (0.7 mL). The reaction mixture was stirred for 1 hour, acidified with 1N HCl (0.7 mL), filtered and dried to yield methyl 1-[(7-cyano(2-naphthyl))methyl]-2-oxo-(3H)—benzimidazole-5-carboxylate (84 mg, 70%) as awhite solid. ES-MS $(M+H)^+$=358.1.

To a suspension of methyl 1-[(7-cyano-2-naphthyl) methyl]-2-oxo-(3H)—benzimidazole-5-carboxylate (82 mg, 0.23 mmol) in $CH_3CN$ (2.5 mL) and methanol (2 mL) was added 1N LiOH (2.3 mL, 10 eq.). The reaction mixture was stirred at room temperature for 3 days, acidified with 1N HCl (2.4 mL), filtered and dried to yield 1-[(7-cyano-2-naphthyl)methyl]-2-oxo-(3H)—benzimidazole-5-carboxylic acid (72 mg, 91%) as a white solid. $^1H$ NMR ($CDCl_3$) δ: 5.16 (s, 2H); 6.77–6.79 (d, 1H); 7.50–7.54 (t, 2H); 7.62–7.64 (dd, 1H); 7.68 (s, 1H); 7.72 (s, 1H); 7.78–7.84 (dd, 2H); 8.11 (s, 1H); 10.8 (s, 1H). ES-MS $(M+H)^+$=344.1.

Example 5

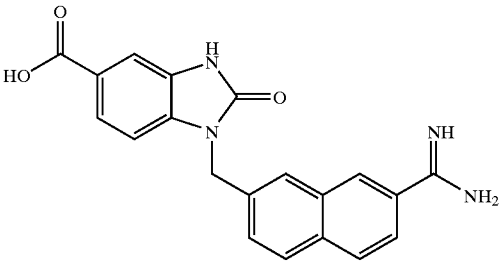

A solution of 1-[(7-cyano-2-naphthyl)methyl]-2-oxo-(3H)—benzimidazole-5-carboxylic acid (70 mg, 0.20 mmol) and hydroxylamine hydrochloride (28 mg, 0.40 mmol) in dry ethanol (4 mL) and DIEA (0.11 mL, 0.61 mmol) was stirred at 55° C. for 8 hours. The reaction was concentrated in vacuo, and the resulting residue redissolved in glacial acetic acid (4 mL). To this solution was added acetic anhydride (0.038 mL, 0.40 mmol). The reaction mixture was stirred at room temperature for 1 hr, followed by addition of methanol (3 mL) and 10% Pd on carbon (24 mg, 0.023 mmol). The mixture was hydrogenated under 1 atm $H_2$ for 17 hours, filtered, and concentrated in vacuo. Purification on a Vydac $C_{18}$ HPLC column yielded 1-[(7-carboxamidino-2-naphthyl)methyl]-2-oxo-(3H)—benzimidazole-5-carboxylic acid (30 mg, 41%) as a white fluffy solid after lyophilization. $^1H$ NMR (DMSO-$d_6$) δ: 5.29 (s, 2H); 7.17–7.19 (d, 1H); 7.56 (s, 1H); etc. ES-MS $(M+H)^+$=361.1.

Example 6

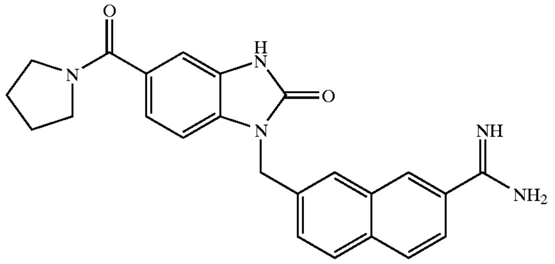

To a suspension of 1-[(7-carboxamidino-2-naphthyl) methyl]-2-oxo-(3H)—benzimidazole-5-carboxylic acid (7 mg, 0.019 mmol) and BOP reagent (10 mg, 0.023 mmol) in DMF (0.8 mL) and N,N-diisopropylethylamine (10 mL, 0.057 mmol) was added neat pyrrolidine (2 μL, 0.024 mmol). The resulting solution was stirred at room temperature under argon for 4 hours. The reaction was concentrated and purified by HPLC to yield 7-{[2-oxo-5-(pyrrolidinylcarbonyl)—(3H)—benzimidazolyl] methyl}naphthalene-2-carboxamidine (6 mg, 75%) as a white fluffy solid after lyophilization. ES-MS $(M+H)^+$=414.1.

Example 7

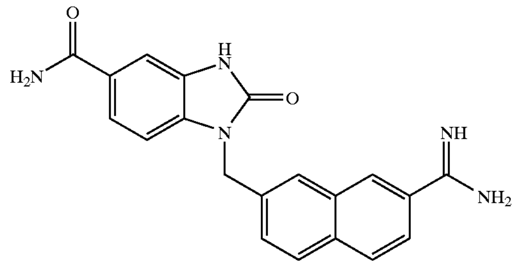

Using a method similar method to that used in Example 6, 1-[(7-carboxamidino-2-naphthyl))methyl]-2-oxo-(3H)-benzimidazole-5-carboxamide was synthesized from the carboxylic acid via a BOP coupling with ammonium hydroxide. ES-MS $(M+H)^+=360.1$.

Example 8

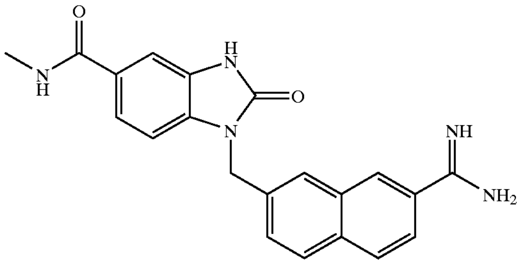

Using a method similar to that used in Example 6, 7-{[5-(N-methylcarbamoyl)-2-oxo-(3H)-benzimidazolyl] methyl}naphthalene-2-carboxamidine was synthesized from the carboxylic acid via a BOP coupling with methylamine. ES-MS $(M+H)^+=374.1$.

Example 9

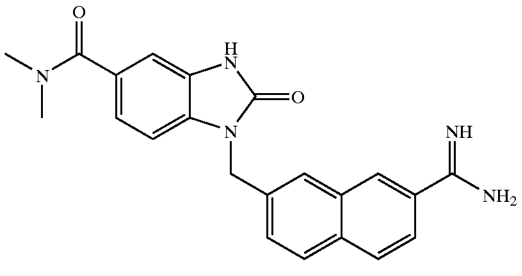

Using a method similar to that used in Example 6, 7-{[5-(N,N-dimethylcarbamoyl)-2-oxo-(3H)-benzimidazolyl]methyl) naphthalene-2-carboxamidine was synthesized from the carboxylic acid via a BOP coupling with dimethylamine. ES-MS $(M+H)^+=388.1$.

Example 10

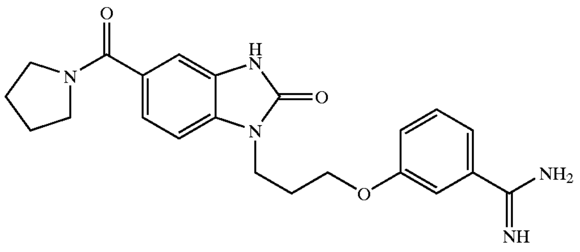

Using a method similar to that used in Example 6, 3-{3-[2-oxo-5-(pyrrolidinylcarbonyl)-(3H)-benzimidazolyl] propoxy) benzamidine was synthesized by alkylation with 3-(3-bromopropoxy)benzenecarbonitrile, saponification, BOP coupling with pyrrolidine, and hydroxylamine method for conversion of nitrile to amidine. ES-MS $(M+H)^+=408.1$.

Example 11

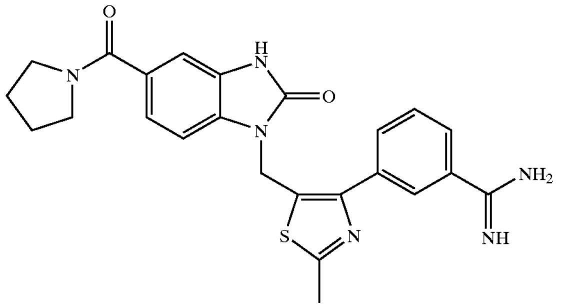

Using a method similar to that used in Example 6, 3-(2-methyl-5-{[2-oxo-5-(pyrrolidinylcarbonyl)-(3H)-benzimidazolyl)]methyl}-1,3-thiazol-4-yl)-benzamidine was synthesized by alkylation with 3-[5-(chloromethyl)-2-methyl-1,3-thiazol-4-yl]benzenecarbonitrile, saponification, BOP coupling with pyrrolidine, and hydroxylamine method for conversion of nitrile to amidine. ES-MS $(M+H)^+=461.0$.

Example 12

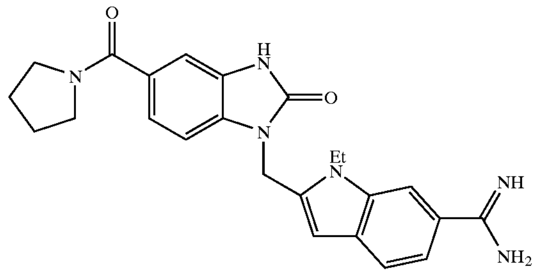

Using a method similar to that used in Example 6, 1-ethyl-2-{[2-oxo-5-(pyrrolidinyl-carbonyl)-(3H)-benzimidazolyl)]methyl}indole-6-carboxamidine was synthesized by alkylation with 2-(chloromethyl)-1-ethylindole-6-carbonitrile, saponification, BOP coupling with pyrrolidine, and hydroxylamine method for conversion of nitrile to amidine. ES-MS $(M+H)^+$=431.1.

Example 13

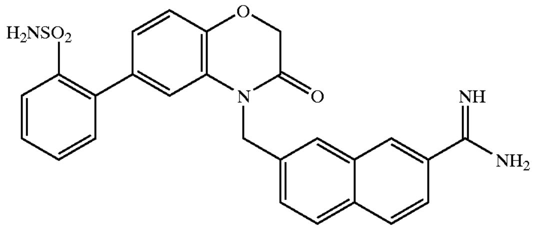

Part 1. To a solution of 2H-1,4-Benzoxazin-3(4H)-one (1.86 g, 12.5 mmol, 1.0 equiv) in 25 mL of $CHCl_3$ at 0° C. was added $Br_2$ (2.0 g, 1.0 equiv) dropwise. After stirring at room temperature overnight, the solvent was evaporated and the residue was recrystallized from $EtOH/H_2O$ to give the product in 95% yield. LRMS found for $C_8H_7BrNO_2$ $(M+H)^+$: 227.9.

Part 2. A solution of the product from Part 1 (103 mg, 0.4 mmol, 1.0 equiv), 2-(t-butylaminosulfonyl)phenylboronic acid (91.2 mg, 1.0 equiv), $PdCl_2$(dppf) (32.6 mg, 0.1 equiv), and triethylamine (279 μL, 5.0 equiv) in 10 mL of DME was degassed with argon for 15 min, then heated to reflux overnight. After cooling to room temperature, the mixture was diluted with ethyl acetate, washed with water, dried over $MgSO_4$, and concentrated. Flash chromatography on silica gel gave the product in 21% yield. LRMS found for $C_{18}H_{21}N_2O_4S$ $(M+H)^+$: 361.1.

Part 3: A solution of the product from Part 2 (36 mg, 0.1 mmol, 1.0 equiv) in 2 mL of DMF was treated with 2-bromomethyl-7-cyanonaphthalene (40 mg, 75%, 1.2 equiv) and $Cs_2CO_3$ 65 mg, 2 equiv) for 0.5 h. The mixture was diluted with ethyl acetate, washed with water and subjected to flash column chromatography on silica gel to give the desired product in 95% yield. LRMS found for $C_{30}H_{28}N_3O_4S$ $(M+H)^+$: 526.2.

Step 4: The compound obtained in Step 3 (50 mg, 0.1 mmol, 1.0 equiv) was dissolved in 5 mL of methanol. The reaction mixture was cooled to 0° C. and HCl gas was bubbled in until saturation, and the mixture was stirred at room temperature overnight. The solvent was evaporated and the resulting residue was treated with ammonium acetate and 10 ml of methanol at reflux temperature for 2 hr. The solvent was removed at reduced pressure and the crude benzamidine was purified by HPLC (C18 reversed phase) eluting with 0.5% TFA in $H_2O/CH_3CN$ to give the desired salt in 80% yield. LRMS found for $C_{26}H_{23}N_4O_4S$ $(M+H)^+$: 487.1.

Example 14

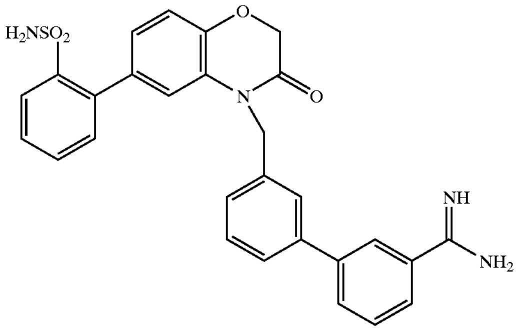

Step 1: The product from Example 13, Step 2 (36 mg, 0.1 mmol, 1.0 equiv) in 2 mL of DMF was treated with 2-bromomethyl-2'-cyanobiphenyl (41 mg, 1.5 equiv) and $Cs_2CO_3$ (65 mg, 2 equiv) for 0.5 hr. The mixture was diluted with ethyl acetate, washed with water and purified by flash column chromatography to give the desired product in 91% yield. LRMS found for $C_{32}H_{30}N_3O_4S$ $(M+H)^+$: 552.2.

Step 2: The product from Step 1 (50 mg, 0.09 mmol, 1.0 equiv) was dissolved in 5 mL of methanol. The reaction mixture was cooled to 0° C., HCl gas was bubbled in until saturation, and the mixture was stirred at room temperature overnight. The solvent was evaporated and the resulting residue was treated with ammonium acetate and 10 ml methanol at reflux temperature for 2 hr. The solvent was removed under reduced pressure and the crude benzamidine was purified by HPLC (C18 reversed phase) eluting with 0.5% TFA in $H_2O/CH_3CN$ to give the desired salt in 77% yield. LRMS found for $C_{28}H_{25}N_4O_4S$ $(M+H)^+$: 513.2.

Example 15 and 16

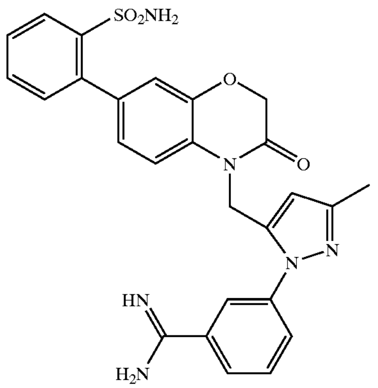

+

-continued

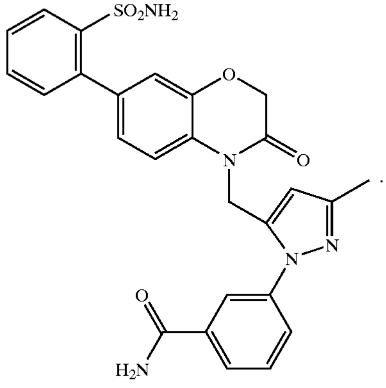

Part 1. A solution of 2-nitro-5-bromophenol (2.53 g, 18.2 mmol) in 15 mL of ethanol was treated with $SnCl_2.H_2O$, and the reaction was heated at reflux for 3 h. The solvent was evaporated to give a white residue, which was used in the next step without further purification. LRMS: $C_9H_{10}NO_3$ $(M+H)^+$: 180.1.

Part 2. A solution of 2-amino-5-bromophenol (2.53 g, 18.2 mmol, 1.0 equiv) in 15 mL of isobutylmethyl ketone and 15 mL of water was cooled to 0° C., $NaHCO_3$ (3.67 g, 2.4 equiv) and then chloroacetyl chloride (2.36 g, 1.67 mL, 1.15 equiv) were added. The mixture was heated to reflux overnight, then cooled to room temperature. The mixture was diluted with ethyl acetate, washed with water, dried over $MgSO_4$, and concentrated in vacuo. Flash chromatography on silica gel gave 7-bromo-3,4-dihydro-2H-1,4-benzoxazin-3-one in 77% yield. LRMS found for $C_9H_{10}NO_3$ $(M+H)^+$: 180.1.

Part 3. A solution of 7-bromo-3,4-dihydro-2H-1,4-benzoxazin-3-one (103 mg, 0.4 mmol, 1.0 equiv), 2-t-butylaminosulfonyl phenyl boronic acid (91.2 mg, 1.0 equiv), $PdCl_2$(dppf) (32.6 mg, 0.1 equiv), and triethylamine (279 $\mu$L, 5.0 equiv) in 10 mL of DME was degassed with argon for 15 min, then heated to reflux overnight. After cooling to room temperature, the mixture was diluted with ethyl acetate, washed with water, dried over $MgSO_4$, evaporated. Flash chromatography on silica gel gave the product in 21% yield. LRMS found for $C_{18}H_{21}N_2O_4S$ $(M+H)^+$: 361.1.

Part 4. The product from Part 3 (36 mg, 0.1 mmol, 1.0 equiv) in 2 mL DMF was treated with 1-(3-cyanophenyl)-3-methyl-5-chloromethyl pyrazole (35 mg, 1.5 equiv) and $Cs_2CO_3$ (65 mg, 2 equiv) for 0.5 hr. The mixture was diluted with ethyl acetate, washed with water and purified over silica gel to give the desired product in 91% yield. LRMS found for $C_{30}H_{29}N_5O_4S$ $(M+H)^+$: 556.1.

Part 5. The compound from Part 4 (50 mg, 0.09 mmol, 1.0 equiv) was dissolved in 5 mL of methanol. The reaction mixture was cooled to 0° C., HCl gas was bubbled in until saturation, and the mixture was stirred at room temperature overnight. The solvent was evaporated and the resulting residue was treated with ammonium acetate and 10 ml of methanol at reflux temperature for 2 hr. The reaction was concentrated in vacuo and the crude benzamidine was purified by HPLC (C18 reversed phase) eluting with 0.5% TFA in $H_2O/CH_3CN$ to give the desired amidine (Example 15) in 77% yield. LRMS found for $C_{26}H_{24}N_6O_4S$ $(M+H)^+$: 516.2. Example 16 was obtained as a byproduct in 15% yield. LRMS found for $C_{26}H_{23}N_5O_5S$ $(M+H)^+$: 517.1.

Example 17

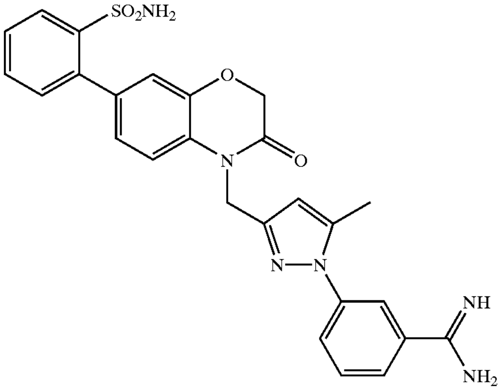

Part 1: The product (36 mg, 0.1 mmol, 1.0 equiv) obtained in Part 3 of Example 15 in 2 mL DMF was treated with 1-(3-cyanophenyl)-3-methyl-5-chloromethyl pyrazole (41 mg, 1.5 equiv) and $Cs_2CO_3$ 65 mg, 2 equiv) for 0.5 h. The mixture was diluted with ethyl acetate, washed with water and purified over silica gel to give the desired product in 91% yield. LRMS found for $C_{32}H_{30}N_3O_4S$ $(M+H)^+$: 552.2.

Part 2: The compound obtained in Part 1 (50 mg, 0.09 mmol, 1.0 equiv) was dissolved in 5 mL of methanol. The reaction mixture was cooled to 0° C., HCl gas was bubbled in until saturation, and the mixture was stirred at room temperature overnight. The solvent was evaporated and the resulting residue was treated with ammonium acetate and 10 ml of methanol at reflux temperature for 2 hr. The solvent was removed at reduced pressure and the crude benzamidine was purified by HPLC (C18 reversed phase) eluting with 0.5% TFA in $H_2O/CH_3CN$ to give the desired salt in 77% yield. LRMS found for $C_{28}H_{25}N_4O_4S$ $(M+H)^+$: 513.2.

Example 18

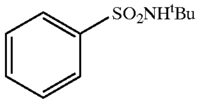

To a solution of tert-butylamine (41.4 g, 566 mmol) and triethylamine (118 mL, 849 mmol) in DCM (1000 mL) in an ice bath, was added benzenesulfonyl chloride (100 g, 566 mmol) dropwise, and the mixture was stirred at room temperature overnight. Water was added to the mixture and organic layer was washed with water, sat. NaCl, dried over $Na_2SO_4$, filtered and filtrate evaporated in vacuo to give the title compound as light yellow solid (117.63 g, 97.6%). ES-MS (M+H)+=214.5.

Example 19

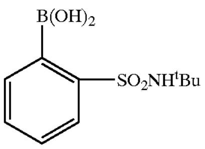

A solution of the compound from example 18 (53.25 g, 250 mmol) in THF (600 mL) was cooled with an ice water bath, and a 2.5 M solution of n-butyllithium in hexane (200 mL, 500 mmol) was added dropwise. A thick precipitate was formed when the reaction mixture was warmed up to 10° C. Triisopropylborate was added, keeping the temperature below 35° C. After 1 hr., the mixture was cooled in an ice bath, 1N HCl (405 mL) was added, and the mixture was stirred overnight. The mixture was extracted with ether (3x100 mL), and the combined organic extracts were extracted with 1N NaOH (3x130 mL). The aqueous extracts were acidified to pH 1 with 12 N HCl, and then extracted with ether (3x140 mL). The combined ether extracts were dried over $MgSO_4$, and solvents were evaporated in vacuo. Hexane and ether were added and a white precipitate formed. The solid was collected and washed with 10% ether/hexane to give the title compound. ES-MS (M+H)+=b Example 20

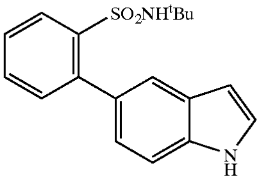

To a solution of 5-bromoindole (1.96 g, 10 mmol) in DME (40 mL) and $H_2O$ (10 mL), was added the compound from Example 19 (3.85 g, 15 mmol), $NaHCO_3$ (1.68 g, 20 mmol) and tetrakis(triphenylphosphine)palladium(0) (0.58 g, 0.5 mmol). The mixture was heated to reflux overnight, then cooled to room temperature and diluted with ethyl acetate. The organic layer was washed with water, dried with $MgSO_4$, filtered and concentrated. The residue was purified by silica gel column chromatography using 25% ethyl acetate in hexane as eluent to give the title compound (1.52 g, 46%). ES-MS $(M+Na)^+$ 351.1.

Example 21

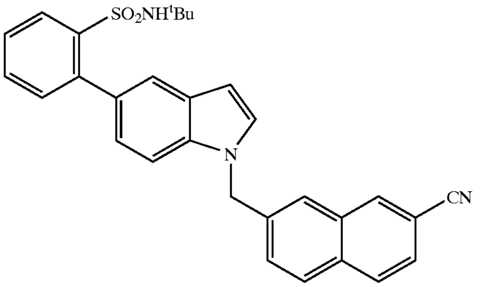

To a solution of the compound from Example 20 (328 mg, 1 mmol) in DMF (10 mL) was added 7-cyano-2-bromomethylnaphthalene (296 mg, 1.2 mmol) and $Cs_2CO_3$ (1.3 g, 4 mmol), and the mixture was stirred at room temperature overnight. The reaction mixture was partitioned between water and ethyl acetate, and the organic layer was washed with water, 1N HCl, sat. NaCl, dried over $Na_2SO_4$ and concentrated in vacuo. The residue was subjected to flash column chromatography on silica gel using 50% ethyl acetate in $CH_2Cl_2$ followed by 100% $CH_2Cl_2$ as eluent to give the title compound (237 mg, 48%). ES-MS $(M+H)^+$= 494.2.

Example 22

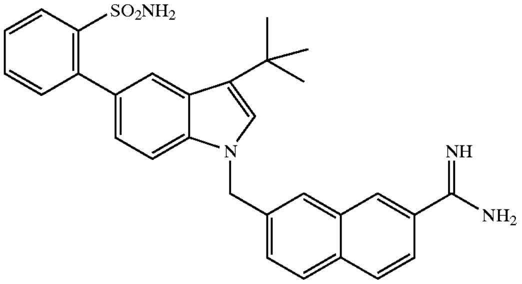

A solution of the compound from example 21 (115 mg, 0.23 mmol) in 20% MeOH/ethyl acetate (10 mL) was treated with a stream of HCl gas for 10 min. at 0° C. The resulting solution was capped, stirred at room temperature overnight, then concentrated in vacuo.

The residue was reconstituted in MeOH (10 mL) and the mixture was treated with ammonium acetate (350 mg, 4.6 mmol). The reaction mixture was heated at reflux for 2 hrs, then concentrated in vacuo. The residue was purified by prep HPLC to give the title compound as a white powder. ES-MS $(M+H)^+$=511.2.

Example 23

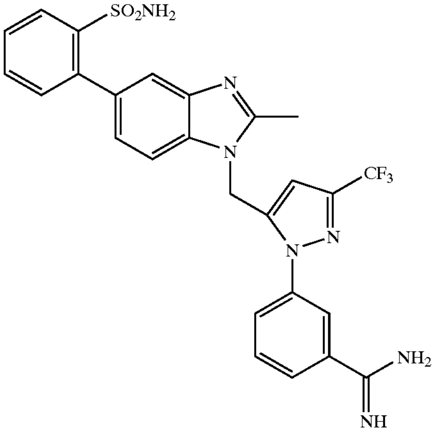

Part 1. A solution of 4-bromo-2-nitroaniline (2.97 g, 13.7 mmol) in 100 mL of dichloromethane was treated with N,N-diisopropylethylamine (2.38 mL, 13.7 mmol) and 4-dimethylaminopyridine (167 mg, 1.37 mmol). Di-tert-butyldicarbonate (3.88 g, 17.8 mmol) was then added in small portions. The mixture was stirred at room temperature overnight under argon, then diluted with 400 mL of dichloromethane and washed with water (x2). The organic phase was dried over $MgSO_4$, concentrated in vacuo and purified by flash column chromatography. The desired product was obtained as a yellow solid in 48% yield (2.07 g).

Part 2. To a mixture of the product from Part 1 (1.02 g, 3.22 mmol), the boronic acid from Example 19 (827 mg, 3.22 mmol), and tetrakis(triphenylphosphine)palladium(0) (186 mg, 0.161 mmol) in 60 mL of benzene was added a solution of sodium hydroxide (515 mg, 12.9 mmol) in 5 mL of water. The mixture was degassed using an argon stream for 15 minutes and then heated at reflux for 24 hours. The solution was concentrated in vacuo, the residue was dissolved in ethyl acetate, passed through a bed of celite, and washed with water (×2). The organic phase was dried over $MgSO_4$, concentrated in vacuo, then purified by flash column chromatography. The desired product was obtained as a solid in 60% yield (0.87 g).

Part 3. The product from Part 2 (72 mg, 0.16 mmol) and the bromide from Example 24 (80 mg, 0.24 mmol) were dissolved in 4 mL of dry DMF, and cesium carbonate (156 mg, 0.48 mmol) was added. The resulting mixture was stirred overnight, then diluted with 100 mL of ethyl ether, washed with water (×2), and dried over $MgSO_4$. Filtration and concentration in vacuo gave a residue, which was subjected to flash column chromatography. The desired product was obtained in 43% yield (48 mg).

Part 4. The product from Part 3 (90 mg, 0.13 mmol) was dissolved in 5 mL of ethyl alcohol, and tin(II) chloride dihydrate (116 mg, 0.52 mmol) was added. The mixture was heated to reflux for 3 hours, and the ethanol was removed in vacuo. The residue was dissolved in ethyl acetate, washed with 1N aqueous NaOH and water. The organic phase was dried over $MgSO_4$, concentrated in vacuo and pumped to dryness to give the desired product in quantitative yield (84 mg).

Part 5. The crude product from Part 4 (84 mg) was dissolved in 7 mL glacial acetic acid, and the mixture was stirred at 80° C. overnight. The mixture was concentrated with toluene to remove traces of acetic acid, and the residue was purified by preparative HPLC.

Part 6. The product from Part 5 (20 mg, 0.034 mmol) was dissolved in 5 mL anhydrous methanol, and a vacuum-distilling adapter, equipped with a rubber septum and with a balloon on its side-arm, was placed on the reaction flask. The solution was chilled in ice, and HCl gas was bubbled through the solution via a long needle immersed in the solution until the balloon expanded, and this reaction mixture was stirred overnight. The reaction was concentrated to dryness in vacuo, then dissolved in 5 mL of anhydrous methanol, and dry ammonium acetate (21 mg, 0.27 mmol) was added. The mixture was heated at reflux for 2 hours, then purified by preparative HPLC to afford the title compound. LRMS $(M+H)^+=553$.

Example 24

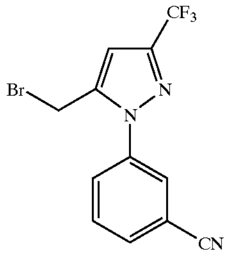

Part 1. A mixture of 1,1,1-trifluoro-2,4-pentanedione (5.43 mL, 44.7 mmol) and 3-bromophenylhydrazine HCl (10.0 g, 44.7 mmol) in 100 mL of ethanol was heated to reflux overnight. The reaction mixture was concentrated in vacuo, and the residue was dissolved in ethyl ether and washed with water (×2). The organic phase was dried over $MgSO_4$, concentrated and subjected to flash column chromatography, giving 12.83 g (94%) of the desired product as an oil, which was a mixture of the two possible regioisomers.

Part 2. The mixture of isomers from part 1 (12.83 g, 41.9 mmol), KCN (5.45 g, 83.8 mmol), CuI (798 mg, 4.19 mmol) and tetrakis(triphenylphosphine)palladium(0) (2.42 g, 2.09 mmol) in 100 mL of acetonitrile was degassed using an argon stream for 30 minutes. The mixture was heated at reflux for 15 hours, then passed through a silica plug on a Buchner funnel using ethyl acetate as eluent. The filtrate was concentrated and dissolved in dichloromethane, washed with water (×2), and dried over $MgSO_4$. Filtration and concentration gave a residue, which was subjected to column chromatography. The regioisomeric products were separable at this stage, giving 3.93 g (37%) of the 3-methyl and 4.0 g (38%) of the 5-methyl isomers.

Part 3. A mixture of the 5-methyl isomer (1.67 g, 6.63 mmol), NBS (1.41 g, 7.95 mmol), and AIBN (543 mg, 3.31 mmol) in 50 mL carbon tetrachloride was degassed using an argon stream for 15 minutes. The reaction was heated at reflux for 2 days, periodically adding additional small amounts of AIBN. The resulting mixture was diluted with dichloromethane, washed with water (×2), and dried over $MgSO_4$. Filtration and concentration gave a residue, which was subjected to flash column chromatography. The desired bromomethyl product was obtained in 1.06 g (48%), along with 1.06 g of recovered starting material.

Examples 25 and 26

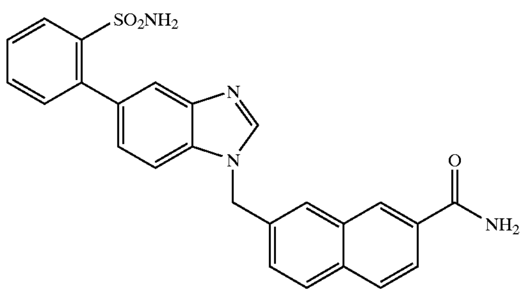

+

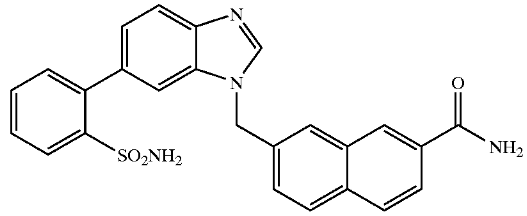

Part 1. The nitro compound from Part 2 of Example 23 (2.70 g, 6.01 mmol) was dissolved in 60 mL of ethanol, and tin(II) chloride dihydrate (5.43 g, 24.0 mmol) was added. The mixture was heated at reflux for 1 hour, then concentrated on the rotovap. The residue was washed through a plug of silica gel and concentrated to give another residue, which was dissolved in 20 mL of formic acid (88%) and stirred at 55° C. for 1 hour. Traces of formic acid were removed by evaporation with toluene in vacuo, and the desired product was obtained by flash column chromatography to give 516 mg (26%) of the desired benzimidazole. LRMS $(M+H)^+=330$.

Part 2. The benzimidazole from Part 1 (62 mg, 0.188 mmol) was dissolved in 5 mL of DMF, followed by the addition of 2-bromomethyl-7-cyanonaphthalene (93 mg, 0.376 mmol) and cesium carbonate (184 mg, 0.564 mmol). The mixture was stirred overnight, then diluted with ethyl acetate and washed with water (×2). The organic phase was dried over $MgSO_4$, concentrated in vacuo, and the desired products were obtained as a mixture of two regiosomers by flash column chromatography.

Part 3. The mixture of isomers from Part 2 (90 mg, 0.18 mmol) was dissolved in 10 mL of dry methanol. A vacuum-distilling adapter, equipped with a rubber septum and with a balloon on its side-arm, was placed on the reaction flask. The solution was chilled in ice, and HCl gas was introduced via a long needle immersed in the solution until the balloon began to inflate. The mixture was stirred overnight and then concentrated to dryness in vacuo. The residue was dissolved in 5 mL anhydrous methanol, and dry ammonium acetate (139 mg, 1.8 mmol) was added. The mixture was heated at reflux for 2 hours, then purified by preparative HPLC to afford the two title compounds. LRMS $(M+H)^+$=457.

Example 27

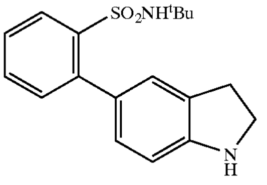

Part 1. To a solution of 5-bromoindoline (1.0 g, 5 mmol) in 10 ml of dioxane was added 5 mL of a 1N NaOH solution and 5 mL of water. This mixture was cooled with an ice bath, and di-tert-butyl dicarbonate (1.2 g, 5.5 mmol) was added in one portion. The reaction was allowed to warm to room temperature, stirred for 4 hours, and then concentrated. The residue was extracted with ethyl acetate (2×25 mL), and the combined organic phases were washed with water (2×25 mL), saturated aqueous NaCl (2×25 ml), then dried over $MgSO_4$. Filtration and concentration in vacuo gave N-Boc-5-bromoindoline (1.33 g, 89%) as a light brown powder after drying. $^1H$ NMR ($CDCl_3$) δ: 1.541 (s, 9H); 3.03–3.08 (t, 2H); 3.92–3.96 (t, 2H); 7.23–7.27 (m, 3H).

Part 2. To a solution of N-Boc-5-bromoindoline (104 mg, 0.35 mmol) in 5 ml of anhydrous dioxane were added the boronic acid from Example 19 (100 mg, 0.39 mmol), cesium carbonate (228 mg, 0.7 mmol) and tris (dibenzylideneacetone)dipalladium(0)-chloroform adduct (10 mg, 0.01 mmol). The reaction flask was thoroughly flushed with argon, and tri-tert-butylphosphine (0.006 mL, 0.025 mmol) was added via syringe. The reaction was heated to 80° C. and stirred overnight. The reaction was then cooled to room temperature, diluted with 25 mL of diethyl ether, flushed through a pad of Celite and concentrated in vacuo to give a brown residue. This residue was subjected to flash column chromatography on silica gel using 25% ethyl acetate in hexane to give the desired biphenylamine (150 mg, 100%) as a light brown oil after drying. $^1H$ NMR ($CDCl_3$) δ: 1.02 (s, 9H); 1.22 (s, 9H); 3.10–3.15 (t, 2H); 4.02, (t, 2H); 7.25–8.14 (m, 7H).

Part 3. The product from Part 2 was treated with 10 ml of 20% trifluoroacetic acid in dichloromethane for 10 minutes. The reaction mixture was concentrated in vacuo, redissolved in 25 mL of dichloromethane, washed with 1N NaOH (2×25 ml), dried over magnesium sulfate, filtered and concentrated in vacuo to give the desired biphenylamine as a brown oil after drying. ES-MS $(M+H^+)$: 330.5

Example 28

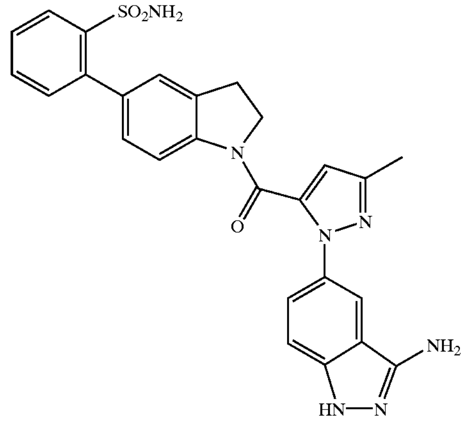

Part 1. 3-Cyano-4-fluoronitrobenzene (9.50 g, 57 mmol) was dissolved in 250 mL of ethanol, 5% Pd/C (2.0 g) was added, and the black slurry was stirred under a hydrogen balloon for 2 days. The reaction mixture was filtered through a celite bed and concentrated in vacuo to give the amino compound in 95% yield (7.37 g). LRMS $(M+H)^+$ m/z 137. $R_f$ 0.62 (2:1 ethyl acetate/hexane).

Part 2. The amino compound from Part 1 (4.00 g, 29 mmol) was slurried in 28 mL of conc. HCl and chilled in an ice bath. Sodium nitrite (2.00 g, 29 mmol) was dissolved in 10 mL of water and chilled in ice bath, and this solution was added dropwise to the cold slurry of the amino compound. The reaction mixture was then stirred at 0° C. for 30 min. Tin chloride dihydrate (19.7 g, 29 mmol) was dissolved in 10 mL of conc. HCl and chilled in ice bath, and this solution was added dropwise to the previous reaction mixture. After completion, the mixture was chilled and the solid hydrazine product was isolated by filtration through a Buchner funnel. This material was washed with cold brine (60 mL) and cold hexane (60 mL) to give 5.85 g of a yellow solid, which was used in the next step without further purification.

Part 3. Ethyl 2,4-dioxovalerate (20.0 g, 127 mmol) was dissolved in 100 mL of ethanol, and methoxylamine hydrochloride (11.1 g, 133 mmol) was added. The mixture was heated at reflux for 20 hours, followed by concentration of the reaction mixture in vacuo. The residue was dissolved in ethyl acetate, and washed with water and brine. The separated organic phase was dried over $MgSO_4$ and evaporated in vacuo to give 19.3 g (81%) of the desired imine as an oil. LRMS $(M+H)^+$ m/z 188.

Part 4. A solution of the product from Part 2 (5.85 g) and the product from Part 3 (3.80 g, 20.3 mmol) in acetic acid (100 mL) and THF (50 mL) was heated at reflux overnight, and the reaction mixture was concentrated in vacuo. The residue was taken up in ethyl acetate and washed with water and brine. The organic phase was dried, filtered, and concentrated and the residue was subjected to flash column chromatography to yield the desired 5-carboethoxy isomer (4.45 g, 56% for two steps) and the undesired 3-carboethoxy isomer (1.00 g, 12% over two steps). LRMS $(M+H)^+$ m/z 274. 5-Carbomethoxy isomer $R_f$ 0.66 (1:1 ethyl acetate/hexane). 3-Carbomethoxy isomer $R_f$ 0.50 (1:1 ethyl acetate/hexane).

Part 5. The biphenylamine from Example 27, Part 3 (90 mg, 0.27 mmol) was dissolved in 2 mL of dichloromethane, and trimethylaluminum (0.7 mL of a 2.0 M solution in hexane, 1.35 mmol) was added at room temperature. The mixture was stirred for 30 minutes, and then a solution of the 5-carbomethoxy ester from Part 4 (77 mg, 0.28 mmol) in 3 mL of dichloromethane was added dropwise to the reaction. The resulting mixture was stirred under argon overnight. The reaction was then quenched by the careful addition of aqueous sat. Rocheile's salt, and the reaction was extracted with dichloromethane (×3). The organic layer was concentrated and the residue was subjected to flash column chromatography to afford the desired coupling product (90 mg, 60%). LRMS $(M+H)^+$ m/z 558. $R_f$ 0.29 (1:1 ethyl acetate/hexane).

Part 6. The product from part 5 (83 mg, 0.15 mmol) was dissolved in 2 mL of ethanol, hydrazine monohydrate (40 μL, 0.75 mmol) was added dropwise, and the reaction mixture was heated at reflux overnight. Concentration in vacuo gave a residue, which was dissolved in 2 mL of trifluoroacetic acid and heated at reflux for 30 minutes. The resulting mixture was concentrated and purified by prep HPLC [(C18 column, standard $H_2O$ to $CH_3CN$ gradient (0.1% TFA)] to give the desired compound. LRMS $(M+H)^+$ m/z 514.

Example 29

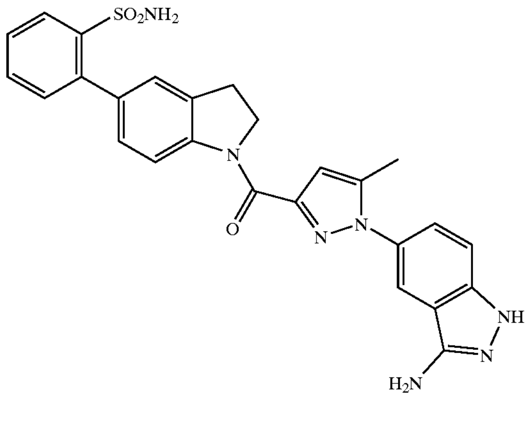

This compound was prepared from the 3-carbomethoxy intermediate from Part 4 of Example 28 in a manner similar to that in Parts 4 and 5, Example 28.

Example 30

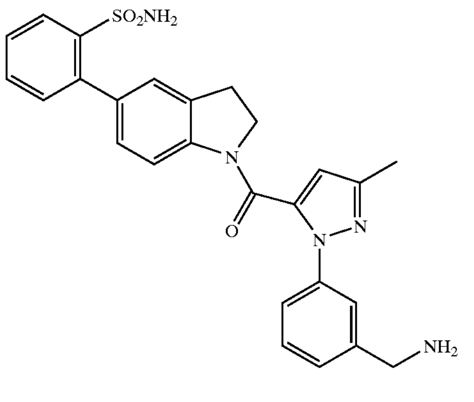

Part 1. 3-Bromophenylhydrazine hydrochloride (6.80 g, 30.4 mmol) and the product from Example 28, Part 3 (2.84 g, 15.2 mmol) were dissolved in 60 mL of acetic acid and 30 mL of THF, and the reaction mixture was heated at reflux overnight. The solvent was removed in vacuo, the residue was dissolved in ethyl acetate, and the solution was washed with water and sat. NaCl. The organic layer was dried over $MgSO_4$, evaporated in vacuo, and purified by flash column chromatography to give the desired pyrazole in quantitative yield. LRMS $(M+H)^+$ m/z 309, 311. $R_f$ 0.47 (1:4 ethyl acetate/hexane).

Part 2. The product from Part 1 was dissolved in 60 mL of acetonitrile, and KCN (2.91 g, 44.8 mmol), CuI (0.43 g, 2.2 mmol) and $Pd(Ph_3P)_4$ (1.3 g, 1.1 mmol) were added. The mixture was degassed by bubbling argon through the solution for 30 minutes, and the reaction mixture was heated under argon at reflux overnight. The black mixture was then passed through a silica plug, and the filtrate was concentrated to give a residue, which was taken up in ethyl acetate and washed with water (×2). The organic layer was dried, concentrated and subjected to flash chromatography to yield the desired nitrile as a white solid (2.69 g, 10.5 mmol, 69% for two steps). LRMS $(M+H)^+$ m/z 256. $R_f$ 0.68 (1:1 ethyl acetate/hexane).

Part 3. The product from Part 2 (2.00 g, 7.8 mmol) was dissolved in 40 mL of methanol, and water (20 mL) and LiOH monohydrate (0.66 g, 15.7 mmol) were added. The mixture was stirred for 1 hour, then acidified with 5N HCl to a pH of 1. The methanol was removed in vacuo, and the mixture was extracted with ethyl acetate (×3). The combined organic phases were dried and evaporated to give the desired acid as a white solid (1.38 g, 78%). LRMS $(M+H)^+$ m/z 228, $(M+Na)^+$ m/z 250.

Part 4. The acid from part 3 (200 mg, 0.88 mmol), the biphenyl amine from Example 25, Part 3 (290 mg, 0.88 mmol), and 4,4-dimethylaminopyridine (10 mg) were dissolved in 4 mL of pyridine and chilled in ice bath. To the mixture was added $POCl_3$ (0.25 mL, 2.6 mmol), and the reaction was stirred in the cold for 1 hour. The reaction was quenched with ice water, diluted with ethyl acetate, and the organic phase was washed with sat. NaCl (×2). The organic layer was dried, concentrated, and subjected to flash column chromatography to yield the desired amide (240 mg, 51%). LRMS $(M+H)^+$ m/z 540. $R_f$ 0.37 (1:1 ethyl acetate/hexane).

Part 5. The product from Part 4 (140 mg, 0.26 mmol) was dissolved in 10 mL of anhydrous DMF and chilled in ice bath. To the reaction mixture was added NaBH4 (80 mg, 2.08 mmol) and anhydrous $CoCl_2$ beads (68 mg, 0.52 mmol). The mixture was stirred for 30 minutes in the cold, then quenched with ice water and diluted with ethyl acetate. The mixture was filtered through a pad of celite, and the filtrate was washed with sat. NaCl (×2). The organic phase was dried, and concentrated in vacuo to give a residue, which was dissolved in 2 mL of trifluoroacetic acid and stirred at 60° C. for 30 minutes. The mixture was purified by prep HPLC [(C18 column, standard $H_2O$ to $CH_3CN$ gradient (0.1% TFA)] to afford the desired aminomethyl compound. LRMS $(M+H)^+$ m/z 488.

Examples 31 and 32

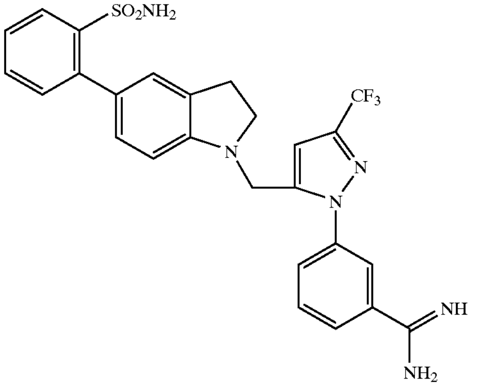

+

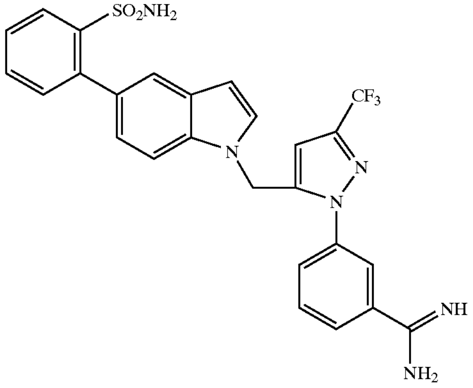

Part 1. A solution of the product from Example 27, Part 2 (80 mg, 0.2 mmol) in 4 mL of $CH_2Cl_2$ was treated with 1 mL of trifluoroacetic acid, and the solution was stirred at room temperature for 10 min. The reaction mixture was then concentrated, and again concentrated from heptane to remove traces of trifluoroacetic acid. The residue was dissolved in 5 mL of DMF, and the bromomethyl compound from Example 24, Part 3 (80 mg, 0.24 mmol) was added, together with 195 mg of cesium carbonate, and the solution was stirred at room temperature for 1 hr. The reaction was diluted with ethyl acetate (25 mL), washed with water and sat. NaCl, and the organic layer was dried over $MgSO_4$. Filtration and concentration gave a brown oil, which was used in the next reaction without further purification.

Part 2. The material from Part 1 (0.2 mmol) was taken up in 10 mL of absolute ethanol, and hydroxylamine hydrochloride (164 mg, 1.5 mmol) and triethylamine (0.2 mL, 1.5 mmol) were added. The solution was heated to 60° C. for 5 hours, then concentrated to give a residue, which was taken up in 5 mL of acetic acid, and acetic anhydride (0.2 mL) was added. The reaction mixture was stirred at room temperature for 30 min, then concentrated to dryness, followed by concentration with heptane to remove traces of acetic acid. The residue was used in the next reaction without further purification.

Part 3. The crude product from Part 2 was taken up in 5 mL of absolute ethanol, 1 drop of acetic acid was added, followed by 10% Pd/C (5 mg), and the reaction was placed under a balloon of hydrogen. After 4 hours, the starting material was gone by HPLC, so the reaction mixture was filtered and subjected directly to preparative HPLC [C 18 column, standard $H_2O$ to $CH_3CN$ (0.1% TFA) gradient]. Two products were isolated, the expected indoline product, and a product where the indoline ring had been oxidized to an indole ring. Indoline product: LRMS $(M+H)^+$ m/z 541.1. Indole product: LRMS $(M+H)^+$ m/z 539.1.

Example 33

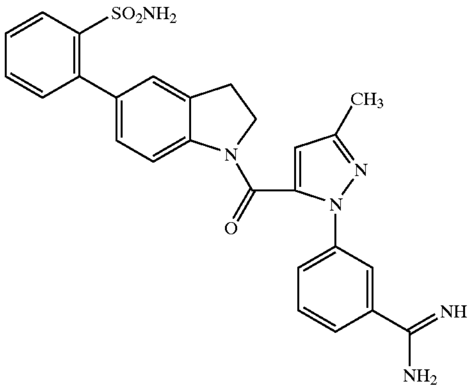

A solution of the product from Example 30, Part 4 (75 mg, 0.19 mmol) was treated with methanol and HCl, followed by ammonium acetate in a manner similar to that in Example 23, Part 6. Preparative HPLC gave the desired product.

Example 34

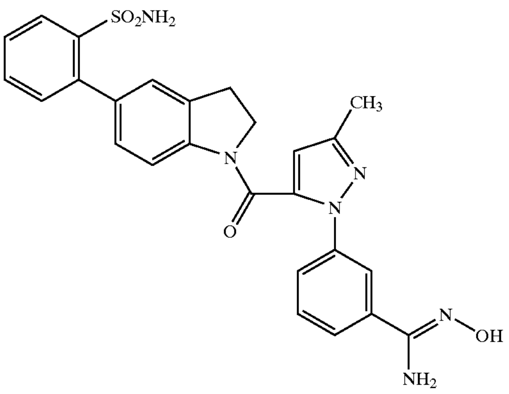

Treatment of the product from Example 30, Part 4 with hydroxylamine hydrochloride and triethylamine gave the above amidoxime.

Example 35

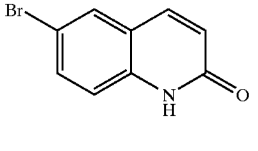

A solution of 4-bromoaniline (15 g, 87 mmol) and $K_2CO_3$ (181 g) in 170 mL of water was cooled to 5° C. A solution of cinnamoyl chloride (18.2 g, 109 mmol) in acetone (87 mL) was added dropwise, resulting in the formation of a light brown solid. After 1 hour, the solid was recovered by filtration, washed with cold water, once with cold ether and dried overnight at 80° C. at 20 mm Hg to give the desired product (23.8 g, 90%). A portion of this amide (10 g, 33 mmol) was suspended in chlorobenzene (220 mL) and aluminum chloride (26 g, 195 mmol) was added portionwise. The solution was heated at reflux for 2 hr, the solution was concentrated in vacuo to one half of its original volume, and the solution was poured into 1L of ice water. The resulting solid was collected by filtration and recrystallized from methanol to give 6-bromoquinolin-2-one (5.0 g, 71%) as a brown solid.

Example 36

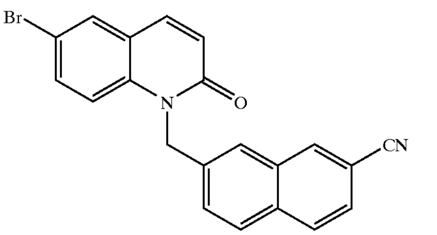

A solution of 6-bromohydroquinolin-2-one (1 g, 4.46 mmol), 2-bromomethyl-7-napthonitrile (1.16 g, 4.46 mmol), and cesium carbonate (1.5 g, 5.35 mmol) in 15 mL of DMF was stirred at room temperature for 18 h. The reaction mixture was diluted with water and ethyl acetate and filtered through celite. The organic layer was washed with water (×2), then with sat. NaCl, dried over $MgSO_4$, and concentrated in vacuo. The residue was subjected to flash column chromatography on silica gel, using 100% $CH_2Cl_2$ as eluent to give 7-[(6-bromo-2-oxohydroquinolyl)methyl]naphthalene-2-carbonitrile (876 mg, 50%) as a white solid. ES-MS $(M+H)^+$=389, 391.

Example 37

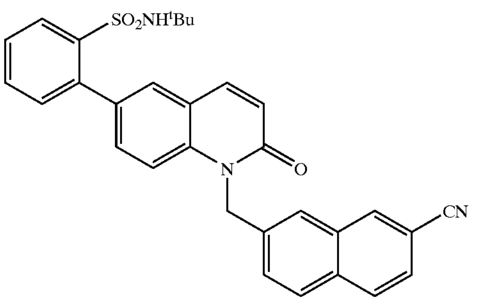

To a solution of 7-[(6-bromo-2-oxohydroquinolyl)methyl]naphthalene-2-carbonitrile (30 mg, 0.077 mmol), 2-{[(tert-butyl)amino]sulfonyl}phenylboronic acid (20 mg, 0.077 mmol), $Pd_2(dba)_3$ (1 mg, 1.5 mol %), and cesium carbonate (25 mg, 0.093 mmol) in dry dioxane (300 $\mu$L) was added tri-t-butylphosphine (0.7 uL, 3.6 mol %). The reaction was heated to 75° C. for 11 h, cooled to room temperature, and diluted with $CH_2Cl_2$ (2 mL). The solution was then filtered through celite, washed with 1N HCl and sat. NaCl, dried over $MgSO_4$, and concentrated in vacuo to afford 7-{[6-(2-{[(tert-butyl)amino]sulfonyl}phenyl)-2-oxohydroquinolyl]methyl}naphthalene-2-carbonitrile (34 mg, 85%). ES-MS (M+H)+=522.2.

Example 38

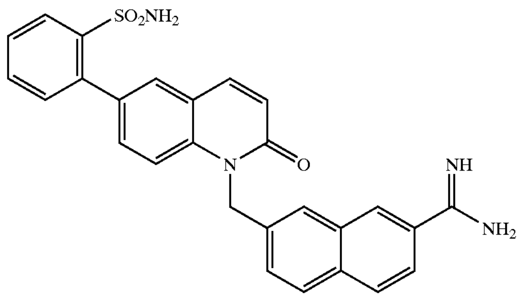

A solution of the nitrile from Example 37 (34 mg, 0.64 mmol) in ethyl acetate (5 mL) containing MeOH (150 $\mu$L) was cooled to −78° C. and HCl gas was bubbled in until saturation. The solution was stirred while warming to room temperature over 18 h. The solvent was removed in vacuo, the residue was taken up in methanol (2 mL), and dried $NH_4OAc$ (50 mg, 0.64 mmol) was added. The mixture was heated to 80° C. for 1 h, cooled, and purified by preparative HPLC [(C18 column, water/$CH_3CN$ gradient (0.1% TFA)]. The appropriate fractions were combined and lyophilized to give the desired amidine (5.6 mg, 19%) as a white powder. LRMS $(M+H)^+$ m/z 484.

Example 39

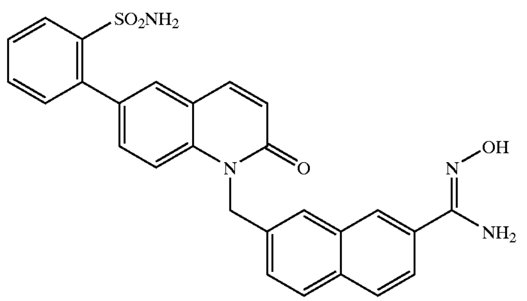

A solution of the nitrile from Example 37 (53 mg, 0.10 mmol) in methanol (0.5 mL) and DMF (0.25 mL) was treated with hydroxylamine hydrochloride (97 mg , 0.20 mmol), N,N-diisopropylethylamine (71 $\mu$L, 0.20 mmol). The solution was heated to 40° C. for 18 h, then concentrated in vacuo. The residue was stirred with TFA (2 mL) for 1 h, then concentrated in vacuo, and this residue was purified by preparative HPLC [(C18 column, water/$CH_3CN$ gradient (0.1% TFA)]. The appropriate fractions were combined and lyophilized to give the desired amidoxime (17 mg, 32%) as a white powder. LRMS $(M+H)^+$ m/z 499.

Example 40

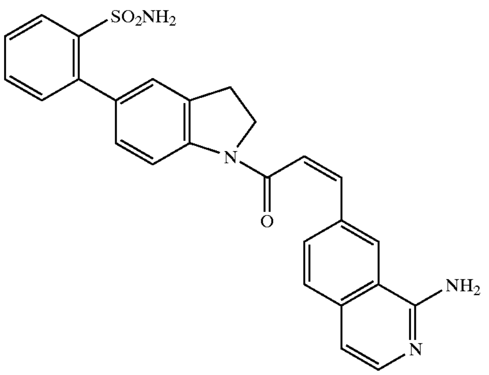

Part 1. 7-Bromoisoquinoline

This compound was prepared as a 60:40 mixture with 5-bromoisoquinoline as in *J. Am. Chem. Soc.*, 1939, 61, 183.

Part 2. 7-Bromoisoquinoline N-oxide Hydrochloride

This compound was prepared by a procedure analogous to that for 6-bromoisoquinoline N-oxide hydrochloride as in PCT WO 98/47876. A solution of 7.8 g (37.5 mmol) of a 60:40 mixture of 7-bromo and 5-bromoisoquinoline in 125 mL of $CH_2Cl_2$ was treated portionwise with 9.7 g (~39.4 mmol) of 3-chloroperoxybenzoic acid (~70% purity). The solution, which was initially homogeneous, deposited a voluminous precipitate over 1 hr. Then 100 mL of methanol were added, and the reaction was concentrated to a volume of about 100 mL. Gaseous HCl was then bubbled through the solution for about 10 min, during which time the solution became warm and all of the precipitate dissolved. A few minutes later, another voluminous precipitate began to form. To this solution was added 100 mL of ether, and the mixture was stirred in an ice-water bath for 20 minutes. The resulting product was isolated by filtration, washed thoroughly with ether, and air-dried to give 8.07 g (83%) of the desired compound as a white solid, which was still a 60:40 mixture of the 7- and 5-bromo isomers.

Part 3. 7-Bromo-1-chloroisoquinoline

This compound was prepared by a procedure analogous to that for 6-bromo-1-chloroisoquinoline as in PCT WO 98/47876. A solution of 8.07 g (31 mmol) of the mixture from Part B was taken up in 50 mL of $POCl_3$, and the mixture was heated at 90° C. for 2 hr. The reaction mixture was concentrated to remove most of the $POCl_3$, and the residue was taken up in 100 mL of $CH_2Cl_2$. The solution was carefully basified to pH 10 by the slow addition of 1N NaOH, and the organic layer was washed with 100 mL of $H_2O$, 100 mL of sat. NaCl, and dried over $MgSO_4$. Filtration and concentration gave a light yellow solid, which was subjected to flash column chromatography on silica gel first with 5% and then with 10% ethyl acetate in hexanes. A total of 3.62 g (48%) of the desired 7-bromo-1-chloroisoquinoline was isolated from this chromatography free of the 5-bromo isomer.

Part 4. 7-Bromo-1-phenoxyisoquinoline

A solution of 3.60 g (14.8 mmol) of 7-bromo-1-chloroisoquinoline and 1.5 g of solid KOH in 11.2 g of phenol was heated at 140° C. for 2 hr. The reaction was cooled to room temperature, then partitioned between 100 mL of $CH_2Cl_2$ and 100 mL of 3N NaOH. The organic layer was washed with another 2×100 mL of 3N NaOH, then with 100 mL of $H_2O$, and dried over $MgSO_4$. Filtration and concentration gave a yellow oil, which was subjected to flash column chromatography on silica gel 30% $CH_2Cl_2$ in hexanes, giving 3.42 g (77%) of the desired product as a light yellow solid.

Part 5. 1-Amino-7-bromoisoquinoline

A mixture of 3.40 g (11.3 mmol) of 1-amino-7-bromoisoquinoline and 7.65 g of ammonium acetate was heated at 150° C. for 15 hr. The reaction was cooled, and the residue was partitioned between 200 mL of ethyl acetate and 200 mL of 3N NaOH. The organic layer was extracted with 2×100 mL of 2N HCl, and the combined aqueous extracts were basified to pH 10 using 50% NaOH. This solution was extracted with 2×100 mL of ethyl acetate, and the organics were then washed with 100 mL of sat. NaCl and dried over $MgSO_4$. Filtration and concentration gave 1.68 g (66%) of the desired amino compound as a yellow solid.

Part 6. 1-[Bis(t-butoxycarbonyl)amino]-7-bromoisoquinoline

A solution of 740 mg (3.32 mmol) of 1-amino-7-bromoisoquinoline in 50 mL of acetonitrile was treated with 1.4 mL of N,N-diiospropylethylamine and 100 mg of 4-(N,N-dimethylamino)pyridine, followed by 3.0 g (4.1 eq) of di-t-butyldicarbonate, and the reaction was stirred at 40° C. for 1 hr. By HPLC analysis, there was still some starting amino compound that remained, so another 1.0 g of di-t-butyldicarbonate were added, and the reaction was stirred at 40° C. for another 30 min. The reaction mixture was concentrated to give a dark oil, which was subjected to flash column chromatography on silica gel with 20% ethyl acetate in hexanes to give 736 mg of the desired product as a light yellow solid. Also isolated were 156 mg of product as a somewhat less pure fight yellow solid, making the total yield 64%.

Part 7. 1-[Bis(t-butoxycarbonyl)amino]isoquinoline-7-carboxaldehyde

A solution of 400 mg (0.95 mmol) of 1-[bis(t-butoxycarbonyl)amino]-7-bromoisoquinoline in 50 mL of anhydrous THF was cooled with a liquid nitrogen/methanol slush bath (−98° C.), and 0.55 mL of a 2.43 M solution of n-BuLi in hexanes (1.3 eq) was added dropwise over 1 min. The solution was stirred in the cold for 5 min, then a solution of 5 mL of anhydrous DMF in 10 mL of anhydrous THF was added rapidly. The solution was allowed to warm to about 0° C., then poured into 50 mL of 0.5 N HCl, and 50 mL of ethyl acetate were added. The aqueous layer was brought to pH 6 with 1N NaOH, 25 mL of sat. NaCl were added, and the layers were shaken and separated. The organic layer was dried over $MgSO_4$, filtered, and concentrated to give an oily residue. This residue was subjected to flash column chromatography on silica gel with 20% ethyl acetate in hexanes to give 190 mg (54%) of the desired aldehyde as a yellow semisolid.

Part 8. (2Z)-3-{[1-bis(t-butoxycarbonyl)amino]isoquinolin-7-yl}acrylic Acid, 2-(Trimethylsilyl)ethyl Ester A solution of 117 mg (0.29 mmol) of [bis(2,2,2-trifluoroethoxy)phosphinyl]acetic acid, 2-(trimethylsilyl) ethyl ester (*J. Org. Chem.*, 1991, 56, 4204) and 400 mg of 18-crown-6 in 25 mL of anhydrous THF was cooled with a dry ice-acetone bath under argon, and 0.75 mL of a 0.5 M solution of potassium bis(trimethylsilyl)amide in toluene were added dropwise over 2 min. The reaction was stirred in the cold for 15 min, then a solution of 100 mg (0.27 mmol) of 1-[bis(t-butoxycarbonyl)amino]isoquinoline-7-carboxaldehyde in 25 mL of anhydrous THF was added dropwise over 10 min. The reaction was then allowed to warm to room temperature overnight, then partitioned between 100 mL of $CH_2Cl_2$ and 50 mL of $H_2O$. The organics were washed with aqueous NaCl, and dried over $MgSO_4$. Filtration and concentration gave an oily residue, which was subjected to flash column chromatography on silica gel with 25% ethyl acetate in hexanes to give 33 mg of the desired product as a clear, colorless oil.

Part 9. (2Z)-N-[5-(2{[(N-1,1-dimethylethyl)amino] sulfonyl}phenyl)-1-indolinyl]-3-{[1-bis(t-butoxycarbonyl) amino]isoquinolin-7-yl}acrylamide A solution of 498 mg (0.97 mmol) of (2Z)-3-{[1-bis(t-butoxycarbonyl)amino]isoquinolin-7-yl}acrylic acid, 2-(trimethylsilyl)ethyl ester in 5 mL of DMF was treated at room temperature with 1.2 mL (1.25 eq) of a 1.0 M tetrabutylammonium fluoride in THF, and the reaction was stirred for 5 hr. The reaction mixture was diluted with 100 mL of ether, and the solution was washed with 100 mL of water. The aqueous layer was again extracted with 100 mL of ether, and the combined organic layers were dried over $Na_2SO_4$. Filtration and concentration gave 350 mg of an off-white solid, which was used without further purification. A solution of 50 mg of this carboxylic acid and 44 mg of 2-indolin-5-ylbenzenesulfonamide from Example 27, Part 3 in 3 mL of DMF was treated with 100 $\mu$L of N,N-diisopropylethylamine and 60 mg of HATU, and the reaction was stirred at room temperature overnight. The reaction mixture was diluted with 100 mL of ethyl acetate and washed with sat. $NaHCO_3$ (2×25 mL), and the organic layer was dried over $MgSO_4$. Filtration and concentration gave an orange oil, which was subjected to flash column chromatography on silica gel, using 20% ethyl acetate in hexanes as eluent to give 62 mg of the desired product as a yellow oil.

Part 10. (2Z)-N-[4-(2{aminosulfonyl}phenyl)-1-indolinyl]-3-{aminoisoquinolin-7-yl}acrylamide A solution of the yellow oil from Part 9 in 2 mL of trifluoroacetic acid was stirred at room temperature overnight. The reaction mixture was concentrated with $CH_2Cl_2$ to remove most of the TFA, then purified directly by prep HPLC to give 15 mg of the desired product was obtained as an off-white solid. LRMS $(M+H)^+$=470.

Example 41

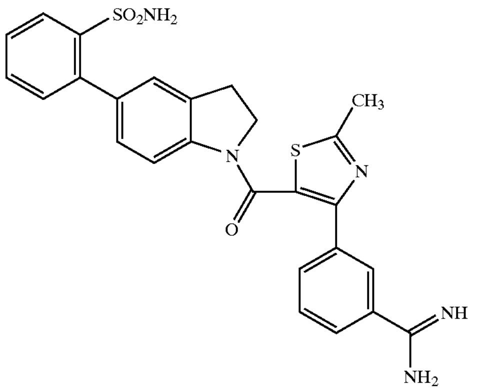

This compound was prepared by a method similar to that used in Example 23, Part 6.

Example 42

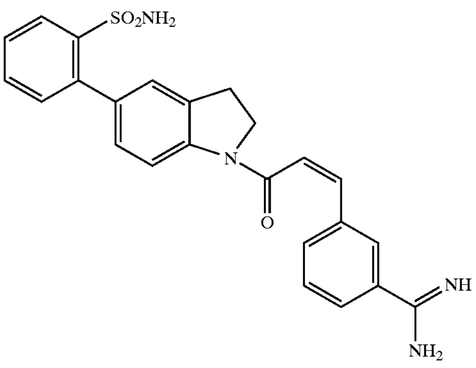

This compound was prepared by a method similar to that used in Example 23, Part 6.

Example 43

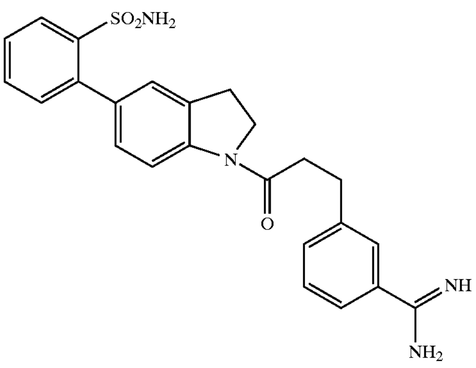

This compound was prepared by catalytic hydrogenation of the compound from Example 42.

BIOLOGICAL ACTIVITY EXAMPLES

Evaluation of the compounds of this invention is guided by in vitro protease activity assays (see below) and in vivo studies to evaluate antithrombotic efficacy, and effects on hemostasis and hematological parameters.

The compounds of the present invention are dissolved in buffer to give solutions containing concentrations such that assay concentrations range from 0 to 100 $\mu$M. In the assays for thrombin, prothrombinase and factor Xa, a synthetic chromogenic substrate is added to a solution containing test compound and the enzyme of interest and the residual catalytic activity of that enzyme is determined spectrophotometrically. The $IC_{50}$ of a compound is determined from the substrate turnover. The $IC_{50}$ is the concentration of test compound giving 50% inhibition of the substrate turnover. The compounds of the present invention desirably have an $IC_{50}$ of less than 500 nM in the factor Xa assay, preferably less than 200 nM, and more preferred compounds have an $IC_{50}$ of about 100 nM or less in the factor Xa assay. The compounds of the present invention desirably have an $IC_{50}$ of less than 4.0 $\mu$M in the prothrombinase assay, preferably less than 200 nM, and more preferred compounds have an $IC_{50}$ of about 10 nM or less in the prothrombinase assay. The compounds of the present invention desirably have an $IC_{50}$ of greater than 1.0 $\mu$M in the thrombin assay, preferably greater than 10.0 $\mu$M, and more preferred compounds have an $IC_{50}$ of greater than 100.0 $\mu$M in the thrombin assay.

Amidolytic Assays for Determining Protease Inhibition Activity

The factor Xa and thrombin assays are performed at room temperature, in 0.02 M Tris.HCl buffer, pH 7.5, containing 0.15 M NaCl. The rates of hydrolysis of the paranitroanilide substrate S-2765 (Chromogenix) for factor Xa, and the substrate Chromozym TH (Boehringer Mannheim) for thrombin following preincubation of the enzyme with inhibitor for 5 minutes at room temperature, and were determined using the Softmax 96-well plate reader (Molecular Devices), monitored at 405 nm to measure the time dependent appearance of p-nitroaniline.

The prothrombinase inhibition assay is performed in a plasma free system with modifications to the method described by Sinha, U. et al., Thromb. Res., 75, 427–436 (1994). Specifically, the activity of the prothrombinase complex is determined by measuring the time course of thrombin generation using the p-nitroanilide substrate Chromozym TH. The assay consists of preincubation (5 minutes) of selected compounds to be tested as inhibitors with the complex formed from factor Xa (0.5 nM), factor Va (2 nM), phosphatidyl serine:phosphatidyl choline (25:75, 20 μM) in 20 mM Tris.HCl buffer, pH 7.5, containing 0.15 M NaCl, 5 mM $CaCl_2$ and 0.1% bovine serum albumin. Aliquots from the complex-inhibitor mixture are added to prothrombin (1 nM) and Chromozym TH (0.1 mM). The rate of substrate cleavage is monitored at 405 nm for two minutes. Eight different concentrations of inhibitor are assayed in duplicate. A standard curve of thrombin generation by an equivalent amount of untreated complex are used for determination of percent inhibition.

Antithrombotic Efficacy in a Rabbit Model of Venous Thrombosis

A rabbit deep vein thrombosis model as described by Hollenbach, S. et al., Thromb. Haemost. 71, 357–362 (1994), is used to determine the in-vivo antithrombotic activity of the test compounds. Rabbits are anesthetized with I.M. injections of Ketamine, Xylazine, and Acepromazine cocktail. A standardized protocol consists of insertion of a thrombogenic cotton thread and copper wire apparatus into the abdominal vena cava of the anesthetized rabbit. A non-occlusive thrombus is allowed to develop in the central venous circulation and inhibition of thrombus growth is used as a measure of the antithrombotic activity of the studied compounds. Test agents or control saline are administered through a marginal ear vein catheter. A femoral vein catheter is used for blood sampling prior to and during steady state infusion of test compound. Initiation of thrombus formation begins immediately after advancement of the cotton thread apparatus into the central venous circulation. Test compounds are administered from time=30 min to time=150 min at which the experiment is terminated. The rabbits are euthanized and the thrombus excised by surgical dissection and characterized by weight and histology. Blood samples are analyzed for changes in hematological and coagulation parameters.

Effects of Compounds in Rabbit Venous Thrombosis Model

Administration of compounds in the rabbit venous thrombosis model demonstrates antithrombotic efficacy at the higher doses evaluated. There are no significant effects of the compound on the aPTT and PT prolongation with the highest dose (100 μg/kg+2.57 μg/kg/min). Compounds have no significant effects on hematological parameters as compared to saline controls. All measurements are an average of all samples after steady state administration of vehicle or (D)-Arg-Gly-Arg-thiazole. Values are expressed as mean ± SD.

Without further description, it is believed that one of ordinary skill in the art can, using the preceding description and the following illustrative examples, make and utilize the compounds of the present invention and practice the claimed methods.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference. Briefer NOTE: All claims moved to end of this section of the patent The claimed invention is:

1. A compound according to the formula:

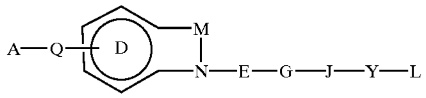

wherein:

A is selected from the group consisting of:

(a) $C_1$–$C_6$-alkyl;

(b) $C_3$–$C_8$-cycloalkyl;

$—N(—R^2,—R^3—C(=N—R^2)—, (—R^2, —R^3)N—C(=N—R^2)—(—R^2, —R^3)N—C(=N—R^2)—N(—R—)—$ (d) phenyl, which is independently substituted with 0–2 $R^1$ substituents;

(e) naphthyl, which is independently substituted with 0–2 $R^1$ substituents; and (f) a monocyclic or fused bicyclic heterocyclic ring system having from 5 to 10 ring atoms, wherein 1–4 ring atoms of the ring system are selected from the group consisting of N, O and S, and wherein the ring system may be substituted with 0–2 $R^1$ substituents;

$R^1$ is selected from the group consisting of:

Halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, $—NO_2$, $R^2—C(=N—R^3)—$, $(—R^2, —R^3)N—C(=N—R^2)—$, $—(CH_2)_mNR^2R^3$, $—C(=O)—N(—R^2, —R^3)$, $—SO_2N(—R^2, —R^3)$, $—SO_2R^2$, $—CF_3$, $—OR^2$, and a 5–6 membered aromatic heterocyclic system containing from 1–4 heteroatoms selected from the group consisting of N, O and S, wherein from 1–4 hydrogen atoms on the aromatic heterocyclic system may be independently replaced with a member selected from the group consisting of halo, $C_1$–$C_4$-alkyl, —CN $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl and $—NO_2$;

$R^2$ and $R^3$ are independently selected from the group consisting of:

H, $—OR^2$, $—N(—R^2, —R^3)$, $—C_{1-4}$alkyl, $—C_{2-6}$ alkenyl, $—C_{2-6}$alkynyl, $—C_{3-8}$cycloalkyl, $—C_{0-4}$ alkyl$C_{3-8}$cycloalkyl, $—C_{0-4}$alkylphenyl and $—C_{0-4}$ alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —$NO_2$;

or $R^2$ and $R^3$ taken together can form a 3–8 membered cycloalkyl or a heterocyclic ring system, wherein the heterocyclic ring system may have from 5 to 10 ring atoms, with 1 to 2 rings being in the ring system and contain from 1–4 heteroatoms selected from the group consisting of N, O and S, wherein from 1–4 hydrogen atoms on the heterocyclic ring system may be independently replaced with a member selected from the group consisting of halo, $C_1$–$C_4$—alkyl, —CN—$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl and —$NO_2$;

m is an integer of 0–2;

Q is a member selected from the group consisting of:

a direct link, —CH2—, —C(=O)—, —N($R^4$)—, —N($R^4$)CH2—, —C=N(R4)—, —C(=O)—N($R^4$)—, —N($R^4$)—, C(=O)—, —$SO_2$—, —O—, —$SO_2$—N($R^4$)— and —N($R^4$)—$SO_2$—;

$R^4$ is selected from the group consisting of:

H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —$NO_2$;

D is a phenyl, which is independently substituted with 0–2 $R^{1a}$ substituents;

$R^{1a}$ is selected from the group consisting of:

Halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —$NO_2$, $(CH_2)_m NR^{2a}R^{3a}$, $SO_2NR^{2a}R^{3a}$, $SO_2R^{2a}$, $CF_3$, $OR^{2a}$, and a 5–6 membered aromatic heterocyclic system containing from 1–4 heteroatoms selected from the group consisting of N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

$R^{2a}$ and $R^{3a}$ are independently selected from the group consisting of:

H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

M is a member selected from the group consisting of:

—C(—$R^{17}$,—$R^{18}$)—C(=O)—, —C(—$R^{17}$,—$R^{17a}$)—C(—$R^{18}$,—$R^{18a}$)—, —C(—$R^{17}$)=C(—$R^{18}$)—, —C(=O)—C(=O)—and —C(=C($R^{17b}$, —$R^{17c}$))—C(=O)—, wherein the first named atom of the chain is directly attached to D, and wherein D, M and the N atom attached to the last chain atom of M collectively form a bicyclic ring structure;

$R^{17}$, $R^{17a}$, $R^{18}$ and $R^{18a}$ are each independently selected from the group consisting of:

hydrogen, halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —$NO_2$, $(CH_2)_m NR^2R^3$, $SO_2NR^2R^3$, $SO_2R^2$, $CF_3$, $OR^2$ , and a 5–6 membered aromatic heterocyclic system containing from 1–4 heteroatoms selected from the group consisting of N, O and S, wherein from 1–4 hydrogen atoms on the aromatic heterocyclic system may be independently replaced with a member selected from the group consisting of halo, $C_1$–$C_4$-alkyl, —CN, $C_{1-4}$alkyl, $C_{2-6}$alkenyl, $C_{2-6}$alkynyl, $C_{3-8}$cycloalkyl, $C_{0-4}$alkyl$C_{3-8}$ cycloalkyl and —$NO_2$;

$R^{17b}$ and $R^{17c}$ are each independently a member selected from the group consisting of:

hydrogen, —halo, hydroxy, —$C_{1-4}$alkyl, $C_{2-6}$alkenyl, —$C_{2-6}$alkynyl, —$C_{3-8}$cycloalkyl, —$C_{0-4}$alkyl—$C_{3-8}$cycloalkyl, —CN, —$NO_2$, —$(CH_2)_m NR^2R^3$, —$SO_2NR^2R^3$, —$SO_2R^2$, —$CF_3$, —$OR^2$, phenyl, and a 5–6 membered aromatic heterocyclic ring containing from 1–4 heteroatoms selected from the group consisting of N, O and S, wherein from 1–4 hydrogen atoms on the cycloalkyl, the phenyl ring, or the aromatic heterocyclic ring may be independently replaced with a member selected from the group consisting of halo, $C_1$–$C_4$-alkyl, —CN, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl and —$NO_2$;

E is a member selected from the group consisting of:

a direct link, —C(=O)—, —C(=O)—N($R^5$)—, —C(—$R^{5a}$,—$R^{6a}$)— and —C(—$R^{5b}$,—$R^{6b}$)—C(—$R^{5c}$,—$R^{6c}$)—;

wherein $R^5$, $R^{5a}$, $R^{6a}$, $R^{5b}$, $R^{6b}$, $R^{5c}$ and $R^{6c}$ are independently selected from the group consisting of: p2 H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl, $C_{0-4}$alkylnaphthyl, $C_{0-4}$alkylheteroaryl, $C_{1-4}$alkylCOOH and $C_{1-4}$alkylCOO$C_{1-4}$alkyl, wherein from 0–4 hydrogen atoms on the ring atoms of the phenyl, naphthyl and heteroaryl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —OH, —O—$C_{1-4}$alkyl, —SH, —S—$C_{1-4}$alkyl, —CN and —$NO_2$;

G is selected from the group consisting of:

a direct link, —C($R^7$,$R^8$)—, —C($R^{7a}$,$R^{8a}$)—C($R^{7b}$, $R^{8b}$)— and —C($R^{7c}$)=C($R^{8c}$)—;

wherein $R^7$, $R^8$, $R^{7a}$, $R^{8a}$, $R^{7b}$, $R^{8b}$, $R^{7c}$ and R8 c are independently a member selected from the group consisting of:

hydrogen, halogen, $C_{1-4}$alkyl, $C_{2-6}$alkenyl, $C_{2-6}$alkynyl, $C_{3-8}$cycloalkyl, $C_{0-4}$alkyl —$C_{3-8}$ cycloalkyl, $C_{0-4}$alkylphenyl, $C_{0-4}$alkylnaphthyl, —$OR^9$, —N($R^9R^{10}$), —$C_{0-4}$alkylCOOR$^9$, —$C_{0-4}$ alkylC(=O)$NR^9R^{10}$, —$C_{0-4}$alkylC(=O)$OR^9$, —$C_{0-4}$alkylC(=O)$NR^9$—$CH_2$—$CH_{2—O—R}{}^{10}$, —$C_{0-4}$alkylC(=O)$NR^9$(—$CH_2$—$CH_2$—O—$R^{10}$—)$_2$, —N($R^9$)$COR^{10}$, —N($R^9$)C(=O)$R^{10}$,—N($R^9$) $SO_2R^{10}$, a naturally occurring or synthetic amino acid side chain, and $C_{0-4}$alkylheterocyclic ring having from 1 to 4 hetero ring atoms selected from the group consisting of N, O and S, $CH_2COOC_{1-4}$alkyl, $CH_2COOC_{1-4}$alkylphenyl and $CH_2COOC_{1-4}$ alkylnaphthyl, wherein from 1–4 hydrogen atoms on the $CO_{0-4}$alkylheterocyclic ring may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

wherein from 1–4 hydrogen atoms on the ring atoms of the phenyl and naphthyl moieties may be independently replaced with a member selected from the group consisting of halo, —$OR^9$, $C_{1-4}$alkyl, $C_{2-6}$alkenyl, $C_{2-6}$alkynyl, $C_{3-8}$cycloalkyl, $C_{0-4}$alkyl—$C_{3-8}$cycloalkyl, —CN and —$NO_2$;

$R^9$ and $R^{10}$ are independently selected from the group consisting of:

H, $C_{1-4}$alkyl, $C_{0-4}$alkylphenyl, $C_{0-4}$alkylnaphthyl, $C_{3-8}$cycloalkyl, and $C_{1-4}$alkyl—O—$C_{1-4}$alkyl, $C_{1-4}$alkyl—COOH wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl—$C_{3-8}$cycloalkyl, —CN and —$NO_2$, and wherein $R^9$ and $R^{10}$ taken together can form a 5–8 membered heterocylic ring;

J is a member selected from the group consisting of:

a direct link, —O—, —O—C(—$R^{11}$, —$R^{11a}$)—, —S—, —S(═O)—, —S(═O)$_2$—, —S—C(—$R^{11}$, —$R^{11a}$)—, —S(═O)—C(—$R^{11}$, —$R^{11a}$)—, —S(═O)$_2$—(—$R^{11}$, —$R^{11a}$)—, —C(═O)—, —C(═O)—N($R^{11b}$)—, —N($R^{11b}$)—C(═O)—, —N($R^{11b}$)—, —N($R^{11b}$)—C(—$R^{11}$, —$R^{11a}$)— O and a monocyclic aromatic or non-aromatic heterocyclic ring having from 5 to 8 ring atoms, wherein 1–4 ring atoms of the ring system are selected from the group consisting of N, O and S, and wherein the ring system may be substituted with 0–2 $R^{11}$ substituents;

$R^{11}$, $R^{11a}$, $R^{11b}$, and $R^{11}$ are a member independently selected from the group consisting of:

hydrogen, halo, —$CF_3$, —CN, —$NR^9R^{10}$, —$SO_2$Me, —$NO_2$, —OH, —O—$C_{1-4}$alkyl, —O—$C_{2-6}$alkenyl, —O—C—$_{2-6}$alkynyl, —O—$C_{3-8}$cycloalkyl, —O—$C_{1-4}$alkyl, —O—$C_{1-4}$alkyl, —O—$C_{1-4}$ alkyl—COOH, —O—$C_{1-4}$alkyl-phenyl, —COOH, —C(═O)—O—$C_{1-4}$alkyl, —C(═O)—O—$C_{2-6}$ alkenyl, —C(═O)—O—$C_{2-6}$alkynyl, —C(═O)—O—$C_{3-8}$cycloalkyl, $C_{1-4}$alkyl, $C_{2-6}$alkenyl, $C_{2-6}$alkynyl, $C_{3-8}$cycloalkyl, $C_{0-4}$alkyl—$C_{3-8}$ cycloalkyl, $C_{0-4}$alkylphenyl, $C_{0-4}$alkylnaphthyl, $C_{0-4}$alkylC(═O)$NR^9R^{10}$, $C_{0-4}$alkylC(═O)$OR^9$, $C_{0-4}$alkylheterocyclic ring having from 1 to 4 hetero ring atoms selected from the group consisting of N, O and S, $CH_2COOC_{1-4}$alkyl, $CH_2COOC_{1-4}$alkylphenyl and $CH_2COOC_{1-4}$alkylnaphthyl; wherein from 1–4 hydrogen atoms on the $C_{0-4}$alkylheterocyclic ring may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl-phenyl, $C_{0-4}$alkyl$C_{3-8}$cycloalkyl, —CN and —$NO_2$;

wherein from 1–4 hydrogen atoms on the ring atoms of the phenyl and naphthyl moieties may be independently replaced with a member selected from the group consisting of halo, —$OR^9$, $C_{1-4}$alkyl, $C_{2-6}$alkenyl, $C_{2-6}$alkynyl, $C_{3-8}$cycloalkyl, $C_{0-4}$alkyl—$C_{3-8}$cycloalkyl, —CN and —$NO_2$;

Y is a member selected from the group consisting of:

(a) phenyl, which is independently substituted with 0–2 $R^{1b}$ substituents;

(b) naphthyl, which is independently substituted with 0–2 $R^{1b}$ substituents; and (c) a monocyclic or fused bicyclic heterocyclic ring system having from 5 to 10 ring atoms, wherein 1–4 ring atoms of the ring system are selected from the group consisting of N, O and S, and wherein the ring system may be substituted with 0–2 $R^{1b}$ substituents;

$R^{1b}$ is a member selected from the group consisting of:

halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —$NO_2$, $NR^{2b}R^{3b}$, $SO_2NR^{2b}R^{3b}$, $SO_2R^{2b}$, $CF_3$, $OR^{2b}$, O—$CH_2$—$CH_2$—$OR^{2b}$, O—$CH_2$—$COOR^{2b}$, N($R^{2b}$)—$CH_2$—$CH_2$—$OR^{2b}$, N(—$CH_2$—$CH_2$—$OR^{2b}$)$_2$, N($R^{2b}$)—C(═O)$R^{3b}$, N($R^{2b}$)—$SO_2$—$R^{3b}$, and a 5–6 membered aromatic heterocyclic system containing from 1–4 heteroatoms selected from the group consisting of N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkyl-phenyl, —CN and —$NO_2$;

$R^{2b}$ and $R^{3b}$ are independently selected from the group consisting of:

H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, —$OR^9$, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

L is selected from the group consisting of:

H, —CN, C(═O)$NR^{12}R^{13}$, —$(CH_2)_n$$NR^{12}R^{13}$, C(═$NR^{12}$) $NR^{12}R^{13}$, $OR^{12}$, —$NR^{12}$C(═$NR^{12}$) $NR^{12}R^{13}$, and $NR^{12}$C(═$NR^{12}$)—$R^{13}$;

n is an integer from 0 to 8;

$R^{12}$ and $R^{13}$ are independently selected from the group consisting of: <hydrogen, —$OR^{14}$, —$NR^{14}R^{15}$, $C_{1-4}$alkyl, $C_{0-4}$alkylphenyl, $C_{0-4}$alkylnaphthyl, $COOC_{1-4}$alkyl, COO—$C_{0-4}$alkylphenyl and COO—$C_{0-4}$alkylnaphthyl, wherein from 1–4 hydrogen atoms on the ring atoms of the phenyl and naphthyl moieties may be independently replaced with a member selected from the group consisting of halo, —OH, —O—$C_{1-4}$alkyl, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —$NO_2$;

$R^{14}$ and $R^{15}$ are independently selected from the group consisting of:

H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —$NO_2$;

and all pharmaceutically acceptable isomers, salts, hydrates, solvates and prodrug derivatives thereof.

2. a phrmaceutical composition for preventing or treating a condition in a mammal characterized by undesired thrombosis comprising a therapeutacally acceptable carrier and a therapeutically effective amount of a compound of cliam 1.

3. A method for preventing or treating a condition in a mammal characterized by undesired thrombosis comprising administering to said mammal a therapeutically effective amount of a compound of claim 1.

4. The method of claim 3, wherein the condition is selected from the group consisting of:

acute coronary syndrome, myocardial infarction, unstable angina, refractory angina, occlusive coronary thrombus occurring post-thrombolytic therapy or post-coronary angioplasty, a thrombotically mediated cerebrovascular, syndrome, embolic stroke, thrombotic strroke, transent ischemic attacks, venous thrombosis, deep venous thrombosis, pulmonary embolus, coagulopathy, dissemination intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catherization, intra-aortic ballon pump, coronary stent, or cardiac valve, and conditions required the fitting of prosthettic devices.

5. A method for inhibiting the coagulation of biological samples, comprising the administration of a compound of claim 1.

6. A compound of claim 1, wherein:

A is selected from the group consisting of:

(a) $C_1$–$C_6$-alkyl;

(b) $C_3$–$C_8$-cycloalkyl;

(c) phenyl, which is independently substituted with 0–2 $R^1$ substituents;

(d) naphthyl, which is independently substituted with 0–2 $R^1$ substituents; and (e) a monocyclic or fused bicyclic heterocyclic ring system having from 5 to 10 ring atoms, wherein 1–4 ring atoms of the ring system are selected from the group consisting of N, O and S, and wherein the ring system may be substituted with 0–2 $R^1$ substituents;

$R^1$ is selected from the group consisting of:

halo, —$C_{1-4}$alkyl, —$C_{2-6}$alkenyl, —$C_{2-6}$alkynyl, —$C_{3-8}$ cycloalkyl, —$C_{0-4}$alkyl$C_{3-8}$cycloalkyl, —CN, —$NO_2$, —$(CH_2)_m NR^2R^3$, —$SO_2NR^2R^3$, —$SO_2R^2$, —$CF_3$, —$OR^2$, and a 5–6 membered aromatic heterocyclic system containing from 1–4 heteroatoms selected from the group consisting of N, O and S, wherein from 1–4 hydrogen atoms on the aromatic heterocyclic system may be independently replaced with a member selected from the group consisting of halo, —$C_1$–$C_4$-alkyl, —CN, —$C_{1-4}$alkyl, —$C_{2-6}$ alkenyl, —$C_{2-6}$alkynyl, —$C_{3-8}$cycloalkyl, —$C_{0-4}$ alkyl$C_{3-8}$cycloalkyl and —$NO_2$;

$R^2$ and $R^3$ are independently selected from the group consisting of:

H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —$NO_2$;

m is an integer of 0–2;

Q is a member selected from the group consisting of:

a direct link, —C(=O)—, —$N(R^4)$—, —C(=O)—N($R^4$)—, —N($R^4$)—C(=O)—, —$SO_2$—, —O—, —$SO_2$—N($R^4$)— and —N($R^4$)—$SO_2$—;

$R^4$ is selected from the group consisting of:

H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —$NO_2$;

D is a phenyl, which is independently substituted with 0–2 $R^{1a}$ substituents;

$R^{1a}$ is selected from the group consisting of:

halo, $C_{1-4}$alkyl, $C_{2-6}$alkenyl, $C_{2-6}$alkynyl, $C_{3-8}$cycloalkyl, $C_{0-4}$alkyl$C_{3-8}$, —CN, —$NO_2$, $(CH_2)_m$ $NR^{2a}R^{3a}$, $SO_2NR^{2a}R^{3a}$, $SO_2R^{2a}$, $CF_3$, $OR^{2a}$, and a 5 . 6 membered aromatic heterocyclic system containing from 1–4 heteroatoms selected from the group consisting of N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

$R^{2a}$and $R^{3a}$are independently selected from the group consisting of:

H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

M, D and N collectively form a bicyclic ring structure selected from the group consisting of:

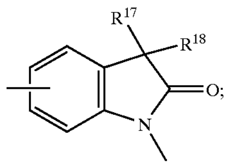

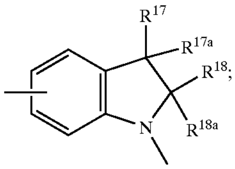

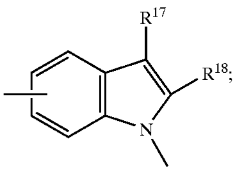

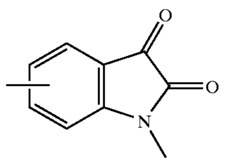

and

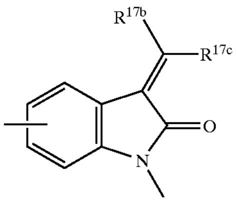

wherein 0 to 2 of the hydrogen atoms on the D portion of the bicyclic ring may be replaced by $R^{1a}$ substituents as defined above;

$R^{17}$, $R^{17a}$, $R^{18}$ and $R^{18a}$ are each independently selected from the group consisting of:

halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —$NO_2$, $(CH_2)_mNR^2R^3$, $SO_2NR^2R^3$, $SO_2R^2$, $CF_3$, $OR^2$, and a 5–6 membered aromatic heterocyclic system containing from 1–4 heteroatoms selected from the group consisting of N, O and S, wherein from 1–4 hydrogen atoms on the aromatic heterocyclic system may be independently replaced with a member selected from the group consisting of halo, $C_1$–$C_4$-alkyl, —CN, $C_{1-4}$alkyl, $C_{2-6}$alkenyl, $C_{2-6}$alkynyl, $C_{3-8}$cycloalkyl, $C_{0-4}$alkyl$C_{3-8}$ cycloalkyl and —$NO_2$;

$R^{17b}$ and $R^{17c}$ are each independently a member selected from the group consisting of: <hydrogen, —halo, hydroxy, —$C_{1-4}$alkyl, $C_{2-6}$alkenyl, —$C_{2-6}$ alkynyl, —$C_{3-8}$cycloalkyl, —$C_{0-4}$alkyl—$C_{3-8}$ cycloalkyl, —CN, —$NO_2$, —$(CH_2)_mNR^2R^3$, —$SO_2NR^2R^3$, —$SO_2R^2$, —$CF_3$, —$OR^2$, phenyl, and a 5–6 membered aromatic heterocyclic ring containing from 1–4 heteroatoms selected from the group consisting of N, O and S, wherein from 1–4 hydrogen atoms on the cycloalkyl, the phenyl ring, or the aromatic heterocyclic ring may be independently replaced with a member selected from the group consisting of halo, $C_1$–$C_4$-alkyl, —CN, $C_{1-4\ 4}$ alkyl, $C_{2-6}$alkenyl, $C_{2-6}$alkynyl, $C_{3-8}$cycloalkyl, $C_{0-4}$alkyl$C_{3-8}$cycloalkyl and —$NO_2$;

E is a member selected from the group consisting of:
a direct link, —C(=O)—, —C(=O)—N($R^5$)—, —C(—$R^{5a}$,—$R^{6a}$)— and —(—C(—$R^{5b}$,—$R^{6b}$)—C (—$R^{5c}$,—$R^{6c}$)—;

wherein $R^5$, $R^{5a}$, $R^{6a}$, $R^{5b}$ $R^{6b}$, $R^{5c}$ and $R^{6c}$ are independently selected from the group consisting of:
H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl, $C_{0-4}$alkylnaphthyl, $C_{0-4}$alkylheteroaryl, $C_{1-4}$alkylCOOH and $C_{1-4}$alkylCOO$C_{1-4}$alkyl, wherein from 0–4 hydrogen atoms on the ring atoms of the phenyl, naphthyl and heteroaryl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —OH, —O—$C_{1-4}$alkyl, —SH, —S—$C_{1-4}$alkyl, —CN and —$NO_2$;

G is selected from the group consisting of:
a direct link, —C($R^7$,$R^8$)—, —C($R^{7a}$,$R^{8a}$)—C($R^{7b}$, $R^{8b}$)— and —C($R^{7c}$)=C($R^{8c}$)—;

wherein $R^7$, $R^8$, $R^{7a}$, $R^{8a}$, $R^{7b}$, $R^{8b}$, $R^{7c}$ and $R^{8c}$ are independently a member selected from the group consisting of:
hydrogen, halogen, $C_{1-4}$alkyl, $C_{2-6}$alkenyl, $C_{2-6}$alkynyl, $C_{3-8}$cycloalkyl, $C_{0-4}$alkyl—$C_{3-8}$ cycloalkyl, $C_{0-4}$alkylphenyl, $C_{0-4}$alkylnaphthyl, —$OR^9$, —N($R^9R^{10}$), —$C_{0-4}$alkylCOOR$^9$, —$C_{0-4}$ alkylC(=O)$NR^9R^{10}$, —$C_{0-4}$alkylC(=O)$NR^9$—$CH_2$—$CH_2$—O—$R^{10}$, —$C_{0-4}$alkylC(=O)$NR^9$(—$CH_2$—$CH_2$—O—$R^{10}$—$)_2$, —N($R^9$)CO$R^{10}$, —N($R^9$)C(=O)$R^{10}$, —N($R^9$)$SO_2R^{10}$, and a naturally occurring or synthetic amino acid side chain, wherein from 1–4 hydrogen atoms on the ring atoms of the phenyl and naphthyl moieties may be independently replaced with a member selected from the group consisting of halo, —$OR^9$, $C_{1-4}$alkyl, $C_{2-6}$alkenyl, $C_{2-6}$alkynyl, $C_{3-8}$cycloalkyl, $C_{0-4}$alkyl—$C_{3-8}$cycloalkyl, —CN and —$NO_2$;

$R^9$ and $R^{10}$ are independently selected from the group consisting of:
H, $C_{1-4}$alkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl—$C_{3-8}$ cycloalkyl, —CN and —$NO_2$, and wherein $R^9$ and $R^{10}$ taken together can form a 5–8 membered heterocylic ring;

J is a member selected from the group consisting of:
a direct link, —O—, —O—C(—$R^{11}$, —$R^{11a}$)—, —S—, —S(=O)—, —S(=O$)_2$—, —S—C(—$R^{11}$, —$R^{11a}$)—, —S(=O)—C(—$R^{11}$, —$R^{11a}$)—, —S(=O$)_2$—(—$R^{11}$, —$R^{11a}$)—, —C(=O)—, —C(=O)—N($R^{11b}$)—, —N($R^{11b}$)—C(=O)—, —N($R^{11b}$)—, —N($R^{11b}$)—C(—$R^{11}$,—$R^{11a}$)— and a monocyclic aromatic or non-aromatic heterocyclic ring having from 5 to 8 ring atoms, wherein 1–4 ring atoms of the ring system are selected from the group consisting of N, O and S, and wherein the ring system may be substituted with 0–2 $R^{11c}$ substituents;

$R^{11}$, $R^{11a}$, $R^{11b}$ and $R^{11c}$ are a member independently selected from the group consisting of:
hydrogen, halo, —CN, —$NO_2$, —OH, —O—$C_{1-4}$ alkyl, —O—$C_{2-6}$alkenyl, —O—$C_{2-6}$alkynyl, —O—$C_{3-8}$cycloalkyl, —COOH, —C(=O)—O—$C_{1-4}$alkyl, —C(=O)—O—$C_{2-6}$alkenyl, —C(=O)—O—$C_{2-6}$alkynyl, —C(=O)—O—$C_{3-8}$ cycloalkyl, $C_{1-4}$alkyl, $C_{2-6}$alkenyl, $C_{2-6}$alkenyl, $C_{3-8}$cycloalkyl, $C_{0-4}$alkyl—$C_{3-8}$cycloalkyl, $C_{0-4}$alkylphenyl, $C_{0-4}$alkylnaphthyl, $C_{0-4}$alkylheterocyclic ring having from 1 to 4 hetero ring atoms selected from the group consisting of N, O and S, $CH_2COOC_{1-4}$alkyl, $CH_2COOC_{1-4}$ alkylphenyl and $CH_2COOC_{1-4}$alkylnaphthyl;

Y is a member selected from the group consisting of:
(a) phenyl, which is independently substituted with 0–2 $R^{1b}$ substituents;
(b) naphthyl, which is independently substituted with 0–2 $R^{1b}$ substituents; and
(c) a monocyclic or fused bicyclic heterocyclic ring system having from 5 to 10 ring atoms, wherein 1–4 ring atoms of the ring system are selected from the group consisting of N, O and S, and wherein the ring system may be substituted with 0–2 $R^{1b}$ substituents;

$R^{1b}$ is a member selected from the group consisting of:
halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —$NO_2$, $NR^{2b}NR^{3b}$, $SO_2NR^{2b}R^{3b}$, $SO_2R^{2b}$, $CF_3$, $OR^{2b}$, O—$CH_2$—$CH_2$—$OR^{2b}$, O—$CH_2$—$COOR^{2b}$, N($R^{2b}$)—$CH_2$—$CH_2$—$OR^{2b}$, N(—$CH_2$—$CH_2$—$OR^{2b}$$)_2$, N($R^{2b}$)—C(=O)$R^{3b}$, N($R^{2b}$)—$SO_2$—$R^{3b}$, and a 5–6 membered aromatic heterocyclic system containing from 1–4 heteroatoms selected from the group consisting of N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

$R^{2b}$ and $R^{3b}$ are independently selected from the group consisting of:
H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

L is selected from the group consisting of:

H, —CN, C(=O)$NR^{12}R^{13}$, $(CH_2)_nNR^{12}R^{13}$, C(=$NR^{12}$)$NR^{12}R^{13}$, $OR^{12}$, —$NR^{12}$C(=$NR^{12}$)$NR^{12}R^{13}$, and $NR^{12}$C(=$NR^{12}$)—$R^{13}$;

n is an integer from 0 to 8;

$R^{12}$ and $R^{13}$ are independently selected from the group consisting of:

hydrogen, —$OR^{14}$, —$NR^{14}R^{15}$, $C_{1-4}$alkyl, $C_{0-4}$alkylphenyl, $C_{0-4}$alkylnaphthyl, $COOC_{1-4}$alkyl, COO—$C_{0-4}$alkylphenyl and COO—$C_{0-4}$alkylnaphthyl, wherein from 1–4 hydrogen atoms on the ring atoms of the phenyl and naphthyl moieties may be independently replaced with a member selected from the group consisting of halo, —OH, —O—$C_{1-4}$alkyl, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —$NO_2$;

$R^{14}$ and $R^{15}$ are independently selected from the group consisting of:

H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —$NO_2$;

and all pharmaceutically acceptable isomers, salts, hydrates, solvates and prodrug derivatives thereof.

7. A pharmaceutical composition for preventing or treating a condition in a mammal characterized by undesired thrombosis comprising a therapeutically acceptable carrier and a therapeutically effective amount of a compound of claim 6.

8. A method for preventing or treating a condition in a mammal characterized by undesired thrombosis comprising administering to said mammal a therapeutically effective amount of a compound of claim 6.

9. The method of claim 8, wherein the condition is selected from the group consisting of:

acute coronary syndrome, myocardial infarction, unstable angina, refractory angina, occlusive coronary thrombus occurring pos-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, and conditions requiring the fitting of prosthetic devices.

10. A method for inhibiting the coagulation of biological samples, comprising the administration of a compound of claim 6.

11. A compound of claim 1, wherein:

A is selected from the group consisting of:

(a) $C_1$–$C_6$-alkyl;

(b) $C_3$-$C_8$-cycloalkyl;

(c) phenyl, which is independently substituted with 0–2 $R^1$ substituents;

(d) naphthyl, which is independently substituted with 0–2 $R^1$ substituents; and (e) a monocyclic or fused bicyclic heterocyclic ring system having from 5 to 10 ring atoms, wherein 1–4 ring atoms of the ring system are selected from the group consisting of N, O and S, and wherein the ring system may be substituted with 0–2 $R^1$ substituents;

$R^1$ is selected from the group consisting of: halo, $C_{1-4}$alkyl, —CN, —$NO_2$, $(CH_2)_mNR^2R^3$, $SO_2NR^2R^3$, $SO_2R^2$, $CF_3$, $OR^2$, and 5–6 membered aromatic heterocyclic system containing from 1–4 heteroatoms selected from the group consisting of N, O and S;

$R^2$ and $R^3$ are independently selected from the group consisting of:

H, $C_{1-4}$alkyl, $C_{0-4}$alkylphenyl and $C_{0-4}$alkylnaphthyl;

m is an integer of 0–2;

B is a member selected from the group consisting of:

a direct link, —C(=O)—, —N($R^4$)—, —C(=O)—N($R^4$)—, —N($R^4$)—C(=O)—, —$SO_2$—, —O—, —$SO_2$—N($R^4$)— and —N($R^4$)—$SO_2$—;

$R^4$ is selected from the group consisting of:

H, $C_{1-4}$alkyl, $C_{0-4}$alkylphenyl and $C_{0-4}$alkylnaphthyl;

D is phenyl, which is independently substituted with 0–2 $R^{1a}$ substituents;

$R^{1a}$ is selected from the group consisting of:

halo, $C_{1-4}$alkyl, —CN, —$NO_2$, $(CH_2)_mNR^{2a}R^{3a}$, —$SO_2NR^{2a}R^{3a}$, —$SO_2R^{2a}$, $CF_3$, —$OR^{2a}$, and a 5–6 membered aromatic heterocyclic system containing from 1–4 heteroatoms selected from the group consisting of N, O and S;

$R^{2a}$ and $R^{3a}$ are independently selected from the group consisting of:

H, $C_{1-4}$alkyl, $C_{0-4}$alkylphenyl and $C_{0-4}$alkylnaphthyl;

M, D and N collectively form a bicyclic ring structure selected from the group consisting of:

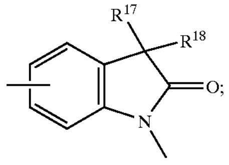

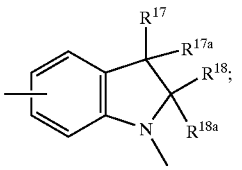

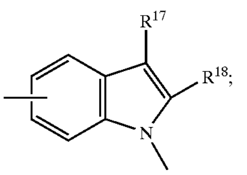

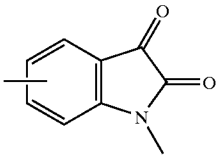

and

-continued

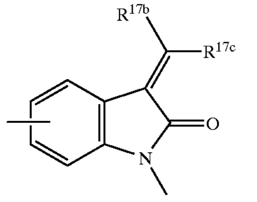

wherein 0 to 2 of the hydrogen atoms on the D portion of the bicyclic ring may be replaced by $R^{1a}$ substituents as defined above;

$R^{17}$, $R^{17a}$, $R^{18a}$ and $R^{18a}$ are each independently selected from the group consisting of:

halo, $C_{1-4}$alkyl, —CN, —$NO_2$, $(CH_2)_mNR^2R^3$, $SO_2NR^2R^3$, $SO_2R^2$, $CF_3$, $OR^2$, and a 5–6 membered aromatic heterocyclic system containing from 1–4 heteroatoms selected from the group consisting of N, O and S;

$R^{17b}$ and $R^{17c}$ are each independently a member selected from the group consisting of:

hydrogen, -halo, hydroxy, —$C_{1-4}$alkyl, —CN, —$NO_2$, —$(CH_2)_mNR^2R^3$, —$SO_2NR^2R^3$, —$SO_2R^2$, —$CF_3$, —$OR^2$, phenyl, and a 5–6 membered aromatic heterocyclic ring containing from 1–4 heteroatoms selected from the group consisting of N, O and S;

m is an integer from 0–6;

E is a member selected from the group consisting of:

a direct link, —C(=O)—, —C(=O)—N($R^5$)—, —C(—$R^{5a}$,—$R^{6a}$)— and —(—C(—$R^{5b}$,—$R^{6b}$)—C (—$R^{5c}$,—$R^{6c}$)—;

wherein $R^5$, $R^{5a}$, $R^{6a}$, $R^{5b}$ $R^{6b}$, $R^{5c}$ and $R^{6c}$ are independently selected from the group consisting of:

H, $C_{1-4}$alkyl, $C_{0-4}$alkylphenyl, $C_{0-4}$alkylnaphthyl, $C_{0-4}$alkylheteroaryl, $C_{1-4}$alkylCOOH and $C_{1-4}$alkylCOO$C_{1-4}$alkyl, wherein from 0–2 hydrogen atoms on the ring atoms of the phenyl, naphthyl and heteroaryl moieties may be independently replaced with a member selected from the group consisting of halo, $C_{1-4}$alkyl, —OH, —O—C,$_4$alkyl, —SH, —S—$C_{1-4}$alkyl, —CN and —$NO_2$;

G is selected from the group consisting of:

a direct link, —C($R^7$,$R^8$)—, —C($R^{7a}$,$R^{8a}$)—C ($R^{7b}$, $R^{8b}$)— and —C($R^{7c}$)=C($R^{8c}$)—;

wherein $R^7$, $R^8$, $R^{7a}$, $R^{8a}$, $R^{7b}$, $R^{8b}$, $R^{7c}$ and $R^{8c}$ are independently a member selected from the group consisting of:

hydrogen, halogen, $C_{1-4}$alkyl, $C_{0-4}$alkyl-$C_{3-8}$ cycloalkyl, $C_{0-4}$alkylphenyl, $C_{0-4}$alkylnaphthyl, —$OR^9$, —N($R^9R^{10}$), —$C_{0-4}$alkylCOO$R^9$, —$C_{0-4}$ alkylC(=O)$NR^9R^{10}$, —$C_{0-4}$alkylC(=O)$NR^9$—$CH_2$—$CH_2$—O—$R^{10}$, —$C_{0-4}$alkylC(=O)$NR^9$(—$CH_2$—$CH_2$—O—$R^{10}$—$)_2$, —N($R^9$)CO$R^{10}$, —N($R^9$)C(=O)$R^{10}$,—N($R^9$) $SO_2R^{10}$, and a naturally occurring or synthetic amino acid side chain;

$R^9$ and $R^{10}$ are independently selected from the group consisting of:

H, $C_{1-4}$alkyl, $C_{0-4}$alkylphenyl and $C_{0-4}$alkylnaphthyl;

J is a member selected from the group consisting of:

a direct link, —O—, —O—C(—$R^{11}$, —$R^{11a}$)—, —S—, —S(=O$)_2$—, —S—C(—$R^{11}$, —$R^{11a}$)—, —S(=O$)_2$—(—$R^{11}$, —$R^{11a}$)—,—C(=O)—N ($R^{11b}$)—, —N($R^{11b}$)—,—N($R^{11b}$)—C(—$R^{11}$,—$R^{11a}$)— and a monocyclic aromatic or non-aromatic heterocyclic ring having from 5 to 8 ring atoms, wherein 1–4 ring atoms of the ring system are selected from the group consisting of N, O and S, and wherein the ring system may be substituted with 0–2 $R^{11c}$ substituents; $R^{11}$, $R^{11a}$, $R^{11b}$ and $R^{11c}$ are a member independently selected from the group consisting of:

hydrogen, halo, —CN, —$NO_2$, —OH, —O—$C_{1-4}$ alkyl, —O—$C_{3-8}$cycloalkyl, —COOH, —C(=O)—O—$C_{1-4}$alkyl, —C(=O)—O—$C_{3-8}$ cycloalkyl, $C_{1-4}$alkyl, $C_{3-8}$cycloalkyl, $C_{0-4}$alkyl-$C_{3-8}$ cycloalkyl, $C_{0-4}$alkylphenyl, $C_{0-4}$alkylnaphthyl, and a $C_{0-4}$alkylheterocyclic ring having from 1 to 4 hetero ring atoms selected from the group consisting of N, O and S, $CH_2COOC_{1-4}$alkyl, $CH_2COOC_{1-4}$alkylphenyl and $CH_2COOC_{1-4}$alkylnaphthyl;

Y is a member selected from the group consisting of:

(a) phenyl, which is independently substituted with 0–2 $R^{1b}$ substituents;

(b) naphthyl, which is independently substituted with 0–2 $R^{1b}$ substituents; and (c) a monocyclic or fused bicyclic heterocyclic ring system having from 5 to 10 ring atoms, wherein 1–4 ring atoms of the ring system are selected from the group consisting of N, O and S, and wherein the ring system may be substituted with 0–2 $R^{1b}$ substituents;

$R^{1b}$ is a member selected from the group consisting of:

halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —$NO_2$, $NR_{2b}R^{3b}$, $SO_2NR_{2b}R^{3b}$, $SO_2R^{2b}$, $CF_3$, $OR^{2b}$, O—$CH_2$—$CH_2$—$OR^{2b}$, O—$CH_2$—COO$R^{2b}$, N($R^{2b}$)—$CH_2$—$CH_2$—$OR^{2b}$, N(—$CH_2$—$CH_2$—$OR^{2b})_2$, N($R^{2b}$)—C(=O)$R^{3b}$, N($R^{2b}$)—$SO_2$—$R^{3b}$, and a 5–6 membered aromatic heterocyclic system containing from 1–4 heteroatoms selected from the group consisting of N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

$R^{2b}$ and $R^{3b}$ are independently selected from the group consisting of:

H, $C_{1-4}$alkyl, $C_{3-8}$cycloalkyl, $C_{0-4}$alkyl$C_{3-8}$cycloalkyl, $C_{0-4}$alkylphenyl and $C_{0-4}$alkylnaphthyl;

L is selected from the group consisting of:

H, —CN, C(=O)$NR^{12}R^{13}$,$(CH_2)_nNR^{12}R^{13}$, C(=$NR^{12}$)$NR^{12}R^{13}$, $OR^{12}$, —$NR^{12}$C(=$NR^{12}$) $NR^{12}R^{13}$, and $NR^{12}$C(=$NR^{12}$)—$R^{13}$;

n is an integer from 0 to 6;

$R^{12}$ and $R^{13}$ are independently selected from the group consisting of:

hydrogen, —$OR^{14}$, —$NR^{14}R^{15}$, $C_{1-4}$alkyl, $C_{0-4}$alkylphenyl, $C_{0-4}$alkylnaphthyl, COO$C_{1-4}$alkyl, COO—$C_{0-4}$alkylphenyl and COO—$C_{0-4}$alkylnaphthyl, wherein from 0–4 hydrogen atoms on the ring atoms of the phenyl and naphthyl moieties may be independently replaced with a member selected from the group consisting of halo, —OH, —O—$C_{1-4}$alkyl, $C_{1-4}$alkyl, $C_{3-8}$cycloalkyl, $C_{0-4}$alkyl$C_{3-8}$cycloalkyl, —CN, and —$NO_2$;

$R^{14}$ and $R^{15}$ are independently selected from the group consisting of:

H, $C_{1-4}$alkyl, $C_{0-4}$alkyl$C_{3-8}$cycloalkyl, $C_{0-4}$alkylphenyl and $C_{0-4}$alkylnaphthyl;

and all pharmaceutically acceptable isomers, salts, hydrates, solvates and prodrug derivatives thereof.

12. A pharmaceutical composition for preventing or treating a condition in a mammal having undesired thrombosis comprising a therapeutically acceptable carrier and a therapeutically effective amount of a compound of claim 11.

13. A method for preventing or treating a condition in a mammal having undesired thrombosis comprising administering to said mammal a therapeutically effective amount of a compound of claim 11.

14. The method of claim 13, wherein the condition is selected from the group consisting of:

acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombolic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, and conditions requiring the fitting of prosthetic devices.

15. A method for inhibiting the coagulation of biological samples, comprising the administration of a compound of claim 11.

16. A compound of claim 1, wherein:

A is selected from the group consisting of:

(a) phenyl, which is independently substituted with 0–2 $R^1$ substituents; and (b) a monocyclic or fused bicyclic heterocyclic ring system having from 5 to 10 ring atoms, wherein 1–4 ring atoms of the ring system are selected from the group consisting of N, O and S, and wherein the ring system may be substituted with 0–2 $R^1$ substituents;

$R^1$ is selected from the group consisting of:

halo, $(CH_2)_mNR^2R^3$, $SO_2NR^2R^3$ and $SO_2R^2$;

$R^2$ and $R^3$ are independently selected from the group consisting of:

H and $C_{1-4}$alkyl;

m is an integer of 0–2;

Q is a member selected from the group consisting of:

a direct link, —C(=O)—, —$SO_2$—, and —O—;

D is phenyl, which is independently substituted with 0–2 $R^{1a}$ substituents;

$R^{1a}$ is selected from the group consisting of:

halo and $C_{1-4}$alkyl;

M, D and N collectively form a bicyclic ring structure selected from the group consisting of:

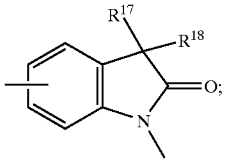

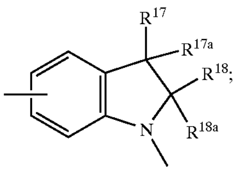

-continued

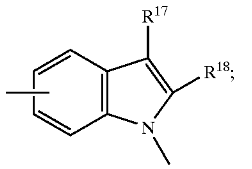

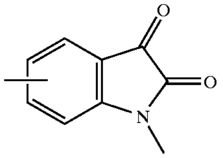

and

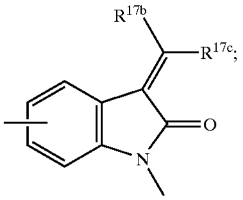

$R^{17}$, $R^{17a}$, $R^{18}$ and $R^{18a}$ are each independently selected from the group consisting of:

halo, $C_{1-4}$alkyl, —CN, —$NO_2$, $(CH_2)_mNR^2R^3$, $SO_2NR^2R^3$, $SO_2R^2$, $CF_3$ and $OR^2$;

$R^{17b}$ and $R^{17c}$ are each independently a member selected from the group consisting of:

hydrogen, -halo, hydroxy, —$C_{1-4}$alkyl, —CN, —$NO_2$, —$(CH_2)_mNR^2R^3$, —$SO_2NR^2R^3$, —$SO_2R^2$, —$CF_3$, —$OR^2$, phenyl, and a 5–6 membered aromatic heterocyclic ring containing from 1–3 N atoms;

E is a member selected from the group consisting of:

a direct link, —C(=O)—, —C(=O)—N($R^5$)—, —C(—$R^{5a}$,—$R^{6a}$)— and —(—C(—$R^{5a}$,—$R^{6a}$)—C(—$R^{5c}$,—$R^{6c}$)—;

wherein $R^5$, $R^{5a}$, $R^{6a}$, $R^{5b}$ $R^{6b}$, $R^{5c}$ and $R^{6c}$ are independently selected from the group consisting of:

H, $C_{1-4}$alkyl, $C_{0-4}$alkylphenyl, $C_{0-4}$alkylnaphthyl, $C_{0-4}$alkylheteroaryl, $C_{1-4}$alkylCOOH and $C_{1-4}$alkylCOO$C_{1-4}$alkyl;

G is selected from the group consisting of:

a direct link, —C($R^7$,$R^8$)—, —C($R^{7a}R^{8a}$)—C($R^{7b}$, $R^{8b}$)— and —C($R^{7c}$)=C($R^{8c}$)—;

wherein $R^7$, $R^8$, $R^{7a}$, $R^{8a}$, $R^{7b}$, $R^{8b}$, $R^{7c}$ and $R^{8c}$ are independently a member selected from group consisting of:

hydrogen, halogen, $C_{1-4}$alkyl, $C_{0-4}$alkyl-$C_{3-8}$cycloalkyl, $C_{0-4}$alkylphenyl, $C_{0-4}$alkylnaphthyl, —$OR^9$, —N($R^9R^{10}$), —$C_{0-4}$alkylCOO$R^9$, —$C_{0-4}$alkylC(=O)N$R^9R^{10}$, —$C_{0-4}$alkylC(=O)N$R^9$—$CH_2$—$CH_2$—O—$R^{10}$, —$C_{0-4}$alkylC(=O)N$R^9$(—$CH_2$—$CH_2$—O—$R^{10}$—)$_2$, —N($R^9$)CO$R^{10}$, —N($R^9$)C(=O)$R^{10}$,—N($R^9$) $SO_2R^{10}$, and a naturally occurring or synthetic amino acid side chain;

$R^9$ and $R^{10}$ are independently selected from the group consisting of:

H, $C_{1-4}$alkyl, $C_{0-4}$alkylphenyl and $C_{0-4}$alkylnaphthyl;

J is a member selected from the group consisting of:

a direct link, —O—, —S—, —C(=O)—N($R^{11b}$)—, —N($R^{11b}$)—, —N($R^{11b}$)—C(—$R^{11}$, —$R^{11a}$)— and a monocyclic aromatic or non-aromatic heterocyclic ring having from 5 to 8 ring atoms, wherein 1–4 ring atoms of the ring system are selected from the group consisting of N, O and S, and wherein the ring system may be substituted with 0–2 $R^{11c}$ substituents;

$R^{11}$, $R^{11a}$, $R^{11b}$ and $R^{11c}$ are a member independently selected from the group consisting of:

hydrogen, halo, —CN, —$NO_2$, —OH, —O—$C_{1-4}$alkyl, —O—$C_{3-8}$cycloalkyl, —COOH, —C(═O)—O—$C_{1-4}$alkyl, —C(═O)—O—$C_{3-8}$ cycloalkyl, $C_{1-4}$alkyl, $C_{3-8}$cycloalkyl, $C_{0-4}$alkyl—$C_{3-8}$cycloalkyl, $C_{1-4}$alkylphenyl, $C_{0-4}$alkylnaphthyl, and a $C_{0-4}$alkylheterocyclic ring having from 1 to 4 hetero ring atoms selected from the group consisting of N, O and S, $CH_2COOC_{1-4}$alkyl, $CH_2COOC_{1-4}$alkylphenyl and $CH_2COOC_{1-4}$alkylnaphthyl;

Y is a member selected from the group consisting of:

(a) phenyl, which is independently substituted with 0–2 $R^{1b}$ substituents;

(b) an aromatic heterocyclic ring having from 5 to 10 ring atoms, wherein 1–4 ring atoms of the ring system are selected from the group consisting of N, O and S, and wherein the ring may be substituted with 0–2 $R^{1b}$ substituents;

(c) a fused aromatic bicyclic heterocyclic ring system having from 5 to 10 ring atoms, wherein 1–4 ring atoms of the ring system are selected from the group consisting of N, O and S, and wherein the bicyclic ring system may be substituted with 0–2 $R^{1b}$ substituents;

$R^{1b}$ is a member selected from the group consisting of: halo, —$C_{1-4}$alkyl, —OH, —OBn, —O—$CH_2$—$CH_2$—OH, —O—$CH_2$—$CH_2$—$OCH_3$, —O—$CH_2$—COOH, —O—$CH_2$—C(═O)—O—$CH_3$, —$NH_2$, —NH—$CH_2$—$CH_2$—O—$CH_3$, —NH—C(═O)—O—$CH_3$ and —NH—$SO_2$—$CH_3$;

L is selected from the group consisting of: H, —C(═O)$NR^{12}R^{13}$, —$(CH_2)_n NR^{12}R^{13}$ and —C(═$NR^{12}$)$N^{12}R^{13}$;

n is an integer from 0 to 6;

$R^{12}$ and $R^{13}$ are independently selected from the group consisting of:

hydrogen and $C_{1-4}$alkyl;

and all pharmaceutically acceptable isomers, salts, hydrates, solvates and prodrug derivatives thereof.

17. A pharmaceutical composition for preventing or treating a condition in a mammal having undesired thrombosis comprising a therapeutically acceptable carrier and a therapeutically effective amount of a compound of claim 16.

18. A method for preventing or treating a condition in a mammal having undesired thrombosis comprising administering to said mammal a therapeutically effective amount of a compound of claim 16.

19. The method of claim 18, wherein the condition is selected from the group consisting of:

acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, and conditions requiring the fitting of prosthetic devices.

20. A method for inhibiting the coagulation of biological samples, comprising the administration of a compound of claim 16.

21. A compound of claim 1, wherein A is a member selected from the group consisting of:

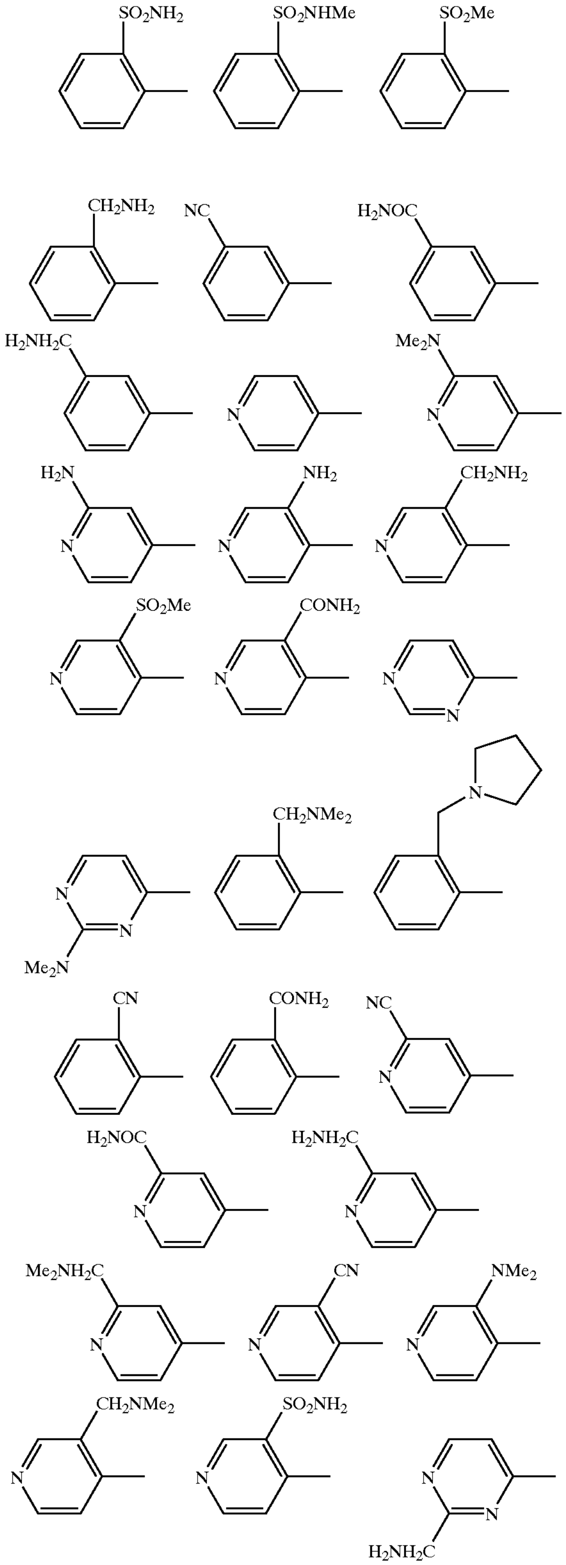

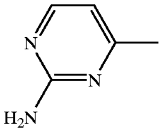

and

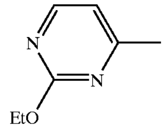

Q is a member selected from the group consisting of:

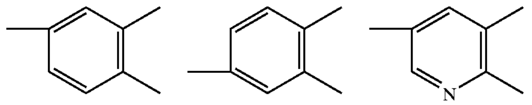
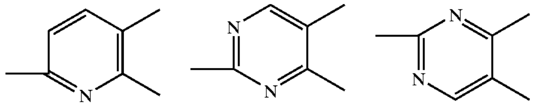
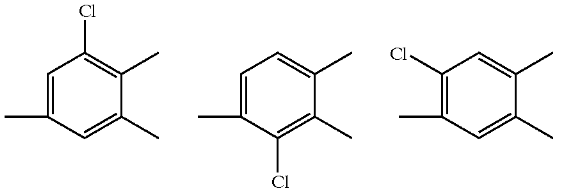
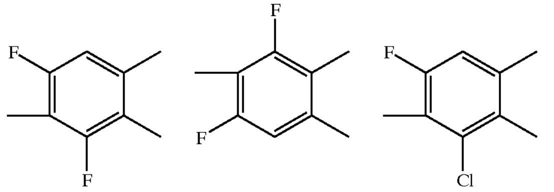
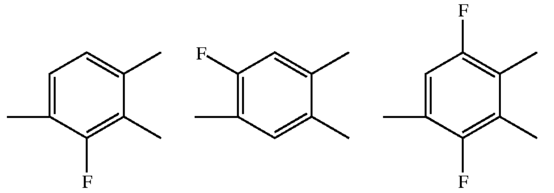
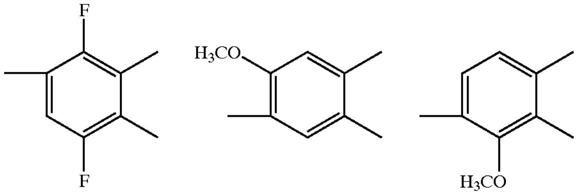
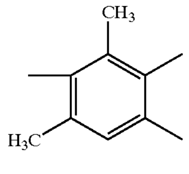

and

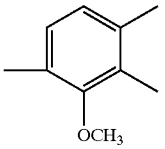

E is a member selected from the group consisting of:

a direct link, —C(=O)—, —C(=O)—N($R^5$)—, —C($R^{5a}$,—$R^{6a}$)— and —(—C(—$R^{5a}$,—$R^{6a}$)—C(—$R^{5c}$,—$R^{6c}$)—; wherein $R^5$, $R^{5a}$, $R^{6a}$, $R^{5b}$ $R^{6b}$, $R^{5c}$ and $R^{6c}$ are independently selected from the group consisting of:

H, $C_{1-4}$alkyl, $C_{0-4}$alkylphenyl, $C_{0-4}$alkylnaphthyl, $C_{0-4}$alkylheteroaryl, $C_{1-4}$alkylCOOH and $C_{1-4}$alkylCOO$C_{1-4}$alkyl;

G is selected from the group consisting of:

a direct link, —C($R^7$,$R^8$)—, —C($R^{7a}$,$R^{8a}$)—C($R^{7b}$, $R^{8b}$)— and —C($R^{7c}$)=C($R^{8c}$)—;

wherein $R^7$, $R^8$, $R^{7a}$, $R^{8a}$, $R^{7b}$, $R^{8b}$, $R^{7c}$ and $R^{8c}$ are independently a member selected from the group consisting of:

hydrogen, halogen, $C_{1-4}$alkyl, $C_{0-4}$alkyl-$C_{3-8}$cycloalkyl, $C_{0-4}$alkylphenyl, $C_{0-4}$alkylnaphthyl, —$OR^9$, —N($R^9R^{10}$), —$C_{0-4}$alkylCOOR$^9$, —$C_{0-4}$alkylC(=O)NR$^9R^{10}$, —$C_{0-4}$alkylC(=O)NR$^9$—$CH_2$—$CH_2$—O—$R^{10}$, —$C_{0-4}$alkylC(=O)NR$^9$(—$CH_2$—$CH_2$—O—$R^{10}$—$)_2$, —N($R^9$)COR$^{10}$, —N($R^9$)C(=O)R$^{10}$,—N($R^9$)SO$_2$R$^{10}$, and a naturally occurring or synthetic amino acid side chain;

$R^9$ and $R^{10}$ are independently selected from the group consisting of:

H, $C_{1-4}$alkyl, $C_{0-4}$alkylphenyl and $C_{0-4}$alkylnaphthyl;

J is a member selected from the group consisting of:

a direct link, —O—, —S—, —C(=O)—N($R^{11b}$)—, —N($R^{11b}$)—, —N($R^{11b}$)—C(—$R^{11}$, —$R^{11a}$)— and a monocyclic aromatic or non-aromatic heterocyclic ring having from 5 to 8 ring atoms, wherein 1–4 ring atoms of the ring system are selected from the group consisting of N, O and S, and wherein the ring system may be substituted with 0–2 $R^{11c}$ substituents;

$R^{11}$, $R^{11a}$, $R^{11b}$ and $R^{11c}$ are a member independently selected from the group consisting of:

hydrogen, halo, —CN, —$NO_2$, —OH, —O—$C_{1-4}$alkyl, —$C_{1-4}$alkyl, —COOH, phenyl, and benzyl wherein the aromatic ring of the phenyl or benzyl is substituted with 0–2 members independently selected from the group consisting of halo, —CN, —$NO_2$, —OH, —O—$C_{1-4}$alkyl, —$C_{1-4}$alkyl, —COOH and —C(=O)—O—$C_{1-4}$alkyl;

Y and L taken together are a member selected from the group consisting of:

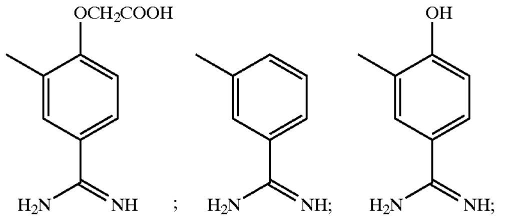
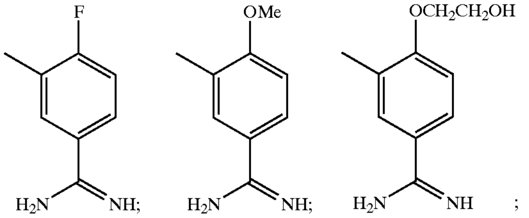
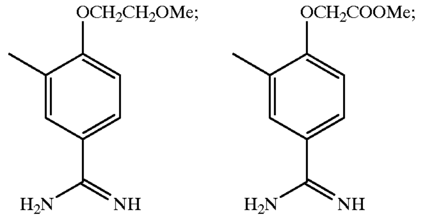
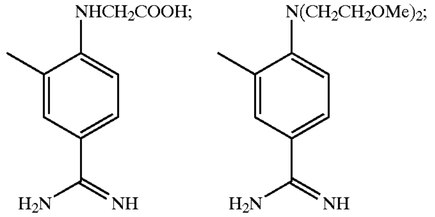

-continued

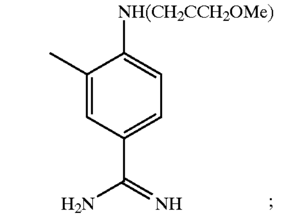
;
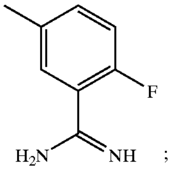
;
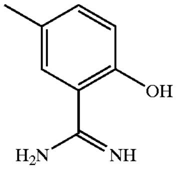
;
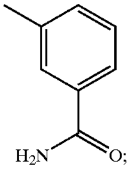
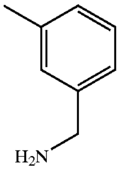
;
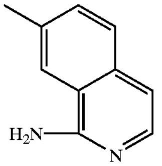
;
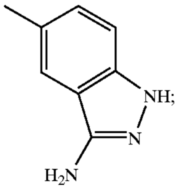
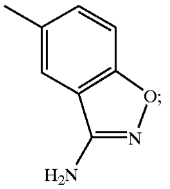
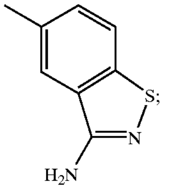
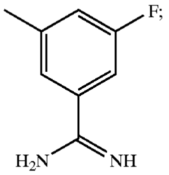
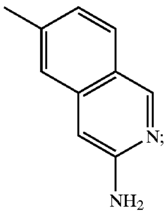
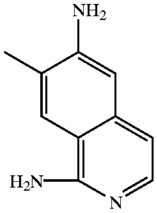
;
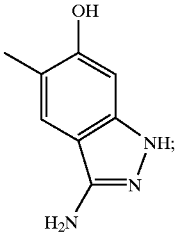
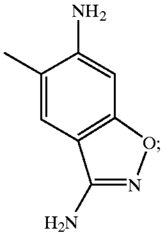
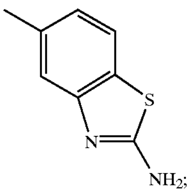
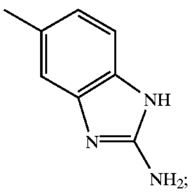
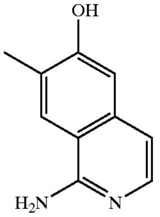
;
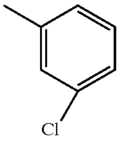
;
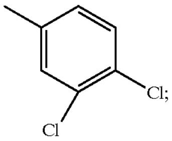
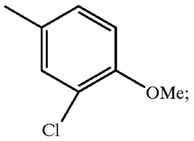

-continued

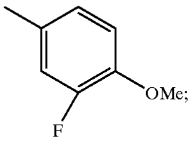
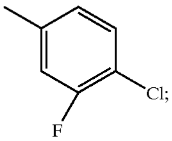
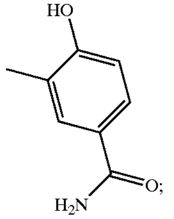
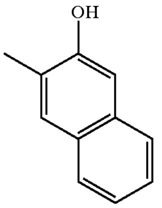
;
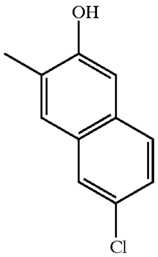
;
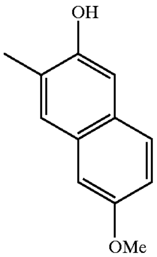
;
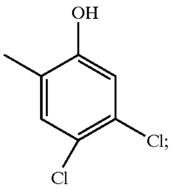
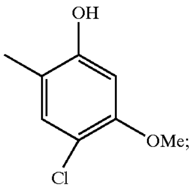
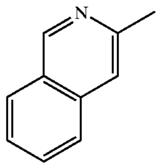
;
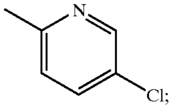
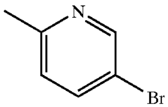
and
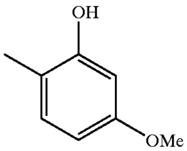

and all pharmaceutically acceptable isomers, salts, hydrates, solvates and prodrug derivatives thereof.

22. A pharmaceutical composition for preventing or treating a condition in a mammal having undesired thrombosis comprising a therapeutically acceptable carrier and a therapeutically effective amount of a compound of claim 21.

23. A method for preventing or treating a condition in a mammal having undesired thrombosis comprising administering to said mammal a therapeutically effective amount of a compound of claim 21.

24. The method of claim 23, wherein the condition is selected from the group consisting of:

acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, and conditions requiring the fitting of prosthetic devices.

25. A method for inhibiting the coagulation of biological samples, comprising the administration of a compound of claim 21.

26. A compound of claim 1, having the formula:
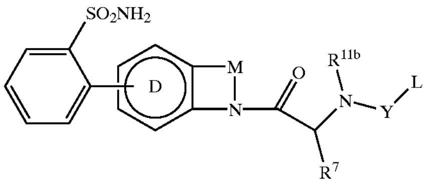
wherein the following portion of said formula
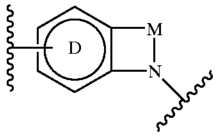
is selected from the group consisting of:
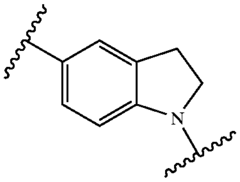 ; 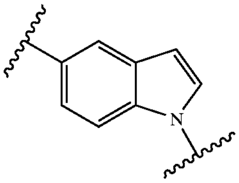 ;
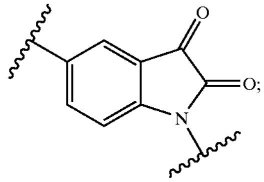 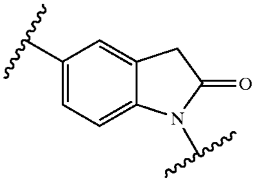 and
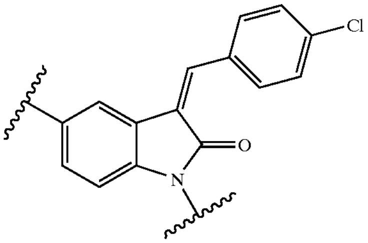
wherein Y and L, taken together, are selected from the group consisting of:
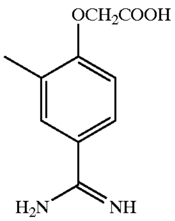 ; 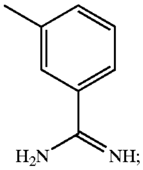 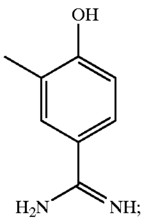
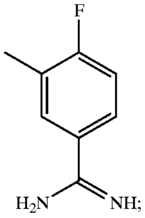 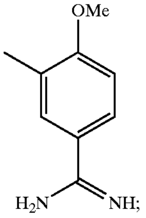 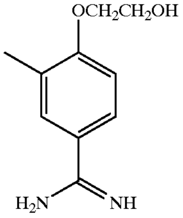 ;
-continued
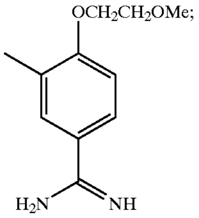 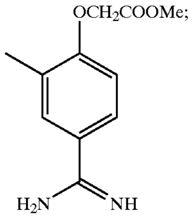
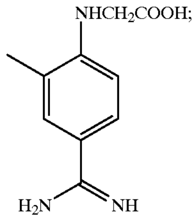 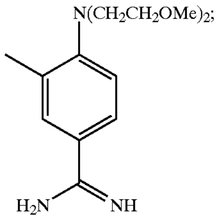
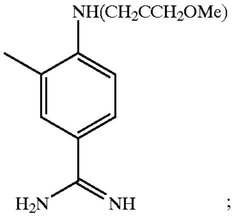 ; 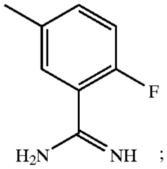 ;
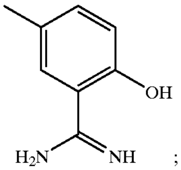 ; 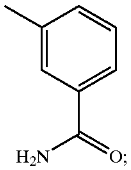 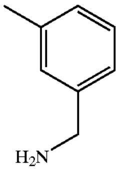 ;
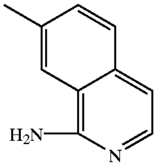 ; 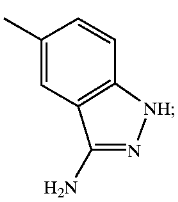 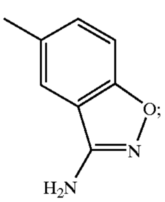
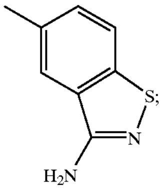 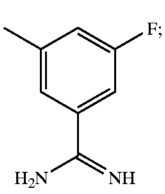 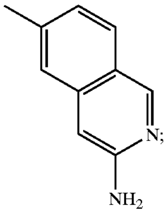
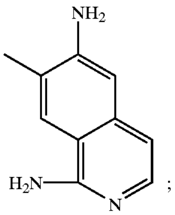 ; 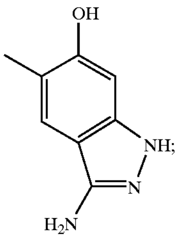 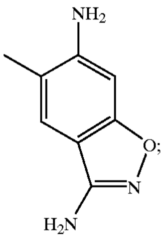

-continued
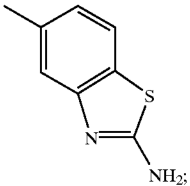
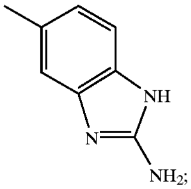
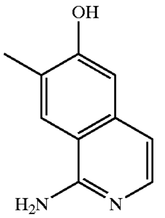
;
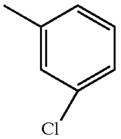
;
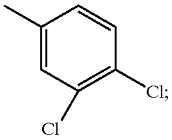
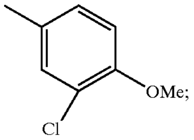
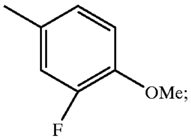
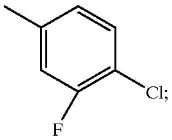
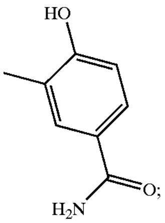
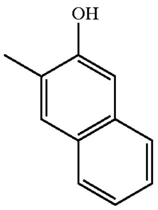
;
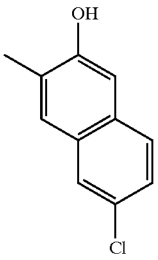
;
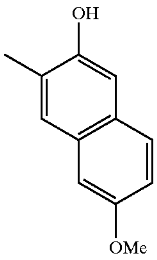
;
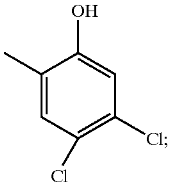
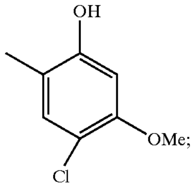
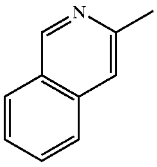
;
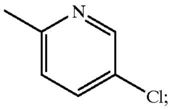
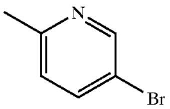
and
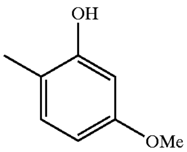
wherein $R^{11b}$ is selected from the group consisting of: H, Me, Ph, OMe, F, OH, Br, $NH_2$, $OCH_2Ph$, $OCH_2CH_2OMe$,
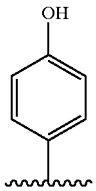
;
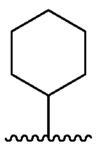
;
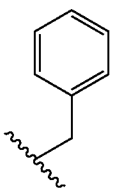
;
-continued
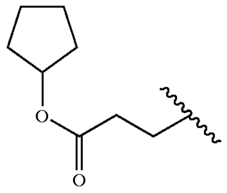
;
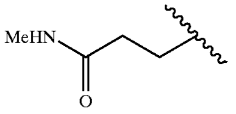
;
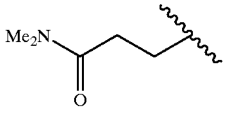
and
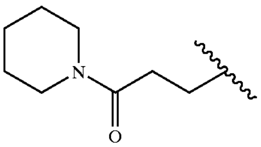
and wherein $R^7$ is selected from the group consisting of: H; Me; Et; Ph;
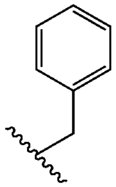
;
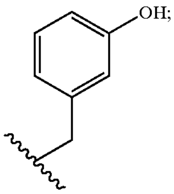
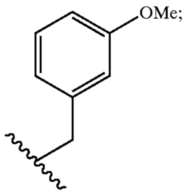
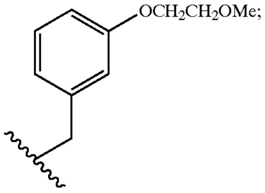
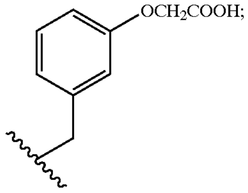
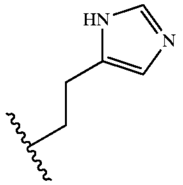
and
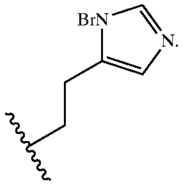
27. A compound of claim 1, having the formula:
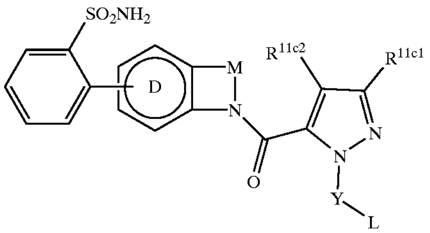
wherein the following portion of said formula
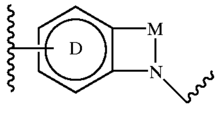

is selected from the group consisting of:
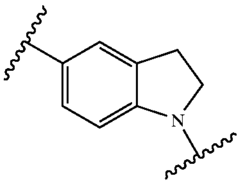 ; 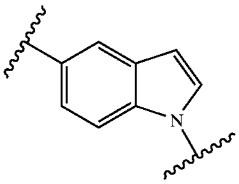 ;
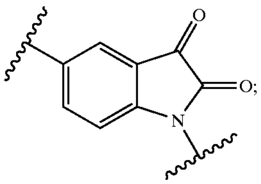 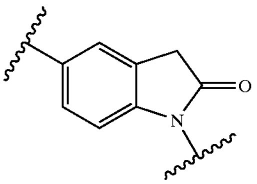 and
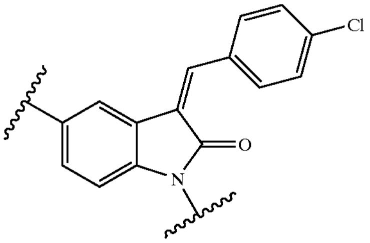
wherein Y and L, taken together, are selected from the group consisting of:
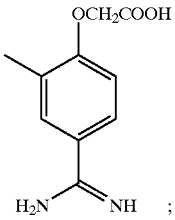 ; 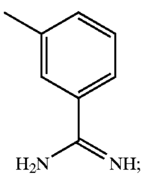 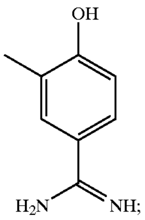
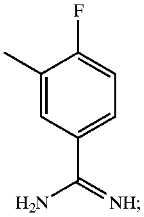 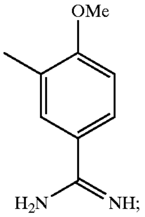 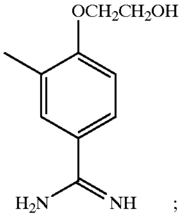 ;
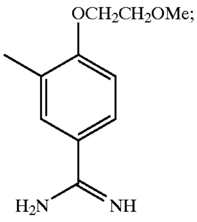 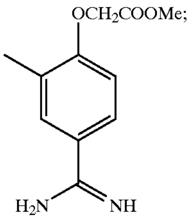
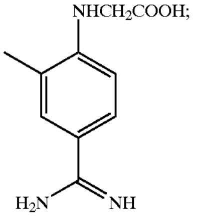 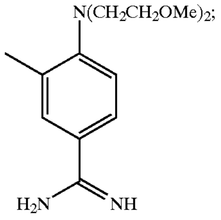
-continued
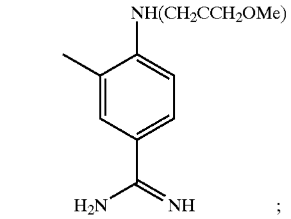 ; 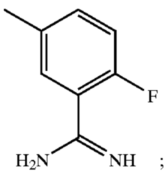 ;
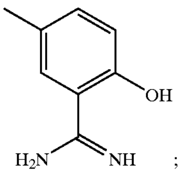 ; 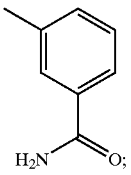 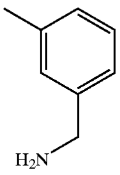 ;
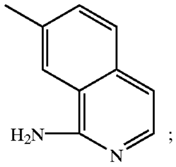 ; 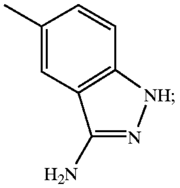 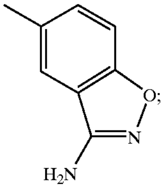
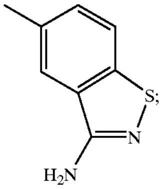 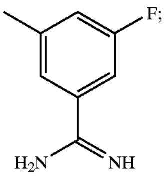 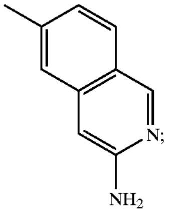
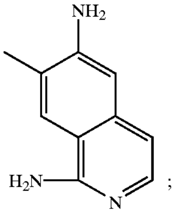 ; 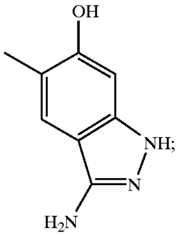 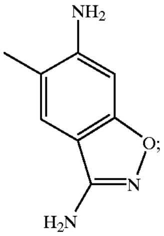
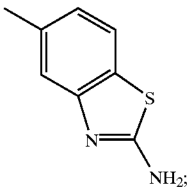 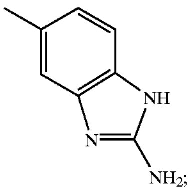 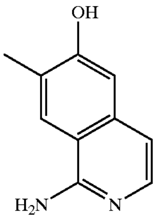 ;
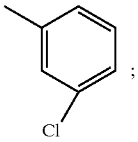 ; 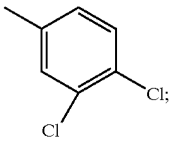 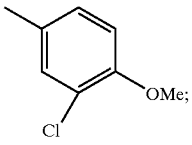

-continued

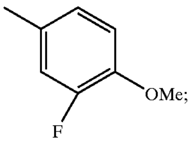
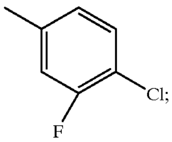
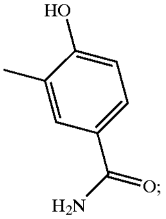

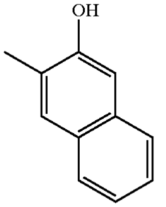
;
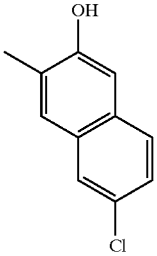
;
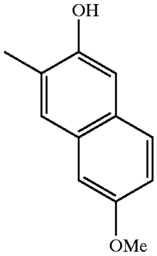
;

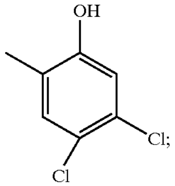
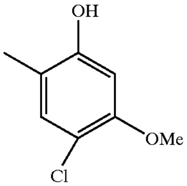
and

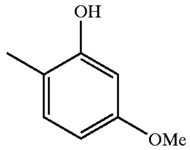

wherein $R^{11c1}$ is selected from the group consisting of:

H; Me; Et; Ph; OMe; $CF_3$, F; OH; Br; $NH_2$; $SO_2Me$; $OCH_2Ph$; $OCH_2CH_2OMe$;

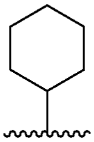
;
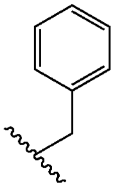
;
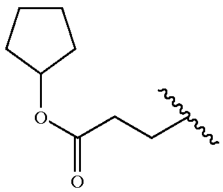
;

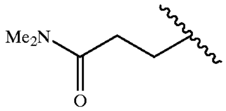
and
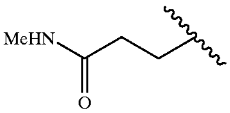

and wherein $R^{11c2}$ is selected from the group consisting of:

H; Me; Et; Cl; Br; F; Ph;

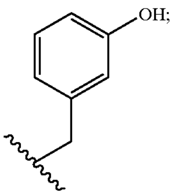
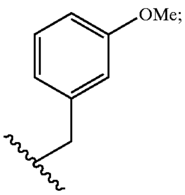

-continued

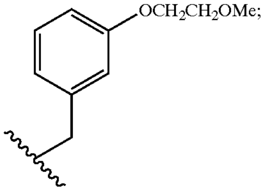
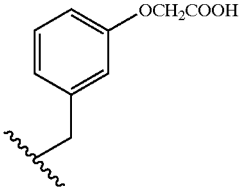
and

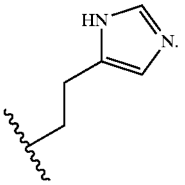

28. A compound of claim 1, having the formula:

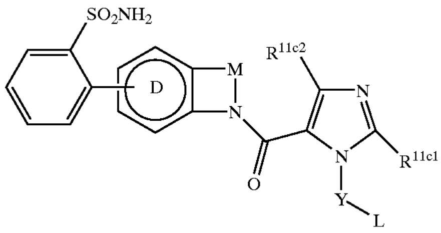

wherein the following portion of said formula

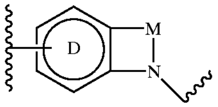

is selected from the group consisting of:

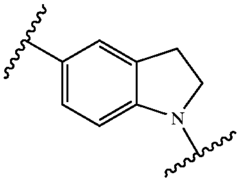
;
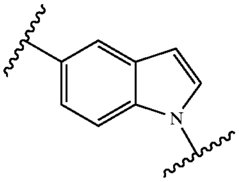
;

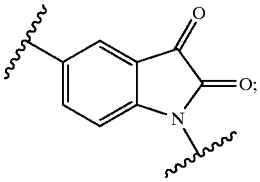
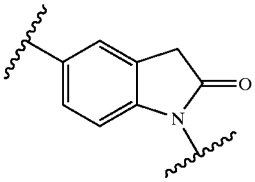
and

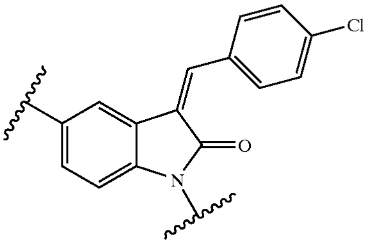

wherein Y and L, taken together, are selected from the group consisting of:

-continued
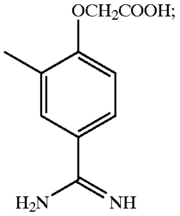
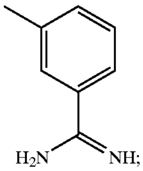
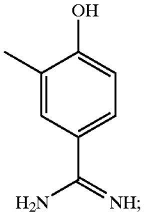
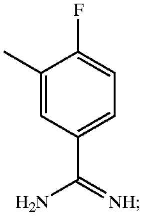
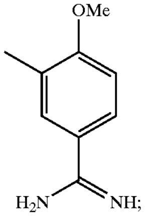
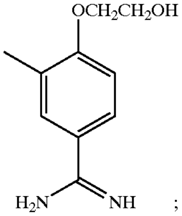
;
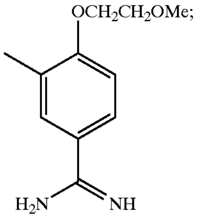
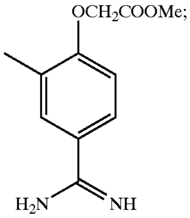
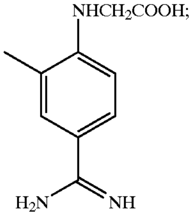
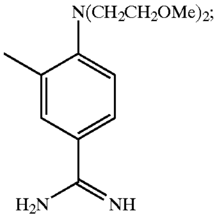
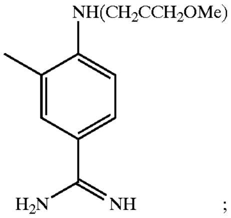
;
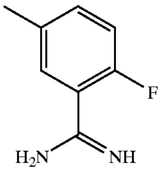
;
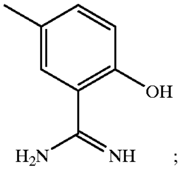
;
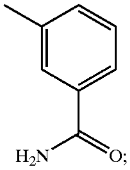
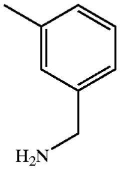
;
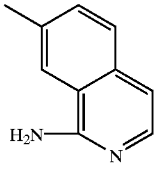
;
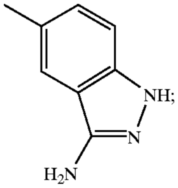
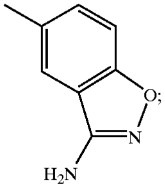
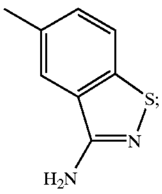
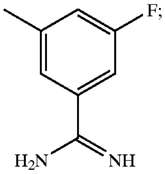
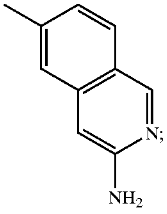
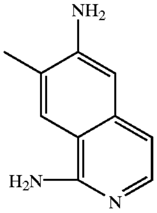
;
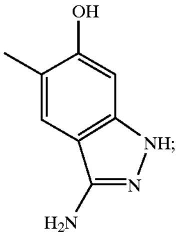
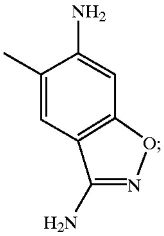
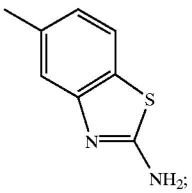
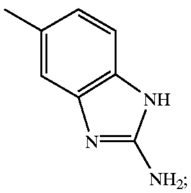
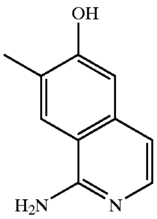
;
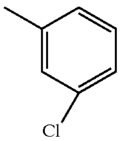
;
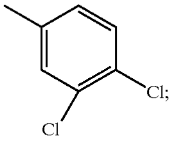
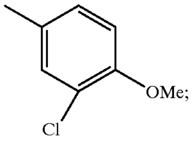
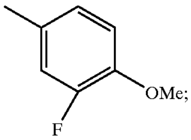
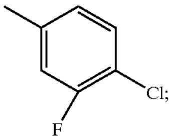
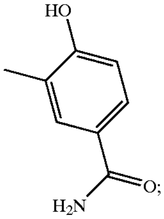
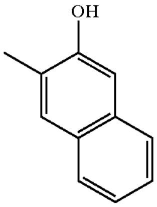
;
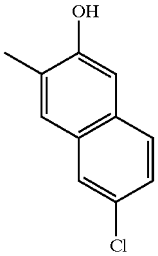
;
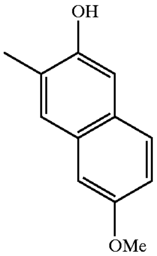
;
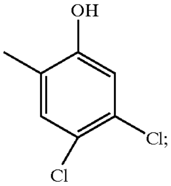
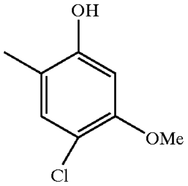
and -continued

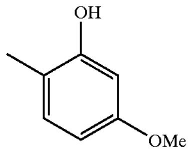

wherein $R^{11c1}$ selected from the group consisting of:

H, Me, Ph, OMe, F, OH, Br, $NH_2$, $OCH_2Ph$, $OCH_2CH_2OMe$,

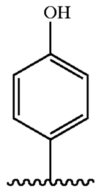 ; 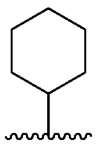 ; 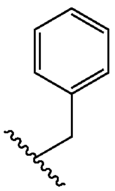 ;

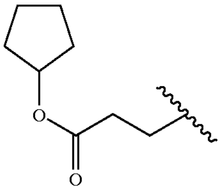 ; 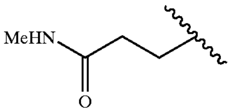 ;

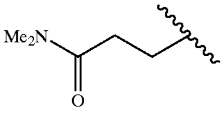 and 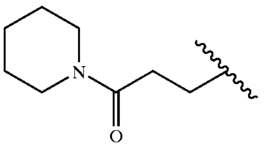

and wherein $R^{11c2}$ is selected from the group consisting of:

H; Me; Et; Ph;

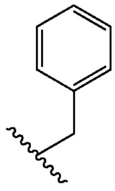 ; 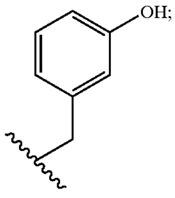 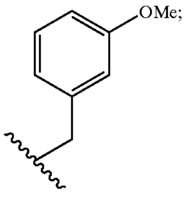

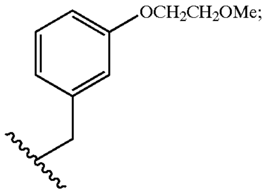 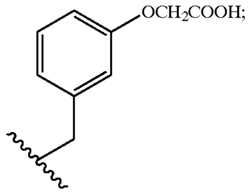

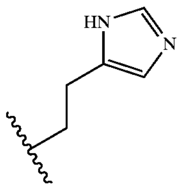 and 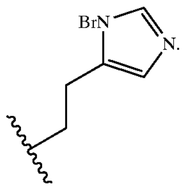

29. A compound of claim 1, having the formula:

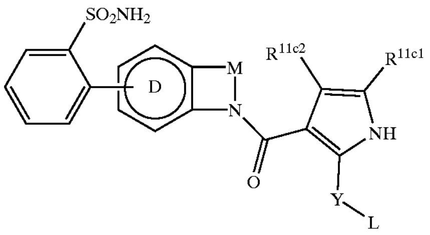

wherein the following portion of said formula:

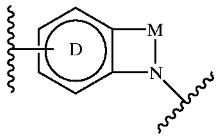

is selected from the group consisting of:

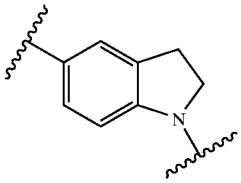 ; 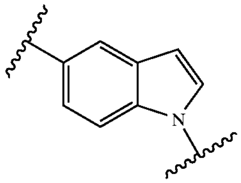 ;

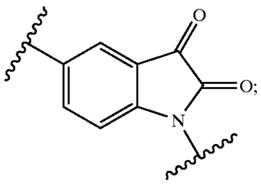 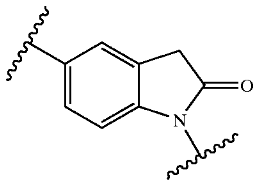 and

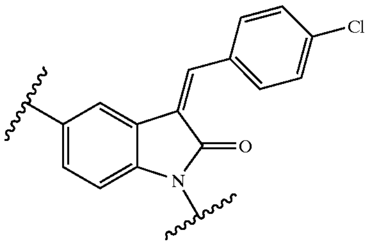

wherein Y and L, taken together, are selected from the group consisting of:

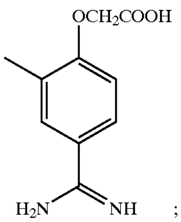 ; 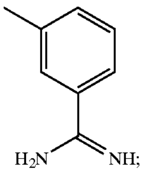 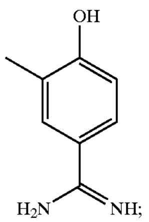

-continued
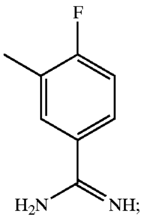
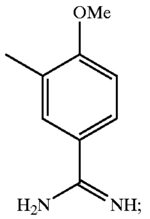
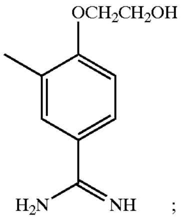
;
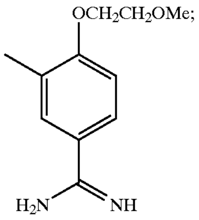
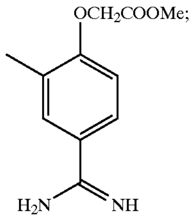
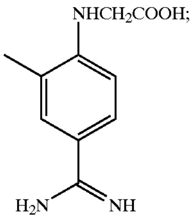
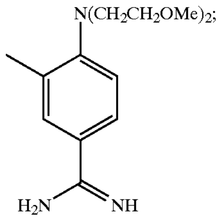
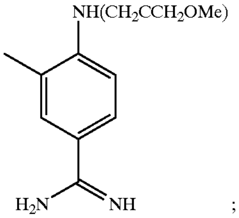
;
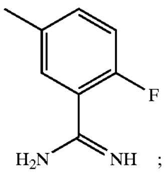
;
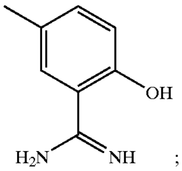
;
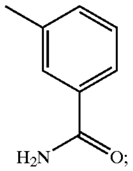
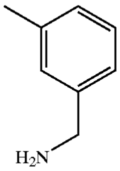
;
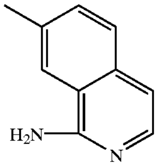
;
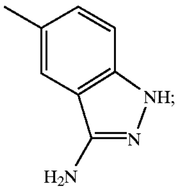
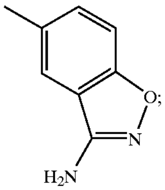
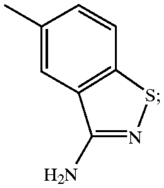
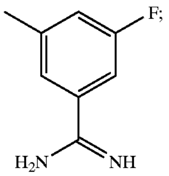
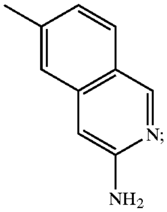
-continued
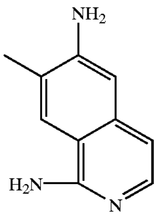
;
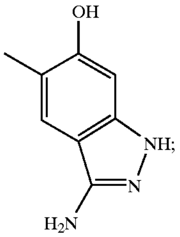
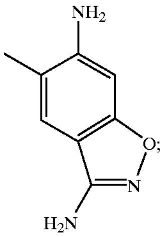
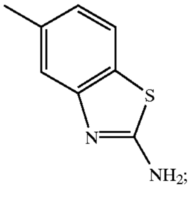
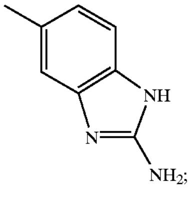
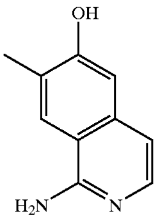
;
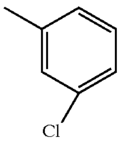
;
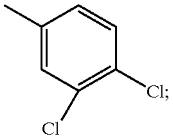
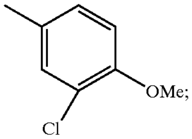
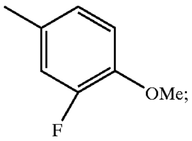
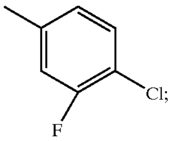
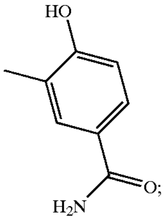
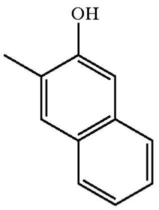
;
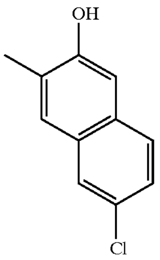
;
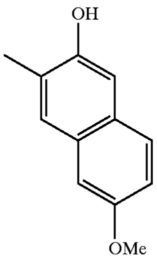
;
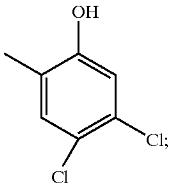
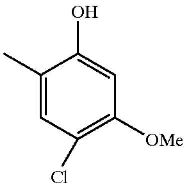
and
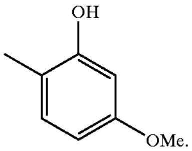
wherein $R^{11c1}$ is selected from the group consisting of:
H, Me, Ph, OMe, F, OH, Br, $NH_2$, $OCH_2Ph$, $OCH_2CH_2OMe$,

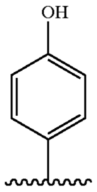 ; 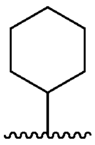 ; 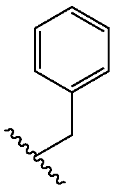 ;
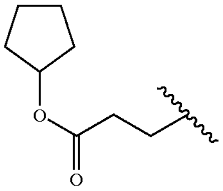 ; 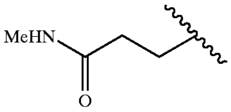 ;
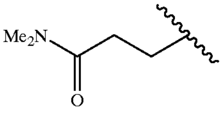 and 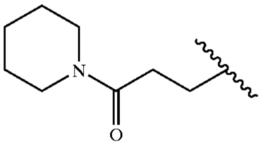
and wherein $R^{11c2}$ is selected from the group consisting of:
H; Me; Et; Ph;
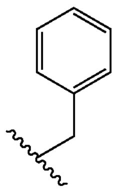 ; 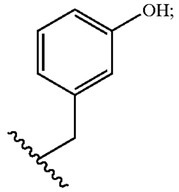 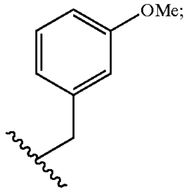
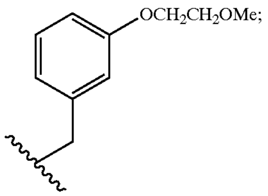 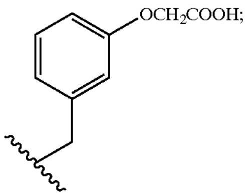
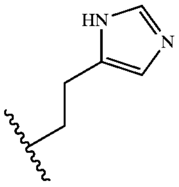 and 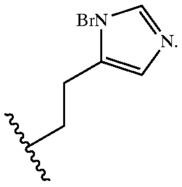
30. A compound of claim 1, having the formula:
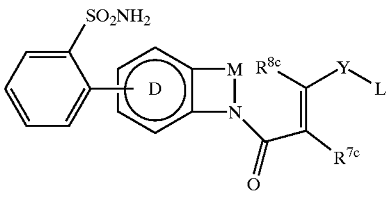
wherein the following portion of said formula
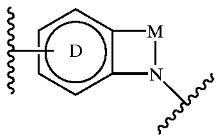
is selected from the group consisting of:
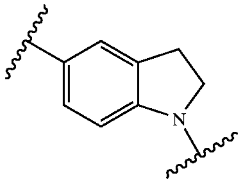 ; 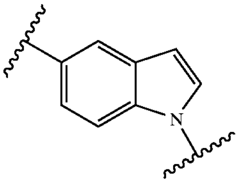 ;
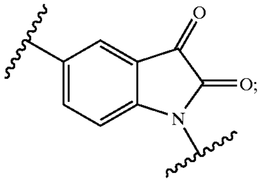 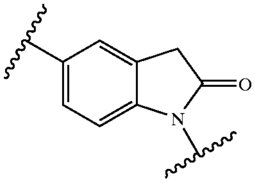 and
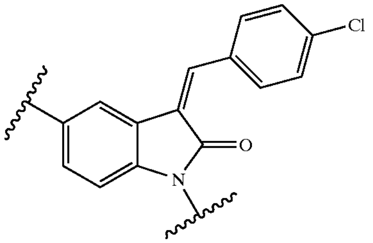
wherein Y and L, taken together, are selected from the group consisting of:
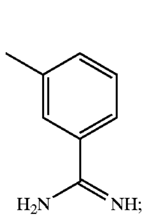 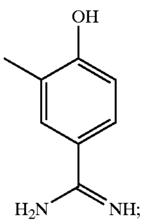 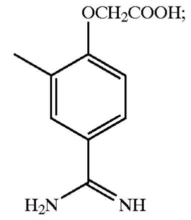

-continued
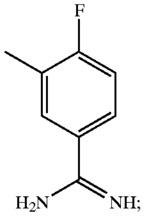
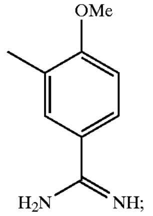
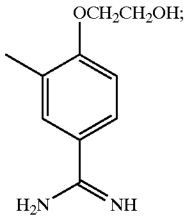
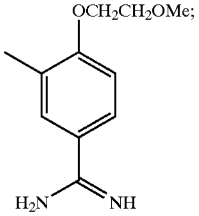
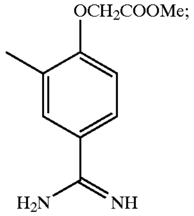
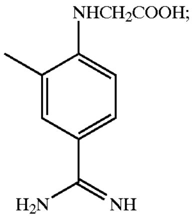
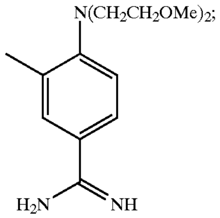
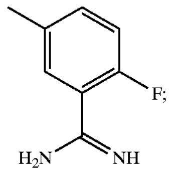
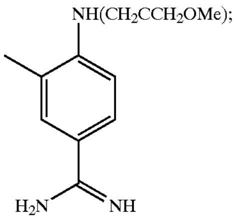
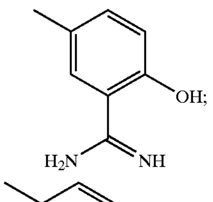
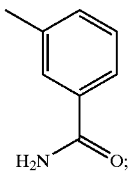
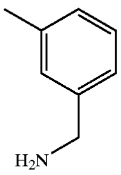
;
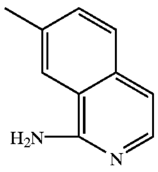
;
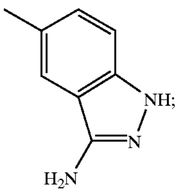
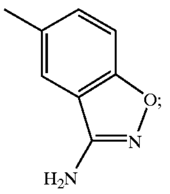
-continued
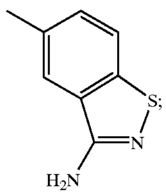
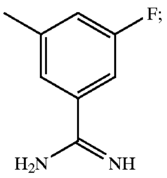
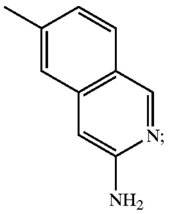
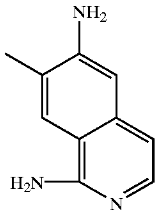
;
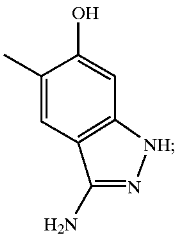
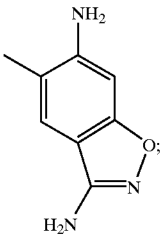
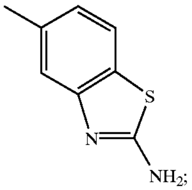
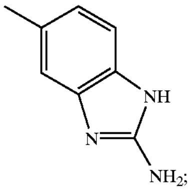
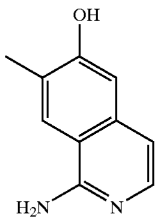
;
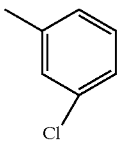
;
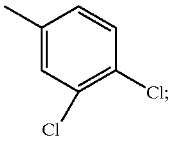
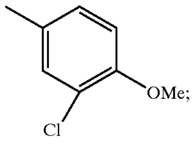
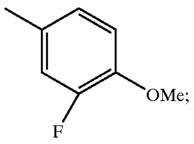
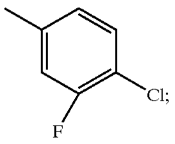
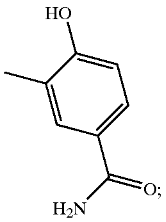
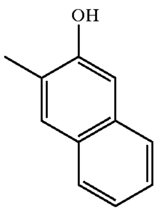
;
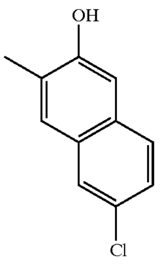
;
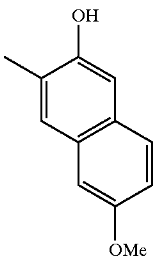
;
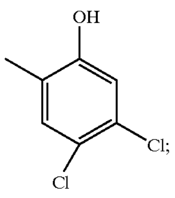
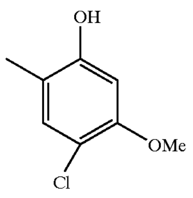
and -continued

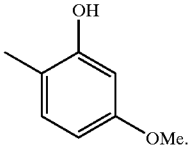

wherein $R^{7c}$ is selected from the group consisting of: H, Me, Ph, OMe, F, OH, Br, $NH_2$, $OCH_2Ph$, $OCH_2CH_2OMe$,

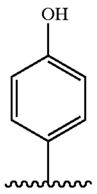 ; 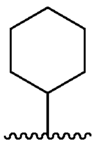 ; 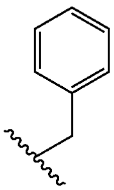 ;

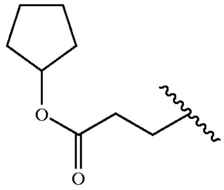 ; 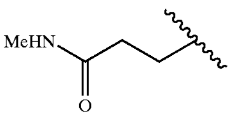 ;

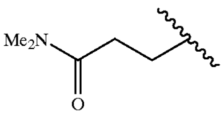 and 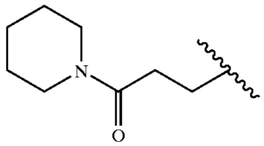

and wherein $R^{8c}$ is selected from the group consisting of: H; Me; Et; Ph;

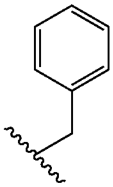 ; 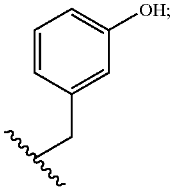 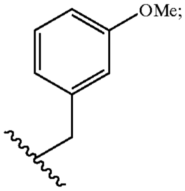

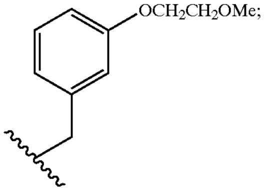 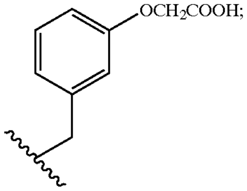

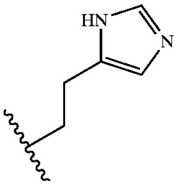 and 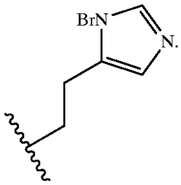

31. A compound of claim 1, having the formula:

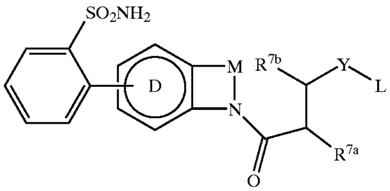

wherein the following portion of said formula

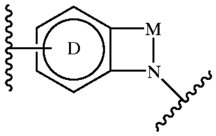

is selected from the group consisting of:

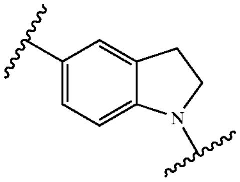 ; 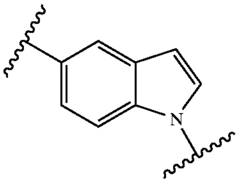 ;

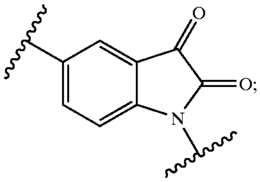 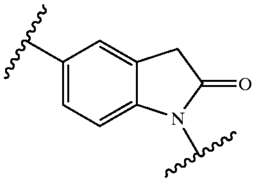 and

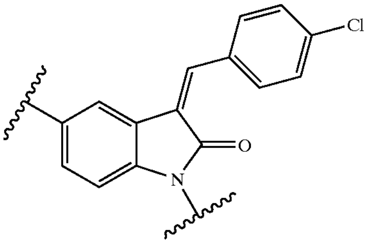

wherein Y and L, taken together, are selected from the group consisting of:

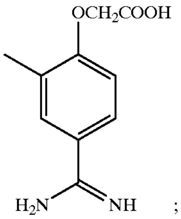 ; 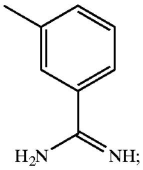 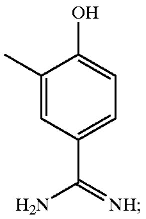

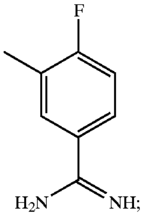 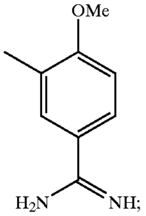 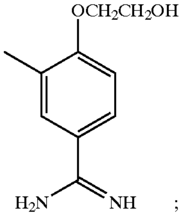 ;

-continued
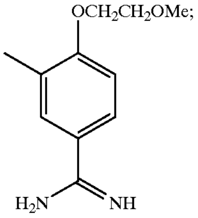
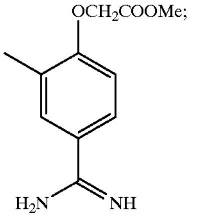
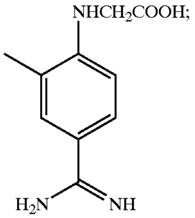
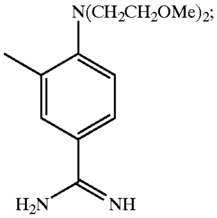
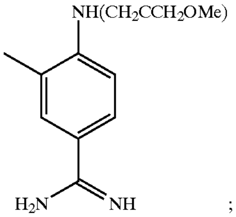
;
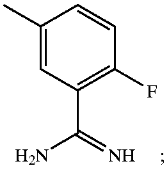
;
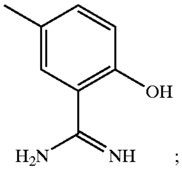
;
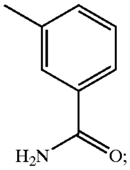
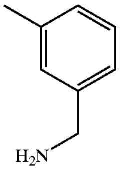
;
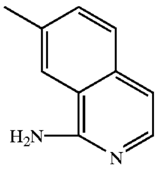
;
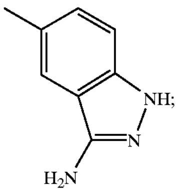
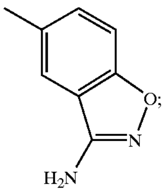
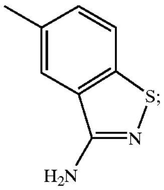
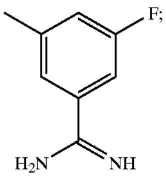
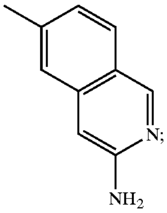
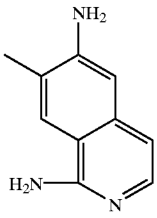
;
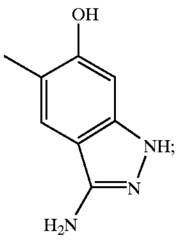
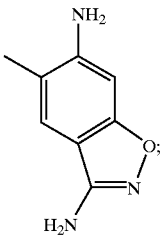
-continued
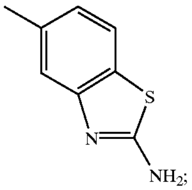
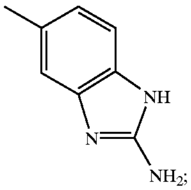
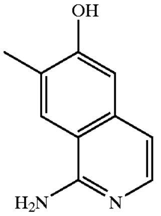
;
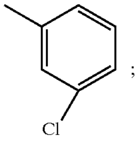
;
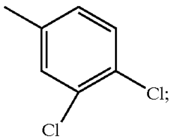
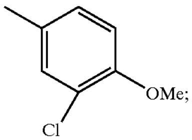
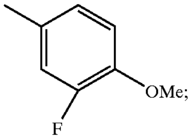
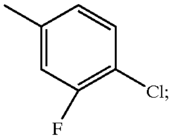
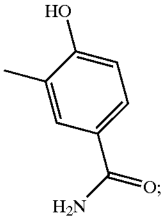
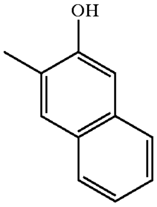
;
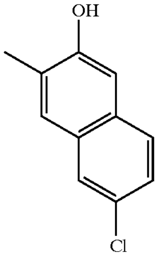
;
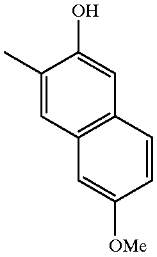
;
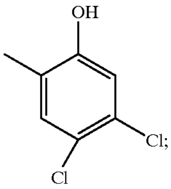
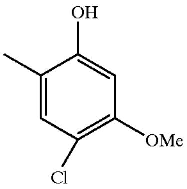
and
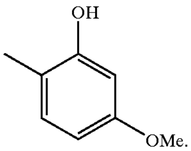
wherein $R^{7a}$ is selected from the group consisting of:
H, Me, Ph, OMe, F, OH, Br, $NH_2OCH_2Ph$, $OCH_2CH_2OMe$,
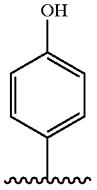
;
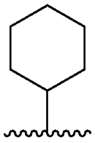
;
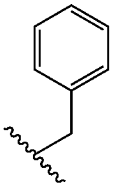
;

-continued
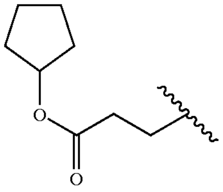 ; 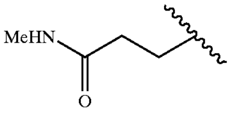 ;
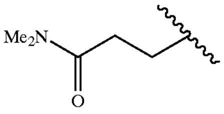 and 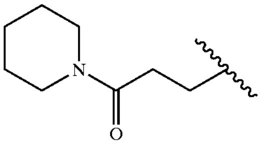
and wherein $R^{7b}$ is selected from the group consisting of: H; Me; Et; Ph;
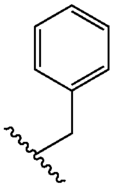 ; 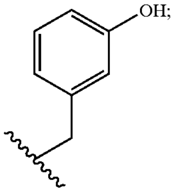 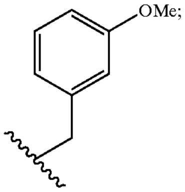
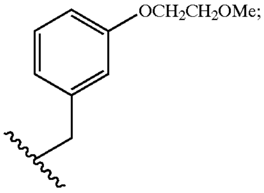 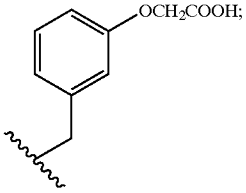
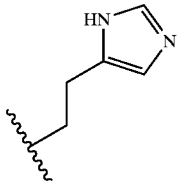 and 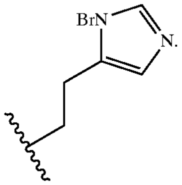
32. A compound of claim 1, having the formula:
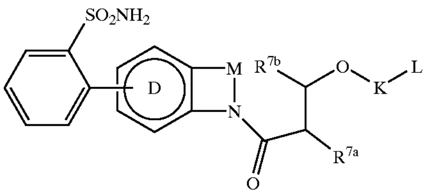
wherein the following portion of said formula
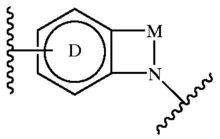
is selected from the group consisting of:
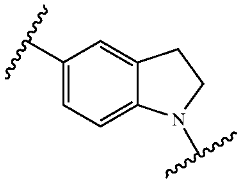 ; 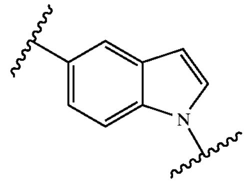 ;
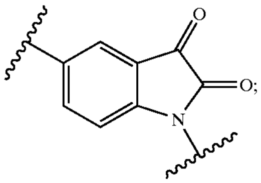 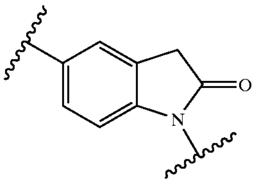 and
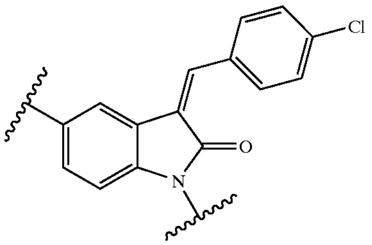
wherein Y and L, taken together, are selected from the group consisting of:
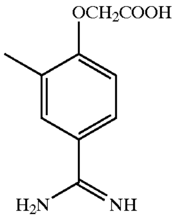 ; 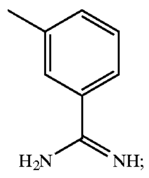 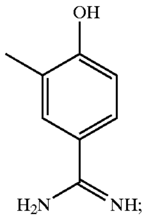
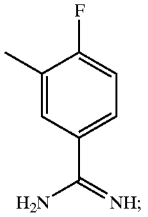 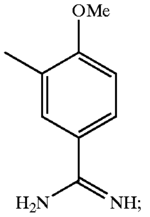 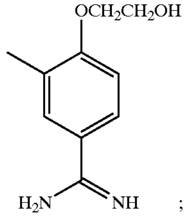 ;
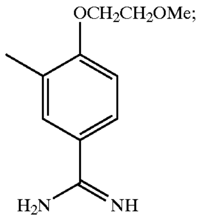 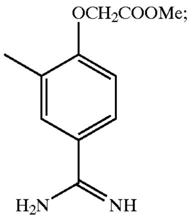
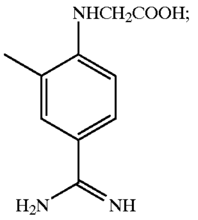 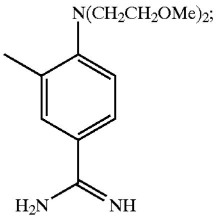

-continued
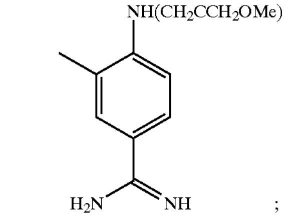
;
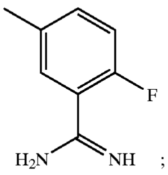
;
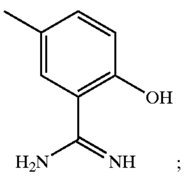
;
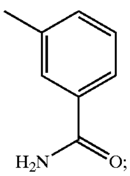
;
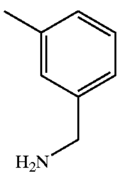
;
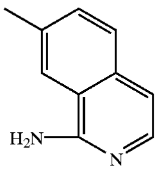
;
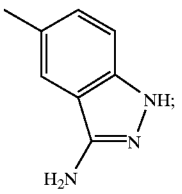
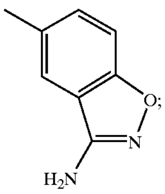
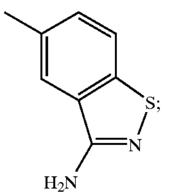
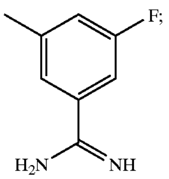
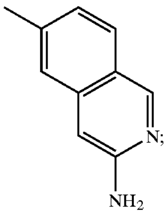
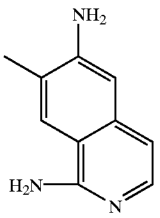
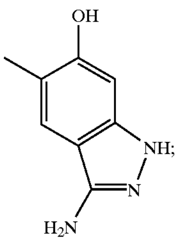
;
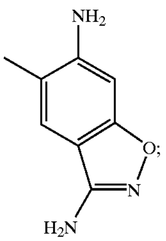
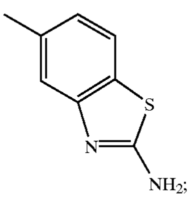
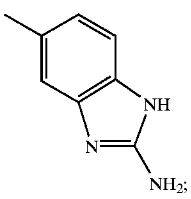
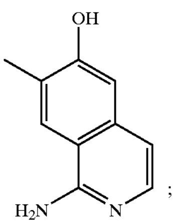
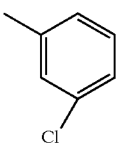
;
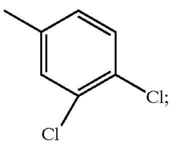
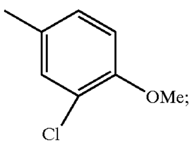
-continued
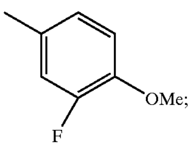
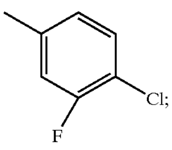
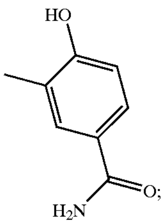
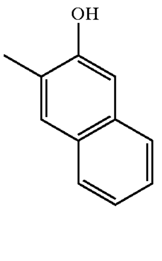
;
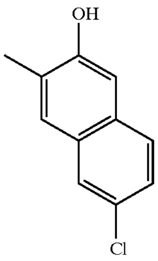
;
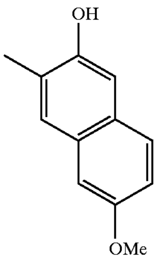
;
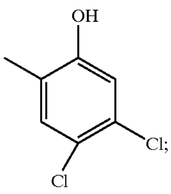
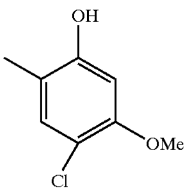
and
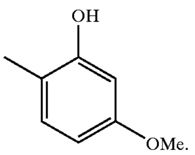
wherein $R^{7a}$ is selected from the group consisting of:
H, Me, Ph, OMe, F, OH, Br, $NH_2$, $OCH_2Ph$, $OCH_2CH_2OMe$,
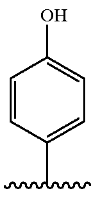
;
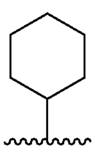
;
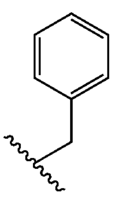
;
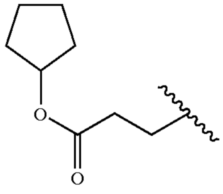
;
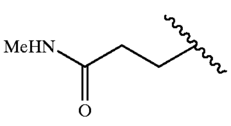
;
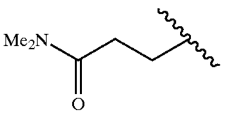
and
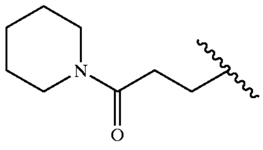
and wherein $R^{7b}$ is selected from the group consisting of:
H; Me; Et; Ph;

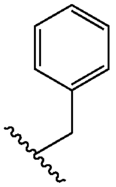
;
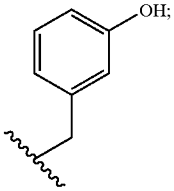
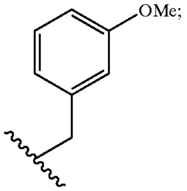
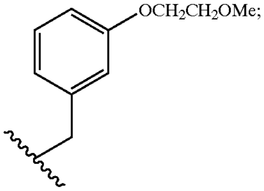
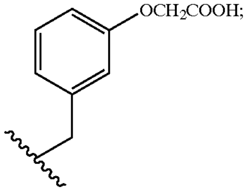
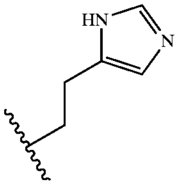
and
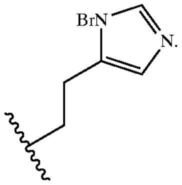
33. A compound of claim 1, having the formula:
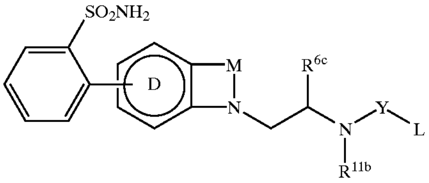
wherein the following portion of said formula
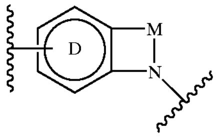
is selected from the group consisting of:
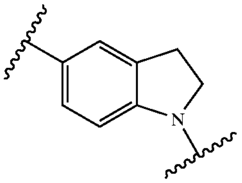
;
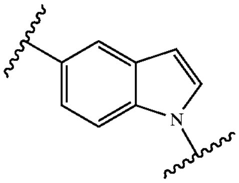
;
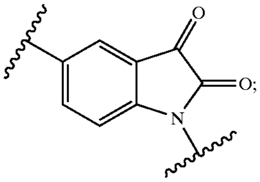
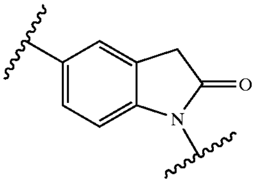
and
-continued
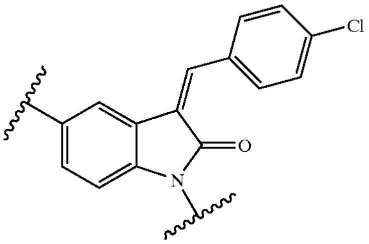
wherein Y and L, taken together, are selected from the group consisting of:
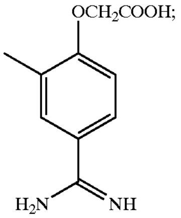
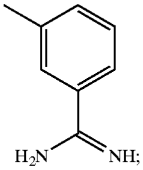
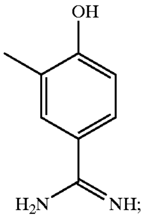
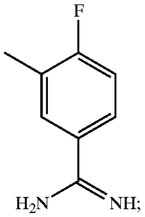
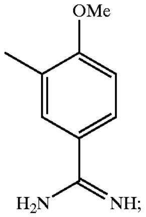
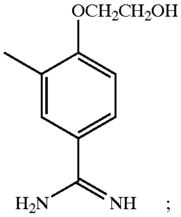
;
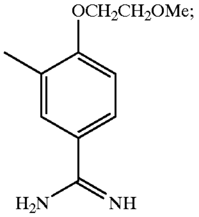
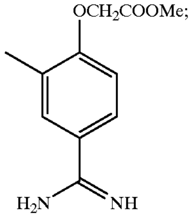
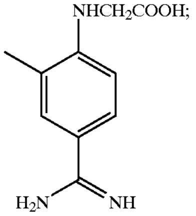
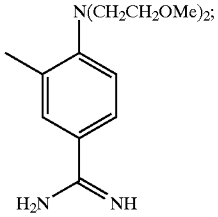
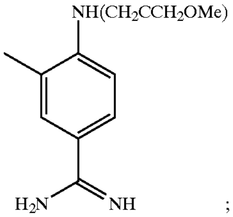
;
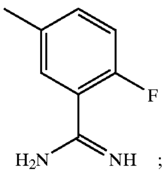
;
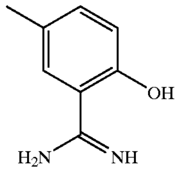
;
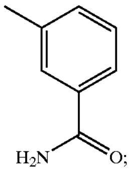
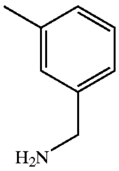
;

-continued
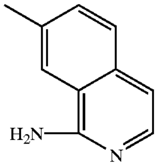 ; 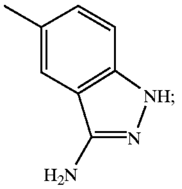 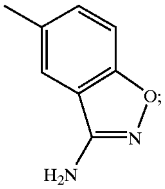
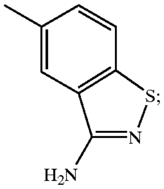 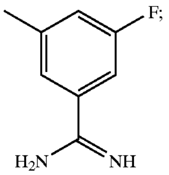 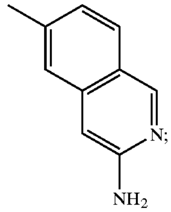
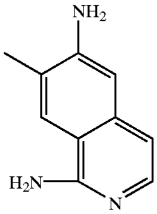 ; 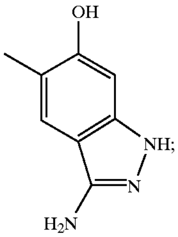 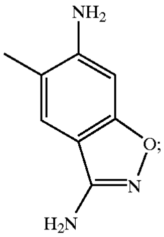
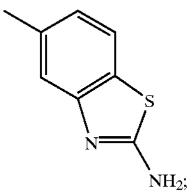 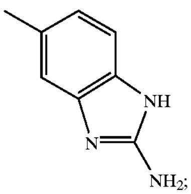 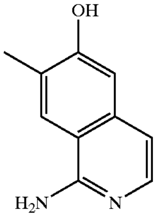 ;
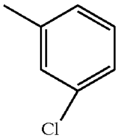 ; 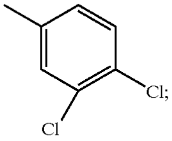 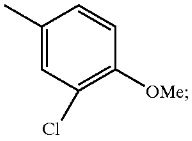
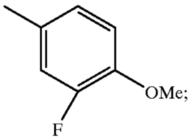 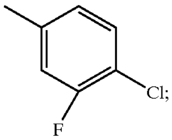 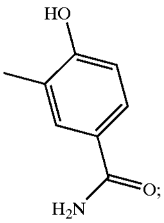
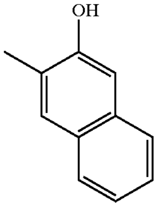 ; 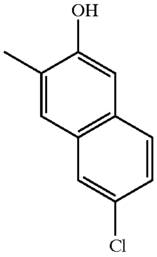 ; 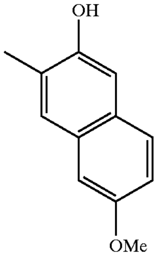 ;
-continued
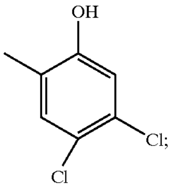 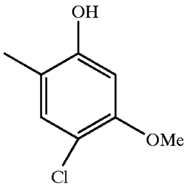 and
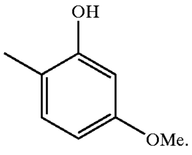
wherein $R^{6c}$ is selected from the group consisting of:
H, Me Et; Ph; OMe; F; OH; Br; $NH_2$; $SO_2Me$; $OCH_2Ph$; $OCH_2CH_2OMe$;
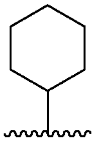 ; 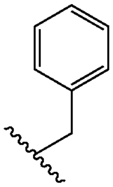 ; 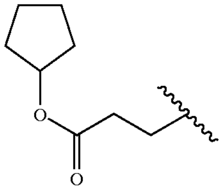 ;
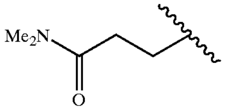 and 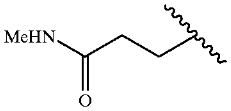
and wherein $R^{11b}$ is selected from the group consisting of:
H; Me; Et; Cl; Br; F; Ph;
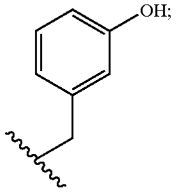 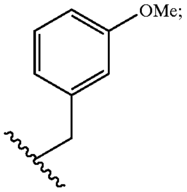
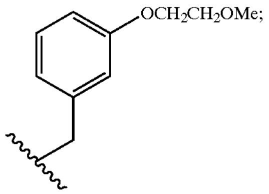 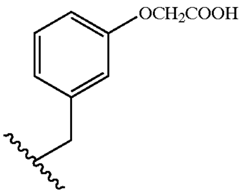 and
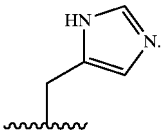

34. A compound of claim 1, having the formula:
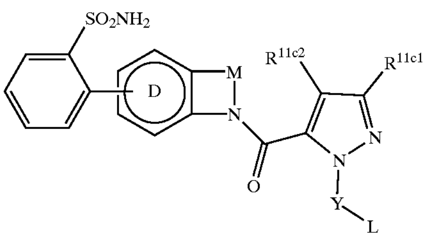
wherein the following portion of said formula
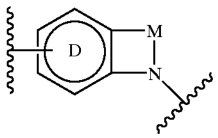
is selected from the group consisting of:
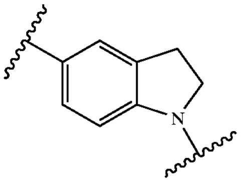 ; 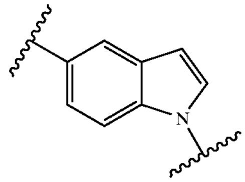 ;
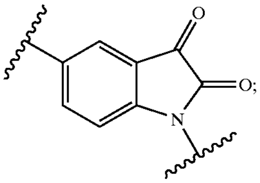 ; 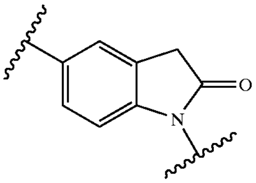 and
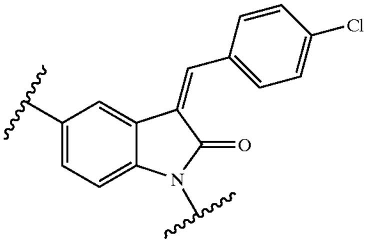
wherein Y and L, taken together, are selected from the group consisting of:
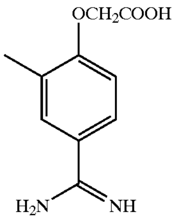 ; 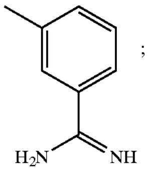 ; 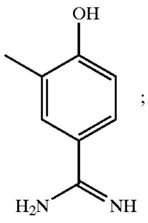 ;
-continued
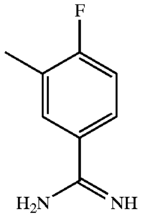 ; 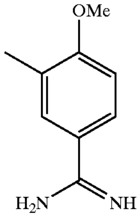 ; 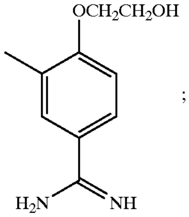 ;
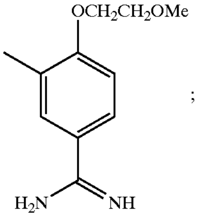 ; 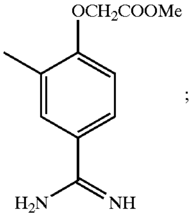 ;
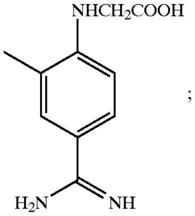 ; 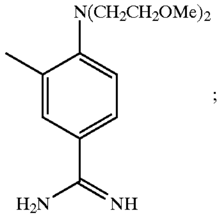 ;
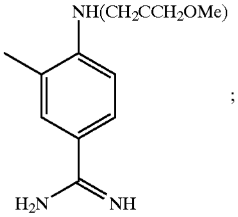 ; 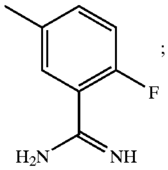 ;
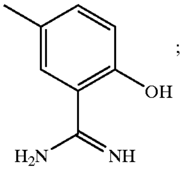 ; 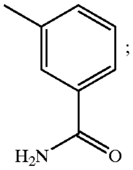 ; 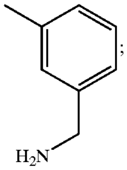 ;
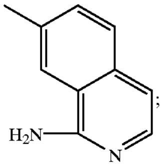 ; 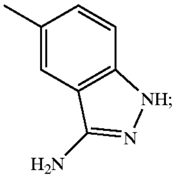 ; 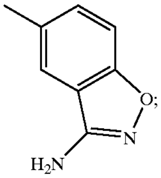 ;
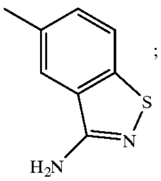 ; 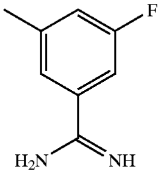 ; 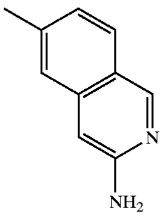 ;
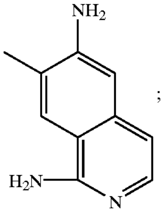 ; 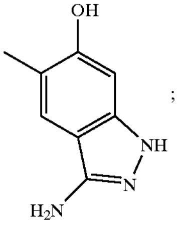 ; 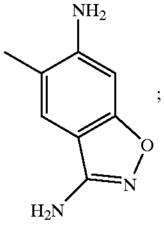 ;

-continued
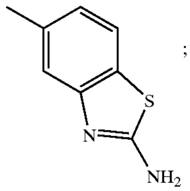 ; 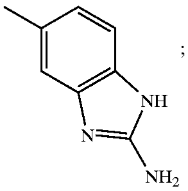 ; 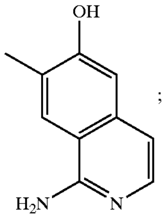 ;
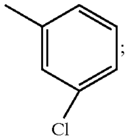 ; 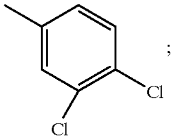 ; 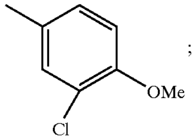 ;
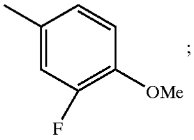 ; 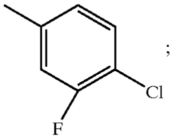 ; 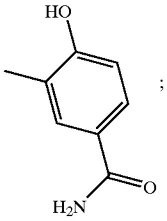 ;
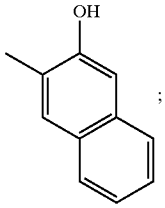 ; 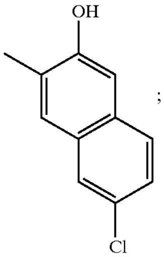 ; 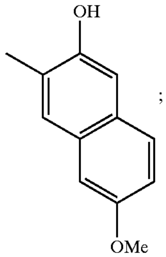 ;
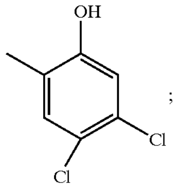 ; 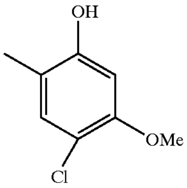 and
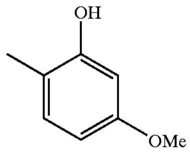
wherein $R^{11c1}$ is selected from the group consisting of:
H; Me; Et; Ph; OMe; F; OH; Br; $NH_2$; $SO_2Me$; $OCH_2Ph$; $OCH_2CH_2OMe$;
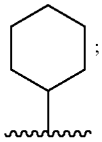 ; 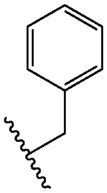 ; 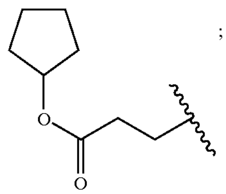 ;
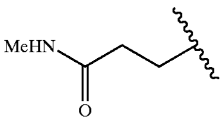 and 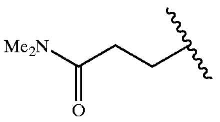
and wherein $R^{11c2}$ is selected from the group consisting of:
H; Me; Et; Cl; Br; F; Ph;
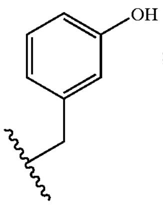 ; 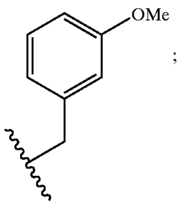 ;
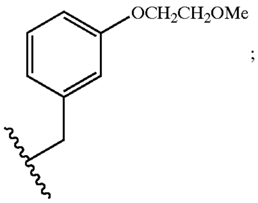 ; 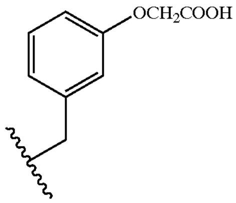 and
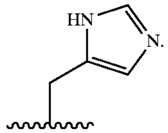
35. A compound of claim 1, having the formula:
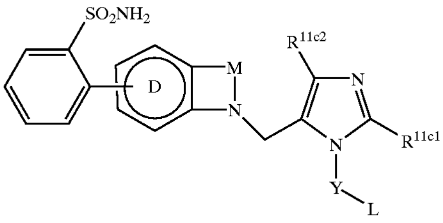
wherein the following portion of said formula
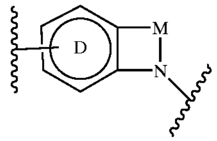
is selected from the group consisting of:
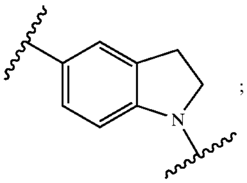 ; 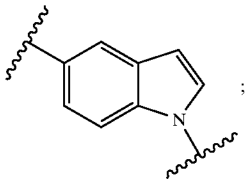 ;
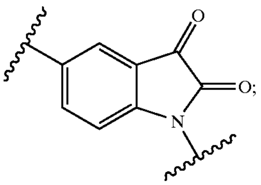 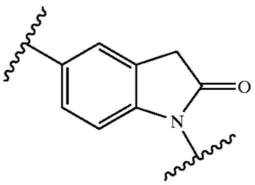 and -continued
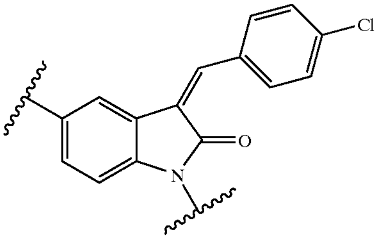
wherein Y and L, taken together, are selected from the group consisting of:
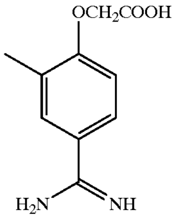 ; 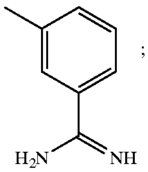 ; 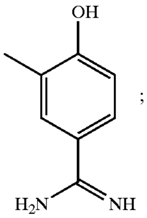 ;
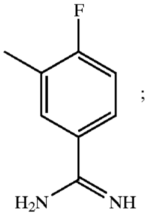 ; 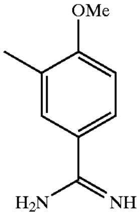 ; 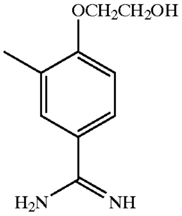
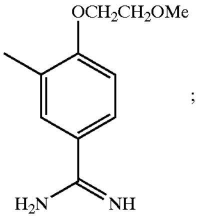 ; 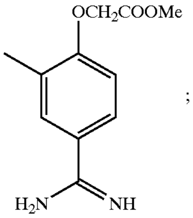 ;
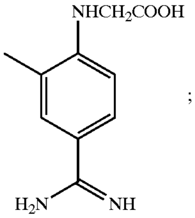 ; 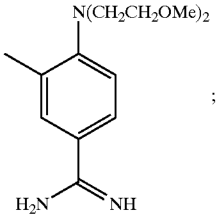 ;
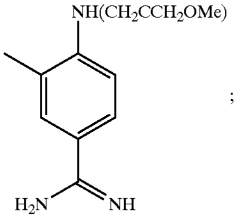 ; 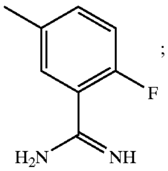 ;
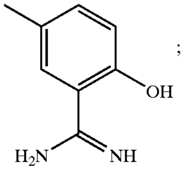 ; 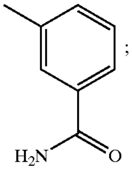 ; 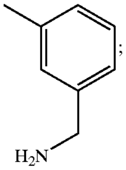 ;
-continued
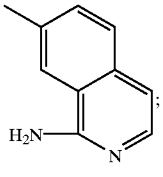 ; 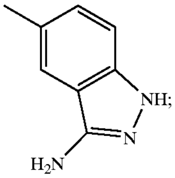 ; 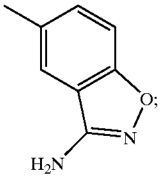 ;
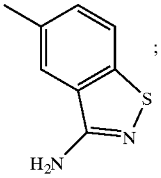 ; 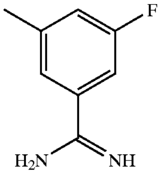 ; 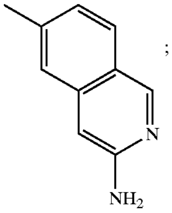 ;
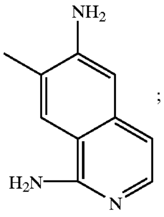 ; 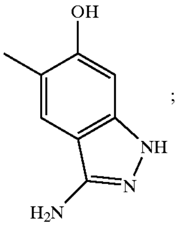 ; 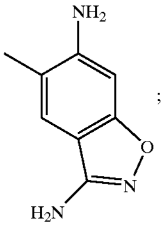 ;
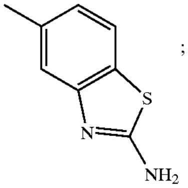 ; 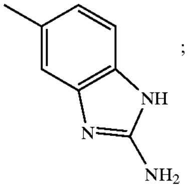 ; 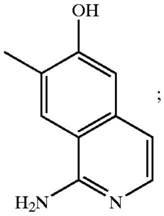 ;
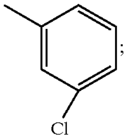 ; 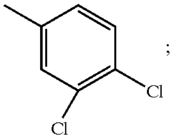 ; 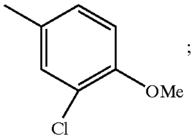 ;
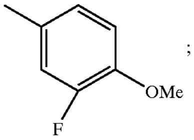 ; 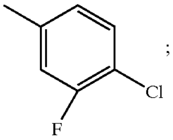 ; 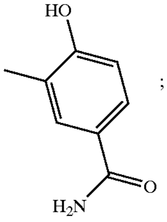 ;
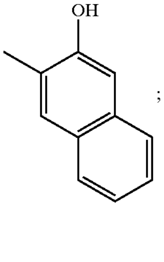 ; 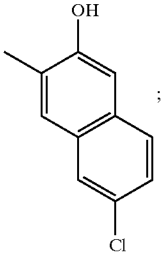 ; 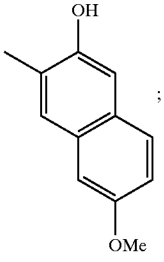 ;
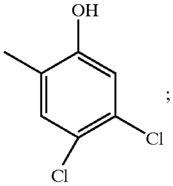 ; 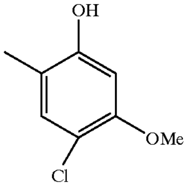 and -continued

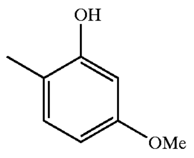

wherein $R^{11c1}$ is selected from the group consisting of:

H; Me; Et; Ph; OMe; F; OH; Br; $NH_2$; $SO_2Me$; $OCH_2Ph$; $OCH_2CH_2OMe$;

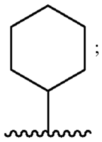 ; 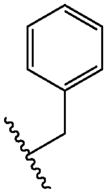 ; 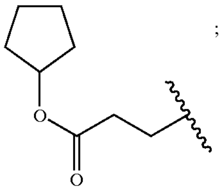 ;

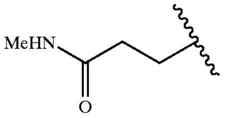 and 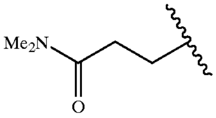

and wherein $R^{11c2}$ is selected from the group consisting of:

H; Me; Et; Cl; Br; F; Ph;

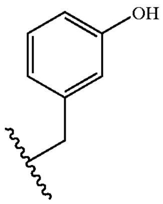 ; 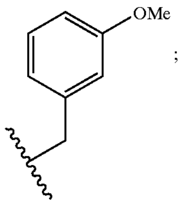 ;

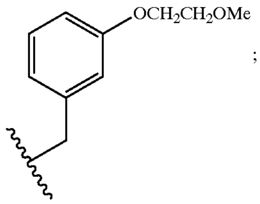 ; 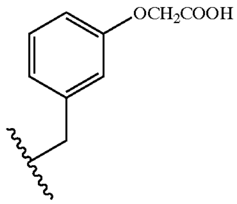 and

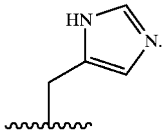

36. A compound of claim 1, having the formula:

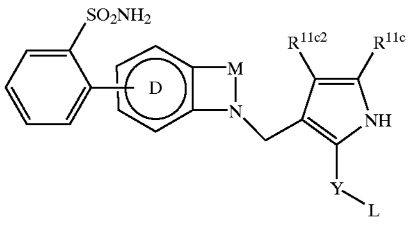

wherein the following portion of said formula

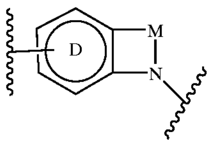

is selected from the group consisting of:

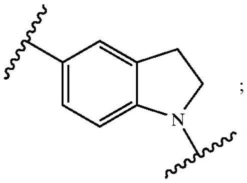 ; 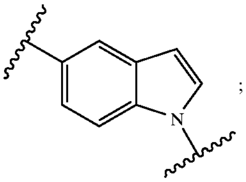 ;

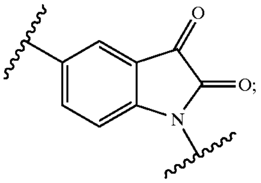 ; 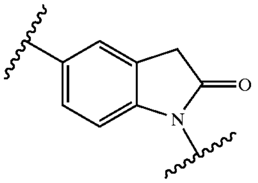 and

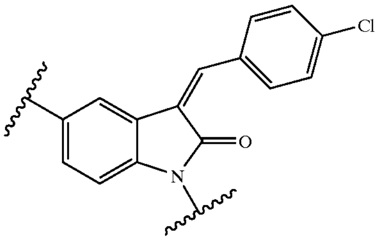

wherein Y and L, taken together, are selected from the group consisting of:

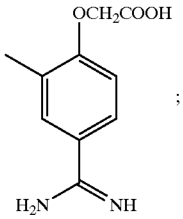 ; 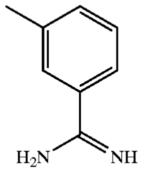 ; 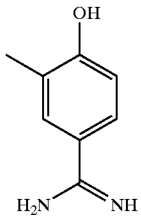 ;

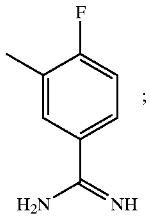 ; 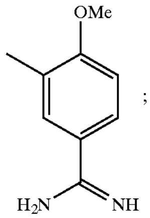 ; 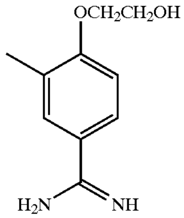

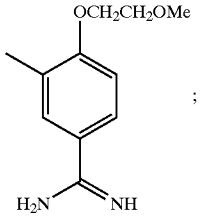 ; 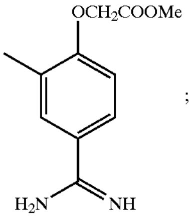 ;

-continued
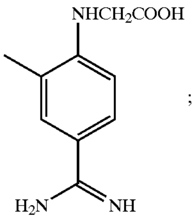 ; 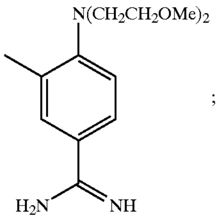 ;
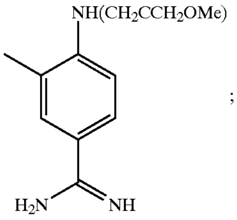 ; 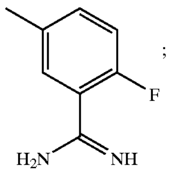 ;
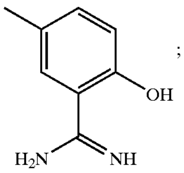 ; 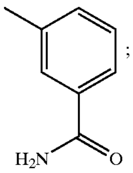 ; 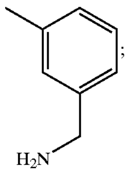 ;
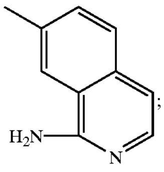 ; 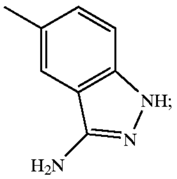 ; 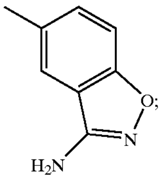 ;
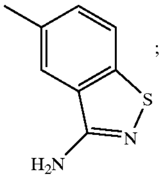 ; 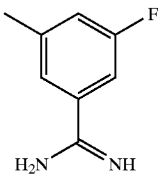 ; 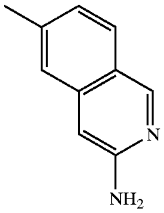 ;
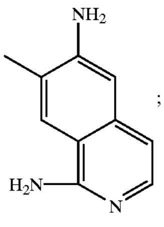 ; 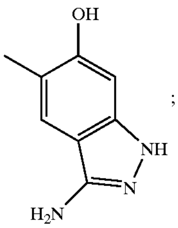 ; 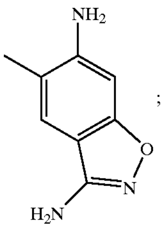 ;
-continued
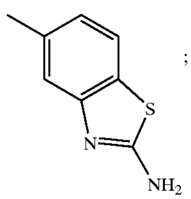 ; 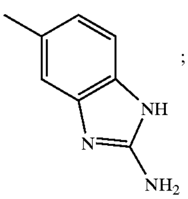 ; 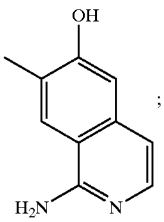 ;
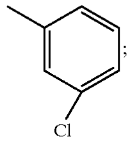 ; 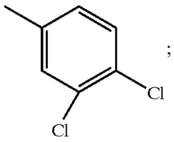 ; 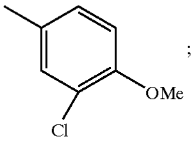 ;
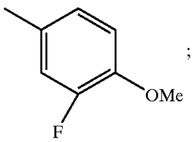 ; 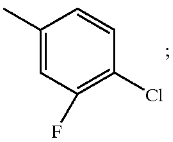 ; 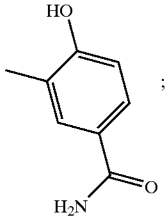 ;
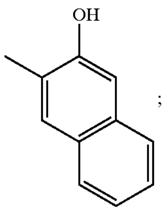 ; 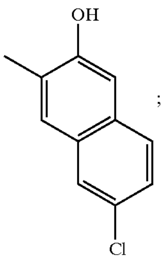 ; 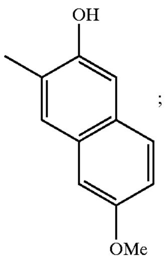 ;
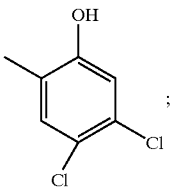 ; 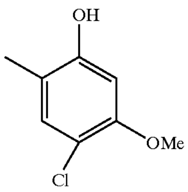 and
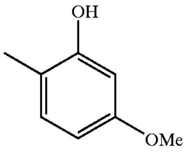
wherein $R^{11c1}$ is selected from the group consisting of: H; Me; Et; Ph; OMe; F; OH; Br; $NH_2$; $SO_2Me$; $OCH_2Ph$; $OCH_2CH_2OMe$;
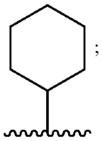 ; 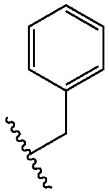 ; 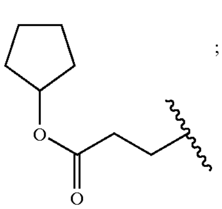 ;
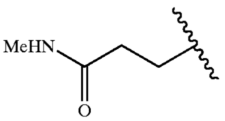 and 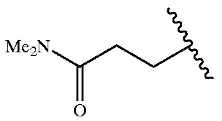

and wherein $R^{11c2}$ is selected from the group consisting of:
H; Me; Et; Cl; Br; F; Ph;
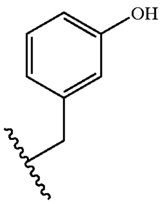
;
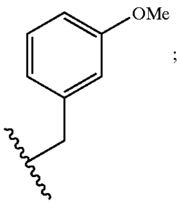
;
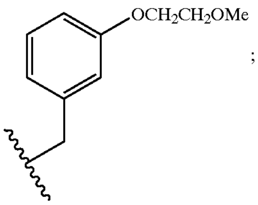
;
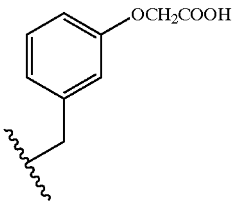
and
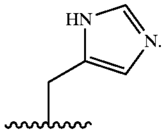
37. A compound of claim 1, selected from the group consisting of:
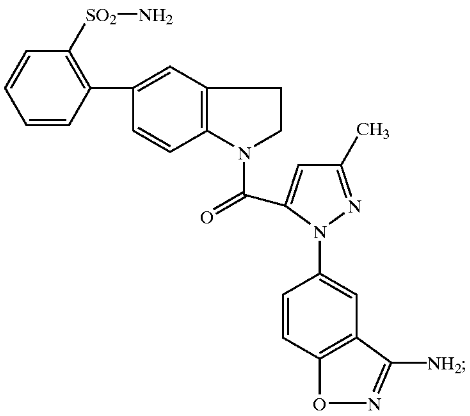
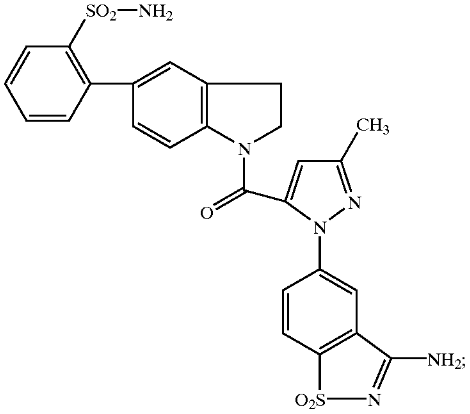
-continued
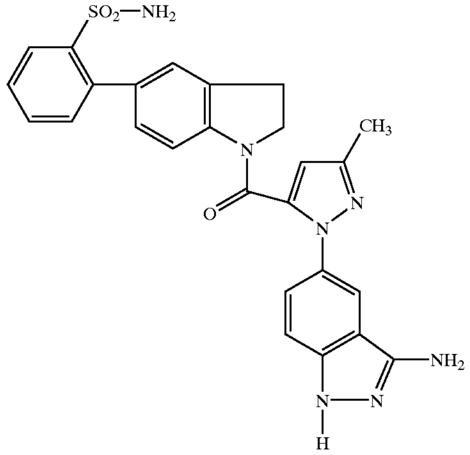
and
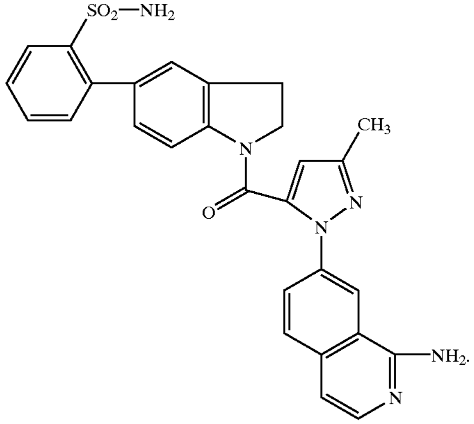
38. A compound according to the formula:
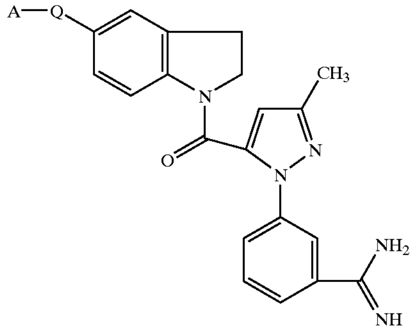
wherein A—Q— is selected from the group consisting of:
t-Bu; O-t-Bu; —$(CH_2)_{0-5}$-amino; OH; carboxylic acid ester; carboxamide;
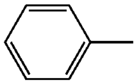
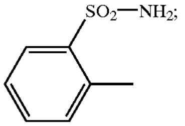
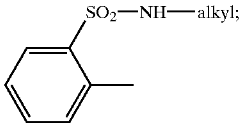
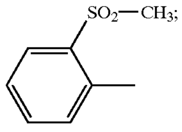

-continued
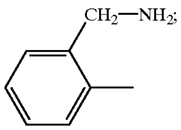
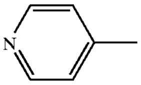
;
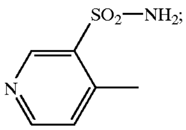
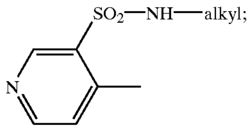
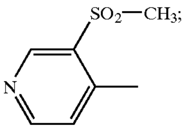
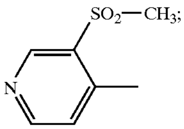
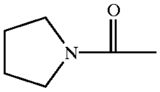
;
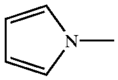
;
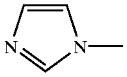
;
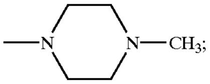
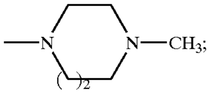
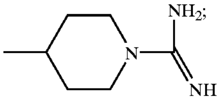
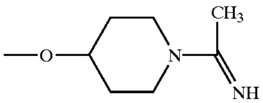
and
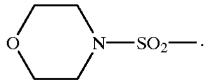
39. A compound of claim 1, selected from the group consisting of:
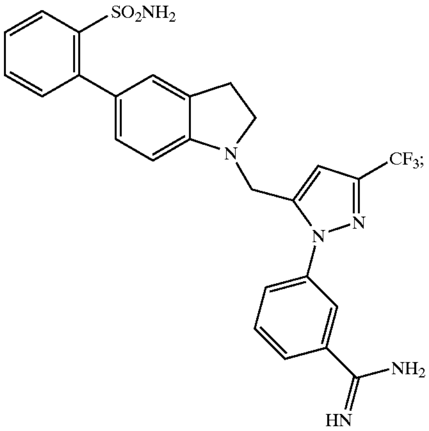
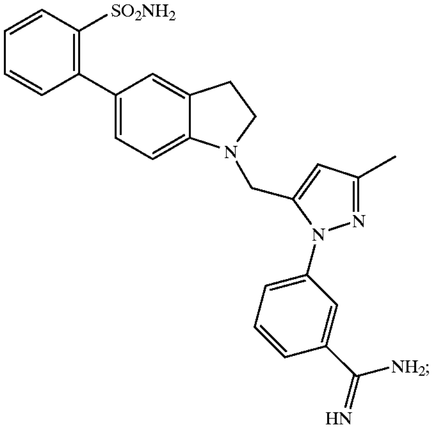
-continued
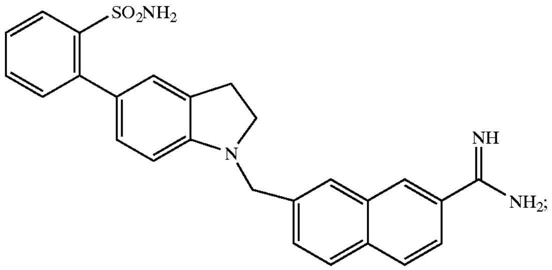
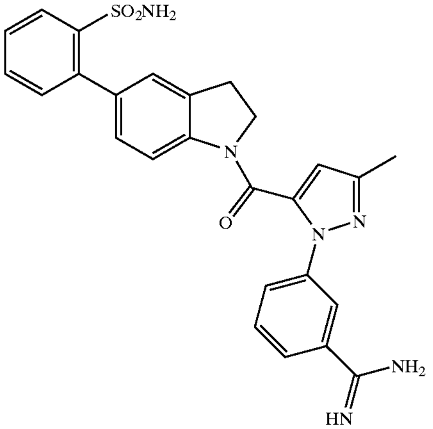
and
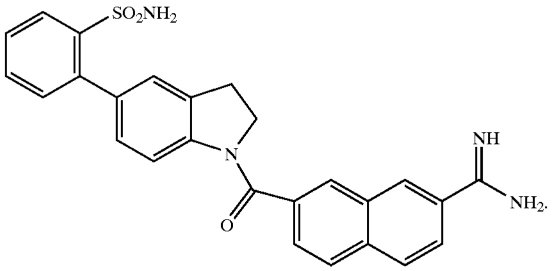
40. A compound of claim 1, selected from the group consisting of:
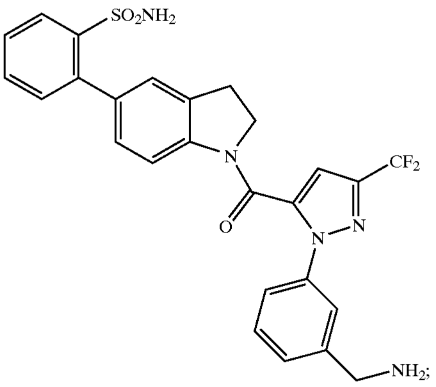

-continued
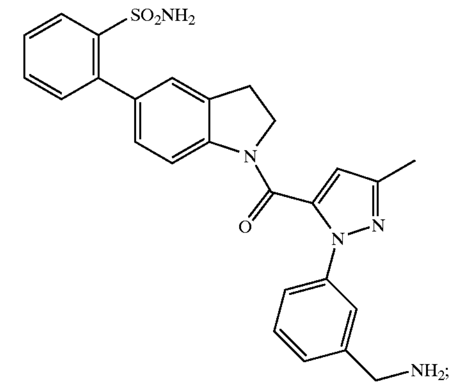
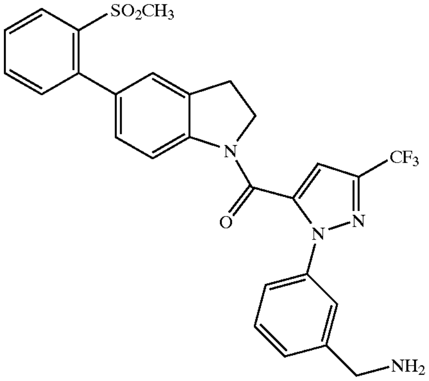
and
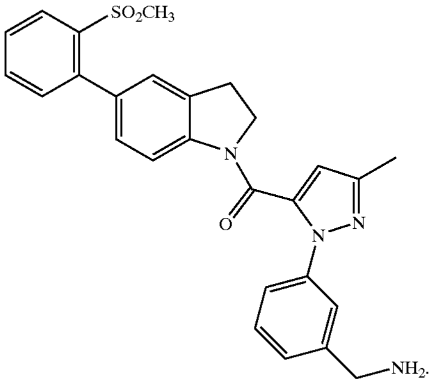
41. A compound of claim 1, selected from the group consisting of:
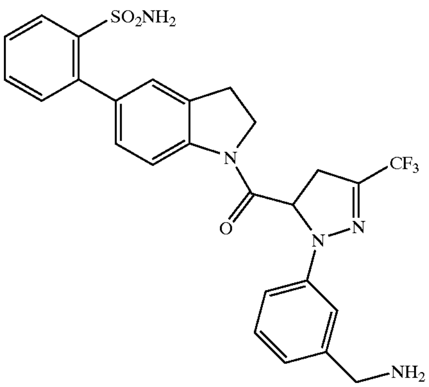
and
-continued
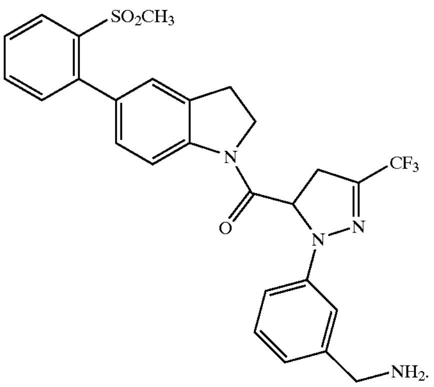
42. A compound, selected from the group consisting of:
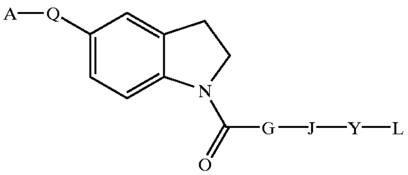
and
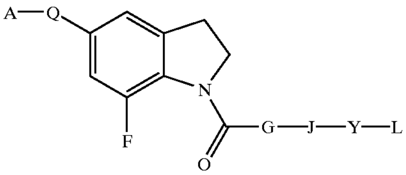
wherein Q is a direct link, and A is a member selected from the group:
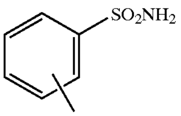
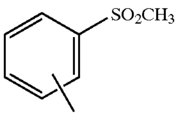
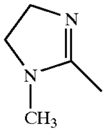
and
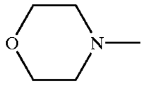
;
or Q is a —C(═NH)— group, and A is a member selected from the group:
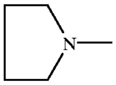
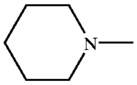
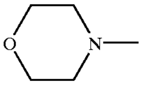
and
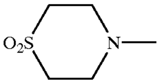
;

G is a direct link;
J is a member selected from the group:
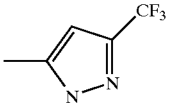
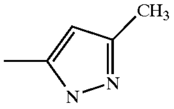
and
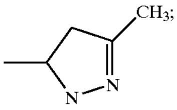
; and
Y—L is a member selected from the group:
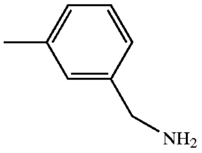
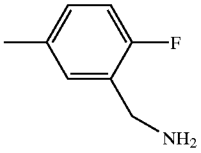
-continued
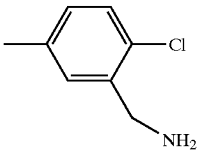
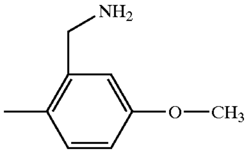
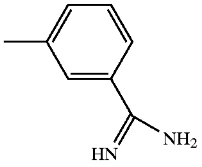
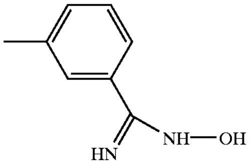
and
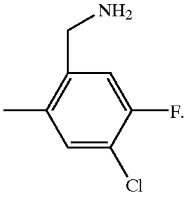
.
* * * * *

UNITED STATES PATENT AND TRADEMARK OFFICE

CERTIFICATE OF CORRECTION

PATENT NO. : 6,534,535 B1
DATED : March 18, 2003
INVENTOR(S) : Zhu et al.

It is certified that error appears in the above-identified patent and that said Letters Patent is hereby corrected as shown below:

Column 402,
Lines 24-29, replace

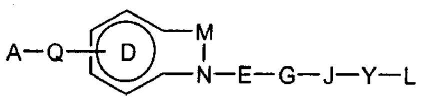

with

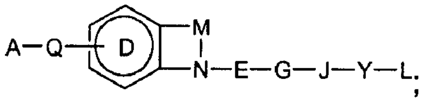

Lines 34-36, replace "$-N(-R^2,-R^3)-C(=N-R^2)-,(-R^2, -R^3)N-C(=N-R^2)-(-R^2, -R^3)N-C(=N-R^2)-N(-R-)-$" with -- $-N(-R^2,-R^3), R^3-C(=N-R^2)-,(-R^2, -R^3)N-C(=N-R^2)-, (-R^2, -R^3)N-C(=N-R^2)-N(-R-)-$ --;

Column 404,
Line 36, remove "p2";
Line 51, replace "R8 c" with -- $R^{8c}$ --;
Line 59, replace "$-C_{0-4}alkylC(=O)NR^9-CH_2-CH_{2-O-R}{}^{10}$" with -- $-C_{0-4}alkylC(=O)NR^9-CH_2-CH_2-O-R^{10}$ --;

Column 405,
Line 29, remove "O";
Line 41, replace "$-O-C_{1-4}alkyl, -O-C_{1-4}alkyl$" with -- $-O-C_{1-4}alkyl-O-C_{1-4}alkyl$ --;

Column 406,
Line 42, remove "<" before "hydrogen";
Line 64, replace "a phramceutical" with -- A pharmaceutical --;
Line 66, replace "therapeutacally" with -- therapeutically --;
Line 67, replace "cliam" with -- claim --;

Column 407,
Line 11, remove "," after "cerebrovascular";
Line 12, replace "strroke" with -- stroke --;
Line 22, replace "required" with -- requiring --;

Column 408,
Line 14, replace "$C_{0-4}alkylC_{3-8}$" with -- $C_{0-4}alkylC_{3-8}cycloalkyl$ --;
Line 16, replace, "5 . 6" with -- 5-6 --;
Line 28, add -- , -- after "$C_{0-4}alkylC_{3-8}cycloalkyl$";

Column 409,
Line 12, remove "<";
Lines 23-24, replace "$C_{1-4\ 4}alkyl$" with -- $C_{1-4}alkyl$ --;

UNITED STATES PATENT AND TRADEMARK OFFICE

CERTIFICATE OF CORRECTION

PATENT NO. : 6,534,535 B1

DATED : March 18, 2003

INVENTOR(S) : Zhu et al.

It is certified that error appears in the above-identified patent and that said Letters Patent is hereby corrected as shown below:

<u>Column 410,</u>
Line 29, replace "$C_{2-6}$alkenyl, $C_{2-6}$alkenyl" with -- $C_{2-6}$alkenyl, $C_{2-6}$alkynyl --;
Line 49, replace "$NR^{2b}NR^{3b}$" with -- $NR^{2b}R^{3b}$ --;

<u>Column 411,</u>
Line 50, replace "pos-thrombolytic" with -- post-thrombolytic --;

<u>Column 413,</u>
Line 42, replace "-O-$C_{,4}$alkyl" with -- -O-$C_{1-4}$alkyl --;

<u>Column 414,</u>
Line 31, replace "$NR_{2b}R^{3b}$, $SO_2NR_{2b}R^{3b}$" with -- $NR^{2b}R^{3b}$, $SO_2NR^{2b}R^{3b}$ --;

<u>Column 416,</u>
Line 30, replace "-(-C(-$R^{5a}$,-$R^{6a}$)-C" with -- -(-C(-$R^{5b}$,-$R^{6b}$)-C --;
Line 49, replace "$CH_2$-$CH_2$-O-$R^{10-)}{}_2$" with -- $CH_2$-$CH_2$-O-$R^{10}$-$)_2$ --; and <u>Column 459,</u>
Line 58, replace "$R^{11c}$" with -- $R^{11c1}$ --.

Signed and Sealed this

Twenty-sixth Day of August, 2003

JAMES E. ROGAN

*Director of the United States Patent and Trademark Office*